US007285641B2

(12) United States Patent
Fu et al.

(10) Patent No.: US 7,285,641 B2
(45) Date of Patent: Oct. 23, 2007

(54) ANTIBODIES AGAINST GENE PRODUCTS RELATED TO WERNER'S SYNDROME

(76) Inventors: Ying-Hui Fu, 7417 28th Ave. Northwest, Seattle, WA (US) 98117; Chang-En Yu, 5709 60th Ave. Northeast, Seattle, WA (US) 98105; Junko Oshima, 5200 Ravenna Ave. Northeast, Seattle, WA (US) 98105; John T Mulligan, 5823 17th Ave. Northeast, Seattle, WA (US) 98105; Gerard D Schellenberg, 7031 19th Ave. Northwest, Seattle, WA (US) 98117

( * ) Notice: Subject to any disclaimer, the term of this patent is extended or adjusted under 35 U.S.C. 154(b) by 309 days.

(21) Appl. No.: 10/374,077

(22) Filed: Feb. 25, 2003

(65) Prior Publication Data

US 2004/0006779 A1 Jan. 8, 2004

Related U.S. Application Data

(60) Division of application No. 09/618,166, filed on Jul. 17, 2000, now Pat. No. 6,583,112, which is a continuation of application No. 08/781,891, filed on Dec. 27, 1996, now Pat. No. 6,090,620, which is a continuation-in-part of application No. 08/632,175, filed on Apr. 12, 1996, now abandoned, which is a continuation-in-part of application No. 08/594,242, filed on Jan. 30, 1996, now abandoned, which is a continuation-in-part of application No. 08/580,539, filed on Dec. 29, 1995, now abandoned.

(60) Provisional application No. 60/009,409, filed on Dec. 29, 1995, provisional application No. 60/010,835, filed on Jan. 30, 1996.

(51) Int. Cl.
*C07K 16/00* (2006.01)

(52) U.S. Cl. ............................ 530/387.1; 530/387.15; 435/326

(58) Field of Classification Search ............... 435/69.1, 435/325
See application file for complete search history.

(56) References Cited

U.S. PATENT DOCUMENTS 6,090,620 A 7/2000 Fu et al. ..................... 435/325

FOREIGN PATENT DOCUMENTS

WO WO 97/24435 7/1997

OTHER PUBLICATIONS

Martin, GM. Cell, 2005, vol. 120, p. 523-532.*

Bosch et al. Journal of Virology, Nov. 1987, vol. 61 (11):3607-3611.*

Coleman et al. Research in Immunology, 1994; 145(1): 33-36.*

GenBank Accession No. T39125, "EST27,19 WATM1 *Homo sapiens* cDNA clone 27m mRNA sequence," located at http://www.ncbi.nlm.nih.gov.

Goto et al., "Genetic linkage of Werner's syndrome to five markers on chromosome 8," *Nature 355*: 735-738, 1992.

Houdebine, Journal of Biotechnology, vol. 34, pp. 269-287, 1994.

Imamura et al., "Cloning of a mouse homoloque of the human Werner Syndrome gene and assignment to 8A4 by fluorescence in Situ hybridization," *Genomics 41*:298-300, 1997.

Kappel et al., *Current Opinion in Biotechnology*, vol. 3, pp. 548-553, 1992.

Kurimasa et al., "Construction of 110 cosmid markers and a 4.5-Mb YAC cotig on human chromosome 8p12-q11," *Genomics 28*: 147-153, 1995.

Lombard and Guarente, "Cloning the gene for Werner syndrome: a disease with many symptoms of premature aging," *Trends in Genetics 12*(8): 283-286, 1996.

Nakura et al., "Genetic association between chromosome 8 microsatellites and Werner syndrome (WRN)," *American Journal of Human Genetics 57*(4 Suppl.): A266, Abstract No. 1544, 1995.

Oshima et al., "Homozygous and compound heterozygous mutations at the Werner syndrom locus," *Human Molecular Genetics 5*(12): 1909-1913, 1996.

Puranam and Blackshear, "Cloning and characterization of RECQL, a potential human homoloque of the *Escherichia coli* DNA helicase RecQ," *Journal of Biological Chemistry 269*(47): 29838-29845, 1994.

Seki et al., "Molecular cloning of cDNA encoding human DNA helicase Q1 which has homology to *Escherichia coli* Rec Q helicase and localization of the gene at chromosome 12p12," *Nucleic Acids Research 22*(22): 4566-4573, 1994.

Srojek & Wagner, Genetic Engineering: Principles and Methods, vol. 10, pp. 221-246, 1988.

Thweatt et al, "A novel cDNA overexpressed in Werner Syndrome (WS) fibroblasts inhibit colony formation in normal human fibroblasts and in HeLa Cells," *FASEB Journal 9*(6): A1270, Abstract No. 84, 1995.

Umezu et al., Proceedings of the National Academy of Sciences, USA, vol. 87, pp. 5363-5367, Abstract only, Jul. 1990.

Wall, *Theriogenology*, vol. 45, pp. 57-68, 1996.

Ye et al., "Genetic association between chromosome 8 microsatellite (MS8-134) and Werner Syndrom (WRN): Chromosome Microdissection and homozygosity mapping," *Genomics 28*: 566-569, 1995.

Yu et al., "Linkage disequilibrium and haplotype studies of chromosome 8p 11.1-21.1 markers and Werner Syndrome," *Am. J. Hum. Genet. 55*: 356-364, 1994.

Yu et al., "Positional cloning of the Werner's Syndrome gene," *Science 272*: 258-262, 1996.

Yu et al., "Mutations in the consensus helicase domains of the Werner Syndrome gene," *Am. J. Hum. Genet. 60*: 330-341, 1997.

Bradley et al., Biotechnology, vol. 10, pp. 534-539, May 1992.

(Continued)

*Primary Examiner*—Christina Chan
*Assistant Examiner*—Yunsoo Kim
(74) *Attorney, Agent, or Firm*—Seed IP Law Group PLLC

(57) ABSTRACT

The present invention discloses antibodies that specifically bind to a WRN gene product or a portion thereof.

6 Claims, 77 Drawing Sheets

OTHER PUBLICATIONS

Genbank Accession No. R58879, "NIB2278R Normalized infant brain, Bento Soares *Homo sapiens* cDNA 5' end, mRNA sequence," located at http://wwwncbi.nlm.nih.gov.

Seki et al., Nucleic Acids Research, vol. 22, pp. 4566-4573, Abstract only, Nov. 11, 1994.

Irino, N. et al., "The recQ gene of *Escherichia coli* K12: primary structure and evidence for SOS regulation," *Molecular and General Genetics*, 205:298-304, 1986.

Koyama, K. et al., "Isolation of 115 Human Chromosome 8-Specific Expressed-Sequence Tags by Exon Amplification," *Genomics*, 26:245-253, 1995.

Lecka-Czernik, B. et al., "An Overexpressed Gene Transcript in Senescent and Quiescent Human Fibroblasts Encoding a Novel Protein in the Epidermal Growth Factor-Like Repeat Family Stimulates DNA Synthesis," *Molecular and Cellular Biology*, 15(1):120-128, Jan. 1995.

Nakura, J. et al., "Homozygosity Mapping of the Werner Syndrome Locus (WRN)," *Genomics*, 23:600-608, 1994.

Wood, S. et al., "Sequence identity locates CEBPD and FGFR1 to mapped human loci within proximal 8p," *Cytogenetics and Cell Genetics*, 70:188-191, 1995.

* cited by examiner

```
TGTGCGCCGGGGAGGCGCCGGCTTGTACTCGGCAGCGCGGAATAAAGTTTGCTGATTTG    60
GTGTCTAGCCTGGATGCCTGGGTTGCAGCCCTGCTTGTGGTGGCGCTCCACAGTCATCCG   120
GCTGAAGAAGACCTGTTGGACTGGATCTTCTCGGGTTTTCTTTCAGATATTGTTTTGTAT   180
TTACCCATGAAGACATTGTTTTTTGGACTCTGCAAATAGGACATTTCAAAGATGAGTGAA   240
AAAAAATTGGAAACAACTGCACAGCAGCGGAAATGTCCTGAATGGATGAATGTGCAGAAT   300
AAAAGATGTGCTGTAGAAGAAAGAAAGGCATGTGTTCGGAAGAGTGTTTTTGAAGATGAC   360
CTCCCCTTCTTAGAATTCACTGGATCCATTGTGTATAGTTACGATGCTAGTGATTGCTCT   420
TTCCTGTCAGAAGATATTAGCATGAGTCTATCAGATGGGGATGTGGTGGGATTTGACATG   480
GAGTGGCCACCATTATACAATAGAGGGAAACTTGGCAAAGTTGCACTAATTCAGTTGTGT   540
GTTTCTGAGAGCAAATGTTACTTGTTCCACGTTTCTTCCATGTCAGTTTTTCCCCAGGGA   600
TTAAAAATGTTGCTTGAAAATAAAGCAGTTAAAAAGGCAGGTGTAGGAATTGAAGGAGAT   660
CAGTGGAAACTTCTACGTGACTTTGATATCAAATTGAAGAATTTTGTGGAGTTGACAGAT   720
GTTGCCAATAAAAAGCTGAAATGTACAGAGACCTGGAGCCTTAACAGTCTGGTTAAACAC   780
CTCTTAGGTAAACAGCTCCTGAAAGACAAGTCTATCCGCTGTAGCAATTGGAGTAAATTT   840
CCTCTCACTGAGGACCAGAAACTGTATGCAGCCACTGATGCTTATGCTGGTTTTATTATT   900
TACCGAAATTTAGAGATTTTGGATGATACTGTGCAAAGGTTTGCTATAAATAAAGAGGAA   960
GAAATCCTACTTAGCGACATGAACAAACAGTTGACTTCAATCTCTGAGGAAGTGATGGAT  1020
CTGGCTAAGCATCTTCCTCATGCTTTCAGTAAATTGGAAAACCCACGGAGGGTTTCTATC  1080
TTACTAAAGGATATTTCAGAAAATCTATATTCACTGAGGAGGATGATAATTGGGTCTACT  1140
AACATTGAGACTGAACTGAGGCCCAGCAATAATTTAAACTTATTATCCTTTGAAGATTCA  1200
ACTACTGGGGGAGTACAACAGAAACAAATTAGAGAACATGAAGTTTTAATTCACGTTGAA  1260
GATGAAACATGGGACCCAACACTTGATCATTTAGCTAAACATGATGGAGAAGATGTACTT  1320
GGAAATAAAGTGGAACGAAAAGAAGATGGATTTGAAGATGGAGTAGAAGACAACAAATTG  1380
AAAGAGAATATGGAAAGAGCTTGTTTGATGTCGTTAGATATTACAGAACATGAACTCCAA  1440
ATTTTGGAACAGCAGTCTCAGGAAGAATATCTTAGTGATATTGCTTATAAATCTACTGAG  1500
CATTTATCTCCCAATGATAATGAAAACGATACGTCCTATGTAATTGAGAGTGATGAAGAT  1560
TTAGAAATGGAGATGCTTAAGCATTTATCTCCCAATGATAATGAAAACGATACGTCCTAT  1620
GTAATTGAGAGTGATGAAGATTTAGAAATGGAGATGCTTAAGTCTTTAGAAAACCTCAAT  1680
AGTGGCACGGTAGAACCAACTCATTCTAAATGCTTAAAAATGGAAAGAAATCTGGGTCTT  1740
CCTACTAAAGAAGAAGAAGAAGATGATGAAAATGAAGCTAATGAAGGGGAAGAAGATGAT  1800
GATAAGGACTTTTTGTGGCCAGCACCCAATGAAGAGCAAGTTACTTGCCTCAAGATGTAC  1860
TTTGGCCATTCCAGTTTTAAACCAGTTCAGTGGAAAGTGATTCATTCAGTATTAGAAGAA  1920
AGAAGAGATAATGTTGCTGTCATGGCAACTGGATATGGAAAGAGTTTGTGCTTCCAGTAT  1980
CCACCTGTTTATGTAGGCAAGATTGGCCTTGTTATCTCTCCCCTTATTTCTCTGATGGAA  2040
GACCAAGTGCTACAGCTTAAAATGTCCAACATCCCAGCTTGCTTCCTTGGATCAGCACAG  2100
TCAGAAAATGTTCTAACAGATATTAAATTAGGTAAATACCGGATTGTATACGTAACTCCA  2160
GAATACTGTTCAGGTAACATGGGCCTGCTCCAGCAACTTGAGGCTGATATTGGTATCACG  2220
CTCATTGCTGTGGATGAGGCTCACTGTATTTCTGAGTGGGGGCATGATTTTAGGGATTCA  2280
TTCAGGAAGTTGGGCTCCCTAAAGACAGCACTGCCAATGGTTCCAATCGTTGCACTTACT  2340
GCTACTGCAAGTTCTTCAATCCGGGAAGACATTGTACGTTGCTTAAATCTGAGAAATCCT  2400
CAGATCACCTGTACTGGTTTTGATCGACCAAACCTGTATTTAGAAGTTAGGCGAAAAACA  2460
GGGAATATCCTTCAGGATCTGCAGCCATTTCTTGTCAAAACAAGTTCCCACTGGGAATTT  2520
GAAGGTCCAACAATCATCTACTGTCCTTCTAGAAAAATGACACAACAAGTTACAGGTGAA  2580
CTTAGGAAACTTAATCTATCCTGTGGAACATACCATGCGGGCATGAGTTTTAGCACAAGG  2640
AAAGACATTCATCATAGGTTTGTAAGAGATGAAATTCAGTGTGTCATAGCTACCATAGCT  2700
```

*Fig. 2A-1*

TTTGGAATGGGCATTAATAAAGCTGACATTCGCCAAGTCATTCATTACGGTGCTCCTAAG 2760
GACATGGAATCATATTATCAGGAGATTGGTAGAGCTGGTCGTGATGGACTTCAAAGTTCT 2820
TGTCACGTCCTCTGGGCTCCTGCAGACATTAACTTAAATAGGCACCTTCTTACTGAGATA 2880
CGTAATGAGAAGTTTCGATTATACAAATTAAAGATGATGGCAAAGATGGAAAAATATCTT 2940
CATTCTAGCAGATGTAGGAGACAAATCATCTTGTCTCATTTTGAGGACAAACAAGTACAA 3000
AAAGCCTCCTTGGGAATTATGGGAACTGAAAAATGCTGTGATAATTGCAGGTCCAGATTG 3060
GATCATTGCTATTCCATGGATGACTCAGAGGATACATCCTGGGACTTTGGTCCACAAGCA 3120
TTTAAGCTTTTGTCTGCTGTGGACATCTTAGGCGAAAAATTTGGAATTGGGCTTCCAATT 3180
TTATTTCTCCGAGGATCTAATTCTCAGCGTCTTGCCGATCAATATCGCAGGCACAGTTTA 3240
TTTGGCACTGGCAAGGATCAAACAGAGAGTTGGTGGAAGGCTTTTTCCCGTCAGCTGATC 3300
ACTGAGGGATTCTTGGTAGAAGTTTCTCGGTATAACAAATTTATGAAGATTTGCGCCCTT 3360
ACGAAAAAGGGTAGAAATTGGCTTCATAAAGCTAATACAGAATCTCAGAGCCTCATCCTT 3420
CAAGCTAATGAAGAATTGTGTCCAAAGAAGTTTCTTCTGCCTAGTTCGAAAACTGTATCT 3480
TCGGGCACCAAAGAGCATTGTTATAATCAAGTACCAGTTGAATTAAGTACAGAGAAGAAG 3540
TCTAACTTGGAGAAGTTATATTCTTATAAACCATGTGATAAGATTTCTTCTGGGAGTAAC 3600
ATTTCTAAAAAAAGTATCATGGTACAGTCACCAGAAAAAGCTTACAGTTCCTCACAGCCT 3660
GTTATTTCGGCACAAGAGCAGGAGACTCAGATTGTGTTATATGGCAAATTGGTAGAAGCT 3720
AGGCAGAAACATGCCAATAAAATGGATGTTCCCCCAGCTATTCTGGCAACAAACAAGATA 3780
CTGGTGGATATGGCCAAAATGAGACCAACTACGGTTGAAAACGTAAAAAGGATTGATGGT 3840
GTTTCTGAAGGCAAAGCTGCCATGTTGGCCCCTCTGTTGGAAGTCATCAAACATTTCTGC 3900
CAAACAAATAGTGTTCAGACAGACCTCTTTTCAAGTACAAAACCTCAAGAAGAACAGAAG 3960
ACGAGTCTGGTAGCAAAAAATAAAATATGCACACTTTCACAGTCTATGGCCATCACATAC 4020
TCTTTATTCCAAGAAAAGAAGATGCCTTTGAAGAGCATAGCTGAGAGCAGGATTCTGCCT 4080
CTCATGACAATTGGCATGCACTTATCCCAAGCGGTGAAAGCTGGCTGCCCCCTTGATTTG 4140
GAGCGAGCAGGCCTGACTCCAGAGGTTCAGAAGATTATTGCTGATGTTATCCGAAACCCT 4200
CCCGTCAACTCAGATATGAGTAAAATTAGCCTAATCAGAATGTTAGTTCCTGAAAACATT 4260
GACACGTACCTTATCCACATGGCAATTGAGATCCTTAAACATGGTCCTGACAGCGGACTT 4320
CAACCTTCATGTGATGTCAACAAAAGGAGATGTTTTCCCGGTTCTGAAGAGATCTGTTCA 4380
AGTTCTAAGAGAAGCAAGGAAGAAGTAGGCATCAATACTGAGACTTCATCTGCAGAGAGA 4440
AAGAGACGATTACCTGTGTGGTTTGCCAAAGGAAGTGATACCAGCAAGAAATTAATGGAC 4500
AAAACGAAAAGGGGAGGTCTTTTTAGTTAAGCTGGCAATTACCAGAACAATTATGTTTCT 4560
TGCTGTATTATAAGAGGATAGCTATATTTTATTTCTGAAGAGTAAGGAGTAGTATTTTGG 4620
CTTAAAAATCATTCTAATTACAAAGTTCACTGTTTATTGAAGAACTGGCATCTTAAATCA 4680
GCCTTCCGCAATTCATGTAGTTTCTGGGTCTTCTGGGAGCCTACGTGAGTACATCACCTA 4740
ACAGAATATTAAATTAGACTTCCTGTAAGATTGCTTTAAGAAACTGTTACTGTCCTGTTT 4800
TCTAATCTCTTTATTAAAACAGTGTATTTGGAAAATGTTATGTGCTCTGATTTGATATAG 4860
ATAACAGATTAGTAGTTACATGGTAATTATGTGATATAAAATATTCATATATTATCAAAA 4920
TTCTGTTTTGTAAATGTAAGAAAGCATAGTTATTTTACAAATTGTTTTTACTGTCTTTTG 4980
AAGAAGTTCTTAAATACGTTGTTAAATGGTATTAGTTGACCAGGGCAGTGAAAATGAAAC 5040
CGCATTTTGGGTGCCATTAAATAGGGAAAAAACATGTAAAAAATGTAAAATGGAGACCAA 5100
TTGCACTAGGCAAGTGTATATTTTGTATTTTATATACAATTTCTATTATTTTTCAAGTAA 5160
TAAAACAATGTTTTTCATACTGAATATTAAAAAAAAAAAAAAAAAAA 5208

*Fig. 2A-2*

MSEKKLETTAQQRKCPEWMNVQNKRCAVEERKACVRKSVFEDDLPFLEFTGSIVYSYDAS 60
DCSFLSEDISMSLSDGDVVGFDMEWPPLYNRGKLGKVALIQLCVSESKCYLFHVSSMSVF 120
PQGLKMLLENKAVKKAGVGIEGDQWKLLRDFDIKLKNFVELTDVANKKLKCTETWSLNSL 180
VKHLLGKQLLKDKSIRCSNWSKFPLTEDQKLYAATDAYAGFIIYRNLEILDDTVQRFAIN 240
KEEEILLSDMNKQLTSISEEVMDLAKHLPHAFSKLENPRRVSILLKDISENLYSLRRMII 300
GSTNIETELRPSNNLNLLSFEDSTTGGVQQKQIREHEVLIHVEDETWDPTLDHLAKHDGE 360
DVLGNKVERKEDGFEDGVEDNKLKENMERACLMSLDITEHELQILEQQSQEEYLSDIAYK 420
STEHLSPNDNENDTSYVIESDEDLEMEMLKHLSPNDNENDTSYVIESDEDLEMEMLKSLE 480
NLNSGTVEPTHSKCLKMERNLGLPTKEEEEDDENEANEGEEDDDKDFLWPAPNEEQVTCL 540
KMYFGHSSFKPVQWKVIHSVLEERRDNVAVMATGYGKSLCFQYPPVYVGKIGLVISPLIS 600
LMEDQVLQLKMSNIPACFLGSAQSENVLTDIKLGKYRIVYVTPEYCSGNMGLLQQLEADI 660
GITLIAVDEAHCISEWGHDFRDSFRKLGSLKTALPMVPIVALTATASSSIREDIVRCLNL 720
RNPQITCTGFDRPNLYLEVRRKTGNILQDLQPFLVKTSSHWEFEGPTIIYCPSRKMTQQV 780
TGELRKLNLSCGTYHAGMSFSTRKDIHHRFVRDEIQCVIATIAFGMGINKADIRQVIHYG 840
APKDMESYYQEIGRAGRDGLQSSCHVLWAPADINLNRHLLTEIRNEKFRLYKLKMMAKME 900
KYLHSSRCRRQIILSHFEDKQVQKASLGIMGTEKCCDNCRSRLDHCYSMDDSEDTSWDFG 960
PQAFKLLSAVDILGEKFGIGLPILFLRGSNSQRLADQYRRHSLFGTGKDQTESWWKAFSR 1020
QLITEGFLVEVSRYNKFMKICALTKKGRNWLHKANTESQSLILQANEELCPKKFLLPSSK 1080
TVSSGTKEHCYNQVPVELSTEKKSNLEKLYSYKPCDKISSGSNISKKSIMVQSPEKAYSS 1140
SQPVISAQEQETQIVLYGKLVEARQKHANKMDVPPAILATNKILVDMAKMRPTTVENVKR 1200
IDGVSEGKAAMLAPLLEVIKHFCQTNSVQTDLFSSTKPQEEQKTSLVAKNKICTLSQSMA 1260
ITYSLFQEKKMPLKSIAESRILPLMTIGMHLSQAVKAGCPLDLERAGLTPEVQKIIADVI 1320
RNPPVNSDMSKISLIRMLVPENIDTYLIHMAIEILKHGPDSGLQPSCDVNKRRCFPGSEE 1380
ICSSSKRSKEEVGINTETSSAERKRRLPVWFAKGSDTSKKLMDKTKRGGLFS 1432

*Fig. 2B*

```
                                                  TTTGGAATTGGG    12

CTTCCAATTTTATTTCTCCGAGGATCTGGTCTCACTCTGTTGCTCAGTCTGTAGTGCAGT    72

GGTGTCATCATAGCTCACTGCAGTCTTGATCTCCTGAGCTCAAACGATTCTCCTGCCTCA   132

GCTCCTGCTTCAGCCTCCTGAGTAGCGGAACAACAGAATTCTCAGCGTCTTGCCGATCAA   192

TATCGCAGGCACAGTTTATTTGGCACTGGCAAGGATCAAACAGAGAGTTGGTGGAAGGCT   252

TTTTCCCGTCAGCTGATCACTGAGGGATTCTTGGTAGAAGTTTCTCGGTATAACAAATTT   312

ATGAAGATTTGCGCCCTTACGAAAAAGGGTAGAAATTGGCTTCATAAAGCTAATACAGAA   372
MetLysIleCysAlaLeuThrLysLysGlyArgAsnTrpLeuHisLysAlaAsnThrGlu    20

TCTCAGAGCCTCATCCTTCAAGCTAATGAAGAATTGTGTCCAAAGAAGTTTCTTCTGCCT   432
SerGlnSerLeuIleLeuGlnAlaAsnGluGluLeuCysProLysLysPheLeuLeuPro    40

AGTTCGAAAACTGTATCTTCGGGCACCAAAGAGCATTGTTATAATCAAGTACCAGTTGAA   492
SerSerLysThrValSerSerGlyThrLysGluHisCysTyrAsnGlnValProValGlu    60

TTAAGTACAGAGAAGAAGTCTAACTTGGAGAAGTTATATTCTTATAAACCATGTGATAAG   552
LeuSerThrGluLysLysSerAsnLeuGluLysLeuTyrSerTyrLysProCysAspLys    80

ATTTCTTCTGGGAGTAACATTTCTAAAAAAAGTATCATGGTACAGTCACCAGAAAAAGCT   612
IleSerSerGlySerAsnIleSerLysLysSerIleMetValGlnSerProGluLysAla   100

TACAGTTCCTCACAGCCTGTTATTTCGGCACAAGAGCAGGAGACTCAGATTGTGTTATAT   672
TyrSerSerSerGlnProValIleSerAlaGlnGluGlnGluThrGlnIleValLeuTyr   120

GGCAAATTGGTAGAAGCTAGGCAGAAACATGCCAATAAAATGGATGTTCCCCCAGCTATT   732
GlyLysLeuValGluAlaArgGlnLysHisAlaAsnLysMetAspValProProAlaIle   140

CTGGCAACAAACAAGATACTGGTGGATATGGCCAAAATGAGACCAACTACGGTTGAAAAC   792
LeuAlaThrAsnLysIleLeuValAspMetAlaLysMetArgProThrThrValGluAsn   160

GTAAAAAGGATTGATGGTGTTTCTGAAGGCAAAGCTGCCATGTTGGCCCCTCTGTTGGAA   852
ValLysArgIleAspGlyValSerGluGlyLysAlaAlaMetLeuAlaProLeuLeuGlu   180

GTCATCAAACATTTCTGCCAAACAAATAGTGTTCAGACAGACCTCTTTTCAAGTACAAAA   912
ValIleLysHisPheCysGlnThrAsnSerValGlnThrAspLeuPheSerSerThrLys   200
```

*Fig. 3A*

```
CCTCAAGAAGAACAGAAGACGAGTCTGGTAGCAAAAAATAAAATATGCACACTTTCACAG   972
ProGlnGluGluGlnLysThrSerLeuValAlaLysAsnLysIleCysThrLeuSerGln   220

TCTATGGCCATCACATACTCTTTATTCCAAGAAAAGAAGATGCCTTTGAAGAGCATAGCT  1032
SerMetAlaIleThrTyrSerLeuPheGlnGluLysLysMetProLeuLysSerIleAla   240

GAGAGCAGGATTCTGCCTCTCATGACAATTGGCATGCACTTATCCCAAGCGGTGAAAGCT  1092
GluSerArgIleLeuProLeuMetThrIleGlyMetHisLeuSerGlnAlaValLysAla   260

GGCTGCCCCCTTGATTTGGAGCGAGCAGGCCTGACTCCAGAGGTTCAGAAGATTATTGCT  1152
GlyCysProLeuAspLeuGluArgAlaGlyLeuThrProGluValGlnLysIleIleAla   280

GATGTTATCCGAAACCCTCCCGTCAACTCAGATATGAGTAAAATTAGCCTAATCAGAATG  1212
AspValIleArgAsnProProValAsnSerAspMetSerLysIleSerLeuIleArgMet   300

TTAGTTCCTGAAAACATTGACACGTACCTTATCCACATGGCAATTGAGATCCTTAAACAT  1272
LeuValProGluAsnIleAspThrTyrLeuIleHisMetAlaIleGluIleLeuLysHis   320

GGTCCTGACAGCGGACTTCAACCTTCATGTGATGTCAACAAAAGGAGATGTTTTCCCGGT  1332
GlyProAspSerGlyLeuGlnProSerCysAspValAsnLysArgArgCysPheProGly   340

TCTGAAGAGATCTGTTCAAGTTCTAAGAGAAGCAAGGAAGAAGTAGGCATCAATACTGAG  1392
SerGluGluIleCysSerSerSerLysArgSerLysGluGluValGlyIleAsnThrGlu   360

ACTTCATCTGCAGAGAGAAAGAGACGATTACCTGTGTGGTTTGCCAAAGGAAGTGATACC  1452
ThrSerSerAlaGluArgLysArgArgLeuProValTrpPheAlaLysGlySerAspThr   380

AGCAAGAAATTAATGGACAAAACGAAAAGGGGAGGTCTTTTTAGTTAAGCTGGCAATTAC  1512
SerLysLysLeuMetAspLysThrLysArgGlyGlyLeuPheSer>>>              395

CAGAACAATTATGTTTCTTGCTGTATTATAAGAGGATAGCTATATTTTATTTCTGAAGAG  1572

TAAGGAGTAGTATTTTGGCTTAAAAATCATTCTAATTACAAAGTTCACTGTTTATTGAAG  1632

AACTGGCATCTTAAATCAGCCTTCCGCAATTCATGTAGTTTCTGGGTCTTCTGGGAGCCT  1692

ACGTGAGTACATCACCTAACAGAATATTAAATTAGACTTCCTGTAAGATTGCTTTAAGAA  1752

ACTGTTACTGTCCTGTTTTCTAATCTCTTTATTAAAACAGTGTATTTGGAAAATGTTATG  1812

TGCTCTGATTTGATATAGATAACAGATTAGTAGTTACATGGTAATTATGTGATATAAAAT  1872

ATTCATATATTATCAAAATTCTGTTTTGTAAATGTAAGAAAGCATAGTTATTTTACAAAT  1932
```

*Fig. 3B*

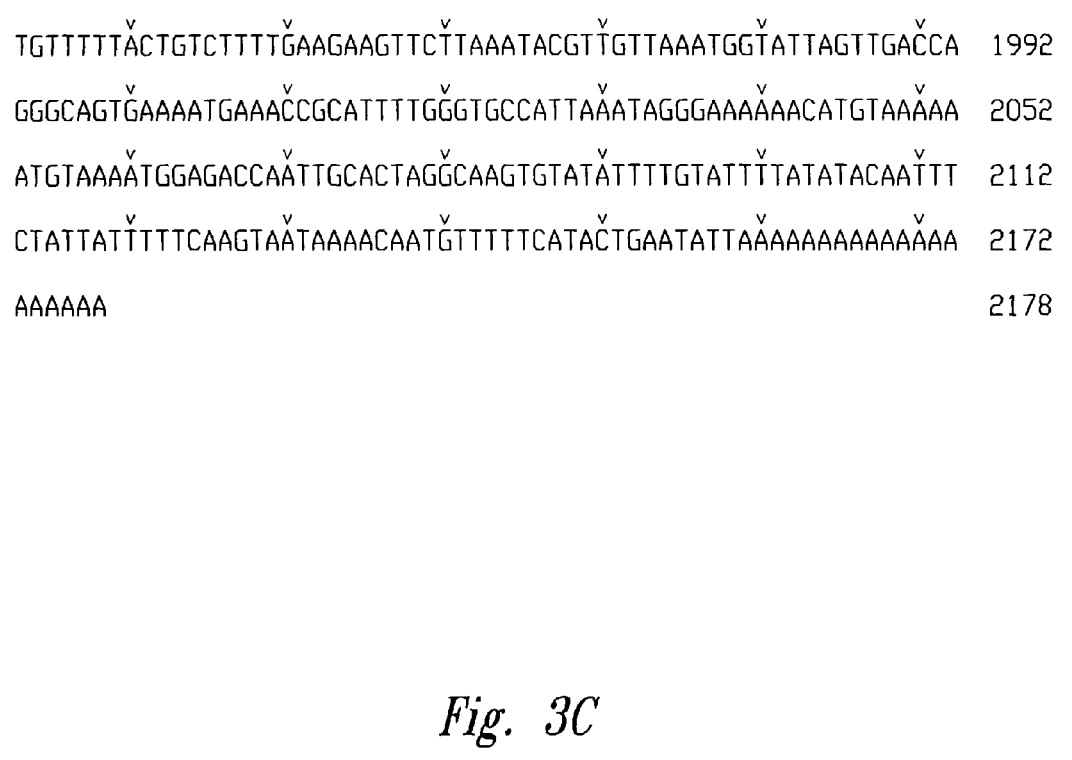

```
TGTTTTTACTGTCTTTTGAAGAAGTTCTTAAATACGTTGTTAAATGGTATTAGTTGACCA  1992

GGGCAGTGAAAATGAAACCGCATTTTGGGTGCCATTAAATAGGGAAAAAACATGTAAAAA  2052

ATGTAAAATGGAGACCAATTGCACTAGGCAAGTGTATATTTTGTATTTTATATACAATTT  2112

CTATTATTTTTCAAGTAATAAAACAATGTTTTTCATACTGAATATTAAAAAAAAAAAAAA  2172

AAAAAA                                                        2178
```

*Fig. 3C*

```
                                                      1                                                     50
agein.12.27_helicases.msf{Agein.12.27.f2.pro}         .......... .......... .......... .......... ..........
    agein.12.27_helicases.msf{recq_ecoli.pro}         .......... .......... .......... .......... ..........
    agein.12.27_helicases.msf{YABC_SCHPO.pro}         .......... .......... .......... .......... ..........
    agein.12.27_helicases.msf{recq_human.pro}         .......... .......... .......... .......... ..........
           agein.12.27_helicases.msf{BLM.pro}         MAAVPQNNLQ EQLERHSART LNNKLSLSKP KFSGFTFKKK TSSDNNVSVT
                                                      51                                                   100
agein.12.27_helicases.msf{Agein.12.27.f2.pro}         .......... .......... .......... .......... ..........
    agein.12.27_helicases.msf{recq_ecoli.pro}         .......... .......... .......... .......... ..........
    agein.12.27_helicases.msf{YABC_SCHPO.pro}         .......... .......... .......... .......... ..MTVTKTNL
    agein.12.27_helicases.msf{recq_human.pro}         .......... .......... .......... .......... ..........
           agein.12.27_helicases.msf{BLM.pro}         NVSVAKTPVL RNKDVNVTED FSFSEPLPNT TNQQRVKDFF KNAPAGQETQ
                                                      101                                                  150
agein.12.27_helicases.msf{Agein.12.27.f2.pro}         .......... .......... .......... .......... ..........
    agein.12.27_helicases.msf{recq_ecoli.pro}         .......... .......... .......... .......... ..........
    agein.12.27_helicases.msf{YABC_SCHPO.pro}         NRHLDWFFRE SPQKIENVTS PIKTLDFVKV KVSSSDIVVK DSIPHKSKNV
    agein.12.27_helicases.msf{recq_human.pro}         .......... .......... .......... .......... ..........
           agein.12.27_helicases.msf{BLM.pro}         RGGSKSLLPD FLQTPKEVVC TTQNTPTVKK SRDTALKKLE FSSSPDSLST
                                                      151                                                  200
agein.12.27_helicases.msf{Agein.12.27.f2.pro}         .......... .......... .......... .......... ..........
    agein.12.27_helicases.msf{recq_ecoli.pro}         .......... .......... .......... .......... ..........
    agein.12.27_helicases.msf{YABC_SCHPO.pro}         FDDFDDGYAI DLTEEHQS.. .......... ...SSLNNLK WKDVEGPNIL
    agein.12.27_helicases.msf{recq_human.pro}         .......... .......... .......... .......... ..........
           agein.12.27_helicases.msf{BLM.pro}         INDWDDMDDF DTSETSKSFV TPPQSHFVRV STAQKSKKGK RNFFKAQLYT
                                                      201                                                  250
agein.12.27_helicases.msf{Agein.12.27.f2.pro}         .......... .......... .......... .......... ..........
    agein.12.27_helicases.msf{recq_ecoli.pro}         .......... .......... .......... .......... ..........
    agein.12.27_helicases.msf{YABC_SCHPO.pro}         KPIKKIAVPA SESEEDFDDV DEEMLRAAEM EVFQSCQPLA VNTADTTVSH
    agein.12.27_helicases.msf{recq_human.pro}         .......... .......... .......... .......... ..........
           agein.12.27_helicases.msf{BLM.pro}         TNTVKTDLPP PSSESEQIDL TEEQKDDSEW LSSDVICIDD GPIAEVHINE
```

*Fig. 4A*

```
                                                   251                                                    300
agein.12.27_helicases.msf{Agein.12.27.f2.pro}      .......... .......... .......... .......... ..........
     agein.12.27_helicases.msf{recq_ecoli.pro}     .......... .......... .......... .......... ..........
     agein.12.27_helicases.msf{YABC_SCHPO.pro}     STSSSNVPRS LNKIHDPSRF IKDNDVENRI HVSSASKVAS ISNTSKPNPI
     agein.12.27_helicases.msf{recq_human.pro}     .......... .......... .......... .......... ..........
            agein.12.27_helicases.msf{BLM.pro}     DAQESDSLKT HLEDERDNSE KKKNLEEAEL HSTEKVPCIE FDDDDYDTDF
                                                   301                                                    350
agein.12.27_helicases.msf{Agein.12.27.f2.pro}      .......... .......... .......... .......... ..........
     agein.12.27_helicases.msf{recq_ecoli.pro}     .......... .......... .......... .......... ..........
     agein.12.27_helicases.msf{YABC_SCHPO.pro}     VSENPISATS VSIEIPIKPK ELSNNLPFPR LNNNNTNNNN DNNAIEKRDS
     agein.12.27_helicases.msf{recq_human.pro}     .......... .......... .......... .......... ..........
            agein.12.27_helicases.msf{BLM.pro}     VPPSPEEIIS ASSSSSKCLS TLKDLDTSDR KEDVLSTSKD LLSKPEKMSM
                                                   351                                                    400
agein.12.27_helicases.msf{Agein.12.27.f2.pro}      .......... .......... .......... .......... ..........
     agein.12.27_helicases.msf{recq_ecoli.pro}     .......... .......... .......... .......... ..........
     agein.12.27_helicases.msf{YABC_SCHPO.pro}     ASPTPSSVSS QISIDFSTWP H.....QNLL QYLDILRDEK SEISDRIIEV
     agein.12.27_helicases.msf{recq_human.pro}     .......... .......... .......... .......... ..........
            agein.12.27_helicases.msf{BLM.pro}     QELNPETSTD CDARQISLQQ QLIHVMEHIC KLIDTIPDDK LKLLDCGNEL
                                                   401                                                    450
agein.12.27_helicases.msf{Agein.12.27.f2.pro}      .......... .......... .......... .......... ..........
     agein.12.27_helicases.msf{recq_ecoli.pro}     .......... .......... .......... .......... ..........
     agein.12.27_helicases.msf{YABC_SCHPO.pro}     MERYPFSSRF KEWIPKRDIL SQKISSVLEV LSNNNNSNNN NGNNGT....
     agein.12.27_helicases.msf{recq_human.pro}     .......... .......... .......... .......... ..........
            agein.12.27_helicases.msf{BLM.pro}     LQQRNIRRKL LTEVDFNKSD ASLLGSLWRY RPDSLDGPME GDSCPTGNSM
                                                   451                                                    500
agein.12.27_helicases.msf{Agein.12.27.f2.pro}      .......... .......... .......... .......... ...EDGFEDG
     agein.12.27_helicases.msf{recq_ecoli.pro}     .......... .......... .......... .......... ..........
     agein.12.27_helicases.msf{YABC_SCHPO.pro}     .......... ..VPNAKTFF TPPSSITQQV PFPSTIIPES TVKENSTRPY
     agein.12.27_helicases.msf{recq_human.pro}     .......... .......... .......... .......... ..........
            agein.12.27_helicases.msf{BLM.pro}     KELNFSHLPS NSVSPGDCLL TTTLGKTGFS ATRKNLFERP LFNTHLQKSF
```

*Fig. 4B*

```
                                                   501                                                550
agein.12.27_helicases.msf{Agein.12.27.f2.pro}    VEDNKLKENM ERACLMSLDI TEHELQILEQ QSQEEYLSDI AYKSTEHLSP
  agein.12.27_helicases.msf{recq_ecoli.pro}      .......... .......... .......... .......... ..........
  agein.12.27_helicases.msf{YABC_SCHPO.pro}      VNSHLVANDK ITATPFHS.. .......... ......EAVV SPLQSNIRNS
  agein.12.27_helicases.msf{recq_human.pro}      .......... .......... .......... ......MASV SALTEEL.DS
       agein.12.27_helicases.msf{BLM.pro}        VSSNWAETPR LGKKNESSYF PGNVLTSTAV KDQNKHTASI NDLERETQPS

                                                   551                                                600
agein.12.27_helicases.msf{Agein.12.27.f2.pro}    NDNENDTSYV IESDEDLEME MLKHLSPNDN ENDTSYVIES DEDLEMEMLK
  agein.12.27_helicases.msf{recq_ecoli.pro}      .......... .......... .......... .......... ..........
  agein.12.27_helicases.msf{YABC_SCHPO.pro}      DIAEFDEFDI DDADFTFNTT DPINDESGAS SDVVVIDDEE DDIENRPLNQ
  agein.12.27_helicases.msf{recq_human.pro}      ITSELHAVEI QIQELTERQQ ELI....... ........QK KKVLTKKIKQ
       agein.12.27_helicases.msf{BLM.pro}        Y..DIDNFDI DDFDDDDDWE DIMHNLAASK SSTAAYQPIK EGRPIKSVSE

                                                   601                                                650
agein.12.27_helicases.msf{Agein.12.27.f2.pro}    SLENLNSGTV EPTHSKCLKM ERNLGLPTKE EEEDDENEAN EGEEDDDKDF
  agein.12.27_helicases.msf{recq_ecoli.pro}      .......... .......... .......... .......... .....AQAEV
  agein.12.27_helicases.msf{YABC_SCHPO.pro}      ALKASKAAV. ...SNASLLQ SSSLDRPLLG EMKDKNHKVL MPSLDDPM..
  agein.12.27_helicases.msf{recq_human.pro}      CLEDSDAGA. ...SNE..YD SSPAAW.... .......... ......NK..
       agein.12.27_helicases.msf{BLM.pro}        RLSSAKTDCL PVSSTAQNIN FSESIQNYTD KSAQNLASRN LKHERFQS..

                                                   651                                                700
agein.12.27_helicases.msf{Agein.12.27.f2.pro}    LWPAPNEEQV TCLKMYFGHS SFKPVQWKVI HSVLEERRDN VAVMATGYGK
  agein.12.27_helicases.msf{recq_ecoli.pro}      LNLESGAKQV ..LQETFGYQ QFRPGQEEII DTVLSG.RDC LVVMPTGGGK
  agein.12.27_helicases.msf{YABC_SCHPO.pro}      LSYPWSKEVL GCLKHKFHLK GFRKNQLEAI NGTLSG.KDV FILMPTGGGK
  agein.12.27_helicases.msf{recq_human.pro}      EDFPWSGKVK DILQNVFKLE KFRPLQLETI NVTMAG.KEV FLVMPTGGGK
       agein.12.27_helicases.msf{BLM.pro}        LSFPHTKEMM KIFHKKFGLH NFRTNQLEAI NAALLG.EDC FILMPTGGGK

                                                   701                                                750
agein.12.27_helicases.msf{Agein.12.27.f2.pro}    SLCFQYPPVY VG....KIGL VISPLISLME DQVLQLKMSN IPACFLGSAQ
  agein.12.27_helicases.msf{recq_ecoli.pro}      SLCYQIPALL LN....GLTV VVSPLISLMK DQVDQLQANG VAAACLNSTQ
  agein.12.27_helicases.msf{YABC_SCHPO.pro}      SLCYQLPAVI EGGASRGVTL VISPLLSLMQ DQLDHLRKLN IPSLPLSGEQ
  agein.12.27_helicases.msf{recq_human.pro}      SLCYQLPAL. ...CSDGFTL VICPLISLME DQLMVLKQLG ISATMLNASS
       agein.12.27_helicases.msf{BLM.pro}        SLCYQLPA.. ..CVSPGVTV VISPLRSLIV DQVQKLTSLD IPATYLTGDK
```

*Fig. 4C*

```
                                                  751                                                    800
agein.12.27_helicases.msf{Agein.12.27.f2.pro}     SE....NVLT DI..KLGKYR IVYVTPE... YCSGNMGLLQ QLEADIGITL
     agein.12.27_helicases.msf{recq_ecoli.pro}     TREQQLEVMT GC..RTGQIR LLYIAPE... ..RLMLDNFL EHLAHWNPVL
     agein.12.27_helicases.msf{YABC_SCHPO.pro}     PADERRQVIS FLMAKNVLVK LLYVTPEGLA SNGAITRVLK SLYERKLLAR
     agein.12.27_helicases.msf{recq_human.pro}     SKEHVKWVHD EMVNKNSELK LIYVTPEKIA KSKMFMSRLE KAYEARRFTR
            agein.12.27_helicases.msf{BLM.pro}     TDSEATNIYL QLSKKDPIIK LLYVTPEKIC ASNRLISTLE NLYERKLLAR

                                                  801                                                    850
agein.12.27_helicases.msf{Agein.12.27.f2.pro}     IAVDEAHCIS EWGHDFRDSF RKLGSLKTAL PMVPIVALTA TASSSIREDI
     agein.12.27_helicases.msf{recq_ecoli.pro}     LAVDEAHCIS QWGHDFRPEY AALGQLRQRF PTLPFMALTA TADDTTRQDI
     agein.12.27_helicases.msf{YABC_SCHPO.pro}     IVIDEAHCVS HWGHDFRPDY KQLGLLRDRY QGIPFMALTA TANEIVKKDI
     agein.12.27_helicases.msf{recq_human.pro}     IAVDEVHCCS QWGHDFRPDY KALGILKRQF PNASLIGLTA TATNHVLTDA
            agein.12.27_helicases.msf{BLM.pro}     FVIDEAHCVS QWGHDFRQDY KRMNMLRQKF PSVPVMALTA TANPRVQKDI

                                                  851                                                    900
agein.12.27_helicases.msf{Agein.12.27.f2.pro}     VRCLNLRNPQ ITCTGFDRPN LYLEVRRKTG NILQDLQPFL VKTSSHWEFE
     agein.12.27_helicases.msf{recq_ecoli.pro}     VRLLGLNDPL IQISSFDRPN IRYMLMEK.. ..FKPLDQLM RYVQEQRGKS
     agein.12.27_helicases.msf{YABC_SCHPO.pro}     INTLRMENCL ELKSSFNRPN LFYEIKPK.. ..KDLYTELY RFISNGHLHE
     agein.12.27_helicases.msf{recq_human.pro}     QKILCIEKCF TFTASFNRPN LYYEVRQKPS NTEDFIEDIV KLINGRYKGQ
            agein.12.27_helicases.msf{BLM.pro}     LTQLKILRPQ VFSMSFNRHN LKYYVLPKKP KKVAF..DCL EWIRKHHPYD

                                                  901                                                    950
agein.12.27_helicases.msf{Agein.12.27.f2.pro}     GPTIIYCPSR KMTQQVTGEL RK.LNLSCGT YHAGMSFSTR KDIHHRFVR.
     agein.12.27_helicases.msf{recq_ecoli.pro}     G..IIYCNSR AKVEDTAAAL QS.KGISAAA YHAGLENNVR ADVQEKFQR.
     agein.12.27_helicases.msf{YABC_SCHPO.pro}     S.GIIYCLSR TSCEQVAAKL RNDYGLKAWH YHAGLEKVER QRIQNEW.QS
     agein.12.27_helicases.msf{recq_human.pro}     S.GIIYCFSQ KDSEQVTVSL QN.LGIHAGA YHANLEPEDK TTVHRKW.SA
            agein.12.27_helicases.msf{BLM.pro}     S.GIIYCLSR RECDTMADTL QRD.GLAALA YHAGLSDSAR DEVQQKWINQ

                                                  951                                                   1000
agein.12.27_helicases.msf{Agein.12.27.f2.pro}     DEIQCVIATI AFGMGINKAD IRQVIHYGAP KDMESYYQEI GRAGRDGLQS
     agein.12.27_helicases.msf{recq_ecoli.pro}     DDLQIVVATV AFGMGINKPN VRFVVHFDIP RNIESYYQET GRAGRDGLPA
     agein.12.27_helicases.msf{YABC_SCHPO.pro}     GSYKIIVATI AFGMGVDKGD VRFVIHHSFP KSLEGYYQET GRAGRDGKPA
     agein.12.27_helicases.msf{recq_human.pro}     NEIQVVVATV AFGMGIDKPD VRFVIHHSMS KSMENYYQES GRAGRDDMKA
            agein.12.27_helicases.msf{BLM.pro}     DGCQVICATI AFGMGIDKPD VRFVIHASLP KSVEGYYQES GRAGRDGEIS
```

*Fig. 4D*

```
                                                   1001                                                   1050
agein.12.27_helicases.msf{Agein.12.27.f2.pro}      SCHVLWAPAD INLNRHLL.. TEIRNEKFRL YKLKMMAKME KYLHS.SRCR
    agein.12.27_helicases.msf{recq_ecoli.pro}      EAMLFYDPAD MAWLRRCL.. EEKPQGQLQD IERHKLNAMG AFAEA.QTCR
    agein.12.27_helicases.msf{YABC_SCHPO.pro}      HCIMFYSYKD HVTFQKLIMS G.DGDAETKE RQRQMLRQVI QFCENKTDCR
    agein.12.27_helicases.msf{recq_human.pro}      DCILYYGFGD IFRISSMVVM E.NVG..... ..QQKLYEMV SYCQNISKSR
           agein.12.27_helicases.msf{BLM.pro}      HCLLFYTYHD VTRLKRLIMM EKDGNHHTRE THFNNLYSMV HYCENITECR

                                                   1051                                                   1100
agein.12.27_helicases.msf{Agein.12.27.f2.pro}      RQIILSHFED KQVQKASLGI MGTEKCCDNC RSRLDHCYSM DDSEDTSWDF
    agein.12.27_helicases.msf{recq_ecoli.pro}      RLVLLNYFGE .......... .GRQEPCGNC DICLDPPKQY DGSTD.....
    agein.12.27_helicases.msf{YABC_SCHPO.pro}      RKQVLAYFGE N.FDKV.HCR K....GCDIC ..CEEATYIK QDMTEFSLQA
    agein.12.27_helicases.msf{recq_human.pro}      RVLMAQHFDE V.WNSE.ACN K....MCDNC ..CKDSAFER TNITEYCRDL
           agein.12.27_helicases.msf{BLM.pro}      RIQLLAYFGE NGFNPD.FCK KHPDVSCDNC ..CKTKDYKT RDVTDDVKSI

                                                   1101                                                   1150
agein.12.27_helicases.msf{Agein.12.27.f2.pro}      GPQAFKLLSA VDI....... LGEKFGIGLP ILFLRGSNSQ RLAD.QYRRH
    agein.12.27_helicases.msf{recq_ecoli.pro}      ...AQIALST IGR....... VNQRFGMGYV VEVIRGANNQ RIRDYGHDKL
    agein.12.27_helicases.msf{YABC_SCHPO.pro}      IKLLK...S. .......... ISGKATLLQL MDIFRGSKSA KIVENGWDRL
    agein.12.27_helicases.msf{recq_human.pro}      IKILKQAEE. .......... LNEKLTPLKL IDSWMGKGAA KLRVAG....
           agein.12.27_helicases.msf{BLM.pro}      VRFVQEHSSS QGMRNIKHVG PSGRFTMNML VDIFLGSKSA KIQSGIFGK.

                                                   1151                                                   1200
agein.12.27_helicases.msf{Agein.12.27.f2.pro}      SLFGTGKDQT ESWWKAFSRQ LITEGFLVEV SRYNKFMKIC ALTKKGRNWL
    agein.12.27_helicases.msf{recq_ecoli.pro}      KVYGMGRDKS HEHWVSVIRQ LIHLGLVTQ. .......... ..........
    agein.12.27_helicases.msf{YABC_SCHPO.pro}      EGAGVGKLLN RGDSERLFHH LVSEGVFVEK VEANRRG.FV SAYVVP.GRQ
    agein.12.27_helicases.msf{recq_human.pro}      ...VVAPTLP REDLEKIIAH FLIQQYLKED YSFTAYA.AI SYLKIG.PKA
           agein.12.27_helicases.msf{BLM.pro}      .....GSAYS RHNAERLFKK LILDKILDED LYINANDQAI AYVMLG.NKA

                                                   1201                                                   1250
agein.12.27_helicases.msf{Agein.12.27.f2.pro}      HKANTESQSL ILQANEELCP KKFLLPSSKT VSSGTKEHCY NQVPVELSTE
    agein.12.27_helicases.msf{recq_ecoli.pro}      NIAQHSALQL TEAARPVLAE SSLQLAVPRI V......... ........AL
    agein.12.27_helicases.msf{YABC_SCHPO.pro}      TIINSVLAGK RRIILDVKES SSKPDTSSRS LSRSKTLPAL REYQLKSTTA
    agein.12.27_helicases.msf{recq_human.pro}      NLLNNEAHAI TMQVTKSTQN SFRAESSQTC HS........ .........E
           agein.12.27_helicases.msf{BLM.pro}      ...QTVLNGN LKVDFMETEN SS.......S VKKQKALVA. ..........
```

*Fig. 4E*

```
                                                 1251                                                   1300
agein.12.27_helicases.msf(Agein.12.27.f2.pro)   KKSNLEKLYS YKPCDKISSG SNISKKSIMV QSPEKAYSSS QPVISAQEQE
   agein.12.27_helicases.msf(recq_ecoli.pro)    KPKAMQK... .......SFG GNYDRK.... .......... ..........
   agein.12.27_helicases.msf(YABC_SCHPO.pro)    SVDCSIGTRE VDEIYDSQMP PVKPSLIHSR NKIDLEELSG QKFMSEYEID
  agein.12.27_helicases.msf(recq_human.pro)     QGDKKNGGKK IQATSRRRLQ TCFSNLV... ..LRIQELRK EKSM......
         agein.12.27_helicases.msf(BLM.pro)     .......... .......... .......... .KVSQREEMV KKCLG..ELT

                                                 1301                                                   1350
agein.12.27_helicases.msf(Agein.12.27.f2.pro)   TQIVLYGKLV EAR.QKHANK MDVPPAILAT NKILVDMAKM RPTTVENVKR
   agein.12.27_helicases.msf(recq_ecoli.pro)    ....LFAKLR KLR.KSIADE SNVPPYVVFN DATLIEMAEQ MPITASEMLS
   agein.12.27_helicases.msf(YABC_SCHPO.pro)    VMTRCLKDLK LLR.SNLMAI DDSRVSSYFT DSVLLSMAKK LPRNVKELKE
  agein.12.27_helicases.msf(recq_human.pro)     .....MPDMN VTKFSN.... .......... .......... ..........
         agein.12.27_helicases.msf(BLM.pro)     EVCKSLGKVF GVHYFNI... ........FN TVTLKKLAES LSSDPEVLLQ

                                                 1351                                                   1400
agein.12.27_helicases.msf(Agein.12.27.f2.pro)   IDGVSEGKAA MLA.PLLEVI KHFCQTNSVQ TDLFSSTKPQ EEQKTSLVAK
   agein.12.27_helicases.msf(recq_ecoli.pro)    VNGVGMRKLE RFGKPFMALI RAHVDGDDEE .......... ..........
   agein.12.27_helicases.msf(YABC_SCHPO.pro)    IHGVSNEKAV NLGPKFLQVI QKFIDEKEQN LEGTELDPSL QSLDTDYPID
  agein.12.27_helicases.msf(recq_human.pro)     .......... .......... .......... .......... ..........
         agein.12.27_helicases.msf(BLM.pro)     IDGVTEDKLE KYGAEVISVL QKYSE..... ........WT SPAEDSSPGI

                                                 1401                                                   1450
agein.12.27_helicases.msf(Agein.12.27.f2.pro)   NKICTLSQSM AITYSLFQEK KMPLKSIAES RILPLMTIGM HLSQAVKAGC
   agein.12.27_helicases.msf(recq_ecoli.pro)    .......... .......... .......... .......... ..........
   agein.12.27_helicases.msf(YABC_SCHPO.pro)    TNALSLDHEQ GFSDDSDSVY EPSSPIEEGD EEVDGQRKDI LNFMNSQSLT
  agein.12.27_helicases.msf(recq_human.pro)     .......... .......... .......... .......... ..........
         agein.12.27_helicases.msf(BLM.pro)     SLSSSRGPGR SAAEELDEEI PVSSHYFASK TRNERKRKKM PASQRSKRRK

                                                 1451                                                   1500
agein.12.27_helicases.msf(Agein.12.27.f2.pro)   PLDLERAGLT PEVQKIIADV IRNPPVNSDM SKISLIRMLV PENIDTYLIH
   agein.12.27_helicases.msf(recq_ecoli.pro)    .......... .......... .......... .......... ..........
   agein.12.27_helicases.msf(YABC_SCHPO.pro)    QTGSVPKRKS TSYTRPSKSY RHKRGS...T SYSRKRKYST SQKDSRKTSK
  agein.12.27_helicases.msf(recq_human.pro)     .......... .......... .......... .......... ..........
         agein.12.27_helicases.msf(BLM.pro)     TASSGSKAKG GSATCRKISS KTKSSSIIGS SSASHTSQAT SGANSKLGIM
```

*Fig. 4F*

```
                                                  1501                                                1550
ageín.12.27_helicases.msf{Ageín.12.27.f2.pro}     MAIEILKHGP DSGLQPSCDV NKRRCFPGSE EICSSSKRSK EEVGINTETS
    ageín.12.27_helicases.msf{recq_ecoli.pro}     .......... .......... .......... .......... ..........
    ageín.12.27_helicases.msf{YABC_SCHPO.pro}     SANTSFIHPM VKQNYR.... .......... .......... ..........
    ageín.12.27_helicases.msf{recq_human.pro}     .......... .......... .......... .......... ..........
           ageín.12.27_helicases.msf{BLM.pro}     APPKPINRPF LKPSYAFS.. .......... .......... ..........
                                                  1551                                                1600
ageín.12.27_helicases.msf{Ageín.12.27.f2.pro}     SAERKRRLPV WFAKGSDTSK KLMDKTKRGG LFS*AGNYQN NYVSCCIIRG
    ageín.12.27_helicases.msf{recq_ecoli.pro}     .......... .......... .......... .......... ..........
    ageín.12.27_helicases.msf{YABC_SCHPO.pro}     .......... .......... .......... .......... ..........
    ageín.12.27_helicases.msf{recq_human.pro}     .......... .......... .......... .......... ..........
           ageín.12.27_helicases.msf{BLM.pro}     .......... .......... .......... .......... ..........
```

*Fig. 4G*

```
TATATTATGG CTATTTTTCT TTCTTATCTA TTTGTATTTT TATTGTTATT ACCTAAAAAA   60
AAATTTTCTA TGTCTTATCA CTAATTCTTC CCTAAAATTT CCCACAATTG TGTAAACTTA  120
CCTCAGTATA TTCATAGATA TGAGACATTC TATCAATTTT ACCCTCTTAA AGATGCAGAA  180
ATAATGCATT ATGTTTCATC CCACCATCTT TAATGAGAAG CTTCCATCTT AGATTAATAT  240
TAGAGAATGT TAAAATACTC TGCAATCAGG TAAGGACGCT TGAAACTTCA TCATAATGCA  300
AAAGTTTTCT TTAACACAAT AAATATTTTG AACCCCTTTT GTGTCTTGTA TTCATAGGAG  360
TTCAGATAGA CCACTTTATT TACTATTTTT TATAGAGAGT GAACAGAAAT CCCATTTCTA  420
GTCACCAGTC CTTAATCTGT AAATCAGGCA GATAATCTGT AAATGATTGG TTGAAATCAC  480
ATTGAATTCC ACTTTGTGCC AGGGACTTAA GTTAACGAAC AAATTATTCT TACAAAAAGG  540
TATAAATGTA AGGTTTTCAT TCCGCTAAAT ATGTTTGTCA AACTGTGTTG TGATTTGTTC  600
TCAGTGTGTC ATAGCTACCA TAGCTTTTGG AATGGGCATT AATAAAGCTG ACATTCGCCA  660
AGTCATTCAT TACGGTGCTC CTAAGGACAT GGAATCATAT TATCAGGAGA TTGGTAGAGC  720
TGGTCGTGAT GGACTTCAAA GTTCTTGTCA CGTCCTCTGG GCTCCTGCAG ACATTAACTT  780
AAATAGGTAA AAAAAATTTA TTGTTTTTAC TCTTGCAGAT TTCTTTCTTT CTTTCCATAT  840
AAACCTCAAA AGTGTTTGAG GCTATTTCCA GTATCCCAAG TAATTTGTGA GTGCATTTAA  900
AGTAAAAAAA AAAAAAAAAG AAAAATAAAA CCTCCCCAAA TCCAGAGGAC ATGTAAGAAG  960
AACATTTGTG GTAAGAGTTG CCACTTGGAG ATGAGCTAAT TTCAGCATGC CTTAGTTAGT 1020
GTGAGGAATT AACTAAATCA GGACAATACT TGGGCCTGTC ACAGAGATCC TATGGAATAC 1080
TTTCCTACCA TTGTGCATTA ATGAACAGGT TCTTTTCCTC TCCTCAGATC CTGTCAAGTT 1140
GCGATGTCTT CAGCCATAGT TACTTCAACT ACCACTGATT TTGTTACTGA TTCTTTCTTC 1200
CCATGCTACA GTGGTGATTA TTCCAGAGGA TTTCTCTCAG TCCCTATTTG ACTCTTGTTA 1260
CTATTTGTTT TCTTGGTTAG TTCCATGAGA CCATGCCAGT TCTCCTTGAC TGTGTATGAA 1320
TCATTGTGTT GCACTGTACT GACAGACTGC CGTAAGTCAA TATTAAGTGT TCAGTATCTA 1380
AGTGCAGGAG AACCTTTCTA CTTAAGTACT CAACAAGTAG TTTGTTGGCA CTTAAGTTCT 1440
ATGAGATTTT TTGTTGTAAA GGAAAACATT ATCTTGCAAA GATTTTGGGG CAGCATTTAC 1500
CAATACTTTG TTCCTTCATC CGTAGGAAAA AGAATCTCAG GAGAAAAACC TATACATGGT 1560
AACCAATGGG GCTGCCAAGC TGATGAAGTA TTTTCAGAGT ACACCTTTGT GTAGCTGAAT 1620
AAATTGAGAT CTTGAATGGA CATATTAGCT CATTTTAGTA AAATGATAAG AGAGTGCCTC 1680
CCACTACAGT TTTTGTTTTT ATGCATCATT AAACAATGTG TTTTTGATTG TCCACTGTGT 1740
TCCATGAACT ATGCTATGTG TGGGAGATAT AGTAGTAAAG AAAAGCAAAG TACCTGCTTC 1800
CATAGAATTC AGTATAATGG GAATGGTAAT TCTTTAGAGA ATCACATAAC TATGGATACA 1860
TAGGCTTCAT TTTACTGTTC TCCTTTTGTG TTTGAAAATG TCAACAATCA AAATTTTGTA 1920
AAAAAGGAAT CATGCAACAT ATTTAAAATT ATAACTGTGT TAAGTGTAAT GAAGGGAAAT 1980
TGCACTGAGT AGTAAGAATA TATAATGGTG TGTGGTATTT CCCAAGTTAA AAAGGTCAGA 2040
TAAGGCTTCC TTGTGGAAGT GATAGTTCAA ATCTGAAAGA AGAATAGGAA TTAATTAGGT 2100
AAAAATGTTT GATGCAAATT TTAAGATTTT CCTTCTGAGT AGTCAGTAGC TTTTCCTTCT 2160
TAACATAGAA GATGACAAAA CCATCCTTTT TTTGTACATA ACAATTCTTG TTTTCCTTTA 2220
GACAGTTGTA TCTGTCAAGC TTCTTATGAT CTAATTTAAA TAATTGGGAT AGAACACAGC 2280
TGTACATGTT ACTATTAAAT ATGGAATATA TCAAACATAA GTTGATTCCT ACCAGTTCTG 2340
ATTTTATTTG TGTATTTTGT TAAAGGTACT GAGGACATTA ATATCCAGTT TTATATTGTG 2400
CATTTGAAGG TTCATCAATA AATACAATTC TTGTTTCTCT GGGTCTTAAA AGATATTTTA 2460
AATGGTTATC TCATTAAGAT TTAACAGGAA ATAACAGTGA TTCAAATCAA ATAGTGGTGC 2520
CAGAAACCCA TACTTGAATT TTGGGTATAG ACAGGTTACC CTTTGCATCA ATCCTGAGGA 2580
AACTAAAACT ATAGGATTAA TCAGGATAAA AAAGAATTGA GCAAGGATTC AGGAGGGATC 2640
TGTATCATCC TGGTGACAAC CCTCTTCTAG AAAAAACTAG AAAGTCTAAG AATAAATGAA 2700
GTTGCTGGTT CTCACCTGGA AAGGTCAGTT ACTCACAAAA TTTTTAGAGT CTATCTTATG 2760
CCATAATTCT ATCACTGAGA GAAGAAACTT GTCCAGTCAT CATGTAATCT TCATGTAAAT 2820
TTATGTTTTT AATTGCAGAA TTCATACCAC AGGCAAAGTC CCAATGTCTG CATTTGCTGT 2880
TACCTTAAAT AGTCAAACCC CAAAGTTATT GTAATCTTTT TTTAACAGAG AATAATTTGC 2940
AGAGTAATCT CGGTCCGGTA GATCTTTCAG TGGATCCCAA ATGATTGCCA TGAATGGTTT 3000
AGAATTTTTT TAATTTTCAA GTTGTTTTTA TTCTGTGGAA TACTGGCTTA TTTTTGTAGT 3060
CCCAAAAGAA AAATAAATAT TTATTTATTT GCCGTTAAGA GTTGTAGTTT TGTTTTCTCA 3120
AATTTGTCCT GACACTGACG AGATTAGTTA AATGTAGGTC ATCTGAACCA AATACAAGGA 3180
AGGAAGGACC CAGTTCTGAA GAGTGTGGGC ATTTCTTTTC TTGTTTTTTT TTTTTTTTTT 3240
TTTTTTTTTT CTATAGGAGG GGAACGAGGT GAACTAAACA AACAAAATAA AGCAAAAAAG 3300
AACTGATTTT TATCCCTTGA GGTAGAAAGA ATGAGATTAC AGTGGACCCC CTTGTCTGCA 3360
TTTTCACTTT CTATGTTTTA GTTACTCACA ACCACGTCCA AAATGTTAAA TAGAAAATTC 3420
CAGAAATAAA CAATTTATAA ATTTTAAATC AGTGGTGGCT TTGAGTACTG TAATGAAATT 3480
TTGTGCCATC CCACTCAGTC GGCCTCGACT TCCCTTAGAA TCATCCCTTT GTCCGGTGCA 3540
TTCACGTTGT ATTTACTCCC TGTCTGTTAG TCACTTGTTG CAGTATCACA GTGCTTGTGT 3600
TCAAGTAACG CTTATTTTAC TTAAGAATGA CCCCAAAGCA CAAGAGTACT GTGCCTAATT 3660
TATAAATTAA ACTTTTTCAT AGGTATATAC ATATAGGAAA AAACATAATA CATACAGGAT 3720
TTGGTTGGTA CTATTCTGCG GCTTCAGGCA TCCACTGGAC GTCTTGGAAT GTATCCCTTG 3780
TGGATAAGGA GGAACTGTAT ATGGTTAACC TAGGAGCTAG AGTCAACAGT TGGAAGAGAC 3840
TTTGGGGATA ATTACATGGA AGGGCATGGT GGGTGGTCGT TTCAGATGAC AAGAATGTTT 3900
TTGAATAACG GATCATTTGT GTCTTCAGAC TTTCCAGAAC TCCTTGAGAA TTATGCAGAG 3960
GTATTTAATC AGTCAGAAGG TTGAATAGTC AAATTATTAG TGAGTGAAGT CTATTTTGAT 4020
GAGGATTTTA CTAATGCTGT CCCTTAGATG TTATAAGTAA ATCGTTGTTT TCTTTTGAAA 4080
TATCTGAAAC CTAGTTAACA TGGACTTTCA TTTGTTCTTG TAAAGATATG CAAAGCTATT 4140
TGGGAGATTG TCATCATCTG ATATTTGATA TTCATGGGCT TTCTTCACAG AAGACTAGAA 4200
```

*Fig. 5A*

```
ATTAACAGAG TCATGATGAA TTATGGCTGC ATTGACTTTA AAAAACAAAC ACCTCCTTAA   4260
TGTTATTTAA CAATTTTGAA TAAATTTGAT ATGGCAAACA AATCAGTTAT AATCGATTGA   4320
GAAAGGAACT TAATTCTAAT ACTTGACTGG TGTCCCATAA TAACCCATAA TACTAAGAGA   4380
CAGTTTTGGA GGGCGAGAAG TCCTGAAGAG CTGATAGAGA TAAAGGTTCA AATTTGAGCT   4440
TCTTTCAGTG TTCCTTACGT CAATGCTTTT AGTTTCTCAT ACAAAATAAA ATAAAGAATA   4500
ACCTTTTTAC TGGGAAAAGG TAAAAATTAA TAAATTGTAG AAGCATTGTT TGAAGCCAAA   4560
AAGTGTGTGA CATGTAAATT GAAATGAAAA ACCTTAGAGT TTTTGATACT TTTTCAAAGC   4620
AGCTAAAGAA TTGATACTTG GACACAGGAA GAATTTTTTT TCAAAAGCAA TTTTTATAAA   4680
ATCAGAAAAA TGTTTACCTC TTGTTGGGGG CATTGACTGG AAAGGAATAC AACAGAACTT   4740
TCTGAGATGC TAGAAATGTT TTTTTATCTT GATGGGGTGT GGGTTTTGTA GATAATGAAA   4800
AATAAACAGT AAAAAATAAG TAAAAAAAAA AGTAAGAAAG TTGCCAATAC AGTTTTACAT   4860
ATTCCTGTGA TGTTTTTAAT CGACAGGCAC CTTCTTACTG AGATACGTAA TGAGAAGTTT   4920
CGATTATACA AATTAAAGAT GATGGCAAAG ATGGAAAAAT ATCTTCATTC TAGCAGATGT   4980
AGGAGACAGT ATGTATTATT TATTTTATGC CAATAGTATG GATTTATGGA TGATGCTCTT   5040
TTAAGACAAC AATTTGGCTA AATAATTATC AGTATTTTGA AAAAATATTT TGTTGCTGTT   5100
ACATGTGTGC TGAATTTTTA AGGCTAACTT CTTTGTGTCT GAGTAAACTG AAGTCAAATA   5160
ATGAAGTCCC AAGTGAATCA ATTAATGGTG ATTTTACCTC ATTATTTTCA GGAATGAACT   5220
TAACATATAC GTTTCTGTTC TTTTATTTAA TTTAAAATTT TGTCTTGGGT AGAATCATCT   5280
TGTCTCATTT TGAGGACAAA CAAGTACAAA AAGCCTCCTT GGGAATTATG GGAACTGAAA   5340
AATGCTGTGA TAATTGCAGG TCCAGGTAAA GATTTCTTAT TATAGATGGA CATTCTAAAA   5400
GTCTTTCTTT CTCTTCCTTT TCATGTTTAA CTGAATTTTT GTTGAATGAT AAGTATTTCA   5460
GTTTTTTAAA CAAAACAATG AATGTGTTTA GATATGAGAA AGCAAACAAT ATTAAAGTAT   5520
TTTGCTTAAA AAATAGATAA AGCAATAAAA TGGTAGCCCT AAATCTAAAC ATATCAATAG   5580
TTATGTTAAA TGTAAATGAT CTAAAATATT ATTTAAAGGC GTAAATTGTA AGAATTGGTT   5640
TAAAAACATG ACCCTGTTCT GTACGTTGTC CACAAGAAAT CCACTGTAAT TATATAGATA   5700
GGTTTAAAAA AGAATGAAAC ATTACATTCC ATGAAAACAT TAATCAAAAG GAAGTTGGAG   5760
TTACTTTAAT ATCAGACAAT GGACACTTTG GAGCAAAGAA TATTATCAGG ATAAAGAAGG   5820
ATATTATATG ATGTAAAAGA ATCATTTCAC CAATGTATCA GTCAGGGTTC ACCAGAGAAA   5880
TAGGACGATT GATATTATGG AGATATATAT ATATATATAT ATATATATAT ATATATATAT   5940
ATATATATAT ATATATATAT ATGGGGAGGG AAAGGAAGAA CAAATATGGG GAGAGAGGGA   6000
TGAGGCGACT GATTTTGAAG AATTAGCTCA CGAAATTGTG GGGGTTGGCA AGTCTGAAAT   6060
TTGTAGAGCA GGTCAATAGG CTGGAAACTC AGGCAAGAGG TGATGTTGCA GTCTTGAGGC   6120
AGAATTTCTT CTCTAGCAAA CCTAGTTTTT GCCCTTTAGT CCTGCCACTG AGTGGATGAG   6180
GCCCACCCAC ATTATTGACA ATAATCTCCT TTACTTAAAG TCAACTGATT ATAAATGTTA   6240
ATCACGTCTA CAAAATATTT TACAGCAACA TCTAGATTAG TGTTTGACCA AACAACTGAG   6300
CATCATAGGC TAGCCAAGTT GATGCATAAT ATTAATCATC ACAACCAAGA AGACATCATC   6360
CTAAATATAT ATATATATCT ACTTAACAAA AAGACTGACA GAACTGAAAG GAGAAATAGA   6420
GAAATCTACA GTTACATTTG GTGACTTCCA GCATCTCTCA ATAATCAATA AAACTGACAG   6480
ACCAAAAAAT CAGTAAGAAG ACAGAAGAAA TGAACAGGAT TATCAGCATG CTGGATCTCA   6540
TTGACCTTTT TAGAACATTC TACCCAACAA CAGTAGAGTA CACATTCAAG TGCAGATGCA   6600
GTATTCATGA ACATGGATTA TATTCAGAGT CATAAAACAA ACCTTAACAA ATTTAAGAAT   6660
CTTGTATTTG TATATTTTTT GACTAGAATG GAATTAAACT AGAAAACAAT AACAGAAAGA   6720
TAACAGAAAA GTCTCTAAAC CTTAGAAATT AAATAACACA CTTATAAATA AATCCATGAG   6780
TCAAAGAGGA AGTCTCAAGG CAAATCAGAA AATGTTTTGA ACTGAATGAA ATGAAAATAC   6840
AAAATGTGTG AGATGCAGCT AATGCAATAC TGAGAAGGAA ATTTATAGCA TTAAATACCT   6900
ATGTAATAAA AGAAGAAAGG TCTCAAATCA GTACCTAAGC TTACATCTTA AGCAACAAGC   6960
AAATAAGAGC AAAATAAATC AAAATGAAGT AAACATAAGG AAATAACAAA GAACATAAGT   7020
CAATGAATAG AAAAGCTATG GTCATACCAC TGCTGTCCAG CCTGGGTGAC AGAGTGAGAC   7080
CCTATGTCAA AAAAATTTAA AAACAAAGCA GCATGCAGCA TTCATTGTCA GTGAATAGAA   7140
AATGGGAAAA CAATAGAGAA AATCAACTCA AAAGCTCATT CTGTATAAAG ATCAACAAAA   7200
TTGATATAAA CTTCTAACAA GACTGACGGN AAAGANGAAA AGACACAGAA GACCAATACC   7260
AGGAATGAAA GAGGGAATTT CACTACAGAC CTCCCAGGTA TTACTAGGGA TGATAAGGGA   7320
ACACTATGAA CAACTCAGAA CATAACTTTA ATAATTTAGA TGAAATGGAT CAATTTCTTG   7380
ATAATCTCAA GCTAATTAAA CTTACAGTGA ATTAGATAAC CTGCATAGTG TTACAACCAT   7440
TAGAGGGATT GAATTCTATG TTAAAAATCT CTGAAAATAA AATCCCCTAG CCCAAAGAAT   7500
TTCAATGACA AATTCTACCA AACATTTAGA AGACAAAATA ATACCAATTC TATAGCATGA   7560
TTCCATTTAT ATAATAGTCT TTGAAACATA AAACTATACT AGAGGGATGA AGAAAAGATC   7620
AGTGGTTATT AGAGATTGGG GGAGGGAGAA GGTATGATTC CAAAGGATAG TACAAGGCAG   7680
TATTTTGGAG TGATAGATTT ATCGTGCCCT GATTGTGATG GGAGTTAGAT GAATCTATGG   7740
ATATCTTAAA ATGTGTAGAA CTTTACACAT ACATACAACC AATTTGCCTA TGTTAATTGA   7800
AAAAATAAAA TAAAAACAAA TTATTTACCT GGTGGGTTAG CTACGTACCT AAGTTCAATA   7860
GCTGCGTTAC TGTAAGACAA AAGAAGCATT ATTAGGGATG GAGTTGTTNC TCTGTGTAAT   7920
GACAAATACT TCCTTCACTA AGAAGACAGA ATTGTTTTAT GCACCTTTAA AAAAAAACAA   7980
AAACAAAAAA AATACAACCA ACAAACAGTA ACTTGCTGGT GCGGTGGCTC ACACTTGTAG   8040
TATTAGCACT TTGGGAGGCT GAGGTGGGAG GATCACTTGA GACCAGGATT TTTAAGACCA   8100
GTCTGGGCAA AAAACCGAGA CTGTGTCTCT ACAAAAATAA AAAATAAATA AAAAAAATTA   8160
GCTAGGCATA GCATTATGTG CCTCTAGTCC CAGCTACTCT GGAGGCTAAG GTGGAAAGAT   8220
CGCTTGAGCC TGGAAGGTTG AGACTGCAGT TGCAGTGAGC CATGATGGCA CCACTACACT   8280
CCAGGCTGGG CATCAGAGTA AGACTCTGTC TCACATAAAA AAAATAATAA TAATGATAAA   8340
AACTAGTCTG GGCATGGTGG CTCACACCTG TAGTCCCAGT CCTTTGGAAG GCCGAGGCAA   8400
```

*Fig. 5B*

GAGAATTGCT TGAACCCAAG ACTTTGAGAA CAGCCTGGGC AACATAGCAA GACCCCATCT 8460
CTATTTAAAA AAAAAAACAA ACTTAAAAAT CCAGCAAATA CATAAAGCAC AAAGCCGACA 8520
GAAGAGGTGG AGAAATCAAC AAATCCACCA TCAAAGTGGG AGAATTTGAT ATAATTTTAA 8580
GTTATTGGTA GGGTAAACAA TCCAAAAATT AGTACACTGT AGAAAATTTG GTCAACATAG 8640
TAATAAGTTT GCTTATTACT ATTTATCAGT ATACATAGTA TACTGATTTA TCAGATACAT 8700
AGTATATGGA GCCCTAGAGC AAGCAACTAT AGCAGTGTAT CTCAAGTATT TTTACTTCAT 8760
GACCCACATA GCAAATGATA TGTGTATATA ACACACTGGG CTAATTGTCA GAGTTCAGTT 8820
TCTGTCCAAA ACCCTAAGAT CTGGAGTGAT TAACCTTTCA GCACTCTTAG AACTCACTTG 8880
TTTGTAGCAC ACTGATTGAG AAGCACTGAA AGACTTCACT CCTCAAACAT ACATGGAATA 8940
TTTCTAAAAA CTATGTATTG GGCCGGGTGC AGTGGCTCAT GCCTGTAATC CCAGCACTTT 9000
GGGAGGCCGA GGCGGGTGGA TCCCGAGGTC AGGAGATCGA GACCATCCTG GCTAACATGA 9060
TGAAACGCCG TCTCTACTAA AAATACAAAA AATTAGCCGG ATGTGGTGGC GAGTGCCTGT 9120
AGTCCCAGCT ACTCGGGAGG CTGAGGCAGG AGAATGGTGT GAACCCAGGA GGCGGAGTTG 9180
CAGTGAGCCG AGATCGTGCC ACTGCACTCC AGCCTGGGCA ACAGAGCGAG ACTCTGTCTC 9240
AAAAAAAACC AACCAACTGA ACAAACAAAA AAACTAAAAA ACAAAAACAA AAAAACTATG 9300
TATTAGAGCA TGGGTTGGCA AACTATGGCC TGTAGGCAAA TCTGCATGCT GTTTTATTTT 9360
TTTTATTTTT TTGACATAGG GTCACTACAG GCTGTCACAC AGGCTGGAGA GCAGTGGTAT 9420
GATCATAGCT CACTGTAACC TCAAATTCCT GGGCTCAAGC AATTCTCTTG CCTCACCTCA 9480
GCTTCCCAAG TAGCTACAGG CATGCACTAC CAGACCCAGT TAATTAAAAC AAATTTTTTT 9540
TTGGTAGAGA CAGTCTCAGT ATGTTGCCCA GGCTGGTTTT CAAACTCCTT GCCTCAATCA 9600
GTCCTCCTAC TTCAGCCTCC TAAAGTGCTG GGATTATAGG CCTGAGCCAT CACGCTTGAC 9660
TAATGTTTTT GTAAATAAAG TTTTCTCAGA ACACAGCCAT GCCTTTTGTT TATGTGTTAT 9720
GTAGGGCTGC CTGAGTTAAG TAGTTGGCTA CAAAGCCTAT CATGGCCTAT AAAGCCTGAA 9780
ATACTTACTA TCTGGTCCTT TATAGAAAGT GTTTTCTGAC CCTGTACTAG ACTAGCTTGT 9840
CTCAAAATTC TTCAATGAAT TTGGAAGTTT TCTCACCACA TTTTCTGACC ATAATGCACT 9900
TGAGTTAGAA GTAAATAAGC AGATAAACAA CAAAATCCTC ATGCATTTGG AAATTAAAAA 9960
TAACACTTAA ATAATTCATA TTCAAAGAAA AAATCAAACT GGAAATTAAA AAAAATTTTA 10020
AACCTACAGA TAACTACATT AATATGCATT AACATTTTTA GAACTTAGGG ATAGTTACAA 10080
TGATATACAT TAAAACTGGT AAGAGGCTGG GTGCGTTGGC TCACGCCTGT AATCCCAGCA 10140
CTTTGGGAGG CCGAGGCTGG GGGATCACGA GGTCAAGAGA TTGAAACCAT CCTGGCCAAC 10200
ATGGTGAAAT CCCGTCTCTA CTAAAAATAC AAAAATCAGC TGGGCGTGGT GGCACGCGCC 10260
TGTAGTCCCA GCTACTTGGG AGGCTGAGGC AGGAGAATCG CTTGAACCTG GGAGGCGGAG 10320
GTTGCCGTGA GCCGAGATTG GGCCACTGCA CTCCAGCCTG GCGACAGAGC GACACTCTTG 10380
TCTCAAAAAA AAAACAAAAA AAAAAACAAA AAAAAAAACT AGTAAGAGGT CCCAGTGGCT 10440
CACACCTGTC ATTCTAGCTC TTTGGGAGAC TGAGGAGAGA GGATCAGTTG AGGCCAGGAT 10500
TCAAGACCAG TCTGGGCAAC ATAACGAGAC CGCATCTCTA CAAAATTTTA ATAACAACAA 10560
CAAAAAAACT GGTAAGAGGC AACATTGAAT AGTACTTTGT GGGAGTTTAT TAGCTTGAAA 10620
TACTCATAAT AGAAAAGAAA ATTAATCAGC TAAGCATCTC ACTAAAGAGA TTAGGAGAAT 10680
AAACCTAAGC ATAGTTTTTT TCCCCCAAAC ATTATTATAT CTGGAATATT GAATGCATTC 10740
TTATTGCTAT TTCAAAGATA CTTACTCTAA GGAAAGCAAT TGAATTAGGT AGTTGAACTC 10800
TATAGTAGAT TTTCTTTAAT GAGTCCTTTT GTTCTCAACC TACTTAAATA ATTCTCATTT 10860
GAATTTATGA TAGTTTCAGA TCTACCCAAA GGGTGACTTA GGAATTTAAC TTCTAAATCT 10920
ATTTAAATGA AAGGTTTATA ATCTTTGTGT CATATTTTAC AGTCGTTAGC GTTTAACAAT 10980
TTATAGCATA GGATTTGGGT TTTTTTTTTT TTCATTTTAA AGAAGAAGTT TATTTAAGCA 11040
AGACACTTGA CTAAGGGAAG ACTATCTTGG AGTTATTATT ACTAGAGTAA TTTATTTCTA 11100
CTTAAAGACA GATTGCCCCA CAAGTAACAG CTACATAAAA AACAGTTGTA AAATTGTCCT 11160
TGGTTTTACA ATGATAAATG AAAAACATTA AAATTCTCTA ATTGAACAAG GTATGCAAGG 11220
ATTTTTATAT TGTTTTTTGC TAAAACTATG ACAGCAAAAT AACATCCTGG AGTATAAAGA 11280
TAAGAGCTGA ATGAGCAGGC CACTAGGGGA CAAAGGGAGT CTTTTCACAG AACCAATGCT 11340
TCTTTTGCCC ACCCCATCTC CATCGAAGTC AATCTAAACA TATTATTGGC CATTTAGTTA 11400
AAAAAAGAAA GAAAAGNAAA AGCAATATGC TTGTGGACAT ACACCAGTTA CTTTATGTGC 11460
AATAAAAGAG TAGGAAGGGG AAGGTGAAAG AATAGAGAAA ACTATGTAGT CAGGATGTGG 11520
TGGAACCAAA TTGCAACTTT CTTTTTTTTT TTTTTTTTTT TTTTTGAGAC AGAGTTTTGC 11580
TCTTGTCACC CAGGCTGGAG TGTAGTGGTG GCCCAATCTT GGCTCACTGC AACCTCCGCC 11640
TCTCAGATTC AAGCCATTCT CCTGCCTCAG CCTTCTGAGT AGCTGGGATT ACAGGTGCAT 11700
GCCACCATGC CTGGCTAATT TTTGTATTTT TAGTAGAGAT GGGTTTTCAC CATGTTGGCC 11760
AGGCTGGTCT TGAATGCCTG ACTTCAAGTG ATCCACCCGC CTCAGCCTCC CAAAGTGCTG 11820
GGATTACAGG CGTGAGCACT GCGCCTGGCC AAATTGTAGC TTTCTAATTG AGACTGTCTT 11880
CTTGGTCTGG AAGAGCAGAG TTCTGCAGTA AAATAACAGG TCCCCCTTTT AGTAGACATC 11940
TCCATGTCTG CTGCTGGAAC ACATCAGTTT TGTCTTAAGC CTCACTTCCA AATGTGCAGA 12000
TGTGTCTGGT TCATTGATTG GCTGCCTGTC AAATTGAAAC CTGATCTGCC TCATTGGCAA 12060
ACCGTGCCCC TTACAATAGG CTTTCATTGG TTTACTAAGC GGTGTGGTGC GTGGCTGTTC 12120
ATCTTAAACT GCACCACAGT TTAAGATGAA CCTTCAAATG AACATTATCC TTGTTCTCAG 12180
TCTTGACTTT CCTTGGGCTT TTTGTGGACC CTGGTGAGTG TGGCAGTCTC CTCAGCTGCT 12240
GCTTCACAAA AGAGGTACCA GGTCTGCCCC GAATGAGTGA GCCCCTAAAC AGGACCAGGA 12300
GTGGCAGAAG AAAGAGGCAG CAACTGAGAT GTGTTTTTTC TAAGCTGAAA GGCTTTTTTT 12360
TTTTTTTTTT GCAACACACC TTTAACACTA AAGTCCAATA TTTATATAAT TNGGTCAAGT 12420
AAGTGGAGCT GTTCTAGCTA TAAATATGGC AACTCTGCTT GCTCGTCCTA TTATTGACAT 12480
TATTCCTTTC TGTGGTCTGA GGTGCCTCCC ATGAAACTTG CTTCTAGGAC ACTAGGATTG 12540
AGAACCATNC AGCGTAACAT ATCTGTTACG CTACAATAGT TTATTTTCAT ATTTTAGCTA 12600

*Fig. 5C*

CTTTACATAC TCGGGTATAA TGAACTTTAT TCATAGCTTC TGAAGCAGTT GGCACATTTG 12660
AGATATTTTT TACTTGGCTA ATTGTTATGC TAAATCTTTT GATTTCTAAA GATACATGCC 12720
TTTGCTAAGC TTTCTTCAAA TGTTATTATT TTTATTTAGA TTGGATCATT GCTATTCCAT 12780
GGATGACTCA GAGGATACAT CCTGGGACTT TGGTCCACAA GCATTTAAGC TTTTGTCTGC 12840
TGTGGACATC TTAGGCGAAA AATTTGGAAT TGGGCTTCCA ATTTTATTTC TCCGAGGATC 12900
TGTAAGTATA TATCTGTGAA TTCCCTTCAT AGATCTTCTT TTACTTCTAT TACACTTTTC 12960
TTCAGAGGTT TGCAGTATTA TGATTGTAAC TTTGACTTCA GATGGGTGAC TAGGAACTCA 13020
TAGAGTCTTA CTAAGTTCCA GTTAAACACT ACATTCATTA CTTTGGATAA AACCCGTGTG 13080
TATGGCATCT TCTGCTGTTT TCATGTTCAA GCCGATGTTC AGCTCTGCAG CTCAGTCTGG 13140
AAGCATTGTG TTAATTTATC ACATTGCATT TGGGTGAATC CCTAGACTAG TCTTGCTTAG 13200
GATAATTAGG AAAAGTTAAC TTTCATTGTA TCAAGGGACA GGTAGAACAA AATTGTCCTT 13260
TTGTCCAGGA AACTATTAAA TTCTTCAAGG AAAACTTTAG TTATAGGGAT TATTTTTTAA 13320
ATGTCTAATT TCAGTAACAA TATTTGGGAC ATATTTATTT TTCCTTCTGT TTCCTATCAG 13380
AAGTATTTAA AGTTATAAGA AAATTGTGGT TTTTGCCTTT ACTAATGAAT AAATAATCAA 13440
TTAAATTCAG TTACTTTTTT TTGGAGTGAT TGATGTTCCA GTATTCTTCT AAACAACCAC 13500
GGGTACAAAT GTGAATAAGA TAGGACCGTT GCAGTCCAAG AGCTTGTTCT GTAGTCCTTT 13560
CCTTTATATG ATTTTTTCCC CTGATTTAGA AGTCTATAAA GCAAAGCTAA GTATTACACA 13620
CTGATAATGG CTGAATAAAT CAAGAGCAAG AGATAGGATA CTTTGCAAAT ATGCATATTT 13680
ATTAAAAATG TACTTTAAAA TAGAGATTAA AATTCTCGTA TTGAATGTAG AATAGGTAAG 13740
CATTTATTTG TGAAATACTC GAATGCTTCA TGTAAATACT TTCTGAGTTT GTATTTTTAG 13800
AAAGGAACAT TTTGGAGGCT GAGGCAGGAG AATGGCGTGA ACGTGGGAGG CGGAGCTTGC 13860
AGTGAGCTGA GATTGTGCCA CTGCACTCCA GCCTGCGCGA CAGAGCAAGA TTCTGTCTCA 13920
ATAAAAAAAA AAAAAGAAAC ATATTTATTA AATTAGTTGT GAAATATTTT TAATGAAATA 13980
TATTGAAAAC TTCTGTTGAT TTTTCATGTA CTGATGTTTT TAGATTCTAA ATGGAGTTTA 14040
AAATTTTGTT TGTAAATCAC AAGTTGGATT AGAAATTTAA TAGTAGAAGT GTTGCCTAAG 14100
GACTATTTTA GGTGCTGTGA GTGAAACTGT ATTTTTTATA ACAAGAATTT TAGTTGTAAG 14160
GGACAGCTTA AATATAATTG AGATCTGTGA AAATGTATTC TGTCTCTATC ACCTTCAGAA 14220
CCTGTGTATC TCAGTTGAAT GTATAATTTA TAAAAATTAT TCTTGTTTTA ATTTGGTGTA 14280
ATCCAGCCAT ATCCAGTATC AACAAATAAG TCTAAGTAGG CTCCTTGACA AACTTGAACT 14340
GGCCACAAGA GAGATCAGAT TTCACCTATT AAAAAACCAA ATCAGACCAC TTACACTGAC 14400
AGTCTCTTCT GGGAGTCCTC AAATTAAGAA GTCTATCCTT TGTGAAATAT TACACTACCC 14460
TTGCTAGATA AAACTTTTCT AAAAGTACCA CTTAATGAAA ATCTGTAGAC ACTAAATGCA 14520
ATGAAAATAA GGCATTGTTT TTTTTTCTCC CCATTTCAGT GATCTTGGTA TCCTGGGATA 14580
TTGTTTTTAA AATTATCGTT ATAATTCCTT TGAGAATTTA GTGAAACGTT CCCTTTAACC 14640
AACTTAGGAA AAATTAATAT CTTTGTACAT GATTTTGAGC TGTAAAATAA ACATTTTAAA 14700
CTGGGAATAA TTGGAGTTTA GTTAAAGAGA TAATGTATAT AAATATATAA CATAGTAGCA 14760
GCATATAATT CTGTCTTACA CAAGATTTTT CTGAATAGTA TAAACAGTTA TGTAGCCTAT 14820
CTAGGAGTTT GTGAATAGAG TTTAAAATTT TGTTTTGAAG CTGCAAATTT GATTAGAAAT 14880
TAAACAGTAA AGTTATTACT TAAGGAACTT CGTTTTAGCT GTCTGAACAA CTTACTGTAT 14940
AAAAATCTTT AAACATTCTG TATAAATATG TGATAAGATA TGCAATGACC TTAATTTTAT 15000
AGATTAGAAA ATAAAAACAC ACTCATTAAT TTACATAACT GACAGATTAA GTGAAACTTC 15060
TCTTCTGATC ACGTTAGCAG AATGCCAAAT CTTGTCGTGG CACTAGAATT AGACGGTAGT 15120
TTTGATAATA CATGATTTGA CTATAGACAT TTGTTGAAAC TATTGGTAGT TTTAATCACT 15180
CTTGTAATTT TCAAACTATC TAACGGGAGA GGATTATCCA TCCTGTTTTC TAGACAAACT 15240
GTTTCATCTG AATGAAATAT ATTCCTAGAG ATAATTATCA CTACTTCATC TTTTGGTTTT 15300
ATTTTGCACA TAGAATTATA GTTCACAATG ACTTTCTGAA GCTCTAAAGT TGCAGCTGTG 15360
AGCTTCTTTG GCCTGTAGGG ACTGGGAAAA AGCACCCCCG TCCTCCCCCA AGCCCCCCCA 15420
CCAAAAAAAG TTAAAGTGTT TTTAACAATA GCTGTGGGCT TTTTGTAGTT TCAGAACTTA 15480
GGAGTTGCCC AGGCTGGAAT GCAGTGGTGT GATCATAGCT TGATGCAGCC TTGAACTCCT 15540
GGGTTCAAGC AATCCTCCCA CCTCAGCCTC CAGAGTAGCT GGGACCACAG GTGCCACCCC 15600
ACCCAGCTAT TTTTTTTATT TTTTAATTTT TTTGTAGGTA TGGGGTCTCC CCATGTTGCC 15660
CTGCCTGTCT CAAACTCCAG GGCTCTCAGG TGATACCCAC CACCCTTGGC CTCCCAAAGC 15720
ACCGAGAGTC ACTGTGCCAG GCTGAGTTTA AAATTTCTTG AGTTGGAGTT TATGGCTATT 15780
TTTTCCACTA GTTATTAAAC ATGTATTTTT GTATAAGGCA CTGTATTACA TTTTGTGGGG 15840
GGATTCAAAG CTAAATTAGA TGAGACGCAT CATCTATTAT GGAAGATGTT ACTTAAGAAG 15900
AAATGAGTGT AATGTAGCAG AGAATTAGAT AAGGGACGTA TGAATACATA TAAATGCTGT 15960
TGAAGTTCTG AAGAGAGAGA GTGTTTAGAG AAATTAGAGG AGTCTTTGTG AAGTTATCAC 16020
TAGAACTTCC TATTTTTGTG GAATATATAG TAGATTTTGG TGTGATACTG TGGATTTGGA 16080
CATTCACTCA GAGAAGGAAT GAGGGAAGAA TGGTGGAGAA GAATGGCATT CACAGTACAA 16140
AAAGCAACTG TGACTTTTAA AGAAGTTAAT ATGGAGAAGT GGCAAGTCTT TTCTTCTCTC 16200
TTCTCTTCTC TTCTCTTCTC TCTTCTTTTT CTTTTTTCTT TTTTTCTCTG TCAGATACTG 16260
TTGTAAAGAC TTTGCTTTTA CCGGAAACTG ATACGTTGGG TCATGTACCC TGGCCAGTCA 16320
GTTCTCTTTA TTCTAACACT TAGCCGATCA ATTAGATTTC CACATTCCAT GATATGTCAG 16380
TTTTGGTGAC CCTTATTTTT CCACCTGGTT TATAAAGGGA AAGAATGTGA TATGTCACCC 16440
AGGCTCTGGA GTACAGTGGC ATGATCATAG GTCACAGCAG CCTCAAAGTT TCCAGTTCAA 16500
GCGATCCTAC CTCCTTGGCT TCCTGAGTAT GTGGCACTAC AGGTGCATGC CACCATGCCC 16560
AGCTAACTTT TTTGTAGAGA CAGGGTCTCC CTATGTTTCC CAGGCTGGTC TTGAACCCCT 16620
GACCTCAAGT GATCCGCCCA CCTTGGCTTC CCAAGATATT GGCATTACAG GCATGAGCCA 16680
CTGTGCCGGC CTGAAAATTT CTCTTTTGAG ATGGCATCCC ACAGAAGTAT ACCTGCTTAG 16740
AGCTAACACT GGTAAAAAGA CTATTTAACC CTATTGCCTT ATTTTACTGT AGTTGAGATT 16800

*Fig. 5D*

GAGTTAAACT GAAAGCTGAA TGACCTGTCC TAGGTCATAC TGTTACTTTG TGCCAGAGTC 16860
AGGATGAGCA AATGGATTTC CTGCCTGCTA GTCTAGTGTC TTTTCTATTT ATTGTGCTGT 16920
AACATACAGT TTTAAATTTG TATTTTTATG CCCAATGGAC ATGGTAGCTC ACACCTGTAA 16980
TTTCAGCACT TTTGGGAAGC CGAGGTGGGG GGATTGCTCG AGACCAGGAG TTCAAGATGA 17040
GCCTGGGCAA CATAGCGAGA CTCCGTCTCT ATAAAAAAAA ATTTAAAAAT TAGCTGAGTG 17100
GTGATGTGTG TGCGTGTAGT CCTCCTTGTG GGAGGTTGAG GTGGGAGGAT CGATTGAATC 17160
TAGGAATTCA GGACTGCAGT GAGCCATGAT TACACCACTG CACTCCAGCC TGGGTGACAG 17220
AGCAATACCC TGTCTCGAAT GAATGAATGA ATGAATGAAT GAATGAATGA ATGCCCAAAT 17280
CCGTAAGCTA TGTTCTGTAT AGCAGCTTTT TCATCATAGG CAGTTTTTAC TCTTATCAGT 17340
GGACAACCTA CAAAATTAAC TAAACACTTA AGCAATTAAC AGAGGAGGCC TTGTTCAGAG 17400
TGAGAAATCA TTAAGCATTT GTTGTTGAAA TTTCTTACTG TACTCTGTTT TAATTCTGTT 17460
TTTTTTTTTT TTTAATGTTA CTTGTTTTAG TTTGGATTCC TAGTTGAAAA GGGAATATGA 17520
TTCCTTTAAA ACAAAGATAC TCTGCTTTAA AGCAAAGGTA TATCATCCTC TTCATGGTGA 17580
TTGCCATGGA AACAAGACAA TGTAAATTTA TTCAAATAGT ACACAGTTTT TATAGTTATT 17640
GATCATGAGG GGAAGGGACA GTTAATCCCT ACTGATCAGA TAAAACCTCA TTGTTTCATA 17700
CTAATAAATG GTTTTTTTAT GCTTATGAAA GGAAAAGCCA GAAGGGTAAT TTTTAGTGTT 17760
TAGAGAGCTA GTGATTCTAG TTAGGGAACT TAATACCTTT GAAGTTATTA GTTTGCAAGC 17820
AATAGAATCT ACTACTACCA AGGTGACCCC TAGCAGATGT AGAGTACCAT TAACAAGTGT 17880
TCCAGGGAAG GAAAGCCAAC TAGATACCAA GTCATGCTTT TTACTCTTAG ATTAAGAAAT 17940
TCAGGTTGAG TTAAAGGATC AGCTGTTAAC TAATAAAAAG CAGATTAATA TTACAGAGCC 18000
AGGCTCTGTC CTGGTTATGG ACTTAATCTT CACAGCATCC TCAAGAGATA AAAATGAATA 18060
TACCTGCATA TTAGATGAGG AAATAGAAGA TAAGTAACTT GCCAGAGCTA TGACGTGAAC 18120
TCAGGTAATG TAGCTTAAGA GCCCCCACAT GTATGTATAT TGGGTGTGTG TGTGGAGGGG 18180
GTGCGTGTGA GTGCTTGTGC ATGCGTGTGG TATAATAAGA AAAAATTAGC ATTTATGCCT 18240
GTAATCCCAG CACTTTGGGA GACCGAGGCA CGAGGATCTC TCAACCCCAG GAGTTCAAGA 18300
CCAGTCTAGG CAACATAGCG AGACCCTACC TCTACAAAAA AAGTTTTAAA AATATTAGCG 18360
GGCATGGTGG AATACACCTG TAGTCTCAGC TGCTTGGGAC GCTGAGGTGG GAGGATCCTT 18420
GAGTCCAGGA GATTGAGGCT ACAGTGAGCT ATGATGACAC CTCTGCACTC CAGCTTGGGT 18480
GACAAAGAGA GACCCTGTCT CCAAAAAAAA AAATTAGAAC TAGTTATCTG GAGGCCTGTG 18540
TTCTAGTCCT AGCTTTAGTA CGGCTACACA GTGACACATT AGGCTACCAT TTAACATCTT 18600
TGAACCTCTG ATAATTTGTT AACAATATGG GTAAAAATGA CTAAGATAAA TCAAAGAGCT 18660
CCAGCATTCC CTCCAGCTCT GAAATTCTAT GATGTTTTAT CTTATTTTAC TTACAAAAAT 18720
AAATTATATT ATGTATATTT AAAGTATACA ATTTGATGTT ATGGGTTACC TATAGTAAAA 18780
TGATTACTAT AATGAAACTA ATTAACATAT CCATCATCTT ATATTGTTAA CCATTTTTTT 18840
GTTTTTGTGG CAAAAGCAGC TGAAATCCAC TCATTTAGCA GGAATCCCAA ATACAGTTCA 18900
GTTGTATTAA TTGTAATTCT CATCTTGTAC ATTCGATCTC TAGACTTGTT TATGCTACAT 18960
ATGTTTGACT TTTAAACATT CTACTCAAAT CAACCCTAAG TCAGGGTTAG CACAGACAGG 19020
ACTTGTTAAC AAGGTAGAAG GTGCCACATT GTACCTGGGT GTTTATATTT CTCTAAATCT 19080
TGTTCTGATC ATATTTTAAT AAATATAATC ATCAGGACAC CAAAATTCAT TCCTTAGCTA 19140
TTAAAAAATT CTATTCTATT TTATTGTTAA GATTTAGGAG AGCATGGTAC AGATTCTCTT 19200
AACTATACCT ATCAGAAGCC TATGTTTTAA GTCCAATGTA TAGGCACTGC TCTGTTTGTC 19260
TCTGGTGGGA ACTTACCCTG CTTTACCTAA TTTCATCCTA GCTTCCTTTT TGTGAAAGAT 19320
CACCCTTGCT TAGCCTATTT TTTGGCAAAT CTACACCTTG GAAATAGTAG TAAATGACAT 19380
AAGCATATTA ATATTTATGA TGTGATTTAT TTTTGTTTTC AAGTCATATA CTGGGGAAGA 19440
TTCTCAAATA TTAAAACAAT GTATCTTTAC ATTTATGTAT GTCGTTCTTG TTCTGTTTTA 19500
GAAGGCTTGT ATTTGCATTT TTAACATTCC AAAAGGTAAA CCTGTAATCA TAATGTTTTC 19560
ATCAATTCAA TAAAACCATT ACGTTTGTAA TAGAGAGCCC TATAGTTGCC TTAGTTAAGT 19620
TTGCTGCAAC TCATTTTATA TATTCTTTTA ATTTTGATCC CTGGATTTTT AATTGATTAT 19680
TAAACCTTCA TTAGGATATA TATGAAATGT AAAAATATTG AGTTATAATC TACCGTTTTC 19740
TAAAATTTTA TACTGCATTT TTATATAGAA ATTCAAATTG CTCATAATCA TTCTAGTGAA 19800
TTTAAGTAGA AAGGTATTTA TTACTAGGTA TTAAATGGCT TATAATATTG TTGACAAGGT 19860
TCCACTGCAA AATAGTTCAC CAAGGGAGCT GTGGCCTCTT CTGTGATCAA GAAGCCATCT 19920
GTCAACTTGG GAAGCTTCCA CTATAGCACC TAACCCCAGA CTACATTGAG TAGGAAGCTG 19980
TAATAATCAG GAAGCTTCTA CCTTTGCATG CTCTGCAAAC CAACGTGAAC CTGCTGTAAT 20040
TTGTAACCAC AAAATGGATG CCTGTTGATA CTTACGAAGC TCATCATTGT ATGCTGGGTT 20100
CTTTGCTAAT ACTTTCTTAT AAAAATTAAA TACCTCCACA ATCATGCATG CTAGCAGAAA 20160
CAGCAGAGGA GTAGCCTTAG CCTCACTTCC TGCTTATACC TGTCATGCAG ATATACAGAA 20220
CCCAGAACCC TAGCTGAAAG GGAGTTTGAG AACTAGTATT TGTATTGTCC CAGATTCTGC 20280
AGTGGAAGAA TTCATAGTGG ATGGAAGTTA GAATGACCCT TGAATTACAA TCGGCCACAT 20340
TCATCACAAA TACATTAAAT AAGAGTAATT TGCCATAAAG CTCTATGTTT GTATACTTCT 20400
TTGTTTTTTT TTTTTTTTTT TTTTTTTTTT GAGACAGGGT CTCACTCTGT TGCTCAGTCT 20460
GTAGTGCAGT GGTGTCATCA TAGCTCACTG CAGTCTTGAT CTCCTGAGCT CAAACGATTC 20520
TCCTGCCTCA GCTCCTGCTT CAGCCTCCTG AGTAGCGGAA CAACAGGTAC ACACCACCAC 20580
ACTTTGCTAA TTTTTTATTT TTTATTTTTT GTAGAGATGT GGGTCTCACT GTGTTGCCCA 20640
GGATGGTCTC GAACTCCTGG GCTTAAGTGA TCCTCCCAAA GTGTTGGGAT TACAGGCATG 20700
AACCACTGTG CCTGGCCCAT ATACTACATA TATTTAAAAG TAGTATTTAA ATGTGTAGGA 20760
TGAATGAAAG AGGCAGTAAG AGAACAAAGT GAATGAAAAA GTATTTCTAT ATGAAGTGAA 20820
AGCAGGAGAG TCCTCTCTGT TAGAGAACAA CAGAATTGCA TATGACAGAC TAGCTTTCTT 20880
AATATTTCTA GAACTTGATG GCTGTGAAGA GCGTCCCGTA GGAATTCTCC CTTCACTTAG 20940
GAAAACATAC CTCAAAACCA TCAGCTGTTT AGCATGCACC TGCTTTTCCT GGTATATCTC 21000

*Fig. 5E*

```
AGTGAAGCAG CTAAATTGTA AATGATTAAG TAAACTTTGC AGTGTATCAT GTGCAAAAGC  21060
ACAGTAAAAA CAAAAATGCA TTGGAAGCTG TGAGTTGTTG CACTGCACTC ATGGATGAAT  21120
AGCTGTTGGT TCGCATTGCG TTTTTTTGTT TTGTTTTGTT TTGTTTTTTT GAGATGGAGT  21180
CTTGCTCTGT TGCCCAGGCT GGAGTGCAGT GGCGTGATCT CGGCTCACTG CAAGCTCTGC  21240
CTCCCAGATT CACGCCATCC TCCTGCCTCA GCCTCCCGAG CAGCTGGGAC CACAGGTGCC  21300
CGCCACAACA CCTGGCTAAT TTTTTGTATT TTTAGTAGAG ACGGGGTTTC ACCATGTTAG  21360
CCATGATGGT CTCAATCTCC TGACCTCGTG ATCTGCCTGC CTTGGCCTCC CAAAGTGCTA  21420
GGATTACAGG CATGCCGCAT TGCGTTTTAT ATAATTCTCA TGGTTCTAGT CTCGAGCTGT  21480
AGGATTTTGA TCACTGTTTC AAACAATAAT GTGAGTTTGC TAAGAGGTCT AAATAACAAA  21540
AGCTAAGTGT CCAAACACAT ATCCAAACCT ATACACTGGG CAATGCATCT GAATTATATG  21600
TGAAATTTCC TGCCATTATT TAAGACACAA AAGGAACATT ATTTTGATAA TGTATTTATT  21660
TGTGAGTGGA GTGTTCAGAA TGAGCACGAT GGGTATAACA TTTTTGTAGG TTTTTAAAGT  21720
TGAAATTTAG TGTAAATCCA AAGAATCAAT AGACAAGTCT GTGTTTTACT TAACCTATAT  21780
GTTTAAATTA GCATTTTTAG ATACTGATTT TATTCCTAAT TTCAGAATTC TCAGCGTCTT  21840
GCCGATCAAT ATCGCAGGCA CAGTTTATTT GGCACTGGCA AGGATCAAAC AGAGAGTTGG  21900
TGGAAGGCTT TTTCCCGTCA GCTGATCACT GAGGGATTCT TGGTAGAAGT TTCTCGGTAT  21960
AACAAATTTA TGAAGATTTG CGCCCTTACG AAAAAGGTAA ACAGTGTAGG AGTCTGCCTG  22020
TTTGACTTAA TTTTGTTTCC CACTCCACAT TAAAAGATCC TTTTTGCTTT TAATAGGGTA  22080
GAAATTGGCT TCATAAAGCT AATACAGAAT CTCAGAGCCT CATCCTTCAA GCTAATGAAG  22140
AATTGTGTCC AAAGAAGTTT CTTCTGCCTA GGTTCATTTT TCAGTTTTTT TCTTGTAACT  22200
TCTGCATTTT TTGTTGCTAT TTATGTGATT CAAATTATAC CAGTTTATAG GCCTCTCACA  22260
AGTAAAATGA ATTGCCTGTT TGTTTTTGTA TGCCTATTTT AGTCAGTTTG GGGGAAGGGA  22320
TCTGTGAGGA AAGGATAAGT CATAGAGCAC TTTTCTTTTT TAAGAGACAG AGTCTCTCTG  22380
TGTTGCTCAA GCTGGAGTGC AGTGGTGCGA TCATAGCTTA CTGCAGCCTC GATCTCGTGG  22440
GCCCAAGTAA TCCTCAGCCA CCTGAGTAGA TGGGACTACA GACATGCACT ACTATGCCCA  22500
GCTAATATAT TTTAATTTTT TGTATAGAGA CAGGGTCTTC TAGTGCTTCC TAGGCTGGTC  22560
TTGAACTCCT GAGCTCAAGT GATCCTCCTG CCTCAGCCTC CCAAACTACT GGGATTACAG  22620
GCATGATCCA CCGCTCCCAG CCAGAACATT TTCTTGGTTG ATGGGAAGTA GCTGACCATG  22680
GTATTTAGAA AACTTCTTTC TCATCGATTA AAGAAGCAGT ACTGAAATCA ATGCGGAGGA  22740
ATCCATATAT CATATTTACT TCTGGTGTGT AGAAGTGGAA AGGGAATACA TTTGTTGCTT  22800
ACTTTTTTGT ACCTTTACAT GTGATTGATC ACTTGTGAGT TTTTTCTTTC AAACATCTTA  22860
AAGCTTCCAG AGCTTTTTCT AGAAAAAAAA ACCAGTTTTA AGAATCACCA GTTCTAAAAG  22920
GGTAATATCT TATTCATCTT TCTGAGAATG GAGTATCATG ATTCATGAAT TAGATACTTG  22980
CATCTTAACA TTTGAAATAA TTTAATTTTA TTATTTTTTA GTTCGAAAAC TGTATCTTCG  23040
GGCACCAAAG AGCATTGTTA TAATCAAGTA CCAGTTGAAT TAAGTACAGA GAAGAAGGTT  23100
TGTTTTAAAG AAATTGTTCT GACTTATTTC ATTCTTTATT GATTCAAATT CTGTTTAAAA  23160
TTTTATATTT TAATTCCTTT CCAATTAAAG AGAAAATGGC ATATATAACA AAGCATAAAA  23220
TTCGGCCAGG GAAGTGATGT GAACAGACTA AAATTTATTG TATATAATTT CTGGGGCTAA  23280
TAAAGAATTG GAGGTATTTG AGAAAGGAAT TAATTTGGGT TCTTTTAAAC CTATCTGCTA  23340
ACTCATTTGG CTTAGAGTAG TCACATGTTA TAATACTTAT AGTTGATCAA AAAATTGATT  23400
CCTAAGTGTT CTTATTAAAG ACACACACAC ACACACACAC ACACACACAC ATTCTTTCTC  23460
TCTCTCTCTC TCACACACAC ACACATGCAC ACACACTTAT GTACTTTCTT GCTTTTTTTG  23520
ACCTAAGATC TTAGATAACT ATTACAGATT AAATACTAAT CCACTGGCAG ACTTCAGCTA  23580
ATTAGAACAC TGGAATAATA GGCAAGCATA GTGAATTACA TTTTCTGGTG AACTTTTTCT  23640
GCTTTATTGA AGTATGCAGA ATGTAAATGA ATTGTTTTTA TAACTTTGGC ACTTGCTGTA  23700
TCTTAGAACA TTCTTTTGAT GATTTATTTT CTGTAGTTTT GGGAGAGATA AGACATTGGA  23760
ATGCGTTTCT AACTACCTTT AGAACTTTAG AAACTGATAA TTTAGGAGGT TATTTTCAGG  23820
TGATTAATTT GACAGCTTGA TTAGGCAAAG AAAAAATTGT GATTTTGAGA TTTTTGTTTC  23880
TTATTTTCTT CACATTTAAA AGTTTTTTGA AACTTTTTTT AATGGACCTT TATATGTTTA  23940
AATGCAGTCT AACTTGGAGA AGTTATATTC TTATAAACCA TGTGATAAGA TTTCTTCTGG  24000
GAGTAACATT TCTAAAAAAA GGTACAGAGT TCCATATTTC TATGTTCTAT ACTTGCTTTA  24060
TGAGTACTTT TTTTTCTAAA GAGAAAGAAC TGTCAGATGT TGGGCTATTT CATTGGCAAA  24120
AGGAAGTTAA ATTTAAAACA TAAGCTTTTC AGTATTAGAA TGATCAAAGT GAGCTATAAA  24180
AGAATAATGT TAATTTAATA GCTAACACTT CTTGGATATT ACTGTTTGTC AGGCATTATG  24240
TTAAATGCTA AGAACTTTAT ATGTGATATC TCATTTAATT CTTACAAGAG TCTAACAGCT  24300
GTTACTATTT ATCGCCATTT TATAGTTGAA GATACCAAGG GTTAAGAAGT TGACAAACTT  24360
GTTCAAGAGC ATACAGCTAA TGGCCGAGCT GGCTTTCAAG TCTATATTTG TCTACCTCTA  24420
GCATCAAGAC ACTATTTATT TTTCTTTGTA TGAAATATAT ACAGGCATAC TTTGTTTTAT  24480
TGTGCCTGGC TTTATTGTGA CTTGCAGATA TTGCATTTCT TATAAATTGA AGGTTTGTGG  24540
CAACCCTGCG TCAAACAGGT CATATTAGCC CCATTTTCCA ATAGCATGTT CTGTTGTCAT  24600
GTCTTTGTGT TATATTTTGG TAGTTCTTGA CTGGCCATTC ACCATTTCTC TCCCTCTCCT  24660
CGGGTCTCCC TGTTCCCTGA GATACAACAA AATTGAAATT AGGCCAATTA ATAACTCTAT  24720
AATAGTCTCT AAGTGTGTTT TTTTTTTTTT TCGAGACTGA GTCTCACTCT GTTGTTCAGG  24780
CTGGAGTGCA GTAGCACAAT CTCGGCTCAC TGCAATCTTC GCCTCCCGGG TTCAAGCGAT  24840
TCTCCTGTCT TAGCCTCCTG AGTAGCTGGG ACTACAGGCG CCCCCCGATC ATGTCTGGCT  24900
AATTTTTGTA TTTTTAGTAG AGATGGGTTT TTGCCGTGTT GGTCAGGTGG ATCTTGAACT  24960
CCTGAACTCA GGTGATCCGC CTGCCTTGGC CTCCCAAAGT GCTGGGATTA CAGGTGTGAG  25020
CCGCTGTGCC TGGCCCATCT CTAAGTGTTT AAGAGAAAGG AAGATTCACA TGTCTCTCAA  25080
TTTAAATCAA AAGCTAAAAG TGATTAGGCT TAGTGAGGAA GCCATGTCGA AAGCTGAGAT  25140
AGGCCAAAAG CTAGGCCCCT TGCACCAAAC AGTTAGTTTG CAAAGGCAAA AGTTCCTGAA  25200
```

*Fig. 5F*

```
GGAAATTAAA AATGCTACCC CAGTGAATAA AACAATGATA AGAAAGCAAA GCAGGCTTTT 25260
TGCTGATATG GAGAAAGTTT TAGTGGTCTT TATAGGAGAT TAAACCAGCC ACAACATTCC 25320
CTTGAGCCAA AGCCTAATCC AGAGCAAAGC CCTAACTCTC TTCAATTCTC TGAAAGCTGA 25380
GAGAGGTGAG GAAGCTGCAG AATAAAAGTT TGAGGCCAGC AGAGGTTGGT TCATGAGGTT 25440
TAAGGAAAGA AGCCATCTCC ATAACATAAA AGTGCAAAGT GAAACAGCAA GTGCTGGTAT 25500
AGAAGCTGTA GCAAGTTATC CAGAAGATCT AGCTAAGATC ATCGATGAAG GTGCCTGCAC 25560
TAACAGACTT TGAATGTAGA CCAAATGCTT TCTACCAGAA GAAGAAGCTG TCTAGTACTT 25620
TCATAGCTAG AGAGAAGTCA ATGCCTGGCT TCAAAGCTTC AAAGGACAAG CTGACTCTCT 25680
TGTTAGAAGC TGATGCAGCT GGTGACTTTA AGTTGAAGCC AGTGCTCAAT TAGCATTCTG 25740
AAAATCCTAG GGCCCTTAAG AATTATGCTA TATCTACTCT GCCTTTGCTA CATACATGTA 25800
ACAACAAAGT CTTGATGATA CCTGTTTACA GCATGGTTTC CTGAATACTT TAAGCCCATT 25860
GTTGAAACCT GCTTAGACAA AAGATTCCTT TCAAAATGTT ATTGCTCATT GACAACACTT 25920
AGTCACCAAG AGCCGTAATG GAGACATACA AGGAGACTAA CGTTGTTTTC ATGCCTGCTC 25980
GCTTAACATC CATTCTGTAG CTCATGGATC AAGAAGTAAA TTAACCTTTT AAGTATTATT 26040
ATTTAAGAAA TACAGTTTGT AATGCTTTAG CTTCTGTAGA TAGTGATTAT CAGAGATGGG 26100
TTTTTAAGAG GTTTTCCAGA AAACCTTCTG GAAAATATTC ACTATTCTAG AAGTCATGAA 26160
GAATATTTGT GATTCAGGAG AGTAGGTCAG AATATCAATA TTAATAGGAA TTTGGAAGAA 26220
GTCGATTCTT ATTAAAATCA AGAGTTTAGT GATAGACATA CTGAGTTTGG GATACCTGTG 26280
GAGTAGTCCA GAAGTTAATT TAAATATATG GGCTTAGTGT ACAGAAGTGA GCAGGGTGCT 26340
TATATATGAA TAAATATTAT TTTAAGATAT ATTTAAATTT TCCTTAAAAT AATACCTATA 26400
CTTGATATAA AAAGTTAATT GGAAATTAGT GGCTTATGAC AAGCATACCA GCCCACACTC 26460
TTCCCAAACC CACTTTGCTC TTATTCATAG AAGCTGTCAT CTTCAAATCT TCCAGCTGAT 26520
TTCCCTGGCG TGTGCCTTCT TATTTCTGAA TGACACGCTT AGAGTACTAT TTTTTTGACT 26580
TAGCAATTTT AGAAATTTTC TACTCATCTC CTATTATGGT AGATTTCCCC TCCTTCATTC 26640
CTCCTCCAAT ATAATTATAT TTCGTCATAT TAATAATTTG TTTATATATA TTTTTAATAT 26700
AATATGATAA TATTGTATTT ATATTATTAA AACTACACAA ATATTATATA CACACTACTA 26760
ACCCAACCGT GTTATTATGG CCACCACTAC CTTTATTTTT TTCCTTGTGT TAGTGATTGT 26820
CTTTGTTTTA TTTTCTTGGT TTTGAGTATT CCTTTTACTA ATTTTCTTTT TTCCTATTTC 26880
AATCTCTCAT TATTTGTTTA CTCATTTGGA GTGTTCCTTG ACTTTTATCC CCTCTTACCT 26940
AGTGACATTT TAATTTTAGT TATCAAATTT TTAATTTCTA AGAATGCTTC TTGTTCTCTT 27000
CTTGTTTCTT CTTCCCCACC AGCCAAAAAT CTATGATGTT ATAGCAAGGA TCATACATTG 27060
TTTCCCAGTA GGTTAAGAAA CCTTGGTTAA AACCTGTTGT ATCCCAGTAA GTTAAAAGAC 27120
GTTAACGTGT CATCTTCAGT ATGGATGAAA GAATATTTTC TTTCAAAAGC AGTTGGTTGA 27180
GGAAGAGAAT GGGACAAATG CTCTTTTTAA AACACCAATT TTGTGATGAA CTCAAATTGC 27240
AATTTTAACT TTACCATTAT AATGAATGTA TTTGATCCAA AATGTTTAAA ATCTAGGCTG 27300
TTGTCATTTA AATAACAAAT TACCTTACTG GTATCATGAA GAATAAATGT TTGTACTGAT 27360
TTGGAAAGAC ATTCTCATTT AGGGGATGAA ATAGAAAGTC AATGAGGAGA AAGAAAAGCT 27420
TTTATTATTT ATTTTCTTTT AAATATTTTA GTATCATGGT ACAGTCACCA GAAAAAGCTT 27480
ACAGTTCCTC ACAGCCTGTT ATTTCGGCAC AAGAGCAGGA GACTCAGGTA AGGCTTTTGT 27540
AAAAAGGTAA TTAGTTTATG ATAGGATAGT TATGATTCTA TGTATGCTTA AAATTCTGTA 27600
TTTTGCCAGC ATTTTAAAAA TTGTTCTTAA GCTAAGAGTC TGAGTTTATA TTTCAGTTTA 27660
TATTCATTCT AAGGAAAAAT GTGGTATCTG AAGCTCTAAA AATAAAGGAC TAGATCTTTT 27720
AAGTACACTT TAAAAAGTGT TGTTTCTTTG TTTTTTGTTC AGATTGTGTT ATATGGCAAA 27780
TTGGTAGAAG CTAGGCAGAA ACATGCCAAT AAAATGGATG TTCCCCCAGC TATTCTGGCA 27840
ACAAACAAGA TACTGGTGGA TATGGCCAAA ATGAGGTAAA CTATCTTTTG CATGTGTTCT 27900
CATTTATTTC CTTCTAACAA AATAGATTTG GAAAATATAT CTAAGTTGAT AATATGACCA 27960
TAGCTTCCAC TGTCACATCT GGGAGGTGAC TCAGATTCCC CCTGCTGCGA TGCTTATCTC 28020
TTTGCCAAGC TTTAGTACCG TGTTTCTGTA TGAATAAAAA CCAGTTACGT TTTCAGCAAT 28080
CATATTCAAT ATTTATAAAA TCTAACTCAT TATTTACCCA CCCTGCATTT TATCCAAATG 28140
CCGAAACTCC TCTTTTTGGA TTCTTTATTT TTGATTATCT TACCATCACA TTTGTAGTCA 28200
GAGGTTCCTA ATGCTTAAAA CCTCTGATCT GAATTTTCTC TCCTCCAATA TAAAACCCCT 28260
TCGTCTTCCT CTTCTTCTTC TTCATTTTTT TTTTTTTTTT TGTCTGAAGA CTTGTCTCAC 28320
TGTGTTGCCC AGGCTGGAGT GTAGTGGTGC GATCACTGCT CACTGCAGCC TTGACCCCCT 28380
GGACTCAAGC TATCCTCGCA CCTCAGCCTC CCGAGTAGCT GGGACTACAG AACATGCCAC 28440
CATGCTCAGC TAATTTTTGT ATTTTTTGTA GAGACAGGGT TTTGCCATAT TGCCTAGGCT 28500
GGTCTTGAAC TCCTAAGCTC AAGCAATCTT CCCGCCTCAG TCTCCAAAGT TCTGGCACTA 28560
CAGGTGTGAG CCACTGTGCC TGGCCTCTTT TTCTCATTTA AATACTTTTC ATACCTTTTG 28620
TAAAACGGGT TCCTTGTTGC CTGTCTATGC CTTCCTCCTC CTTCTTAATG ACACCACGTT 28680
AATTCTGACT GTTTTCCCTT GGCCTGTTGC AGAAGCCTCT TAACTATTAA CCCTTCATTC 28740
TCTCTCTCTG TTTCATCTGA TATATGAGTA CCAAACTAAA TCTTCCTTTA TCATATCTTA 28800
CTTCTGCTTA AATGTTTTTT TTCTAGCTTA GAATTCAAGG CCCTCTATTT ATGAACTTAA 28860
ACTTACTTTT CCCTCTAAGT TACAGAATTT GAAATGGTTT ATCTTACCTG GATTGTTTAT 28920
CACTTGTTGA AGATCCATTT TCAACTTCCA TATATTTATT TACAGTGTTG CTTCTCCTTG 28980
TAGTTTCCTT GATTCCTCAA AACTCCTTTT AAGAATTCTT GAAGATCTCG CTTTATTACT 29040
ATTTCTCGCT TTATTACTGT AAAGACTATG AGAAGGTCTT TCATGATCTT ATCAGCAAAG 29100
TAATTCCTCT CTCTTGAATT CATAGAGGAC TTTCAGATGA ATTCTAAAGA TGCTTCTGTA 29160
GCACTTACCA CACAATNGCT ATATTTTATT TTTTTGTAAT TAGTGGTAAA CAAGTATTAT 29220
TATATCTTNC TAGATTTTAA ACTCCAAATA AAGATACTAG CTCCTTACCT TTTTGTGTGT 29280
CTCCTGTAGC ACCTAGCACA ATGCCTCATA AACAGGAGGT GATCATTAAA TATTTAGAAG 29340
AAATTATTTC CCAAGAATAG TTGCTTGGTA ATTGTATTTG TCTTTTACTT CCTTTTAAAA 29400
```

*Fig. 5G*

```
AATTGTTTCT GTCACTAAAT TGCATCCAAT AGATGTTACT TGAGTGCAGA ATTTTCTAAT 29460
GACATTACAC AGTGCTACAT CTGACACTAA TTCTTTTGTT AAAAAATAAA TATTCTGGCC 29520
GGGCGCTGTG GCTCACGCTT GTAAATCCCA GGACTTTGGG AGGCCGAGGC GGGCGGATCA 29580
CGAGGTTAGG AGATCGAGGC CATCCTGGCT AACACGGTGA AACCCCGTTT CTACTAAAAA 29640
TACAAAAAAT TAGCCGGGCG TGGTGGCGGG TGCCTGTAGT CCCAGTTACT CTGGCGGCTG 29700
AGGCAGGAGA ATGGCGTGAA CCCGGGAGGC GGAGCTTGCA GTGAGCGGAG ATCGCGCCAC 29760
TGCACTCCAG CCTGGGTGAC AGAGCNNNAC TCCGTCTCAA AAAAAAATAA AAAATAAAAA 29820
TAAATAAATA TTCTAAGACC ATACTTTAAT GGAGGTGTTT TTTGTTTTTT TTTGTTTTTT 29880
TTTTTTTTTT TTGGTGATAG AGTTCTCACT CTGTCACCTA GGCTAGAGTG CAGTGGCGCG 29940
ATNCTCNGGC TCACTGCAAC CTCCGCCTCC TGGGTTCAAG CCATTCTCCT GCCTCAGCCT 30000
CCGGAATAGC TGGGACTACA GGTGCGCGCT GCCACCCCCG GCTAATTTTT TGTATTTTAG 30060
TAGAGATGAG GTTTCACTGT GTTGTCCAGG CTGGTGTTGA ACTCCTGAGC TCAGGCAATC 30120
CACCCGCCCC GGCCTCCCAA ATTGTTGGGA TTACAGGCGT GAGCCACAGT GCCTGGCCCA 30180
GAGGAGATAT TTAATGAAAA ATAATAATCA TTAGATAGGC AGATTTTTAG AAGGAGGGCA 30240
TCGAATGGGT TCTTGGATAT TGGACACAAT AAGAAATATT GAGCTAAAAG TCTGAAGGAA 30300
TTGGCAGATA TACTGTTACA GGTAAACACT TTGTAGAAGA AAATAATGAA TGAGACTTTC 30360
TTTTGAGATT TTCTTAGCCT CTTAGTTGTT CCCAGTTAAA GCCTCATATT TTTCCTTTTC 30420
ATGACAATAA AAATAATAAT AAAATCAGTA ATAAAGTGAA TATATGAGAT GTTAACCTGT 30480
TCCTTTATGA CAATGTCCTG TTTACCAATT AACAGTGTGT TTTTGTGGTG ATGGGGGCAA 30540
GACAAATCTT TAAATGGTGG AAAGCAAAGA AAGAAATTAT AAAACATGAT TAGTTGTATT 30600
ATACGTTGTT TTTGGTTGTT GGAAAAACTA TACATTTATT GAGAGAATCA TTAGGAAGCT 30660
GAACATCAGC TATATTGCTG GAGTGATACT GTTTCAGTGG TTTCTTGACC TTTTTGTTGT 30720
TGTTGTTGTT GTTGTTAAAC ACAGACCAAC TACGGTTGAA AACGTAAAAA GGATTGATGG 30780
TGTTTCTGAA GGCAAAGCTG CCATGTTGGC CCCTCTGTTG GAAGTCATCA AACATTTCTG 30840
CCAAACAAAT AGTGTTCAGG TAAAATACTG TGGTTTGCAG GAGCTCTTAG AGAATAAGCA 30900
TTTTTTGTAA CCATTTCAAA AGTACCCTCC AGAAGCAACA TTTGCTCACT TTATTTGCAT 30960
TTCCATACTG GACACTTAGA AAATGAATTA AAATTGTTTT TACAGTCAAT CNNTGTTGTA 31020
AAAACATGTC AGTTATCTAC TTTTAAAGAT GATACTAAAA AGTAGTTGTC CAGGCTGCTG 31080
ATGTCTTTCT ATTTCATTGG GAGGTTTTGT TTTTAAATTG GAAACATTAT TTTAGGTTGA 31140
TAAATTATAA TTTTACATTC AAATGTGGTA GTTGGAATTT AAAGCTGGAA AGTTATCCTT 31200
GCTATGAGTT GGTCAGGAGC TCAGCCACTT TCTTTTGGTT TAGCATCTTC TCTAATCTCC 31260
CTCCCCTTCC AGTAATGCTG TCTTTTGATA GTAAGTGGAT TTCATATTAT TCTCTTCAGT 31320
TTTAATAGTG TTTCCTTCAT ATCCTTTTAT TATTGCTTGT TCTGCCCTAA GTGACCATTT 31380
CCAGAAATGT CATTTAGGNA TTTTCTCTAA ACTCCACGTA GCAGACTCTA TAATGCATAC 31440
TCTGCAGAAG GTGAGGCAGT GGGAGGTAGA GGGGAGACTA CTAGACTAGG AGTCACGGAA 31500
TCAGGACTTT AGTTCTTCCT TACAGTTGTT CACCTGGTGA ACCTGCACAT GTCCTTTAAT 31560
TTCCTTGGGT CTCCATTTCC TCAGCTATAC AATGGAAATG ACACTTCCTC CCCCACATCC 31620
AGGAAACAAC AGATGACATT AGAAAATAGA AGACATGGGA TAAGTATAAA ATGTTGAAAG 31680
AGTTAAACAC ATTCAAGGCA ATATTAAGGG ATTATTTTTT ACTTCCAAGA AGCTCCTGGA 31740
AGCTTTGGGC AGGCACAGTT GGATCCTACT TTAGAAAAAT CTTTCTCTAA CTATAAGTAG 31800
AAAACCCTTC TGCTTTTTGA ATGTAGCATT TCCCTCTTTT GATATAGAGT ATCTTTGGCA 31860
ACTTTGAATT TTCTTTTTCA TACTCTTATA TAAGACATCA TGTGAAAATT CTTATTTCTT 31920
ACTGAGTTTT TGGAAATGAA ATTATAATGT CTTAATAGTT TGAGAAAGAA TATCATACCT 31980
ACCAGCGGTA ATTGAGTAAG TTCCCTCTCT TTGGACACTT GAAAGTAGTA TCTTCTTTCA 32040
TGAATTAGTG ATATTATTTA ATAATGAATG AGTGATCTCT CCTAACTCCC CTTCAGAAGA 32100
GGAAAATGAA GTAGGGGAAA AGGTAAATTC CCCAAGGGAT AGGTATGAAA CCTTTATGAA 32160
CCTTCTGGAT AGAGAAGATG ACTGCTGATT TCTGTGATTA GAAATTATAC TTGGGTTATT 32220
CTGCAAATTG AAATGAATTA TTTAAAAAAA AACAACTTTA ATGTTTATTA AGCAAGTTTT 32280
GTTATTCATG AGTTTCATTA GCCTTTTATT TTTTTTTTAA ATTTTGAAGT AAAATTTCTT 32340
GCTGTCACAA TACACATTAA AAATTACAAA TATGACACAT ATTAAACACA TTAAGATGGC 32400
CGAATAGGAA AAATATGCTA AAATATTTTT ATATAAATAC ATTTTTTGAG AATTTTGAGA 32460
ATTTCTGGAA CAAAGTAATG ATATAATCCA TAAATGTACA ATTAAAGAGT TTAAGGATAT 32520
CCAAAATACT TGGCAAAGTA ATCTGAAATA ATACTCTTAG GAAGGTAGGG CAAGAATGTG 32580
ATTCTAGTAA GCAAAAATGT AATCAAATCG TATTCTAGTC CCAGCTACTC GGGAGGCTGA 32640
GGCAGGAGAA TGGCGTGAAC CTGGGAGGCG GAGCTTGGAG TAAGCCGAGA TCGTGCCACT 32700
GCACTCCAGC CTGGGCGACA GAGCGAGACT CCATCTCAAA AAAAAAAAAA GACTATATGA 32760
ACTTGTATGG CATAAATATG TACAAATATT ATTTATTTTA AAAAAATTCA GGGGTAGGGA 32820
CAGGGTAGTT AGAAAATATC TAAGGATGTT CATGAAATAA TACTGGCTAT GAATGACAGT 32880
TGATGAAACC GGGTGGTGCC CNATCTTATT CCCTCGACTC GTGTATATGT TTGATATATC 32940
CCACAATAAA CCTTAAAAAA AAAAAGNATG AGTGGTCAAT TATAGGAAGA TATAAATAGA 33000
AAAGGCAATA AGGACAAAAG TTGGCAAAGC TTACCTAAGC ACTCTTCAGA TAAAAAGACA 33060
TTTTTGCTAA CTAGATTTGA ATATTATAGT TTAATTGTCA AGGAAAATGC CTCAACTTAA 33120
TCTTTGTTAA GAGACTACTT AAGGCACTAT CAGAAGTTCC CTCATGGCAA GGTGCAATCC 33180
CTCATGCCTG TAATCCCAGC ACTTTGGGAG GCCAAGGCAG GCAGGTTACC TGAGGCCAGG 33240
AGTTAGAAAA CAACCTGGGA AACATAGTGA GACCCGACCT CTACAAAAAC AATTTCTTAA 33300
AATTAGCCAG GCATGGTGGT GCTAGCCTGT AATCCCAGCT ATTTAGGATG CTTAGGCAGG 33360
AGGATTGCTT GAGCCCGGGG ATTTGAGGCT GCAGTGAGCC ATCATTGTGC CACAATACTC 33420
CAGCCTGAGT GATAGAAAAA AAAAAAAAAA GTGTCTTTGT TATATTCCAA ACTTGTTCTC 33480
AACTTTCAGG TGAGCTGGCT TCCTGTATAA CTCTTGTATA GGACAGAACA TACTGGTTGG 33540
GGCAAGTGAA ACTGTCTAGT TGTATGCCTC ATAAATTAAT GAATTTCCTT TCTAATATAT 33600
```

*Fig. 5H*

ACACTGATAT TTATACACAC ATACACATAA AACCAAGCTC AATAGATGGG TAGTGCAGCT 33660
CTATTCCCCA AAACCCAACT ACCCTGTAAC AAGACACATT AGACTTTTGA GATTGCAAGG 33720
ATGAGGACTG AAATGCTGGC CTAGACCATG GTGTTGCCAT AGTGGGGTGA CCAGTCTGAA 33780
TAGCCAACAA TGCTTCCTCA GTAAATACCC ATTTTGTCTT GGTGGGATTT CTACAAATTG 33840
CAAAATGCAG CTATTATGAA GCTGTAAAAG AGNAAACANG AAACATGTAA CACCTGGGAC 33900
TGTTTTATTA GGCCCACCGT ATGCTCAGAA CATGAAATCT CCACTGCTAG GGTTATTTGA 33960
TTGAAATTAT CTTTTGTGTT GATGTGAGAG TTTAGCTCTG AGATTCTTCC ACATGTAAAA 34020
TGTAATCCCC CAAAGTATTT GGCAAGCACA TTTTATTGCC TTGGGTCAGA TAATTGAAAC 34080
ATTAGGCATC ATATATATAG CATGTAAAAA GTAAAACAGA AACATTTATG TTTCTCACCA 34140
AGCAGTAAAT TAGTACTCAA CTAATAAATT TCTTAAACTC CCTAATAACA GAATATGGAA 34200
ACAAAAAATA AATCTTTCCA AAAGAAGAGC TCATGGACAC ATTTCCTCAT ATATGTATAC 34260
ATAATATAGT AGAACACATG ATAAATAACC TATAAAAATG ATACCAATAT CATTCATCAA 34320
GAGACGAGGC TCTTCTTTAA ATTATTAATT TCATCTGTTA CAGGTTTTAT TATGACTGTA 34380
GTATGCTGTT TTCATCTACC TTTTATGTGT AGTTAAAAAA ATAGTTTTCT ATCTCTTTAC 34440
CTTTATTTCA GCCTTTAAAA AGATTCCATT ATTTTTTCAT TAATCTTGTT TTTCAGTTTT 34500
TCCCATTTTT TCTTTTAAAC ATTTCTTAAG GAACCATATT TAAGATTTTA TAGAATACTT 34560
AGATTTCTAG TTGGGATGTA TCATTTAAAA TTAGATATGT AGAGAGAGTG TTATGATATA 34620
TTTCCTTACG ATATATTAGT GGTTATAGTA CCTAAATTTG AATAGTGATT CTGTTCATTC 34680
ATTCATTCAT TCATTCAATA TTCACTTCCA GGAGATTGGG GACTTATTTA AAGACAGAGT 34740
AGTTCACATT ATAGTTCCTT TTTTTAGTCC TTCTTATTCG TTAAAGAAAA GACTAGGAAA 34800
TGTTTGTTAT TACAAATATT TTATTAAAAT TTTGTGTGCT CTAGCATTAT TTTACCTTTT 34860
AAAATCAATA TGTTAAAAAT CCAACTTCTT TTTGAGCTCC CCATAAAAAG GGAATTATTT 34920
GTTGCTTATG GGTTTAACTT GTGTTATTTT TTTCTTAATG GCTAATTATC ATACATATAT 34980
TCTATTATTG TATTGATATT ACTGATCATT TGTGCTACAT TAAAAATTCT GTAGACAGAC 35040
CTCTTTTCAA GTACAAAACC TCAAGAAGAA CAGAAGACGA GTCTGGTAGC AAAAAATAAA 35100
ATATGCACAC TTTCACAGTC TATGGCCATC ACATACTCTT TATTCCAAGA AAAGAAGATG 35160
CCTTTGGTAA GTGTGACTTT CATGTTACAG GGAATTTTTT TAGTTTACTT AAACTTGTGT 35220
TTTATCAGCT TTTTAGTATT AAAGTTCTGA CTTGGGATCA ATTTCCTCCA ACCCTACAAT 35280
AAATCTCAGT TTATCTTTAA TTTTAAAAGA GAATGTTGTT TTCTTTTTCT GTTAAGCCTC 35340
CCTGTTAAGT AATAGCAGCA AGTTTAGTTT GGCCATGAAT ATCTTCTAGA GATTGTATCG 35400
GGGTACTGAT AAACACATTT ATAGCTCAGG GATACTGCAT CAGCCATATT TTAAAATGGG 35460
ACTAACAGTT TAAAAACTAT AAATATTCAC AGTGTTAAGA AACAATCTCA AGATGCATTA 35520
AGAAAAAGGA AGGTGCAAAA CAGAAAAACA AACGTAAACG TGTGTGCATA TGCATGCTTA 35580
TATAGTCACA TATTCTTGTA TGTGTACAAA AAATACACAC TGGATCTCTG CAAGCATAGC 35640
CAAGCAACTG GAAATATGTT TTTAAAAACT TGCTTTTCAT TCTATCTCTT CTAGTACTGT 35700
TTTGATGCTC TTTGAAAACA ATCTAATTGC TGTAACAAAT GACCATACGT AGGCCGGGTG 35760
TGGTGGCTCA TGCCTGTAAT CCCAGCACTT CGGGAGGCTG AGGCAGGCAG ATCATTTGAG 35820
GCCAGGGATT TGAGACCAGT TGGACAACAT AGGGAGACCC TGTCTTTACT AAAAATACAA 35880
AAATTAGCTG GGCGTAGTGA CGCATGCCTG TAATCCCAGA TACTTGGGAG GCGGAGACAT 35940
GGGACTTGCA TGAACCCAGG AGGCAGAGGT TGCAGTGAGC TGAGATTGCG ACACTGCATT 36000
CCAACCTGGG CGACCGAGCA AGACGCGGTC TCCAAAAAAA AAAAAAAAAA AGACCATATG 36060
TAATGTTTCT TCATTGTTCT AAGATAAATC TTTAAGGCTG TTGAGGTTTT TTGTATACAA 36120
AATGGAGAGT AAGTTTTAAT GGGATGGGAC AAAATGAGGC TTACAGTTGA GTTTAATTTG 36180
AGTTCACATC CTGTTGACAT TAAGTTGATT TGGAACAAGT GATATGGTCC AATGCCTGCT 36240
TTTCTATTGT CTGTGGTTCC ATCCACTAGT GCCTGTGTTA CACACCTCTT GTTCAGGTTT 36300
TATCATTTAA AATAAATAAG AATAAACAGT CCATAGCTTA TCTTACTTAC TGAATAAATG 36360
CTCTGATTTG ACAGTCATGT TTCTTAAAGT TCCTTACAAA GGCCATTGCC CAAGAAACCA 36420
AATAATTCCA TTATACTATT TTTGAAATAG AACACATAAT AAATGGGAAT TTTAAGTTCA 36480
GTTTCTTATG TAAACAATAA CTTCTATGTA CATGTTAAAT ATGCCTGTAT ATACCTAATT 36540
TGACCATGTA TGTATAGTAG AAATGAAAAC AGTTACTAAG AAAATTTGTT ATTGGCTCCA 36600
AATTTTCTGA ATTAAGTGTA TTNCTAATGC TCAGCCATAA TATGGGGTTT CATGTGTTAG 36660
TTTATGTATT CATGGTTAAA AATGTGAAGA CTGTTATATC TTCATTTGTG TCTTTTGGTA 36720
TTATTTGGTT GTATTTTATT GTGTGATATG GTGGTATAAT TATCCTTACC TCCCAGGAGT 36780
TTGAGAGGGT CTTGCCAGTT AACCGCAGAA TTAAACATGC CTAGGACTAA TTAATCAGGA 36840
GCAATACTAC AATTAATTGG AGGTAATTTG AAACCTGGTT TCAAATAACC CTGATATTAT 36900
GCACACATGG TGCACACTTT TCTAGTAGAC ATTTAATGAA AGTAATTTAA AACCTACCTT 36960
TGAAGGATGA AAAACATTGC CTTAAATGCT CTATTCTGTG AAAGTATCAA CATTTATGCA 37020
AATACAGTCT AAATTCAGAC TTTGAAAATG TATTGAAAGA GAGGATCATG AAATAAGTTA 37080
GAGCTGAGTG ACAAAGCTTT CTGAGTGTTT AAAAGAATGT TTTACCTAAT AAATATCTGA 37140
AATGTATTTG GAGCCACATT TGTTTAAAGA ACTGTATAAA TATGTAGCAC TGTTCATGTG 37200
AAGTTCAATA GTAGGAAAAT GCTGACAGCC CTTGTGGAAC TGTGGTTATT ATTATTTTAT 37260
GAATAGAGCC AATTTCAAAC ACCTATTAGA GTCTTCTCAG GAACATTTTA TAGAATGCAT 37320
CTGGAGCCTT ATGTTATCTC TAAGCATTTT AGGATTTGTC TTCTTGGAAA TTCATGTAAC 37380
CAAACCACCA TGTGTTATTT CAAGTGTATA TAGTATTGGG TTACAGTTTA CTATGTTTTC 37440
AGAAGGTTGT GACAACTATT AGACTTACAG AGAATGACTT CTCTGCCACT AACGGCTTTC 37500
TAAAGTGAAT AGAGAGGGGC GAGGATTGAA TTCTTCGGTA AAGCTGGGTG ATTTTGTTTT 37560
ATTCAATACA GTATAATAAG TATAAAAAGT AGAACCTATA GAGAGCTATA ATGGGGGTAG 37620
TTTTAAAGAA ATTCTGAAAA TGAAAAACTT AAGTAAAGGT TTAGTTCATT GTTTATTTCA 37680
CACTGAGCAT TTACTACCTG AATGTTTTGG ACATTTTATT TCCATGACTG GAGTGGACAC 37740
TTTTACAACT CACTGGGTTC TTTGCTGATC TTTCTCTAGA AGAGCATAGC TGAGAGCAGG 37800

*Fig. 5I*

ATTCTGCCTC TCATGACAAT TGGCATGCAC TTATCCCAAG CGGTGAAAGC TGGCTGCCCC 37860
CTTGATTTGG AGCGAGCAGG CCTGACTCCA GAGGTTCAGA AGATTATTGC TGATGTTATC 37920
CGAAACCCTC CCGTCAACTC AGGTGAGAGG CATGGCCTAG CTCTGCACCC TTAATGACTT 37980
GATGAAGTAA ACAAGCAATC CACTATATTT TTCACTGTTA ACAGCATTAA TCCTTTATGC 38040
TATTATGAAA ACCTTACTTT TGTGATTCTT TTTCTTGTTT TAGGAAAACA ATCTTTCTTC 38100
CCATTATCAC TCAGAGGAAA GTATACTGAG AAATTTTTTT GTTTTGTTTT GTTTTTTGAG 38160
ACAGAGTCTT GCTCTCTTGT CTAGGCTGGA GTGCAGTGGC GTGATCTTGG CTCGCTGCAA 38220
CCTCTATCTC CCAGGTTCAA GTGATTCTCT TGCCTCAGCT TCCTGAGTAG CTGGGACTAC 38280
AGGCGTGTGC CACCATGCCC AGCTACTTTT TGTATTTTTT GATAGAGACA GGGTTTTCCA 38340
TGTTGGCTAG GCAGGTCTCG AACTCCTGAC CTCTGATGAT CCGCCCACCT CAGCCTCCCA 38400
AAGTGCTGCG ATTACAGGTG TGAGCCATGG CACCTGGCCA ATACACTGAG AAATTTTTAT 38460
TTTCCTTTTC AGCTTAAGGT TACAACTTCC CCACCATCCA AAACGTGCAC TTTCATTTTT 38520
TTTCTAATTT CTATCTCATC ACTTGCAAAA ACCATATTTT TCTCCACATT CATTCCCAGT 38580
AGCTTCCTGA CTCCTAGTTC TTCCCTAAAT CCTTCTGAGT CCTTGTCATT GGTTTCGCTT 38640
GAGTAGCCTT TCTAATCAAC ACAGTCATTG GTATCAGTTA CTGTGACATG GAAGGGACAG 38700
ACCAAGTTCT GTGGGCCGCT ACGTAGAAGG ATTTCCTGTC ACTTTGCTGC AGAACCTCAG 38760
CTCGCGGAGA GCAAGCCCCT TTGCTTGCCC TGTAGAAATA TTTTAAATTA TTATCCTTTT 38820
TTTTTTNAAC AGAAGTAAAT AGGAGATACG TTAGAGGATT TTCTCTCCTA GATGTGTAAA 38880
TACAAACTTG GGGTCTTATA ACTCAATAAA TCTGATAAAT TTCTTTTGAC TGTTAGGATA 38940
GAGCAGTGGC CATACCAATA GCCTCATCTC CAAAGCTGCA GTGAAGATAC TTTTTACTAC 39000
CTTAAAGTCT TTCCCATTTG TGAACAACTT GTGAACAATT CCCCCCAAGA ATTTGGAAGA 39060
TCACTCTCTG AAAGCACAGT CAATACTGTA CTTAAATGGA TCTGAGCAAA AATAAGTCAC 39120
TTAGAAGACA GGATTATTTC TAGACTTGAG TGTGACTTGA CTGAAGGTCT AAAGAACAAA 39180
CAGCTCCTTC ACTTCCATTG ATCACGGTGG AAGCACAGGG AAAGGACAGA CACGGAGGCA 39240
AGTTGGAGTA GTGCTCATCT AAGTTCCAGG GATGCGGGGG AGTGGCCAGG GGACTTCAGG 39300
TATAGTAAAT AAATAACCTA TTTATAAGTT ATGTCAATGT CATGTTTGAA ATAGAAAACC 39360
AAATACTGCA TGTTCTTACT TACAAGCAGG AGCTAAAGTT GGTGCATATG GATATAAAAA 39420
TGAGAACAGG CCGGGCGTGG TGGCTTGTGT CTGTAATCCC AGCACTTTGG GAGACCTAGA 39480
TGGAAGGATT GCTTGAGCTC AGGAGTTCAA GACCAGCCTG AGCAACATAG TGTGACCCCC 39540
ATCTCTACAA AAAATAAGAA AATTAGCCAG ACGTGGTGGC ATATACCTAT AGTCTCAGCT 39600
ACTTGGGAGT CTGAGTCAGG AGGAGTGCTT GAGCTCAGGA GTTTGGGGTT ATAATAAGCT 39660
GTGATCATGC CACTGTGCTC CAGCCTGAGT GACACCCAGA GTGAGAACCT GTCTCAAAAG 39720
GAGAAAAAAA AAAAAGTAAC AGTAGACGCT GGGAACTACT GAGGGGAGGG AAGGAACAAT 39780
GGTTGAAAAG GTGGGAAGGG ACAGTGGTTG AAAAACTACG TGTTGGGTAC TATGCTCACT 39840
ATCTGGGTGA TGGGATCAAT TGTACCTCAA ACCTCAGCAT CCTGCAATAT ACTAATGTTA 39900
CAAACCTGCC CATGTACTAC CTGAATCTAA AGTAAAAGTT ATAATTTAAA AAAATTATAA 39960
TAAAATCAGA AAATAAAGGT CTGAGATGGA AAATTAAAAG ACCAAAGCCA CCCATAAGCA 40020
CAATAAATCC CTCCCCCCAA AAAATTATAT CTATTAAAAA AAGGTGTTGC GCCAGGCACT 40080
GTGGCTCATG CCTATTGCCT ATAATCCTAG CACTTTGGGA GGCCAAGACG GGCAGATGAC 40140
TTGACTTGAG GTCAGGAGTT CAAGACCAGC CTGGCCAACA TGGTGAAACC CTGTCTCTAC 40200
TGAAAATACA AAAATTAGCC AGCAGTGGTG GCATGCGCCT GTAATCCCAG CTACTCAGGA 40260
GACTGAGGCA GGAGAATCGC TTGAACTGGG GAGGCGGAGG TTGCAGTGAG CCGAGATCAT 40320
GCCACTGCAC TTCAGCCTGG GTGACAGAGT GAGACTCTGT CTCAAAAAAA AAAAAAAAAA 40380
AAGACCTTGT ACCCTGACAA GTTTTAGTTT GTGCAGGAAT GACACAATCT AGAATGACTC 40440
AAGATTGGAA AAATCTTTAA ATGTTAATTA CACAATAAGG GTAAAAGGAG AAAAATTACC 40500
TAATGTCATC TGAGCAACAA GAAGAAGAAA TGAAAGGCAT TAAAAATTGG GAAAAATTTA 40560
TATTTGACAG TATCTTAACA ACGAATTCTG CTTCTATATC ACTTCCTAGC TTTCTGATGA 40620
TAACTTCCCG TGCAGATCTG TATGTAAGGA ATGGACGTAG TAGTCATGCT AATCTGAGTA 40680
TTTATCTGTG TGATACTTAC GAATTAACGA TGTAAGTTAA TAAGTTAGCA TTTCGTGAAC 40740
CTGGTTAATA CCATTTGCTA AGGTTAAATT AGCCAAATCC TGAAGTAAGC TGTAAAACAT 40800
CCAAGGTAGG GTAGAGAGGC ATCTTATGAG AAAGCTGGCC AACTCTCCTG GTCACCTTCT 40860
AATCTTCCTA ACTTCAGAAA TCAAGGCAGA GAGAGGAAAA TAGTAATTAC TTTGTAGGAT 40920
TAGATTTATG GTTGTCGAAA CCTTTGTTTC TCCAGTGCAG AATGAGATAG CGTTTTAGGG 40980
AAAGCCAAAG ACTCAGATGT CTTCTTCATG CTCATCGTGT GGAATTTTTC TTCCTTTAGA 41040
AATGTATTGT CTCTCAGGGC TTAAAGCAAT TTGCATCTTT CGATGAGACA TTGAGTAATA 41100
GGCAATATTC TCTGAAATAA TTTGTGCAGG CTGGGCACAG TGGCTCACAC CTGTAATCCC 41160
AGCACTTTGG GAGGCCGAGG CGGGCAGGTC ACTGAGGTCA GGTGTTGGAG ACGAGCCTGA 41220
CCAACATGGT GAAACCCCGT CTCTACTAAA AATACCAAAA TTAGCTGGGC TTGGTGGCAC 41280
ACACCTGTAA TCCCAGCTAC TTGGGAGGCT GAGGCAGGAG AATTGCTTGA ACCCCCATGG 41340
AAGGTGGAGG TTGTGGTGAG CCAAGATTGT GTCATTGTAC TACAGTCTGG ACAACAGAGT 41400
GAGACTCTGT CTCAAAAAAA AAAAAATAGA ATTTGTGCAG TTCCCCCCAC CCCCTTTTTT 41460
TTTTCTGTTG GCATTTTTGC TATCATTTAG CTGCCTTCTT TATATCCTGA AACTTACAGG 41520
TGGTGTTGGT CTAGTCAGTA AGAGCAAAGG CTTTGGGAAT AGATAGATCT GTATTTAGAC 41580
CTTGGCTCTA GCATCTCATT GTTATGTGAC CTCCATCAAG TGACCTAATT TCCCTAATAT 41640
TCAATTTCCT CATCTCTAAG ACAGGGAGTT AATATTGCCT CTCTTATAGA ATTGTGAGAA 41700
ATATAGTCAT GTGTCGCTTG ATGATGGGGA TGAATTCTGA GAAATGTGTT GTTGGGCGAT 41760
TTCATTTTGT GGGAACCTCA CAGGGTGGAC TTAAACAAAC CTAGATGGTA TGGCCTACTA 41820
CACACCTAGG CTGTACGGTA TAGCTCCTGT CTTCAAACCT GTACAGCATG TGACTTTACT 41880
GAACACTGTA GGCAATTATA ACACAGTGGT ATTTGTATAT ATAAACATAG TGAAACATAG 41940
AAAAGGCCCA GTAGAAATAC AGTGTAAAAG NATTTTTTAA AAAAGCTGGG CATGGTGGCT 42000

*Fig. 5J*

CACGCCTGTA ATCCCAGCAC TTTGGGAGGC CGAGGCAGGC AGATCACTTG AGGTCAGGAG 42060
TTCAAGACCA GCCTGGCCAA CATGATGAAA CTCCGTTTCT ACTAAAAGTA CAAAAATTAG 42120
CTGGGCGTGG TGTTGGGTGC CTGTAATCCC AGCTATTCAG GAGGCTGAGG CAGGAGAATT 42180
GCTTGAACCC AGGAGGTGGA GGTTGCAGTG AGTCAAGATT GTGCCACTGC ACTTCAGCCT 42240
GGGAGACAGA GCGAGACTCT GTCTCNAAAA AAAAAAAAAA AAAAAAGAGA TAAAAAGGTA 42300
CATCTGTACA GGGCACTTAC CACGAATGGA GCTTGCACCC TGGGAGTTGC TCTGGGTAAG 42360
TCAGTGAGTG AGCGGTGAGT GAATGTGAAG ACCTAGGACT GTGCACTGCT GTAGACTTTA 42420
TAAACCCTGT GCACTTAGGC CACACTCACC CCTGTGATAC GAGTCTACCT ACTGTATAAC 42480
GTACCTGCAT ATGTACCCTT GAAACTAAAA CAAAAGTTAA AAAATTTATC TTCTTTTGCC 42540
AATAATAAAT TAACCTTAGC TTACTGTAAT GATTTTTCTT TATGAATTAA AATCTTTTTA 42600
CTCTTTTGTA ATAACACTTG GCTTAAAACA CAAACATATT GTACAGCTAT ACAAATATAT 42660
TTTCTTTATA TCCTTCTTCT CTAAGATTTT TTCTGTTTTT GATTTTGTTA AATTTGTTTT 42720
TACTTTTTAC ATTTTTTTTG TTAAAAACCA AGACAAAAAC CCACACATCA GCCTAGGCCT 42780
ACATGGGCTC AGGATCATCA GTCTCACTAT CTTCCACCTC CACATCTTGT CCCACCAGGT 42840
CTTCAGGGGC AGTCATATGC ATGGGGCTGT CATCTCCTGT GATAACAATG CCTTCTTCTG 42900
GACACCTCCA GAAGGGCCTG CGTGTTTTAC AGTGAACTTC TAAAAAATAA TAAAATGTAT 42960
AGTATAGCAA ACACATAAAC ATAGTAACAT AGTCATTTAT TATCATTTTC AAGTATTATA 43020
TACTGTACAT AATTGTACAT GCTAGACTTT TACACAGCTG GCAGCAAGGT GAGTTTGTTT 43080
ACACCATTAC CACCACAAAC ACATGGGTGA TGCTTTGCAT TGTGATGTTA CGATGGCATG 43140
ATGTCACTAG GTGGTAGGAA CTTTTCAGCT CCATGATAAT CTAATGGATA CTTGTTCCTG 43200
TTGGCTGCCC GTCGTTGACT GCAACATCAT TATGTGGTGC ATGACTGTAA ATTAGATACT 43260
GTTCAGAAAG CTTTGGCACA CTGGTAATAG CAAATGGTGG TGGCAAATAT GATGATGATG 43320
ATGATGATGA TTGAAGACAT AGATGGTAAA ATTTTATGGT GTCTTAAAAG TACCCTCTAA 43380
ATATGATTAT TTTTATAGTC TGTCCTTTTG AATAGGCACT TAAGAATGTA TGAACTTAAT 43440
AAGTATATAA GAAAGAATGT TCCCCAAAAT ATATCTTACA GAGGCATACA ATTTAAGAAT 43500
TCAAACAGGT TGTAATGGGG TGTGTGTGTG TGTGCACACG CGCACGCATG CGTGCTCATT 43560
CACACTAAAG AATTCTTGGG CATATGTTCC TGAATGTCCT AAATGGACAT TCTAACATCA 43620
CTTCATTATG GGCAGAGGGA AATGGTAAAG AAAAATTTCA TATTATATTA TTCAGCCACA 43680
TATTGACAGC ATCTGTTTTA TTTGCCTATG GTAAAGAATT GAAGCACTGT TAATTTGCTT 43740
TTTAAATCAT GTAGGCACAA AGTTATCGAA CTTTAGATTT AGAAATGAAA CTGGAAATCA 43800
TTACACTTTC CCTTTCCTAT CCCCACCCTG TTTTGGAGAG AAAGAGTGTG AGGCTTAGAG 43860
AGTTATAAAA CTGTTTTAAT ACCATGTCTA AGATTAATAA CTGAACAAGT TTCTCTTTTT 43920
ACTCGTGTTA AAGTTGTACT GCCAATTAAC TTAAAAGAAA GAAATATGCA ATTTCTAATC 43980
CTGATATAGG ATATGGGTAT ATAAACTCTA ACTTGATGAG TGAAACAAAT TAACTTATTT 44040
ATAATCAGTT TCATATCTTT ATTTATTGAG TGTCTTTAAA TACCCCTTAC CTTTAAAGTA 44100
AGAAATATTA AAATCAAGCA GAATATAATA ATGAAAAATT CTTAAGATAT ACTTACTAAA 44160
AACTTATCGT TCGGTTAATA CACTGTATGT AGGTTGTACA TACAATATGA AAAAGTATAT 44220
TTTTGTAGCC TACTTTTAAA TCCAGAATAG AGGAGGTTAA GAAGGTTGTG ATAACCATGA 44280
GCTCTTTTTT TTTTTTTTTT GAGACAAGGT CTTACTCTGT TTCCCAGGCT GGAGTGCCGT 44340
GGCACAATCA TAGCTTACTG CAGCCTTGAA CTCTTGGGCT CAAGCAAGCC TTCCACTTCA 44400
GCCTTCCAAG TAGCTGGGAC CACACCTGGC TAATTTTTAA GTATTTTTGT AGAGATGAGT 44460
TCTCACTACA TTGCCCAGGC TAGTCTTGAA CCCCTAGCCT TAAGCGATCC TCCCACCTCA 44520
GCCTGCCTAA GTGCTGGGAT TACAGGTGTG AGCCACTGAG CCCAGCCCTC TTTTATTTCT 44580
TTTGATAGTA CACTCATAAT CATTAAACTA TCATTTCTGG ATGTGAGATT GTGCTTTTGG 44640
ATTCTTATTT TTTCTTTATA AAATACTTTT TGTTCTCTTA CTGGAGAAAA CATTGTTGGA 44700
TTATAAATGA TATAACAAGG AATGAGGATA TACATACTAT AATAACGATT CAGATATGTT 44760
ATTTTCATAT TTTATTTAAC TGTAGCCATG CCACAATAAT TTAGAGTTTT AAAGAACAAG 44820
TTTGATTGAA ATCTAAACTT TGTACAATCC TGAATTGAGA AGTTTCCTGT ATTTTATTAT 44880
GACACAATAT TTACCTAAAA ATAGGGTAAT TATGAATTGA GAAAACATAG CTATTAATTT 44940
CATACTCTTA TTTGTTAAGT AGATTTTGTC TGGAAAACTG TTCATATTTA AAGGAGCTTT 45000
GTACCTTTGT ATTCTTTTTG TTTTTCCTTG TTTATATAAT TTTAAACTCT GTTTATGGAT 45060
TTGGGATTCT AACTATGCTA AATAATAAAT TAAGGCATTG AATGAAGTAC CTAGACAGTA 45120
TTTTGATTAA TTTTATTCCC CCATTCTTAA TGTGCATGTA ACTGGAAAAT TAAGAGTGGC 45180
TTCCAAGGGA TCTACTACAA AAGTAAGGTT AATATGATCT CTTTTAAAAC ACTGAAGGCG 45240
TGTAGCCAGT GTTGTCATTA ATTCTGCAGT AGATATTTTC AGCACTTATT TACATGGGAA 45300
GTTAGAGCAG AGTAAGATGC ACCTGTAAAG CTAAATGCCA CTTATTTGCA TATATATAAA 45360
ACGCAGGATG AATTTACCAT AGAAATATAA AGGGTACTTA TAGAAATGTA TTAGAAAAAT 45420
ATATGAATTT TTAACTTATA TCTAGAAGTT AACTTTATAC ATTTAACTTT AAATCATTAA 45480
TAGTGGTTTA ACACCATAAG CGGATGTTTA TGCATCATCA TTTTATGAAC AAAAGACATT 45540
CTAATTTTAG AAATAAAGTG ATTCAAAAGA GAATAAAATA TCTTACTTTT TCTTTTAAAA 45600
TTAATTTGTT TAGCGCATTA CATGATAATA GCTCAAGCTT GTGTGATTTT TCCCTAAAAA 45660
ATTGGTTTAT AAATATTACA TTTATAGTAT GAAGAAATTA ATCATACATA GTTTATTTAT 45720
CTAATTTCTA AATACCCATG GAAGAAAATG AATTTAATGG AATGTAGTTG TGTATTACTT 45780
GGTTTCGAGT GTGGGAAAAT TTATATGGTC TTTCTAAAAC AGCACTGTCA GTAGAAATAC 45840
AATGTGAGCT ACATATGCAA TTTTAAATTT TCTAGTAGCC ACATTTTAAA AAGTAAATGG 45900
ATGCAATTTA TTTTGATAAT ATAATTTAAT TAGTCTACTA TATTTAAAAT TTTATCATTT 45960
CAACATGTAA TCAATATGAA AATTATTAAT GAGATATTTT ACATACTTTT TTCTGTAATA 46020
AGCCTTTGTA ATCAGGTATG TACTTTATAT ATACAACAAA TCTTCTGATG CTAAATTTTA 46080
ACTGGAAATA CTTGATCTGT GTTTAGCTTT TGTAAAATTT ACTGTTGAAC AACGTGGACT 46140
AATGTGCCTA AGTGGTTCCA AACATATTTT AAAATTTGAA GACAAATAAA AGGGAACTCA 46200

*Fig. 5K*

AAGTAAATTG GGATACATAC ATACAACAGA ATACTGAGCC ATTAAAAAAT GATGAAATAG 46260
TAAAATTGGG GGAATTTTGA TGATACTAGG ATGATATAAT GACCAAGAGA CAAATACAAT 46320
TTTAGTTTGG TTGAGAGATG TGATCATCAC GTTGCTGATT TTACTATGTA TAGAGGTTAT 46380
CTTTTCCTTT CTAAGATTTT GAAACTTTAA TTAGTTAACC CACTTACCTA GTTTCTATTA 46440
GCTGTGTAAC TTTCTCTTCC TGTTTTTTGT TTTGTTTTGT TTTGTTTTTT GCTTTTTAAC 46500
TGCAGTATTT TGAGGAGTCT TGGAGTAGCA AGCTAATCTT TGGAAGAAAG GAAAATATAA 46560
ACCTGAAAAC TAATAATTTA AAGAACGTCT TTTCAGGTTG TCATTTGAAA AATANCTTGA 46620
TTTCTGATCN ACNTGATTTG AATTGAGTGT CAAATATTTG ATATGTTTTG TAAATTAGGT 46680
GAAGATGAGT GAGTAGGTTC TAAACTGCTT GGGTTTACCG CACTCTGGAG CATTGCAGGA 46740
GAATGTGATG TTGGAAGGAA GTGCTGAAAC ATAATTATTG GCTTGCCTAT AGGAGGGTGC 46800
TACATAATTT TAGAAGGTGT CAAGAAATTG ACACAGTCTG AATTAGTTCT GTTGAGTTGC 46860
AAAAAATGTA AAGTTTCTTG ATTCTGAAAA TAAGAAATAT GTTCCCAGAA ATCTCATCTA 46920
GTTAATGTGC TTTTAAAATC ATTGATGTCT CTTGTTATTA CAATAATAGC CATTGAAAGA 46980
ATCTTTTTTA TTAGAATGTT ATTTACAGGT ACGATTAGCT TCTATTTAAA TAAATTATTT 47040
TTATACTTGA TCTTAGGCAA AAGGCCAACA AGTGATCAGA ATAAATTATT TTAAGAGNAA 47100
AACTAATTAT AATTGATATT TGGAATTGGA AGCACAATTT CCTTTAGAAC AATTCCACGA 47160
ATGGTTGTTT TGATTCTCAA GGCAGCCCAC AAAAGACAGT TTGAAACACA ATTTATGCAG 47220
TGTCAATAGT ACTGACCTGA CTTTGGATCT TGGAGGCAGG GGCTTCAGGT GATACCCGAG 47280
TGGAGTTTTT ACTCCATTTC CATTCCGTAA GGCTATAGGC ATTTGAAAGA GGAAACTTTT 47340
CTTTGGCAAC CTTCCACCTT CCTTTCTACA GAATATTTCA GTATTTCTAG CTCATAGGTT 47400
TTCTAAAATA TTCTCTGTAA TTTATTTTGA AATGGAGTTT TTTTATCGTT TACAGATATG 47460
AGTAAAATTA GCCTAATCAG AATGTTAGTT CCTGAAAACA TTGACACGTA CCTTATCCAC 47520
ATGGCAATTG AGATCCTTAA ACATGGTCCT GACAGCGGAC TTCAACCTTC ATGTGATGTC 47580
AACAAAAGGA GATGTTTTCC CGGTTCTGAA GAGATCTGTT CAAGTTCTAA GAGAAGCAAG 47640
GAAGAAGTAG GCATCAATAC TGAGGTATTA ATTATATATA GAATTTTCAT AAAGTGTCAG 47700
TTTGTTCAAT TTGCATATCC TAGTACTAGA ATGCTGTATT TTTTTGAACT GTTATGAATT 47760
CTGATATGAT TACTTTCTCT ATGTGCTACA TTTCCTTTGC TTTTCATAAA TATGATCTGA 47820
GAAAAGTGAT TAAAAAAAAG ACAGTAAAAG GGAGGTTTAG TCCATCTGTT TAGCTTATTA 47880
TGTAGAATGT CAGCTTAAAT TTTACCTGTA CCTCATATTG ACCGTATAGC CTGGAAAATC 47940
TTTCGGAGGT ATAGTTAATG GATTTAAGCA TATGGCAGTT TATGTAGTTA ATGAAAGTGA 48000
AAACAAATTG TATTATAAAT ACCTCCCAAA CTGGTTTATT ATCATTCTAT CATTCTTCAT 48060
GCTCTGTTAG TATGATATTG AATATCTGAG GTACCAGGAT TATTGTTGCT TGTGGCTCTG 48120
AGCATTTCGT AGTGCTTTTG CATGATGAGA GAAAGATTAC AAATTTAGTA TTATGTTAGA 48180
TGGTACGTTT TATTAAAATC AAATGCTTCA AAAATAATTG CTCTGTGTAT GGCATGAGAT 48240
AAATAGCAAT CAGATATATT GTTTAATAAT ATGACTCTAT TAAATGATGG CATAAATTTG 48300
AAAATTTGAC CTTCGGTATC TTCCGGGTCT AAAATTATAT GACTCCATTA TAAATATTTT 48360
GGAAATGATT AACTAAAAAA TTGTTTCAAT TCTTAGTTGG TAAATTCAAT GTGGTAGTAG 48420
GTGGTGGTGA TTATTTTGTA TTAGAGAATT AGGAATTACA CTTAGTTCTA AGGTAATCTT 48480
TATAGGATGT CCAGCAATTA AACCCCTACT TTTTTGAATT GCTTAAAAAT AAGGGAACTG 48540
ATCTTTTTAA ATTCTGTACT TGAGTTACGT CTGTATATAT AGTCATGTCC TAGATAATCT 48600
AATGGAACTT AATTAGTTGG AAATCTTTAT ATTGTTTATA ACTGAACTAG CTATAAGAGG 48660
AACATTAAAG AAAACATATT TTGAGTGGAG GTAATGAAAT TTAGCTTCTA ATGCTCAGCC 48720
TTTTATTTCT GTAATCTATA CCAGATACCT AAGACCCTCT TATTGTTTCC CAGCTTCAAC 48780
CTGTCAGTAT AGAAAACGGT GTAACTTACT ATTTTTTCTC AATATTGAAG CACATTTGTA 48840
GTGAAATATT ATTTTAACTA TATATTGCCA TTTTTGCTTT TTCCCTATTT CAGTAACATT 48900
TTTCGCTATT TCAGTAACAT TACATGTCAA CAAGAGAATG GTGGGTATTT TGGGGGGGGT 48960
TGGGTGGGAA GAAATTTTAC TAAGCTTGCT AGATTCTAAA AGGTATACCT TATTTGGCCC 49020
CTTTTCCCCA TTTAGGGGAA CAAGGGTGTT GGGGCTGGGA AGTAGATAAG AGGTGAAGTA 49080
AGTCATCCAA AGCATATGTC TTCATTAGCC TCCCTGTATG AAAAGCTGAT TTCTGTAGAG 49140
TGTTGGAGGC CTACTTTCAG AATCTGTCAT ATGTTAACAT TCATCTTCTC TACTGACCTG 49200
ATTTATATCC CTTAGTCTAT TTCATTTTAT AATTATGACA AAGGATAAAG TCATTAGAAC 49260
AAATTCTTTT TATTAGTTGA CGTATTGTTG TGTTTATATC TCTTGTGTTT GTTATTAAGA 49320
TGGAAGCTCA ATCATGTCCT TGTTTAACAG AAAGGTGATG TCTTGGCATT GATAATTCTG 49380
ATTCAATATC CATAGGTACA TGGTGGATTC TTTAAATATT TAGTATTCTT TTATTTCTGG 49440
AAAGTTTTCT TAAATGATAG TTTTTTTAAA ATTTCATTTC TATAAAGTTT TCTTAAATCA 49500
TACTTTTTAG TGTTTTATTC CATTACTTCA TATTTCTTCT TCAGGAACTC CTGCTATACA 49560
TGTATGTTGG ATCTTCATTA CCCAGCTTCA ATATTTTTCA CTTTTCATGC ATTCTTTTTA 49620
TTTCTTCATT TCTCTTTAAA TTTTTTTCTT CCTTTTCACC TTCTATTTCT CTTTTAACAT 49680
AATTGTATTT ATTTCTGTAT TCCACATAGC TTAGTATTCA CTTATTTTAA AATTATTTTA 49740
AAACGTTTTT TAGATTTAAA AATTCTTTTT TTATTTATAT ATACATATTT TATTTTTACC 49800
AAAGGAGCAA CACTATTAAC TGAAGACTTC TATAATTTTT TTCTTTTATT TCTGATTCTT 49860
TCTTCGGTTT TCCCCCTCAG TTTTGAACTT TTCTAATTTT GATTTGTGAT GTCCTTTTGT 49920
ATTTTAGATA ATTTTCCTAA TGTTTTCCAG CTCATTTGGA AAGGCTACAG TTTTATTCTG 49980
TACCTAAGCA AGTCTTTCTG GTGTCAAAGA TTTGACCTTG ATACTTTTCT TTTGCTCATT 50040
TTCGTATGAG ATTAGTTTTC CTGTACTTTC AAAAGAAGGC GTGGTTCAAG ATGGCTTTCC 50100
CAATTTCACA TCTGTCTCTA ATGTTTTTGT GTAATGTCTA AAATATGGAA ACTTGGTTTA 50160
TGAGATCTAC TCTGCCATTT TTATCTGGGC TTTCTCTTCC TTTTGTCTCT GTTGTACCTG 50220
TCCTGCTTGG TTCTGATTTA ACCCCAGTGG TTTCTCCTGA ATGTGGAGCC TTCTCCTAGA 50280
AGGCAGCCTC GGCTAGTCCC AGGGTTCAGA GTAGCCAGCT GCTCTCTTCA CCTAAGAGAC 50340
CACTGTGGAT TCCTTGTACT CACTTGCTAT TGGCTTGGAC AAAAGCCCTC CCATTTTCAG 50400

*Fig. 5L*

| | | | | | | |
|---|---|---|---|---|---|---|
| ATGCTATTAT | CAGATTAATC | TCTCATTAAT | CTGTCTTTCC | AGTGTATGCC | TGTGGGCTAT | 50460 |
| CTTGGGGTTC | TCTTGTTATC | AGACACCTCC | CTGCTGGCCT | CTGCTTTCTC | CCGTACAGAT | 50520 |
| GTCAGTACTG | TGCAGGTCTT | AATTGCTGTT | GGTGGTTTGC | CCCTACATTC | TTACAGTTTT | 50580 |
| AGTTTCCCAA | GGATACCTTT | AAACTTGGTT | TTATTGTAAA | TGTCGACAAT | GGATTTTGGG | 50640 |
| TTTTACTATC | TAGTTCTGTC | TTAATTCTGG | AATTCAGAAA | GATTAAAAGC | TCTGTTGTTG | 50700 |
| CAGCTGCTGC | CACCTCTTCC | CAGTACCCTC | TCCTCCTATG | TCATTTTTTT | CTTCTTATTT | 50760 |
| TTCTTGACTG | TATAAGAGAG | AATGTATGAC | ATTTCCTGCT | TGACCGCTGA | GTTTGATTAT | 50820 |
| AAATTAAAAT | ACACAATATT | TTATACAAAT | TGTTTTGTAG | AAGATTTATT | TACAGATGCT | 50880 |
| CATTCACAGG | TAAAATTGAC | TTATGAAAAT | AGTTTTCATG | ACAAATGTAT | CAGGCTCGGT | 50940 |
| AACTAAATAT | ATGGATTGAT | CTTGTTTATA | AATGAAATTA | AATGTGAATG | TAACTTACAT | 51000 |
| ATTTCTGTAT | TTGCTTACAT | CCGTATGTAC | ACATATAATC | AGCAAATGAG | TTGATGTTTC | 51060 |
| CTATTCGTAA | CTTAATGGTA | ATAGCTTGGT | AACAGAGTTG | GGAGTATTAA | AAAGATGTAA | 51120 |
| AGAGCCCCTT | AAAATTTTGT | TGCTGGGAAT | TTTAGTGTTC | TACTGATGAA | GGAAATAGAC | 51180 |
| ACTGGAAGGT | GTTGTTTCTA | TTAGGTAACT | TAGATATCAT | ACTGAAGACT | TCAAATACTT | 51240 |
| ATTGTTGACA | CTCAAAAGAC | ACACTTAGTG | TAAGTAAGCA | TTTCCCCGCT | TTTCCCAATG | 51300 |
| AAATAAGATC | ATTATTATAA | TTCCATTATA | AATGCTGATG | ATCATATTTA | TAGAAATATA | 51360 |
| GAAGATAAGA | CTTGAAATGA | TATTCGCTAC | CAATTAATGA | GTTTGAAGAA | GAAATCAGGA | 51420 |
| TGTGTTTTGC | TATTTTACAT | TTATTCTTAT | TTAACTCCAA | AGAATTCAGT | GATGTTATGT | 51480 |
| ACTATTATTT | CCATTTCTCT | GTGAAGACGT | TGAAGCTTAA | GTAACACGCA | TAATAAGGTC | 51540 |
| ATACATTTAG | CAAGTGGCTC | AATTAAAGTT | CAAACCTGGT | TCTGCCTGGT | TTCAAAGTCT | 51600 |
| GTGCTACTCC | ATGGTATTAG | GCTACAACAT | GACTTAGGGT | TTCTTCCTCT | GCTCTATTGC | 51660 |
| TGTTCAGATG | TACTCCTCTT | TTGGCAGAGT | GGGAGAAAAT | TTTTGCAATC | TATGCATCTG | 51720 |
| ACAAAGGCCC | AATATCCAGA | ATCTACAAGG | AACCTAAACA | AATTTACAAG | AAAAAAAAAA | 51780 |
| AAACATTAAA | AAGTGGGCAA | AGGACTTGAT | CAGACACATC | TCAAAAGAAG | ACATTTATGT | 51840 |
| AGCCAACAAA | CATATGAAGA | AAAGCTCAAC | ATCACTGATC | ATTAGAAAGA | TGCAAAATGC | 51900 |
| CTTTTCTGTA | TGCCACCTTA | TATCCCCAGT | ATTTATTATT | TCTAAGTCAT | AGTATCTTAC | 51960 |
| AGTGTATATA | AGTCTCATCC | GTTCTTTTGA | TTTTCTCTTC | CCTGCTTGCA | ATTGGGTACC | 52020 |
| TAGGAACAAA | GTTGCAATCT | TAGCCAGTTT | TTTCTTTAGC | CTTTGCTGAT | GTGTGAAAAG | 52080 |
| CCCTTTTTTC | TACCCTGGAT | TTCTGTACTT | AAGCTGGAAC | AGCTAAGTTT | TTACCTTTTT | 52140 |
| TAAATATAAA | GTTTCAGAGT | CTTCTGCCAA | GGATCTTTTG | CTGTTTTCCT | ACTGTTAAAT | 52200 |
| ATTTCAAAGC | CTTTTTTAAA | CATAGGGAAT | ATAATCAAAC | ATAGCAAGCA | GCTGATGAAC | 52260 |
| AATATCTAGA | TAGTCTTCAT | TATTGAAATG | GAATAAATGG | TATTTTTGTA | TTTTAGGCTA | 52320 |
| ACAGACACCT | TGTACCTTAG | ATAAGGCCAA | CCTTCTCATA | AAATCCCTCA | GTTACTTTTA | 52380 |
| TTAATAATAA | CCAAATTAAC | TCTGGATTCC | AGGGTGTACT | CATGATGGAA | TGATTTCTCT | 52440 |
| GTCATGTTAT | CCTGAGGATC | TAGTACTCTG | AGATAACATA | AGTGTATGAC | ACTTTAGGCT | 52500 |
| TATGAAACAC | TTAGCTACTT | AAATTATTTA | ATTTTTTTTC | ATGTGCAGAT | GGTATTGTAC | 52560 |
| CCAAACACTA | CCTTTGTGTG | TGTGTGTGTG | TGNNCGCCTG | TGTGTGTGTT | TTTGAGACAG | 52620 |
| GGTCTTACTC | TGCTCAGGCT | GGAGTGCAGT | GGCGTGATTA | TAGCTCACTA | CAGCCTTGAC | 52680 |
| CTCCTGGGCT | CCAGTGATCC | TGCCAAAGTG | TTGGGATTGC | AGGCGTGAGC | CACCTCACCC | 52740 |
| AGCCTTAAAT | TATTTTTTTT | TCAAGGATGT | TTAACCTGAG | GGTTAGAGGC | TCTTTGGCAC | 52800 |
| GTGAGCTGCT | GAAATGTGTG | TGAAAGTGTT | GTGCACGTGT | ATGTTTCTCT | TTTTTTCTGG | 52860 |
| GAAGTGGATC | TGTAGTGATT | CTTAGATGAG | TCTATGAGAC | AAGAAACTTT | TATTTTTTTC | 52920 |
| ATTTATTTAG | CGAATGTTTG | TTAAGCGTAC | TATGCCTTGG | CCACTCTACA | GGGTGCTGAT | 52980 |
| TGGACCAGTC | TGTCTACCTA | CCGTTGTAGA | TGTTAGAAGC | TATATTCTTT | TCACATGCCT | 53040 |
| AATATAACTC | TTTGTGTATG | TATACATGCC | CAGGCATGTT | CCTTCCTCAG | AACATTAAAT | 53100 |
| TCACCATTTT | GGTCAACTCA | AAGCAAGTAC | ACCATGGGAC | ACAGATCTGA | AATAATGTCC | 53160 |
| AGATTTTTAC | TTACTGAATG | AGGTGTGTTG | NAGTGTATAA | GACTACATGA | TGAGATGGCA | 53220 |
| AGTAATTGCC | TGAAGAAATG | ATGTAGTGAT | TTTGTGTGTC | TTATATTTAT | TTACTTTTTG | 53280 |
| ATCCAGAAAT | AAATTATATA | GATACCACTA | TTTTGTTTGG | ATGGGGGAGA | AAGGATGGGT | 53340 |
| GTGTATTCAG | GAACTTATGT | TACTTTTTTG | CAACTAATAC | CCCTTCTCAG | TAGTACAAAG | 53400 |
| ATTTGATTTC | TTTTTCTTTC | TATTTCCTAC | AGACTTCATC | TGCAGAGAGA | AAGAGACGAT | 53460 |
| TACCTGTGTG | GTTTGCCAAA | GGAAGTGATA | CCAGCAAGAA | ATTAATGGAC | AAAACGAAAA | 53520 |
| GGGGAGGTCT | TTTTAGTTAA | GCTGGCAATT | ACCAGAACAA | TTATGTTTCT | TGCTGTATTA | 53580 |
| TAAGAGGATA | GCTATATTTT | ATTTCTGAAG | AGTAAGGAGT | AGTATTTTGG | CTTAAAAATC | 53640 |
| ATTCTAATTA | CAAAGTTCAC | TGTTTATTGA | AGAACTGGCA | TCTTAAATCA | GCCTTCCGCA | 53700 |
| ATTCATGTAG | TTTCTGGGTC | TTCTGGGAGC | CTACGTGAGT | ACATCACCTA | ACAGAATATT | 53760 |
| AAATTAGACT | TCCTGTAAGA | TTGCTTTAAG | AAACTGTTAC | TGTCCTGTTT | TCTAATCTCT | 53820 |
| TTATTAAAAC | AGTGTATTTG | GAAAATGTTA | TGTGCTCTGA | TTTGATATAG | ATAACAGATT | 53880 |
| AGTAGTTACA | TGGTAATTAT | GTGATATAAA | ATATTCATAT | ATTATCAAAA | TTCTGTTTTG | 53940 |
| TAAATGTAAG | AAAGCATAGT | TATTTTACAA | ATTGTTTTTA | CTGTCTTTTG | AAGAAGTTCT | 54000 |
| TAAATACGTT | GTTAAATGGT | ATTAGTTGAC | CAGGGCAGTG | AAAATGAAAC | CGCATTTTGG | 54060 |
| GTGCCATTAA | ATAGGGAAAA | AACATGTAAA | AAATGTAAAA | TGGAGACCAA | TTGCACTAGG | 54120 |
| CAAGTGTATA | TTTTGTATTT | TATATACAAT | TTCTATTATT | TTTCAAGTAA | TAAAACAATG | 54180 |
| TTTTTCATAC | TGAATATTAT | ATATATATTT | TTTAGCTTTC | ATTTACTTAA | TTATTTTAAG | 54240 |
| TACCTTTATT | TTTCCAGGAT | GTCAGAATTT | GATTCTAATC | TCTCTTATGT | AGCACATGTG | 54300 |
| ACTTAATTTA | AAACCTATAC | TGTGACACAG | AGTTGGGTAA | ACGATGATTA | TTTAACTTTA | 54360 |
| AGCAGTTCAC | CATCCATTTC | AAAGCCTTTG | ATTGGCTTTT | TTGTAAATAA | AAATAACTTG | 54420 |
| TTAAGAAACA | AATATATCTG | TCATAGAAGA | ACTAGAAAAT | CCAGGGAAGT | GAGAAAAATG | 54480 |
| AAAATAAAAA | NTCATTCATA | GTTTTACTAG | TAGCTAATCA | CAGTCAACCT | CTTTTGTGTA | 54540 |
| TCCCACCAGA | CTTTTTTATA | TTCATTTGTT | TTTAGGTAAA | ATATAAAAGT | CTCGTATATT | 54600 |

*Fig. 5M*

```
CCCATTTTTC TGCATTGCAT TACCAGAAGG TAGTGGCGCC TATTAAATAT GTGATATGTT   54660
GTTGTCCAGC CATGGCTTCT GCATTTGCAT GCTTTTGTGT GTGCATCTGC AATACCCTGT   54720
GAATATCCTG TGTGATGGAG TGGCAAGTAC GCACAGACAC GTCTGCTGCA TGCCTAGGTA   54780
CGAGGCTGTC TCCAGGAGAA GCACTTGTTT GATTATTTGA GTTGCCAATT GAATTTGCTG   54840
CTTTTTTTCA TGGCTTGCCA TTTTCACTGA AAAGAATGAC TAATGAAAAA CGATGATTGG   54900
TTATTAGATT TGGATGTTTG GCAGACATTT TCTCAAAATT GAACTAAGTT GGCCTCTTCA   54960
CGGAAAACAA CTGGTATTTG TTGTGCCAAT GATAAAATTG GAGATTTCTA GCAAAATGTA   55020
TAATTTTGGA AAAGTTGTGT TCCTCCACTG GAAGCTTGAC AGCTTTCCTT AACATAAAGA   55080
CTTCTCTTTC TCTTCGCTTT CACTACTACT ACTACTAATT CTTCTTCTGA TTCTTCTTCT   55140
TCTCCTTCTT CCTTCTTCCT TCCTTCCTCC TCCTCCTCCT TCTTCTTCCT CTTCCTCTTC   55200
TTCTTTCTCT CTTTCCTTCC TTCCCTTCCC TTTCCCTTCC TTCCTTCCTT CCTTCCTGCC   55260
CGTCCGACCG CCCTGCCTTC CTTCCTTCCT TCCTCCCTCC CTCCCTCCCT CCCTCCTTTC   55320
TTTTTCTTTC TCTTTCTTTC TTTCTTTCTC TCTCTCTCTC TCTTTCTTTC TTTTTCTTTC   55380
TCTTTTTCTT TCTTTCAAGC AGTCCTCCCG CCTCAGTCCC CCAAAATAGT GGGATTATAG   55440
GTGTGAGCCA CCATGCACAG CCTTACATAA AGCCTTTTCT AATGAGATGG ATAGTAATTA   55500
ACAAATGTGA GTTTTTGATA TTATATAAAG ATTTTTTCTG TGTTTCGAAG ATCCGTATAA   55560
CTCAGTGAAT CAGTATGTTC TGGATGACTA ATATGTGATG TTAAGAAATC ATGACTGAGG   55620
CCGGGCGCGG TGGCTCACGC CTGTAATCCC AGCACTTTGG GAGGCCGAGG CGGGCGGATC   55680
ACGAGATCAG GAGATCGAGA CCACCCTGGC CAACATGGTG AAACCCCGTC TCTACTAAAA   55740
ATACAAAAAT TAGCTGGGTG TGTTGGTGCG TGCCTATAAT CCCAGCTACT CGGGAGGCTG   55800
AGGCAGGAGA ATCGCTTGAA CTCAGGAGGC GGAGATTGCA GTGAGCTGAG ACTGCGCCAC   55860
TGCACCCCAG CCTGGCGACA GAGCAAGACT CCGTCTCAAA AATAAAAAAA GAAATCATGA   55920
CTGGGTAAAA GATCTGTTCA GAGTACAAGA TGGACCAATG GATTTGATAT ATTTGAATAT   55980
AACAGAGTAT GAAAAAGTTT ATTGATATAG TTTCAGATTA CACACTGCAA CTAATCTTTA   56040
AGAAACTATT ACTTGTCCAC TTTTTGGTAA AATTTCAGAG AACAATGTCC ACCATTATCT   56100
GAACAGGCTA TTAAAATACT CTTCTCTTTT CCAACTACGT GCCTGTGCAA AGTCAGATTT   56160
TTTTCATATA CTTCAGCCAA AACAGCATAT CAAAATGGAT TGAATGCAGA AGTAGATCTG   56220
AGAATACAGC CACTTTTGTT AAGCCAGACA ATGAGATTTG CAAAATGTAA ACAATGCTGC   56280
TGTTCTCAGT TTTTAAAAAT ATGTTTTTTA AAAGTATTTA TGTTAATGTG TACTTGGTTT   56340
ACTACTGCTA TTTTTAAATA AAACAAGAAA CATTTTTAAA TGTCTGTTTT AATTTCTAAA   56400
GTGGTAGTGA TAGATATAAC CCATATTAAT AAAAGCTCTT TGGGGTCCTC AGTGATTTTT   56460
TTTTAAGAGT ATGGAAGGGT TCTCAGACCT AAGAGATTGA GAAATGCTGA TGTAATGTTT   56520
TATTATAAAG GTGTACCATG AATTATGTAC CTTACTTCAT ATTGTTGGAC ATTAAAGTTG   56580
CTTTCAGTTT TTTTGTTTTA AACAGCACTG CTTTGACCTT TTTTAAAAAA TGAGTCAGGG   56640
TCTTGCTGTG TTGCCCAGGT TGGAGTGCAG TGGCTATTCA CAGACATGAT CATAGCATGC   56700
TATAGCCTTG AATTCCTGGG CTCATGTGAT ACTTCTGCTT CAGCCTCCTG AGTAGCTGGG   56760
ACTATAGGCG TGCACCACTA TGCCCAGCTG CTTTGAATAT TCTTGAAATG AAATATGGTA   56820
TAGTCTCATA CCATATCATA GCCAGAGGGG GAGAGAGAGA ATTTTGTTGT TGTTGTTATG   56880
TTATCTGTAG TGGACTTTAT GCCTTCCCAG CATAAATTCT CTCTTTCCCC ATTTTTCGTG   56940
ACCCTTGATT TTTGTTGGGG TTCGTTCCAA GGAGAATAAT TTCCATCTGG ATATTGGATT   57000
GGCACCTGTG ACCTCTTCTG AGCTAGACCC TAGTAACAGC GTTTGGATCT GGGGTAGGTG   57060
TGTGGCCAAC TGAGCTGCTG GTTCATGCCT TTCCTGAAAT GAGCCCTACC TCTGAATATT   57120
TCAGAAACAT GGGACATTAA CTTCCCTTTA CTTACGTTAA ACCCCTTTGA ATGAGGAGTT   57180
GTTTTTCACT TCCAGTTGTG TTCAGTTGTC ACAGAAGCAC AGCGATGTGA TTGGTGGAAG   57240
GACCCGTCAA CAGACCCAGA AGATGTAAAG TGTTTTTAAT CTCAAAGGAT GTGGAATCTC   57300
AGAGATAGTT ACACCGAGTA GAGGATGAAG CGGCTCCTGG ATGGAGGCAG AGGCTTCCTG   57360
GATCTTCAAG TTCTGTATGG GTTGTTGTAT GAGGTTGGTG CAAAAGTGAG GCAGGAGAAT   57420
AGGGTCTGGA GGCAAGGAAA CTAAGGCCGA TTCACACTGA CTTCCTAGAA CTAAATCAAA   57480
AGGAAAACCC CAATTTTCCA GACCTAAATA ACAAAAGTAC CAGATGGCTC CTCCCTTTCA   57540
ACTGCCCCTC CCCCACACCT TTCTGCGTGA CACATGGAAA ATTGAAAGTA TCTCTGGTTG   57600
CTTCTGCGTA GGAATGTAAC TTTGTAACCA ATCAGACGGA TCGCAGGCCA AGTCGCCTGC   57660
ATAGAAATGT AACTTTGTAA CTTCACTTTA GCCTCTGATT GGTTGCTTTC CACAACCAAT   57720
CAGATGCTTG CATAGGGTGT ACCTGTTGTG ACTTCACAAA GTGGTGGAAG TGGTGGAAGT   57780
GGTGGAAGGG TGGAAGGGCT ATTTAAATTT TTATTCATCC TCTGATTGGT TGTTTCACTT   57840
AAGCCTCTAA TTGGTTCTTG AGTCCTGGAG CCTGTGAAGG GTACTTTATT TTCAGTAAAT   57900
GCATGCTTTT TTTGCTTCAT TCTTTCCTTG CTTTGTGCAT TTTGTTCAGT TCTTAGTTCA   57960
AGACACCAAG AGCCTGGACA CCCTCCACTG GTAACAAAAG TAACTGGTGT TTTTGCCATT   58020
AGAAGTAATG GCACAGAACA AGTACATGAG AGCGATTTCT TATGGAAAAT TAAATGGCGC   58080
ATAAGTCGTG TGCTCAGGTA AGGGAGCTGG GAACCGGTAG AGGAAGGTCT CCAACCCACA   58140
CCCGTGGGAT CTCTGAGTCT TTGAAAGTCC GTCCTCACCC TTTGTGAAGA ATGGGAGCAC   58200
GGCTGGACTC GTCACCGGGG GTTTTGGGGG GCTGAACTTG TCATTTGAGG GTGTAGGGAG   58260
GTTGGATGAA TCGCAGGGGT GCAGGGAGGG GGCCCACTGG AGCTCCACCA GGACCCCAGC   58320
ACCCTAGATC CAAACCTGGT CATGCTTCCC ATGCTCAGAG GCAAATCTCC CTCCCCTTGG   58380
GGGGCGGAGT CAGACGAGAC CCCCTCTCCA TCCTTTTCCA GGTCCGGTGG GGGCGGGACT   58440
TTAAAGGTAA AAACAGCAAT TACTTTTGCA CCAACTTATC TTCTAAGTTT CGCTCCCTAC   58500
CACCTGAGTG TGTTTGGAGG CTCTGGCTCA TTGTACCTGC CTGATCACCA GGTGCAAGTA   58560
GCTGGGCCAG AAGGACCTCG GCACGTTACG GAATATTTAC TACAGGAACA GGTGAGCTGA   58620
AGGCGAATTC CCCAGGTGTA GCCTGTGACC ATAGATTCAG ACAAAGCCCT GACTGTTGCC   58680
TGGAATTCAA AAAAGCTGTA GCCCTACCAG ATAGAATAAG AAAAGAATAT AGGATTCTTC   58740
CTATTCAAAT AGGTTGCATA TAATTAAGAG CATGAACGAT CCAATGGAAT GAACTCAAAG   58800
```

*Fig. 5N*

TAGTTTTTGA GTGTAATAGA CTTGAAGTGT CTTATGGAAA AGAATTGCAA AACCACAGAA 58860
ACAGTGAAGA AGGTTAGTTA TAGCCTTGAT GGGGTAGCTG ACTTCAGCAG TCTCAGCTAT 58920
CTGAAAAGTT ATTTACCAGA TTTTGGTTGG GAACATAATC CCTAAATCAT TTGAGATAAT 58980
GTACTTGTTT CCTTACTGGG TAAATGTGTT TAAACCTTGA GNAAAATGTA GACATAAGTA 59040
GNAATATANG AATAAATTAA ACCTTTGGTA GTTATGTTTT AGGATTAAGG ACTAATAAGT 59100
ACATATTTGA TATTTAAGCA TTTGTAATGC TTGAGATAAT TTATCCTACT CAAGTAACAG 59160
ATTACTCTTG TGACTCCAAT GTAAAATATA TCATTGAAAA ATTAGTATCT GCTTGTGATT 59220
TTTAAGTAGA AACCCTGCCA TTTGAAAGGT ATTTGCCTTT ATTATTGGAG ATATTTCATA 59280
TGAATGTTTA ACTTTGTTAT TGCATAGAAG TATTTAAACA GATTTCACTT GCAAGAGAAA 59340
GATATCTAAT AGGTTACTCT TAATCAGTAC TAAATTACTA CAATTACTAT ATTCTATTAA 59400
TATCGATTCA TTAAAACCCA GAGCTTTAAT TATGTCTCAG AAAATTAATT AAACTTTAGC 59460
CTCATAATCA GCTTTATTTT CTAACTCAAT GTTTAAAAAT TGACAAGTAT GTATTATACT 59520
TATTTATGTC TTCATTCAGT AAACATTTGC ATTTGTAGCA TGCAAGACAA CATGCTAGAC 59580
ACACGAAAGA TGGAATAAAT GGAAGAAAAT GCAACACAGA TCTCATGCTT AAGAGGGACA 59640
GATTTACTCT GAAGATTCAA TGAAAAAACA TCCACAAACA ACTTTTCTAC AAGAAACAAA 59700
ACATTTTAAA GAAAACATTT ACTTCAGCCG GGCGCGGTGG CTTACGCCTG TAATCCCAGC 59760
ACTTTGGGAG GGCGAGGTGG GTGCATCACG AGGTCAGAAG TTCGAAACCA GACTGGCCAG 59820
TATGGTGAAA CTGTGTCTCT ACTAAAAATA CAAAAATTAG CCTGGCGTGG TGGTGTGTGC 59880
CTGTGATCCC AGCTACTCAG GAGGCTGAGG CAGGAGAATC GCTTGAACCT GGGAGGCAGA 59940
GGTTGCAGTG AGCTGAGATC AGGCCATTGT GCTCCAGCCT GGGCAACAGA GCGAGACTCC 60000
GACTCAAAAA AAAAAAAAAG AAAAAAAAAA AGAAAACATT TACTTCACAT AATAAGATAT 60060
GAGAAAAAAT GGACTCTCTG AATGAAAAAA AGAGGAGATC ATGTGAAAGA TTTGCGCTTT 60120
TTTTTTTTTT AAAGTTATGG ACTGAAACAC TCCTAATCAT TAACATTTGT TATTTTAGGG 60180
GAGTGGAATT GGAAAGGTGG AAAGGGCTAT TTACATTTTT ATAATCTCCA TGTCTTTTAA 60240
ATCAATATAT ATTGCATTTA TTCTTTTAGT TAAAATTTTA AGAACTCTAT AAAAAATAGA 60300
GACAGGGACT CCCTTTGTTA CCCAGGCTGG TCTCAAACTC CTGGGATTAA GTGATCCTCC 60360
CACCTCAATT AGAAGGGTGG AAGGGCCAGC TGTTTAAGTT TCTATAATCT CTGTTAAATC 60420
AAATGTATAT TGCATTTATT ATTTTAAATT TTAAAAACTT TTTTAAAAAT AGAGATGGGA 60480
TCTTCCTATG TTGTCCAGGC TGGTTGTGAG CTCCTAGGAT CAAGTGATTC TCCCGCCTTG 60540
ACCTTTCAAA GAGCTGGGAT TACAGGCATG AGCCACCATG CCCAGCCTAT TTATTTGTTT 60600
ATTTATTTTT AGAGGCAGGG TCTCACTCTC ACTAGACTGA AGTGCAGTGG TGTGATCATA 60660
GCTCACTGCA GTCTCAAACT CCTGGACTCA AGCAATCAAC TAGCCTCAGC CTCTGAGTAC 60720
TGAGATGACA GGCATGTGCC TTCATACCCA GCTAATATTT TTGTAGAGAT GGGGTCTTCC 60780
TGTGTTGCCC GGAAGAGTCT CAAACTCTTG GCCTCAGCCT CCCAAAGCAC TGGGATTGCA 60840
GGCATGAGCC ACAACACATG GCCCTGCTTT TAAAAAATAT ATAGTGGGCC AGGCTTTCTG 60900
GGATGATGGG CAACCATTAC ATTTGCTTTC TCTCCATTCT GAATGTCAGC CTCCATACAC 60960
CTCTCTTGAG CCATCTCTTG ATGCCCAGGA CTGGCAGGCA AGCAGGATGT TAGGGTGCTG 61020
GCTGGAGGGC TGGAAAGCCC CAGGGCAAGG ATATGAACGT GAAGGATTTT AAGGAGATTC 61080
TTGGACCTCA AGGGAACTTT TGGTCCTGGT TTCCTAGAGT ATGTTAGATC TTCTTGGCCC 61140
CCAAAGAATC AAGGAAAAGC TGAATAGGTG GACCGAATCC TTTCCAGCAC TGAGGCTGGG 61200
AGAACTCTAT GACACCAGTG GGTGCTCATC CTGGTGCTGC CATGGACCTG ACTACCTACT 61260
TCCGCTAAAC TCTCCAGCAG CTGAGCCTTC AAGAGAAGAC GTCCTCCACC TTTTCCATGA 61320
GATGAAGAAT CCTTGGGGCC AGGGGATGTG CTCACTAGCT CACACCTGTC TCCATCCTCT 61380
AGACCATGCT TGCAGTACAC AGGACCCCAG AATGCCTGGC CCAAACACTC GTGAGCCTCC 61440
AGGGGCTGCA GGGGCTTCTG GCCTTGTTTC CCCATCTGAT GAGTTCGTTT CTTGGTCTGA 61500
AAGATTGTGA CAGTTACTAC GAGACTGAAT GAAGGGGGAT GAATGCAGAA ATGAAAACTT 61560
AAGACAAAAG TAACTTTTAA TGAGAGGGGC CGAGGGAAGA AGAAGAGGGC TCCCTGCTTC 61620
TAATGAGCAA AGGCAGCCAC CCTGAGCTTC TACAGCCCTT CGTATTTATT GAGTAGAAAG 61680
AGCAGGGAGG AGGAGGTAAT GATTGGTCAG CTGCTGGATT GATCACAGGT TCATATTATT 61740
GCTAACAGGC TTCAGATGTG CCTGATCACA AGAAACACTT GCGCCTGGGC ATGACTGCCC 61800
TCAGCATTCC TTCTGGGCGG CAGATGCAGT TTGTCAGTTT GCTAACAACC TGCTTTCATG 61860
AGAACAGTTT GCTGCTTACT TACACAGCCA CCAGTGATTT ACTGAGTTGA TCACGACCCT 61920
CACTCTTTCG GCCTCCAACA AAAGACGATC AAAGAATGGT TGTTTGCAGA GGTTATGGAC 61980
AAGACTTGAT GTCCAGGCCG AGTGTCCGTA TGCACAGGAG CCTCTTGGTG GTGCAGAGTG 62040
AAGCCAGAGG AGGAGGAGTG GGTTGTGTCC ATGGGCTGAT TCTCCCTGCA CCAACAGGAC 62100
AGAATCCTAA GGAATCCGAG CATTTGAAAT TCAAATCTGG TCTTACAGGT TGTTATGTAT 62160
TTGTCTAGGT AGGAGGCTAG AATGTATTGA AATGGGGTTA GCCTGACATA TTTATATATT 62220
TCATATTTAG GCTTCCATTT GTTCCTTTGT CTTGGGTCCC AAAAATATAT TAGAGGTGGG 62280
CCTGTCTGTT CTCTTGGACA CGAGGACCTC AACGAGTTTC CACTGTTCTC TGAATGTTTC 62340
CTTCCTGGTT TTCTGTGTAT ACAATAATTC CTAGTTTTCT GTTATTTACA ATTTTACTTC 62400
CACTTTTTAA AGACAAAAAT GTATGTTTTT TTAGTCAATA TTGATATAGT GGACCAATAT 62460
ATTTTACCGT TATTTTTGCT TACTGTTTTT GTTTTTTTGC CTTCCTCATC TTCTCACTAA 62520
GTTTGTCTGA CTACAGCCAC ACACCATTCA TTCAATACCA ACTCTTTTTT ATTTTTATTT 62580
TTTGGAGAGA GGGTCTCACT CTGTCACCCA GGCTGGAGTG CAGTGGCATG ATCTTGGTTC 62640
ACTGCAGTCT CAAACTCTTG GACTCAAATG TTCTTCCTGC CTCAGCCTCC TGAGTAGCTG 62700
GGACCACAGG TGCACACGAC CATGCCTGGC TAATTAAAAA CAAAACAATT TTTTTTTTTT 62760
TAGAGACGGG GTCTCACTAT GTTGCCTAGG CTGGTTTCAA ACTCCTGGGG TCAAGTGATC 62820
CAATACCAAC TCAACACGTG GTGAGACCCA GTGGTCTAGA CAAACAGCCA CATAGCAATA 62880
TGTTTTTCTC CATGATTCAT ATCCATGTTC GTTTGTTACA AAATAACAGG CATGAACATT 62940
TTCTTCAGAG AGGGAGATCC CCACTTATCC ATTAATGACT CATTTGGTGT CCATTCCAAA 63000

*Fig. 50*

```
CTATTAAACT GCAAAAGCAG ACATGAGAAA AGAAACTTAA GTCAATGTTT TTATCACATG 63060
TTGGTGCCAG CCTCCCATAG TGGTGCTAAA TTTATGNAAA TTGCAACAAA ACAAAAACCC 63120
AAACAACCCA ACAACGAAAA GCTATTTAGT GAACACCGTG ACTAACAAGC TTATTAGAAC 63180
TGCTTATCAG AGCTATGTGT GGATTTTGTA GGGGGAAAGA TTTTCTTCCC TCGTAGACAT 63240
TTTGCAAAAT AAAAGTAAAA TATTACCTTT ATGTACGTGG TAGATAGAAT TCCACAAGCT 63300
TCAAATTCAA CGACTCAAAA ATGTTGCTTT TACTTTCCAT ATCTCAGAAG TCACTTTTCT 63360
TTTATTTATT TTTTAGAGAT AGGGTCTCGC TCTGTTGCCC AAGCTGGAGT TGCAGTGGCA 63420
CAATCATAGC TCACTGCAGC CTTGAACTCC TGGGCTCAAG CAGTCCTCTT ATCTCAGCAT 63480
CCTGAGTAGC TGGGACTACA GGCGCATACC ACCACTCCTA GCTGATTTTT AAATTCTGTG 63540
TAGACATAGG ATCTTGCTGT ACTGCCCAGG CTAGTCTTGA ACTCTTGGCC TCAAGTGATC 63600
CTCCCACCTT GGCCTCCTAA AGTGCCGGGA TTGCAGGTGT GAGCCACCAT ACCTGCCCAG 63660
AAATCTCTTA TTTTAAACCC CAATTCCTCC TGATAGTAAA AAAAAAAAAA AAAAAAAAAT 63720
GTCATCTTGG TGTATTTTGG GTAGGCTGGA TCACTTCAAG TTTCCCCCTC CTCCTGAAGC 63780
TCCGACAGAG GCCTGCAAGC CCTGCTGGGA TCTGTCCTCA GTCCCTCTCG GGCTCATCTT 63840
CTACCATCTT GCTGTCACTC CATCTCCCTG TCCTTCCCTT TGCTTCACCC ATACCAGACC 63900
CTGTACTGTT TCTGGAAGAC ACCAGGCATG CTGTGTCTTA GGGGAGAATG TGATTTCACC 63960
AACTAGTGCC GCCCAAGTAA CATGCATTTG CCCTGACTGC TCTTTTCACC TGCTGTGCTG 64020
CTCCCCCAGA TAACCACAGG CAAACCCCGC CAACTCCTAG TTTATTGAAC TATACCATGA 64080
GTAACTTACT TAAAATCTCC ATACCTTGTC CCATTCTCTC TTACCTGTTC CAATACTTAT 64140
TTATGATGTT GATAGATGAT CTCCCTCTAC TAGACTGGAA GCTCCTTGAC AGCGGGGATT 64200
CTTGTCTGTT TTGTTCACTG CTGTGTCTTT AGCACCTGGA GAAATGCCTG GCACACAGCA 64260
GGAACTCAGT AAATAACTGC TGAATAAATA AACATGAATA AATCAATGAA TGGGGATGCC 64320
TAAGTGCTTC GGGATTCTGG TCAAAGCTTT GGCAACTAGG GACGCACAGG GACCCTCATC 64380
ATCTCTGCCT CCTAGGCAGG TATCCACTGA GATCCGCAAT CCCATCTGGT CCTTGGACCA 64440
GTTACCCTTC ATGTTGGCCT CTGTTAAGAT GTCCAGGTTG TATCTGGTCT CCCACACAGC 64500
ATCCCTTTAT TACTACCCCT GGACCTCAGC AGTCAGCCAC ACATTCAGTA AAGGCCACAG 64560
CTCTGCCATC TCCTAGCTAG GGGACTTTGG ACAAATTACT TAGACACTCT GAGCCTCGTT 64620
TGTAACATGC AGAGACGTTG CTGGGATTAG ACACAATGCC TGTAGACCAT TTAACAATTG 64680
CTGTCACACA TGGTTGGTAT TCACTCAGCT GTCGCTATGG AATTAGCAGA CAGAAAAGGC 64740
ACAGCGTCAG TGGCTGGGTG TCCAGAGAGA AGCAGCCTGT CTCTCTAGAT AATACTTGGC 64800
AAAATCACAG CAGTCCGGTG TGTGGCCCTT TACTGACCTT GATTAAAAAT CGGGTGTCAG 64860
CACCCCAAGT GGATCCTTCT TACAGGTGCA GATTCAGACT CATTATCCAA GTTGACAGAG 64920
ACAGAAGTAA ATATTCAACA AATATTTATT GAGCACTTAC TATGTGCCAG GCACTGTTGT 64980
TGTAGGTGCT GGAATACAGC AATGAACAAA AAAAGTGAAA CATTCTTCCT TAGATGGTGG 65040
TAAAGCGATA GGAGGACACA GCAGGGAAGG GGTTTGGACT ATTTCAATTT GGGACAGGAA 65100
ACGCCTTGCT GAGAGAGTGA GGGTTGAGCT CTGGAATTAG CCTGAGTTTG ACCACATGTA 65160
ACTGCAACTT TGAGCAAGTC GATCCACTGT AAGTCTCTTT TATTAACACC ATTGTGTGTA 65220
AGAGGAAATA GAAACTCAGC TAAAGTCGTT GGAGAATTGA ATGTGGTGCA GCATTTAGCA 65280
CAGCGCAGGA ATAATAAAAG CCAGCTGTTC TCATCCTTTG CCCATAGAAA AGCTATCCGG 65340
GAAGCCACAT TATAGTCTGA AGGCTGCCTA CTGGTTTGGT CAAAGAAAGG GCAGTTAGAT 65400
AATTTTCATG TTTAATTAAG GGCACGGGGC TAGATTTCTT GAGGTGCCAG AGTAATGCTT 65460
GCTTTTCATG AACAACGGAT ACAAGATATG GGCATTGCAG AACCTTTAAA GAACATAACT 65520
GGAATAATCA AATAACCGAA AGTTCATGAA ATATTCTGGC TCATGAATTA GTTATCTGGT 65580
AAATCACAGT CTGAAAGTCA CAGAATACAA ATTACTTTAA ATTTCCTCCA AAGCTTACTG 65640
AGTAAGGGGA GGGACATTTA AGATGCGGAG GAAGCGCTGA ACTTGCAAGA GGAACAAGGA 65700
GGACGGTGGC TGCTGGAACT CTGTAACCCT TAGAGAAGAT GTGGGTGGGA TTTGGCAAGC 65760
CCCCTAGACT CTCTTTGTTT TGGGTCTTAA TAGGGACAGT TTATTATTTT TAATGACTCG 65820
CGTGAATTGT ATACTGTTTT AAGCATCCAC CAAAAGCCTT TCGGCTTTTT CCCTAATTAG 65880
ACTCATTCTC ACACAGAGAG GAACTGAACT TTTTACCTCT TTGGTTCAAG AGCACCATCT 65940
ACTGGTCAGA TTTGGTAATT TCGGGTTTAT GGCACTGGAA AATCAAAGAG CATTTTGATT 66000
TGGTTGTGTT TGGTTTTGGT CCATTTATCA ATACAGGTTT TTTGGCGGAC AAAATAATGT 66060
GAAAATCAGG GGAATCAGGT GAGGGCATTG GATGTCTCTG TCACAGACGA TGGGGAGCTC 66120
AGCCGATTTT AAGCTTCTAA CCTCAGCTGG TCTGGAGAAG AGCAAACCTG ACAACCAGCA 66180
CGAAGAAAGT AGCTCTGCCT CTGTGGTGTG CTGGACATTC TGGTTACATA GATGGGAAGA 66240
CGAGGCCCTT TCCGACAAAT ATGCAAATCC CCCACATCTC CAAATTTGGT AGCTCTGGGG 66300
CTTAGGGCAG CTTCTGGAAA CAGAACTCAG ACCTAGCCTG CTGGAGCAGG AAGGGCTTCT 66360
GAGAAGATGA TATCTGGACC ATCTAAGGAG TGTAAATAAG AAATAGCCGC CAGGCATGGT 66420
NGCTCACGCC TGTAATCCCA GCACTTTGGG AGGCTGAGGC GGGCAAGTCG CTTGACAAAG 66480
TCAGGAGTTT GAGTCCAGTC GGGGCAACAT GATGAAACCC CATCTCTACA AAAAATACAA 66540
AAATTAGCTG GGTATGGTGG TGCATGCCTG TAGTCCCAGC TACTCTGGAG GCTGAGGTGG 66600
GAGGATCACT TGAGCCTGAG AGGTTGAGGC TGCAGTGAGT CGTGATGGCT GCACTCCAGC 66660
CCGGGCAACA GAGTGAGACC CTATCTTAAA AAAGAAAGAA AAAAGGAAGA GGTCAGGAGT 66720
TTGAGACCAG CATGGCCAAC ATGATGAAAC CCCATCTCTA CTAAAAATAA AAAAAAAATC 66780
AGCTGGGCGT GGTGCATGCG CCTGTAATCC CAGCTACTGG GGAGGTTGAA ACTGGAGGAT 66840
TCCTTGAACC CGGGAGGCGG ACGTTGCAGT GAGCCGAGAC CACACCACTG CACTCCAGCC 66900
TGGGCGATAG AGCGAGACTC CACCTCAAAA AAAAGAAAAA AGAAAAAGAA AAGAAAAGAA 66960
ATAGCCAGAT GGAGAACAGG GGAAAGGCCA GAAGAGCAGG GGCGTAAAAG GCGTGGAATG 67020
GCATGCGGGG GAGTAACAAG GTTTTTTTTT TTTAAACGGA GTCTCACTCT GTTGCCCAGT 67080
TTGGAGTACA GTGGCGCGAT CTTGGCTCGC TGCAACCTCT ACCTCCCGGG TTCTAGCGAT 67140
TCTCCTGCCT CAGCCTCCTG AGTAGCTGGG ACTACAGGCG TGTGCCACCA CACCTGGCTA 67200
```

*Fig. 5P*

ATTTCTGTAT TTTTAGTAGA GATGGGGTTT CATCATGTTG GCCAGGCTGG TCTCGAACTC 67260
CTGACCTCAA GTGATCTGCC CGCCTCAGCC TCCGAAAGTG CTAGGATTAC AGGCGTGAGC 67320
ACCGTGCCCA GCTAGTAACA AGGTATTGAC TGAACCAGAG TGGGGTGTGT CAAGATCGGG 67380
AATCAGCAAG CAGCACAGGG GGTGTCCTGG GTGGGGATCT GGGGCTCAGG TCTTCCTGCT 67440
ATCCTGCTAC CCACCTGCAC ACTTGTTCGT TTTCTTTCCA CTCATTTTTC TCCCTTGCCC 67500
AGACTTCAGG TCTACCAGCT ACACTTCTTG ATTTCTTTGG CCTTCAAAAT TCGGTTCAAT 67560
AAGGAAAGTT TTAGCATTAT TTTCATATAG GTCCTTGACA TTTCTTGCTA AGGTTATCAT 67620
TAGATTTTTT TTTAATGGTG TAATAGTTCA GGCCTTCACT CAAATGTCAT CTCTCTAGAG 67680
AAGCCTTCCT TAACTACCAT ACCAAAAACG GTTCCAGCGC CGCTACCGTC TATCCCAGCC 67740
TATCCTCTCA CGTCCTGTGG TCCTGAGGTT CTGTGATAAT GTTCTATAAT TCTGTGCTGT 67800
CCAATATGGT AGCCACGAGC CACATGTATT CATATCGTCG TTATTGAGCA CTATATAATG 67860
TGGCTAGTGC AATTGACACA CTACAATTTT AGTTGAATGC AATTTAAATT AATTTACATT 67920
GAAATAGCCA CATGTTTGGC TCACACCTGT AATCCCAGCA CTTTGGGAGG CTGAGGCGGG 67980
TGGATCACCT GAGGTCAAGA GTTCGGGACC AGCCTGGCCA ACATGGTGAA ACCCCATCTC 68040
TACTAAAAAT ACAAAAATTA GCCGGGTGTG GTGGCACGCG CCTGCAATCC CAGCTACTCG 68100
GGAGGCTGAG GCAGGAGAAT CACTTGAACC TGGAGGGTGG AGGTTGCAGT GAGCCAAGAT 68160
TGCACCACTT CACTCCAACC TGGGCAAAAG AGTGACACTC TGTCCAAAAA AAAGAGAAAT 68220
AGCCATATGT GGCTGGTGGC TATTGTATTG GACAGCACAG CTCTGTTTCT CCCACTAGAA 68280
TGTAATTTGA TGAGGGTGGG GACTTGGACT TATTCACAGC TGAATACCTA GAATGGAACA 68340
TAACTGCTAT GTTTTGAATG TTTGTGTCCC TTCCAAAATG TATGTTGAAA CTTAATCCCC 68400
TATATAAGAG TTGAAGAACC TTTTAGAAGG TAATTAGGCC ATGAGGGCAG AGTCCTCATG 68460
GATGGGNATT AGGGTCTTAT AACAGGACTT GAGTCCTCTA TAANGGAACG GAGAGTTCAC 68520
CTTTNCCTTC CCTTCTGCCN ATGTGNAGGA CACAGCGTGT GTCCCCTCTG AAGGACACAG 68580
CGACAAGCCT CCATTTTGGA AGCAGAGAGC AGCCCTCACC AGACACTGAA CCTACTGGCG 68640
CCTTGATCTT GGACCTCCAG CCTCCAGAAC TATGAGAAAT AAACTACTGT TGTTTGTAAA 68700
TTGCCCAGTC TGTGGCATTT TGTTATGAAA ACAGCAAAAA CAGACTAAGA CAAATCAGTT 68760
CTGGCACATA CTAGTAACTC AGTGATTCTT TGTAGAGTGA GCAAACGTGT GAATGAATGA 68820
ATGAATACAT TGTCATGCGC AGCTTTCGTG GGTCGTGAGT ACAAATGAGA AAATACGATC 68880
ATGGTGCCAT TGCAATGGCT TGAAACCCCA GCACTTACTG GCAGGAAGTC TGTCATTTTT 68940
TGCAATTCTC CTTCCCAAGT GTTTCCAGAC TCCCGAGAAG TGCACATGTA TATTTAGGAA 69000
TCAGTTCTCA TCTGCTAGAA CATGGGAAGG GAGTTAGTTG ATAGCAGTTC AGCTGCTTCA 69060
AATGCAGTCC TAGCTGACCC TGGAGGATCC AGGTACCTAT GGGTGCCATC ACGGCCACCT 69120
TTGCACTATC CTGTGAGAAA CTCTCTCCCA TCCTTGGTGA TGTCCTCCTG TGGTAACCTC 69180
AGTGAGAGAA CTCCATTGAT TCCCTAAACC AGAGGTCCCC AACCTTTTTG GCACCAGGGA 69240
CTGGTTTTGT GGGAGACAAT TTTTCCATGG ACCATGGGTG GGGAGGGGGG GATGGTTTTG 69300
GAATAATTCA AGTGCATTAT AATACGTTTA TTGTGTACCT TGTTATTATT ATTACATTGT 69360
AGTATAGAAT AATTATACAA CACACGATAA TGTCTAATCA GTGGGAGCCC TGAGCTTGTT 69420
TTCCTGCAAC TAGACAGTCC CATCTGGGGG TGATGGGACA CAGTGGCAGA TCATCAGGCA 69480
TTAGATTCTC TTAAGGAACA TGCAACCTAG ATCCCTCGCA TACACAGTTC ACAATAGGGC 69540
TCATGCTCCT GTAAGAATCT AACGCTGCTG CTGATCTGAC AGGGGGCGGA GNTCAAGTGG 69600
TAATGTGATG GATGGGGAAC TGCTGTAAAT ACAGTTGAAG CCGCTCACCT CTTGCTTTGT 69660
GGCTGGGGCC TGGGTACCCC TGCCCTAGAC AGTAGACTTC TCAAGGGGAG GGGAAAGAAT 69720
GGGCCAAGGA ACTGTGTCAG TCAAGAGGGC CCCCACTCAA CGGAAACAGA CCAGCCACTG 69780
GTCTCACAGT GCAAGTCAAG GAAGCTGGTC TCAGAGCTGT CCTCAGAGGG GACGCGTGAT 69840
AAGCAGATCA CACCCGGGAA GACTCGGCAT CAAGATGGAG AGGAGGGAAT GCGATGCGCC 69900
TGGTGGCAGC CGTAGGATCT CCTTCCAAGG CCGCACTGGA GGAGAGCTGC CTCCTAAGAA 69960
CAGGAAAGTG AATCAGAGTG AGGCTGTCAT TATAGTAAGA TAAAGAAAGA TGAGTGCTTG 70020
TTTGGGAATC TGGACAGAAT TAGCATCTGC TTGCTTTAGG ATAGTGGCTT CTTTTCTCTC 70080
TTGAACAAAA TACTCTCCTT AATAACTGCA GACCCAGGAT AACATGGAGT CATTGTTCAA 70140
ATTCACCCCG TTGCAGAATT CTCCAGTTAT CAGCATTTGT GTGTGTGTGC GTGTGTACCT 70200
ACATGTGCAC AGATGTATAC ACACACAGAT AAACACACTC CAGGCTTTGG GGAAATCGTA 70260
TTCGTAGATG CCTGTCTCTA CCTTTATTAT GTTAAAGAGA ATTCTGACTC TCAGGTCGTG 70320
GACTTCATTC ATTGTGTTGC TCACATGCAG GAAAAAAAAA AACCAGAATG CAATAAGGAT 70380
AATTCATTGA TTTGTGGGGA AAGAGAAAAT TCATTGTTTT GGGGGGAAAG AGAGAATGTA 70440
TTGATTTGTG GGGAAAGAGT CAATAAGTGA ATGTTTCCTG TTCTAGGACT GGCTTTGCCT 70500
TGTCAATAAT TGATTTTGTT GTTGAGAATA CATTTCAAAG CCTTTAAAGC AGTGTGCAGT 70560
TAAGGATGAT ATTTTTGCTT GAAATGACTA CTTTGCATCA TGTAGAAGGA ATAGTGTCTT 70620
TTAAAGGCAA CAGATGCAAG TCTAGGACCC CAGAGCTTTA GAAGGCTCTG GGCTTCGGGT 70680
ATGTGTCTGA TGTGTTGAGA GTTGCAGGGG ACGGGAGGGA TGTCCACTGT GGGCCAGTTT 70740
CTACCAGCCA CCGAGAAGCT GGAATTTGTT TATTCATTTA TAGAGCAACA GGAACTGGAA 70800
TCGAAATCTG TCAGTCCCTA TGTGCAGGGT GTAATTGAAT TGACTTCTCT GCTCTCAATT 70860
GGAACTTCCT TTGACCTGTA GTGAGAACAT TTTATGGCTC CCTCTAATCT AAAAAGGGTT 70920
TTTTTTTTTT TTTTAACTTT CCTTCCTATT CCCTTGTCTG CTAACCAACA GAGAACTCAG 70980
CCCACAGCCT CACAGACAGA ATGAGAGCAA TGCTTAATCC TTGTTCAGTG AATCTCATGG 71040
CCTCCTCTAG TCTTCAAACT TGGATTCCAA GTGCCTTGAA GAGCCAGACA CAGTGGCTCA 71100
TGCCTGTAAT CCCAACACTA TCGGAGGCTG AGGCAAGGGT GGATCACTTG AGATCAGGAG 71160
TTTAAGACCA GCCTGGCCCA CATGGCGAAA CCCTGATTCT ACAAAACATA CAAAAATTAG 71220
CCAGTCCTAG TGGTGCATGC CTGAAATCCC AGATACTCCA GAGGCTGAGG GAGGAGAATC 71280
ACTTGAACCT GGGAGGTGGA GGTTGCAGTG AGTGGAGATC GCACTACTGC ACTCTACTCT 71340
GTCTCAAATA ATAATAATAT ATATTTTTAA GTGCCTAGAA GAAAGAACTG CACTTCTGCA 71400

*Fig. 5Q*

GAGAGCGCCT CCAAAGCTCA GGGTAAGTGA CATGCTGCTT ACCATCCTAG AATGGAACCA 71460
GGCCACCCAT CCCCAGGTGG GACAACTGCA CTCCCAGGAT AACCCCTGAG TTATGGGCAG 71520
ACTTGTGTCT CTCCCCAGTT CAGATCTTGA AGTCCTAGAC CCAGTGCCTC AGGATGTAAC 71580
TGTAGATTCT TTAAAGAGTG AATTAAGATG AGGCCATTAC TAAAAGCCTA GACCTGACCA 71640
CTATGCAATC TATGCATGTA ACAAAATTGC ACATGTATCC CATCTCTACA AATTAAAATA 71700
AATAAATAAA ACTACGTCAT TACAGTGGGT CCTAATCCAG TATGACTAGT GTTTTTGTGT 71760
TTGTTTTTGT TTTGAGATGG AGTCTCTGTC ACCTAGGCTG GAGTGCAGTG ACACGACCTC 71820
GGCTCACTGC AACCTCCACT TCCCAGGTTC AAGCAATTCT CCTGCCTCAG CCTCCCGAGC 71880
AGCTGGGATT ACAGGCACGT GCCACCACAT TCAGCTAATT GTTTTGTAAT TTTTTTTTGA 71940
AGTTTTTATT TTTTATTTAT TTATTTTTAA TCTTTTTTTA TTTTATTTTA TTTTTTTACT 72000
TTAAGTTTTA GGGTACATGT GCACAACGTG CAGGTTAGTT ACATATGTAT ACGTGTGCCA 72060
TGCTGGTGCG CTGCACCCAC TAACTCGTCA TCTAGCATTA GGTATATCTC CCAATGCTAT 72120
CCCTCCCCCC TCCCCCCAAC CCACAACAGT CCCCAGAGTG TGATGTTCCC CTTCCTGTGT 72180
CCATGTGTTC TCATTGTTCA ATTCCCACCT ATGAGTGAGA ATATGCGGTG TTTGGTTTTT 72240
TGTTCTTGCG ATAGTTTACT GAGAATGATG ATTTCCAAAT AGAGACAGGG TTTCATCGTG 72300
TTGCCCAGGC TGGTCTCGAA CTCCTGACCT CAAGTGAGTT GCCTGCCTTG GCCTCCCAAA 72360
GTGCTGGGAT TACAGGCGTG AGCCACCACT CCCCGCCTGG TGTTATTAGA AGAAGAGATT 72420
AGGACAGAGA CACAGACACA GAGGAAAGGC TGAGTGAGGA CACAGGGAGA AGACAGCCAT 72480
CTGCAAGCCA AGGAGAGAGG CCTCAGAAGA AACCAACCCT ACTGACATCC TGAGCTTGGG 72540
CTTCCAGCAT CTAGAAACTG TGAAAAAATA AATGTCTGCT GTCTAAGCCA CCCAGCCAGT 72600
GGTATTTCGT TGTGGTAGCC CTAACAGACT AATACATGCT GAGTCTCTCA TTGTTCAAAT 72660
CATCCTGTAA AACTGACTCA ACAGGCTTTT TTTGAGCAGG GTTTTCTATT CATGTACTCA 72720
TTAATTTTCC TTAAATTAAA AGTTGCAAAT ACAATATACA AAATTAAAAG TTCAATTAGA 72780
AAAATGAGTT TCTATAATCA GCCTACTCAG AATTAACCAT GGTTTCAAAT AGGGGTTTTG 72840
CTGGTGTTTT TTGTTTTGTT TTGTTTTGAG AGAAAGTTTT GCTCTTGTCT CTCAGGCTGG 72900
AGTGCAATGA CGTGATCTCA TCTCACTGCA ACCTCCACCT CCGGGTTCAA GTGATTCTCC 72960
CGCCTCAGCC TCCCAAGCAG CTGGGATTAC AGGCAAGCGC CACCATGCCC AGCTAATTTT 73020
GTATTTTTAG TAGAGACGGG GTGATCTGCC CTCCTTGGCC TCCCAAAGTG CTGGGATTAC 73080
AGGCGTGAGC CACTGCGCCC GTTAGCTGTT TTGTTTTGAA ATCAACTTTG AAAAATGTTT 73140
TGATATCTCA TCATGTCCCC AATGCCATTT GTAATGGTCA CACAGCATTC TGTTGTATGA 73200
TGTACCATGC TTTATCTAAC CTGTGTCCTA TTTTTGGATA GTTCGAATTT TCCTATTTCT 73260
TTTCACTATT AGAAGCAAGG CTGCAATGGA CATCCTTTTA AATACTTTTT AAAAACAAAA 73320
ACCTTGGTAC AAGTACCTGT ATATAGACTT GCAGGGTCAA AACTTCCCAT TTGATGGCTA 73380
TTGATATGTA CTAACAAATT GTCCTCCAGA AAGTGGTCTT TTCCTCACCC TCATCAGTTC 73440
TTGGTGTTAC CACCTTTTTG CATTTTGCCA AGCTGATAGG TAAAAAAGTG TCTCTTACTA 73500
TTGTATGTAT TGAATTAAAT TTATTTATTT ATTTATTTAG ACAGGGTCTG GTTCTGTCCC 73560
CCAGGTAGGA GTGCAGTGGT GCAATCATAG CTCACTGCAG GCTTCAACTC CTGGGCTCCA 73620
GCAATCCTCC TGCCTCAGCT TCCTAAGTAG CTGGGACTAT AGGTGGGCCC AGCTAATTAA 73680
ATTTTTTTTT TTTTTTTTTT TTTAAGATAC AAGGTCTCAC TACTTCGCCC AAGCTGGTCT 73740
TGAACTCCTG AGCTCAAGAC ATCCTCCCAC CTCAGCCTCC TGAGTTGCTG GGATTACAGG 73800
CAGGAGCCAC TGTGCCTGCT TATTATATAT TTCAAAATAA CGAAAAGAGT GGAATTGCAA 73860
GTTCCTCACA CAAAGAAATG ACAAATGCTT GAGATAATGA TTATCATAAT TATCCTGATT 73920
TGATCACTAC AACTTGTATG CTTATATCAA AATATCACAT ATTTATATTT TTAAAAATTA 73980
TATTTATATT TATGTGATAT TTTGATATAT TTTGTAATGA TCATTTTACA TATGAACATA 74040
TTTATACATA TATACAAACC AAATAAACCA TACATATTTA TACATATGCA CCTATGTACA 74100
AACCAAAGAA ATTGGGATAT AGCTATCCCA GTTCTATTAA AAAATTGAGA TTTTTTTCTT 74160
CTCTATTGAT ATTTCCTACT TTTTTTTTGT TTTGAAAAAT AATTTATCCT TGAGTCAGTT 74220
GTGATGATTT ATACCTGTAT AGAGATTACT AGTTTGATCA AAATCATTTC ATTTATTGTT 74280
AAAAATTGTA TAATGATATT ATCTCCTAAC TGAAAATTTT CCTTTATCTC TGTGATTATA 74340
TTCCATTTCT CATTCATCAT ATTTTCATTT CATTCCAGTT TTCCTTGGTT AGACTTTCCT 74400
ATGATTTGTG TCTTTTACTG TTCTTTTCAA AGAACAGCCT TGGTATTTAT TTATCAATTC 74460
TATTTCTTTT TAATTTCACA ATTAATTGTT TTCTGTTTTT ACCATGACTA ATTCCCACCA 74520
CTGCTTTCAT AGATTAATTT TGTGTTCTTT TTCTAATTTC TTCAATTAAT TTATTTTCAT 74580
TTTTTAAAAA CTTAATAATA AAAGTTCTTA AAGTCCTAAA TCTTTTCCTG AGTACTGTGG 74640
GATTCTTTCC ATGTGCTTCT GCATGTAGTA TGACTATTGC AATTGGTATA GATGGTATTA 74700
CAGTTCTTAC TCCTTCTTAC ATCCAGGGAT TACTAAGGAG ACTGATTTTA AATTTGCAAG 74760
AAGTTTGACT TCTAAAAGTG CCAGGCTCCT TTTTGATGTC AAGTCTCACC TATTTCTTCT 74820
GTTTTTCTCT AGTAACTGAG CTCAGGTTTT GTTGAAGGCA GCAAACTACT GGCTAAAACT 74880
GCTCAATGTT TTCCAGCTAA AATTGCTCAA GTATTTCCTG CAGCTAGTTA GGGCAAGTTA 74940
CCTGGCTCTG TCTAGAGAGA TGGAGGTGCA GGTCCTTGGA GACAGAGTAC CCTCTGAACA 75000
AAAAGGCAAA GACTTACCAG CAGAAAACCC ATTTGCCTTT TCCCTTTCCT CCTCACTGAC 75060
ATGCAAGGGT TATGTCTGGA GGTACGAGAA AAGGAAAGCA TAAGGATAAA ATCTAACAGG 75120
CTAAGAATGA CAGGGCAGAA AGATAGAAAG GATCTGTGTC CCCGATGGCA TCGTTGTACC 75180
AGCAAGACTG ATGATCATGA TGTAAGTCAA ATGAATGCCC AGCTGCTGCT GGCTGTGTTT 75240
TTTGTTATTT GCGGCTGAAT GCATTGCTAA TGTAAACATT ACCTTGCAGC CAGAGAATAC 75300
GGCTTGCCAA AAGTCTAGTT TTGTATGTTA ATCATGATAC ACCAGCCAGA CAGAGTGGCC 75360
CTCAGCTGTA ATCCCAGCAC TTGGGGAGGC CAAGGCAGGC GGATCACTTG AGGTTAGGAG 75420
TTCGAGACCA GCCTGACCAA CATGACAAAC CCCCGTCTCT ACTAAAAATG CAAAAATTAG 75480
CTGGGCATGG TGGCTCCTGC CTGTAGTTCC AGCTACACGG GAGGCTGAGG CAGGAGAATC 75540
GCCTGAATGC AGGAGGAGGA GGTTGCAGTG AGCCAAGATG GTGCCATTGC ACTCCAGCCT 75600

*Fig. 5R*

GGGCGACAGA GTGAGACTCT GTCTCAAAAA ATAAAAATAA TAATAATAAT GATATGCCAA 75660
CTGCTATAGC ACCTAGACTG CAAAATGTAC ATCACAACAG TCCGATTCTC TGTTCTCTTT 75720
GTTCAGGGGT AAGCATGGAG CTTAATTTTG ATCTATGAGT CAACGTGGGA AGTCCGTTAG 75780
GTTAGAAGTG CTTCTGGTCA AGGTTTCTTT GCTTCTAAAA GAGGAATGTG AGGAAAAAGT 75840
CCCTGTCTTG GTGTGGATTT TGGTGTGGGG GGATGTATAT AAAGCCTGTA GCTATTGAAG 75900
CCATCTGGCA AACTTGAAGG GAGCAGCTGA CTCTGAGCTG GTAGAATATA GAAATGGAAA 75960
GGATTTAGAT CTTGATGTGG TTGAGAGGCT GCCCTCCCTT GGGACTTCTT TTTTGTGTGT 76020
GAGTTAACAA GTTTTCCTTA TTGTTAAGTT GCTTTAGTGG GTTTGCTATT ACTTGTAGTC 76080
AAAACATTTA TTATGGCATC ATCTACTTTA TTCTATCCTT CTGCTTTCCT TATTACAAGT 76140
ATATTTACAA GCTCATTGTC ATTCATGTCA TCATTTTAAT CAGCACCAAC AACAGCATCA 76200
CCAGTAACAT TTATTGAGTG TTTTTAAGTG CCAGGCCCTG TTGTTGTCAT TTAAATCTTA 76260
CACCAATCCC TACTGCTCAG ATACTATTCT TTTTAAAAAT TATTTTTTTT TTAGGCACAG 76320
GATCTTGCTC TGTTGCCCAG GCTGGAGTGC AGTGGCATAA TCATAGCTCA CTGCAGCCTC 76380
AAACTCCTGG GCTCCAGTGA TCTTCCTGCT TCAGTTTCCC AAAGTGCTGG GATTACAGGT 76440
GTGACCACTA CCCCCTGTCC TATTATTATT GATTCAGATT TACAGATGAG GAAAATAAGG 76500
CTTAGGAAGG CTACATAATT TCCTAGATTG CTTATTTAGT AAGCGGCAGA GCCAGGATTC 76560
AAACCCAGAC CTGAGGGACT CCTAGACTAG TCCATGCCAC TGTGATATGG CCTTTCACAT 76620
CTCTTCTTTC ATCCGTCATC ATGATATCTT TCTCCTCTGA GTTCTGGGGA AGTTTCTCAA 76680
GTTGGACTGC CAATTTTCTG CAGGATTTTC CTGTGATATA TAACTCCTTC ATTTACTGCT 76740
TCCATTTTAT TTCATATCAC CTACAATTTC CCTTATGTCT AAAACCAATT GCTCCTATAT 76800
CTAAGATGCA ACGTCCTTCT GAATTATAGT GTTAATGCAA TAGGGTATTT TGAAGGTTTC 76860
TGTATGTTTT CTGTAGAAAA GTTATCTCAA AGGGGGATAT ATACTTCCAT TTCCCAGTGG 76920
TCTACTTCTT TTAAGCCACA AATAGGGCAC TTTCTCTTGT TAGTTTAATC CTACGGGTAT 76980
ATAATTTTCA GTATTTCTAG TGTTAGAATT TGAGATTCAG AGAACTATGA GTCTCTGTTT 77040
TAATCTTTCA GTCCTAGGAA AAGGAGAAAT AGGGCTGCCT ATCTTTTCTG TGGTTTTATT 77100
TTGCCATTTA ATTTCTAATT GACTGTGAGA TGTATCAAGA GATCTGTAGC TCAAGGCAGT 77160
TGAATGTCCC AGAGCTTCAC AGCTGAGCCA AGTGACTTCT TTTCCATGTT TATTGTGGCA 77220
GCCAAGGTCA GCAGATGCCA TGCCTCTTGC TCTGAGTGCC TGGACCACCC CCATTAAGAG 77280
CCTCCCACAG CAACAACTCC ACTTGACCCA CGATAAGTGA GGTTGGCACT GTGTCTCTCT 77340
CTTTGTACAT TTTGTTTTCT AAGTTGCTTG TAGGGCCAAG CTTTGAGTCC TTGTTACCAT 77400
CAGCTTAAGC TCCGGCCTCT CTGAATTGGA GGATTTTGTT TGTGTTTGAT TAGAGCCTGT 77460
TGGCAGAAGC AAGTGCCAAA GTCAGACATA AAACAGAAAA CTCTAATGTG GTGTCAAGTC 77520
TTTTCCAGAT GTTACTGATC CTCTTTCTTT TCCTTCTTTT TTTTTTCTTT TTTGTTATTT 77580
TTGATCCCCT TCCTTTTTGC TTCCCTTAGG TTGACCTTTG CTGTCCTACG GGCAGTACAA 77640
AGATTGGGTC TTTCTGTCTC TGCCTCTCCT GCCCTCGGAC TCCTACCATG GGTCTTTTCT 77700
TTTTTTATAG AGATAGGGGT CTCACTTTGT TTATCGTGTT TTTTTTTTTG TTTGTTTTTT 77760
GAGGTGGAGT CTTACTCTGT CACCAGGCTG CAGTGCAGTG GCGTGATCTT GGCTCACTGC 77820
AACCTCCGCC TCCTGGGTTC AAGCGATTCT CCTGCCTCGG CCTCCTGAGT AGCTGGGACT 77880
ACAGGTGTGT GCCACTATGC CCAGTTAATT GTTGTATTTT TACTAGAGAC AAGGTTTCAC 77940
CATGTTGGCC AGGATGGTCT CAATCTCTTG ACCTTGTGAT CCACCCGCCT CAGCTTCCCA 78000
AAGTTCTGGG ATTACAGGTG TGAGCCACAG CGCTCAGCCT GAACTTTTAC TTTTAAGACA 78060
ATTGTAGATT CAAATCCTGT GTCCTCTCTT ACACAGTTTC CTCCAATGGG GGCATTTTAC 78120
AAATATAATA ACCAGGATAT TGACATTGAT ACATTTGATA CAGTCAAGTT ACATTTTCAT 78180
CACCACAAAG ATCCTGGTGT TACTCTTTTA TAGCCATACC TGCCTCCTTC TCCCCTCCCC 78240
CATCCCTCAC GCCGGCAACC ACTAATCTGT TCTCCATTTC TACAATTTTG TCGTTTCAAA 78300
AATGTTATGT AAACAGAATC ATACAGTTTC TCATCTTTAA GATTCGTTCT TTCCTGTTTT 78360
TTTTTTCTTT TTTTTCTTTT CTTTGTTTTT TTGAGATGGA GTCTCACTGT GCCACCCAGG 78420
CTGGAGTGCA CTGGTGTGAT CTCGGCTCAC TGCAACCTCC GCCTCCAAGT TGTGGGTTGA 78480
AGCGATTCTC CTGCCTCAGC CTCCCAAGTA GCTGGGATTA CAGGTGCCTG CCACCACGCT 78540
CGGCTAATTT TTTTTTTGTA TTTTTAGTAC AGACAAGGTT TCACCATGTT GGCCAAGCTG 78600
GTCTCGAGCT CCTGACCTCA GGTGATCTGC CTCGGCCTCC CAACTTGCTG GGATTACAGG 78660
CATGAGCCAC CGCACCCGGC TGAGATTGGC TCTTTCACTC AGCATAATTC CCTGGAGACT 78720
TCATCCAAGT TGTTGCATGT ATCAATAGCT TGTTTCTTTT CATTGCCACC TAGTTTTCAA 78780
TGGTATGAAT GCCGCATTGC TTGTTTCATC AGTCACCTGG TGGAAAACAT CAGGGTTGTT 78840
CCCAGTTTTT AACTATTATG AATAAAGCTG CTATGAACAT TTGTGTACAG GTTTTTGTGT 78900
GAACATATTA TCATTTCTCT GAGATGAATC AATGCCAAAG NAATGCAATG GTATGTTTAG 78960
TTTTATAAGA AACTGCCAAA CTGTTTTCCA GAGTGGCTAT ATGANTTTTG TATTCCTACT 79020
AGCAGTGTAT GAATAATCTA GTTTCTTTAC ATCCTCACCA GCATTTCATG TTCTCAGTAT 79080
TTTTTTTATT TTAGTTAATC CGATATGTAT GTAGTGCAAT ATCACTGTGG TCTTAATTTT 79140
TAGTTCACCA GTGCTAATGA TGTTGAATAT CTTTCATGTA CTTATTTGCC ATCTGTATAT 79200
CCACTTGGTG AAATACTTCA TGTCTTTAAA GAAGACCCAG GATTTCTAAA AAACTGTTGA 79260
GTTTTGAGAA TTTAAGAAAT ATATTCTAGA TACTGGTACT TTGTTGGATA CATGGTTTGT 79320
AAATATGTTC TCCTAGTTTG TAGCTTGTCT TTTCATATGT GTTAAAGCTT ATCTCCCATT 79380
TTATTATTTG TTTTCTGTTT ACTTTGTTTC TTATTCCTCT ATTCTCACTT TGGGTGGATT 79440
ATTTAAAATAT TTTTTAAGGT TTCATCTTGA TTTATTTGTA GCATTTTGGG TACATCTCTT 79500
TGTACACTTT TCTTAGTGGT TGCCCTGGGT GTTACCATAT ACATATGTCA AGAGTCACAT 79560
TCTGCTGGTG TCAGTGTTTT TCCAGTTGAA GGCAAGTGTG GAAAACTTAC CTCCATTTAG 79620
ATTCCTTTAC TCTTCCCATT TTTAAAACAT GTGTCTCAAG TATTCCCTCT ACATTCATTG 79680
ATCAGCACAC TAGAGAGTGT TATTTTGGCT TTAACCTTCA AATATAATTT AAGACACTCA 79740
GGAGAATAGG ATCATCTATT ATGTTTACCC CTGTCTTTGC CTGTTTTGAT GTTCTTCATT 79800

*Fig. 5S*

CTTTTCTAAA GTTTCAAGCA TTCTTCTGTT ATCATTTCCT TTCTGTTTAA AGAACTTCCT 79860
TTAGTCGTTC TTTAAGGACA GATTTACTAG CAACAGATTC TCAGTTTTCC TTCATCTGAG 79920
AATGTCTTTA TTTCCCCTGC ATTCCTGAAG GATATTTTCA CCTGATATGG AATTTGTGAG 79980
TGATAGTTCT TTTTCCTCTA AGCACTTGAA AAATGTTATG CCACTTTCTG CTGTCTTTTA 80040
TGGTTTCCGA AGAGAAATCC ACTTTCATTC AAACTGTCAT TTCCCTGTAA GTAATGGATG 80100
TTTTCTGTCT AGTTGCCTTC AAGACTTTGT CTTTAGTTTT TACAAGTTTA ATTATGATAT 80160
GTCTTGGTGT GAATTTCTTT GAGTTTATCC TGCTTATGAT AGTTCACACA GCTTTTTGAA 80220
ACTGTAGGTT TATGTCTTCC ACCAAATTTT ACTGAATTTC TTCAGTTCTA TGGTCTTGCT 80280
CCTCTTCCTG AAGTATTCCA ATGATACCGT GTTCTCTTTT GTTACGGTCC CACTGGTCTT 80340
TGAGACTCTC TGTTCATTTT ATTTCGGTCT TTCTTTTCTC TGTTGTTCAG ATTGGGTAAA 80400
TTCCATTGAT CTACCTTCAA GCCCACTGAT TCTGTCCTCT ATCATCTCTA TTATTGAGCC 80460
CAACCACACA GTTTTAATTT TGATTATTGT ATTTCTCAGT TCTATAATTT CCATTTGGTT 80520
ATTTTTCAAT GACTTCCATT TTTGCTGAAA TTTTCACTTG TTTCAAGAGA ATTTGTAATT 80580
ACTTGTTGAA GCACTTTTAT AATATCTGTT TAAAATACTT GTCATATAAT TCCAGTAACT 80640
AATTCATCTT GGTGTTGACA TCTGTTTATT GCTCACTTAA AAATAAAAAA TAAAAAACAC 80700
CTAGACTTTA TTTTTTATAG CAGTTTAAGG TTCACAGCAA AATTGAGAAG AAAGTAAAGA 80760
GTGTGCCCAG AAAAATAGTA CCCCTATGCA GAACCTCCCT GATATTGTTT GGCTGTGTCC 80820
CCCACCAAAT CTCATCTTGA ATGGTAGCTC CCACAATTCC CACGTGTTGT GGGAGGGATC 80880
CAGTGGGAGG TAATTGGATA ATGGGGGCGA ATCTTTCCCA TGCTGTTCTC ATGATAGTGA 80940
ATAAGTCTCA TGAGATCTGA TGGTTTTATA AAGAGGGGTT CCCCTGCACA AGTCCTCTCT 81000
TGCCTGGCGC CAGGTAAGAA GTCCCTTTGC TCTTCCTTCA TCTTCCATTA TGATTGCGAG 81060
GTCTCCCCAG CCATGTGGAA CTGTAAGTCC ATTAAACCTC CTTTTCTGTA TAAAGTACCC 81120
AGTCTCAGGT ATGTCTTTAT TAGCAGTGTG AGAATGGACT AATACACTCC CTATCAACAT 81180
CCCCTACCAG ATTGGTATGT TTGTTGTAAT CGATGAACCT ATGTCAACAC AGCGTTATTT 81240
CCCAAGCTCC ATAGCTTATA TGAGGATTCG CTCTTGGTGT TTACATTCTG TGAGTATTGA 81300
CAAATGTATG ATGAAATGTA TTGACCATTA TAGTGTCATA CAGAATACAG GATAGTTTCA 81360
CTGTCTTAAA AAATCTTCTG TGCTCCCCTT ATTCATCCCT TCCTTCTGTG TAAGCCCTGG 81420
CAACCACCGA GCTTTTCACT GCCTCCATTG TTTTGCTTTT TCCAGGATGT CATAGAGATG 81480
GACTCATACA GTAGGTAGCC TTTTGAAATT GACTTCTTTC ACTTAGTAAT ATGATTCCTC 81540
CATGTCTTTT CATGGCTTGA TAGCTAATTT CTTTATAGTG CTGAGTAGTA TTCCATTCAC 81600
TTATAATTCC TTGAATTCAT TGTTTGGAAT ATTTTGCAGA TGATATGCTA TTCCCTAACT 81660
TTATGCATCT TCACTCACAG GATTGTTTTT TTCTCACCAA TGCTTATTTA TATAAAAGCC 81720
ATATCAACAA AATTTTACAC ATCAAAAATT TTCAGACTTC TGGTTGCTCC AAAGAAGGAA 81780
TGACCCCATT CTTCTCAGGT CCTCTTCCTC ATGACTAAAA AACTCTGAAC AAAGCACAGA 81840
AAGTTGCGGA AGGCTCTGAA AGGTGAAAGG AGGTGGACTG CCTAGGGACC TCAGGACTTG 81900
GAAAACAACT CAGTGGGGAA TTCCGTGGAT TTCCTTATCA CCTCCCTTAT ATCCTGGACA 81960
CGGAGCTGCA GAAGACTCCA ACCTACAGTC ACCAATGCGC ATAGAAGAAA AAAGCTCCAA 82020
GAAAAGCCTT TTCCTCCTGG CCAGATGACT GGACAAGGGT GGCCTGACAA CAGAAAACCC 82080
ACAACAAGGA ATTACAGGTA ACTCCAGAGA GGATCAGCTT GAGTGGTTAA AACAAGTACA 82140
TGGAAAACAA AAAGAAGCAT TTTTCTTTTT TTGTAAAAGA GCTTGTACTG TAATAACTTT 82200
GATTTTGTTT TTTGTTTTTT GTTTTTTGTT TTTTTTTTGA GACTGAGTCT CACTCTATTG 82260
CCCAGGCTAG AGTGCTGTGG CGCAATCTTG GCTTACTGCA ACTTTTGCCT CCTGGGTTCA 82320
AGTGATTCTC ATGTCTCAGC TTCCTGAGTA GTTGGGATTA CAGGCATGCA CCACCACACC 82380
AACTAATTTT TGTATTTTTA GTAGAGATGG GGTTTGACCA TGTTGGCCAG ACTGGTCTTG 82440
AACTCCTGAC CTCAAATGAT CTGCCCACCT TGGCCTCCCA AAGTGCTGAG ATTACAAGCC 82500
TGAGCCACCG CACCTGGCCA ACTTGGACTT ATTTTTATAA TAAGTAGATA TTGTTCACTG 82560
TAGATATTGA ATCAATTTTT ATTTAATCTT GATTTTTTTT CTTGAGCTGC ATTAGAAATT 82620
CATTACAATA TTTCAATTTA TAAATCTTAT TAAAAATTAC TACTACCTAG ATCTCATTGT 82680
TTTCTTTTTT CTTTTTTGAG ACATGGTCTT GCTCTGTCAA GCAGGAGTGC AGTGGGACAA 82740
TCATAACTCA CTGTAGCCTC CAACTCCTGG GCTCAAACGA TCCTGCTACC TCAGCCTCCT 82800
GAGTAGGTGG GACTATAGGT GCACGCCACC CATGTGTGGC TAATTTTCTT TATTTTTTTT 82860
TGTAGAGACA AGGTCTCACT GTGTTGCCCA AGCTGGTCTT GAATTCCTGG CTTCAATCAA 82920
TCCTCCCGCC TCAGCCTCCC AAGGTGTTGG GATTTCAGAC GTGAGCCACT GCACACCTGG 82980
CCCCATTTTT TTTCCTTGAA TAAAGTGTAC TGGTAAATTT TAGGCTCATG AGGGTATATA 83040
TGCATTATTT TCTTCAAATC AAGCCTGAAT CAAAGAAACT TCTGCTTTAG TTTTAGTGAT 83100
ATTTGTCCCA AATGTTTAAA GACTGTATCA TTCTGATGAA TTGGATATTC CCATTGAGAG 83160
ATATTCAATA GGCCTTGATT GAAATGTTCT TCATTTTCTT TTTAAATTCT ATTTACAGTA 83220
GTCTGCATGT GTTAGAACTT TCAGAAAGGG AGAGATTTCT GTCTGGGCTG TCCCCACCAG 83280
CCAGAAGGGT CTGAGAGGCA CTGACTTGCC CTGGGGTGAT ATTTCTGCAG GACTTTGCTC 83340
CTCTGTAGGA AGACAGCCTA GAACAGAGGT GAAGGATGCC TCGGGCCTGC CTAGACCAAC 83400
AGCCATTCCC TGGTGATGCT GTAGTGTGAA GACCCTTGTC TTTCCCAACA CCTGTGATAG 83460
CTTTCAAATT ATTCTTTTCA GACAAACTTT ATGCCTGTTT CTTTATCTCT ATTTTGCATC 83520
CTAACAGAAA AAGCCAATCA CCTAGAAGGG AAAGTCAGAC TGGTCCCTGC TGCTTTCCCC 83580
ACATCTCCAC TGCCCCCAAT ATTGAATGCC GTGACAATGG AATGAAATTC CAATGTCCAT 83640
GAAATTCTGA GGGGAGACAT TTTGACTCAA GATTATATAC TCAGTGAAGA TGTCCTTTAT 83700
TTATTTATTA AATTAATTTT TTTTGAGATG GAGTCTCTCT CTGTCTCCCA GTTTGGAGTG 83760
CAGTGGTGCG ATCTCGGCTC ACTGCAACCT CTGCCTCCTG GGTTAAAGTG ATTCTCCTGC 83820
TGCAGCCTCC TGAATAGCTG GGACTATAGG TACTCACCAC CACACCTAGC TAATTTTTTT 83880
TTTTTTTTTT TTTTTTTTGG TAAAGATGGG GTTTCACCAT GTTGGCCCGT CTGGTCTTGA 83940
ACTCCAGACC TCAGGTGATC TGCCCGCTTT GGCCTCCCAA AGTGCTGGGA TTACAGGCGT 84000

*Fig. 5T*

```
GAGCCACCTT GTCTGGCCAA AGACGTCCTT TAACTAAAGA CTTCTGGTGT ATGTTACCTT   84060
AAAAATATAA ATATAAAAGC ATGAAGAAAA TACAACCTCC ATGGAATTTT TTTGCCAATG   84120
AATCTAGAAA AATAAGAATT GATTCAAAAT AATGAATAGG GAAGCTGTAA TAAAATGACT   84180
TGAGGGTTCA TTGAGTCCAT TTAAATATAT ATCTCTTACT AAAATCACTA AGGGTCATAA   84240
TTAGACAATG AAGTAAGTGC CATAAATCTA AACAATGTAA ATAACAATAT ATCTAAAAAA   84300
AAAAAACTAA GGAGTTTGGA GAGAGGATAC GGGAGGATGT GTTCTTTCAT AGTAGGGAAT   84360
TAGTTAATAT TCTTTAAAAT GGAAACATGT AAGAAAAAAG ACCCTAATGA CTGAAAACTA   84420
AGTTTTCCTC AATCTTTTTT TCATATCCTT TGAAGGCTAT TTTAAGAAAT AATATCTAAA   84480
GAACATCGAT TTGATGTTCA CAATTCCAGT TGATTTTCCT TCTGTGAAAT TCAAATGAAA   84540
TTAAATAAAT ATGTTTTGTT AAAAATGGTG TCATCCCATT TAAGTAAATG TCCTTTCTTT   84600
TACCTATTTA TCCATCTATA ATCTGTATCT ATTCATCCAT CAATGGATAC ATGTGCACAG   84660
ATAAATGGCC CCTTTGGTGA AGGGCTGAGA GGGTATTGTT TTCTAACCCC AACCTGTGAC   84720
GGCTTCCATG AGGCCAATGG AATCATTTTG AAATGTGTTT ACCACAGCAG GGAGACACAG   84780
AAGACTGGGG TCTCACACCT GTGTGGGAAC TCCAGAGGGT GAGAAAAGGG CCAATGAACT   84840
GCTCCGGTGA CACAGCAGGG AGGGTGGCTG CCGTGCTGGG TGCGGCCTGC CTTCCTAGAG   84900
AATGTCAGGG AAAGGGATGT GGGGTCATTT CCTGTGGACA CATTTAAGCC AAGTAGGGGA   84960
GAGGTCTGGT ATGGGGTCCT CTTGGGGCCT GTTGGACAGG GTTGACCAGC AGAGAGAGGA   85020
TGCCCAAGGA TTGAAGGAGG AGTGGGTAAG AGGTTCTCTA GGTCATGGGA ACTTCTGAAT   85080
TTCCCATGGA AAGCACCACC ATAATCTGTG TGCAATGAAC AGCCAGACCC ACGTGGGAAT   85140
TCTAGGCCAG CAAGAATCCC TTACTTGCTC ACTGGCTGCC ACGTGGCTCT GACCATGGAG   85200
AGGTCTGGAA CTGTAGCTTC CCAGTGGGGG AGAAGTAGGC TGGGAGAGAG AAGGGGACAG   85260
AGGAACCACA CCCTCCTTCC CCACCTCCAA ACAGAAGCCA GTAAAAATTG AGGGATGGAG   85320
AAAAATATAA GGCTAAATTA AGTTTTGGAA CTTTGGCATG ATCAAGGCTC ACTGCAGCCT   85380
CAACCTCCTG GGCTCAAACA ATCCTCCCTT CTCAGCCTCC TGAGTAGCTG GGACTACAGG   85440
CACATACAAC CATGCTCACC TTTTTTTTTT TTTTTTTTTT GTAGAGATGG GGTATTGCTA   85500
TGTTGCTCAG GGCTGGTCTC AAACTCCTGG GCTCAAGCAA TTCTCCTGCC TCAGCCTCCA   85560
AAAGTGCTGG GATTACAGGT GTAAGCCATT GGCCCTGCCA AGTTTAAGAA CTTTTACAGT   85620
TATAAGAGAC TAGATATTTT AATTATTATT ATTATTTTTT AGACAGAGTC TTACTCCGTA   85680
TCCAGGCTGG AGTGCGGTGG CACAATCTTG GCTCACTGTA ACCTCCACCT TCTAGGTTTA   85740
AGCGATTCTC CTGTCTCGGC CTCCTGAGTA GCCAGAATTA GTAGAGACGG GGATTCGCCA   85800
TGTTGATCAG GCTGGTCTCG AACTCCTGAC CTCAAGTAAT CCACCTGCCT TAGCCTCCCA   85860
AAGTGCTGGG ATTACAGTAG ATATTTTAAT TTTTTTGCAT GGAGGCTATT TTTACTACTA   85920
AAAGTGAATG AAGTATATTT TGTATCTTCC AGGAGTTTGG AAAGTCAAGT CTATTTGCAC   85980
CCAGCCACGT GCCTGCCATG GTGCCCGCGG CCTCTCAATT TTTGACCTTT GTTTATGCTG   86040
CTCTGTCTAC CCAGAATGCT CTCCATCGAG GGAAACCTAC TCTCTCTTCA AGGCCAAATT   86100
CCAGCATCAC CTCCGCCATG AAGCCTTCAT AGATCTACTC AANGTAGAAA CTTCTTAACC   86160
CCTCTAAACT GTCTTAGCAT CTTGGTTGTA GTATTGGTTT AGAATAGCAC AAATTCTACC   86220
CAAAATCTCA CTAAGTCTAT TCTAAGCAAA TCTTGGATAA TTTGCTAACA CTAAAATTAA   86280
ACCTGTTCTC TTTTGGTTTT TTGCTAACAA TGAAACAAAC TTGGTCTTAC TCTTTTGCTC   86340
AAGCTGGAGT ACAGTGGTGT AATCATGTCT CACTGCAGCC AGGAATTCCC GGACTCAAGG   86400
GATCGTCCTA CCTCAGCCTC CTGAGTAGCC GGGACTACAG GTGTGCATAA CCGTGCCTGG   86460
CCAGTTTTAA AATTTTTATT TAGGGACAGA GTTTTGCTAT GTTGTCCAGG CTGGTCTTGA   86520
ACTATTGACC TCAAGTGATC CTCCCACCTT GGCCTTTCAA AGTGCTGGGA TTAGAGGTGT   86580
GAGCTGCCAC ACCCAGCCCC GTTCTCTCTT TTGCATCTAT ATTAGTCTCT GTGCTCTTGG   86640
GAAAAGTGGA CCAATATCAT TTCAAAACTT GATGAAAAAG AAAATTAAAA TCTCATCCTC   86700
GGGAACTGAA ATCACAAACC ACCCAGCAAG GTCCACACCT CTAGGAGACT GGCATTTAGA   86760
AGACAGGACC ACAGTTGAAG CAACGGTTCT TTCTTTACCC TCCCTGCCTG TGACAGACTG   86820
CATGTGCTGA TTATCCCTGC GTTTTCTGCA GAGCTTGCCT TCCTGGTGAT ACAGTACTTT   86880
ATTTTATTCT GAGGGCCCCT TCCTGCCAGG GGATATCTGT CAGGGGATAC ATAAAACTGC   86940
ACAAAATGGA ACAAGTTATA GGTCATATAA AATTTCAGGA CATTGTTGAG AAGGAGAAGT   87000
TGCTAAATTG GAGACACCAT GATGTGAAAT CCCAGGGTCC CAGAATATTG ATGGAACTAG   87060
TATGTTTTTC TTATGTAATA TTTTATGGTG TCTGGGAAAT GGAGTTGCCT AAGTGAACTC   87120
ATTTTTTATG TCTAGGGGAA TAGCAACATA ACTATCATCT AACACTAAAT AAAGAGGAGC   87180
AAAATGTGCT ACATTTAGAA AGTGATGGTA TTATCCCCAG CTGAGGCAGA CTTAGTGATG   87240
GTGTTAGAAA TAAAGTATGG TAGGAGGCTG AGGCAGGTGG ATTGCATGAG CTCAGGAGTT   87300
TGAGACCAGA CTGGGCAACA TGGCGGAAAC CCCATCTCTA CAAAAATCCA              87350
```

*Fig. 5U*

GTATAAAGTT AGTAAATGTG AGGCCTCTCT CGATGCCTGG GTCCTGGGCT TTGGTTCTCA 60

GTCCTCCATA AATCATCCTG CTGGAGGAGA AGACCCTTAG ATCTGGCTCT TCTCAGGGGC 120

ATTTTAAAGA CAAATGAAAA TAAA ATG GAA ACC ACT TCA CTA CAG CGG AAA 171
Met Glu Thr Thr Ser Leu Gln Arg Lys
1 5

TTT CCA GAA TGG ATG TCT ATG CAG AGT CAA AGA TGT GCT ACA GAA GAA 219
Phe Pro Glu Trp Met Ser Met Gln Ser Gln Arg Cys Ala Thr Glu Glu
10 15 20 25

AAG GCC TGC GTT CAG AAG AGT GTT CTT GAA GAT AAC CTC CCA TTC TTA 267
Lys Ala Cys Val Gln Lys Ser Val Leu Glu Asp Asn Leu Pro Phe Leu
30 35 40

GAA TTC CCT GGA TCC ATT GTT TAC AGT TAT GAA GCT AGT GAT TGC TCC 315
Glu Phe Pro Gly Ser Ile Val Tyr Ser Tyr Glu Ala Ser Asp Cys Ser
45 50 55

TTC CTG TCT GAA GAC ATT AGC ATG CGT CTG TCT GAT GGC GAT GTG GTG 363
Phe Leu Ser Glu Asp Ile Ser Met Arg Leu Ser Asp Gly Asp Val Val
60 65 70

GGA TTT GAC ATG GAA TGG CCG CCC ATA TAC AAG CCA GGG AAA AGA AGC 411
Gly Phe Asp Met Glu Trp Pro Pro Ile Tyr Lys Pro Gly Lys Arg Ser
75 80 85

AGA GTC GCA GTG ATC CAG TTG TGT GTG TCT GAG AGC AAA TGT TAC TTG 459
Arg Val Ala Val Ile Gln Leu Cys Val Ser Glu Ser Lys Cys Tyr Leu
90 95 100 105

TTT CAC ATT TCT TCC ATG TCA GTT TTC CCC CAG GGA TTA AAA ATG TTA 507
Phe His Ile Ser Ser Met Ser Val Phe Pro Gln Gly Leu Lys Met Leu
110 115 120

CTA GAA AAC AAA TCA ATT AAG AAG GCA GGG GTT GGG ATT GAA GGG GAC 555
Leu Glu Asn Lys Ser Ile Lys Lys Ala Gly Val Gly Ile Glu Gly Asp
125 130 135

CAG TGG AAA CTT CTG CGT GAT TTT GAC GTC AAG TTG GAG AGT TTT GTG 603
Gln Trp Lys Leu Leu Arg Asp Phe Asp Val Lys Leu Glu Ser Phe Val
140 145 150

GAG CTG ACG GAT GTT GCC AAT GAA AAG TTG AAG TGC GCA GAG ACC TGG 651
Glu Leu Thr Asp Val Ala Asn Glu Lys Leu Lys Cys Ala Glu Thr Trp
155 160 165

AGC CTC AAT GGT CTG GTT AAA CAC GTC TTA GGG AAA CAA CTT TTG AAA 699
Ser Leu Asn Gly Leu Val Lys His Val Leu Gly Lys Gln Leu Leu Lys
170 175 180 185

GAC AAG TCC ATC CGC TGC AGC AAT TGG AGT AAT TTC CCC CTC ACT GAG 747
Asp Lys Ser Ile Arg Cys Ser Asn Trp Ser Asn Phe Pro Leu Thr Glu
190 195 200

*Fig. 6-1*

```
GAC CAG AAA CTG TAT GCA GCC ACT GAT GCT TAT GCT GGT CTT ATC ATC    795
Asp Gln Lys Leu Tyr Ala Ala Thr Asp Ala Tyr Ala Gly Leu Ile Ile
            205                 210                 215

TAT CAA AAA TTA GGA AAT TTG GGT GAT ACT GCG CAA GTG TTT GCT CTA    843
Tyr Gln Lys Leu Gly Asn Leu Gly Asp Thr Ala Gln Val Phe Ala Leu
        220                 225                 230

AAT AAA GCA GAG GAA AAC CTA CCT CTG GAG ATG AAG AAA CAG TTG AAT    891
Asn Lys Ala Glu Glu Asn Leu Pro Leu Glu Met Lys Lys Gln Leu Asn
    235                 240                 245

TCA ATC TCC GAA GAA ATG AGG GAC CTA GCC AAT CGT TTT CCT GTC ACT    939
Ser Ile Ser Glu Glu Met Arg Asp Leu Ala Asn Arg Phe Pro Val Thr
250                 255                 260                 265

TGC AGA AAT TTG GAA ACT CTC CAG AGG GTT CCT GTA ATA TTG AAG AGT    987
Cys Arg Asn Leu Glu Thr Leu Gln Arg Val Pro Val Ile Leu Lys Ser
                270                 275                 280

ATT TCA GAA AAT CTC TGT TCA TTG AGA AAA GTG ATC TGT GGT CCT ACA    1035
Ile Ser Glu Asn Leu Cys Ser Leu Arg Lys Val Ile Cys Gly Pro Thr
            285                 290                 295

AAC ACT GAG ACT AGA CTG AAG CCG GGC AGT AGT TTT AAT TTA CTG TCA    1083
Asn Thr Glu Thr Arg Leu Lys Pro Gly Ser Ser Phe Asn Leu Leu Ser
        300                 305                 310

TCA GAG GAT TCA GCT GCT GCT GGA GAA AAA GAG AAA CAG ATT GGA AAA    1131
Ser Glu Asp Ser Ala Ala Ala Gly Glu Lys Glu Lys Gln Ile Gly Lys
    315                 320                 325

CAT AGT ACT TTT GCT AAA ATT AAA GAA GAA CCA TGG GAC CCA GAA CTT    1179
His Ser Thr Phe Ala Lys Ile Lys Glu Glu Pro Trp Asp Pro Glu Leu
330                 335                 340                 345

GAC AGT TTA GTG AAG CAA GAG GAG GTT GAT GTA TTT AGA AAT CAA GTG    1227
Asp Ser Leu Val Lys Gln Glu Glu Val Asp Val Phe Arg Asn Gln Val
                350                 355                 360

AAG CAA GAA AAA GGT GAA TCT GAA AAT GAA ATA GAA GAC AAT CTG TTG    1275
Lys Gln Glu Lys Gly Glu Ser Glu Asn Glu Ile Glu Asp Asn Leu Leu
            365                 370                 375

AGA GAA GAT ATG GAA AGA ACT TGT GTG ATT CCT AGT ATT TCA GAA AAT    1323
Arg Glu Asp Met Glu Arg Thr Cys Val Ile Pro Ser Ile Ser Glu Asn
        380                 385                 390

GAA CTC CAA GAT TTG GAA CAG CAA GCT AAA GAA GAA AAA TAT AAT GAT    1371
Glu Leu Gln Asp Leu Glu Gln Gln Ala Lys Glu Glu Lys Tyr Asn Asp
    395                 400                 405

GTT TCT CAC CAA CTT TCT GAG CAT TTA TCT CCC AAT GAT GAT GAG AAT    1419
Val Ser His Gln Leu Ser Glu His Leu Ser Pro Asn Asp Asp Glu Asn
410                 415                 420                 425
```

*Fig. 6-2*

GAC TCC TCC TAT ATA ATT GAA AGT GAT GAA GAT TTG GAA ATG GAG ATG 1467
Asp Ser Ser Tyr Ile Ile Glu Ser Asp Glu Asp Leu Glu Met Glu Met
430 435 440

CTG AAG TCT TTA GAA AAC CTA AAT AGT GAC GTG GTG GAA CCC ACT CAC 1515
Leu Lys Ser Leu Glu Asn Leu Asn Ser Asp Val Val Glu Pro Thr His
445 450 455

TCT ACA TGG TTG GAA ATG GGA ACC AAT GGG CGT CTT CCT CCT GAG GAG 1563
Ser Thr Trp Leu Glu Met Gly Thr Asn Gly Arg Leu Pro Pro Glu Glu
460 465 470

GAA GAT GGA CAC GGA AAT GAA GCC ATC AAA GAG GAG CAG GAA GAA GAG 1611
Glu Asp Gly His Gly Asn Glu Ala Ile Lys Glu Glu Gln Glu Glu Glu
475 480 485

GAC CAT TTA TTG CCG GAA CCC AAC GCA AAG CAA ATT AAT TGC CTC AAG 1659
Asp His Leu Leu Pro Glu Pro Asn Ala Lys Gln Ile Asn Cys Leu Lys
490 495 500 505

ACC TAT TTC GGA CAC AGC AGT TTT AAA CCG GTT CAG TGG AAA GTC ATC 1707
Thr Tyr Phe Gly His Ser Ser Phe Lys Pro Val Gln Trp Lys Val Ile
510 515 520

CAT TCT GTA TTA GAA GAG AGA AGA GAT AAT GTT GTT GTC ATG GCA ACT 1755
His Ser Val Leu Glu Glu Arg Arg Asp Asn Val Val Val Met Ala Thr
525 530 535

GGA TAT GGG AAG AGT CTG TGC TTC CAG TAT CCG CCT GTT TAT ACA GGC 1803
Gly Tyr Gly Lys Ser Leu Cys Phe Gln Tyr Pro Pro Val Tyr Thr Gly
540 545 550

AAG ATT GGC ATT GTC ATT TCA CCT CTC ATT TCC TTA ATG GAA GAC CAA 1851
Lys Ile Gly Ile Val Ile Ser Pro Leu Ile Ser Leu Met Glu Asp Gln
555 560 565

GTC CTC CAG CTT GAG CTG TCC AAT GTT CCA GCC TGT TTA CTT GGA TCT 1899
Val Leu Gln Leu Glu Leu Ser Asn Val Pro Ala Cys Leu Leu Gly Ser
570 575 580 585

GCA CAG TCA AAA AAT ATT CTA GGA GAT GTT AAA TTA GGC AAA TAT AGG 1947
Ala Gln Ser Lys Asn Ile Leu Gly Asp Val Lys Leu Gly Lys Tyr Arg
590 595 600

GTC ATC TAC ATA ACT CCA GAG TTC TGT TCT GGT AAC TTG GAT CTA CTC 1995
Val Ile Tyr Ile Thr Pro Glu Phe Cys Ser Gly Asn Leu Asp Leu Leu
605 610 615

CAG CAA CTT GAC TCT AGT ATT GGC ATC ACT CTC ATT GCT GTG GAT GAG 2043
Gln Gln Leu Asp Ser Ser Ile Gly Ile Thr Leu Ile Ala Val Asp Glu
620 625 630

GCT CAC TGC ATT TCA GAG TGG GGC CAT GAT TTC AGA AGT TCA TTC AGG 2091
Ala His Cys Ile Ser Glu Trp Gly His Asp Phe Arg Ser Ser Phe Arg
635 640 645

*Fig. 6-3*

ATG CTG GGC TCT CTT AAA ACA GCG CTC CCA TTG GTT CCA GTC ATT GCA 2139
Met Leu Gly Ser Leu Lys Thr Ala Leu Pro Leu Val Pro Val Ile Ala
650 655 660 665

CTC TCC GCT ACT GCA AGC TCT TCC ATC CGG GAA GAC ATT ATA AGC TGC 2187
Leu Ser Ala Thr Ala Ser Ser Ser Ile Arg Glu Asp Ile Ile Ser Cys
670 675 680

TTA AAC CTG AAA GAC CCT CAG ATC ACC TGC ACT GGA TTT GAT CGG CCA 2235
Leu Asn Leu Lys Asp Pro Gln Ile Thr Cys Thr Gly Phe Asp Arg Pro
685 690 695

AAT CTG TAC TTA GAA GTT GGA CGG AAA ACA GGG AAC ATC CTT CAG GAT 2283
Asn Leu Tyr Leu Glu Val Gly Arg Lys Thr Gly Asn Ile Leu Gln Asp
700 705 710

CTA AAG CCG TTT CTC GTC CGA AAG GCA AGT TCT GCC TGG GAA TTT GAA 2331
Leu Lys Pro Phe Leu Val Arg Lys Ala Ser Ser Ala Trp Glu Phe Glu
715 720 725

GGT CCA ACC ATC ATC TAT TGT CCT TCG AGA AAA ATG ACA GAA CAA GTT 2379
Gly Pro Thr Ile Ile Tyr Cys Pro Ser Arg Lys Met Thr Glu Gln Val
730 735 740 745

ACT GCT GAA CTT GGG AAA CTG AAC TTA GCC TGC AGA ACA TAC CAC GCT 2427
Thr Ala Glu Leu Gly Lys Leu Asn Leu Ala Cys Arg Thr Tyr His Ala
750 755 760

GGC ATG AAA ATT AGC GAA AGG AAG GAC GTT CAT CAT AGG TTC CTG AGA 2475
Gly Met Lys Ile Ser Glu Arg Lys Asp Val His His Arg Phe Leu Arg
765 770 775

GAT GAA ATT CAG TGT GTT GTA GCT ACT GTA GCT TTT GGA ATG GGC ATT 2523
Asp Glu Ile Gln Cys Val Val Ala Thr Val Ala Phe Gly Met Gly Ile
780 785 790

AAT AAA GCT GAC ATT CGC AAA GTT ATT CAT TAT GGT GCG CCT AAG GAA 2571
Asn Lys Ala Asp Ile Arg Lys Val Ile His Tyr Gly Ala Pro Lys Glu
795 800 805

ATG GAA TCC TAT TAC CAG GAA ATT GGT AGA GCT GGC CGG GAT GGA CTT 2619
Met Glu Ser Tyr Tyr Gln Glu Ile Gly Arg Ala Gly Arg Asp Gly Leu
810 815 820 825

CAG AGT TCC TGT CAC TTG CTC TGG GCT CCA GCA GAC TTT AAC ACA TCC 2667
Gln Ser Ser Cys His Leu Leu Trp Ala Pro Ala Asp Phe Asn Thr Ser
830 835 840

AGG AAT CTC CTT ATT GAG ATT CAC GAT GAA AAG TTC CGG TTA TAT AAA 2715
Arg Asn Leu Leu Ile Glu Ile His Asp Glu Lys Phe Arg Leu Tyr Lys
845 850 855

TTA AAG ATG ATG GTA AAG ATG GAA AAA TAC CTT CAC TCC AGT CAG TGT 2763
Leu Lys Met Met Val Lys Met Glu Lys Tyr Leu His Ser Ser Gln Cys
860 865 870

*Fig. 6-4*

AGG CGA CGA ATC ATC TTG TCC CAT TTT GAG GAC AAA TGT CTG CAG AAG 2811
Arg Arg Arg Ile Ile Leu Ser His Phe Glu Asp Lys Cys Leu Gln Lys
875 880 885

GCC TCC TTG GAC ATT ATG GGA ACT GAA AAA TGC TGT GAT AAT TGC AGG 2859
Ala Ser Leu Asp Ile Met Gly Thr Glu Lys Cys Cys Asp Asn Cys Arg
890 895 900 905

CCC AGG CTG AAT CAT TGC ATT ACT GCT AAC AAC TCA GAG GAC GCA TCC 2907
Pro Arg Leu Asn His Cys Ile Thr Ala Asn Asn Ser Glu Asp Ala Ser
910 915 920

CAA GAC TTT GGG CCA CAA GCA TTC CAG CTA CTG TCT GCT GTG GAC ATC 2955
Gln Asp Phe Gly Pro Gln Ala Phe Gln Leu Leu Ser Ala Val Asp Ile
925 930 935

CTG CAG GAG AAA TTT GGA ATT GGG ATT CCG ATC TTA TTT CTC CGA GGA 3003
Leu Gln Glu Lys Phe Gly Ile Gly Ile Pro Ile Leu Phe Leu Arg Gly
940 945 950

TCT AAT TCT CAG CGT CTT CCT GAT AAA TAT CGG GGT CAC AGG CTC TTT 3051
Ser Asn Ser Gln Arg Leu Pro Asp Lys Tyr Arg Gly His Arg Leu Phe
955 960 965

GGT GCT GGA AAG GAG CAA GCA GAA AGT TGG TGG AAG ACC CTT TCT CAC 3099
Gly Ala Gly Lys Glu Gln Ala Glu Ser Trp Trp Lys Thr Leu Ser His
970 975 980 985

CAT CTC ATA GCT GAA GGA TTC TTG GTA GAA GTT CCC AAG GAA AAC AAA 3147
His Leu Ile Ala Glu Gly Phe Leu Val Glu Val Pro Lys Glu Asn Lys
990 995 1000

TAT ATA AAG ACA TGT TCC CTC ACA AAA AAG GGT AGA AAG TGG CTT GGA 3195
Tyr Ile Lys Thr Cys Ser Leu Thr Lys Lys Gly Arg Lys Trp Leu Gly
1005 1010 1015

GAA GCC AGT TCG CAG TCT CCT CCG AGC CTT CTC CTT CAA GCT AAT GAA 3243
Glu Ala Ser Ser Gln Ser Pro Pro Ser Leu Leu Leu Gln Ala Asn Glu
1020 1025 1030

GAG ATG TTT CCA AGG AAA GTT CTG CTA CCA AGT TCT AAT CCT GTA TCT 3291
Glu Met Phe Pro Arg Lys Val Leu Leu Pro Ser Ser Asn Pro Val Ser
1035 1040 1045

CCA GAA ACG ACG CAA CAT TCC TCT AAT CAA AAC CCA GCT GGA TTA ACT 3339
Pro Glu Thr Thr Gln His Ser Ser Asn Gln Asn Pro Ala Gly Leu Thr
1050 1055 1060 1065

ACC AAG CAG TCT AAT TTG GAG AGA ACG CAT TCT TAC AAA GTG CCT GAG 3387
Thr Lys Gln Ser Asn Leu Glu Arg Thr His Ser Tyr Lys Val Pro Glu
1070 1075 1080

AAA GTT TCT TCT GGG ACT AAC ATT CCT AAA AAA AGT GCC GTG ATG CCG 3435
Lys Val Ser Ser Gly Thr Asn Ile Pro Lys Lys Ser Ala Val Met Pro
1085 1090 1095

*Fig. 6-5*

```
TCA CCA GGA ACA TCT TCC AGC CCC TTA GAA CCT GCC ATC TCA GCC CAA       3483
Ser Pro Gly Thr Ser Ser Ser Pro Leu Glu Pro Ala Ile Ser Ala Gln
        1100                1105                1110

GAG CTG GAC GCT CGG ACT GGG CTA TAT GCC AGG CTG GTG GAA GCA AGG       3531
Glu Leu Asp Ala Arg Thr Gly Leu Tyr Ala Arg Leu Val Glu Ala Arg
    1115                1120                1125

CAG AAA CAC GCT AAT AAG ATG GAT GTA CCT CCA GCT ATT TTA GCA ACA       3579
Gln Lys His Ala Asn Lys Met Asp Val Pro Pro Ala Ile Leu Ala Thr
1130                1135                1140                1145

AAC AAG GTT CTG CTG GAC ATG GCT AAA ATG AGA CCG ACT ACT GTT GAA       3627
Asn Lys Val Leu Leu Asp Met Ala Lys Met Arg Pro Thr Thr Val Glu
                1150                1155                1160

AAC ATG AAA CAG ATC GAC GGT GTC TCT GAA GGC AAA GCT GCT CTG TTG       3675
Asn Met Lys Gln Ile Asp Gly Val Ser Glu Gly Lys Ala Ala Leu Leu
            1165                1170                1175

GCC CCT CTG TTG GAA GTC ATC AAA CAT TTC TGT CAA GTA ACT AGT GTT       3723
Ala Pro Leu Leu Glu Val Ile Lys His Phe Cys Gln Val Thr Ser Val
        1180                1185                1190

CAG ACA GAC CTC CTT TCC AGT GCC AAA CCT CAC AAG GAA CAG GAG AAA       3771
Gln Thr Asp Leu Leu Ser Ser Ala Lys Pro His Lys Glu Gln Glu Lys
    1195                1200                1205

AGT CAG GAG ATG GAA AAG AAA GAC TGC TCA CTC CCC CAG TCT GTG GCC       3819
Ser Gln Glu Met Glu Lys Lys Asp Cys Ser Leu Pro Gln Ser Val Ala
1210                1215                1220                1225

GTC ACA TAC ACT CTA TTC CAG GAA AAG AAA ATG CCC TTA CAC AGC ATA       3867
Val Thr Tyr Thr Leu Phe Gln Glu Lys Lys Met Pro Leu His Ser Ile
                1230                1235                1240

GCT GAG AAC AGG CTC CTG CCT CTC ACA GCA GCC GGC ATG CAC TTA GCC       3915
Ala Glu Asn Arg Leu Leu Pro Leu Thr Ala Ala Gly Met His Leu Ala
            1245                1250                1255

CAG GCG GTG AAA GCC GGC TAC CCC CTG GAT ATG GAG CGA GCT GGC CTG       3963
Gln Ala Val Lys Ala Gly Tyr Pro Leu Asp Met Glu Arg Ala Gly Leu
        1260                1265                1270

ACC CCA GAG ACT TGG AAG ATT ATT ATG GAT GTC ATC CGA AAC CCT CCC       4011
Thr Pro Glu Thr Trp Lys Ile Ile Met Asp Val Ile Arg Asn Pro Pro
    1275                1280                1285

ATC AAC TCA GAT ATG TAT AAA GTT AAA CTC ATC AGA ATG TTA GTT CCT       4059
Ile Asn Ser Asp Met Tyr Lys Val Lys Leu Ile Arg Met Leu Val Pro
1290                1295                1300                1305

GAA AAC TTA GAC ACG TAC CTC ATC CAC ATG GCG ATT GAG ATT CTT CAG       4107
Glu Asn Leu Asp Thr Tyr Leu Ile His Met Ala Ile Glu Ile Leu Gln
                1310                1315                1320
```

*Fig. 6-6*

AGT GGT TCC GAC AGC AGA ACC CAG CCT CCT TGT GAT TCC AGC AGG AAG 4155
Ser Gly Ser Asp Ser Arg Thr Gln Pro Pro Cys Asp Ser Ser Arg Lys
1325 1330 1335

AGG CGT TTC CCC AGC TCT GCA GAG AGT TGT GAG AGC TGT AAG GAG AGC 4203
Arg Arg Phe Pro Ser Ser Ala Glu Ser Cys Glu Ser Cys Lys Glu Ser
1340 1345 1350

AAA GAG GCG GTC ACC GAG ACC AAG GCA TCA TCT TCA GAG TCA AAG AGA 4251
Lys Glu Ala Val Thr Glu Thr Lys Ala Ser Ser Ser Glu Ser Lys Arg
1355 1360 1365

AAA TTA CCC GAG TGG TTT GCC AAA GGA AAT GTG CCC TCA GCT GAT ACC 4299
Lys Leu Pro Glu Trp Phe Ala Lys Gly Asn Val Pro Ser Ala Asp Thr
1370 1375 1380 1385

GGC AGC TCA TCA TCA ATG GCC AAG ACC AAA AAG AAA GGT CTC TTT AGT 4347
Gly Ser Ser Ser Ser Met Ala Lys Thr Lys Lys Lys Gly Leu Phe Ser
1390 1395 1400

TAANATGACN ACGATGGAAC AGTTTGTGTG TCCTACATCT TCATTCCTAT AAAGAATGAA 4407

NAGAAATATT TTAACCTCAA AATTATTTAA AGTCCAAAGT GAAGCTCACC TAAACGTCGA 4467

GCCATAGAGT CTTTAATTGN CCGTTGGCAG TTGAGCTACA GTATCTGAAC CTTCTGAGAC 4527

CCGGAGTGCA GCATAGACTG TGAAGTCGGC TTCCTTTCCG ATTGCCTTCC GAACCCGTGT 4587

CACTGTCAGG TTGCAGTCTT TCTCTTCTTG CAGCAGTGTG TGTTGGAAAT GGAGGCTGTG 4647

TCGCTTTGAC ATATAGAACA GATCAGTANT TGCATAGGGA CAGATATGAA GATNCAGCCG 4707

GTCTTTGCTT TCTTATGCAG ATGCCTGTAT GACAGTATCA GTGCACCAGC CCAGCCAGGG 4767

AGACATCAGC TTCCATTTAA AAAGG 4792

*Fig. 6-7*

Genomic sequnce

>01459 01459

```
TGAGGTTATT CTTTGAAGGG GACAGAATCC CATTTCACTT TTACTAGATA AGAATTTAGA     60
ACCTAACATC TGCCACCGTA GACTCTGAGT TATTAAATTG AGAGGAAATG GCCAAAGTGT    120
ATCCTGTAAT GAAATAATCC TCATATGAAA TTGTTCTTAT ATGACATTGG AAGACCTGTC    180
TTGCTCTGTC TTTTCAGTTT TGGATACATT TTCTTGACAC AAACCGGTAT CAGAGCCAGA    240
CTCTTTTCTG CTCTAACATC TTGCTTCTGT ACGTTATAAT CCTCAGTCCT CAAGCGGTCT    300
CTAACATCTT GCTTCTGTAC GTTATAATCC TCAGTCCTCA AGCGGTCTTC GGCGACGTCA    360
GCTACTCTTT TTTTGTACAG AGTGATGGTT ATAAAGTCTT CTTGTTGAAA ATCACTGTGA    420
ACTTAGTAGC TATAGTAAAA TTTTCATAAA GATCCGTAGA AATTAAAATT ATAGCATAAA    480
TATACAACTA GCTTTTTCTA ACATTTTGTT ATCAGATTTC AGAATAATCA TACATTTTTT    540
ACATTTTTAC TAAAAAATGA GTATTTACAT ATTTGACCAA AATAAAATTG AACCATTTTA    600
GATAATTATT GAAACAATTT CCACATTAAG CAGTATAACT GCCAATTAGT TAATTGCTGA    660
ATGATTACAT ATTAGTTATT AATATTGTCT AGCAACAACT TTATCTTATA CTCAAAATGA    720
TTATATTGGC CATTTAACTT AATTAAGTTT CTCGCTTTTT TAATGCTTTT AGAAAAGATT    780
GGGATGCCTT ATTTAGTTTA GCCCTCAAGC AATTAGGTGA GGCAATTACC ATGGTAACAG    840
AAGGTATTCA TTTCCTTACC TTAGCTAAAG GTTTTGGGAA CAAAGAAACC TCTCAGCTCA    900
TCCATTGAAA CCCAACTTTC TCCTGAGCCT GGCATTAAGT GTTTGTTCTC TAAAAGAGGA    960
CTTAATTTTA AGTGGGGAAA ACATGCCCCT GAGCTGAGTC TCTTTGTCAT AGGGCGATTA   1020
AAAAGCTACC TCTTCTTAAT AGGAAGTGTG GTCTTAACTT TTATATTTCA CATTTTATAT   1080
TGAGAATTTC TACACTCATA TAATGTTTTG ATCAAACTTT CCCTTTAAAT CCTTGCCTTC   1140
CCTATCCTCT TTCTTCCTTT GTTTCCTTCT TTGTTTGTTT CTCTCTCTCT CTCTCTCTCT   1200
CTCTCTCTCT CTCTCTCTCT CTCTTTCTTT CTTTCCTTCA AATGCCCTGA ACGTCCTTAC   1260
GCTGCTTCTC GCTGCATGAG TACAGGATCA CCTGAGATAC CTACCTAGCT GTCAGGAACC   1320
ACATCCTGAA GAAGACAGAC CCTTGCTTCC CCAGTGGCTG GCTATCTGTT GCCAATACTG   1380
TAGGCTTCAT GAGCTTCCCC TCAGTGCACG CTGAGATTTG GCTGGCTTGA TTTTTTTGCA   1440
TGCAGACATA GCCTCTGAGA TGGACAATAA TCCTGCCAAC AGTCTTCCTG CCCCTCTTCT   1500
GCAATGATTC CCAAGCCTTG TGACATGGGA GTCACATTTA GAGCTGGTCA GTTTTTGTTC   1560
TTTTTTCTTT TGTTTTGAAT TAAACTCGAA ATCTCATTGG TATGCTCTCT TTTGACAAAA   1620
GGATACCAGA CCACCTCTCC TAACGGTCTA ATTGCTGTCA AATAAAATCA CTTAAGGTGT   1680
ATTTTTCAAC ACATAATTTA TAGTTTTTGA CAGGTAATTT ATTAATATTT ATTTGGCTAG   1740
TTCTACCATT CCCAAGCAGA AAGTCTACTT ACTAAATTAG CTATCATGAG GCAAATTTTG   1800
TAACTAATTT ATCAAAAATT CTGGTCATGG TGGTGCATAT CTATAATCCT ATCACCCAGG   1860
ATTGTGGTTC AAGGCCAATC TCAAAGGAAA CTTTGTCTCA AAACAAACAA ACAAACAAAC   1920
AAACAAATTA ACATGAAACA GAACACATTA AAAAAACCCA GGGTTTTTAC CAGAAATTTA   1980
ATTATTAAAT ATATCTTGGA AATTAAAACC AGACAACAAC AACAACAACA TCAACCCACC   2040
CTGAGTATGC TGTTAAAAAT ACCAGTACTA GAGGCCTGGA GACATTGCTC ATGCTTGAGA   2100
CTATTAAGCA TTCTTACAGA AGAATGGGTT CTGTTTCTTG CAACCTCATG GTGGCTCACA   2160
GCTCCCAGTA TATGGACATC TGAGACTGGA AATGATAGGA AGAATTAAGG CTTTACACAA   2220
ATATCTGTCT AAAAACACGC ATGCGCCAGG CTGTCTATAT ACAGCGACTC CTGAATATTC   2280
ACACTTGCAT TTAATTTGAA TTCTGCATTG TGATGCCATA TAAACTGTTA AGTGCAGTGG   2340
AATTCAGGAA CTTGTGGTAC TTTCTGTTTA GTTTAAGATT AAAAGTGCAG TTACTATGTA   2400
GTGGGTAAAG GTGCTTGCTT TGCAAGCCTG ACAGCCTGGC TCAGGGTTCA GCCTCTGTGT   2460
GATGTAGGAG AGAAGCACAC CAGAGCATCA GTAACACTGT CAGGCATTGG TGCCTCTCAT   2520
GAGCTGGATC CCAAGTTGGG CCTGTCATTC CTGTTCCCCA GGCTCTTCTC CATATTTTTC   2580
CCTGCAGTTC CTTTAGACAG GAACAATTCT GAGTCAGAGT TTTTGACTGT GGGATGACAA   2640
CCCCATCCCT CCACTTGGTG CCCTGTCTTT CTATTGGAGG TGGACTCTAC AAGTTCCCTC   2700
TCCCCACTTT TGAGCATTTC GTCTAAGGTC CCTTGCTTTG AGTCCTGAGA GTCTCTCACC   2760
TCCGAGGTCT CTGGTACTTT CTAGAGGGTC CCCCCATTTG AGGGCAACTG ACAGTGCATT   2820
GAGCTTACCA AATATTTTGT AAACTTCTTG TTGTTCAGAT TTAATTACAT CTTTAAAGAG   2880
TTTTGTCCCT AGCTATCGTT CTCGCCGGCA AGAACACACG CGGACAACCG GATTCTTCTG   2940
CGGCAAGCTT TATTGCTTCT TAAGGAGGGA AGACCCAGAC CCTGGAAAAT GGTGCTGCTT   3000
ATATAGCCCT CAGCGTGGCG TTTCAGCACC TGATGTGGCA TGTCACCTCC TGATTTGTTG   3060
CTCGCCCATC ACTTCATTAC TATGCCCCGA GATGGGCAGT GACTAGGCGT GAGTTCACTC   3120
TTGCACTTGC GCACAAGGCT TGTTTATTAG GCACAGCGGA AGCCAGCGCC ATCTTATAAT   3180
```

*Fig. 7-1*

```
GGTGATTACT CGCGGCACGG CTCTCCACAG AGTTTACCAG AAAATGTATT CATAAAATGA   3240
GTGTTATATT ACTTTCCTGT TATATTTATT CCCAATAATA TTGTTTATTT TATTGTATAG   3300
CTTTTTGCTA TTGTAAATAT AATTTTGACT CTGCCCTAAT TTCTGAGGAT GCATTGTCAT   3360
ATCAGAAAAA GTTTTATTAT AGTTTCTATT GTGTTTCTAT AGTTTTTATT ATAGTTTCTA   3420
GTTCAAACCA TATTACTGTT TTCTTTATCA ATTGAAAAAG AGCTACTTTT TAAATTATAG   3480
GCTCCTTGGT TCTCTGGTTA TAAACAATGG TATGCAAAAT AAAACCATTT ACCACTGTGT   3540
CTCTTAAAAA GAAAGTAGGA GATAACTGAC TTCACAAAGT TGCTCTGTGA TCCCCCACGC   3600
ATGTGTCATG GTGGGAGCTT GCTGGCATTC AAACATAAAC ATATCACAAA CGCACACACA   3660
TGCACACATA CTCTCTCTCT CTCACACATG CACACACACA CAATTTGTTA TTTCACTATT   3720
GAAGTCTTGA GAGACCAAAA GAAGGTTTTA CACTAAAAGG AACATTTTTA ATTATCCCCT   3780
CTGTTTCCTT TTTGAAGACT TGTAATATAA TTACATTATA GTTAAAACTG TAGCAATCAC   3840
AGATCACAGG GAAGATGCCC TGATAGCCCA GAAGTAGTAG CATGAAACAA TGTTTAATTA   3900
ATGCTGTCTG ACTCTCAAAT AATAACTAAT AGTACTAACA GAGCAGATGA GAGCTTTTAA   3960
TAGTATTTTG AAAATATTTT ATATAAAATT TAGTCATATT CAAAGCTGTC TATATGATTG   4020
GAAGGAATTA ACATGTCTCC TCTTTAAGGA AACAGAGACT CTCTTAGCTT TAAGGGCTTT   4080
GTGCCCTTGG TAATCCATGT AAGGGGCCTG AACTGCTGCA CAGCAGTTGG TTGTAAAGAA   4140
GTTTTTAGAC TGCCAAGCGA GACACTCCTC CTGCTGTTTG CTACCACTTG ATTAGAAAAT   4200
AGTTTGTGTG GTGGTTGTTA AATAAAATTC AAGTCATGAT CAAAAGTAAG CATAAAGTCC   4260
AATATATAGT AACCTTAATA ATGGGGGGAG GAGAGTGAGT ACTTGTCGAG TGTTCAAGAA   4320
GTCTCAGGTT CCGTCCACAG TCCCACATAC ACCAGGCACA GGGGCACAGA CCTGTCATCT   4380
CATCTCAGTA CGCGGGCAAG AAAATCAGGA GTTCAAAGCC ATCCTTGGCT ACATAGCAAG   4440
TTTGAGGCCA GCGTAGACGT CATGACATTC TGTCTCAATA AAACAAGCAA CAACAAGAAC   4500
ACTCCCCAAA CAACAACCTT CCCTCAAGTC CAAAGAAGAC TGAGACATGC GAGATGCACA   4560
GTAAACTAAG GTCATCAGGA GTGTGAGGGG CTTAGAGAGG ATGGGTGGGG GGGACTACAC   4620
TGTATGAAGC TGTCACAAAG ATGCACACTA GACAAGGGAA AATGTCTTTA AAATGCAGAC   4680
ATATAATCTT ATTTATTATT GTGTGTGAGT GTGGGTAGAC ACATGCCATG GCATGCATGT   4740
CAACTTTGTG GAGTTGCTTC TCTTTTTCTA CCTTTCCATG GATTCTGAGT CTCCAATTCA   4800
GGTCACCACA CCTGTGGAGT TAATACCCTT ATCTGCTGGG CTGTCTCATC AGCGCCAAAG   4860
AACTTGTTTT TAATACTGCC TGTGAATGAG ATGAATGGCA CTACTGAAAA ACTGTAAATT   4920
AATATAAATT ATGCTGATCC CTGCTTAGCC TCAAATGAAT GAGACCCAAA CTATAATTTA   4980
TTTATTGGGC TCTGCTCAAT TACCTCGGGA TGACCCCAAA TCTATTCTCT AATGCTAGTC   5040
TGGCTACTTC CCCAACTGTG CTCCCCAAAT ACTTGCCGTC TGAATCTTCC TGGGTGATTC   5100
CTGCTCTAGC AGCCTGGTGT CCCAGGAAGG CATTTCACTC AGGCAGTGCT GCTGGTCCAT   5160
CAGGACTAAT GGAGATCTCC TCTTTTCTAT GTCTTCTTCC CCATTCCCAC CCCACCCTTG   5220
TAATTGGTTG TTGCCAGTTT TACTTAACTA ATAGTTTTAA ATTGGATAAG TTTGCACAAC   5280
AAAGGTGGGT TGTAACTAGG GATTTGCTTG TCTTGGCGCA ACCAGATCAT GGAGTACAGA   5340
ATTTAACATA TGGATACAAG TAGCACCAGA CCAACCCACA ATAAAAAACA GACAAAAAAA   5400
AAAAAAAAAA AAAAAACCAG CAAAAAAAAC CCCCATAGAC AGTCTTTAAA TGATAAGAGC   5460
GGAAAAGTTG TAGGTGGTAA TAGATGGTTA GACAGGATAA TTTCAGGGAA GATTTAAGTT   5520
ATTTAAAAAA AATCTATTTA TATATGCATG CAATTGTGTG TGAGTGTGTG TGTGCGCACG   5580
TGATTGTATG AGTATGTGAT GGCCAGTGCT CTTGGAGGTC AGGGTGTCAG ATCTGGTAGC   5640
TGGAGTCTCA ACTTGGGTAG AAACTTTTAA CCTCTGAGCC ATCTTTCTAG CCCCAAGATA   5700
CTGGTTTTGT AAATAAATTT ACCTTTAAAT TCTCTTCCTG GGGGGTATCT AGATCCAATT   5760
TTGTACGTAA GCAGATATTT CAAATTAAAA TGATGCTGGT GTCACACAGC TGCCGATTAG   5820
TTACTGAGAT TTACGTTTGC TTCAACATTG TGCTGAACTA CATGCATAGC TTTTGTAAAA   5880
GGTTATTTGC TGAAACTAGC TTTCTGGTAT TTCACCAGTA ATATACTCTG GGCACAGAAC   5940
AAACTTGTTT TCTGACTCAA TATAAATATA TTGCGTGTGT GTGTGTGTGT GTGTGTGTGT   6000
GTGTGTGTGT GTGTGTGTGC ATGTTATAAA ATCCTGTCTT CTGCTCATGA CATAGCTGTT   6060
TCATTAACTC ACAGCAGTTT GTATTTGCCT GCATGAGACC TATATAAGAT CAAGCCAGTC   6120
TGAATCCCAG CATGCAAAGG GGAGATGCTA TCTGGGACCC ACCCTTCATG GGAGATACAG   6180
GAATTGGTGG CTCCTGGGGG AGGGAAGAGT AATTTTTCTT TGGGAGTGTG GCCATTGTCA   6240
TCTTGTCCAT GTTCCAGTGG ATAGCCCTAC ACTCATACAC AGAAGCAACA GTAACTGGAC   6300
TTAGTGGGTT ATAAAAAATA TTAGAAATGG AATTTGTATA CAACCGAGCC GTATCACTCC   6360
TGATCATATA CCCAAAGGAC TTTACCATAC AATAGAAGTA TTTGCTTAGC CATGTTTATT   6420
GCTAATCTTT TCATAATAGT GAGTATGTGA ATAAGTGGAT GAGTGGATAG AGAGTCTGGA   6480
```

*Fig. 7-2*

ACTAGGTAGG AGACCATGAA CGGGAACAGT AGGTGTTGAG AAGGGGCAGG AGCAGAAAGC 6540
AAAAGGTCAC ATTGGGCATT GTCTTAGTTA GGCTTACTAT CGTTGTGACA AAACACAAAA 6600
TAAAATCTCC AAAAGCAACT TGGGGAGGAA AAGATTAGAA TTTACGACTC TTGAGTTCAT 6660
ACTCCATCAC TGTGGGAAGT CAGAGCAGGA ACTCTAGGCA GGAACTGAAG GAGAGGCCAA 6720
GGAGGAACAC TGCTTACTGG CTTTCTCTTC ATGGCTTGCT CAGCCTGTTT TCTTAGACAC 6780
CAAGAACAAC CTGCCCTGGG GTGACATCAC TTACTGTAGA CCAGGCCCTC CCACATTAAT 6840
CATGTGTCAA GAAAATGTCC CACATGCTTT CTTTAAGGCC AATCTTATAG AGCTGTGGGA 6900
AGCCACATGT GCCGTTGCAG AGTGGCACCG GCTACTGCTG GCTACCACGC ATAAGTTTGG 6960
ACAAACAACC AATGTGTACA TATGCAGTAA AGCTTTTTGC CAAGTCACTG CCTGGCCCCG 7020
GCATGTTAAT GAGGTACTGA GAATATAACC AATCAGATGT GAGACATGCA AATGAGGTAT 7080
GATAATGAGG TTCTGTGAGG TACTGAGAGA GAGTAGCCAA TCAGATGAGG AACATGCAAA 7140
TGAGGCATAG TGCATAACCA ATCCGTGTGT GAGACACGCC TCTCCTAGGC CTATATAAGC 7200
AGCACCAGTT CTGGGCTCAG GGTCTCTTTG CCTCTGCAAT CAAGCTCTCC CAGAAGGATC 7260
CTGTTGCAGC GTCGTTCTTG CTGGTCAAGT CGGGCGAGCA CAAAATAGAG CCTTTTTTTT 7320
TTTTTAAATT GAGAGTCCCT CCTCCCAAAT GACTCCCGCT TGTGTCAGGT GGACAGTAAA 7380
CTAGCCAGGA CAGATGACCC CCTTGTCAAC TTGGCACACC AGTACTTATT ATGAAAACAT 7440
AACCTTTCCC TTTTTGTTCA TTTTTAAGGT CTCATATTAA TATTATAATA TAAGCTATAA 7500
ATAACTTTAA AAGTTTCATA TTCTTTAAAA ATTCAAAAAA TTTACAAGTT AAGTCTCTTT 7560
AAAATATCCA AAATTTCTCT AAAATTACCA AGTTTCTTTG AAATATCCAA GGCCTCATAA 7620
ATGGATGTTT CTGTAAAATT AAAATAAATT ACTTTCTTAT TCCAAGAGAG AAGAAGCAGG 7680
GCACAGCCAC AGAAAATTCT GAGTGCACAT TAATAACTAA GTAAGATAAT GCCCCATAGG 7740
GTTGTCTTCT GTCGGCCTGT CTTACAGAGG CAATTTCTCA ATTATGCTTC CCTTTTCTCA 7800
GACAACACAT ACTTGTGTCA CATTGGCAAA AATCTAGCCA ACAAAGGCTT GAAAGCAGAA 7860
GGCTACTGGG GATGGCAGGG CTCAAGGACT GGGGACTTGG TGATTAGGGA GAAATAGGGC 7920
ATAGGAAGAG AAACCGCAAA AACAAAAATT TCTTGTAAAA ATGCTACAAT GAAACCTAAT 7980
CATCTGTATA TAATAAAAAG TGAATAGAAC AGATTGTACA TCTGTAATTT GCTATCATCT 8040
TTTGACTTCT GTTAGTGGTT TTGAAATCTT GGCAAAAAGC AACTTAACCA TTAACAGTTC 8100
TAAATTGCTT TAGGGTTTAT AAAACCTGCA TTTTCACATG AGATTGTCTT ATTACATTAA 8160
AGTTGGGTGG ATCTGGGAAG AGTTACACTA TGTATGCAAT TCTCAAAGAA CCGAGGAAAG 8220
GAAGATAAAA TTTCTTTATA TTATTTAATA GTGCTGAGTG TAGTAGGCTG TTCCTCCATC 8280
TTAAATGCGT GCTCTGATTT CTTCATGGTA ACAGAGGTTT CATCAGGAGA CTCTTCCAAA 8340
ACATATTTAA AACTTTACTC CCCACAAGAC ATTTGGGTAA CAGGAACTTT CCGGANGTGT 8400
GAGGAGTTTA TTACTTGGCT TTAGTATAAA TCATGTAGGA GCATGGATGC ATTTCATTAT 8460
TGAAAAAATA ATATATTTGG AGTCTCATAC TTGAAGTCTG GGTTATATTC CAGAGAGCCC 8520
TCAAAACTAG TAACAGCTTA AGAGAAAGAT CATCCAAGAA ACCCTTTCTT TTTAGGGAAG 8580
TGTCTCTTAC TCAGCCAAGA GCACAGTGAA AGGGCTTAGT ATTGGACAGC TATTATATCT 8640
TCAAAACTAG GTCTTTATTT TATTTTACGA ATAAATCCAG TAGTTGCTCT GAGTCAGCTT 8700
ATACCTTATG AGAGATGATA ATTATACAGA AAATCAAAGA TGCTGAAAAT GTAATACCTC 8760
ACATACTGAG GGATCCTGTT CATTAAGGAG ATAAAAATTA TTCTTTTGAA GGAGCAAAGC 8820
TATACACATA ACATATTAGA ATTTTGAAAC AGCCACAATC ATAGAACTTA ATTTGTTATA 8880
AAAGGAAGAA GTAATGTATA GTTAATAAGT GGTTTAAGCC TTGTCCTTGA GGCTAGATGT 8940
TATAACTCAT ACTAAATATG TATGTTTGTT TCAGGCTAGG TATCATATCC TACACGAAAT 9000
ATGTATGTAT GTTTCAGGTT AGATGCTATA TCCTACACTA ATTATATATG TTTGTTTCAT 9060
TTTCAGTCCT ATCTATGGAG CTGTCTCTGA GCTTTCTATC AAATATTTGT CATATTTATT 9120
CATAGATATT GTTTATTGGA ATTTGCAAAC AGGGCATTTT AAAGACAAAT GAAAATAAAA 9180
TGGAAACCAC TTCACTACAG CGGAAATTTC CAGAATGGAT GTCTATGCAG AGTCAAAGAT 9240
GTGCTACAGA AGAAAAGGTA ATTGTTCATT GATTATTTGT CTAAATGGGC AATCTTGTTT 9300
GAGTTTGACT ATGCAGTGAG TCACATCATT GCTTGTGAGC TTTGGGTCAT TGTTGAGGTA 9360
AAACTTTCTG TTGTGTGAAT GAACCAGAAC TAAGTTGTTC AAAGGTAAAT GAGACTCAAT 9420
TTTATACATG TTTTATAAAA TGAGATTCCC TAGAGTATAT TCTTTCTTTT TATAGTTAGC 9480
ATTCTTAGTT GAAGTTATTG GTTTGTTCAA ATTCAAGTAA TAATTTATAC AATATTAATG 9540
TTGGCATTTT TTGGTTAAAA TAGTTTGAGT CCTTAGAGGC TTAAGATCTG ATAATTAGCC 9600
ACCAACATTT TTTTGTTTTC TTTTTCAATA TTTTATTAGA TATTTTCTTC ATTTACGTTT 9660
CAAATGCTAT CCCGAAAGTC CCTTATACTC CCTCACTCCA CCCACTCCCC TACCCACCCA 9720
CTCCCACTTC TTGGCCCTGG CGTTTCCCTG TACTGGGGCA TATAAAGTTT GCAAGACCAA 9780

*Fig. 7-3*

GGGGCCTCTC TTCCCAATGA TGGCTGACTA GGACATCTTC TGCTACATAT GCATCTAGAG 9840
ACATGAGCTC TGGGGGGTAC TGGTTAGTTC ATATTGTTGT TCTACCTATA GGGTTGCAGA 9900
TCCCCCCAGC TCCTTGGGTA CTTTCTCTAG CTCCTCCATT GGGGGCCCTG TGATCCATCC 9960
TATAGATGAC TGTGAGCATC CACGTCTGTG TTTGCCAGGC ACTGGCATAG CCTCACACGA 10020
GACAGCTATA TCAGGGTCCT TTCAGCAAAA TCTTGCTGGC ATGTGCAATA GTGTCTGCGT 10080
TTGGTAGCCA CCAACATTTT AAGGTTACAT TATTGCATCT AGCATGCTAA TATAATTATG 10140
AGGAAAAAAC AAGTAAATTA AGTGACTTCA CAAAAGAAAG ATTGGATGTT TGAAAATAGA 10200
ATTGTGTGGA AAAATAACTT TATGTTTACC CTTGTTAATC TGACCTTATG AATTCTTACT 10260
CTATAATATA AAATGTAGTG CTATAAATTT CTTCAGTGAA CTTTATTATT TCAGTTAACA 10320
CTACAACTTA CTGTGATATT TATTTGTGCC TGTTTTGAAT TTTGCTCAAC TCAAGGCCTG 10380
CGTTCAGAAG AGTGTTCTTG AAGATAATCT CCCATTCTTA GAATTCCCTG GATCCATTGT 10440
TTACAGTTAT GAAGCTAGTG ATTGCTCCTT CCTGTCTGAA GACATTAGGT AAGGGATTGG 10500
AAGTTCTTAC CATTAAGTTT GTACCCGTAA GAAATAGCGA TATTTATGAG TGCCTAGTTT 10560
TACAATGGAA GTATATCTCA GAAGTATATT TACATACATC ATATCACAGT TGTATTCTAC 10620
TTTTTAAAAT ATAAAATAAA CTCACTAAAT TAAATTAGTA AGGTTCCTAT TTGTTAATTA 10680
GTAACCTTTT CTACTTTATT AGATACTTTT TTTTTCTTTT AGTGCTTTAG ATGTAAATAC 10740
AGGTAAAACT ATTGAAGACA ACTGTTTACC AATTTAGGAA AAAATGGAAA ATGTTATTTA 10800
ATGTCGAACT ATTTTCATAT CTTAAAACAT CAATGTATTA AGTAATGTTT ATGATTCTCT 10860
GTTTTATTTT TTTTAATTTA TTTTTAGCTT TTAAAATTGT GTTAGGATGC CTCCTCTGCG 10920
TGTATGTTTG TATACCACAT GGTTACGGTG TCCACAGAGG CCAGGAGAGG GCTTTGGATC 10980
CCCTTGAACT GGAGTTGTGA GCGATCTTAT GGGTGCCGGG AATCAAGCCT AGGTTCTCTG 11040
GAAGAGCAGC CAGTGCATTC AGCTGCTGAA CCATTTTAAA AGATAGTGAT AGTTCCTGCA 11100
AATGGTCCAT GAAAAGAGCT TTAGCAATGA CTGTTGGTAC TTTAAGAGTT GCCTGTCTTT 11160
GTTTTTCTAA GGCTATAACA AAATCCATGG CCTGAGTAAA TTATAAAAAA ATACATATAA 11220
GTAAATTCAT AAATAAATTT ATTCCTTACA GTTTTGGAGG CTATAGAGCC CCCAGAGAAT 11280
GGGATTGGCA TTTGTAAGGG GACCATTTTT TTTTTTAAAT TGGATATTTT CTTTATTTAC 11340
ATTTCAAATG TTATCATCTT TTCTGGTTTC CTTCCCTCCT GGAAACCCCC TATCACATCC 11400
TCCGTCTCTC TGCTTCTGTA AGAGTGTTCC TCTACCCACC CACCCACCCA CCCACCCACT 11460
CCCACCTTCC TGCCCTTGAT TCACCTACAC TGATGCATCT ATTGAGCCTT CATAGGACCA 11520
CGGACATCTC CTCCCACTGA TGAATGACAA GGCCATCCTC TGCAACATAT GCAGCTGGAG 11580
CTATGTGTAC TCCTTGGTTG ATGGCTTAGT CCCTAGTTTT CTGGGGGTGG GGGAGGTGTG 11640
ATCTGGTTGG TTTATGTTGT TGTTCTTCCT ATGGGATTTC AAACCCTTTC AACTCTTTCA 11700
GTCCCTTCTC TAACTCCTCT ATTAAGGACC CTGCGCTCAG TCCAATGGTT GGCTGTTAAC 11760
ATCCACCTCT GTATTTGTAA GGCTCTGGCA GGGCCTCTCA GGAGCAGGCT CCTTTCAGCA 11820
TGCACTTCTT GGCATCCACA ATAGTGTCTG GGTTTGGTAA CTGTATATGG AATGAATCCC 11880
CAGGTGAGAC AGTTTCTGGG TGGTCTTTCC TTCAGTCTCT GCTCTTCACT TTATCTCCAT 11940
ATTTGCTCCT GTGAGTATTT TGTTCTCCTT CTAAGAAGGA CCGAAGCACC CCCACTTTGG 12000
TCTTCTTTCT TATTGACCTT CATGTAGTCT GTGAATTGTA TCCTGGTCAT TTGGAGCTTT 12060
TGGGCTAATA TCCACTTATC AATGAGTGTA TAATATTTGT GTTCTTCTGC GATTGGGTTA 12120
CCTCACTCAG GATGATATTT TCTGTCCATT TGCCTAAGAA TTTCATGAAT TCATCATTTT 12180
TAATAGCTGA GTAGTAAGTA CTCCATTGTG TAAATGTACC ACATTTTCTG TATCTATTCC 12240
TCTTTTGAAG GACATCTGGC TTCCTTCCAG CTCCTGGCTA TTATAAATAA ATATATAAAC 12300
ATAGTGGAGC ATGTGTTCTT ATTACATATT GGAACAGAAA GAGCAATTTG CAAATTCATT 12360
TGGAATAACA AAAAAAAAAA AAAAAAAAAC CCAGGATAGC GAAAACTATT CTCAACAATA 12420
GAAGAACTTC TGGGGGAATC ACCATCCTGA CCTCAAGTTG TATTACAGAG CAATAGTGAT 12480
AAAGACTGCT TGGTAATGGT TCAGAGACAG GCAGGAAGAT CAATGGAATA GAATTGAAGA 12540
CCCAGAAATG AACCCACACT CATATGGTCA CTTAATCTTT GACAAAGGAG CTAAAACCAT 12600
CCAGTGGAAA AATGACAGCA TTTTTAACAA ATGGTGTTAG TTTAACTGGT AGTCAGCATG 12660
TAGAAGAATG CAAATCGACC CATTTTTTTC TTTTCTTTTC TTTATTTACA TTTCAAATGT 12720
TATTCCCTTT CCTGGTTTCC CCTCTAACCC CCCCCCCCCC CCACACACAC ACACACACAC 12780
ACCAACCCAC TGGCTTCCTC TTCCTGGCCC TGGCATTCCT CTATACTGGG GCATAGAGCC 12840
TTCAAAAGAC CAAGGGCCTC TCCTCCCATT GATGACCAAC TAGGCCATCC TCAGCTACAT 12900
ATGTAGCTGA AGCCATGAGT GTGCTCTTTG GTTAGTGGTT TAGTCTCTGA GAGCTCTGGT 12960
GGTACTGGTT AGTTCATATT GTTGTTCCTC CAATGGGGCT GCAAACCTCT GCTACTCCTT 13020
GGTTACTTTC TCTAACTCCT TCACTGGGGA TCCTGTGCTC AGTCCAATGG ATGGCTGTGA 13080

*Fig. 7-4*

GCATCCATTT CTGTATTTGA AGTTGACCCA TTCTTACCTC CTTGTACAAA GCTCAAGTCC 13140
AAGTGGATCA AGGACCTTCA CATAAAACCA GATACACTGA AACTTATAGA GAAGAAAGTG 13200
GGGAAGAGCC CCAAACATAT GGGCACAGGG GAAAAATTCC TGAACAGAAC ACCAATGGCT 13260
TATGCTGTAA GATAAAGAAT CAACAAATGG GACCTCATAA AATTGCAAAG CTTCTGTAAG 13320
GCAAAGCACA TTGTCAATAA GAAAAAAAGG CCACCAACAG ATTGGGAAAA GATCTTTACC 13380
AATCCTACAT CTGATAGAGG GCTAATATCC AATATATTCA AAGAACTCAA GAAGTTAGAC 13440
TTCAGAGAAC CAAATAACCC TATTAAAAAT GGGGTTCAGA GCTGTCTTAG TCAGGGTTTC 13500
TATTCCTGCA CAAACATCAT GACCAAGAAG CAAGTTGGGG AGGAAAGGGT TTATTCGGCT 13560
TACATTTCCA TATTGCTGTT GATCACCAAA GGATGCAGGA CTGGAACTCA AGCAGGTCAG 13620
AAAGCAGGAG CTGATGCAGA GACCATGGAG GGATGTTCTT TACTGGCTTG CTTCCCCTGG 13680
CTTGCTCAGC CTGCTCTCTT ATAGAACCCA AGACTACCAG CCCAGAGATG GTTCCACCTA 13740
CAAGGGGCCT TTCCCCCTTT ATCACTAATT GAGAAAATGC CTTAGAGTTG GATCTCATGG 13800
AGGCATTTCC TCAACTGAAG CTCCTTTCTC TGTGATAACC CCAGCTGTGT CAAGTTGACA 13860
CAAAACCAGC CAGTACAAGA GCTAAACAAA GAATTTTCAA CTGAGGAATA CTGAATGGCT 13920
GAGAAGCACC TAAAGAAATG TTCAACATCC TTAATGATCA GGGAAATGCA AATCAAAACA 13980
ACCATGAGAT TCCACCTCAC ACCAGTCAGA ATGGCTAAGA TCAAAAACTC AGGTGACAGC 14040
AGATGCTGGC AAGGATGTGG AGAAAGAGGA ACACTCCTCC ATTGCTGGTG GGATTGCAGG 14100
CTTGTACAAC CACTCTGGAA ATCAGTCTGG CGGTTCCTCA GAAAACTGAA CATAGTACCT 14160
ACTACCTGAG GACCCAGCTA TACCACTCCT GGGCATATAT CCAGAAGATG CTGCAACATC 14220
TAAGGGAACT TTGTACTGCG TCTGTATCAG GGTAGAGGCT AAGATGGGTT GGGATTAAGC 14280
CAGTTCTCTG GATACCTGTT CTGGGAGTGG AGCCCTGATG AGCCAAACAC TTGTGTTTAG 14340
GCCCCACCTC CACGCCCTGC TCCATTAAGG ATTCCATTTT AACAGGGACT ATGAATAGGA 14400
TATTCATGAC CCAGCACCTT GTGTAATTCG GGTTCTGGAG TAATGCAATC TAAGCCTCTT 14460
GATGCAACTT ACACTGAGAA GTAGTAAATC AATTCAGATC ATTGAAATGA CTGCGTGTGT 14520
CCTTTTGGTT TTTAACTATT TTCATGAAAA GCAGAAGTGA ATAAAGTTGT TCATCAGTGC 14580
CCTCCTGGTG GTTGGTAAAT GTGATCTAGA AGTGGCATTT AGGTATCTTT ACTTCCACTG 14640
CATTTACTGG TTATGTGTGG GCTTCATTTT GCTGAACTAA AATTAGACTT ACAGAATAAG 14700
TAAATCTATT ACACACGGTT ATATATTGTC CTCACCATGT TACCTTTGTC TTCCTACGGT 14760
ATGACATGTG TTTTATTAGT CAGAGGGTTT TTTTTTTTTG GTTTGTTTGT TTATCTTTTG 14820
TTTTTAAAGG AATAGAACTG GCAGAATGAA CGTATATATA TATCAAACAG GGATTTATTA 14880
GTGTGGCTTT GCAGACTGAG GTCTCTTGTC CAACAATGGC TGTGCCTCAT CAAAGCCAAG 14940
AATCCTTTTT TCTCGTAGTT GTTCATTCGA GGAGCCTGGG TGTCTAAGTC AGTCTTCAGT 15000
CTGCATGGGC TTCCTGAAGA AGGAATTTCT AACACCAGCT AAGTAGTGCC TTAGTAGCAA 15060
GACAGACGAA CTTGCCAGCC AGACTGAGGA CAGGCTGACA AAAAGCCAAA GCTTCCCTCT 15120
TCCGTGCCCC TTCAGAAGTG GGCCGCCATC AGAAAGCGTA ACCTAGATTT AGGATGCTCT 15180
TCTCCTGTCA CATAATCTAA TCAAGAAAAG CCCTCATAGG TGAGCCCAGG GCTTATATTT 15240
TAGATGATTC CAAATGGAGT CAGGTTGCCA GCCAAGATCA GCTCAGCACA GTAAGTTGAA 15300
GTGGTCTGAA TGAAGCTCTG TGTTCATTTT GAAGTGCAAG ACGGGCTTGG TTTGCTTTGC 15360
ATTACTTTTC ATATGGCCAC TTTGGAGATC CTCGCATCAG GGGCTGGAAA CATGGCCCCC 15420
CATTAAGAGC AGGAAGCGCT ATTGCAGAGG ACCCCAGTCT GGTTCCCAGT ACCCATAATG 15480
GTGGCTCACA GACCTCTGTT TTCTATGACT CCAGCTCCAG GGTGCTGAGT CCCTCTTCTG 15540
CCCTCTACAG GCACCTGTGC TTATGTGCAC ATATGTACCC CTCTTCCCAT ACACACCTGG 15600
TTAGAAAAAT AAAAATCTTA AAGAATATTT TTACACCAGG GCCAGTGACA TGGCTCAGCG 15660
GGTAACAGGG CCTGCCACCA AGACTGGAGA TCTGAGTTCT AATCCCATTT CAACCTCAGA 15720
GGCTCATGGT GGAAGCCAAG AGCTGATCCT GAATTCAACA TGCATGGGGC CACCAAAAAA 15780
GAAAGAAAGA AAGAAAGCAA TTTAAAAAGA TGTTTACCCC ATGGGGTTTC AACAGTTTGA 15840
TATGACATAC CTTTGTGTGC TGAAGTTTGT GCTGATCCTG CTTGGGGACC ATCGACCTTT 15900
TTTTTTTTTT TTTTTAAATT TGTGGGTTTA ATAGTTTTTG TCCAATTTGA AAATCATCTT 15960
CAGTTTTTAT TTTTTTCAGT ACTGTGCTTT TCTGGGACTC TGATATACAT ACACTAGGTT 16020
GCTGGATACT ATGTCTTAAC TTCTTTTCTC TTTTTGTTTA TGCTTTGGTT TGAATGTTTC 16080
TTCTGCTGTG TCTTTAAGTT AATCACCTAT ATTTCTTCTG TAGTGGCTGA TCTACTGTAT 16140
ATCCTCCCTG TGTATTTTTA ATTTTCATTG TGTTTTTCTC TTTTTTGTTA TTGAAAATGA 16200
TTTTTTTAAA AATACAACAC ATTTGGACTG TGGTTTCCCT TTCCACAACT CACCCCAAAT 16260
CCTCTCCACC TCAACAGAAA AAGAAAGGGC CAGAGAAGAA GCACAGGAAA CACATACAGA 16320
TGCAGGCCAC ACACGTGTAC ACACAGGAAT CTCATAAGTA CACAAAATCA GAAACCAGAT 16380

*Fig. 7-5*

ATATAAAAAT TATATAAGCA AAAGACTTGC TAGATTAACA AAATAAAGGT TCATTCTCTG 16440
TTGGCCATTT ACTGCTGGGC CTAGGGCCTG CTGGTGAGTG TGGTTTGTAT ACCCAGTGAG 16500
TCTGGTGGAG AAACTAGTTT TTCCTTTGTG AGTGGTTATA AATAGGAGAT AATTTCTGGG 16560
TGAGGGATAG GATCGGCGCT GGGACTTTAT CTGGTTAGAC CTGGGTAGAC CCTGTGTGTG 16620
CTCCCACATG AAAGCTCTTC TGTGCTTTAT CAGCCCTGCT GTGTCTTGAA GGGCTTCTTG 16680
CCTTGGTGTC TTCCATCCCA CTGGGTCTTA CAACCTCTCT GCCCCCTCTT TTGCAAAGTT 16740
CCCTGAGCCA TGCGGGGAGG GGTCTGTCAT TGTTCCCATC TCCTGCAGGA GGCAGTGTCT 16800
CTGACATTGG CTGGGCAAGA CACTGAGCCA TGAGCATAAA AAAACCCTGC CAATTTGCTA 16860
TTCATTGTGT GCATGCTTTC CTTTAAATTC CTGAACATAT TTACAATTTA TAATAGTTTT 16920
CGTTTGTCTT GTTTTGAGCA GGGGCTTATG TAGCCTAGGC TGGCCTTGAA TGTACTCTGT 16980
CGCCAAGGCT GATCTTAGTT CCTGATCCTA TTGCCTATGC CACCAAGTGC TGGGATCACT 17040
GACTTGTGCC AGCAGGCCCT GCTGTGACCA TAATGCAAAT TTCAGTGATA TTTTAGCTCT 17100
ATTTTTGCCT CTATTGAGTG ATCACCCCGC CAACTGATTA TGTTTATGTT TGATATGTGT 17160
CAGGGCTGTT GAGGTTTTTT TTCTTTTTCT TTTTTTTTTT TTTTTTTTGG TCTGCTGTTG 17220
TGATTTTACC TTGCTCAATA TATATATATA TATATATATA TATATATATT TTTTTTTTTT 17280
TAGTTTGCTT TCTAAGAAAA GAGGTTTTGC CAGAGGGCTC ACCCAGAGAT GGGTTTTGTA 17340
TTCGGAGGCT TGCTTTTAGA CCTCATTAGG CCGGCAATTG CTTTTCCTCC AAAGGTAATT 17400
TAGTTCTCTC AGGTGCGATC ATAAGGGAGG CTGCTGCATG TTCCTAGAGT TCAGCAAGAA 17460
TGTCTGCTGG GACTTGGGAA CTTACGCTCT TACCTCTGTC TGTGTCCCCA CCTCAGGGCT 17520
GTCCTTTCTC TGTTGTCTGT AAGGCATTCT AGGAGAACCA GGGACAACGA CAGAGACTGT 17580
CCTCTTGTTC AGAGAACAGT AAATTTAGAC GTGTTTGTAC AATTTATTGT TTCTTTTTAG 17640
TGGAAAAAGA AGTACTTGTA AATTTTATCT TAGCCTGAGG TATTAGTTGA TATTCTTTTA 17700
TGTTTGTAAT AAATTTTTAA TCAAAACTTG TGAACTAGGC ATAGAAACAA TAGTAAACAA 17760
AACCGTATCT TCTTATTTAA TTATATCAAA TCTTTATTAT TTAGTGTGTA TGTGTGTGTG 17820
CTCATGTATG TAGATATATA CTTGGTCAGA GGACAACTTT CAGGAGTAGT TTTCTTCTAT 17880
TATTTATGTC TAAAATTAAA TAGAAAATAA AAGCTCATGT ATACCCTTTT TAATTTATTT 17940
TCTTCCAACC CCCGTGCTAC TTTAAATAAC ATGTCATGAA TTTAGTATTT ATCATTTCTT 18000
TATATTGTGT TATTTGCCAA CTTAGAAACT ATATGGTTTT CCTGAAGCTT GTCTTTTTCA 18060
CTCAAGTTTT GAGAATTTTT CATTTTGATA TATGTAGTTC CATTATTTTA TATGCTATAT 18120
TATGTTTTGG CATGCCACAA TTTCTTTATT TTTTTGTTTT ATGGAAACAT AGTTTTTCCA 18180
ATTCCCCCGT CTGCAAAAGG ATCAGGGTTG TAGTGAACAT TCTTTCTTTG CTGTGTTGGT 18240
TAGTGTTTCT TGTCCATTTG GCACAGCCTA GAGTCGTCTG AGGCTAAGGA ACCCAACTGA 18300
GAGAATGCCC CATCAGATTG GTGTATAGGC AAGCGTGGGA ATAGGGTTTT CTTGACTGAT 18360
GATTGATGTG GGAGGGACCA GCTCACCTTG GGCAATGTCA TCCCTTGGGA GTTGGTCCTA 18420
CCTTGTATAA GAAAGCAAAC CTAGCAAGCC AGTTAGCAGT GTTTCTCCAT GGCCTCTACT 18480
TCCGCTCCTG CTTCTAGGGA CCTGCCTTGA GTTCCTGCCC TGACTTCCTT TTCTTCCCAA 18540
ATTGCTTTTG GACATGGTGA TGATCACAGC AATAGATGGC AAACTAAGAC ATTAATCAAT 18600
TGAGCTGTCT CACCTTTTAG AGTGGTTTGA ATAAGCATGG CCCTCAAAGG CTCATATATA 18660
GAATGGCTAA TCACCGAGGA GTGGAACTCT TTGATAGGAT TGGAACAGTG GTTCTCAACT 18720
TGAGAGTCTT GATGTCTTTG GACATTAAGC GACCCTTTCA CAGATATCCT GAATATCAGG 18780
TATTTACATC GTGATTCATA GCAGTAACAA AATTACAGTT ATGAAGTACC AATGAAATCA 18840
TTTTATGGTT GGCGTCATTA GGAAGGTTGA CAACCACTGG ATTAGAAGAA TTAGGACTTA 18900
TGACCTTGTT GGGGGAAGTG TGTCACTTGG GGTGGGCTTT GAGGCTTCAA AAGCCTAGAC 18960
TTTGAACAGA CCTTTTGCAC AAGAACAGGC CTCTTGTTCT CTCTACTGCT GCTCAGGGTA 19020
TAGCTCTCAG CTGCTGCCGC AGTGCCGTGC TTTACACCAT GATAATGGAC TAAGCCTCTG 19080
AGCTGTAAGC CAGCCACCAA TTACATGCTT TCTTTTATGA GAGTTGCCAT GGTCATGGTG 19140
TCTCTGCAGC AGTACAACAG TGACTAAGAC AGAAGGAAAC ATAGAAACAT TCACGCAGTT 19200
AATCCACACA ATTTTTCCTT TGATAGCATG CGTCTGTCTG ATGGCGATGT GGTGGGATTT 19260
GACATGGAAT GGCCGCCCAT ATACAAGCCA GGGAAACGAA GCAGAGTCGC AGTGATCCAG 19320
TTGTGTGTGT CTGAGAACAA ATGTTACTTG TTTCACATTT CTTCCATGTC AGGTTGGTAT 19380
CTCTGCTTCA TTGTCATATG GCCATCAATA ATACCATATC AACTTTCTTC CTGCAAAGTT 19440
AAGTTCTTTC ATTAGCAGGC CTTCTTTCAT GATCTTGTAT TTGTTTAAGT ATTTATATTT 19500
TTACTTGATT TTTATACCTT TTCCCTTGGT TAGAGAATAG AGAACTGAAG TTTAGAGGTG 19560
TAAATGACTA GGAATAATAC CCTATTACTG TTACTACAGG TGGCGTTCGA ACTCATTCTA 19620
TCTAGTCAAA TTTCAGTCTG GACTCTGCAT TAGCTAAGAA AAGAGATAGT TAAGGTGAAT 19680

*Fig. 7-6*

GTGATTCTAA ATTTAAGCTT AATATAAACA GTTTACCACA CATTCCGTGT GCATTAAAAT 19740
AGTAAATCCA TTATATTAAA GAGTTTTATG GAAATAATAA TGAAATGTTT TAGTTTTCCC 19800
CCAGGGATTA AAAATGTTAC TAGAAAACAA ATCAATTAAG AAGGCAGGGG TTGGGATTGA 19860
AGGGGACCAG TGGAAACTTC TGCGTGATTT TGACGTCAAG TTGGAGAGTT TTGTGGAGCT 19920
GACGGATGTT GCCAATGAAA AGGTAGGCGT AATAAATGCA GTATTTTAAT AAACATGATA 19980
ACCTGAGTTT CATAGAATGT GCATTTTCAT CTAAATGTTA AGTTTCTTTT TTTTTCCATT 20040
TTTTATTAGG TATTTAGCTC ATTTACATTT CCAATGCTAT ACCAAAAGTC CCCCATACCC 20100
ACCCACCCCC ACTCCCCTGC CCACCCACTC CCCCTTTTTG GCCCTGGCGT TACCCTGTAC 20160
TGGGGCATAT AAAGTTTGCA AGTCCAATGG GCCTCTCTTT CCAGTGATGG CCGACTAGGC 20220
CATCTTTTGA TATATATGCA GCTAGAGTCA AGAGCTCCGG GGTACTGGTT AGTTCATAAT 20280
GTTGTTCCAC CTATAGGGTT GCAGATCCCT TTAGCTCCTT GGCTACTTTC TCTAGCTCCT 20340
CCATTGGGAG CCCTATGATC CATCCATTAG CTGACTGTGA GCATCCACTT CTGTGTTTGC 20400
TAGGCCCCGG CATAGTCTCA CAAGAGACAG CTACATCTGG GTCCTTTCAA TAAAATCTTG 20460
CTAGTGTATG CAATGGTGTC AGCGTTTGGA TGCTGATTAT GGGGTGGATC CCTGGATATG 20520
GCAGTCTCTA CATGGTCCAT CCTTTCATCT CAGCTCCAAA CTTTGTCTCT GTAACTCCTT 20580
CCATGGGTGT TTTGTTCCCA AATCTAAGGA AGGGCATAGT GTTCACACTT CAGTCTTCAT 20640
TCTTCTTGAG TTTCATGTGT TTAGCAAATT ATATCTTATA TCTTGGGTAT CCTAGGTTTG 20700
GGGCTAATAT CCACTTATCA GTGAGTACAT ATTGTGTGAG TTTCTTTGTG AATGTGTTAC 20760
CTCACTCAGG ATGATGCCCT CCAGGTCCAT CCATTTGGCT AGGAATTTCA TAAATTCATT 20820
CTTTTTAATA GCTGAGTAGT ACTCCATTGT GTAGATGTAC CACATTTTCT GTATCCATTC 20880
CTCTGTTGAG GGGCATCTAG GTTCTTTCCA GCTTCTGGCT ATTATAAATA AGGCTGCTAT 20940
GAACATAGTG GAGCATGTGT CCTTCTTACC AGTTGGGGCA TCTTCTGGAT ATATGCCCAG 21000
GAGAGGTATT GCTGGATCCT CCGGTAGTAA ATATGTCCAA TTTTCTGAGG AACCGCCAGA 21060
CTGATTTCCA GAGTGGTTGT ACAAGCCTGC AATCCCACCA ACAATGGAGG AGTGTTCCTC 21120
TTTCTCCACA TCCACGCCAG CATCTGCTGT CACCTGAATT TTTGATCTTA GCCATTCTGA 21180
CTGGTGTGAG GTGGAATCTC AGGGTTGTTT TGATTTGCAT TTCCCTGATG ATTAAGGATG 21240
TTGAACATTT TTTCAGGTGT TTCTCTGCCA TTCGGTATTC CTCAGGTGAG AATTCTTTGT 21300
TCAGTTCTGA GCCCCATTTT TTAATGGGGT TATTTGATTT TCTGAAGTCC ACCTTCTTGA 21360
GTTCTTTATA TATGTTGGAT ATTAGTCCCC TATCTGATTT AGGATAGGTA AAGATCCTTT 21420
CCCAATCTGT TGGTGGTCTT TTTGTCTTAT TGACGGTGTC TTTTGCCTTG CAGAAACTTT 21480
GGAGTTTCAT TAGGTCCCAT TTGTCAATTC TCGATCTTAC AGCACAAGCC ATTGCTGTTC 21540
TGTTCAGGAA TTTTTCCCCT GTGCCCATAT CTTCAAGGCT TTTCCCCACT TTCTCCTCTA 21600
TAAGTTTCAG TGTCTCTGGT TTTATGTGAA GATCCTTGAT CCACTTAGAT TTGACCTTAG 21660
TACAAGGAGA TAAGTATGGA TCGATTCGCA TTCTTCTACA CGATAACAAC CAGTTGTGCC 21720
AGCACCAATT GTTGAAAATG CTGTCTTTCT TCCACTGGAT GGTTTTAGCT CCCTTGTCGA 21780
AGATCAAGTG ACCATAGGTG TGTGGGTTCA TTTCTGGGTC TTCAATTCTA TTCCATTGGT 21840
CTACTTGTCT GTCTCTATAC CAGTACCATG CAGTTTTTAT CACAATTGCT CTGTAGTAAA 21900
GCTTTAGGTC TGGCATGGTG ATTCCGCCAG AAGTTCTTTT ATCCTTGAGA AGACTTTTTG 21960
CTATCCTAGG TTTTTTGTTA TTCCAGACAA ATTTGCAAAT TGCTCCTTCC AATTCGTTGA 22020
AGAATTGAGT TGGAATTTTG ATGGGGATTG CATTGAATCT GTAGATTGCT TTTGGCAAGA 22080
TAGCCATTTT TACAATGTTA ATCCTGCCAA TCCATGAGCA TGGGAGATCT TTCCATCTTC 22140
TGAGATCTTC CTTAATTTCT TTCTTCAGAG ATTTGAAGTT TTTATCATAC AGATCTTTCA 22200
CTTCCTTAGT TAGAGTCACG CCAAGATATT TTATATTATT TGTGACTATT GAGAAGGGTG 22260
TTGTTTCCCT AATTTCTTTC TCAGCCTGTT TATTCTTTGT ATAGAGAAAG GCCATTGACT 22320
TGTTTGAGTT TATTTTATAT CCAGCTACTT CACCGAAGCT GTTTATCAGG TTTAGGAGTT 22380
CTCTGGTAGA ATTTTTAGGG TCACTTATAT ATACTATCAT ATCATCTGCA AAAAGTGATA 22440
TTTTGACTTC CTCTTTTCCA ATTTGTATCC CCTTGATCTC CTTTTCTTGT CGAATTGCTC 22500
TGGCTAATAC TTCAAGTACT ATGTTGAAAA GGTAGGGAGA AAGTGGGCAG CCTTGTCTAG 22560
TCCCTGATTT TAGTGGGATT GCTTCCAGCT TCTCTCCATT TACTTTGATG TTGGCTACTG 22620
GTTTGCTGTA GATTGCTTTT ATCATGTTTA GGTATGGGCC TTGAATTCCT GATCTTTCCA 22680
ACACTTTTAT CATGAATGGG TGTTGGATCT TGTCAAATGC TTTTTCTGCA TCTAACGAGA 22740
TGATCATGTG GTTTTTGTCT TTGAGTTTGT TTATATAATG GATTACATTG ATGGATTTTC 22800
GTATATTAAA CCATCCCTGC ATCCCTGGAA TAAAACCTAC TTGGTCAGGA TGGATGATTG 22860
CTTTAATGTG TTCTTGGATT CGGTTAGCGA GAATTTTATT GAGGATTTTT GCATCGATAT 22920
TCATAAGAGA AATTGGTCTG AAGTTCTCTA TCTTTGTTGG GTCTTTCTGT GGTTTAGGTA 22980

*Fig. 7-7*

TCAGAGTAAT AGTGGCTTCA TAAAATGAGT TGGGTAGAGT ACCTTCTACT TCTATTTTGT 23040
GAAATAGTTT GTGCAGAAGT GGAATTAGAT CTTCTTTGAA GGTCTGATAG AACTCTGCAC 23100
TAAACCCATC TGGTCCTGGG CTTTTTTTGG TTGGGAGACT ATTAATAACT GCTTCTATTT 23160
CTTTAGGTGA TATGGGACTG TTTAGATAGT CAACTTGATC CTGATTCAAC TTTGGTACCT 23220
GGTATCTTTC CAGAAATTTG TCCATTTCGT CCAGGTTTAC CAGTTTTGTT GAGTATAGCC 23280
TTTTGTAGAA GGATCTGATG GTGTTTTGGA TTTCTTCAGG ATCTGTTGTT ATGTCTCCCT 23340
TTTCATTTCT GATTTTGTTA ATTAGGATTT TGTCCCTGTG CCCTCTAGTG AGTCTAGCTA 23400
AGGGTTTATC TATCTTGTTG ATTTTCTCAA AGAACCAGCT CCTCGTTTGG TTAATTCTTT 23460
GAATAGTTCT TCTTGTTTCC ACTTGGTTGA TTTCACCCCT GAGTTTGATT ATTTCCTGCC 23520
GTCTACTCCT CTTGGGTGAA TTTGCTTCCT TTTTTTCTAG AGCTTTTAGA TGTGTTGTCA 23580
AGCTGCTAGT ATGTGCTCTC TCCCGTTTCT TCTTGGAGGC ACTCAGAGAT ATGAGTTTTC 23640
CTCTTAGAAA TGCTTTCATT GTGTCCCATA GATTTGGGTA CGTTGTGGCT TCATTTTCAT 23700
TAAACTCTAA AAAGTCTTTA ATTTCTTTCT TTATTCCTTC CTTGACCAAG GTATCATTGA 23760
GAAGAGTGTT ATTCAGTTTC CACGTGAATG TTGGCTTTCC ATTATTTATG TTGTTATTGA 23820
AGATCAGCCT TAGGCCATGG TGGTCTGATA GGATACATGG GACAATTTCA ATATTTTTGT 23880
ATCTATTGAG GCCTGTTTTG TGACCAATTA TATGGTCAAT TTTGGAGAAG GTCCCGTGAG 23940
GTGCTGAGAA GAAGGTATAT CCTTTTGTTT TAGGATAAAA TGTTCTGTAG ATATCTGTCA 24000
GGTCCATTTG TTTCATAACT TCTGTTAGTT TCACTGTGTC CCTGTTTAGT TTCTGTTTCC 24060
ACGATCTGTC CTTTGAAGAA AGTGGTGTGT TGAAGTCTCC CACTATTATT GTGTGAGGTG 24120
CAATGTATGC TTTGAGCTTT ACTAAAGTGT CTCTAATGAA TGTGGCTGCC CTTGCATTTG 24180
GTGCGTAGAT ATTCAGAATT GAGTGTTCCT CTTGGAGGAT TTTACCTTTG ATGAGTATGA 24240
AGTGTCCCTC CTTGTCTTTT TTGATAACTT TGGGTTGGAA GTCGATTTTA TCCGATACTA 24300
AAATGGCTAC TCCAGCTTGT TTCTTCAGTC CATTTGCTTG GAAAATTGTT TTCCAGCCTT 24360
TTACTCTGAG GTAGTGTCTG TCTTTTTCCC TGAGATGGGT TTCCTGTAAG CAGCAGAATG 24420
TTGGGTCCTG TTTGTGTAGC CAGTCTGTTA GTCTATGTCT TTTTATTGGG GAATTGAGTC 24480
CATTGATATT AAGAGATATT AAGGAAAAGT AATTGTTGCT TCCTTTTATT TTTGTTGTTA 24540
GAGTTGGCAT TCTGTTCTTG TGGCTTTCTT CTTTTTGGTT TGTTGAATGA TTACTTTCTT 24600
GGTTGTTCTA GGGCGTGATT TCCGTTCTTG TATTGCTTCT TTTCTGTTAT TATCCTTTGA 24660
AGGGCTGGAT TCGTGGAAAG ATATTGTGTG AATTTGTTTT TGTCGTGGAA TACTTTGGTT 24720
TCTCCATCTA TGGTAATTGA GAGTTTGGCC TGGTATAGTA GCCTGGGCTG GCATTTGTGT 24780
TCTCTTAGTT TCTGTATAAC ATCTGTCCAG GCTCTTCTGG CTTTCATAGT CTCTGGTGAA 24840
AAGTCTGGTG TAATTCTGAT AGGCCTTCCT TTATATGTTA CTTGACCTTT CTCCCTTACT 24900
GCTTTTAATA TTCTATCTTT ATTTAGTGCA TTTGTTGTTC TGATTATTAT GTGTCGGGAG 24960
GAATTTCTTT TCTGGTCCAG TCTATTTGGA GTTCTGTAGG CTTCTTGTAT GATCATGGGC 25020
ATCTCTTTTT TTATGTTTGG GAAGTTTTCT TCTATTATTT TGTTGAAGAT ATTAGCTGGC 25080
CCTTTAAGTT GAAAATCTTC ATTCTCATCA ATTCCTATTA TCCGTAGGTT TGGTCTTCTC 25140
ATTGTGTCCT GGATTACCTG GATGTTTTGA GTTAGGATCC TTTTGCATTT TGTATTTTCT 25200
TTGACTGTTG TGTCGATGTT CTCTATGGAA TCTTCTGCAC CTGAGATTCT CTCTTCCATT 25260
TCTTGTATTC TGTTGCTGAT GCTCGCATCT ATGGTTCCAG ATCTCTTTCC TAGGATTTCT 25320
ATCTCCAGCG TTGCCTCGCT TTGGGTTTTC TTTATTGTGT CTACTTCCCC TTTTAGTTCT 25380
AGTATGGTTT TGTTCATTTC CATCACCTGT TTGGATGTGT TTTCCTGTTT TTCTTTAATG 25440
ATTTCTACCT GTTTGGCTGT GTTTTCCTGC TTTTCTTTAA GGGCCTGTAA CTCTTTAGCA 25500
GTGCTCTCCT GTAATTCTTT AAGTGACTTA TGAAAGTCCT TCTTGATGTC CTCTATCATC 25560
ATCATGAGAA ATGTTTTTAA ATCTGGGTCT AGATTTTCGG TTGTGTTGGG GTGCCCAGGA 25620
CTAGGTGGGG TGGGAGTGCT GCGTTCTGAT GATGGTGAGT GGTCTTGATT TCTGTTAGTA 25680
GGATTCTTAC GTTTGCCTTT CGCCATCTGG TAATCTCTGA AGCTAGCTGT TTTAGTTGTC 25740
ACTGTTAAGA GCTTGTTCTT CAGGTGACTC TGTTAGCCTC TATAAGCAGA CCTGGAGGGC 25800
AGCACTCTCC TTAGTTTCAG TGAGCAGAGT ATTCTCTGCA GGCAAGCTCT CTTCTTGCAG 25860
GGCAGGTACC CAGATATCTG GTGTTCGAAC CAGACTCCTG GCAGAAGTTG TGTTCCACTC 25920
ACTAGAGGTC TTAGGATCTT GTGTGGAATC CTGTGTGGGC CCTTGCAGGT GTCAGGCGAC 25980
TCTGCTGGCA AGGTAGCCCG GGGCTCGAGT CGAGTGGAAG GGACTTGTGC CCCAGATCAG 26040
GCCCGGGTAG CCTGCTTCCC TATGTACTGC AGTCTCAGGT TCCGCGCGAT TGGATTGGGG 26100
CAGGCACTGT GTTCCACTCA TCAGAGGTCT TAGGATCCTG TGGGGGGTCC CGTGTGGGCC 26160
CTTGCGGGTG TTGGGCAAAC TCTGCTGGCA AGGTAGCCCT GGGCTCGAGT CGAGCGGAAG 26220
GGACTTGTGC CCCAGATCAG GCCAGGGTAG CCTGCTTCCC TATGTACTGC AGTCTCAGGT 26280

*Fig. 7-8*

TCCGCGCGAT TGGATTGGGG CAGGCGCTGT GTTCCACTCA CCAGAGGTCT TAGGATCCCG 26340
TGGGGGGTCC CGTGTGGGCC CTTTCGGGTG TTGGGCAAGA CTCTGCTGGC AAGGTAGCCC 26400
GGGGCTCGAG CTCTTTTTTT TTCTTTAAAA AAAAATTTTT TTTATTAGGT ATTTTCCTCA 26460
TTTACATTTC CAATGCTATC CCAAAAGTCC CCCATACCCT CCCCCTGACT CCCCTACCCA 26520
CCCACTGCCA CTTCTTGGCC CTGGCGTTCC CCTGTACTGA GGCAGATAAA GTTTGCACGA 26580
CCAATGGGCC TCTCTTTCCA CTGATGGCCT GCTAGGCCAT CTTCTGCTAC ATATGCAGCT 26640
AGAGACAAGA GCTCCAGGGG GTACTGGTTA GTTCATATTG TTGTTCCACT TATAGGGTTG 26700
CAGATCCCTT TAGCTCCTTG GATACTTTCT CTAGCTCCTC CATTGGTGCC CTGTGATCCA 26760
TCCAATAGCT GACTGTGATC ATCCACTTCT GTGTTTGCTA GGCCCCGGCA TAGTCTCACA 26820
AGAGACAGCT ATATCAGGGT CCTTTCAGCA AAATCTTGCT AGTGTATGCA ATGGTATCTG 26880
TGTTTGGCGG CTGATTATGG GATGGATCCC CGGATATGGT AGTCTCTAGA TGGTCCATCC 26940
TATTGTCTCA GCTCCAAACT TTGTCTCTGT AACTTCTTCC ATGGGTGTTT TGTTCCCAAT 27000
TCTAAGAAGG GGCAAACTGT CCACACTTTG GTCTTCATTC TTCTTGAGTT TCATGTGCAT 27060
TGTATCTTGT ATCTTGGGTA TTCTAAGTTT CTGGGCTAAT ATCCACTTAT CAGTGAGTAC 27120
ATATCATGTG AGTTCTTTTG TGATTGGGTT ACCTCACTCA GGATGATGCC CTCCAGGACA 27180
ATCCATTTGC CTAGGAATTT CATAAATTCA TTCTTTTTAA TAGGTGAGTA GTACTCTGTT 27240
GTGTAAATGT ACCACATTTT CTGTATCCAT TCCTCTGTTG AGGGGCATCT GGGTTCTTTC 27300
CATCTTCTGG CTATTATAAA TAAGGCTGCT ATGAACATGG TGGGGCATGT GTCTTTCTTA 27360
CCAGTTGGAA CATCTTCTGG ATATATGCCC AGGAGAGGTA TGTCGGGATC CTCTGGTAGT 27420
ACTATGTCCA TTTTTCTGAG GAACCGCCAG ACTGATTTCC AGAGTGGTTG TACAGCTTTC 27480
AATCTGACCA GCAATGGAGG AGTGTTCCTC TTTCTCCACA TCCTCACCAG CATCTGCTGT 27540
CACCTGAATT TTTGATCTTA GCCATTCTGA CTGGTGTGAG ATGGAATCTC AGGGTTGTTT 27600
TGATTTGCAT TTCCCTGATG ATTAAGGATG CTGAACATTT TTTCAGGTGC TTCTCGGCCA 27660
TTCGGTATTC CTCAGGTGAG AATTCTTTGT TTAGCTCTGA GCCCCATTTT TAATGGGGTT 27720
ATCTGATTTT CTGGAGTCCA CCTTCTTCAG TTCTTTATAT ATATTAGATA TTAGTTCACT 27780
ATCTGATTTA GGATAGGTAA AGATCCTTTC CCAGTCTGTT GGTGGCCTTT TTGTCTTATT 27840
GACGGTGTCC TTTGCTTTAC AGAAGCTTTG CAATTTTATG AGGTTCCATT GGTCAATTCT 27900
AGATCTTACA GCACAAGCCA TTGCTCTTCT ATTCAGGAAT TTTTCCCCTG TGCCCATATC 27960
TTCAAGGCTT TTCCCCACTT TCTCCTCTAT AAGTTTAAGT GTCTCTGGTT TTATGTGGAG 28020
TTCCTTGATC CTATTAGATT TAACCTTAGA ACAAGGAGAT AGGAATGGAT TAATTCGTAT 28080
TCTTCTATAT GTTAACCACC AGTTGTGCCA GCACCATTTG TTGAAAATGC TGTCATTTTT 28140
CCACTGGATG GTTTTAGCTC CCTTGTCAAA GATCAAGTGA CCATAGGTGT GTGGGCTCAT 28200
TTTTGGGTCT TCAATTCTAT TCTACTGGTC TACTTGTCTG TCACTATACC AGTACCATGC 28260
AGTTTTTATC ACAATTTAGG TCAGGCATGG TGATTCCACC AGAGGTTCTT TTATCCTTGA 28320
GAAGAGTTTT TGCTAACCTA GGGTTTTTGT TATTCCAGAT GAATTTGCAG ATTGCTCTAA 28380
TTCATTGAAG AATTGAGTTG AAATTTTGAT AGGGATTGCA TTGAATCTAT AGATTGCTTT 28440
TGGGAAGATA GCCATTTTTA CTATATTGAT CCTGCCAATC CATGAGCATG GGAGATCTTT 28500
CCATCTTCTG AGATCTTCTT TAATTTCTTT CTTCAGAGAC TTGAAGTTTT TTTTCATACA 28560
GATCTTTCAC TTAGTTAGAG TCACACCAAG GTATTTTATA TTATTTGTGA CTATTGAGAA 28620
GGGTGTTGTA TCCCTAATTT CTTTCTCAGC CTTTTTATTC TTTGTGTAGA GAAAGGCCAT 28680
TGACTTGTTT GAGTTAATAT CCAGCCACTT CACCGAAGCT GTTTATCAGG TTTAGGAGTT 28740
CTCTGGTGGA ATTTTTAGGG TCACTTATAT ATACTATCAT ATTATCATCT GCAAAAAGTG 28800
ATATTTTGAC TTCTTCTTTC CAATTTGTAT CCCCTTGATC TCCTTTTCTT GTCGAATTGC 28860
TCTGGCTAGG ACTTCAAGTA CAATGTTGAA TAGGTAGGGA GAAAGTGGGC AGCCTTGTCT 28920
AGTCCCTAAT TTTAGTGGGA TTGCTTCCAG CTTCTCACCA TTTACTTTGA TGTTGGCTAC 28980
TGGTTTGCTG TAGATTGCTT TTATCATGTT TACGTATGGG TCTTGAATTC CTGATCTTTC 29040
CAAGACTTTT ATCATGAATG GGTGTTGGAT TTTGTCAAAT GCTTTCTCCT CTTCTAACAA 29100
GATGATCATG TGGTTTTTGT CTTTGAGTTT GTTTATATAA TGGATTACGT TGCTGGATTT 29160
CCATATATTA AACCATCCCT GCATCCCTGA AATAAAATCT ACTTGGTAAG GATGGATGAT 29220
TGTTTTAATG TGTTCTTGGG TTCGGGTAGC GAGAATTTTA TTGCTTATTT TTGCATCAAT 29280
ATTCATAAGG GAAATTGGTC TGAAGTTCTC TATCTTTGTT GGATCTTTCT TTGTTTTAGG 29340
TATCAGAGTA TTGTGTCTTC ATAGAATGAA TTGGGTAGAG TACCTTCTGC TTCTATTTTG 29400
TGGAATAGTT TGTGCAGAAC TGGAATTAGA TATTCTTTGA AGGTCTGATA GAACTCTGCA 29460
TTAAACCCAT CTGTCCCTGG GCTTTTTTTG GTTGGCAGAC TATTAACGAC TGCTTCTATT 29520
TCTTTAGGGG ATATAGGATT GTTTAGATCA TTAACCTGAT CTTGATTTAA TTTTGGTACC 29580

*Fig. 7-9*

TGGTATCTGT CTAGAAACTT GTCC 29604
>00109 00109
TGTTCTTGTG GCTGTCTTTT TGGTTTGTTG AAGGATTACT TTCTTATTTT TTCTAGGGCG 60
TGGTTTCTAT CCTTGTATTG GGTTTTTTTT TTTTTTCTGT TATTATCCTT TGAAGGGCTG 120
GATTCGTGGA GAGATAATGT GTGAATTTGG TATTGTCATG GAATACTTTG TTTTCTCCAT 180
CTATGGCAAT TGAGAGTTTG GTTGGGTATA GTAGCCTGGG CTGGCGTTTG TGTTCTCTTA 240
GGGTCTTTAT AACATCTGTC TAGGATCTTC TGGCTTTCAT AGTCTCTGGT GCAAAGGTCT 300
GGTATAATTC TGATAGGCCT GCCTTTATAT GTTACTTGAC TTTTTTCCCT TACTGCTTTT 360
AATATTCTAT CTTTATTTAG TGCACTTGTT GTTCTGATTA TTATGTGTGG GGAGGAATTT 420
CTTTTCTGGT CCTGTCTATT TGGAGTTCTG TAGGCTTCTT GTATGTTCAT GTGCATCTCT 480
TTAAGTTTGG GAAGGTTTCT TCTATTATTT TGTTGAAGAT ATTTGTTGGC CCTTTAAGTT 540
GAAAATCTTC ATTTTCATCT ACTCCTATTA TCCGTANGTT TGGACTTCTC ATTGTGTCCT 600
GAATTTCCTG GATGTTTTAA GTTAGGATCT TTTTGCATTT TGCATTTTCT TTGATTGTTG 660
TGCCTATGTT CTCTATGGAA TCTTCTGCAC CTGAGATTCT CTCTTCCATG TCTTGTATTC 720
TGCTGCTGAT GCTTGCATCT ATGGTTCCAG ATTTCTTTCC TAGGGTTTCT ATCTCTAGCG 780
TTGCCTCATT TTGGGTTTTC TTTATTGTGT CTACTTCGCT TTTTAGGTCT ACTATGGTTT 840
TGTTCATTTC CATCACCTAT TTGGATGTGT TTTCCTGTTT TTCTTTAAGG ACTTCTACCT 900
GTTTGGTTAT TTTTTCGTGT TTTTCTTTAA GGACTTGTAA CTCTTTAGCA GTGTTCTCCT 960
GTATTTCTTT GAGTTATTAA AGTCCTTCTT GATGTCCTCT ACTATCATCA TGAGATATGC 1020
TTTTAAATCC GGGTCTAGCT TTTCGGGTGT GTTTGGGTGC CCAGGACTGG GTGAGGTGGG 1080
AATGCTGCAT TCTGATGATG GTGAGTGGTC TTGGCTTCTG TTACTAAGAT TCTTACGTTT 1140
GCCTCTCACC ATCCAGTAAT CTCTGGAGTC AGTTGTTATA GTTGTCTCTG GTTAGAGCTT 1200
GTTCCTCTTG TGATTCTGTT AGTGTCTATC AGCAGACCTG GGAGACTAGC CTTCTCCTGA 1260
GTTTCAGTAG TCAGAGCACT CTCTGCAGAT AAGCTCTCCT CTTGTAGGGA CGGTGCCCAG 1320
ATATCTGGCA TTTGAACCTG CCTCCTGGCA GATTTTGTGT TCCACTCACC AGAGGTCCTA 1380
AGATCTCGTG GAGAGTGTTC TGGGTACCTT GGGGGTGTCC GACAACTCCG TGTCCGACAA 1440
TTCTAGTGCT GGGGCCGACT GGAAGGGACC TCTTTTTCTT TTATAAAGTA ATGAAAGCTA 1500
TGTGTTGATT TTGGTGGCAA AAGAGAAGTT CAAAGTGCAA TAATGAAACC CTCCATTTCT 1560
GAAACTCCAT CTCAGCGTCC AGTTGCCTGA ACTAACGCCC GTTCATCTTT CCTGCCAACC 1620
TTAGTATTTT GTATATTGCA CACTTGAATG TTTATTGTAT CTAACGGATT TATTCCAATA 1680
GCACGTCTTT GGAAAAGATG ACTACAGGGC AACTCTCAAT ATAGAATGTT GAGTGTCTGT 1740
TTGACCTTTA ACATCATCAC CTATGTTTCC ATCATTTTAT TGATGAGATG ATTACATCCT 1800
TATATTCAGC CACGTATTCA TTTGGTTTTG AGATCAAAAC CATTCTTGCC TATTCCGCTG 1860
CCTTCTAGGA ACAGCATCTT TAACGTTTCA GCCCTTTGAT ACCCACATTA TGGAACCTCG 1920
GAGTTAAATT CCTACTGTCC ACTATGAATG AGGTCTCAGA TGGGAGGCTT GTTTTTTTTG 1980
TGGTCCCTGG GGACAGCTGA CTATGACTGT GAATGTTTGC TCTGTCCCCC TTTCACTCCT 2040
TCCAGTTGAA GTGCGCAGAG ACCTGGAGCC TCAATGGTCT GGTTAAACAC GTCTTAGGGA 2100
AACAACTTTT GAAAGACAAG TCCATCCGCT GCAGCAATTG GAGTAATTTC CCCCTCACTG 2160
AGGACCAGAA ACTGTATGCA GCCACTGATG CTTATGTATG TATTTAAAGA CCTTTAATAT 2220
GACATCATTC TCATTTCTCG GACCAAATCA CTTTAGTAAA AATGTATTGG GGTTATGTCC 2280
TTAGCTGAAA TATTTTATTA TAGTTTGGCA TTAAAATTTG CTTAGGAATA CATCAAGTGA 2340
AATTCTTCAT GTTAATTAGA AAATACCAAT TAATAGGTTG TTTAGCAGTA GTTATTTCTA 2400
CTATTACGAT GTAAAGTGAT GTCCAATTCC TGTGTAAAAG AATGTGAACT TACTGAAAAC 2460
ATGAAAGGCT TTGAGCTTAG CAGGCACAAA TAGTTTGATG ATGTATTTTG TATATAAGCA 2520
ACTCAGAATC AGAAAAATCA CAGGCTTTCC ATATTTAAAC TAGCCTTATT CCCTACATTT 2580
ATATTTAAAA TGTGGAAATT TAGATAAATT GCCTCCAAAT TTAGTTGCTG CTGTTCTTAG 2640
ATGTATTTTC ATATGTGTAA TCTGTACATA CTGGCATCTA GGCTTGTCTT TATATATAGT 2700
ACTGTGGTCT GTGTGTGCTT TACCTTAAGA AATGTTTCTT TTGTAAATTT CTTTGCCCTA 2760
GATCATACTT ATTGCTCATA TTTAAATAGT ATTTATTGAT AAATATCTTG TTAATTTTCC 2820
ACCTTACATT TATTTTTAAG ACATCGATAC TCTAACTTTT AGCCAGAAAA ACAAAGGAAA 2880
ACCAACTGTC TTAGTCAGGG TTTCTATTCC TGCACAAACA TCATGACCAA GAAGCAAGTT 2940
GGGGAGGAAA GGGTTTATTC AGCTTACACT TCCATACTGC TGTTCATCAC CAAGGAAGTC 3000
AGGGCTGGAA CTCAAGCAGG TCAGAAAGCA GGAGCTGATG CAGAAGCCAT GGAGGGATGT 3060
TCTTTACTGG CTTGCTTCCC CTGGCTTGCT CAGCCTTCTC TCTTATAGAA CCCAAGACTA 3120
CCAGCCCAGA GATGGTCCCA CCCACAAGGT GTCTTTCCCC CTTGATCACT AATTGAGAAA 3180

*Fig. 7-10*

| | | | | | | |
|---|---|---|---|---|---|---|
| ATACCCCACA | GCTGGATCGC | ATGTAGGCAC | TTCCTCAACT | GAAGCTCCTT | TCTCTGTGAT | 3240 |
| AACTCCAGCC | TGTGTCAAGT | TGACACAAAA | CTAGCCAGTA | CAGCAACAGA | TGCTTTTTGT | 3300 |
| CAGGAGAACA | GCTGGATGAG | TTGGGATGTG | CTGTTGTTCC | TTTGGCTTCC | TTTGCTTCCT | 3360 |
| TGCTTACTTG | CTTTAAAAAA | AATAACAGAC | TCTCTTGCAG | CTTATTCCAC | TCTTGAACTG | 3420 |
| TTCATGCAGC | CGAGGCTGCC | CTTAATGTCC | AGATCCTCTT | GCCCCTGTTT | CCTTGCTATG | 3480 |
| GAGATTACAG | GCTGTAGTGT | CTATATTCTT | GACAGTTTGT | ATGACTTGAT | CAAGTCTGTG | 3540 |
| AAAAATACCC | AGCATGCATT | GTTGTTCATA | CACTGACCAG | CATTCTCAGT | TGGTTTAATG | 3600 |
| AAATCTCAAG | AATTGGATAG | GATCTGTCAC | CAAAACAGAT | GTTTCTTACT | AGATGGTAGT | 3660 |
| TATTAGATTT | TGTTTACAGA | TCATTTCATT | TGGATACCTA | TTTACAATAC | TGAAAATTAG | 3720 |
| TAAGTGAAAA | TTTAAAGCTG | TATTTTATAG | CCTAGGCAGC | TTTTGTTTCC | CCATTGGGTA | 3780 |
| GTGCTTACAT | GAAGACCCGA | GTCTTTGCAT | ACTGAAATAG | TTTTACTTCA | TTTTTGGAGA | 3840 |
| GTATTTTGGA | AATCATTCTT | GTAGATGTTG | CTTGAGATAT | CACATATATA | TATTTATTTT | 3900 |
| GGTAATCTTT | AACTTGCACT | TTGTTTTTCT | TTTGTCTTTT | TATAGGCTGG | TCTTATCATC | 3960 |
| TATCAAAAAT | TAGGAAATTT | GGGTGATACT | GTGCAAGTGT | TTGCTCTAAA | TAAAGGTATG | 4020 |
| TTGTGGCCTA | AAATAAAAGA | TAAAAATATG | AATTTGCTAT | TTTGTGAGAT | TCATTTAAAA | 4080 |
| AAGTCAAAGT | ATTATGTATC | TTTGCAAAGT | ATTATGGTAC | TTCTTAAATG | TCTGAGCAGT | 4140 |
| GTTGCTGTAA | AGGTGACATC | CATCAGGATC | AGAAATTAGA | GTTGTAGATC | TTCCCTTGTG | 4200 |
| AAAAGCAGGG | ATTCCATTGC | TAGTTTGATA | GTGTTGCTGC | TCTTCTTGTC | CATGGAGTGG | 4260 |
| CCATGTTATT | GTCCTTGATA | ACATCAGTTA | GCCAGCCAGC | TGCCTCTTGG | CTGGTAACAT | 4320 |
| CCACATTCTT | TCTACACTTG | TTTAAAACGG | ATTTGCCTCG | ACTATTCCTG | TGTATATGGT | 4380 |
| GCACTGTAGT | GTTCTGCCTT | TCTGTGTTCG | GTTGCTGTTT | TCTTCACTCA | GCTTCATTGA | 4440 |
| CCTTGTCAGA | TGCTTTGATC | TGTTAGTGAT | TACAGGCAGA | GTCAGCCAGT | AGGTGGATAA | 4500 |
| GCACCAGCTT | TTGTGCTGCA | GAACCTCTGT | GGTGGAGCCT | TAGCCATCTG | ACCTGTAAGA | 4560 |
| TGTCCCTTTC | CCCATGCTTG | TAATGTGGAC | AATAGATAAG | TGTCTATCTC | ATGGATTGGT | 4620 |
| TGTGACCACT | AAAGGGACAG | ATGTTCAAAG | TAAGATGGTC | AGAGAAAATT | GTTAAATAGA | 4680 |
| TTGAACAGTC | CTATAATACA | TGATCTGAAA | TGCTTTGAAA | TCGGAAACTT | TTTGGTGATA | 4740 |
| ACATGATTTA | CGTATTCATT | AGTATATTTC | ATTGAAAATA | TTTCCTGGAA | GAAGCAATAC | 4800 |
| TTGAGAAGCC | TGAAATAGGA | ACAGAAATTT | GCCAGCCAAA | GCCAGAGGGA | AAGTGATAGA | 4860 |
| CAGGTACAAA | GCCTCAGAGG | GCAGCTCTCT | GGAACTTATG | CAGTGTAAGG | AAACTGTTGA | 4920 |
| CTGTGACAGT | GTAATGTAGG | AGAAGCAGAA | AAATGAGACA | GGCCTCACTA | AAGAGGTTAC | 4980 |
| ATGTAGCCTT | CCAAAGAGCA | AATTGAAGCT | GTTATTGACG | GTTCTAAATG | TGGAAGTGAA | 5040 |
| ATGCGCTGGA | TTGAAAACAA | GCTAACAAAA | CAAGCTGTAG | AATAAAACAC | ACTAACTAAG | 5100 |
| CGAGCCACAG | AGAAAGAAAG | TGGATCTTAG | GATTACAAAA | GAATGGTGGG | AAAGGCTTTT | 5160 |
| TGGAGGCTAT | GATGGTAAGC | CAAGAAAGAG | GAATTGGTAC | CTTGAATTGG | TTATTTGTGT | 5220 |
| CAAGGGTCGG | CACAGTGGGT | AGCGTCANCC | TACATTTAAT | GGAGGCAACA | GAATCTGCTG | 5280 |
| TAATGACAGG | CACACGCCAA | GGATCCTCCT | GGCTTTTGGC | TGCACGACAG | ATTAAAATCC | 5340 |
| AGGGTAAAGA | CTCACTTTAT | ATAGACCAGG | CTGGCCTAGA | ACTCAGAGAC | CTACCTGCCT | 5400 |
| CTGCCTCCTG | AGTGCTGGGA | TTAAAGGTGT | GCACCACCAC | CACTCAGCTG | GAAGTAAAGT | 5460 |
| TTTATAGTTG | TTTTTTTAGA | CATGTTCAAG | GAGAGTAACA | TCTCAGGTAG | CAAGAGGGTT | 5520 |
| GTAGCCTGTG | GACACCTAGA | TATGTAGGTT | GTATCTCAGA | AGACAGTTTG | TCTGAGATAA | 5580 |
| AATGTAAGCA | CTAAGTGTCC | TAAGAAACTG | CTGGCGTCTA | ATCTTTGTGT | GGGGGAGGGG | 5640 |
| ACCCTATAGG | AGTTGCCCTG | GGTGTGGAAG | GAGATGAGAA | AGTGCTGGAC | AATTCAAGTA | 5700 |
| CCAGTGTGCT | GAAAGTCAAG | GGAGGGCTAG | GTTTGAGGGA | GGAGGATGTT | ATCAACTGCT | 5760 |
| TTGAATTCTG | CTGAGATTTT | GGCAAAGTGA | AGGCTTGTAG | GCAATCATCA | GATTTGGCAC | 5820 |
| AATGGCCACT | ATCATTTGTA | ACCTTCTACA | CCAGTGGTTC | TCAACCTTCC | TGTACTGTGA | 5880 |
| CCCTTTAATA | CAGTTCCTCG | TGCTGTGATG | GCACCAACCA | TGACATTATT | TCCTTTGCTA | 5940 |
| CTTCTTGACT | GTAATTTTGC | CACCGTTATG | AATTGTGATG | TAACTATCTG | ATATACAGGA | 6000 |
| TGTTTGATTT | GTAAACCCTG | TGAAAGAGCC | ATTTGATCAA | TCATTGTTCT | GTGCTCTACT | 6060 |
| TCTGGTGTCC | TGGGTGTTGA | CAAAAGAGTA | TTGCAATCAG | AGGGTGAACT | TCTAGAGCAG | 6120 |
| ACAGGGTCCA | GAGGCTTTGG | TAGTATAAAA | ATATTATAGG | CATAGCAAGA | ATAAAGTAGT | 6180 |
| TTAATGAGGT | AGGTAGAAAC | CAGTACTAAA | ATTATATCAA | TCATATTACT | GCAAATAGTG | 6240 |
| GAGAAAGATG | TAAGGAATTG | ATTTTAAGTG | TATATAAATA | ATATTTTTTA | AAGACTTAAT | 6300 |
| TTAGAAAGGG | AACGTTCATA | AAACACAGGT | TTGTCTAGTG | TTTGCTATAT | TTTAGTGTTC | 6360 |
| ATTATGTATT | GATTTTATTT | GACAAGCAAG | GTAACATGCT | ATTTGGCTCT | CTGAAGGAAG | 6420 |
| AGAGCCAAAT | GCTTAGAGCT | GAGAAAGTAC | AAAGCCACTG | AGGGCAACTG | CTTCCCTAGT | 6480 |

*Fig. 7-11*

GTAAGGAACA GAAATATAAC CAAAGAGAAA CGAGTGTGAG GGAGACTTGT AGGAAACAAG 6540
GCTGGAAAAG AGGCTTGGGG CCAGTCAGTT AGGGCATCAG ATTGTGTGAA TTGGACTTGA 6600
TGTTTTAATA CTCAAAACCA TCAACAACCA CGGTACAACG ATGGCCAATA GGAAACCCTT 6660
AGTTTGGGTG TGTGGAGCAG CAGAGTAAAA TGATCCAGAT TTTGTCTTAA AGTGTTTTTT 6720
TTTTCTCACT GCTGTAAGAA GGTCAGGAAG TTAGATAGGA GGCTTTTTCA ATTGTCCAGA 6780
AATAGAAGAT AGTTGTACTG GGCCAGTGGA GGTAGCAAGA AATGTAAATG CAGTAGGTAT 6840
TCTGAAGGCA TACACTGAAG AATTCTAGGT GAATTCCTTA TAAAGGGTGA GGAAAAGACT 6900
GCTAGGATGG CCAAGGTATT TTTCTTTTCT TTTCTTTTTC AGTTTTTCGA GACAGGGTTT 6960
CTCTGTGTAG CCCTGGCTGT CCTGGAGCTC ACTCTGTAGA CCAGGCTGGC CTTGAACTCA 7020
GAAATCTGCC TATCTGCGCC TCTCAAGTGT TGGGATTAAA GGCGCCCGGC TTAAGGTATT 7080
TTTCTTGAAT GACCTGATGA CTGGCAGTGC AGGATGATAT GAAGAGTATG TTTTGGTTGG 7140
AAAAAATCCA CCAAAGTTGC AACGTGGACA TGAAAAAAAA CTAGAGGTGG ATTTTGATAT 7200
CCACGAACGG CTCCATACTA GTTATTTTCT GTTACTGTGA TAAAACACCG TGACCAGAGA 7260
GGTCTTTAAG GAAAGGAGTT TCTTTTTGCT CACAGTCCCA GAGGGAAGTC TTCAGTGGCT 7320
CTGCGGGAGC ATGGCAGAAA GCAGCCGGCT TGGCAGTGGG GCAGGAAACT GTTAGGTCAC 7380
ATCTTGAACA GCAGTCTTGA AGCAGAGAGA GCAAACAGGA AGTAGGGTGA AGCTGTGCAC 7440
TCTCAAAGCC ACCCCCAGTG TCAAACTTAC TCCCGGAAGG TTGCACCACC TAAACCTCTC 7500
CAAATGGAGT CACCAACTGA GCATCCAGTG TTCCACTGCC CGCGAGCCTG TGGGAAATAT 7560
TTCCCACCTA ACCACCACTG CACTGTGAGA AATGGAATTC CAGAGTACAC GGCGGAAGTT 7620
GGGGTTAGAA ATATAGATTG TCCAGTGGTG AAACTGGAGA TAAAACTGGG AGTGAATAAA 7680
CTGAAGAATA TAGGTGGTGT CAGCTTCAAG GTCACACTGA CATTTAGAAA ATGAGAGTGG 7740
CTTGAGGGCG GAGACGGGGC ATCAGTGAAT GAGGAGGGGG GCGAAGGACA TGCTTTAAAT 7800
AGGAAGGAGA CATCAGCCCC TTAAACCTCG GAGGAGTTGA ACGATGCACA GATCGTGGAT 7860
TAACTATTAG GGTTGATAAT GTGGTAGCCT TCCCAGAGGA AGCTGTGCTG CTGAGGGCAA 7920
AACTCTTGAG TTGGAGTTAG TTTAGGAGAA AATAAGAGCA GAACATTCGA GGATGAGCAG 7980
CAGGCGTTGG AAACGTAAAA GAGAAAGAAG AGGTGTAAAA TTGTCATCTT AAGATAAGCG 8040
GGGTCTGCGT CATGAGTTTA AAACTAAACC GGCCATTATC ATTTTGTTTT AATTTCAAGA 8100
ATGTCCAGCT ACTTAGGCAC CGATTAGCTA AAGAAGTTGA GTATGATTAG AGTAGATTTT 8160
GCCCCGTGAG TTCCACGGAG TTGGGTAAAG AAGGCAGAAG TGGAGAGTCT GTATCAAATG 8220
AATGGCTAAG AAAGGAAAGG AGACCAGGTA GGGAGAGTAG GAGTGGGTGC TGGAGGGGGC 8280
GGATTCAACA GGTTTCATTC TGAAGTGTTA ACTCACTGAG CTGGGGTAAG CAAGCCAGAA 8340
AGAGCGGTGG GATGGCTCTA TTTATGGTGG AAAGTGTTTG TAATAGAAGG TTTGGGTGCA 8400
GTGGAGGTTT TATTGGGCAG TTTTAAGGTC GAGAGTCTGA TTGTGGGAAT GAGTAGCTCA 8460
GATTAGATGA GGAAGATTGT TGGAATGAAG GGTGACCCTT GGGCAAGGGT TCCAAACGGT 8520
GTTAAGTTTG AACGTGCCTG GATTGGGGCT TACTGACTTC CAAGTCAGAA ACAGTGTCGG 8580
GTGAGTTTAG AGTCCCAGGC TTGTCCTCTG GCCCAGGTCA GTAACATTTA GATTGGATAA 8640
TGTATACATT TGGAATTCAC TCTAAATTTC AAATAGCAAA AATTTGAAAG GAACATTAAA 8700
ACAAGGGAGT AAAGAGGAAA GTGATTTAGA GATCCGAGAG GGAAGTGTTC TGTTAGAATT 8760
CATTGTGCGA ATAGATGAAA ATCTGGATAC TAATACTATG CTGTGATGTG GTTAAATAAA 8820
ATCTCTGCTT TCTAATTTTA ATATTAATCT TTTCTCTCTC TCTCTCTCTC TCTCTCTTTC 8880
TCTCTCTCTC TCTCTCTTCT TTTATTTAGC AGAGGAAAAC CTACCTCTGG AGATGAAGAA 8940
ACAGTTGAAT TTAATCTCCG AAGAAATGAG GGATCTAGCC AATCGTTTTC CTGTCACTTG 9000
CAGAAATTTG GAAACTCTCC AGAGGTTAAA TATTGTGCTT TTTAAAATAT TTATTTTATT 9060
TTTAATTGTA TGTGTATGCG CGTTCAGTCA CCTTTTATGC TATTTTCTTA AACATGGAAT 9120
TCTGATTTTT ACAGAATGCC TGCTTGTTAT AAATTACATA TACCTACAGC TTGGCTTTAT 9180
AACAGCAAGT TAAGTAGGAT TTATTAGCAT CAAGAACTCA CAACAGAGTG GTTTGAAGTT 9240
TATTGTAGGA AGGAACAGTT GTTTTTGTCT CAGAGGACCC TAATAGAATC GATGTGATTT 9300
AGTATTGTTT AGTCATTTAT TTACATTCAG TGTGCTGCGG TGTTGCTGCA GTGTGATTAG 9360
CACTCTACTG GCTGTTGAGC TTGTCTGCTG CTAACTAATG AGCAGGATAG AAATCTTAAG 9420
GAAGGAAATG TGCATGCCAC CATGTATGCC TTCCTAGTCC AGCCTTTAAC GTTAGAGTAA 9480
GTGGTTATGT CTTACTCTGA TGTGAGTGCT TGGTAAATAA GATATTATAA TAGTATCACT 9540
GTTGCTATAG CAACACATTT ATTTCACAAT TAAATTGAAT CATAACTTCT CATACCATAT 9600
TATTTATACA CAGTTGTTAT ATATAAGCAG TATATGTATA TACATATAAT TATATACTGT 9660
GTATGTAGTA AAATTTACAA AATTGCCAGG CACCACGGTA CATACCTGTA ATCTGTGCAT 9720
TCAGGAGGCA GAGGCAGGAG AATTCCAAGC TCAAGGCCAG CCTGACTAAT AAAAAGCTTT 9780

*Fig. 7-12*

ATAAATTTTT ATTATTTTAA AATAACTTGT TATTAGATTT TGAATTTAGT TAATAGTTTT 9840
AAAAGTTTTT TTTTTGTATC ATTTTATGTG TATGGCTGTC TTTGCCTGCA TGTATGTCTC 9900
TGTACAACTT ATGTGATGTA TTCCTGAGAG GTGCAGAGGA GGGTATTGGA TCTTCTGGAA 9960
CTGGTGTTAC ACACAGTTGA AAGCTGCCAT GTGGGTGCTG GGAATCAAAC CTGGGTCCTC 10020
TAGAAGAGCA GCCAATGCTC TTAACTGCTG AGCTATCTTT CCAGCCCTGA ATTTAATTTT 10080
GATCTTGATT TTTGCTTATG TTAATATAGA CTTTGACAGT TTAAGGTTGA GCTAAAGTTG 10140
GGAGAGTTGA TAATTGTGTA GTTTTGTTTT TTTGAGTATT TTTGTACATT TTATTATGAT 10200
CATAATTACT TTCCATTACA CTCTCTTATC CCCCTGATTC CTGCTGACTC CCTCTTACTT 10260
AAGTAGCTCC TTTCCTTCTT TCACGTCTCA TGTGTGTTTG TGTATTTGTG TGTGCATGTG 10320
TGTGCATGTG TGTGTGTGTG TGTGTGAGTG TGTGTGAGTG GCACTGTGTT TATTTAGGAG 10380
TATTTGTATG AGCATGGTTA AGAGGCTGCT GACTAAGCAC TGGCAACTTT ACCAGTGACT 10440
ACTGAAGAGA ATGATGACTG TTTGCCTAGA AGCCAAGCAA AAGCTCCCTA GGGAAGGATG 10500
GGGTGGGTCA CTTTTGAGCT TCACCATCCA CGTGGGAGCG GCAGAAGGCC CTGTGTTTTG 10560
TGGGTTTTAT GCAGATATCC ATAGCTGCTG CGTGTTTATG ATTTCAGTAG CCATGCAATG 10620
TCTACATGGC AATGTTTCAC AGCACTCCCC CACATCGTCT GACTCTTACG GTTTGTCCAT 10680
CCATCCTGTT ATGTCCACTG GGCCATTGAA GGAGTTTTAT GTACAGGCTG GTCCCAATTC 10740
AGGCAGAGCA CCCAGTATTC ATTTATGCTC AACACTTTGA TCATTGTGAG TCTTCTTTAG 10800
CCAAAAGCTT CTTTGACCAA GACTGAGAGT AGCACTCTGG ATAAGAACAA GAGTTCGAAG 10860
GCAATATGAT ATGTGTCTAT CTAGCAATGT GTCAGCAGTT GGTACCCCTC TGCTATGGCC 10920
TGTGATCTCC CCAGCCAAAG GCTTCTGACC AGATTTATAC TTCCAGTCAC GTATTCCCTC 10980
CTGAAGGTCC AGGCTTCAAA TGCCTCGATT GCTGATTGAT GTGACCCACC CCCAGTCATG 11040
TCATTGGTTC TCCAGCAGAC ATACCTTGCC TGGCAGGTTG GTACTGTAGC ATGCAGGGTA 11100
CAGAGTTGGG TAAGACCCTT GATGACCATC GCCACCCCTC CCCCCTGGCA GGTGGCATAG 11160
TACCTTTTCC AAGTATGAAT GCTGACTGGC AGGATGAAAC TGAAGCATCC GGTCAGTTCC 11220
AGTTTGATTT TTCTGTGTCT TGTAAGAATG AGCTCCCAGT GTAGGACCAA CCCCTGGACA 11280
AACTCAGACT TTGATGGTTT ATTCTCATAG AAGAGCAGAG TTTCATCTGA ACCATTAAAA 11340
TAAAAATTAG CTGGAACTAC CTGAACATTT CTGGTTTTAT AAATCATTGA GTTAAATATT 11400
GGAAAATTAG AATACATAGT CCAAAGCACT TATTACATAA CAACATACGT CTCTTTGTTT 11460
ATTACCATCT TTTGTCTTTC TCTAATTTCC TCACTTATTT AGGTAATTTT TCTTTCTTTA 11520
GTGCTGAGGA TTGAGCTTGA AGCCTTGTGC ACTCCAGGCA AGCATCACAG AGTTGTCTTT 11580
AAAGTAGTCC TGTTGTTTGG TGTTCTGCAC AGTGTTTCTT ATTTACACTA CGTTCAGAAT 11640
GTATTACCTA CAATTTCTAC TTTTAGTTTC TTTAAAGTGG AATGATAATT CAATATACTT 11700
GAAGTCATGT GACTACAAAG TCCTAAGAAT TTTTAAGTTT TTTTCTTATG AGCTTTTGCA 11760
GTTATTTTGA CTATGGGGCA TAATTTTTTG ATTATAATTT TTATGTAATA GATAATTATA 11820
TTTTTCCTAT CCCCCAACCC TTTCCAGATC CTAACCACCT CCCTATCCAC CCAAGGTTTG 11880
AGCCCCTTTC TATCAACAAT GAACAATCTA ACAAAGAAAA ATCAGAACAA AAAACCAGTA 11940
AGGAAAAACA GATACCTCAA CAAAATGAAA TTAAAAGCCT ACAAAAAAAA AAAAAAAAAA 12000
AAAAACCAAA ACAAAACAAG GCGTTCATTT TGTGTTGGTT ATCTTCTCCT GGGCATGGGG 12060
CCTGCCCTGG ACTGTTGCCA ATACATCCAG TGACACGTAA TTAGAGAAAG CAGATTTTTT 12120
TTCTTTCCCA GCTTTTGCAA AGAAGTTTTT AGTTAGGAGT GCTGGGATTT TGTCTAGATT 12180
GAACCTTTGC TATTCATGTG CAAGCTACCA CAGTCTCTGG GAGTTCATAT GTGCATCAGT 12240
CTTGTGTCTG GAAGACAGTG TTTCTGTGTC ATTTTATTGT AAAATTTACT ACTTAACTGA 12300
GAGTTATCAA TAATTTTTTT TTCTTTTTTA GTTTTGTTTT TTGACTTTGT TATTTTGTGG 12360
TTAAAGTGTG GCTTGCTTCC TCCTCTTCTG ATTTACTGGT CTGGGATTGT TCCTTCTGTT 12420
TTCTTGGATG TGATTAACTG CTTCAGACTA AAGTTTTCCT TCTAATGCCT TCAGTAGTGT 12480
TGGTTTAGTA GACTGATATG CTTAAAATTG GTTTAATCAC AGAATGTCCC CCTCGCCCCC 12540
AAGCTACTGT GATTGATAGT TTTGCTGGGT ATAGTAGTCT GGGCAGGGAT TTGTGATCTT 12600
TCAGAGCTTG TAGACTATTT GCCCAGGTCC TTTATGGGTT TTTAAAATCT CCATTTAAAA 12660
GCCAGAAGAT ATTTTAATAG CTCTGCCTTT ATATGTTATA TGGTCTTTAA ACCTTGTAGC 12720
CTTTAATATT CTTTCTTTCC TCTGTATGTT TAGTATTTTG ATTATGTGGC GAGGGATTTC 12780
TATTCCTATC TATTTTGTTT TCTGTATACT TCTTGTACCT TAAAACGCAT TTCCTGCTTT 12840
AGATTGGGAG AAATTTCTTG TATGGTTTTG TTAATAATAT TTTCTGTGAC TTTACATGGA 12900
TTTCTTCTCC TTCCTTTATA TCTACTTTTT ATAAGTTTGA TCCTTTCATT GTATTACAGG 12960
ATTTCCAAAT GGCTTGTGCC TGCGTCTTTT TAGATTTAAC ATTTTTTGAC TGAACTGTAC 13020
ATTTTTTTCT ACCTTGTTTT TAAGACTTGA ACTTCATTCT TCCATGTTGT GTGATATGTT 13080

*Fig. 7-13*

```
GATGACACTT ACCTCTCAAG TTTTTCTTTA ACACCCTGAG TTTTTCATTT TAGAAAATTT   13140
ATTAACAAAT AACAAATTTA CGAACAGAAC TTTATTGGCT TTTCCCATGT GTTTAGTCCA   13200
GAATAGAATG AAATAGTTTT TGCTTTGTTT TTTGTCATAT CTTATTGCTG CAGTTTACAT   13260
TTCATTAAAT TAATTATCAA AAAGGGCCAT CTGGCATAAA GGGGATGGGG ACTCAGAGTT   13320
AGTAAACTCT GAGTGAGTAT GCAAGGCTAC TTCTACAATG AGAAGCACCT GATCACACAG   13380
GCAAGTTGGC TGTTACTCAT ATTCACGTGT GGCCACATGG AAATAAGGAA CAGTTTTAGT   13440
CCCAATGGGT CTCCTCAGTA AGCCTTCGTT CAGTAAGAAC TTTTAAAGCT CATCTTTACA   13500
ATGAATAAAA TTAGAGCTGA ATAATGCTTA TTGAATTTTT TTTAGGGTTC CTGTAATATT   13560
GAAGAGTATT TCAGAAAATC TCTGTTCATT GAGAAAAGTG ATCTGTGGTC CTACAAACAC   13620
TGAGACTAGA CTGAAGCCGG GCAGTAGTTT TAATTTACTG TCATCAGAGG ATTCAGCTGC   13680
TGCTGGAGAA AAAGAGAAAC AGATTGGAAA ACATAGTACT TTTGCTAAAA TTAAAGAAGA   13740
ACCATGGGAC CCAGAACTTG ACAGTTTAGT GAAGCAAGAG GAGGTTGATG TATTTAGAAA   13800
TCAAGTGAAG CAAGAAAAAG GTGAATCTGA AAATGAAATA GAAGATAATC TGTTGAGAGA   13860
AGATATGGAA AGAACTTGTG TGATTCCTAG TATTTCAGAA AATGAACTCC AAGATTTGGA   13920
ACAGCAAGCT AAAGAAGAAA AATATAATGA TGTTTCTCAC CAACTTTCTG AGGTACTGAA   13980
TCAAGAGGGA ATAATATATT CATCAGTGGT TGGTTTACTT TGTTGTATAA ATGCACAAAG   14040
AACAAATATT TTAGTTTTTG TGGGATGCAT GGTCTCTGTT GTACCTATCC AGTTCATCCG   14100
TTGTAAAGCT GCCATAGACA CATGCAAGCA GTGGTACCTG TGTGCTTCAG TAAAACTTTA   14160
TTTAAAAATA CAAACAGAGG GCCATGTTAA CTTGTGAGAT CCACTTAATA CAATAAGTAG   14220
AATTGTATAA GTGAAAAATT TTGCTGCTTT ACTATTTATG TTTTTTATAT GATAGGTAAT   14280
AGTTTTTTGG TGGATTCTTC CTAAGTATTT ACTCATTCAA ACTTGATTTG GGGGGTGGGT   14340
GGGTTTTATT CCTTCAAATA GAAATTATTT GTTAGGGTGA AAGGGTCCTT TGATTTACAG   14400
GCATCCATAC TGTGACCTGG AGAGCCAGGA AGCTCTTGTC TCCTTCCTAA TTCTTATTAG   14460
CTTGCAAATT ACTGAAGACA TTTATCATTT CTGGGAGGTT TTTCTTTTTC TTTTCTTTTC   14520
TTTTCTTTTC TTTTTTTTTC TTTTCTCTTC TCTCTTTTTT TTTGCAATAA CAAATTTCAT   14580
TTTAGATTTT GAAAAGATTG TATAGGTTTA AACCTCTCAA TTTCATTACA GAAGTGGAAA   14640
CCCAGTCTTA TATACAATTC TTTGATTTTT TTTTTACAGG AGTTTTTCAA TTGTTTCTAT   14700
TGAGTATATA AATGTAAATT GTTTTAAAAA TTTCAAAATA TTCTCATTCT AATTTTTTGT   14760
GAACCAGATT CCCTCTCTAG AAAATGCTGT CTTTCACTTA CATGTGCATC ATTCTAATTC   14820
TGTAGAAATT TCTAATTAGA TCTGCACTTT CATATTTTTA TATATTAGAG AATTATGCTC   14880
ATGAGTTTGA TTTGACTGAT ATCTTTTATA TCAATTATTG CCATTTTATT ATGTAATGAT   14940
TAGCATCATT TTTATTATTT AAGACTGCGT TTAGAAGTCA AGAAAACCTT ACTCAGTTAA   15000
AAGTGTACTT TAATACATTT TAATAGCTTT AAATTAGCAT GTTAATTAAG GCTATTTTCA   15060
TTTTCCCATT AACAAATTAA ATATGAAGCA TTTGGGGAGA TATTCCTTCA AGTTTCTTCT   15120
TGATTTGTGT GTGTGTGTGT GTGTGTGTGT GTGTGTGTGT GTGTGAAGGG TAGATTTGCA   15180
GCTTGTTAGG CACCCGGTTC CTTGGGATTG CCAAATTATT GTAAAGATTC TTCATATCCA   15240
AACATCAACA ACAGATCAAG AAAATAATAT ATTTAGTATT TTTTCAAATA GATGGTCTTT   15300
GTAAAACACT AATTTATTGA AAGATTATTA TGTATTAGTC TTTGGTATTT TTAAGTCAGT   15360
GTATGTAAGA AAACCATTGA TTTTCTTGGT TTGTACAGAC TTTTTTCAAC ATTGATTAGA   15420
ATGCCATCTA TTGGAAAGTT GGGGAGACCC AGGTTGACCT GGTTGACCTT CAACTTGCAC   15480
TTTCTCTTCT TTTGCATGTA GATTCTACTT GACGTCTGTT TATCTAACTT GCCTGTCTTT   15540
TTAATTACGC TCTCTCTCTC TCTCTCATTA TTTGAAGATT AAAACACTCA TTCTCCTTTC   15600
TCTCCCGTCC TCTCTGTGCT CATGCTGTGA ACATATAAAT ATGCTTTAAA CATCTGCCTA   15660
TTAAAGAAGA GGAAGATGTC TAAATACTTC AGTGAAAGCA GCTGAGAGCA TAGTGTCACT   15720
CTCGCAGAAC GTTAATCTTT GAAATCCTTT TCTTTAAAGC ATTTATCTCC CAATGATGAT   15780
GAGAATGACT CCTCCTATAT AATTGAAAGT GATGAAGATT TGGAAATGGA GATGCTGAAG   15840
GTATGTTTGA ACACAAGAGA AAGTTACTTC AAGTTTTTAA AAGAACACTT TAATAATTAA   15900
AATATTATCC ACTTCCAAAT CAGATGCCAC CACAATGATA TTCATACCCA TTATTTAATG   15960
TTAGACTTTA AGTTTTCAAT TTACATGTCC TCATCTGTAA GTAGTCTTAG GTGTAACGTT   16020
GGGAGTTCTC ACGGGAGTTC TGTGTCCTCA TACGTCTCTC TCTCTGGAAA CTGGGCAGTA   16080
ACTAAGCACT TGAGCAGGAA ACTCATTATT TCTTCTTCTT CTTCTTCTTC TTCTTCTTCT   16140
TCTTCTTCTT CTTCTTCTTC TTCTTCTTCT TCTTCTTCTT CTTCTTCTTC TTCTCCTTCT   16200
ACTCCTCCTC CTCCTCCTCC TCCTCCTGCT CCTGCTCCTC CTCCTCCTGC TCCTCCTGCT   16260
CCTCCTCCTC CTGCTCCTGC TCCTCCTCCT GCTCCTCCTC CTCCTCCTGC TCCTCCTGCT   16320
CCTCCTCCTC CTCCTGCTCC TCCTGCTCCT GCTCCTCCTC CTGCTCCTGC TCCTGCTCCT   16380
```

*Fig. 7-14*

```
CCTCCTCCTC CTGCTCCTGC TCCTCCTCCT CCTCCTCCTG CTCCTGCTCC TCCTCCTGCT    16440
CC                                                                   16442
>00275      00275
GCTCCTCCTC CTCCTGCTCC TCCTGCTCCT GCTCCTGCTC CTCCTCCTCC TCCTGCTCCT       60
GTTCCTGCTC CTGCTCCTCC TCCTCCTCCT CCTCCTCCTC CTGCCCCTCC TTCTCCTCCT      120
TCTCCTTCTC CTCCTTCTCC TCCTCCTCCT GCTCCTCCTC CTCCTCCTGC TCCTCCTTCT      180
TCTCCTCCTC CTCCTCTTCC TCCTCCTCCT CCTGCTCCTC CTCCTCCTCC TCCTCCTCCT      240
CCTCCTCCTC CTCCTCCTCC TTCTTCATGT ATTTGTTGTG TTTTAGACAT TCTGTGTTTT      300
ACTCATTCAA TCATTTACAG GGTCTGGATT TTCTTATTGT GTGTTTTTTT TTTTTTAAAT      360
ACTGATTATA TATAATGGCT GTTTACTCTG TTATCAAAGC TGAAGTATGG ATCTGTGCAT      420
TTCTATCCTG TCACTCATCC TCCAGCTTAT CAAGTGTCGT AAGCCATGTG CAGACAGAAA      480
AATCCAGACT GAGAGAGTAA GGGAAAGCAC AGTTTAGTTA AATCAAATGA AAAATAAAAA      540
GAAATAGAAG TATGCTTTTG TGTCTGCCTT TTAAGCTGCC ACCTGTAGGT TAGTGTGCTT      600
TTTCTTTTCA TTAAATGAGA GTAATTTTCT AGTTCTTTAG TTTTGAGTTT TAGATAAATA      660
AGGATAAATA AAGATGTGGA TTCCTAATTG AATGTAGACC TGAGTCCTCC CTTCCCCATT      720
GGTGTCCATT GCTAACATCA CAGTTTACCA GGGAGCCTGT CTCCTATTTA AGAAATATGA      780
GCTAAATCAC AATCTATTCA CTAGGTATCC ATTTTTCTAG TGCATTCAGT TCAAGTGGTA      840
CCAAGTGTAG GATGCTTGTA GACATCTGTA CCATATATTA TACACTGGAC ATCTCTGTTC      900
TCTGGATATG TTGGTAGAGT TAAAGAAATA TCATCACCTC TTTTTTCCCC TCATTTTTCT      960
TTTATAGGAC GGAAATATTA TACTTTAAAG GACATTCTTA AAACCAAACT AAAAAATAGA     1020
ACGCCTCATA AAAAGTGAAG ATAACTTGTG TTAAATGAAT AGTCTATGTA ACTCCTTAGT     1080
AAAAAGTTTT ATAGATACAG CGATTTGAAA TATACTAATA TTTTTGAAAT AGTGGAGAAA     1140
ATACATATCA AAACACCTTT TTTTCACATC AGTAATATTT CTTTCCTAAA ATTATTTGAA     1200
TCCTTTTTTA CAATTCCAAA ACACATTTAT TGCTTGCTCA TAATTTAAGC ATCATCTTTA     1260
CTCAAGAAAA ATGCAATTGA CATGTAACAT AGAGAAATCT ATGATAAAAA TAGCATTAAA     1320
ATGTTTCATT TTACCACTTA GAATTCTAAA ACGTTGAAGT CCAATAAGAA AAACTGGTTA     1380
AATTATGCAA ATTTTAAATT TACGATACGT TTCCCAGAGG CCGTTCATTA TGTGCTATTA     1440
CTGAACCTTG TTTATGCTGG CCATGCTCCA TCCTGGCCTC GTGCCTTGGA GCATCTTCAG     1500
CACGTATTTA TAGAGGAGCA CACATGTTCT TTTGTGCTGT TGTTTGCACA TCTGCCGGTT     1560
TTCAACCAAA TTGTAGGCTT TGTTAATAAC CCTCCTTTTG TACTCAGTAA AAAGATACTG     1620
TATTGTCAGT GTTCTGCCTC AAATTTCTTT TAAACTTCCA GTCTTTAGAA AACCTAAATA     1680
GTGACATGGT GGAACCCACT CACTCTAAAT GGTTGGAAAT GGGAACCAAT GGGTGTCTTC     1740
CTCCTGAGGA GGAAGATGGA CACGGAAATG AAGCCATCAA AGAGGAGCAG GAAGAAGAGG     1800
GTAAGAATCA GGGTGGAAAC AAACTCACCT TTCATGGATT TCGTGTCAGT TTTCCCGTGT     1860
TTGGAAGTTT AACAAGTTGG TGGCACGTAG TTACTTATCC AGTCTATAAA CCAACCACTT     1920
AAGTCCTTAG TGCTCCTGTC TCTCGGGAAC TGTGGATGAT GAAACCTTTA ATCCTGAAGT     1980
GAAAGATTTG GTTTGGGTCC CAATGACAGT GGTGAAATAG TTTACTAATT GTTCATATTG     2040
AATGCCCTTG TTGGTGATAC AAATACATGC AGTCTGCTAC CCACCAGGAG CTTATGGTTT     2100
AAACAAGTGC CACACCATAT GTTCAATTAA ATGTATAGAA TAGTAAATGA GTGTGCAAGT     2160
GATAGAACTG TCATCTACGT GTAACCAATC ATGGTCATTC GGTCAACTTT GTAGTACTAT     2220
CACTATACTT ACAATATATT GTGGTGGGAA AATGTGGGCA TTTCAAAATC ATTTTGTAGG     2280
TAGAAGGTAC TTATAAATGT ATTGATGAGT TATTCTCCTT TGTTTCCTTT TATTAAGTGT     2340
AGCCATCTGT TTGTTAAGAT GTGCCATAGC ACTTATTTTT CATGTTTAAT GATAGCTTAT     2400
CTAGAATCTG TGTTTTATCC TTTCTTGGCT GCTTGTGAAT CTTTGCATCA ATGGACAGAC     2460
AGTGGTGGGA CTTAGGGAGA GCTAACATAG TCCACCATGT GGTACCATTA AAATTTTTGG     2520
CTAAAGATTT AAGTAGCTAT ATTAACCTAA CTAAATAGGA TAGGTAGCTA AATTAGATCC     2580
AGGTAACTTA ATTTATATAA CTAGATTTAG TTTTAAACAG CTAAATGAAA ATTTTATTTT     2640
TTTTCTGTAC ACTTAATTTG GGATACTAAT ATAATTCATG TTTATCATTA ATTGAAAATT     2700
ACTTCTAATA TAAAATTTTT ATCGGCATTT CTATTGTTTG CTTGGTTCGC TTCATTCTGG     2760
ATTGTAGATC CTGCAAGTTT CCCAATTACA GGATGTTGGG CCTCTTCTTA CCACTATTGC     2820
TAAAGCGGGC CACAAGGATA GGTCTAGTTT GTAAGTAGTG ATCAGAGGAT TTGCCTGGTG     2880
TCATGCTAGA TATCTGTAGA GTCAAGTGTG ACTGGGATGG AAACAGTGGA TGTCACCCAT     2940
CACTCTGTTC TTTATCACAG CAATGGAATG AACATTTTCC TCTTCTTGCA TAGCATATTT     3000
GCTTTTGAAC ATAAATGTCA ATTTTATTAT TTTATTTATT TTTAAGACCA TTTATTGCCG     3060
GAACCCAACG CAAAGCAAAT TAATTGCCTC AAGACCTATT TCGGACACAG CAGTTTTAAA     3120
```

*Fig. 7-15*

```
CCGTGAGTAT GATCTCAATT AACTATATTA TGTACATATT TTTTTTTCAC AAAGAGAAAG 3180
AGTAAATAAT CCATCCCCAT ATCCTAACAG CAGCAGCCTA ATTTTATTGT AGGCATATAT 3240
GTCAGGTATA GATTATATAC AACTGTAAAA TTATTGGAAA TATTAATTAC ATAAGTTTCT 3300
TTGTCCTTTT AATAGGAAAG GAAGCGGTTC TATTTTTCTT TAACTGAGTG CTTCTATGCA 3360
AAAACTATAT AATAATAAAA AAAGAATTTT TCTCACTGCT GAGTTATCTT TTATTGAGTA 3420
TGAATTCAGA GGAAAGGCAC ATTGCTTACT GCTTTCTGCA GGTGTTGCAA GGCACACTGT 3480
TGTGAGTCTC TGAGAGAACA GTTTGAGAAG CTGAAGGTTT ATTGTTTTAA CATTTCAAAA 3540
TATATTTCCA TCTAAAGGGC TGTCTTAGTC CATGTCCCAT TGTCGTGAAG GGACACCATG 3600
ACTACAGCAA CTCCGATAAA GGAAAACATT TGATCAGGGC TGGCTTACCA GTTCAGAGGT 3660
TTAGTCCATT ATCATGGAAG GCATGGCAGT GTACAGGCAG ACATGGTGCT GGAGAAGGAG 3720
CTGAGAGTTC TACATCCCAA TTGGCGGGCA GGAGGAAGAG AGAGTGAGAC ACTGGTTGTG 3780
GCTTGAGCTT TTGACACCTC AAAGCTCACA TCTGGTGACA TACTTCCTCC AACAAGGCCA 3840
CACCTGGTCC AACAAGGCCA CACCTCCTAA TCTGTTCAGA TACTGCCAAT CCCTGTGAGC 3900
CTTAGGGGAG TGTTTTCATT CCAACCATCA CAAGGGCACA CTAATAACTA GAAACAATGA 3960
GATGAACACA AACGAGATTA GGAACAAGTG CATTTGAATA AGACCAGTAA GTAACTAACA 4020
ATCTAGACAG GGTTTTTTCA ATTTTTTTTA TAACTTTTTT TTGGGGGGGG GTGCGTGTTT 4080
CGAGACAGGG TTTCTCTGTG TAGCCCTGGC TGTCCTGGAA CTCACTCTGT AGACCAGGCT 4140
GACTTTGAAC TCAGAAATCT GCCTGCCTCT GCCTCCCAAG TCCTGGGATT AAAGGCGTGC 4200
ATCACCACTG CCCGTTTTTT GTTTTTTTTT TTAAATAACT TTAAAAAGAA TTCATCGGAA 4260
CATTTTTCCT TCTTTTAATA AACTATCACC TCCAGTTGAT TTCACCTTAG TCCATCACTT 4320
TACACAGGTC TCATTTCAAA CCTATAGCAG TCCTCTTATT TATTCTAAAA TATTAACTTT 4380
TCGGTCTATA GTACAAAGCT GGGTATTTGT TTTATACTTT AGATATATGT AATAAAATTA 4440
CATATACATA CTATATGGCA ACTCATGGTT ATTCAGTCAG TCTGAATGAA AAGTTAATCA 4500
AATGATCAAA TTTTTTCTCT CAAATTTCTA GGATTTGAAT ATATTTTTAT AGGTAGCTCC 4560
AAAAAAAAAT CTGAGTTTAT TGGAGAGAAG TTAAATAGAT TTGAACTTGT GCTTTGGATG 4620
CTATTGATAA AACATTTTAC TTTGTACCTT CAAGGGTTCA GTGGAAAGTC ATCCATTCTG 4680
TATTAGAAGA GAGAAGAGAT AATGTTGTTG TCATGGCAAC TGGTAAGCTA TACTTAAAGT 4740
AAATAATTTA ATCATCTAAA AGTCATAAAG GGTCTAAAGT GCTTAATCTT TCAGAAACTT 4800
ATAAAATATA GGAAGGAATG ATTGGGGGAA AAGCCTTCAA ACTTATGCAT GAATTACCAT 4860
GTCAGTCCAC TTATTCTGCT ATATAAGCAC ACTGTAAGAA GAAAGTAAAG CATCAAGAGT 4920
TTCTTTTTAT TTTTTTGTGT TATTTTTTTT TTATTCAAGG ATATGGGAAG AGTCTGTGCT 4980
TCCAGTATCC GCCTGTTTAT ACAGGCAAGA TTGGCATTGT CATTTCACCT CTCATTTCCT 5040
TAATGGAAGA CCAAGTCCTC CAGCTTGAGT AAGTAATGCT TGCACTGCTG CAGCGTCGCC 5100
TTGGATAAGC AAGTGGAAAG AACATGGCAA GGCAGGATCT TACTACACAG GCTTAGCTAG 5160
GCTCTTCTCT CAGTGCAGTG GCCCTTTGCC CAGTTGTCCC TCTCTGTTCT ATCGATGAAA 5220
TATCAGAAGA TGAACGTGAA TCTAGGTCAC AGGATTACGT TTTGGGAAGT AACTTGATCT 5280
TCTTTATTTC TATTTTTAAT TTTTGAGATA GGGTCTTGAT ATATATATAG TCCAGGGTGG 5340
TGTCGCTCTG GCCTCTTGCC TTGCCCTTCA TGCCTTGGGC TCACAGAGCA TGCACTAGCA 5400
CCCCTGGCTG CATTCATTAG TAGCAAACGA AGTGTTAGTG GAAGAGTTTA CATTCATTCT 5460
TGAGGTCTCC AATGCAAGGC TACCTGTTTT CTCTGATCAG GGTTTAAAAG GACTGATTGC 5520
TTTATGCTAG TTAGCTGTCT CAAATTCTTT TTTTTTTGTT CTGCTCTCTG GGCTCCCAAG 5580
CTTGCAATGA GATATATATA AAAGTTTACT TTTTAAGATA TGTTTTTATT AGTTCTTTGA 5640
AAATCTCCTA CATGTTTTGA TTATAGTCAC CCCTCTTCTA ACCCTAAGTT CACCTTTCTA 5700
TTCCTTCTTG AAAGATCCAC ATTAAAGACT TGCCTCCTCA TCAGGCTTTT GAAGGAATAT 5760
ATCAAGTTAT ATAGACACAA AAAGGAAGAA CATTAGAAAG ATGAGGAACA TAGGAGGTTC 5820
ATGTTTATGT GTGTATTCAT CAGAGCGTTT GTCTCTTGTA GGCTATCCAA TGTTCCAGCC 5880
TGTTTACTTG GATCTGCACA ATCAAAAAAT ATTCTAGGAG ATGTTAAATT GTGAGTAACT 5940
TATATCATGT CACATAATAT TGTAAGATGT ATATAGAGTA AGAGAATTTT GTATATATGT 6000
TTACTTATAT GAGTAAATTG CCCATATTTG AAAACATACT TTAAAAAGCC TTATTTCTGA 6060
AATAATAACA TAGTTCCATT TCTTCCTTTC CTTTCTTCCT TCCAAACTCT GCCAAACATC 6120
CTTCCTTGTT CTCTTTCAGA TTGATGGATT TTTTTCCCAT TAGTTGTCAT TACATGGATC 6180
CATGTTTATA CATATGTATT ACCAAATGCC CCGTTTTTTC TCAGCAGAAG TCATGTAAAA 6240
CTCCTTTATC CTTAAGATAA ATATTCACTT TTGGGGGGCT GGTAAGATGG CTCAGTGGTT 6300
GAGAGCATAC TGAGTGCTTT TCTGGAGGTT ATGAGTTCAA ATCCCAGCAA CCACATGGTG 6360
GCTCACAACC ATCTGTAATG AGAAACAAAT AAAAAAAATC CCTATGGGCC AGAACGAGTG 6420
```

*Fig. 7-16*

GGGCCCCGGA GTGAGTGGGG TCAGAGCAAG AGGGAGAGAA AGGGAAGTGG ATTTTTATTC 6480
ACTTTTTGTT TAAATTATTA TTGTATTTGT ATTATTAACT TGTCTTCCAT TATCTTATTG 6540
TATCATATCT AGTATTATAT GTTATACATA TATATCGTAT ATATGTATTT ATATGTATCA 6600
TACTTTATAT TATATGGTTA ATTTGCTATT ATGATAATTT TTATAAAAGA AGGCTAGAAA 6660
TTACTTATGG CATGTCTCTA CCATATAAAA GCAGATAAAA TTAAATTAAA AATTTTAATA 6720
TAAAAGTTCT TTAAGTTTTT AATTTATCTA TTCCACTAGT ATTTTAGTGT CTATTACATG 6780
CTAAACATTA TGTTTTCACT AGTAATTTAT TAGGCATGTA ATAAATTTTA TCGTATCTCC 6840
AGGAAATTGA TGCAGTTTTC TAATTACTGT AAGAAACAAT AAAAATAATG AAGGCTAACA 6900
TCACTGTACC CAGGTTTGGA ATCAGTTCTC CGTCCGACTA GGAAACTGAT CTGAGATGAG 6960
CCAGTCAACT CCAGTGTATC CCAGTTTCTT GAAAATTAGC TGTTTACTTA CAGAGACAGA 7020
CTTAGGACAT CTCAGTTAAG AAACGGACAC TGGAACCTTC ATGGAACCAA AGAGCAGCCA 7080
GGAAAACTAA CACACCCCTG AAAACAAAGA GCATAACTGG GGGCTTGTCA TCGAGACTTG 7140
CAGGCTTTTA CTGTAGCTAC AGCAGCCAAC ACAGGCAGAC GGAGCCACAG AAGCAGATCT 7200
CAGCAAGGAA TCTGCACATG CCTACAAAGC TCATCATCTG AGAAAGGCTC AAAGGTGATC 7260
CAGTGGAAAA GAGACAATCC AGAATAATGG CTTATATGAA AACAATGGCC TTATAAGAAA 7320
AACAAACCAA ACAAACCAAA CCAAAACAAA CAAAACCCCC CAAACTAATA CACCACACAA 7380
TATAAACATT TTTTGCTAAA AGCGAATTAT GCGTCCAAGC ATAAAATTGT GAAATGTTTA 7440
AGGAAAAGCA TGCCATCTTT ATAACCTTCA GTTAGGGAGA CTTCTTAAAT ACCCAAAGCA 7500
AAATCTATAG GAACAAACTA GCAGCTGGAC TTTTACAAAC TGAAAACCTA CTTCTCTTCA 7560
AAAGAATTAT TGAAAAAGGA AGAAAGGCCA TAAACTAGCA AAGTATATGC AAAGTACATA 7620
TCCATACAAG ATTTCTACCT ATAATATAGA AATTACCACC AAAAGAGAAT TAAAAAAAAT 7680
TAAAGTGTCA AAAGATTGGA ACAGACACTA GCACAAAGAT ATACAAACAG CAATAAGTAT 7740
AAGATGCTTA TATAATTGGT CACCAGGCAA AAACAAATTC AAGGTACAGT GAGATTCTTT 7800
CCAAGTGGCT AAAGCCAATG ACTGGCTAAG AAATGTCAGG GGTAGTGAGC AACAAGACTT 7860
TTCACACACC ACTTCTAGGG ATGAGAGATG GTAGAATGTT TGTTTGGGGA GTAGACTGTT 7920
AGAAACCATA ATTTGGCTTA TAATTCCAGC TTAGTGGTGA ATCCTACACA TCAAGAATTG 7980
TTATATTTTA TTTTGGTGAA TTGAAGATAA ATGAAAGGAC TAACATCTGA ATTATGTATA 8040
TATATAAAAT ATTCCTTTGG ATTTTAATAA TCAGCATGAT GCATTACTTA AAAACCTATT 8100
GAATGCTTCT TTCCAGTCTA GGGCAGGGAC CTTAGCTGAC CTTGGGTGCT AACTCTGCAC 8160
CCAGCCCCAC AATACCCAAA GGAAGCTCCA CTTCTAGGCG CTCTAACACG CCAAGTCCGC 8220
AGGATTCCAG GATCCCAGGA ACTTGGTCAC ACCAGGATCT CAGGGTTTTA GAGGAACCTT 8280
GGCTCCCAGG AGCTCTGACA CACCCAGGAT CTCAGGATCA CAGGATCACA GAGACAGCTG 8340
AACTCTGAGA AGGTCTGACA CGACCAGGAT CACAGGAAGG ACAGGCTCCA GTCAGATATA 8400
GTGAAGGCAG GTAGCACTAT AGATAACCAG ATGGTGGGAG GCAAGGGGAA GAACATAAGC 8460
AACAGAAACC AAGGTTACTT GGCATCATCA GAACCCAGTT CTCTCACCAT AGCAAGTCCT 8520
GGATACCCCA ACACACTGGA AAAGCAAGAT TCAGATCTAA AAATCACTTC TCAGGATGAT 8580
GATAGAGGAC ATTAAGAAGG ACATCAACAA CTCCCTTAAA GAATACAGGA GAACACAAGT 8640
AAACAACTAG AAGCCCTTAA AGAGGAAACA CAAAAATCTT TTAAAGAACT ACAGGAGAAC 8700
AAAATCAAAC AGGTGAAGGA AATGAACAAA ACCATCCAGG ATCTAAAAAT GGAACTAGAA 8760
ACAATAAAGA AATCACAAAG GGAGACAACG CTGGAGACAG AAAACCTAGG AAAGAGATCA 8820
GCAGTCATAT ATACAAGCAT CACCAACAGA ATACAAGAGA TAGAAGAGAG AATCTCAGGT 8880
GCAGAAGATA CCATAGAAAA CATTGACACA ACAGTCAAAG AAAATACAAA ATGCAAAAAG 8940
CTCCTAACCC AAAACATCCA GGAAATATAG GACACAATGA GAAAATGAAA CCTAAGGATA 9000
ATAGGTATAG AAGAAAGTGA AGATTCCCAA CTCAAAGGGC CAGTAAATAT CTTCAACAAA 9060
ATTATAGAAG AAAACTTCCA TAACCTAAAG AAAGCGATGT CCATGAACAT ACAAGAAACC 9120
TCCAGAACTC CAAATAGACT GGACAAGAAA AGAATTCCTC CTGTCACATA ATAATTGAAA 9180
CATCAAATGC ATTAAACAAA GAAAGAATAA TGAAAGCAGT AAGGGAAAGA AGTCAAGTAA 9240
CATATAAAGG CAGACCTATC AGATATAGGA CTAGACTTCT CACCAGAGAC TATGAAAGCT 9300
AGAAGATCCT AGGCAGATGT CATACAGACC CAAAGAGAAC ACAAATGCCA GCCCAGGCTA 9360
CTATACCCAG CAAAACTCTG AATTATCATA GATGGAGAAA CCAAGATATT CCATGACAAA 9420
ACCAAATTTA CACAATATCA TTCCACAAAT CCAGCTCTAA AAAGGATAAT AGATGGAAAA 9480
CACCAACACA AGGAGGGAAA CTACACCCTA GAAGAAGCAA GAAAGTAATC TTTCAACAAA 9540
CCCAAAAGAA GATAGCCACA CAAACATAAT TCCACCTCTA ACAACAACAA AAATAACAGG 9600
AAGTAACAAT CACTTTTCCT TAATATCTCT TAACATCAAT GGACTCAATT CCTCAAAAAA 9660
GGACATAGAC TAACAGACTG GATGTGTAAG CAGGACCCAG CATTTTGCTG CATACAGGAA 9720

*Fig. 7-17*

ATGCACCTCA GTGACAAAGG CAGACACTAC CTCAGAGTTC AAGGTTGGAA AACAATTTTC 9780
CAAGCAAATG GTTGTTTCCC AAGAAACAAG CTGGAGTAGC CATTCTAATA TGGAATAAAT 9840
TCAACTCTCA ACCAAGTTAT CAAAAAAAAA AAAAGATAAG GAAGGACACT TCATACTGGT 9900
CAAAGGAAAC ATCTGCCAAG ATGAACTCTC AATTCTGAAC ATGTATGCTA CAAATGCAAG 9960
GGCACCCACA TTCATAAAAG AAACTTTACT AAATCTCAAA GCACACATCA CACCCGATAC 10020
AATAATAGTG GGAGATTTCA GCACCCCACT CTCAGCAATG GACAGGATCA CGGAAACAGA 10080
AACTAATCAG AGACACAGTG AAACTAACAG ATGTTATGAA CCAAATGGAT CTAACAGATA 10140
TTTATAGAAC ATGTCATCCA AAAGCAATAA ATATACCTTC TTCTCAGCAC CTCATGGAAC 10200
CTTCTCCAAA ACTGACCATA TAGCTGGTCA CAAAACAGAC TTCTACAGAT TCAAGATGAT 10260
GGAAATCATC CCATGCACCC TATCATCAGA CCACCACGGC CTAAGATTGG TCTTAAATAC 10320
CAACACAAAC AACGGAAAGC ACACATACAT ATGGAAGCTG AACAGCGCTC TACTCAATGA 10380
TACCTTGGTC AAGGCAGAAA TGAAAATGAA GACACATCAT ACCAAAACTT CCGGGACACA 10440
GTGAAAGCAG TGGTAGGAGG AAAACTCATA GCTCTAAGTG CTTCCAAAAA GAAACTGAAG 10500
AGAGCTTACA CTAGCAGCTT GACAGCTCAC CTGAAAACTC TAGAACTAAA AGAAGCAAAA 10560
ACACTCAAGA GGAGTAGACT GCAGGAAATG ATCAAACTCA GGGCTGAAAT CAACCAAATA 10620
GAAGCAAAAA GAACTATACA AAGAATCAAC AAAACCAGGA GCTCGTTCTT TCAAGAAATC 10680
AACAAGATAG ATAAATCCTT AGCCAGAGTA ACCAGAGGGT ACAGAAACAG TATCCAAATT 10740
AATAAAATCA GAAAGGAAAA AGGAAACATA ACAACAAAGT ATATCTTAAA ATAACTATTC 10800
TGTTTGTTGA ATATCAATAG TTGAAAATAT TAAAATCATG TTCTACAAAC ATCATGGAAA 10860
TATTATTGAT AATTTTTCTC ACTGTGCTTG AAATTAGCAT TTTCTTAATG TTTATGTCAA 10920
AGTGTTTTTG CTATTTTGAA ATGTTTAAAA TATACTTACT GATAAAATAA TTTCTCTCCT 10980
AGAAACACTG ATAATCTTTT TTCTGTAAAC TGATTTTTGG ACAATGTACA CAGATATAAA 11040
ATGTGTTTTA AATACTCTCT CACTATGTCA GGTGTTATTA TATAAAGGCT TTCAAATATA 11100
TTTCTTAGTG ATTCTTTTTA AATATTTTAT GCTCTTTTAC TATGCCTAGC TCCCAAAGAA 11160
TATTCTGTAT GTTTTGAAAC AATTTAGTAT TCAATATTAG GTACAGGATC CTCAGTTATG 11220
GATAGTATTA AATATTAATT AATGATATTT TTAGGATATG AAAGGATATG AATATAAAAG 11280
TTGGACAAAA TTTTAAAGTA TTATCTGATA TCAAAATACT CAATATTATT GATATGTTTG 11340
ATGTATAAAA TACATTTAAA TAATAAGTTT TAAAAAATGT CTATTGAACA TTTTGATTTT 11400
GTTATCATTC ATTGACTGCC TTTTTTTCCT ATTAGAGTGT TTCAATTTAT GTTTCTATTT 11460
TTGTTTGTCT TTACAGAGGC AAATATAGGG TCATCTACAT AACTCCAGAG TTCTGTTCTG 11520
GTAACTTGGA TCTACTCCAG AAACTTGACT CTAGTATTGG TAAGTAATGA AGTAGGACTT 11580
CGGTGAATAC AAAGTAACCC ATTTATGGTT GAAGACCAGA TTCCAGTTTT GTTAAAGGCT 11640
TATTTCAAAC ATTTGCTCCT CTAGGAAATT TCTAATCAGT TTTACATTTG TCCCATTTTA 11700
CAATGCTGTA TAATTCCTCA TTCCATAGAG GTGGTACTCC TGGGTGGGTG TCATATTTGT 11760
ATATAAGCAT GTATGTATCC CTGTCACACT CAACCCTTTT GAGGCTTCTC TGCTCTTACT 11820
GGCCTCCCAA CTCCTTCATG CAGGATGTGG CACACAGTTG TCTATCCTGT GCATTGCTGC 11880
ATGAACGCTG AGTCTTGTTT CATATTCTGA GTCTAAATGA AATCAGTGTG TGGTTCCTCA 11940
TTCTTGCTCG TCAGAATCGC CCTTCAAGCT CTAGAACAAT GCTGTTAAAT GGCGTATTTC 12000
TTAGAAAATA TAAATATAAA ATAGGTTAAA TGCTGTGATA TTGTTTATGC TGAAACTTTT 12060
GTTTTTTGGT GGTGGAAGTG TGGTCAGGTT TAGCTAAGAG CTCCAAAGGA AACAAACATT 12120
ATCCATATTC AAAACTTTCA TTTAAATTTT ATCCAACTTA TCAGATAAAA TTGTTTTCCC 12180
AATTTGTGGG ATTTTCGTTT TTGAAGAATT AGGTATTAAG TAATTTCATA TAGGTTAAGT 12240
TTTCAGTATT GTACTGGACT AGCTAGTGGA GTGTCAACTT GATTTAAGCT ATGGTCTTCA 12300
AAGAGGAGGA AACTCAGTTA AGAAAATGTC TCCTTAAGTC AAGATGAAGG CAATCCTGTA 12360
GAACATTTTC TCAATTACGG ATTGATGGTA GAGGGCCATT GTGGATGGTA CTATCTCTGG 12420
CCTGGTGGTC TTGGGTGCTA TAAGAAAACA GGCTGAACAT GCCATGGAGA GCAAGCCTGT 12480
AAGCAGCATC CCTCCGTGGG CTCTGCATCA GCTTGTATTG ATTGGTGTTG CTTGTTGGTG 12540
CCACAGTAGA GAGAGGAGCT CACCAAGTTC CTAAGCCATC CTTTTTGGAA GGAGCAGAGG 12600
GGTTCAGCCT TCCTGGGAAG GCTCACTCCA GTTACTTTAT TCAAGCATTG TTCAAGGTTA 12660
ATTGGGGCTG GGAAAGGTTT CAACCACCAC AGTTGTTATC TTGTGTTTGC TGCTCAAGAG 12720
ACAACATGAC CCACACAGAT CTTAGTCCCT TTTGACCATG GCTAGGCATA ATCAAAGGTA 12780
AGAACTCCAG GTTTGCCAGG AGTGTCTTAG GACCAAGGTT GATGCAGCTG CAGGCCTTCA 12840
GGTAGTACTG AGTGCAGACT TTGCAGGGAG ACAACATTTC TTCAAATAAT CTCAAAACAA 12900
TTTCTCAGCC TCTACTCATT AACCCAAACA CAGCAGAGGC TTCGCTGAAA CATTTCACTC 12960
AAAGCTAGGC ACAAAGGCTT CACTGAACAT TTCACTTCAG GCTCCTGCCT CCAGGTCGCT 13020

*Fig. 7-18*

TCCCTGCTTG AGTTCCCACA TTGGCTTCCA TCAATAATGA GGATGATGTG GAAGTGTAAG 13080
CCAAATAAAC CCTTCCTCCA CAAATCGCTT TGGTCATGGT AACAAAGACA TGTACCCTAT 13140
CACTTAATAG TATTTCTCTT ATCAGGCATC CATGGGAGGA GGGGCCCTTG GTCCTGTGAA 13200
GGCTCCATGC CCCAGTGTAG GGGAATTCGA GGCTAGGGAG GCAGGAGTCG GGGGTGGGGG 13260
GAACACCCTT ATGGAGGCAG GGGGATGGAG AATGGGACAG GGGATAACAT TTGAAATGTA 13320
AATAATGAAA ATATCCAATA AAAATAAATA AATAAATAAA TAAATAAATA AGGAAATTGA 13380
AAAAAAAAAC AAAACAAAAA GAGAGTAGAC TTTTATATTT CAGTATGTGT TGAAAGCAGC 13440
AAAGAATGAG GACCTACATT AATATTTATG GAAATATATT ATCACAGTGT ACCTATGCTC 13500
TCTCTCTGTT AGCTCTCATT GCCATGTTTT TGCCTGTAAT GGAAAACAAG TTTGATGTCC 13560
AGTCTGTAAT AGCTGGAAGG TGTTCCTTCA AGCATCTCTC TATGGGTTTA GCCTTATAGA 13620
TTTACCTTAT AGATCTATAG CCTTATAGAT CTACCTTATA GGTCAATTTC ATGGTTGGAT 13680
CTAAAAACCT GGTTATCAGT AACTCTGTAT TCTGAGTATA TTTTTTTCCA CTTTCAGTGT 13740
TTATTTGTTT TAATTTATAA TGATGTTAAA TTAATAACTC CTGTAAGTAA ATAAACATTA 13800
AGAGCCTTTG ACAAGTAGTT ATAACTTTTT ATGAGGTAAA TGGTCATTGC TGCCGAGCTG 13860
AGGACACTGT TCAATGATTC TGTTTGCCTA GCATGTTCCA GGCCTGGCTT CAAACCTCAT 13920
TCAGTTTCAC TTATTTTTGT TTTTACTCCA TGTGTTGGTG TTTGTGGTCA CAGGGTAACT 13980
TGAAGGAGAA GGGGAGATGG TCCTCTCCGT CAACCATGTG GGTTCTGGGC ATTTGCTGTT 14040
ATGCCAAAGG GAAGTGGTTT TACCCACTCC CTCTTGCTCA CCTTAGACAC TGTATGTTTT 14100
GTTTATTGTG CTTTTCTCCC CCCCCCCCCG TGAATCAGTT TAGGAGAATG ATACAGGAGG 14160
ATCAGATAGT CTGACCTCCC TTCTGTTTTA AAAACATACA CACAAGTGAG CAAACAAAAC 14220
CAGATAACAC GTGTAAGTTT TTCATCACTA GAGCAGAATT GTTTGCTTTT AATAGATAAA 14280
AATATTTCCC TGGGTGATTT AGAAAAAGGG ATAAGGAAAA TGAAAATTAT TTTTTTTAAA 14340
TATTTCCACT GGCTTTTGTT TGCAGGAAAC AGTAAAAAGT CTACAAAAAT GAATATACTT 14400
GGGATGTTAT TTGTACAGTA GTCTGACATT TAACTAATCA GATTTGTCAT TTTTAGGTAA 14460
ATGTTACATT TTTTTTTAAA GTAGTCCGGG TCTATAACAG AAATAGCAAG CATACTTCAT 14520
GGGGTGCCTT CCCAGGCGTA CTTGTGATTG TCTTTTAACT TTGGGAATGA GACTTGAATG 14580
GCAGATGCCT AAATGAAATC TCTACAGGAC CTTGGAAGAC CCTTGAACTT TTGCATTCAG 14640
AGTGAATTTT GCCAAAGCTT GTCTGAACTA ACTGTGTAGG TGAAAGTTCA ACTCTATTAA 14700
CTGCTTGTCA GATCTCTTTT AACTTAAAGT CTAGCCATGT TAATTTCTAC ATTCAGAATA 14760
AGTGTATGAG TGACACTGGA ATTTCCGCAG TCACTCAGTG GTATAAAGTC AGCGTTTGCC 14820
TCTTCGCTTC CTTCCTTCTC GCAGTCTGAG GACATTGGTG TAATCTCAAT GAGTTGCTCT 14880
TGTTTCTTTT GTTTCCTCTC TGGATTGTGA GACCCTTGAG GTCAAGTATA CTTTGGTTAC 14940
CAAGAAAAGG GTTAATTCAG TTTTCTTATT TAGATAGAGC CTCCAGCAGC TCAGGCCGGT 15000
CTTGAACTTT CTATGTGGCT GAAGAGAGCC TTGAATTCCT GATCCTGAAT TACATGCGTG 15060
TGGCTCTTAA AAGGGCTTTA AATCATAATG ACCATGTAGT AATAACCGCT GAAGTATATT 15120
TTTATTAAGC TCTTTTTGGG CCCATCCTTA TCTGAGTGTT TTATGTGAAT GTTCTAATTT 15180
AACCTTAGAG GAGTAAGAAG TATTAGGTGC TGTTACTACC TACCGTGTTT TATTTTTGCT 15240
TACGATGCTG TTTGTGCTGC TGGTGCTGCT GGGGGTGATG GTGGTGATGG TGATGGTGAT 15300
GGTGGTAGTG GTGGTGATGA TGTTTGTGGT GGTAGTGGTC AGTGTGTGTG TGTGTGTGTG 15360
TGTGAAATAC CACAGTGTGT TTGTAGAGGT CAGAGAACAC CTGTGTAAGT GGGAGACAGT 15420
TCTCTCTGTG GTTTCTGAGG GTTGAACTCA AGTTCTCAGA CTTTTACCCA CTGAGCCTTC 15480
TCAGCAGGTC CACGATGTAG TTTTGAGGAA ACTGAGAACT GAAAAGATTT GTAGCTTGCT 15540
CAAGGCTTTG TGTACAGCTA ATCTAATTCT AAAGCACATG TTTTAAATCA TCTCACTGAT 15600
AGGGTATATC AGCAAATAAC AGAAGGTTAT TTTTCTCTTA AAAGTACTAA TTTGATAAGG 15660
GTAAAGGCAT TACTAGTCAG TTCTTTGAAA TGTCTGAAGA TGTCATGATG ATTACATAAT 15720
GAAGCCCTTT CAGATGCATT AAGACACCAT TGATCTTGTA TTAGTGTGTG GTGTGGGGCC 15780
CCGTGGAGGG TTATGTTCTT TTTCACTACT TACTTTGCAC ACGGTGGGAA TTAGTTCTCC 15840
CCAAGCCGTT TTATGTTAGC CAATGTGGAT GTCATCTCGT CTTCAGTTAT TGGCATTTCA 15900
GAGGAACTTC CTGTAATATG ATATGTGCCG GATTGCAGAT AACGATGTAC TTAATCTCAG 15960
TAGAAATGTG CTGACTATTT GTCTCCGTTG ATAGCTAATC TATGAGATAA GATTAACATT 16020
ATTGCCAAAA AGAAATGGAA CAATTCTTTT GAAAGGATAT TGTTGTAGAT GTTATAAGTG 16080
ATAATTTTGG GACACAGTAA TAATAAGCAA TTTATGTCTT TGAGGAATAG TAATGAAAAC 16140
TGAAAGATAG TGTGTTGTTT CAATTACGAC GTAAATATTT CCTGTATGCG AACCTCTTTT 16200
ATTCATTTCT CCTCTTACCT CCTATTCTGC CTTCGGAAGT TTGATGTTAT CTGGTATTAT 16260
TTATGCTTCT TATATGTGTG TGTGTTTGAG CCCAATACTT TGATTTGACT TATACTTTCT 16320

*Fig. 7-19*

GTGAGGTATA TGTTCTAATA GGAACAGACA ATATTGACTT AGCTAGCATT TTCCTTCTGA 16380
GCCTTATTTC TCCTGTATAT TTTCTTCTGT GTAGGCATCA CTCTCATTGC TGTGGATGAG 16440
GCTCACTGCA TTTCAGAGTG GGGCCATGAT TTCAGAAGTT CATTCAGGAT GCTGGGCTCT 16500
CTTAAAACAG CGCTCCCATT GGTAAGCCTT GCCAGATCTC ATGCCCCCAC CCCACCCATC 16560
TCAGCTGAGG ACTGACCCCA GGGCTCCTAC CACCAGGCTA GACCCTCAAT CCCGAATTTA 16620
CTGAAGTGAC ATTTTCATCA AGGCCTTTCC AGGACTGGGT AATGTCCACC CATCTCAAGA 16680
CTTCTCTATA AAAGGGATCA GATGTGAGCA ATGGGGCATA TTTAGTTTTA AAATTTTTTA 16740
AATTCTCACG CTGGCTTCCT TTTGAGGTTG ACGTGTAGCT TACTAAGGAA TACTCTTAAC 16800
AGGAGTGTCC AGGCTGTGAC ATTGAGCTAC TCCAGTGTCA TCTTCAAGGT TCTCCCTCAA 16860
GAACCACAAA ATTGTGTTAT TCAAAGACAT CACAAAGATG CCTCTGTTTT AGTTCACGTG 16920
TGACTTTGTG TTGTGCCACA TTCCTACTGT CAGGGCACGG GCTGGATGCT CTTCACTAGG 16980
ACAAGAGCTG GAAAACAAGT TTTGAACATG GCAGATAAAA ATGGCAGTTA CTATTCCTTA 17040
GTGAAAGGGG ATACAGTTTC AAGAATCCGT GGATGCCTGG AAACACCCCC TCAGTGTAAA 17100
TTATGCACAG TAGAAGAATT TTTAAAATGA CTATCTGTGA CAATATACTA TAGCAAAAAT 17160
GACCACAGTC ATTATTCTTG ACCGCGTGGC TCATGATTAA GTAGAGTAGG TAGCACCCAA 17220
CCACAAGCAC TTCCTAGTCT CCTAACTGAG ATGGTTAGTC AGTAGGTAAT GGGGGAGGCT 17280
GTGGATTGTG TGGAAACTTT GGACCAAGGG GAGAATGGGG TGATATCTTT GAGAGTACAG 17340
TGCAGAATTT CATCATGTTA CTCAGCACGC CTTTAATCCC AGCACTCGGG AGACAGAAGC 17400
AGGTGGATCT CTGAGTTTGA GGCAGCCTAC TTTAGTCCTG TCTTAGGAGA AAGATAAAGG 17460
AAAATGTAAG TTGGGTTTTA GGTTTTTTTG GTTTTTTTTT TTTTCTATTT GTTTGTTTTT 17520
GTTTTGTTTT TTGTTTTTTG GTATAACTTT TCATTTAGTA TATTCAGATT TGGTTGTTCA 17580
CAAGAATCTG AAATCAGAAA ACGCCATTGT GGATAGAGAA GGTGGGTGTG AAGTGGATGA 17640
GAGGGCGGGT GTGTGGTGGA TAGAGATGGG AGTGTAGTAG ATGGAGGGGG CGGGTGTGTG 17700
GTAAATGGAA AGGGCGGTGC GTAGTATAGT ATGGCTTTCA CATACAGTTC TCTTTTCTTA 17760
AATAGTCCAT AAAAAATGTA GTTACCTGGT GTTCCTCACT AATGGCCTCT GTAAAATGGG 17820
CTGGGGACTG CGATAGTTCT ACTTATCACA GTTTGTAGAA ACTTTTAGGT TGTTTGTTGG 17880
AGTTAGGATA TTATGAATGG GGATACTGTA AACATTTGTC TATAGTCCCA GGGTCCAGGT 17940
CAGCGGTTAC AAAGTTTGTG AACATAAGTT TTAGTTTTCT GGGATAAATG ATGTTCTGGG 18000
TTCTATGGGA AGTGCTGGTT TCACTTTTAG GAAGACCCCA GTGCTACTCT CTAGACTGGC 18060
TGCTCTGTTT TGTATCGTCC CCTCCCCAGC AGCTTAGGAA CAATAGCTTC TTCTCTTTTT 18120
TGCCACTGTT TAGTCTTATT ACTATGTAGT ATTTTAGCAA TTATGATACG AGTGGAGTGG 18180
TAGCTTGTGT TTTCAATTTG CATTTCTCTA ATAGCTAGTG GTGTTGAACA TCTTTTGTGA 18240
GCTTCTTATT TGGTTAAATG CCTAGTTTAA TTGGGTTGTA TTTTTTCTGT TAAGCACATG 18300
GGGGAGGTGG AGGGAGAGAA AGGGAGGGAG AGGGATAAGG AAGGAGAGGA GAGAGAAGGA 18360
AGGAGAGAGG GAGGGGGAGG GTTGTGCTTA TGCACATATA CCTCTGCGGT GTGCTCTACA 18420
GTGCAGCCCC TGCAGGCGCC AGATGTTGAC GCTGCTGTCC TCCTCTGTTA CTCTCTACCC 18480
CATTTTATTT GAAACACAGT CTCAGTAGCC AGGGAGCTCC TCATTTGTGC TAGACTAGCA 18540
GGCCACCAAG CCCCTGGGCT CTTCCTACTT TGGAACATTG GGCTCCTAGG TGTGCACGCT 18600
GTGCCTGGCT TTTCTGTTGG TTCTGGGAAT CCTTGCTCAT GTCCTGATAC TCACTGAGCC 18660
ATCTCTTCAG TCCCTCTGTT AACTGCTAAG AATTAAATGT TTATAAGTGT GAGTTATTGG 18720
TTGGATATTG AGCTTGTAAA TATTTCTTTG TAAATTTTAT TTTTTTCTCC TATTTTCACA 18780
ATCTTTTATA AAAAATATTA TAAGTTGGGT AAAATTCAGA ATATTTTTTT TCCTTTATGG 18840
GCTTTCTTTC TCAGTCTCAG ATCTTGAAAG TTTGTCCCTG TAGTTTTTCC TAAAATGTAA 18900
ATGATGTAAA TTTAGGTCCG ACAGGGTACA GAGATGTCAT GGCAGGTAAA GAGCTTGCCG 18960
TGCAAGTGTG AAGACATGAG CTTGAGTCTG TGAAGTACAG TGACATGTGC CCCATCCCAC 19020
ACTATATGGC AGAGGAGACC CAAGGGCCCA CTCCTCCCCT AACTGGGTAA AAAGAGGGCT 19080
TTTTATCTAC TTAATTGCTT TTGCCTCTTT GTTGAGAATC TTTTGAGTGT GTTTTGTCAG 19140
CCTGTTTCTC TGGGCTGTAG TCATTTGGAT TGAATTAACG AAGCGGCCTA TATTTAGGTC 19200
CTGGTGCTAG AGAGACGGTG TGCACAAGCC TCACAGTTAA ATGGGTCAAA CCAAGAGGAG 19260
CATTCAAAGT TCTTATCCTT TTGGCGAGAT TGTCTGACTT AGTTCCCTTA ATCATCAATC 19320
TTACACATTA ATAGCAAATT GCTATGTTTA AAATGACTTC TTTCTGTTCG GGTTTTCTCG 19380
TCAAGATTTG ATTGAGCAGT GATTAAGTAA GTCAAAAACA GTAGGAGACA GGTAATGCTA 19440
CAGCTAGCAG ATACTACATC AAAGGAAAAG AAACTAATGT ATTTGGGGTC TAAGTATGCG 19500
TCTGGCCTTG GGTCAGACAC TCTTGTCTCA GTCTTCAGGA CTGTTAATTA AGTTAGCTTT 19560
AATGCCATCA TATTTCATCA TTTGTCAAAG GACAGCTCAT TCCCCTTGCT TTCTTTCCCA 19620

*Fig. 7-20*

GCATAACCTT CTCCTCAAGT CTCTTCTGTT CCTTTGTACC TTCTTGTTTT ATTAGGGTTG 19680
GTGTCCTGGT CCCTGTTTTA GACTTACTCT CTCTCTCTTC TGTGCTCTCT TTTCTGTGCA 19740
TAATTGGATA CCATCCATCC CATTATGGAG AACCCTCAAA TCTACAACTT GGATTAGTAC 19800
CAGATGTGAC TGAGTTCCTC CGCCTACTTA CCGGCACTTG CTGTTGTACT ACATTTTGTT 19860
TTAGCAATTT TATTGCATAT AAATCACACA TATTATAGGG GATTTATAGG ATATGTATAT 19920
ATACACAATT GTCAACTTGA GGGTTTGCTC TTTGGGTTCC TAATAGGTAT CTCAAACTTA 19980
ACCCCTCCAA AACTGGCTCC TGATGTTCTT CGCACTCTGA GTGCTTTTCC CGCAGACTCC 20040
ATCACCTTGT TTAATAGCAG CACCAGAGTG TTTTGCTATG CAGCCCGGAC TAAACAAGAG 20100
ATCCTCCTGC CTCAGTGTAC CCAGTTGCCT GGAATGCAAG TGTGTACTAC TCTGCCTGGG 20160
AGCTTGATTA TTGTTACCAC TCTGCAGCAT ACATTTCACC AGTAAGGAAA GCCTGTGAGT 20220
GATCTTCCGA GCCTATACAG CTGCTAATCG CTTCCCTCTT GATCCCTGCC GTAGCCCCGG 20280
TGCTGGCTTA CATCTTCCTT CATGTAGGCT GTTACAATAA TCGCCTGGTT TCCACCTTTA 20340
GTCTATTTCT ATACAGCGTT CAAAGTGATA CTTCTGAATC TGTCCCCTAG TTCTGTGTCT 20400
TCTGTGCAGG ATGTGATGGC ATCGCCCCTC ACTGAGGTTA TGCTATGTCG TCTTTCACTT 20460
TCATGCCCGA ATGGTGATGT TAGCTTCTTA ATGCAATCCA TCAGTGAATT AAGTCTTTGG 20520
GTCAGGTTAC AGCCATCGTT ATCTAATCAC CTCTCCGTGG TTGGGTCTGT GACTTGGGGA 20580
TTTTCACCCT TCTACACACA GAGAGGGCAG TTTGTATCTA AACCATAACA AGAGGGAGTT 20640
TTTCTTTTTC TTTTTGTTTA TATAAGCAGG GGTACTATCT GACTCATAGC AGTTGCTTAA 20700
TAATTACACG AATCAATTAA TTCTGGTCAG AAAGCTGGGA ATTAGCGAAG TAACTTTCCT 20760
ATATAGGTAG TTATAAAAGA GTTGGGTAAT AAATAGCTAT ACCATAATAT ACTGTGCCGA 20820
TTTCAACACA AATGATTTGA AAGAGACAAG CTATATTTTC TACCCTTAGG TAGTTCATAG 20880
CCCCGAGAGG GAGTTGAGAT CCACATCCAG GAAAGTAGAG GCAATAGAAA CAAACTGTGC 20940
ACCATGCATG GAAAGATGAG TAGTGCCCAT AGCACAGTCG CACATGGGAG GGCAAGTGAA 21000
GGTGTCCCAC AGTGCAGTCA CTGAGCGCTG CTCTGAAGGA CTGGTTCCCA CTGACTTAGG 21060
AAGATTTAAT GAGACAGAGC GAGCTGTGGA ATTGAAAAGC AAGAGGATGC TTGTGTAAGC 21120
CTTTCTTAGG CCTTTGATTC TAGGATTGCG TTAAAGGAGT TTTAAATAAT TTAAGTGGTT 21180
CTCAAATATT CTTCAGGTGG AAAAAAAAAG AATTAAATCT TTTATTATAT CTAACTCTGG 21240
ACATAATGAG ATCGCTTTCA GTTCTTGCAG TGATGAAACA GCGTATTCCT TCAGCTGAGA 21300
GTCTTGGCAG GTTGTTCCTC CTGCAGAGGC CGAGGATCCT TAGCCCCTGT GCTTTTAAAG 21360
ATGGACTCTG TTGGGGGTGG TAAGAAACGC CACCTGGTGG ATATTCCTTT TCTTATTGAC 21420
CTTGATCTTA CTGTTTTAAC CCTGTTATGC TGGGATTACT GTTGGGTTCA TTACACCAAA 21480
TTAGTATAGC AAATCTAAAA GTGCTGGAAA CCACCAAACA ATTAACACAG AGGACCCATT 21540
TGGAAGGAAT CACAAAAGTG AGCCCAGAGA GGTGAAAGCC AGGTGAAAGT TCTGCATAGC 21600
CGTCAAAGTT TATATCTAAC CAGGAGGACG GACTTTTGAA GACTATGAGG TATATTGACT 21660
CTTCCCACTA ATTTGTCGTA AGGACCCATT AAAAAGATCA GAATAGTAGA CACTAAATAA 21720
CTGGAAGAAG AGATTAACTA AAATCTGTGT GCAGAGTGTG AAGTAGTTAT GTCATCCAAT 21780
TTAGAAAAAA GATTGTTATG TTTTCTTTCA ACCGTTGTTT CATGGAGCAT GTAGTTAAGA 21840
TTCATCTCAA TGTACAGTGT CATAAGATTA ATCTGCATTA TATATTCATT GGGTTTTGTT 21900
GCTTACTTTG TCAACAACTG GTGTCTCTTA CCAAGGAAAT CAAGGCAGGC AAACTTAAAG 21960
AACAAATTCC TGGTGCTAAG TGCTTGATAT ATGTAGACAC CAGTATAATT CAGCACATGA 22020
CCAGCTTTCT TCTCAAACAG GTTACACTAT TTATAATTGT GCTGTAGCCA CAAAAACGAC 22080
CTGGAAATAG CCCATCCAAC AAGGGCATAT GGTCCCATTT CTCAGTACTG ACCCATGTGC 22140
TATTTGTAAG CATTGTCCTT GACTAAAATT TTCACATTAT AAAATGCTGC AGACTTCTGA 22200
GGGATCCGTT CTAGTCACAT TCATTTTCAT GAAGACTGTT ATTTTTTATT CTACTTTTTA 22260
GTTGGAAGAG CAGTATTCCT CTCTGTGTCT TTGGAATGTT GTAGTGAGTT TACAATATTT 22320
TCCCTGCTAG CAGTCTGCTT GACTTTTTGA GGACCTTATA AGAAAAATGA AAATTTTTAC 22380
TAAAAGATCT ATCAATCTTG TAGCTCTGTG TCTCTCACTT CACTTTTCCT TAAGTTGAGC 22440
CCTTGCTGGA GTCAGTGGGG AATGCGCTAG CATTTGAAAT TCTCCACCAT TGACATTTCC 22500
ATGCAGAAAG AAATGTCTTC TGTTGTTTTG TGACTGCACT AGTTATAAGG AACATTTTAG 22560
GTGCTGGCTC TAATACCCTG AATAGAATTA AGCACTTAGC ATGCTTTTGT AGATATGTTT 22620
ATGTGTTTTG TGTGGAGTCC AGGTGTGTAT AAAGACTACA GGTCATTCTT GGGTGTTGTT 22680
CCTCAGGTAC AATCCACATT GTCTTTGAGA AACAGGATCT TTCACTGGCC TGGAGCTAGC 22740
CAAGTAGGAT GGAGTGACTG GCCCTAGAGT CCTGGGAACC TCCATATTTC TTTTATATTT 22800
GGCATAAGAC CGCTGTCCTT TTTCTTTGAT TCTTAAAATA TTGTTCAGCC TCTTTGCTTA 22860
TGCAAAGGCG ATCTATCAAT CAGTAAAGTT CTGGCCTGAG AAGTCTGTTC AGGAAGACAG 22920

*Fig. 7-21*

GCCATTGGCT GAGATCATCT ACCCAGTGCC GGTATTACAA ACTGGAATTT CAAGTGTGTG 22980
TCACAACATC TAGGTGTGTG TGTGTGTGTG TGTGTACACA TATATATGTA TATATGGTGA 23040
TGCCCAGCGT CCTGAAGGCG CTGTTTGACA AAGTTCCAGT TCTTGGACCA AGCCTTCACT 23100
GCCCTTGGTG GATATTCGCT GCACACCTCT TGCTAGTCTT ATGTTTCTCA CTGTTAAAGG 23160
CCTCTCTCTG AAAGCTAGAG GTGGGATAAC AAGAAGCTAG TGTAAACAAG AATCAAGTTA 23220
ATTAAAGTTC CCTGGGGGGG GGGAAGTTAT GCAGAAAATT GAGTCTCTTC TAAGAAGTTA 23280
TTTCTTAAAT AAACATTTAG ATCATTAATG AATGTTGTTA GTAAGCATGA GATAGAAGAT 23340
TTGAGAAGAA TTATTAAAGA AGTAAAACTT AGGGAGAACT TAGAAGTTGA GAAGTTGTAT 23400
TTGGATTGCT AGGTTTTTAA GGTTCAACTT GAGAAACGAG CAGTTTGTAT GTATAGGACG 23460
GGATTTGGAT CATGCAGGTT TATGACAAGC CTCGGTGCCT TCCTGAAGGC AAAAGTAAGC 23520
AGGTTTAGGA ACCCTGATGT TCTTCTGTTC TTCACAGAAT TGTTGTAAAG ATAGGGATTG 23580
TATTGAAACA AGGGTTCAAG ACAGAGACAC AGAAGAAGGC ACTCTGGCTC AGTGAACTAC 23640
CTGCCTTCCT GAACATGTAA GGTTAAAAAT GTAAATTCCT AGGAAACTGT TATATTTCTT 23700
TTTAAAATGT TAGGTTTTGT TTGTTTGTTT GTTTGTTTTG TTTTTTAGTT TTAGTTTTAC 23760
TTTTTTTTAG ACAGGGTCTC ACTGTGTAGC TGGGGACAAG CTCCACCCCT GTTCCCCTTT 23820
TCCTCACCCT CCTGAGTGCT GGGATCACAG GCGTGTGCCA CCACCCCTGT CAGGGTCCTC 23880
TACACACCCA GGAGTCCTTA CTGTCAGGCT GTGTCTGTTA TCGTATCTTA TATCAACCAC 23940
TAATCAACCA TTGTAATGCT TGATTAGAGA ATCTGATTTC TTCAAAACAA ACAAGGCTCT 24000
GCATGACTTA ATCACTACAT ATACATTCCT AACGCAGAGA GCAGTCGGAT TATTGGCCTG 24060
AAGATTAATG TGGGGTTACA TTTTAAAGTG GTTTCACAAA TTTAAAAATA GACAATACAA 24120
AAAATTATCC TAATTACTTG GTTTCATTGA GTTTATTTTT GTATGACTTT GGATAGGTTT 24180
TAATCTAATT AAGTTATTTT AATCGTAAGA GTAGCTGTTT CTTAATTAAT TTACTGCTGA 24240
AGACCAAACC CAAGGCCTTG ACAGGCTCGT ACATTCCCAA TGAGCCATGC CTTCAGCCAC 24300
TTAACTATTC CTTTCTGTGT GTGACTGAAA ATAAGCTTTA TTTTTCTAAG CCAACAAAAA 24360
TGAAATAATG CTTGAAGCTT TGTCCAAGTC TATATTATTT TATGGGTAAT ATTTATTTTA 24420
TATTGAACAC TTTTATTTTT TAACTATGAA GGTCTTTTAT TTTCATAGAT ATCTATTGCG 24480
GTAAAAATTT AAAGGTAATA AACTATGATA AATTGAGCTA AAGATGTGGC TCAGTGGTTA 24540
GATGTTCATA TTGCTCTTAC ATGAGAGGAG AGTTCAATTC CGATCACCCA CATTAGGTGG 24600
CTCACACCTA ACCATAACCC CAGCTCCAGG GGTGTCTGAA AGCTCTGGCC TTTGAGGAGG 24660
ACTTCACACA CACACACACA CACACACACA CACACACACA CACACACAAA GTAATAAATA 24720
AAAATGATCC CTAAGTACAT AAATCATAAT TGAAGTAACA TTCAATGTTG TTATGGAGGA 24780
TCAGCTTATT GGGAGGTTAT GTAACTATAA TATTTACATT TTTAAAGAAT AGAAAAAATC 24840
TATTTCTATA ACAAAGCTAA CTGAAACAGT AGAATATAAA AGGCAAAAAC ATTGATATTA 24900
ATATTTTGTG AAATTTAAAT AAAAACCAGC AATCAACTGA AACTGAAAAT ACCATAAATG 24960
ACAATGCTCT TTCTTAGGTA TTTCTTAGTA GTTTTGTTTC GCATTCTTAA TTTACATTGT 25020
TGTATAAAGA AGAATAAACC GAGTTACTGA ACAGAGCAGC AAAGCTTGTA ATCTAAAATT 25080
TAAAGATGTT TATGTTTTAG TTTTCGAATT AACAATTTAT AATTCTGAAG ATAATTTTTT 25140
CTTAATTTGT TTATTATCTA AATGCATTTT ATACATCAAC CATATTAATA ATATTGAACA 25200
TTTTGAGACT CAAATAATAC ATAAAAAATT TGTTCAACTT TTATTTTCAT ATCCTGAAAG 25260
TATCATTAAT GAATATTTAA TACTATCCAT AACTGAGGAT CCTATATCTA ATGTTAAATA 25320
CTAAATTGTT TCAAAACATA CAGAATATGC TTAGGGAGTT AAGCATAGTA AAAGAGCATA 25380
GAATATTAAA AATGAATCAT TAAAAAATAC ATTAAAAAGC CCTTATATGA TACCACATGA 25440
CATAGTGAGA GAGTATTTAA AACGCATTAT ATATCTGTGT GCATTGTCTA ACAATCAGTT 25500
TACTTAAAAA AGATTATCAG TGTTTCTAGG AGAGAAATTA TTTTATCAGT AAGTATATTT 25560
TAAAAATTAC AAAATAGCAA AAACTCTTTG AAGTTAACAG TAAGAAAATG CTAATTTCAA 25620
GCACAGTGAG AAAAATTATC AATAATATTT CCATGATGTT TGTAGAACAT GATTTTAATA 25680
TTTTCAAATG TTGATATTCA ATAAACAGAA AAGTTATTTG AAGATATATT TCATTGTTAT 25740
GTCTCCCTTT TAATTTTTGA TTTTATTAAT TTGGATACTG TCTCTATGCC CTCTGGTTAC 25800
TCTGGCTTAG GGTTTATCTA TCTTGTTGAT TTTTTTTTCA AAGAACCAGC TCCTAGTTTT 25860
GTTGATTCTT TGTATAGTTC TTTTTGCTTC TATTTGGTTG ATTTCAGCCC TGAGTTTGAT 25920
TATTTCCTGC AGTCTACTCC TCTTGAGTGT TTTTGCTTCT TTTAGTTCTA GAGTTTTCAG 25980
GTGAGCTGTC AAGCTGCTAG TGTAAGCTCT CTTCAGTTTC TTTTTGGAAG CACTTAGAGC 26040
TATGAGTTTT CCTCCTACCA CTGCTTTCAC TGTGTCCCGG AAGTTTTGGT ATGATGTGTC 26100
TTCATTTTCA TTTCTGCCTT GACCAAGTTA TCATTGAGTA GAGCGCTGTT CAGCTTCCAT 26160
ATGTATGTGT GCTTTCCGTT GTTTGTGTTG GTATTTAAGA CCAACCTTAG TCCGTGGTGG 26220

*Fig. 7-22*

TCTGATGATA GGGTGCATGG GATGATTTCC ATCATCTTGA ATCTGTAGAA GTCTGTTTTG 26280
TGACCAGCTA TATGGTCAGT TTTGGAGAAG GTTCCATGAG GTGCTGAGAA GAAGGTATAT 26340
TTTTTGCTTT TGGATGACAT GTTCTATAAA TATCTGTTAG ATCCATTTGG TTCATAACAT 26400
CTGTTAGTTT CACTGTGTCT CTGCTTAGTT TCTGTTTCCG TGATCCTGTC CATTGCTGAG 26460
AGTGGGGTGC TGAAATCTCC CACTATTATT GTATCAGGTA TGATGTGTGC TTTGAGATTT 26520
AGTAAAGTTT TTTTATGAAT GTGGGTGCCC TTGCATTTGG AGCATACATG TTCAGAATTG 26580
AGAGTTCATC TTGGCAGATG TTTCCTTTGA CCAATATGAA GTGTCCTTCC TTATCTTTTT 26640
TTTGATAACT TGGTTGAGAG TTGAATTTAT TCCATATTAG AATGGCTACT CCAGCTTGTT 26700
TCTTGGGAAA CAACCATTTG CTTGGAAAAT TGTTTTCCAA CCTTGAACTC TGAGGTAGTG 26760
TCTGCCTTTG TCACTGAGGT GCATTTCCTG TATGCAGCAA AATGCTGGGT CCTGTTTACA 26820
CACCCAGTCT GTTAGTCTAT GTCTTTTTTT GAGGAATTGA GTCCATTGAT GTTAAGAGAT 26880
ATTAAGGAAA AGTGATTGTT ACTTCCTGTT ATTTTTGTTG TTGTTAGAGG TGGAATTATG 26940
TTTGTGTGGC TATCTTCTTT TGGGTTTGTT GAAAGATTGC TTTCTTGCTT TTTCTAGGGT 27000
GTAGTTTCCC TCCTTGTGTT GGTGTTTTCC ATCTATTATC CTTTTTAGAG CTGGAAAGAT 27060
ATTGTGTAAA TTTGGTTTTG TCATGAAATA CCTAGCAGCT TGACAGCACA CCTGAACACT 27120
CTAGAACTAA AAGAAGCAAA TACACCCAAG AGGAGTAGAC TGAGATTGGG AGTTTTGCCT 27180
GGGCTGGCAT TTGTGTTCTC TTAGGGTCTG TATGACATCT GCCTAGGATC TTTTAGCTTT 27240
CATAGTTTCT GGTGAGAAGT CTGGTGTAAT TCTGATAGGC CTGCCTTTAT ATGTTACTTG 27300
ACCTTTTCCA TTGCTGCTTT TAATATTCTT TCTTTGTTTA GTGCATTTGG TGTTTTGATT 27360
ATTATGTGAC AGGAGGAATT TCTTTTCTGG TCCAGTCTAT TTGGAGTTCT GGAGGCTTCT 27420
TGCATGTTCA TGGGCATCGC TTTTTTTAGG TTAGGGAAGT TTTCTTCTAT AATTTTGTTG 27480
AAGATATTTA CTGGCCCTTT GAGTTGGGAA TCTTCACTCT CTTCTATACA TATTATCCTT 27540
AGGTTTGGTC TTCTCATTGT GTCCTGGATT TCCTGGATGT TTTGGGTTAG GAGCTTTTTG 27600
CATTTTGTAT TTTCTTTGAC TGTTGTGTCA ATATTTTCTA TGGTATCTTC TGCACCTGAG 27660
ATTCTCTCTT CTATCTCTTG TATTCTGTTT GGTGATGCTT GCATCTCTGA CTCCTGATCT 27720
CTTTCCTAGA TTTTCTAACT CCAGGGTTGT CTCCCTTTGT GATTTCTTTA TTGTTTCTAG 27780
TTCCATTTTT AGACTCTGGA TGGTTTTGTT CATTTCCTTT GCCTGTTTTA AAGTGTTTTC 27840
TGGTAATTCT GTAAGGAATT TTTGTGTTTC CTCTTTAAGG GCTTCTAGCT GTTTACCTGT 27900
GTTCTCCTGT ATTTCTTTAA GGGAATTATT TGTGTCCTTC CTAACGTCCT CTATCATCAT 27960
CATGAGAAGT GATTTTCGAT CTGAATCTTG CTTTTCCAGT GTGTTGGGGT ATCCAGGACT 28020
TGCTATGGTG GGAGAATTGG GTTCTGATGA TGCCAAGTAA CTTTTGTTTC TATTGTTTAT 28080
GTTCTTCAGC TTGCCTCCCG CTATCTGATT ATCTCTAGTG CTACTTGCCC TCGCTCTGTC 28140
TGACTGGAGC CTGTCCTTCC CGTGATCCTG GTTGTGTCAG AACTCCTCAG AGTTCAGCTG 28200
TCTCTGGGAT CCTGTGATTC TGGAATCCTG TGATCCTGAG ATCCTGGGTG TGTCAGAGCT 28260
CCTGGGACTC AAGCTGCCTC TAGGAACCTG AGATCCTGGT GTGACCAAGC TCCTGGGATC 28320
CTGGGATCCT GGGATCCTGT GGACCTGGGT GTGTTAGAGC TCCTGGGAGT AGAGCTTCCT 28380
TTGGGTGTTG TGCTACTGGC TGTGGAGTTT GCTCTCAAGA TCTGCTCTGG GCAACGGCTC 28440
AGAGTGGATG GGACCTGTGC CGCTGGTCAG GTGGAGTTCC TGGGTGCCTG GGTTCCACTG 28500
CTCCCAGTTA CTCCCGGTGT TGGGGCAGAT GTTGTGCCCT CCTCACCTCT GATCCTATGA 28560
TCCTGGGAAT GTTTAGGGCA CTTGGGAGTG AGCTTCCTCT GGGTGTTGTG GGACTGGCTG 28620
CGGAGTTAAT GCCCAAGGTC TCTGCTCAGG GCACTGGCCC TGACTGGAAG GAACCTGTGC 28680
CAGTGGTGGG GCGGATTTCC TGGGCACCAG CCCAGACTGG AACAGAACAC TTTTATTTTT 28740
ATTCATTTAT ATTGTTCAAA ATAATGAGTT TCGTTTCATT TCCATAACAT ATTTAATGTA 28800
CTTTGGTCAT ACTTATTCCC TAAGAGATCG TATTTTGTTT TAATTTTAAG TCAAATTATA 28860
TACATATTTC TTTGTAAATT AGCAAACTGC ATACACATTT ATACTTAGAT ACAAGATAAA 28920
TGCTTAAATT ATTTTATGAG GTATTTACCG TTATGTTTGA ATAATTTTAT TAGGATGTTG 28980
TTTCCTCTAT CTGTAACAGG TAATAAAATA AAAAATTGAA TTCTTAGCAA TAGAATAGCT 29040
AATGATTTAG AAATAAATTT TAAGACAGCC TTTTTCTTTT CTGATAATGA AATGGTTGAG 29100
TACCCTGGTT GAGTGTGTCC CCATTGTAAT AGTTATAAAA CATGAGCCAT CTACATGGAA 29160
GATACCTTGC TCACCTACAT GTGAATTTCT GAACGAAATA TTCATGGTCT TCCTGCCTCC 29220
TATTGTGCCT CTTGATTTTG ATGCTCACCC TATGGAGAAA TGCTAGAAAA TAGCCTATGA 29280
GTCAGTTGCT TAAAGAATCG GGTAGTCATA CATGTCTCAC TTTCTACATA TTGATTACAT 29340
CCAGAATGGC ACTGAGAACT CAGTAAGACA GGAGAGAGGT TGTAATGGCT GTTGGGAGAC 29400
TTGCTTCCAC AGCTGGAAAG CCACATGCCA ATATAATTTT GAAGAACGCT TCTCACAAAA 29460
TAAAAGATAA ATTGTTTTAT GTAGCTAGGC TATTAATTTA TAACCCTGCC AGGGCTTATG 29520

*Fig. 7-23*

TATTGCAAGT TACAGATTAT TAAAAAAGAA CGAGATGTAT TAATCCCCAC TTCTATTAGC 29580
ACTAAAGTAT AAATGGCTAA TAAGTAGTTT TAATTTAGTG GGACAAGATA AATTGCATTG 29640
AAATCTCATG ATTTAGTGTT TGATTTATTA AGTAGGAGAT AACTTTTCTC GTTTAAAAAC 29700
ATTTTTTTTT CTCTTTACGT AGGGCTCGTA GCTTGGTGGT AGAGCACCCA CTAAGCATGC 29760
CCAAGGTCCT GGGTACCATC CCCAACATGA CAAAAAGAAA TAAATATTCT AATAAACCAA 29820
AACGTTAGCA TGTGTGTCTT GGCCATGGTT CCTGTATGGT TGTGACTGTG GATGTGTCAG 29880
AAGACAGTGA GAAGTCAATG CGCCTTTTAA ACGTCCGTTT GTATTGGATT TCCCCCCAGG 29940
TTCCAGTCAT TGCACTCTCC GCTACTGCAA GCTCTTCCAT CCGGGAAGAC ATTATAAGCT 30000
GCTTAAACCT GAAAGACCCT CAGATCACCT GCACTGGATT TGATCGGCCA AATCTGTACT 30060
TAGAAGTTGG ACGGAAAACA GGGAACATCC TTCAGGATCT AAAGCCGTTT CTCGTCCGAA 30120
AGGCAAGGTA AAGATAGGAC GCTAGACGAA AGGATCTTTT AAAGAAGTTA TTTTATTTTT 30180
TTCTATTTCT TTTTTGATA TATATTTAAT GTCTCAAATT TTATGTAGCC TTGGCTCAAA 30240
TGAGTGTAAT ACTACATAAT CAATTCAGTG ACCAATATGA AACCACTAAA AGAAATATTT 30300
CCATTCATTC TTTTAGAATT TCATATAGTA TACTTTGATC ATATCCACCC CTTATTACTT 30360
TCCCAACTTC TCAACGGAAA CTAGCTCTCC CTCTCCCAGA AGCTATCAGC TGTCTACAGT 30420
CTACTGCTTG GTTAGGGGTA GGGGCTTGGT CTAGTGTAGA CAAGGGTTCA TGAGCGCAGT 30480
GGTCCTGCCA TGACCAGGAC ACATGGCTTT GCTTCAGTTT TCTCTGACCA TTGGCCTTTG 30540
TGTTCTATTT GTCCACTCTC CCATGGTGTT CAAAGCATTT GTATTTTGCA AGGGCAGAGG 30600
AGATGTGGCC AGGAACTAAT TTGTCTAATA TTATTTTTCT TTTATATTGT TATTCAAATA 30660
AGAGATATTC TTTTAATAAT TTACAACTAA ATGAACAAAT ATGACATGAG CATTTCTTAT 30720
GAGTTCTGTC TGCTTTCATA TTTAGATGAT CTACCTCTGC TGGAGGGGCT TTTTAATAGT 30780
CAGTATAGAG TCTGTCCATG TTCCAAGGAC TGTCCTAGAT GCTTTATACA AGTGATCTTG 30840
TTAAATCCTC TAGCATAAGG AAGTTCCTGT GTACATCTAT ATTTTACTGA TGAAACTGTC 30900
CATTACACTT CTAAGATTTG TATTTTAAAA TATACTTTAT GCTTTATTTT GTATGCGAAG 30960
AACCTTTGTA ATGCCATTAT TCTCTGTCCT GCCTGCTGAG TTAAAAGTTG ATATTTTCCT 31020
TATATTAAGT ATTCTGAATA ATGAAAAATA ATTTTCTCCT ACCAATACCA ATGCAAACCA 31080
AGTCCAAGCA AGAAAGAGCT GAGAGCATTG TTAGTGTTTT CCTCGTCCAG AAAGGATGTA 31140
AATGGGAAGA GAGATCCTAG GTTAAGGAAG TGATAGTGTT TGTTGTAGAT ACTAGGAAGT 31200
AGTTTAAGTA CCACCTGAGA AGTGCTCGCT ATTCCGAGTA GAATAGGAAG ATGGGGAATG 31260
TATTGATAGG GTTTTGCTGC TCAAGCTGCC TCCTTGAACC TGCTGTTCCA TGGTCCTTTC 31320
CAGTAAAGGA AAAGTTCTCT TGTCAAAGGC TTCTTCTAAA CTGGATGTTT CTACACTCAT 31380
GTCATTACTA ACCCCTGATC TTTTAGTTCT TGTCAATGCA CATTATTTTT AATATCTATG 31440
GCTAATTTTT ATAGTGACCC TCTTCTTTCA TATGTATATG TGTGTGTGTG TGTGAGTGTG 31500
TGTGTGTGTA TGTATATATG TGTGAGTGTG TGTGTATGTA TGTATATGTG TGTGTGTACG 31560
TGAGTGTGTG TGTGAGTGTG TATCTGTGTG TGTGTGTGTG TATGTGTGTA CACACACGTT 31620
AAAGTGCCTT CCCCCATCTT TTCTTGTGAT GTTTTGTTTT CCCATTTTTG GCATCATTTG 31680
CCTTACAATA TCTTATGCAA ATGCCTTCTT CCCAATTTAT ATTGATATTC TGGTAACGAT 31740
GATTAATTTA ATTTTTAGCC CAGATTTTTC TGATCACTCA TAACACATCT ATATCCTCGG 31800
TGCTACTTGA TATATTCCAC AGATAACTTT CAGGTTTATC ATCTGCAGAC ACGTCCTTAA 31860
ACCTTGGAGT AAAATTTTAT TTTTAAACCT TGTATAATAT TTTATGCAAC AGTGAAATTA 31920
TTCTCTCACC TCTTAAATAA GAATAGATTA ATCTATTGTG CTGCCTTTCT AGACTCATTT 31980
TTATCCATAC CTTGTAAGTT TTAGAATCAT TTTTTTCCTA AAACAAAGTG ATTCCTGGTT 32040
TTAACTTTAA TTTGGGCCAA TGTTGAGTGC CAGAGTTTTG CTTTCACACA ATACGTTTCT 32100
ACGTTTGTCT TTCCAGAATG TTCTGGAGTT TCAGGGAGTT GAAGTGTTTT TCAGTCTGCT 32160
GACTTCTTTA AGACTTTTGC TTAGTGAAAG CAAAGATTAT GAAAGATGAA TCCCAAACTG 32220
CGATGAAACA TACATGTAAC AGGCGTGTTT GCTTTCTCTG TCTCCCTACC TCTTCCCCAC 32280
CCTTCCACAG TTCTGCCTGG GAATTTGAAG GTCCAACCAT CATCTATTGT CCTTCGAGAA 32340
AAATGACAGA ACAAGTTACT GCTGAACTTG GGAAACTGAA CTTAGCCTGC AGAACATACC 32400
ACGCTGGCAT GAAAATTAGC GAAAGGAAGG ACGTTCATCA TAGGTTCCTG AGAGATGAAA 32460
TTCAGGTGTG CAGAGCAACC ATCTTTCTCT GAATTCTTCA CAGGAAGTAT ACGTATCTGT 32520
CAAACATTTA TGTCACCAAT TTTTTTTTTA AAATTGTTGT ATTAAGCACA GTTTCACCAC 32580
TCTGATAAAG GTAATGACTG TATAGTGAAA TTGGATTAAA TAAACCCTAC AGCTTAGTGT 32640
AAATAGCAAA GACTGTCATC TGTTACTGGG CTACACAGAG AATCAACACC AGTTCTGTCA 32700
GAGTAGGTTA TGTAATGAGA GTGGTCATCA GGAAGCTGAA ATCTGAGAAG AGTCTTAAGT 32760
ATGTCAAGTT TACCAGGTCA GTAGGTAACG AGGGCTGTAG AGTCCCAGGA AGCAGCAGCA 32820

*Fig. 7-24*

GGTGCAGAGA CACACGTTGA GTGCATCCTG GGCTCAGAGA GGAAGAGCCT GAGGTGATCG 32880
GAGGAGAAGA TGAGCGGTAG GAATGGCACA GTCAGGGGAC ACAATGAGAA GGTTAGACAC 32940
TCTCAGGAAG GCTGCGTTGG ATGGTTGGCC AGCTTAAAGA TGAGAAGGAT CCCTGGTTAA 33000
TGGTGCTCGC CCCCTACCAG AAAGCATCTA TTGTCACTCT TCCTGTAGGA ACGGCACTAA 33060
TGCTTATGAG AGGTTGTTGT GCACACTTAT TAATACTTTT ATTACTTTAG CGACTGGGTC 33120
CTTTGGATGC ATCTGGCATA CTGCCTGTCT TAGGTACTTT TCTGTTCTAC TACTGACTGA 33180
GGCAACTTAC AGAAGAAATA GTTTATTGGG GCCTACAGTT TCAGAGAGGG GGTCTGTGGT 33240
CACTGTGGAG AGTGTGCAGC AAGCAGATAG GCATGGTGCT GGCGCAGCGG GTAGGCAAGG 33300
TGCTGGAGCA GCGGGTAGGC AAGGTGCTGG AGCAGCGGGT AGGCAAGGTG CTGGAGCAGC 33360
GGGTAGGCGT GGTGCTGGAG CAGCGGGTAG GCGTGGTGCT GGAGCAGCGG GTAGGCGTGG 33420
TGCTGGAGCA GGAGCTGGCA GCTTGAGCAC CAAGAGAGAG AGCTAGCTGG AATGGCACGG 33480
ACCTTTGAAA TTTCAAGGCC AGCCTTTAAA GCCTGCTCTT CCCCACAAGG ACACACGTCC 33540
TAACTCTTCC CAAACAGTTC TCTCACCTAT GGATCAGCGT CCAAACATAT GAACCTATCA 33600
GGGCCATTCT TGTTCAAACC ACCACACTGC CAATGTATAA CTTGATTGAA GCATTAAATT 33660
TATATATATT AGTTTTTTGA GACAGGGTTT CTCTGTATAG CCCTAGCTGT TCTGTGGAAG 33720
TATTAATATT TTAAAAGAAG GCTTAAAAAT CTTTAGTGAT CTTTCATTAC AGTTAATTTT 33780
GAAGGTTATC TATCTACCTA CCTACCTACC TACCTACCTA CCTACCTACC TACCTACTTA 33840
TCTACCTACC TACCTACCTA CCTACTTACC TACCTATCTA TATTTTGCAT GCCCTGCTGA 33900
ATTTTCTCTT TCTAGTACAG GAAGTCATCA ATTCGAATCC ATATTATAAA AATTAAAGTT 33960
TAGATGAATA GTTGCATTCT AGGTAGCCCG AGGTAGTGTT TTGTCTAACA GCTGAACCGA 34020
TAGACTCCTT CCTGGTCACA ATTCAGAAGC CTGGCATATG CTTCGAACCT TCCCCTTTCT 34080
TAGCACAGTG AAAGGCATGT TGTCATCAGT GTAGACTTAT CTGGACTCTT AGAGCTGATT 34140
ACTTTTTGTT GGGTGTTCGT TGAGTGCCGA CTGAATTCAT AAATGTAATG ACTTCTAGAT 34200
AGCTACTTCC TGACCATTTT ACAGTGGATT TTTACTGTAT GGCAGGCACA GAGGCTGACC 34260
TCTGTAGCTC TTCATATGTT AGACTGATGC ATAAAGCCAT TTTCTGTTTT ACAATTTTAG 34320
AAACAAAGGG AATTTCCTTT ATGTCATATA TACTCAAATC CCATGCACAT TAGCTTTCCA 34380
TGATTTGTTT ATAACTGTCT GTTCTCAAAT TTTATCCCAA CCCTTAGTTT CGTCCTTCCT 34440
ACATTTGCCA TTTTAAGGTG GCTTTTTAAA AAATGAAATG ATGAATAACT TATTTGGTAG 34500
AATAGTTTTC ATTTATATCT AAAAGTTTAT AGGGACAGTG TGAAAATCTG GTTAATAGAA 34560
TAGTTAACAT CAAATGAAAG AATAATCCGG TGAAGCTTAG AATTCCATTG GTTATTGACT 34620
GCTAGCTGGA CTGAGCTGTT AGAATTCCAT TGGTTATTGA CTGCTCGCTG GACTGAGCTG 34680
TTAGAATTCC ATTGGTTATT GATTGCTCGC TGGACTGAGC TGTTAGAATT CCATTGGTTA 34740
TTGACTGCTA GCTGGACTGA GCTGTTAGAA TTCCATTGGT TATTGACTGC TAGCTGGACT 34800
GAGCTGTTAG AATTCCATTG GTTATTGACT GCTCGCTGGA CTGAGCTGGC TTCTTGCACC 34860
AAAGCTTTTG CTTCCCACGT CTGTGCCGTT ATCCCCGCTC CCTCACCCCT CACCCATCCT 34920
TTGCGTGTTT CCTATGCTCT TCCTTTCTCC TTTCTGTCAA TCTCCTGGGC CATCCTAGAA 34980
CATACCCTAT GAGCTTATTT TACTGTTGTC TCTTCAATGA GGCGTCTTCT CCCCTCCCCT 35040
CTCCTAAGCC TTCGATCTGA CTTTGGAGGT GTTTATTGCT CTACCCTGAC ACAATTTACT 35100
TATACTGCTA TCTTAATTTA TTGTCAGTTT TTATGATTCT CTATTGATTC CCCACTAAAA 35160
ATGCCGGAAA TTCACCAGCC TTTCCTCTGT GTTCCTGCAG CCCTGGACCC CTTTCCCTTT 35220
GCCTGTTGGT TTATATCTTA ATTCTGCTTA AATGTCATAT GGTTATCAAC TTAAGCATCT 35280
TACCTTTAAT TTTTATAATA TATGGTTATA GTTCTCACAT ATATTTTTGT ATTCTTGTTA 35340
TTAAAGGATT TTTTTTCTGA GTATTTGTCC CTAATTCTCC TGTGAGTTTT TTCCAACCAT 35400
ATGAACTTTA TTTTGTTAGG TTCATTCACA TTAGGTCATT TGACAGTTTT ATCCTCTTGG 35460
TATTATACCC GTCTTTTTTG TTTTTGTTTC TGTTTTTGTT TTGTTTTGTT TTGTTGTTTT 35520
CTATTGTACC CATCTTAATG ATGCTTCATT AGCTGTATTT CTCTTTGCAG TAGTGAATGG 35580
TATTATACTT AGATTCTGTC ATCAGGAGAG GACATTCGAA ACTTGATAAT AATACAATAG 35640
TTTTATTCAC TACAGTAACT GTTTCTCATA GCTTCGGGTC TCCAGAGAAA CTCCTTTATT 35700
TGCTCCTTTT TATAGAGATG AAGAGAAGTC ACATTTTTTT TTTTAAAGAC AGGGTTTCTC 35760
TGTATAGCCT TAGCTGTCCT GGAACTCACT CTGTAGATCA GGCTGGCCTC AAACTCAGAA 35820
ATCCGCCTGT CTCTGCCTCC CAAGTGCTGT GATTAAAGGC GTGCACCACC ACTGCCCGGC 35880
CAGAAATCAC ATTTTTATAG CCACTATTTA TCCAAATCTG TATTTGGATA GATTATCTTT 35940
TAGTCTGTAA GTAAAGTTAT ATTTAATTTA GTTTTACACT GGCGGGCAAG CTGCTGTTTT 36000
ATTTTGTAAG TTTTAGTTAA GTTGAAATGT GATTCTTACT CTGCGTTGTT GTTCATTCTC 36060
AGTGTGTTGT AGCTACTGTA GCTTTTGGAA TGGGCATTAA TAAAGCTGAC ATTCGCAAAG 36120

*Fig. 7-25*

TTATTCATTA TGGTGCGCCT AAGGAAATGG AATCCTATTA CCAGGAAATT GGTAGAGCTG 36180
GCCGGGATGG ACTTCAGAGT TCCTGTCACT TGCTCTGGGC TCCAGCAGAC TTTAACACAT 36240
CCAGGTATAA ATGCTTATTG TTTTCACCTT ACAAATTCCT TTTTCCTTTC CAAGAAAGTA 36300
TTTGAGGGAG TATCCAAAAT ATCAAGTGAC CCCTGAGTAT ATTTAAAGGG GTCGCCACCG 36360
GAAAGTGAGC AAAATGAACA GAATATCCCT GAAGAGTGTT TTTGGTAAGT CTTCCCACAT 36420
AGCAGGTGAT CCAGTTGGAG TTAACAAGAT CGGGACTGCA CTTGGACGTA TAACATAGGT 36480
CTTATGGCAT CCTGTCCTAT TGTGCAGCAG TAAGCAGTTC CCACATTTTA AATCCTCCAG 36540
TCATATGGCT CTAGGTTTAA GTAAGTACCA TGTGTCCAGT GCTATAATGG TGGTTATTCT 36600
AAAAGATGTA TCCAATTCTT GTTTAACTCT CTTTACTATT GTTTCTGTGA TTAGTTCCGT 36660
AAGTGCATGC CACTGCTCAT AGACTGAAAA CTCACCTGGT TGATAGTGCC TAAATAATGT 36720
AACAGCGTAG TGTTAGAGTG CTGTCATAAA ATAGTATATG TTCGTGGTTT AAATTCAAGG 36780
AAAGGGAAAC TGCCTACTTA AATGCTAACT AAATTGTAAC TTACATCCTG CCAGATTATA 36840
TTAGAAGCAA CAGCTTCAAT TTCCAAAATC ATAGGGACAT TATTTACCAG TTATCTATCT 36900
ATAGGGAACC AGGAAAAGAA GCCAGTGCAG CCCAGCCAGT GAACGTGCCA ACATAAAGGA 36960
CCTTTCAGTG CTCCTCCAGG CTGATGAGTA AGCTAGACAC TGGTAGCTAA AAGAGTAGGA 37020
TTAGATAAGT AAAAAGGGTT GTTACAAAAT CTAAGATCTT GCTAGGAATA GTCAGTATAT 37080
TTTACTTTGT AATAAGTAGA GCTGAACTCT GATCCCCTGA AAGCAAGCAT TCTTAGCCAC 37140
TGAGCCATCT CTCCAGACCA GGCGCCAGAG TCTTTACCCA GCCTTTTAAA AACCAATTTA 37200
AAGTAAGTTG GATAGAACAC ATCTCTGCAA GCTACTATTA AATTTGGAAT ATATCAAATA 37260
TCACTTGGTT AAGACCAGAT CTTATTTTAT TTGTGTATTA TGCTAACATG CTGGAAACAT 37320
TATAGGCCTG AGTTGTATAA TGCAATCTCA CCCGTGGATA TAGTGTTGAT TTATGTGGGT 37380
TTTGAAAGAT ATGCTGAGTG GTTTATCTCA TTAAGATTGA TCAGGAAATA ATAGTTGTGC 37440
CAGAATACCC GTGCAATTGT TACTTAGTAT CCATGGTGAC TGGTTCTGAG TTCCTTAAGA 37500
TAGAAATAAA TAAATAATCT CCCTATACAT GAGGCTCTTA TACAACATAG TATTTGTATA 37560
CAGGCTGTGT ACTCTTCTAC ATACTATCTT CCTAGCTCAC ATATAACATC TATTATAAAG 37620
TAATTGATGT GTAAGCATTT AGTTTTACAC TGTAATCTTT AGAGAATAAC AATAAGAAGA 37680
ATGTCTCAAT GTGTTTAGTA CAGATGCAAC TACTGTAAGC CTAATTGGGG TTTAACTTGG 37740
GGTTGACCGA CTCTCAAGTG CTGAACTAGT GGGTGCAGAG CTGAACCACT CGCTCTTTTA 37800
GTACAGATAG GCTACTCTGT GTATCAGAGA CAAAGGAGAA AAACTGTAAA AGGATAAACA 37860
GGAGAGAGCC AAGGATTAAG GGTGAGTTTG TACCATCGAG ATCTTGAAGC AGAAGAAAGC 37920
AGTGAGATTC TGGGTCTCAG CTCTAAGGGT CATTGTAACT TATAAAGTTG TAGTCTCGCG 37980
TATGCTAAAA TTCTGTGACA AGGGAAGAGT CTTGTTTGAG GGATCATGCC GTGATTTTAA 38040
CTAACTAATG TTTATTTGTT AGTTTTGTGA TGCTGGGTAT CAAATCTGGG CCACCCTCAT 38100
GCTAGACAGC CTATGTAAGC CACATCCTCA GAGACGATTA TGTAGTTTTA TGTTCCCTTA 38160
TTGTGTGATT TTTGTGTTTC TTACTGCCGA GCCGTAACAA GGCAGTGTCC CAGTGATTAT 38220
GTTTATTATA TTTGTAGTCA TACCCAGTAG TTACTGCCAT CTTTTGTTTC AAAGTGAAGA 38280
ACTTAGAGAA TAATCTCTAA TAAATCTTTG AATTCTCTTA AAGTTAATGA ATTGTTAGAA 38340
TTTATGGTTT TTTTGGTGAA ATAAGTTGTA TTGCGCATTT AATAGTAGCA AAAGAAGAAT 38400
AAACTAATAA ATATTTAATT GAGTTTCTTT TTCTCAAATG AACATGTAAA TGAGCATGGA 38460
TGAAATCAAA TAAATATATT TCATCTCAAT CCAATATACT AAGATATAGT TCTGAGTATT 38520
GTTGACTTTA TCTCTGAAGG ACAAGGGAAC TAAATGAAAC TGATTTTTTT ACAAATCTAT 38580
GATCCATTAA GTATGGGCTT GGATAATAGC TCAGGTTAGT ATTTTTAGTT CAGGGTATTT 38640
GGAGGAGAAA ATTCATGTGA AGGGTGTTAT CCATTGAGAA CATATCTTTG AATAATGGAT 38700
CATTTGTACA TTCAAATTTT CTAGAATAGA GATTGTATAC AGATATTTTG ATTAATCAGA 38760
AGGCTGGATG TTACAAACAT TAGTGAGCAA AGTCCCTAAT GATGAAGTTC AGTATTATCA 38820
TTTAGTTCTT GTATATTAAA TCAGAATGTT ATATTGCAAT ATCTAAAATT CATTTCATGC 38880
AGGTTTTTTT TTATTATTAT TCTTGGAAAG ATGTGGAACA CTGCCTGGAA GATTTCATGG 38940
CCTAATGCAA TAGCACTGAT GTTTAAAGAT AAAAACAAAC ATACTGGTAC TGTTATTTCA 39000
CAATTATAAA CAACTTCATT ATTGTGACCA AAAAAATTCA TTACAACTCA CCAAGGAAAA 39060
CACTCAATTC TAATACTTTA CTCCTGTCCT CAAGGGCTTC GCAATACAGA GGGACAGCTT 39120
TGGAGCTGAG CTGTCCTCTG AAAAGCCAGT AGGAGTAGAT GAAGGTTCAG ACTGGAGTGA 39180
CGGGGATGGA GACTAGAGCG ATGGGGATGA AGGGTCATAC AGACTAATGA GCCTCTTTCA 39240
GTTTTCCTTA CATAGATATT TTAACTTTCT CAGAGAACAT TTATTAAAAT AAAAGATGAA 39300
TTTCCAGTGA AAGGTCCAGG ATCCATGTGC TAGAAGGCTT ACTAGAAACT GTGATGAATG 39360
AGGTCTGTAA ATCAAAAGGA AACCTTGAAA GTTATCAGTG GAACTCTCTT GTCCAGGGCA 39420

*Fig. 7-26*

TGATTAGGAA GAATGCAGGC ATTTGGGGGA GCAAAATAAT AAAATTAACA GTATAATTTT 39480
AGATATTCTT GTGATTTTTC CATTGGCAGG AATCACCTTA TTGAGATTCA TGATGAAAAG 39540
TTCCGGTTAT ATAAATTAAA GATGATGGTA AAGATGGAAA AATACCTTCA CTCCAGTCAG 39600
TGTAGGCGAC GGTATGTATT ACCTGCTTTT TCCAATTGGA AGCATAGGTC TTTAGCTGGT 39660
ACTTTTTTTG TTGTTTGTTT TTTTGAGACA GGGTTTCTCT GTGTAGCCCT GGCTGTCCTG 39720
GAACTCACTC TGTAGACCAG GCTGGCCTCG AACTCAGAAA TCTGCCTACC TCTGCCTCCT 39780
GAGTGCTGGG ATTAAAGGCG TGTGCCACCA CTGCCCGGCT AGATGGTACT TTTTTTTTTT 39840
TAAAGTTAAT TAAAAGTGTT TTTAAAGAAT GTTTGCTGTA TACATGCTGA ACTTTAGGGC 39900
AGGCTTATTT CTGTTTAAAT AAATTAATAT GAAATAATGC TGAGACAAGT AAATACAGTA 39960
GTGGTACTAT CGTGTCATTT TGGGTGGTGG GTGTAGTATG TCTATATTTG TTCTTTAATT 40020
TAAGATTTTC CCTTCATCAG AATCATCTTG TCCCATTTTG AGGACAAATG TCTGCAGAAG 40080
GCCTCCTTGG ACATTATGGG AACTGAAAAA TGCTGTGATA ATTGCAGGCC CAGGTAAAAA 40140
TATCTTCCTG ACGAACCTTC TAGAAACTGT CGATTCTCTT TCTGTTCAAC TCCTGCTTCA 40200
TTAAATTTTT GTTTAATATA AGTATTTTAG GTTTTGTTTT GTTTTGTTTT GTTTTGTTTT 40260
TTTCGAGACA GGGTTTCTCT GTATAGCCCT GGCTGTCCTG GAACTCATTT TGTAGACCAG 40320
GCTGGCCTCG AACTCAGAAA TCCACCTGCC TCTGCCTCCC GAGTGCTGGG ATTAAAGACA 40380
TGCTATTTTA GTTTTTTTAA ATGACATAGT TACTTTATTT AAAATAAAAC AAAGTGAAGA 40440
GGTTTACTTT TATACAATAA AGTCTTAAAA CGGTAGGCCT AGTTAGTCAA TAGTTGCGTT 40500
TCAATATGAT TAGCCTAAAA ATACTCATTA AAGGCATAAT TTATCAAAAT TGATTTGAAA 40560
GGCATTCTAC TTGATGTTTA CCATAAGGGC AAGTACAATT ATGTAGATAG TTTTAAAAAA 40620
TGAAATAGAA AACACTGCAA AAACACTAGC CAAAAGAAAC CGTACGTTAC TGTTTTAGTA 40680
TTTAGTGGTA TGGACTTTGG AGCAAAGCAT GCTATCAGGG ATGAATCAAG ACACCGACCA 40740
GTGTGAAGTA TCAGCGTTCT GCAGAGAAGT GGCACCAAGG AGAGAGCAAG AGGGGCAGGA 40800
GAGGTGTGGG ATGGAAAGAA CAGGACAGAG GTGACAGGCA TCAGTGAGGT GGCAAATCTT 40860
AAAACTTGTA GCCAAGTTTT GGTCTGAACC CTGCGTCAGG CACACGCTAA TGTTAGTGTT 40920
GAAACAAAGT TTATTGCCCA GCAAGCTTGT TTGTATTAAG GCTTTCAACC CAAAGAGGGT 40980
AGTTATTGGG CATGATTTCC ATTGTTGAAG TCGTCTCATC ATAAGTAATA TTCACATCTA 41040
CAAAATACAT TTGCTGTGGC ATCTAAATTA TTTTCTGATC AAACAACAGC CCCACTTTGA 41100
CATGCAAGCT ATACAGCCCA GAAGACATAA TCCCAAGTGG GCACATAAGA ACCTGCACAT 41160
AAGAACCTGC ACATAAGTAC CACAGAAGCA GAAGGCGGGG GGATCAGAAA CCCACGTGTA 41220
TTAGGTGACG TCGGCGTCTG CTTACAAGGC AGTGGAATTA ATGGACAAGA ATGAGTAGGG 41280
CTGCGGGGAG CGATGGGCGT GTCTGCAATG GCAAATTCAG AGGTTCAGAC GGGAGATCAA 41340
GAGACTGAGA CCAGCCTGTG ATGCAAGTGA TCTCAAAAAG AACCCAGGTC CCATAGTGAG 41400
ACTGTGTCTC AAGATCCCGA GAACAAAAGC AAGCGTAAGA CTCAACAGCA AGCATGACCC 41460
ACCCCAAAGC CCCCAAACAG CCCCCTACCC CCACCCCACT GACTCTATGA GGAGATGAAG 41520
GAATGAAGAG GGTGTCAGCA AACCAGTTCT AATTAATTTC TTGAAAGCAT TTCAGCCACT 41580
TGTTCCAATG GCGGCTTATA CACACATGTT TACATAAAGC TAACCTTGAC AAATGAGGAA 41640
CTATTCGATT TGGATCAAGT ATGCTTTTTG CTTTAATGGC ATCAATCTAG AAAGCAGCAG 41700
TGGGAAGAAA AGAGAAATCT CCAAACCCTT AGAAACCGTA CCTCCAAATA ATCTTACAGC 41760
CACTCAGAAA ATGATCTGAA CCGACGAAGA AGAATATGAA GTACCTGGGA TACAGCTAGA 41820
ATGACTCTGC AAAGATAATT TATAGTGTTA ATACAACATG GAAGAGCACA GGCTTCAGAC 41880
ACATAACTAG CATTCACTTT AAGAAACGGG CAGAGCCGGG CGTGGTGGCA CAAAACAAAC 41940
AAACAAACAA ACAAACAAAA AACAAAAAAC AAAAACAAAA AAGAAATGGG CAAATATGAG 42000
GAAGATGAAC AGGAAGGGAG TTAAAAAGAG AAGTGCGTAG ATCAATGCCG TAGACGACAA 42060
AGCCAATAGA GGGGAGTCGG CGAGCTCACA GGCTTCATAT TTTCCAAGAC TGGTGGGGAA 42120
AGGGGAGGAC AGTACCAATA TCAAAATGAA GGAATTTCAC TGCAGACCCC ATGAATGCTC 42180
TGAACAAGCC AGGTTACTGG AAATGCAGTA AAACTGATCT AATAGACCAG TTTCTTAGTG 42240
GGCTCTAATT GACAGTGCTC AGGCATGGTG AAACTTAGGA AGAATACTCC TCTAACTGTT 42300
ATAAGGATTG AGTTCTTCCT TAAAAAACCT CTGAAAAGAG AACTCTCTAG CCCACCTGGC 42360
TTTAGTGACA AATTCCAGCA CCAGAAGAGG ACATCAAACT CATTACAGAT GGTTGTGAGT 42420
CACCATGTGG TTGCTGGGAT TTGAACTCAG GACCTTCAGA AGAGCTGTCA GTGCTGAACC 42480
ACTGAGCCAT CTCGCCAGCC CTCCAGCAAA CATTTAAATG AGGAGATATC CCTGCTTCTG 42540
TAGTGTGGCT GCACATGCAC ACTCTCTGAA AGGCAGAGCT GTAGGGAAGA TCAGCCGCTG 42600
GCAGAGGTTA AAGGCAGGCA GAATAGATCT GAGAGCAGGG CATTCAGTGG GTCTTGAGTG 42660
TGACGAAGGT TCGATGGGTC TGCTTATAGG GATATGTACG CTTTATTATA CTGTAAATAA 42720

*Fig. 7-27*

AATAAGTATA AGTGGTGCCT CTTTGAGTTA ATCGTGTCTC TAGGTACAGT AGCTGTATGC 42780
CAGAAGCAGC GCTGTTAGAG ATAGAAATCT AAAGATGTTT GGAAATTAGT GATAACCACA 42840
ATAACATATA TTTAAGGTGG TAAGATAATA TGTATAGGTC ATACTTCATG GGAACTTGAT 42900
AACTTTAAAT TCTCTGAAGA AAGTCACCTG AGCATCCTAC TAAAGAGGTA AATGGGAGAA 42960
TAAACCTAAG GCAGGGGATT TCTTCTTTAA ATCAAAACAT AATGGCTTTA ACTGGAATAC 43020
TGACTGCATT CTTATTGCTA CTTTAAAGAT ATATGTGATG TGGAAAGTAG TTGAATTTCG 43080
TAATTGAATA TATTAGTTGA TAGTCTCTAA GGACTTCTTT TGTTCTCAAG CTAAAAAAAA 43140
AATCCTCATT TACACCAATG ATAATTTTAC ATCTACTTGG AGGATGACTA AGGAATTTAA 43200
CTGCTGAATG TACCAGCAGG ACAAGCTTAT AGGCTCGGTG CTCTGTTGTA AAATTATTAG 43260
GGTTCAAGCT AACATGTTAC TGCATAGCAG CTTTTTACTT AAAACCAATT TTACCCTTCC 43320
TGGTGTAACG TAGCACAAGC TTCCGTATTT ATATAACTGA TCGTGTGGAG CTGCCCTAGC 43380
CGGGATGCTT TCCTTGAGCC TGGCATCTTC CCAGCGCCTC CATAACATTT AGCTTCTGGG 43440
TGCCACAAGA AAGCGCTGTC TGTAGTGCCG TATTTGTTAT TTGTGTCTCA TACGCATAGA 43500
TCACACACAT GCCCTTGATT GTAATAAGCT TTATGTGTAG AGTTGGAAGT GTCAGACACA 43560
TTTGAGAATT TTTTTTTTTA CGTGGTCTAT GTTTGTATCT TTCTATTTCT AAGGGGAGCAT 43620
GCTTTTGTCA GTGTTTTCTT AGGCTGTTCT TACTTTCCTT CAGGCTGAAT CATTGCCTTA 43680
CTGCTAACAA CTCAGAGGAC GCATCCCAAG ACTTTGGGCC ACAAGCATTC CAGCTACTGT 43740
CTGCTGTGGA CATCCTGCAG GAGAAATTTG GAATTGGGAT TCCGATCTTA TTTCTCCGAG 43800
GATCTGTGAG TGTATCTGTG ATAGCTCCTG GGACTGTTTC TGACAGTGCT TTCCACTGTG 43860
TGGCTATGGC TTTGGCTTTC TTTAGATGGC TAACTAGCAA CCCGTGTTAG CAACACCTTG 43920
AGTTCCATCC TAACCCTGCA TTCATTGTCT TGGACAAATC TTGTCTCACG TCAGACGCTG 43980
TTTTGCTATG TTGGATGCTG GCGGTCAGCT GTGTGCTGCA GTCTGAAAAT AGCCTATTCG 44040
TTTACCACAC TGCAATTGCA TTAATCCCTA GACTGGTTTT TCTTAGGATA ATTAGGGAAA 44100
GTTAACTCCC AGTGTGTCAA GGGACTGGTA GAACAAAGTT GCAGCTTCTG GTGCCCAGAT 44160
ACGATTATGT TCTTTGCGCA AAACTTGAAT TTCAGGGATT ATGTTGTCAG AGGCTGGGTT 44220
CAGCAACAGT GTACAGCAAC ATAGTCTCCC TCCGATGGTG TTTTATGTCA GAAGTACTTA 44280
ACATGCTAAG AAAGGGCTTT TGCTTGTTTT AGTGGTTTAC CAGTGAATAC CTGATTTAAC 44340
TGGACTCCTT TCTGTTTTGA GTGATTCATG TGGCCTCATT ATGCTGCCAA ATGTCACTTA 44400
CAAAGTGACA ATAATAAGGT ACAAATACAC ATACAGAGCT GGTTTTCTGT AGTCCTTCTG 44460
CTTTTATGAT AATTTTATTT CTGAATTAAG AGTCTGTAAA TTTAAGAATT GTATATTAAT 44520
ATCACTTAAA TAAACCAAGA GTAGAAGAAG GCAGAGTACT TTGTAGATGG ATCTATCTGC 44580
TTATTTAAAA CATGCTTTAG AGTAGAGGCT AAATGTTCAT TTTGTATATA GAATTTTAAA 44640
ATAATTTAGG TAAGCTTTTG CTGCTTAAAT ACTCAAGAGC TTCATGTAAA TGCATTTGCT 44700
TGTGCTTGCT TGTGCTTAGA AAGTAATCTA TGGAGTTAGT TATGAAATAT TTTTAATGAA 44760
ACACATTGAA AACTTGTACT ATCCTTTCAA GTGTCAGTGC TTTCAAGATA ATAGAGTTTA 44820
AATTTTTGGT TTTAAATGGC AAAAAAGCAT ATAAATGTAA CAATAGAAGT GTTACTTAAG 44880
CAGTTTTTAT TTCTATCAGC TCTGCAAGAA ATCTCAAATG CCACTGAAAT CCGTACATTC 44940
GTTTTCTATC TTTGTCACCT TTAAAATCCC TGTAGCCAGT GTGAGTATTT AATTTATGAA 45000
AAGTGTCCTT GTTTTGGTTT GGTGCGATCT AGCTGTATCC AATATCAATA AATAAGTTTG 45060
TTTCTCGTCA AACTTTCAGT GGTCACAGGA GGGATCAGGT TTCACTTATT ATTTGAAAAC 45120
CAAGTCAGAC GTCCTCTACC GGCAGTGTCT TCTGGGAGTC CTCAAATTAA GCAGTTCATC 45180
CTTAGTGAAA CTTTATACTA CCCTTGCTAG CGCAACGTGT AAAGCTTTTA AAAAGTATCA 45240
CTTAATGAAA ATGTGTAGAT GCTAACAATA GTGAAAATAA GACAGGCTTC CTTTCTCTGC 45300
TTTCAGTGAC TTTGATATCT ATTGGGATAT CGGTGAAAAA GTATGACTGT AATTCTCTTG 45360
AGAACTGAGC AAGTTGTTCC CCTTAACCAA TTTAGGACAA GCTAATACCT TTGTAATTTT 45420
AATTTGTAAG ATGATATATC AAACTGTCTT GGAGTTATTT TGAAGAGATA ATTTTTATAA 45480
GCATAAATTC GGTTTTGGTA GTGCTTGATT CTCTCCTACA TGTTTTTTTA ATATTATAAA 45540
CACTTAATTT ATCCATAAAT TTGTTAAATT TAGTTTAAAA ATTTGTTTTA ATGTGTCTAA 45600
TTAGAAAGTA ACCAAGATTG TCTAGAGAAC TTTGTTTTAA CTGACTAAAC AGTTCACCAT 45660
GTTCAGCAAT CTTTGACATT GCTCAAACGT GTCATAACAT AATCAATAGC CATAATTTAA 45720
GGGAAAAAAA CCACATTGAT CATTTGCATA CCAAGATTAG CATCTTCCCA AATGCCTTAT 45780
CCAAGTGCTA ATCTTTATCA TGGCCTCAGG AGTAGGTACC ACTTAATATT TTAGGATGTG 45840
TGTATATGCA CGTGTTCAGG TGCTCTCACA TCTGTGTGTG CATATGAACA CCAGAGGTGG 45900
ACATTGGATG TCTCCCTCTG GTACCCTCCA TTTCATTCGT ACTCTTTTGA CCCAGTTTGT 45960
CACCGAACCA GGAGCTCAGT GTCTTGGTTA GACTGGCTTG CCATTAGTCC CTGACATTCT 46020

*Fig. 7-28*

CCTGCCTCCG TTTCCTGCCA GCCAGCTGAC ACTGTAGTAA CAGCACCCAG CTTGTCTTCT 46080
TAAATTATAG TTTACTGGCG TTTCAAGAAC ATCATAACGG ATGCAGTGTA TTTTGGTTAT 46140
AATCAACCTC AGTATTCTCC CAGCTCTTCC CAGACTGATC CCACTGCCTC TTCACCAATC 46200
CCAACTTTAT GACCTCCCCC GCCCAACTTC CCCAGCCATG GGTATGGGCA TCTGTTAGAA 46260
TGTGGTCAAC CTATCAGGAG CTATGCCCGT AAAGAATGAC GATCTCCCTG AAGAGCCGTC 46320
AGCTGTGAAT AGTTGTTCCC CAGGAGCTCC TGAACCCTTT TCTCCATCCC TTGATGAAAA 46380
TTTTGCTAAC TTGGTTCTGT GCAGGCAGCC ACAGATGCTG TGGGTTAACG GGTGCAGTGG 46440
TCTGTCATGC CCAAAAGACA CTGTTTGGTT CTGGTTCTAC ATGACCTCTG GCTCTAACAA 46500
TCTCCTTTTG GGACGAACCC TGAGCCTTGA GGGAAAGGAG TGTGACCCAG ATCTCCCATT 46560
TGTAGATGAA CACTCTATAT AGACAATATC CTCTGTGCTG TGCTTTGACC AGATGTGAGA 46620
TTCTGCGTTA ACCGCCATCC ACTGCACAAA GAACCTTCTC TGATGAGGCT TGAGAGTGGG 46680
ACCAATCTAT GGCTATAGGA ACAGGAACTT AGAGACAAGT ATAATTCTAT GTCAGTTTAG 46740
CAAAATAATA GTAAGAAATA TACTGCTGGG GCCGTGAGCT CCTTGACCAA ATGTTCTGGC 46800
CAGATTTACA GCATCCTGTA TGGAATGGGT GTGGGAACGG TAGGGAGAGG ATGGTACTTC 46860
TTAAATCCTG TCAGAAAGTG CTATGATATT GAGGCCACTT TTGCACCCAT GGGCATATCT 46920
GCCATGCTGG TTGTCATTTT AGTGTACAGG GTTAATAACT GGAGGAGAAA TTGACTTTTT 46980
CTTCCCCAGT AGCCTGCATA GCACCTTCTG GTATTGTGAA AGCTAGCCAG CAGAAAGGAA 47040
ACTTCTGGGC CAGGACCAGC GTGATTTCTC CATGTTCTAT GGCCAAAGCA GGTGGTGTCT 47100
TCAGCAATAC AGCCTTACCA CTAAGTTCTG ATGAGAAACC AAGAACAGTA GCGGTGACCT 47160
GTATTATTTG AGGTGGGGCA TCTGTAGGAA AAACTGAGCA ACAGTTTGAG AGGAGGTATC 47220
TCACACTGGA CTATTTGTTT GGTGACCTGT GGCTTCCTTG AGTAACATTA GCTTTTATGT 47280
AGCCTGATTC CAATTAAACT CTTATATAAG TGTGTGTGAG TTTAGGAAGC TTATAAATAG 47340
TAAGTTTCCA TATGGGTTTT AATTTTTTTT TAATTTTATT TTGTGATTTT ACTAATTCGC 47400
TTTACATCCC GCTCACTGCC CTACTCCTGG TCACTCCCTC CCACAATCCT TTCCTTATCC 47460
CTCCTCCCCC CTTCTCCTCT GAGAAGTTGG GCCCCCCTGG GTATCCCTCC ACCCTGGCAC 47520
TTCAAGTCTA TGCGAGGATA GGGTCTTCCT CTCCAATTGA GGCCAGACAA GGTAGCCCAG 47580
CTAGTAGAAC ATATCCCACG TACGGGCAAC AGCTTTGGGA TAGCCCCCAC TCCAGTTGTT 47640
TGGGACCCAC ATGAAGACCA AGCTGGACAC CTGCTACATA TGTGTAAGGA AACCTAGCTC 47700
CATATGTTCT TTGGTTCGTG GTACAGTTTC TGAGAGCTCC AAGGGTCAGG TTAGTTGGCT 47760
CTGTTGGTTT TCCTGTGGAG TTCTATCCCT TTCTGGGCTG CAATCCGTCT TCCTAGTTTT 47820
CCAAGAGTCC CCAAGCTCCA TTCACTGTTT GGCTGTGGGT GTCTGCATCT GTCTAAGTCA 47880
GCTGCTGTGT GGAGCCTCTC AAAAGACAAC ATGCTCCTGT CTGCAAGCAT AACAGAATAT 47940
CATTAATAGT GTCAAGGATT GGTGCTTGCC CATGGGATGG GTCTCAAGTT GGACCGGTTA 48000
TTGGTTGGCC ATTCCCTCAG TCTCTGCTCC CTCCCCTGTG CCTATATTAC TTGTAGACAG 48060
GATAAATTTT GGGTTGATAA TTTTGTGGGT GGGTCAGTGT CTTTATTGCT CTACTTGGGT 48120
TGCTGCCTGG CTACAGGAGG TGGCCTCTTC AAGTTCCATA TCCCCAGTGT AGTAAGTCAC 48180
AGCTAAGGTC ACACCTATTA ATCCTTGGAT GCCTCCCTTA TCCCAGGTTT CTGTCTCATC 48240
CTGTAAATGC CACCCACTTC CCCACTTTTC CTCTGCAGAT TTCCATTCAT TCTCATTACA 48300
TCTAGCTCTC TCCCTGCCCT TCCCTACACC CAATCCTGAA CTCCCATCTC CCTCCGCATC 48360
CCCCGTCCTA GTTCCCTCTT TCCATGTGCC TCTTATAACT ATTTTATTCC CACTTCTAAA 48420
TGAGATTCAA GCATCCTTCT GCCTTCCTTC TTGTTTAGCT TCTTTGGGTC TATGGAGTGT 48480
ACCATGGTAC TTGTATGTTT TGGCTAATGT CCGCTTATAA GTAAGTACAT ATCATGCATC 48540
TCCTTTTGGG GTTGGGTCAC CTCACTCAGG ATGATATTCT CAAGTTCCAG CCATTGGCTT 48600
GCAAAATTCA TGATGTCTTT CTTTTTAATA GCGGAATGGT ATTCCATTCT GTAGATGTAT 48660
CACATTTTAT CCATTCTTCA GTTGAGGGAC AGCTAGGTTG TTTCCAGCTT CTGGCTATTA 48720
TGAATAAAGC TTTAGGAACA TAGTTGGGTA TGTGTCTTTA TGGGATGTTG GAGCATCTTT 48780
TGGGTATGTG CCCAGGAATG GTATAGCTGG GTCTTGAGGT AGGACTATTC CCAGTTTTCT 48840
GAGAAACTGC CAAAGTTTCA AGTGGTTGTA TAAGTTCCCC TCACTCCACA CCCTTGCCAG 48900
CCTGTGTTAT CTTTTGAGTT TTTGATCTTA GCTATTCTGA TGGGTATAAG ATGGAACATC 48960
AATGTTGTTT TGATTTGCAT TTCCCTCATG ACTAAGGACT TTGAACATTT CTCTAAGTGC 49020
CTTTCAGCCA TTTGAGAGTC CTCTTTTGAG AATTCTCTGT TTAGCTCTGT TTCCCATTTT 49080
TAAATTGGGT TATTTGGGTC ATTGTTGTCC AACTTCTTGA ATTCTTCGTA AATTTTAGAT 49140
ATTTGCCTTC TGTCCGATGT AGGATTGGTG AAGATTCTTT TCCAATCTGA AGATTGCCTT 49200
CTTGTCCTAT TGACAGTGTC CTTTGCCTTA CAGAAGCTTT GCAATTTCTT GGGGTCCTAT 49260
TTATCAGTTG TTGATCTTAG AGCCTGAGCC ATTGGTGTTC TGTTCAGGAA CTTGTCTTCT 49320

*Fig. 7-29*

GTACCAATGC ATTCAAGGTA TTTCCCTCTT TCTCTTCTAT GATATTTAGT GTATATAGTT 49380
TTAAGTCGAG GTCTTTCATC CACTTGGACT TGACTCTTTT AATAAATGTG TGTGTGTGTG 49440
TATGTGTGTG TTTAGGAAGC TTATAAATAG TAAATTTCCA TGTGTTTTTT TTAAACTTTT 49500
TTTTTTACCT CTCTCTCTCT CCCTACCTCT CCACTCTGCC CTCGCATCCC ACTCTACACC 49560
TTAAACCTCT TCCCCCTTTA TATCACATAT TGTTCCAGTA TCCCCGTCAT AATGTTTTTT 49620
TCTTTCACCT ACCTCTACCA ATAAATGGTC CCTTTCTAGT TTCTTGGATT CTTCAGGCAC 49680
TCCAAGTTAA ACACACTATG TGAAACATTC AATGGTAGGA TCACATGTGC GAACATGTGA 49740
TGATGTTTGT CCTTCTGGGT CTGGGTTCCC TGAATCACTA TTGTTCCCCA GCTCCATCAG 49800
TTTCCCTGCA AATTGTTATG ATTGTAGTTT TCTTTATAGC CAAATAAAAC GGCATTGTGT 49860
ATAGGTGGTC CCACACTTTC GTGATCTATT TTGTAATTTA ATGGCTGTTT TCATGTCCTA 49920
GCAGTCATGA ACATAGCAGC TAGACCATGG CTGAGCATGC ATCTCTCTGG TAGGAAATAG 49980
AGGCCTTTGG TTATATACCC AGGGGTGATT TATGTGGGCC ATCGGATTCA TCATTTTAGC 50040
TGTTTGAGGA TTCTCTTTAC TGATTTCGAA GGAGCTGCAC CAGCTTTCTG TCTCACCAAC 50100
GGTGCACAGG GGTTCCCCAG ATCATCACCT GCATTTCTTG TCTTTTATGT TTTTTAATCT 50160
TATCCTCGAA GTAGTTTCAA CTTGAGTTAA GGATGGTAAA CTCTCCTGAA AGCATTTCAT 50220
TTCCTAGGCA CCTGCATTTC TTCTTCTGCA ACTTCTGTTT CATTCTATAA CTCACTTTTT 50280
GTTTTTAGTT TTTTCAACTC TTTTTTGTAT TCTGTAGACT AACCCTCTGT CAGATGTGTA 50340
GCTGGAATTA TACTCTAGGC TGCTCCTTTG GTCATGTAAT GGTTTCTTTC TTAGTAGCAC 50400
CTTTTCATTT ATAAAATTCT ATTTGTTGAT TAGTGGTCAT ATTTTGTAGA TGACAGGGCT 50460
CCTTTTCAGA GTCCTTACCT GAGCTGGTAT ACTGAGGCAT ACTTCACATT CTTCTGGGAG 50520
TTTCAGATCT AGCATTGAAA CCTTTGATTT CATTTGGAAT TTATTTGCCA TATCTTACAG 50580
GTCCTGGGGA TCCAATCTCA GGTGCTTATA TTTAGACATA GAGCCCTTTG TCTCATGAGC 50640
TATCTCCCCA ACCCAGATAA TGCTTTTAAG AAAAGATTGG ACCTATTCAG CTGTTAGAAC 50700
TGTTGATAGA TTTGTGTGTG TATGTGTGTG TGTGTGTGTG TGTGTGTGTG TGTACATGTG 50760
TGTACCTATA TGCACACATC TGTATGTATC TATTTTAAAG ACAAGATCAT GCCTAGGTTG 50820
ACTCTCACTC AACTGGAAAT TCTCCTGTCT AAGCCTCCTG ATTACAGCAG TAGGATTACA 50880
GGCATGTACT ACTATAGTCA ACGGCAATTG CTGTAGTTCT AATCACTCTC CAAAGTTATA 50940
AGAACATGTA GCTGGGGTGG GCTATTTCGT TTAATTTTCT AGACAAATAT TGAGTCTGAT 51000
AGAAATATAT TACTATGGGT TAGGTCTGCT TTTCAGGACT AAAGAACTTG GCTAAATGCA 51060
CAAGGCACTT GGTTCATGAA GAATTACCTA TTGAACCCCT GAAATGGCAG CTGGGACTAT 51120
CTCTGGACTA TAGGAGCTGG AAAGGGGCAG GGCTGGTGGG AGGAGAAGGT GGAGAGGGTA 51180
GCTAGGAACT TAAATGTCTT TGAGCTATTG AGCATCTGTT TTTATGTAAG GCATGACATT 51240
GATTTTGTAG AGGATACAC 51259

*Fig. 7-30*

```
      1                                                      50
MOUSE .....METTS LQRKFPEWMS MQSQRCATEE .KACVQKSVL EDNLPFLEFP
HUMAN MSEKKLETTA QQRKCPEWMN VQNKRCAVEE RKACVRKSVF EDDLPFLEFT

      51                                                    100
MOUSE GSIVYSYEAS DCSFLSEDIS MRLSDGDVVG FDMEWPPIYK PGKRSRVAVI
HUMAN GSIVYSYDAS DCSFLSEDIS MSLSDGDVVG FDMEWPPLYN RGKLGKVALI

      101                                                   150
MOUSE QLCVSESKCY LFHISSMSVF PQGLKMLLEN KSIKKAGVGI EGDQWKLLRD
HUMAN QLCVSESKCY LFHVSSMSVF PQGLKMLLEN KAVKKAGVGI EGDQWKLLRD

      151                                                   200
MOUSE FDVKLESFVE LTDVANEKLK CAETWSLNGL VKHVLGKQLL KDKSIRCSNW
HUMAN FDIKLKNFVE LTDVANKKLK CTETWSLNSL VKHLLGKQLL KDKSIRCSNW

      201                                                   250
MOUSE SNFPLTEDQK LYAATDAYAG LIIYQKLGNL GDTAQVFALN KAEENLPLEM
HUMAN SKFPLTEDQK LYAATDAYAG FIIYRNLEIL DDTVQRFAIN KEEEILLSDM

      251                                                   300
MOUSE KKQLNSISEE MRDLANRFPV TCRNLETLQR VPVILKSISE NLCSLRKVIC
HUMAN NKQLTSISEE VMDLAKHLPH AFSKLENPRR VSILLKDISE NLYSLRRMII

      301                                                   350
MOUSE GPTNTETRLK PGSSFNLLSS EDSAAAGEKE KQIGKHSTFA KIKEEPWDPE
HUMAN GSTNIETELR PSNNLNLLSF EDSTTGGVQQ KQIREHEVLI HVEDETWDPT

      351                                                   400
MOUSE LDSLVKQEEV DVFRNQVKQE KGESENEIED NLLREDMERT CVIP.SISEN
HUMAN LDHLAKHDGE DVLGNKVERK EDGFEDGVED NKLKENMERA CLMSLDITEH

      401                                                   450
MOUSE ELQDLEQQAK EEKYNDVSHQ LSE....... .......... ..........
HUMAN ELQILEQQSQ EEYLSDIAYK STEHLSPNDN ENDTSYVIES DEDLEMEMLK
```

*Fig. 10-1*

```
       451                                                 500
MOUSE  HLSPNDDEND SSYIIESDED LEMEMLKSLE NLNSDVVEPT HSTWLEMGTN
HUMAN  HLSPNDNEND TSYVIESDED LEMEMLKSLE NLNSGTVEPT HSKCLKMERN

       501                                                 550
MOUSE  GRLPP.EEED GHGNEAIK.E EQEEEDHLLP EPNAKQINCL KTYFGHSSFK
HUMAN  LGLPTKEEEE DDENEANEGE EDDDKDFLWP APNEEQVTCL KMYFGHSSFK

       551                                                 600
MOUSE  PVQWKVIHSV LEERRDNVVV MATGYGKSLC FQYPPVYTGK IGIVISPLIS
HUMAN  PVQWKVIHSV LEERRDNVAV MATGYGKSLC FQYPPVYVGK IGLVISPLIS

       601                                                 650
MOUSE  LMEDQVLQLE LSNVPACLLG SAQSKNILGD VKLGKYRVIY ITPEFCSGNL
HUMAN  LMEDQVLQLK MSNIPACFLG SAQSENVLTD IKLGKYRIVY VTPEYCSGNM

       651                                                 700
MOUSE  DLLQQLDSSI GITLIAVDEA HCISEWGHDF RSSFRMLGSL KTALPLVPVI
HUMAN  GLLQQLEADI GITLIAVDEA HCISEWGHDF RDSFRKLGSL KTALPMVPIV

       701                                                 750
MOUSE  ALSATASSSI REDIISCLNL KDPQITCTGF DRPNLYLEVG RKTGNILQDL
HUMAN  ALTATASSSI REDIVRCLNL RNPQITCTGF DRPNLYLEVR RKTGNILQDL

       751                                                 800
MOUSE  KPFLVRKASS AWEFEGPTII YCPSRKMTEQ VTAELGKLNL ACRTYHAGMK
HUMAN  QPFLV.KTSS HWEFEGPTII YCPSRKMTQQ VTGELRKLNL SCGTYHAGMS

       801                                                 850
MOUSE  ISERKDVHHR FLRDEIQCVV ATVAFGMGIN KADIRKVIHY GAPKEMESYY
HUMAN  FSTRKDIHHR FVRDEIQCVI ATIAFGMGIN KADIRQVIHY GAPKDMESYY

       851                                                 900
MOUSE  QEIGRAGRDG LQSSCHLLWA PADFNTSRNL LIEIHDEKFR LYKLKMMVKM
HUMAN  QEIGRAGRDG LQSSCHVLWA PADINLNRHL LTEIRNEKFR LYKLKMMAKM

       901                                                 950
MOUSE  EKYLHSSQCR RRIILSHFED KCLQKASLDI MGTEKCCDNC RPRLNHCLTA
HUMAN  EKYLHSSRCR RQIILSHFED KQVQKASLGI MGTEKCCDNC RSRLDHCYSM

       951                                                1000
MOUSE  NNSEDASQDF GPQAFQLLSA VDILQEKFGI GIPILFLRGS NSQRLPDKYR
HUMAN  DDSEDTSWDF GPQAFKLLSA VDILGEKFGI GLPILFLRGS NSQRLADQYR
```

*Fig. 10-2*

```
       1001                                                   1050
MOUSE  GHRLFGAGKE QAESWWKTLS HHLIAEGFLV EVPKENKYIK TCSLTKKGRK
HUMAN  RHSLFGTGKD QTESWWKAFS RQLITEGFLV EVSRYNKFMK ICALTKKGRN

       1051                                                   1100
MOUSE  WLGEASSQSP PSLLLQANEE MFPRKVLLPS SNPVSPETTQ HSSNQNPAGL
HUMAN  WLHKANTES. QSLILQANEE LCPKKFLLPS SKTVSSGTKE HCYNQVPVEL

       1101                                                   1150
MOUSE  TT.KQSNLER THSYKVPEKV SSGTNIPKKS AVMPSPGTSS SPLEPAISAQ
HUMAN  STEKKSNLEK LYSYKPCDKI SSGSNISKKS IMVQSPEKAY SSSQPVISAQ

       1151                                                   1200
MOUSE  ELDARTGLYA RLVEARQKHA NKMDVPPAIL ATNKVLLDMA KMRPTTVENM
HUMAN  EQETQIVLYG KLVEARQKHA NKMDVPPAIL ATNKILVDMA KMRPTTVENV

       1201                                                   1250
MOUSE  KQIDGVSEGK AALLAPLLEV IKHFCQVTSV QTDLLSSAKP HKEQEKSQEM
HUMAN  KRIDGVSEGK AAMLAPLLEV IKHFCQTNSV QTDLFSSTKP QEEQKTSLVA

       1251                                                   1300
MOUSE  EKKDCSLPQS VAVTYTLFQE KKMPLHSIAE NRLLPLTAAG MHLAQAVKAG
HUMAN  KNKICTLSQS MAITYSLFQE KKMPLKSIAE SRILPLMTIG MHLSQAVKAG

       1301                                                   1350
MOUSE  YPLDMERAGL TPETWKIIMD VIRNPPINSD MYKVKLIRML VPENLDTYLI
HUMAN  CPLDLERAGL TPEVQKIIAD VIRNPPVNSD MSKISLIRML VPENIDTYLI

       1351                                                   1400
MOUSE  HMAIEILQSG SDSRTQPPCD SSRKRRFPSS AESCESCKES KEAVT.ETKA
HUMAN  HMAIEILKHG PDSGLQPSCD VNKRRCFPGS EEICSSSKRS KEEVGINTET

       1401                                        1440
MOUSE  SSSESKRKLP EWFAKGNVPS ADTGSSSSMA KTKKKGLFS*
HUMAN  SSAERKRRLP VWFAKGS... ..DTSKKLMD KTKRGGLFS*
```

*Fig. 10-3*

SEQUENCE LISTING (1) GENERAL INFORMATION:

(iii) NUMBER OF SEQUENCES: 209

(2) INFORMATION FOR SEQ ID NO: 1:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 1:

CTGGCAAGGA TCAAACAGAG AG 22

(2) INFORMATION FOR SEQ ID NO: 2:

(i) SEQUENCE CHARACTERISTICS:

-continued

```
        (A) LENGTH: 23 base pairs
        (B) TYPE: nucleic acid
        (C) STRANDEDNESS: single
        (D) TOPOLOGY: linear

   (xi) SEQUENCE DESCRIPTION: SEQ ID NO: 2:

CTTTATGAAG CCAATTTCTA CCC                                      23


(2) INFORMATION FOR SEQ ID NO: 3:

    (i) SEQUENCE CHARACTERISTICS:
        (A) LENGTH: 22 base pairs
        (B) TYPE: nucleic acid
        (C) STRANDEDNESS: single
        (D) TOPOLOGY: linear

   (xi) SEQUENCE DESCRIPTION: SEQ ID NO: 3:

TGGCAAATTG GTAGAAGCTA GG                                       22


(2) INFORMATION FOR SEQ ID NO: 4:

    (i) SEQUENCE CHARACTERISTICS:
        (A) LENGTH: 26 base pairs
        (B) TYPE: nucleic acid
        (C) STRANDEDNESS: single
        (D) TOPOLOGY: linear

   (xi) SEQUENCE DESCRIPTION: SEQ ID NO: 4:

AAATAACTAT GCTTTCTTAC ATTTAC                                   26


(2) INFORMATION FOR SEQ ID NO: 5:

    (i) SEQUENCE CHARACTERISTICS:
        (A) LENGTH: 22 base pairs
        (B) TYPE: nucleic acid
        (C) STRANDEDNESS: single
        (D) TOPOLOGY: linear

   (xi) SEQUENCE DESCRIPTION: SEQ ID NO: 5:

CTCCCGTCAA CTCAGATATG AG                                       22


(2) INFORMATION FOR SEQ ID NO: 6:

    (i) SEQUENCE CHARACTERISTICS:
        (A) LENGTH: 26 base pairs
        (B) TYPE: nucleic acid
        (C) STRANDEDNESS: single
        (D) TOPOLOGY: linear

   (xi) SEQUENCE DESCRIPTION: SEQ ID NO: 6:

CTGTTTGTAA ATGTAAGAAA GCATAG                                   26


(2) INFORMATION FOR SEQ ID NO: 7:

    (i) SEQUENCE CHARACTERISTICS:
        (A) LENGTH: 21 base pairs
        (B) TYPE: nucleic acid
        (C) STRANDEDNESS: single
        (D) TOPOLOGY: linear

   (xi) SEQUENCE DESCRIPTION: SEQ ID NO: 7:

GAGCTATGAT GACACCACTG C                                        21


(2) INFORMATION FOR SEQ ID NO: 8:

    (i) SEQUENCE CHARACTERISTICS:
        (A) LENGTH: 21 base pairs
```

-continued (B) TYPE: nucleic acid
(C) STRANDEDNESS: single
(D) TOPOLOGY: linear (xi) SEQUENCE DESCRIPTION: SEQ ID NO: 8:

ACTGAGCAAC AGAGTGAGAC C 21

(2) INFORMATION FOR SEQ ID NO: 9:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 9:

GGATCTGGTC TCACTCTGTT GC 22

(2) INFORMATION FOR SEQ ID NO: 10:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 10:

TTGCCTAGTG CAATTGGTCT CC 22

(2) INFORMATION FOR SEQ ID NO: 11:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 11:

AGTGCAGTGG TGTCATCATA GC 22

(2) INFORMATION FOR SEQ ID NO: 12:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 12:

CCTATTTAAT GGCACCCAAA ATGC 24

(2) INFORMATION FOR SEQ ID NO: 13:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 13:

CAGTCTATGG CCATCACATA CTC 23

(2) INFORMATION FOR SEQ ID NO: 14:

(i) SEQUENCE CHARACTERISTICS:
(A) LENGTH: 22 base pairs
(B) TYPE: nucleic acid

-continued (C) STRANDEDNESS: single
(D) TOPOLOGY: linear (xi) SEQUENCE DESCRIPTION: SEQ ID NO: 14:

ACCGCTTGGG ATAAGTGCAT GC 22

(2) INFORMATION FOR SEQ ID NO: 15:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 15:

GAGAAGAAGT CTAACTTGGA GAAG 24

(2) INFORMATION FOR SEQ ID NO: 16:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 16:

TTCTGGTGAC TGTACCATGA TAC 23

(2) INFORMATION FOR SEQ ID NO: 17:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 17:

CCAAAGGAAG TGATACCAGC AAG 23

(2) INFORMATION FOR SEQ ID NO: 18:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 18:

ACAGCAAGAA CATAATTGTT CTGG 24

(2) INFORMATION FOR SEQ ID NO: 19:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 19:

GAACTTTGAA GTCCATCACG ACC 23

(2) INFORMATION FOR SEQ ID NO: 20:

(i) SEQUENCE CHARACTERISTICS:
(A) LENGTH: 24 base pairs
(B) TYPE: nucleic acid
(C) STRANDEDNESS: single -continued (D) TOPOLOGY: linear (xi) SEQUENCE DESCRIPTION: SEQ ID NO: 20:

GCATTAATAA AGCTGACATT CGCC 24

(2) INFORMATION FOR SEQ ID NO: 21:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 21:

CATTACGGTG CTCCTAAGGA CATG 24

(2) INFORMATION FOR SEQ ID NO: 22:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 22:

GATGGATTTG AAGATGGAGT AGAAG 25

(2) INFORMATION FOR SEQ ID NO: 23:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 23:

TGAAAGAGAA TATGGAAAGA GCTTG 25

(2) INFORMATION FOR SEQ ID NO: 24:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 24:

GTAGAACCAA CTCATTCTAA ATGCT 25

(2) INFORMATION FOR SEQ ID NO: 25:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 25:

AATTTGCGTG TCATCCTTGC GCA 23

(2) INFORMATION FOR SEQ ID NO: 26:

(i) SEQUENCE CHARACTERISTICS:
(A) LENGTH: 22 base pairs
(B) TYPE: nucleic acid
(C) STRANDEDNESS: single
(D) TOPOLOGY: linear -continued (xi) SEQUENCE DESCRIPTION: SEQ ID NO: 26:

TCCTAGTCAC CCATCTGAAG TC 22

(2) INFORMATION FOR SEQ ID NO: 27:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 27:

CATGAAACTT GCTTCTAGGA CAC 23

(2) INFORMATION FOR SEQ ID NO: 28:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 28:

CCCAGGAGTT CGAGACCATC C 21

(2) INFORMATION FOR SEQ ID NO: 29:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 29:

TTACAATCGG CCACATTCAT CAC 23

(2) INFORMATION FOR SEQ ID NO: 30:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 30:

TGTAATCCCA ACACTTTGGG AGG 23

(2) INFORMATION FOR SEQ ID NO: 31:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 31:

AGTGGAAGAA TTCATAGTGG ATGG 24

(2) INFORMATION FOR SEQ ID NO: 32:

(i) SEQUENCE CHARACTERISTICS:
(A) LENGTH: 24 base pairs
(B) TYPE: nucleic acid
(C) STRANDEDNESS: single
(D) TOPOLOGY: linear -continued (xi) SEQUENCE DESCRIPTION: SEQ ID NO: 32:

TAGCTTTATG AACCAATTTC TACC 24

(2) INFORMATION FOR SEQ ID NO: 33:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 33:

AATCCAAAGA ATCAATAGAC AAGTC 25

(2) INFORMATION FOR SEQ ID NO: 34:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 34:

GCTTGAAGGA TGAGGCTCTG AG 22

(2) INFORMATION FOR SEQ ID NO: 35:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 35:

TGTTCAGAAT GAGCACGATG GG 22

(2) INFORMATION FOR SEQ ID NO: 36:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 36:

CTTGTGAGAG GCCTATAAAC TGG 23

(2) INFORMATION FOR SEQ ID NO: 37:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 37:

GGTAAACAGT GTAGGAGTCT GC 22

(2) INFORMATION FOR SEQ ID NO: 38:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 38:

-continued

GCCATTTTCT CTTTAATTGG AAAGG 25

(2) INFORMATION FOR SEQ ID NO: 39:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 39:

ATCTTATTCA TCTTTCTGAG AATGG 25

(2) INFORMATION FOR SEQ ID NO: 40:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 40:

TGAAATAGCC CAACATCTGA CAG 23

(2) INFORMATION FOR SEQ ID NO: 41:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 41:

GATTAATTTG ACAGCTTGAT TAGGC 25

(2) INFORMATION FOR SEQ ID NO: 42:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 42:

TGAAATATAA ACTCAGACTC TTAGC 25

(2) INFORMATION FOR SEQ ID NO: 43:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 43:

GTACTGATTT GGAAAGACAT TCTC 24

(2) INFORMATION FOR SEQ ID NO: 44:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 44:

-continued

GATGTGACAG TGGAAGCTAT GG 22

(2) INFORMATION FOR SEQ ID NO: 45:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 45:

GGAAAAATGT GGTATCTGAA GCTC 24

(2) INFORMATION FOR SEQ ID NO: 46:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 46:

AAGTGAGCAA ATGTTGCTTC TGG 23

(2) INFORMATION FOR SEQ ID NO: 47:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 47:

TCATTAGGAA GCTGAACATC AGC 23

(2) INFORMATION FOR SEQ ID NO: 48:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 48:

GTTGGAGGAA ATTGATCCCA AGTC 24

(2) INFORMATION FOR SEQ ID NO: 49:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 49:

TGTTGCTTAT GGGTTTAACT TGTG 24

(2) INFORMATION FOR SEQ ID NO: 50:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 50:

TAAAGGATTA ATGCTGTTAA CAGTG 25

-continued (2) INFORMATION FOR SEQ ID NO: 51:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 51:

TCACACTGCG CATTTACTAC CTG 23

(2) INFORMATION FOR SEQ ID NO: 52:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 52:

GTAATCATAT CAGAATTCAT AACAG 25

(2) INFORMATION FOR SEQ ID NO: 53:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 53:

CTTTGGCAAC CTTCCACCTT CC 22

(2) INFORMATION FOR SEQ ID NO: 54:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 54:

GCAAAGGAAA TGTAGCACAT AGAG 24

(2) INFORMATION FOR SEQ ID NO: 55:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 55:

AGGCTATAGG CATTTGAAAG AGG 23

(2) INFORMATION FOR SEQ ID NO: 56:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 56:

GTAGGCTCCC AGAAGACCCA G 21

-continued (2) INFORMATION FOR SEQ ID NO: 57:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 57:

GAAAGGATGG GTGTGTATTC AGG 23

(2) INFORMATION FOR SEQ ID NO: 58:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 58:

TTTTAATAGG GTAGAAA 17

(2) INFORMATION FOR SEQ ID NO: 59:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 59:

TTTTAATACG GTAGAAA 17

(2) INFORMATION FOR SEQ ID NO: 60:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 60:

GAAGCTAGGC AGAAACAT 18

(2) INFORMATION FOR SEQ ID NO: 61:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 61:

GAAGCTAGGT AGAAACAT 18

(2) INFORMATION FOR SEQ ID NO: 62:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO: 62:

TTGGAGCGAG CA 12

-continued (2) INFORMATION FOR SEQ ID NO: 63:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO: 63:

TTGGAGTGAG CA 12

(2) INFORMATION FOR SEQ ID NO: 64:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 64:

AAGAAGTTTC TTCTG 15

(2) INFORMATION FOR SEQ ID NO: 65:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 65:

AAGAAGTTGC TTCTG 15

(2) INFORMATION FOR SEQ ID NO: 66:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO: 66:

CCTTCATGTG AT 12

(2) INFORMATION FOR SEQ ID NO: 67:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO: 67:

CCTTCACGTG AT 12

(2) INFORMATION FOR SEQ ID NO: 68:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 68:

CTGTAGACAG ACACCTC 17

(2) INFORMATION FOR SEQ ID NO: 69:

-continued (i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO: 69:

CTGTAGACAC CTC 13

(2) INFORMATION FOR SEQ ID NO: 70:

(i) SEQUENCE CHARACTERISTICS:
(A) LENGTH: 5208 base pairs
(B) TYPE: nucleic acid
(C) STRANDEDNESS: single
(D) TOPOLOGY: linear (xi) SEQUENCE DESCRIPTION: SEQ ID NO: 70:

TGTGCGCCGG GGAGGCGCCG GCTTGTACTC GGCAGCGCGG GAATAAAGTT TGCTGATTTG 60

GTGTCTAGCC TGGATGCCTG GGTTGCAGCC CTGCTTGTGG TGGCGCTCCA CAGTCATCCG 120

GCTGAAGAAG ACCTGTTGGA CTGGATCTTC TCGGGTTTTC TTTCAGATAT TGTTTTGTAT 180

TTACCCATGA AGACATTGTT TTTTGGACTC TGCAAATAGG ACATTTCAAA GATGAGTGAA 240

AAAAAATTGG AAACAACTGC ACAGCAGCGG AAATGTCCTG AATGGATGAA TGTGCAGAAT 300

AAAAGATGTG CTGTAGAAGA AAGAAAGGCA TGTGTTCGGA AGAGTGTTTT TGAAGATGAC 360

CTCCCCTTCT TAGAATTCAC TGGATCCATT GTGTATAGTT ACGATGCTAG TGATTGCTCT 420

TTCCTGTCAG AAGATATTAG CATGAGTCTA TCAGATGGGG ATGTGGTGGG ATTTGACATG 480

GAGTGGCCAC CATTATACAA TAGAGGGAAA CTTGGCAAAG TTGCACTAAT TCAGTTGTGT 540

GTTTCTGAGA GCAAATGTTA CTTGTTCCAC GTTTCTTCCA TGTCAGTTTT TCCCCAGGGA 600

TTAAAAATGT TGCTTGAAAA TAAAGCAGTT AAAAAGGCAG GTGTAGGAAT TGAAGGAGAT 660

CAGTGGAAAC TTCTACGTGA CTTTGATATC AAATTGAAGA ATTTTGTGGA GTTGACAGAT 720

GTTGCCAATA AAAAGCTGAA ATGTACAGAG ACCTGGAGCC TTAACAGTCT GGTTAAACAC 780

CTCTTAGGTA AACAGCTCCT GAAAGACAAG TCTATCCGCT GTAGCAATTG GAGTAAATTT 840

CCTCTCACTG AGGACCAGAA ACTGTATGCA GCCACTGATG CTTATGCTGG TTTTATTATT 900

TACCGAAATT TAGAGATTTT GGATGATACT GTGCAAAGGT TTGCTATAAA TAAAGAGGAA 960

GAAATCCTAC TTAGCGACAT GAACAAACAG TTGACTTCAA TCTCTGAGGA AGTGATGGAT 1020

CTGGCTAAGC ATCTTCCTCA TGCTTTCAGT AAATTGGAAA ACCCACGGAG GGTTTCTATC 1080

TTACTAAAGG ATATTTCAGA AAATCTATAT TCACTGAGGA GGATGATAAT TGGGTCTACT 1140

AACATTGAGA CTGAACTGAG GCCCAGCAAT AATTTAAACT TATTATCCTT TGAAGATTCA 1200

ACTACTGGGG GAGTACAACA GAAACAAATT AGAGAACATG AAGTTTTAAT TCACGTTGAA 1260

GATGAAACAT GGGACCCAAC ACTTGATCAT TTAGCTAAAC ATGATGGAGA AGATGTACTT 1320

GGAAATAAAG TGGAACGAAA AGAAGATGGA TTTGAAGATG GAGTAGAAGA CAACAAATTG 1380

AAAGAGAATA TGGAAAGAGC TTGTTTGATG TCGTTAGATA TTACAGAACA TGAACTCCAA 1440

ATTTTGGAAC AGCAGTCTCA GGAAGAATAT CTTAGTGATA TTGCTTATAA ATCTACTGAG 1500

CATTTATCTC CCAATGATAA TGAAAACGAT ACGTCCTATG TAATTGAGAG TGATGAAGAT 1560

TTAGAAATGG AGATGCTTAA GCATTTATCT CCCAATGATA ATGAAAACGA TACGTCCTAT 1620

GTAATTGAGA GTGATGAAGA TTTAGAAATG GAGATGCTTA AGTCTTTAGA AAACCTCAAT 1680

AGTGGCACGG TAGAACCAAC TCATTCTAAA TGCTTAAAAA TGGAAAGAAA TCTGGGTCTT 1740

-continued

```
CCTACTAAAG AAGAAGAAGA AGATGATGAA AATGAAGCTA ATGAAGGGGA AGAAGATGAT   1800
GATAAGGACT TTTTGTGGCC AGCACCCAAT GAAGAGCAAG TTACTTGCCT CAAGATGTAC   1860
TTTGGCCATT CCAGTTTTAA ACCAGTTCAG TGGAAAGTGA TTCATTCAGT ATTAGAAGAA   1920
AGAAGAGATA ATGTTGCTGT CATGGCAACT GGATATGGAA AGAGTTTGTG CTTCCAGTAT   1980
CCACCTGTTT ATGTAGGCAA GATTGGCCTT GTTATCTCTC CCCTTATTTC TCTGATGGAA   2040
GACCAAGTGC TACAGCTTAA AATGTCCAAC ATCCCAGCTT GCTTCCTTGG ATCAGCACAG   2100
TCAGAAAATG TTCTAACAGA TATTAAATTA GGTAAATACC GGATTGTATA CGTAACTCCA   2160
GAATACTGTT CAGGTAACAT GGGCCTGCTC CAGCAACTTG AGGCTGATAT TGGTATCACG   2220
CTCATTGCTG TGGATGAGGC TCACTGTATT TCTGAGTGGG GGCATGATTT TAGGGATTCA   2280
TTCAGGAAGT TGGGCTCCCT AAAGACAGCA CTGCCAATGG TTCCAATCGT TGCACTTACT   2340
GCTACTGCAA GTTCTTCAAT CCGGGAAGAC ATTGTACGTT GCTTAAATCT GAGAAATCCT   2400
CAGATCACCT GTACTGGTTT TGATCGACCA AACCTGTATT TAGAAGTTAG GCGAAAAACA   2460
GGGAATATCC TTCAGGATCT GCAGCCATTT CTTGTCAAAA CAAGTTCCCA CTGGGAATTT   2520
GAAGGTCCAA CAATCATCTA CTGTCCTTCT AGAAAAATGA CACAACAAGT TACAGGTGAA   2580
CTTAGGAAAC TTAATCTATC CTGTGGAACA TACCATGCGG GCATGAGTTT TAGCACAAGG   2640
AAAGACATTC ATCATAGGTT TGTAAGAGAT GAAATTCAGT GTGTCATAGC TACCATAGCT   2700
TTTGGAATGG GCATTAATAA AGCTGACATT CGCCAAGTCA TTCATTACGG TGCTCCTAAG   2760
GACATGGAAT CATATTATCA GGAGATTGGT AGAGCTGGTC GTGATGGACT TCAAAGTTCT   2820
TGTCACGTCC TCTGGGCTCC TGCAGACATT AACTTAAATA GGCACCTTCT TACTGAGATA   2880
CGTAATGAGA AGTTTCGATT ATACAAATTA AAGATGATGG CAAAGATGGA AAAATATCTT   2940
CATTCTAGCA GATGTAGGAG ACAAATCATC TTGTCTCATT TTGAGGACAA ACAAGTACAA   3000
AAAGCCTCCT TGGGAATTAT GGGAACTGAA AAATGCTGTG ATAATTGCAG GTCCAGATTG   3060
GATCATTGCT ATTCCATGGA TGACTCAGAG GATACATCCT GGGACTTTGG TCCACAAGCA   3120
TTTAAGCTTT TGTCTGCTGT GGACATCTTA GGCGAAAAAT TTGGAATTGG GCTTCCAATT   3180
TTATTTCTCC GAGGATCTAA TTCTCAGCGT CTTGCCGATC AATATCGCAG GCACAGTTTA   3240
TTTGGCACTG GCAAGGATCA AACAGAGAGT TGGTGGAAGG CTTTTTCCCG TCAGCTGATC   3300
ACTGAGGGAT TCTTGGTAGA AGTTTCTCGG TATAACAAAT TTATGAAGAT TTGCGCCCTT   3360
ACGAAAAAGG GTAGAAATTG GCTTCATAAA GCTAATACAG AATCTCAGAG CCTCATCCTT   3420
CAAGCTAATG AAGAATTGTG TCCAAAGAAG TTTCTTCTGC CTAGTTCGAA AACTGTATCT   3480
TCGGGCACCA AAGAGCATTG TTATAATCAA GTACCAGTTG AATTAAGTAC AGAGAAGAAG   3540
TCTAACTTGG AGAAGTTATA TTCTTATAAA CCATGTGATA AGATTTCTTC TGGGAGTAAC   3600
ATTTCTAAAA AAAGTATCAT GGTACAGTCA CCAGAAAAAG CTTACAGTTC CTCACAGCCT   3660
GTTATTTCGG CACAAGAGCA GGAGACTCAG ATTGTGTTAT ATGGCAAATT GGTAGAAGCT   3720
AGGCAGAAAC ATGCCAATAA AATGGATGTT CCCCCAGCTA TTCTGGCAAC AAACAAGATA   3780
CTGGTGGATA TGGCCAAAAT GAGACCAACT ACGGTTGAAA ACGTAAAAAG GATTGATGGT   3840
GTTTCTGAAG GCAAAGCTGC CATGTTGGCC CCTCTGTTGG AAGTCATCAA ACATTTCTGC   3900
CAAACAAATA GTGTTCAGAC AGACCTCTTT TCAAGTACAA AACCTCAAGA AGAACAGAAG   3960
ACGAGTCTGG TAGCAAAAAA TAAAATATGC ACACTTTCAC AGTCTATGGC CATCACATAC   4020
TCTTTATTCC AAGAAAAGAA GATGCCTTTG AAGAGCATAG CTGAGAGCAG GATTCTGCCT   4080
```

-continued

```
CTCATGACAA TTGGCATGCA CTTATCCCAA GCGGTGAAAG CTGGCTGCCC CCTTGATTTG   4140

GAGCGAGCAG GCCTGACTCC AGAGGTTCAG AAGATTATTG CTGATGTTAT CCGAAACCCT   4200

CCCGTCAACT CAGATATGAG TAAAATTAGC CTAATCAGAA TGTTAGTTCC TGAAAACATT   4260

GACACGTACC TTATCCACAT GGCAATTGAG ATCCTTAAAC ATGGTCCTGA CAGCGGACTT   4320

CAACCTTCAT GTGATGTCAA CAAAAGGAGA TGTTTTCCCG GTTCTGAAGA GATCTGTTCA   4380

AGTTCTAAGA GAAGCAAGGA AGAAGTAGGC ATCAATACTG AGACTTCATC TGCAGAGAGA   4440

AAGAGACGAT TACCTGTGTG GTTTGCCAAA GGAAGTGATA CCAGCAAGAA ATTAATGGAC   4500

AAAACGAAAA GGGGAGGTCT TTTTAGTTAA GCTGGCAATT ACCAGAACAA TTATGTTTCT   4560

TGCTGTATTA TAAGAGGATA GCTATATTTT ATTTCTGAAG AGTAAGGAGT AGTATTTTGG   4620

CTTAAAAATC ATTCTAATTA CAAAGTTCAC TGTTTATTGA AGAACTGGCA TCTTAAATCA   4680

GCCTTCCGCA ATTCATGTAG TTTCTGGGTC TTCTGGGAGC CTACGTGAGT ACATCACCTA   4740

ACAGAATATT AAATTAGACT TCCTGTAAGA TTGCTTTAAG AAACTGTTAC TGTCCTGTTT   4800

TCTAATCTCT TTATTAAAAC AGTGTATTTG GAAAATGTTA TGTGCTCTGA TTTGATATAG   4860

ATAACAGATT AGTAGTTACA TGGTAATTAT GTGATATAAA ATATTCATAT ATTATCAAAA   4920

TTCTGTTTTG TAAATGTAAG AAAGCATAGT TATTTTACAA ATTGTTTTTA CTGTCTTTTG   4980

AAGAAGTTCT TAAATACGTT GTTAAATGGT ATTAGTTGAC CAGGGCAGTG AAAATGAAAC   5040

CGCATTTTGG GTGCCATTAA ATAGGGAAAA AACATGTAAA AAATGTAAAA TGGAGACCAA   5100

TTGCACTAGG CAAGTGTATA TTTTGTATTT TATATACAAT TTCTATTATT TTTCAAGTAA   5160

TAAAACAATG TTTTTCATAC TGAATATTAA AAAAAAAAAA AAAAAAAA               5208
```

(2) INFORMATION FOR SEQ ID NO: 71:

(i) SEQUENCE CHARACTERISTICS:
(A) LENGTH: 1432 amino acids
(B) TYPE: amino acid
(C) STRANDEDNESS: <Unknown>
(D) TOPOLOGY: linear (xi) SEQUENCE DESCRIPTION: SEQ ID NO: 71:

```
Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
            20                  25                  30

Ala Cys Val Arg Lys Ser Val Phe Glu Asp Asp Leu Pro Phe Leu Glu
        35                  40                  45

Phe Thr Gly Ser Ile Val Tyr Ser Tyr Asp Ala Ser Asp Cys Ser Phe
    50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
        115                 120                 125

Glu Asn Lys Ala Val Lys Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160
```

-continued

```
Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
        275                 280                 285

Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met
        435                 440                 445

Leu Lys His Leu Ser Pro Asn Asp Asn Glu Asn Asp Thr Ser Tyr Val
    450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Glu Asp Asp
            500                 505                 510

Glu Asn Glu Ala Asn Glu Gly Glu Glu Asp Asp Asp Lys Asp Phe Leu
        515                 520                 525

Trp Pro Ala Pro Asn Glu Glu Gln Val Thr Cys Leu Lys Met Tyr Phe
    530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
```

-continued

```
            580                 585                 590

Leu Val Ile Ser Pro Leu Ile Ser Leu Met Glu Asp Gln Val Leu Gln
        595                 600                 605

Leu Lys Met Ser Asn Ile Pro Ala Cys Phe Leu Gly Ser Ala Gln Ser
    610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
        675                 680                 685

Ser Leu Lys Thr Ala Leu Pro Met Val Pro Ile Val Ala Leu Thr Ala
    690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
            740                 745                 750

Phe Leu Val Lys Thr Ser Ser His Trp Glu Phe Glu Gly Pro Thr Ile
        755                 760                 765

Ile Tyr Cys Pro Ser Arg Lys Met Thr Gln Gln Val Thr Gly Glu Leu
    770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
            820                 825                 830

Ile Arg Gln Val Ile His Tyr Gly Ala Pro Lys Asp Met Glu Ser Tyr
        835                 840                 845

Tyr Gln Glu Ile Gly Arg Ala Gly Arg Asp Gly Leu Gln Ser Ser Cys
    850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
            900                 905                 910

Ile Leu Ser His Phe Glu Asp Lys Gln Val Gln Lys Ala Ser Leu Gly
        915                 920                 925

Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
        995                 1000                1005
```

-continued

```
Asp Gln Thr Glu Ser Trp Trp Lys Ala Phe Ser Arg Gln Leu Ile Thr
    1010                1015                1020

Glu Gly Phe Leu Val Glu Val Ser Arg Tyr Asn Lys Phe Met Lys Ile
1025                1030                1035                1040

Cys Ala Leu Thr Lys Lys Gly Arg Asn Trp Leu His Lys Ala Asn Thr
                1045                1050                1055

Glu Ser Gln Ser Leu Ile Leu Gln Ala Asn Glu Glu Leu Cys Pro Lys
            1060                1065                1070

Lys Phe Leu Leu Pro Ser Ser Lys Thr Val Ser Ser Gly Thr Lys Glu
        1075                1080                1085

His Cys Tyr Asn Gln Val Pro Val Glu Leu Ser Thr Glu Lys Lys Ser
    1090                1095                1100

Asn Leu Glu Lys Leu Tyr Ser Tyr Lys Pro Cys Asp Lys Ile Ser Ser
1105                1110                1115                1120

Gly Ser Asn Ile Ser Lys Lys Ser Ile Met Val Gln Ser Pro Glu Lys
                1125                1130                1135

Ala Tyr Ser Ser Ser Gln Pro Val Ile Ser Ala Gln Glu Gln Glu Thr
            1140                1145                1150

Gln Ile Val Leu Tyr Gly Lys Leu Val Glu Ala Arg Gln Lys His Ala
        1155                1160                1165

Asn Lys Met Asp Val Pro Pro Ala Ile Leu Ala Thr Asn Lys Ile Leu
    1170                1175                1180

Val Asp Met Ala Lys Met Arg Pro Thr Thr Val Glu Asn Val Lys Arg
1185                1190                1195                1200

Ile Asp Gly Val Ser Glu Gly Lys Ala Ala Met Leu Ala Pro Leu Leu
                1205                1210                1215

Glu Val Ile Lys His Phe Cys Gln Thr Asn Ser Val Gln Thr Asp Leu
            1220                1225                1230

Phe Ser Ser Thr Lys Pro Gln Glu Glu Gln Lys Thr Ser Leu Val Ala
        1235                1240                1245

Lys Asn Lys Ile Cys Thr Leu Ser Gln Ser Met Ala Ile Thr Tyr Ser
    1250                1255                1260

Leu Phe Gln Glu Lys Lys Met Pro Leu Lys Ser Ile Ala Glu Ser Arg
1265                1270                1275                1280

Ile Leu Pro Leu Met Thr Ile Gly Met His Leu Ser Gln Ala Val Lys
                1285                1290                1295

Ala Gly Cys Pro Leu Asp Leu Glu Arg Ala Gly Leu Thr Pro Glu Val
            1300                1305                1310

Gln Lys Ile Ile Ala Asp Val Ile Arg Asn Pro Pro Val Asn Ser Asp
        1315                1320                1325

Met Ser Lys Ile Ser Leu Ile Arg Met Leu Val Pro Glu Asn Ile Asp
    1330                1335                1340

Thr Tyr Leu Ile His Met Ala Ile Glu Ile Leu Lys His Gly Pro Asp
1345                1350                1355                1360

Ser Gly Leu Gln Pro Ser Cys Asp Val Asn Lys Arg Arg Cys Phe Pro
                1365                1370                1375

Gly Ser Glu Glu Ile Cys Ser Ser Ser Lys Arg Ser Lys Glu Glu Val
            1380                1385                1390

Gly Ile Asn Thr Glu Thr Ser Ser Ala Glu Arg Lys Arg Arg Leu Pro
        1395                1400                1405

Val Trp Phe Ala Lys Gly Ser Asp Thr Ser Lys Lys Leu Met Asp Lys
    1410                1415                1420
```

-continued

```
Thr Lys Arg Gly Gly Leu Phe Ser
1425                1430

(2) INFORMATION FOR SEQ ID NO: 72:

     (i) SEQUENCE CHARACTERISTICS:
          (A) LENGTH: 2178 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 313..1497

    (xi) SEQUENCE DESCRIPTION: SEQ ID NO: 72:

TTTGGAATTG GGCTTCCAAT TTTATTTCTC CGAGGATCTG GTCTCACTCT GTTGCTCAGT     60

CTGTAGTGCA GTGGTGTCAT CATAGCTCAC TGCAGTCTTG ATCTCCTGAG CTCAAACGAT    120

TCTCCTGCCT CAGCTCCTGC TTCAGCCTCC TGAGTAGCGG AACAACAGAA TTCTCAGCGT    180

CTTGCCGATC AATATCGCAG GCACAGTTTA TTTGGCACTG GCAAGGATCA AACAGAGAGT    240

TGGTGGAAGG CTTTTTCCCG TCAGCTGATC ACTGAGGGAT TCTTGGTAGA AGTTTCTCGG    300

TATAACAAAT TT ATG AAG ATT TGC GCC CTT ACG AAA AAG GGT AGA AAT TGG    351
              Met Lys Ile Cys Ala Leu Thr Lys Lys Gly Arg Asn Trp
                1               5                  10

CTT CAT AAA GCT AAT ACA GAA TCT CAG AGC CTC ATC CTT CAA GCT AAT      399
Leu His Lys Ala Asn Thr Glu Ser Gln Ser Leu Ile Leu Gln Ala Asn
     15                  20                  25

GAA GAA TTG TGT CCA AAG AAG TTT CTT CTG CCT AGT TCG AAA ACT GTA      447
Glu Glu Leu Cys Pro Lys Lys Phe Leu Leu Pro Ser Ser Lys Thr Val
 30                  35                  40                  45

TCT TCG GGC ACC AAA GAG CAT TGT TAT AAT CAA GTA CCA GTT GAA TTA      495
Ser Ser Gly Thr Lys Glu His Cys Tyr Asn Gln Val Pro Val Glu Leu
                 50                  55                  60

AGT ACA GAG AAG AAG TCT AAC TTG GAG AAG TTA TAT TCT TAT AAA CCA      543
Ser Thr Glu Lys Lys Ser Asn Leu Glu Lys Leu Tyr Ser Tyr Lys Pro
             65                  70                  75

TGT GAT AAG ATT TCT TCT GGG AGT AAC ATT TCT AAA AAA AGT ATC ATG      591
Cys Asp Lys Ile Ser Ser Gly Ser Asn Ile Ser Lys Lys Ser Ile Met
         80                  85                  90

GTA CAG TCA CCA GAA AAA GCT TAC AGT TCC TCA CAG CCT GTT ATT TCG      639
Val Gln Ser Pro Glu Lys Ala Tyr Ser Ser Ser Gln Pro Val Ile Ser
     95                 100                 105

GCA CAA GAG CAG GAG ACT CAG ATT GTG TTA TAT GGC AAA TTG GTA GAA      687
Ala Gln Glu Gln Glu Thr Gln Ile Val Leu Tyr Gly Lys Leu Val Glu
110                 115                 120                 125

GCT AGG CAG AAA CAT GCC AAT AAA ATG GAT GTT CCC CCA GCT ATT CTG      735
Ala Arg Gln Lys His Ala Asn Lys Met Asp Val Pro Pro Ala Ile Leu
                130                 135                 140

GCA ACA AAC AAG ATA CTG GTG GAT ATG GCC AAA ATG AGA CCA ACT ACG      783
Ala Thr Asn Lys Ile Leu Val Asp Met Ala Lys Met Arg Pro Thr Thr
            145                 150                 155

GTT GAA AAC GTA AAA AGG ATT GAT GGT GTT TCT GAA GGC AAA GCT GCC      831
Val Glu Asn Val Lys Arg Ile Asp Gly Val Ser Glu Gly Lys Ala Ala
        160                 165                 170

ATG TTG GCC CCT CTG TTG GAA GTC ATC AAA CAT TTC TGC CAA ACA AAT      879
Met Leu Ala Pro Leu Leu Glu Val Ile Lys His Phe Cys Gln Thr Asn
    175                 180                 185

AGT GTT CAG ACA GAC CTC TTT TCA AGT ACA AAA CCT CAA GAA GAA CAG      927
Ser Val Gln Thr Asp Leu Phe Ser Ser Thr Lys Pro Gln Glu Glu Gln
190                 195                 200                 205
```

-continued

```
AAG ACG AGT CTG GTA GCA AAA AAT AAA ATA TGC ACA CTT TCA CAG TCT      975
Lys Thr Ser Leu Val Ala Lys Asn Lys Ile Cys Thr Leu Ser Gln Ser
            210                 215                 220

ATG GCC ATC ACA TAC TCT TTA TTC CAA GAA AAG AAG ATG CCT TTG AAG     1023
Met Ala Ile Thr Tyr Ser Leu Phe Gln Glu Lys Lys Met Pro Leu Lys
            225                 230                 235

AGC ATA GCT GAG AGC AGG ATT CTG CCT CTC ATG ACA ATT GGC ATG CAC     1071
Ser Ile Ala Glu Ser Arg Ile Leu Pro Leu Met Thr Ile Gly Met His
        240                 245                 250

TTA TCC CAA GCG GTG AAA GCT GGC TGC CCC CTT GAT TTG GAG CGA GCA     1119
Leu Ser Gln Ala Val Lys Ala Gly Cys Pro Leu Asp Leu Glu Arg Ala
    255                 260                 265

GGC CTG ACT CCA GAG GTT CAG AAG ATT ATT GCT GAT GTT ATC CGA AAC     1167
Gly Leu Thr Pro Glu Val Gln Lys Ile Ile Ala Asp Val Ile Arg Asn
270                 275                 280                 285

CCT CCC GTC AAC TCA GAT ATG AGT AAA ATT AGC CTA ATC AGA ATG TTA     1215
Pro Pro Val Asn Ser Asp Met Ser Lys Ile Ser Leu Ile Arg Met Leu
            290                 295                 300

GTT CCT GAA AAC ATT GAC ACG TAC CTT ATC CAC ATG GCA ATT GAG ATC     1263
Val Pro Glu Asn Ile Asp Thr Tyr Leu Ile His Met Ala Ile Glu Ile
            305                 310                 315

CTT AAA CAT GGT CCT GAC AGC GGA CTT CAA CCT TCA TGT GAT GTC AAC     1311
Leu Lys His Gly Pro Asp Ser Gly Leu Gln Pro Ser Cys Asp Val Asn
        320                 325                 330

AAA AGG AGA TGT TTT CCC GGT TCT GAA GAG ATC TGT TCA AGT TCT AAG     1359
Lys Arg Arg Cys Phe Pro Gly Ser Glu Glu Ile Cys Ser Ser Ser Lys
    335                 340                 345

AGA AGC AAG GAA GAA GTA GGC ATC AAT ACT GAG ACT TCA TCT GCA GAG     1407
Arg Ser Lys Glu Glu Val Gly Ile Asn Thr Glu Thr Ser Ser Ala Glu
350                 355                 360                 365

AGA AAG AGA CGA TTA CCT GTG TGG TTT GCC AAA GGA AGT GAT ACC AGC     1455
Arg Lys Arg Arg Leu Pro Val Trp Phe Ala Lys Gly Ser Asp Thr Ser
            370                 375                 380

AAG AAA TTA ATG GAC AAA ACG AAA AGG GGA GGT CTT TTT AGT             1497
Lys Lys Leu Met Asp Lys Thr Lys Arg Gly Gly Leu Phe Ser
            385                 390                 395

TAAGCTGGCA ATTACCAGAA CAATTATGTT TCTTGCTGTA TTATAAGAGG ATAGCTATAT   1557

TTTATTTCTG AAGAGTAAGG AGTAGTATTT TGGCTTAAAA ATCATTCTAA TTACAAAGTT   1617

CACTGTTTAT TGAAGAACTG GCATCTTAAA TCAGCCTTCC GCAATTCATG TAGTTTCTGG   1677

GTCTTCTGGG AGCCTACGTG AGTACATCAC CTAACAGAAT ATTAAATTAG ACTTCCTGTA   1737

AGATTGCTTT AAGAAACTGT TACTGTCCTG TTTTCTAATC TCTTTATTAA AACAGTGTAT   1797

TTGGAAAATG TTATGTGCTC TGATTTGATA TAGATAACAG ATTAGTAGTT ACATGGTAAT   1857

TATGTGATAT AAAATATTCA TATATTATCA AAATTCTGTT TTGTAAATGT AAGAAAGCAT   1917

AGTTATTTTA CAAATTGTTT TTACTGTCTT TTGAAGAAGT TCTTAAATAC GTTGTTAAAT   1977

GGTATTAGTT GACCAGGGCA GTGAAAATGA AACCGCATTT TGGGTGCCAT TAAATAGGGA   2037

AAAAACATGT AAAAAATGTA AAATGGAGAC CAATTGCACT AGGCAAGTGT ATATTTTGTA   2097

TTTTATATAC AATTTCTATT ATTTTTCAAG TAATAAAACA ATGTTTTTCA TACTGAATAT   2157

TAAAAAAAAA AAAAAAAAAA A                                             2178
```

(2) INFORMATION FOR SEQ ID NO: 73:

(i) SEQUENCE CHARACTERISTICS:
(A) LENGTH: 395 amino acids
(B) TYPE: amino acid (D) TOPOLOGY: linear (ii) MOLECULE TYPE: protein (xi) SEQUENCE DESCRIPTION: SEQ ID NO: 73:

```
Met Lys Ile Cys Ala Leu Thr Lys Lys Gly Arg Asn Trp Leu His Lys
  1               5                  10                  15

Ala Asn Thr Glu Ser Gln Ser Leu Ile Leu Gln Ala Asn Glu Glu Leu
             20                  25                  30

Cys Pro Lys Lys Phe Leu Leu Pro Ser Ser Lys Thr Val Ser Ser Gly
         35                  40                  45

Thr Lys Glu His Cys Tyr Asn Gln Val Pro Val Glu Leu Ser Thr Glu
     50                  55                  60

Lys Lys Ser Asn Leu Glu Lys Leu Tyr Ser Tyr Lys Pro Cys Asp Lys
 65                  70                  75                  80

Ile Ser Ser Gly Ser Asn Ile Ser Lys Lys Ser Ile Met Val Gln Ser
                 85                  90                  95

Pro Glu Lys Ala Tyr Ser Ser Ser Gln Pro Val Ile Ser Ala Gln Glu
            100                 105                 110

Gln Glu Thr Gln Ile Val Leu Tyr Gly Lys Leu Val Glu Ala Arg Gln
        115                 120                 125

Lys His Ala Asn Lys Met Asp Val Pro Pro Ala Ile Leu Ala Thr Asn
    130                 135                 140

Lys Ile Leu Val Asp Met Ala Lys Met Arg Pro Thr Thr Val Glu Asn
145                 150                 155                 160

Val Lys Arg Ile Asp Gly Val Ser Glu Gly Lys Ala Ala Met Leu Ala
                165                 170                 175

Pro Leu Leu Glu Val Ile Lys His Phe Cys Gln Thr Asn Ser Val Gln
            180                 185                 190

Thr Asp Leu Phe Ser Ser Thr Lys Pro Gln Glu Glu Gln Lys Thr Ser
        195                 200                 205

Leu Val Ala Lys Asn Lys Ile Cys Thr Leu Ser Gln Ser Met Ala Ile
    210                 215                 220

Thr Tyr Ser Leu Phe Gln Glu Lys Lys Met Pro Leu Lys Ser Ile Ala
225                 230                 235                 240

Glu Ser Arg Ile Leu Pro Leu Met Thr Ile Gly Met His Leu Ser Gln
                245                 250                 255

Ala Val Lys Ala Gly Cys Pro Leu Asp Leu Glu Arg Ala Gly Leu Thr
            260                 265                 270

Pro Glu Val Gln Lys Ile Ile Ala Asp Val Ile Arg Asn Pro Pro Val
        275                 280                 285

Asn Ser Asp Met Ser Lys Ile Ser Leu Ile Arg Met Leu Val Pro Glu
    290                 295                 300

Asn Ile Asp Thr Tyr Leu Ile His Met Ala Ile Glu Ile Leu Lys His
305                 310                 315                 320

Gly Pro Asp Ser Gly Leu Gln Pro Ser Cys Asp Val Asn Lys Arg Arg
                325                 330                 335

Cys Phe Pro Gly Ser Glu Glu Ile Cys Ser Ser Ser Lys Arg Ser Lys
            340                 345                 350

Glu Glu Val Gly Ile Asn Thr Glu Thr Ser Ser Ala Glu Arg Lys Arg
        355                 360                 365

Arg Leu Pro Val Trp Phe Ala Lys Gly Ser Asp Thr Ser Lys Lys Leu
    370                 375                 380

Met Asp Lys Thr Lys Arg Gly Gly Leu Phe Ser
```

-continued

```
385                 390                 395

(2) INFORMATION FOR SEQ ID NO: 74:

     (i) SEQUENCE CHARACTERISTICS:
          (A) LENGTH: 1269 amino acids
          (B) TYPE: amino acid
          (C) STRANDEDNESS: single
          (D) TOPOLOGY: linear

    (xi) SEQUENCE DESCRIPTION: SEQ ID NO: 74:

Glu Asp Gly Phe Glu Asp Gly Val Glu Asp Asn Lys Leu Lys Glu Asn
1               5                   10                  15

Met Glu Arg Ala Cys Leu Met Ser Leu Asp Ile Thr Glu His Glu Leu
            20                  25                  30

Gln Ile Leu Glu Gln Gln Ser Gln Glu Glu Tyr Leu Ser Asp Ile Ala
        35                  40                  45

Tyr Lys Ser Thr Glu His Leu Ser Pro Asn Asp Asn Glu Asn Asp Thr
    50                  55                  60

Ser Tyr Val Ile Glu Ser Asp Glu Asp Leu Glu Met Glu Met Leu Lys
65                  70                  75                  80

His Leu Ser Pro Asn Asp Asn Glu Asn Asp Thr Ser Tyr Val Ile Glu
                85                  90                  95

Ser Asp Glu Asp Leu Glu Met Glu Met Leu Lys Ser Leu Glu Asn Leu
            100                 105                 110

Asn Ser Gly Thr Val Glu Pro Thr His Ser Lys Cys Leu Lys Met Glu
        115                 120                 125

Arg Asn Leu Gly Leu Pro Thr Lys Glu Glu Glu Glu Asp Asp Glu Asn
    130                 135                 140

Glu Ala Asn Glu Gly Glu Glu Asp Asp Asp Lys Asp Phe Leu Trp Pro
145                 150                 155                 160

Ala Pro Asn Glu Glu Gln Val Thr Cys Leu Lys Met Tyr Phe Gly His
                165                 170                 175

Ser Ser Phe Lys Pro Val Gln Trp Lys Val Ile His Ser Val Leu Glu
            180                 185                 190

Glu Arg Arg Asp Asn Val Ala Val Met Ala Thr Gly Tyr Gly Lys Ser
        195                 200                 205

Leu Cys Phe Gln Tyr Pro Pro Val Tyr Val Gly Lys Ile Gly Leu Val
    210                 215                 220

Ile Ser Pro Leu Ile Ser Leu Met Glu Asp Gln Val Leu Gln Leu Lys
225                 230                 235                 240

Met Ser Asn Ile Pro Ala Cys Phe Leu Gly Ser Ala Gln Ser Glu Asn
                245                 250                 255

Val Leu Thr Asp Ile Lys Leu Gly Lys Tyr Arg Ile Val Tyr Val Thr
            260                 265                 270

Pro Glu Tyr Cys Ser Gly Asn Met Gly Leu Leu Gln Gln Leu Glu Ala
        275                 280                 285

Asp Ile Gly Ile Thr Leu Ile Ala Val Asp Glu Ala His Cys Ile Ser
    290                 295                 300

Glu Trp Gly His Asp Phe Arg Asp Ser Phe Arg Lys Leu Gly Ser Leu
305                 310                 315                 320

Lys Thr Ala Leu Pro Met Val Pro Ile Val Ala Leu Thr Ala Thr Ala
                325                 330                 335

Ser Ser Ser Ile Arg Glu Asp Ile Val Arg Cys Leu Asn Leu Arg Asn
            340                 345                 350
```

-continued

```
Pro Gln Ile Thr Cys Thr Gly Phe Asp Arg Pro Asn Leu Tyr Leu Glu
        355                 360                 365

Val Arg Arg Lys Thr Gly Asn Ile Leu Gln Asp Leu Gln Pro Phe Leu
    370                 375                 380

Val Lys Thr Ser Ser His Trp Glu Phe Glu Gly Pro Thr Ile Ile Tyr
385                 390                 395                 400

Cys Pro Ser Arg Lys Met Thr Gln Gln Val Thr Gly Glu Leu Arg Lys
                405                 410                 415

Leu Asn Leu Ser Cys Gly Thr Tyr His Ala Gly Met Ser Phe Ser Thr
            420                 425                 430

Arg Lys Asp Ile His His Arg Phe Val Arg Asp Glu Ile Gln Cys Val
        435                 440                 445

Ile Ala Thr Ile Ala Phe Gly Met Gly Ile Asn Lys Ala Asp Ile Arg
    450                 455                 460

Gln Val Ile His Tyr Gly Ala Pro Lys Asp Met Glu Ser Tyr Tyr Gln
465                 470                 475                 480

Glu Ile Gly Arg Ala Gly Arg Asp Gly Leu Gln Ser Ser Cys His Val
                485                 490                 495

Leu Trp Ala Pro Ala Asp Ile Asn Leu Asn Arg His Leu Leu Thr Glu
            500                 505                 510

Ile Arg Asn Glu Lys Phe Arg Leu Tyr Lys Leu Lys Met Met Ala Lys
        515                 520                 525

Met Glu Lys Tyr Leu His Ser Ser Arg Cys Arg Arg Gln Ile Ile Leu
    530                 535                 540

Ser His Phe Glu Asp Lys Gln Val Gln Lys Ala Ser Leu Gly Ile Met
545                 550                 555                 560

Gly Thr Glu Lys Cys Cys Asp Asn Cys Arg Ser Arg Leu Asp His Cys
                565                 570                 575

Tyr Ser Met Asp Asp Ser Glu Asp Thr Ser Trp Asp Phe Gly Pro Gln
            580                 585                 590

Ala Phe Lys Leu Leu Ser Ala Val Asp Ile Leu Gly Glu Lys Phe Gly
        595                 600                 605

Ile Gly Leu Pro Ile Leu Phe Leu Arg Gly Ser Asn Ser Gln Arg Leu
    610                 615                 620

Ala Asp Gln Tyr Arg Arg His Ser Leu Phe Gly Thr Gly Lys Asp Gln
625                 630                 635                 640

Thr Glu Ser Trp Trp Lys Ala Phe Ser Arg Gln Leu Ile Thr Glu Gly
                645                 650                 655

Phe Leu Val Glu Val Ser Arg Tyr Asn Lys Phe Met Lys Ile Cys Ala
            660                 665                 670

Leu Thr Lys Lys Gly Arg Asn Trp Leu His Lys Ala Asn Thr Glu Ser
        675                 680                 685

Gln Ser Leu Ile Leu Gln Ala Asn Glu Glu Leu Cys Pro Lys Lys Phe
    690                 695                 700

Leu Leu Pro Ser Ser Lys Thr Val Ser Ser Gly Thr Lys Glu His Cys
705                 710                 715                 720

Tyr Asn Gln Val Pro Val Glu Leu Ser Thr Glu Lys Lys Ser Asn Leu
                725                 730                 735

Glu Lys Leu Tyr Ser Tyr Lys Pro Cys Asp Lys Ile Ser Ser Gly Ser
            740                 745                 750

Asn Ile Ser Lys Lys Ser Ile Met Val Gln Ser Pro Glu Lys Ala Tyr
        755                 760                 765

Ser Ser Ser Gln Pro Val Ile Ser Ala Gln Glu Gln Glu Thr Gln Ile
```

-continued

```
    770                 775                 780

Val Leu Tyr Gly Lys Leu Val Glu Ala Arg Gln Lys His Ala Asn Lys
785                 790                 795                 800

Met Asp Val Pro Pro Ala Ile Leu Ala Thr Asn Lys Ile Leu Val Asp
                805                 810                 815

Met Ala Lys Met Arg Pro Thr Thr Val Glu Asn Val Lys Arg Ile Asp
            820                 825                 830

Gly Val Ser Glu Gly Lys Ala Ala Met Leu Ala Pro Leu Leu Glu Val
        835                 840                 845

Ile Lys His Phe Cys Gln Thr Asn Ser Val Gln Thr Asp Leu Phe Ser
    850                 855                 860

Ser Thr Lys Pro Gln Glu Glu Gln Lys Thr Ser Leu Val Ala Lys Asn
865                 870                 875                 880

Lys Ile Cys Thr Leu Ser Gln Ser Met Ala Ile Thr Tyr Ser Leu Phe
                885                 890                 895

Gln Glu Lys Lys Met Pro Leu Lys Ser Ile Ala Glu Ser Arg Ile Leu
            900                 905                 910

Pro Leu Met Thr Ile Gly Met His Leu Ser Gln Ala Val Lys Ala Gly
        915                 920                 925

Cys Pro Leu Asp Leu Glu Arg Ala Gly Leu Thr Pro Glu Val Gln Lys
    930                 935                 940

Ile Ile Ala Asp Val Ile Arg Asn Pro Pro Val Asn Ser Asp Met Ser
945                 950                 955                 960

Lys Ile Ser Leu Ile Arg Met Leu Val Pro Glu Asn Ile Asp Thr Tyr
                965                 970                 975

Leu Ile His Met Ala Ile Glu Ile Leu Lys His Gly Pro Asp Ser Gly
            980                 985                 990

Leu Gln Pro Ser Cys Asp Val Asn Lys Arg Arg Cys Phe Pro Gly Ser
        995                 1000                1005

Glu Glu Ile Cys Ser Ser Ser Lys Arg Ser Lys Glu Glu Val Gly Ile
    1010                1015                1020

Asn Thr Glu Thr Ser Ser Ala Glu Arg Lys Arg Arg Leu Pro Val Trp
1025                1030                1035                1040

Phe Ala Lys Gly Ser Asp Thr Ser Lys Lys Leu Met Asp Lys Thr Lys
                1045                1050                1055

Arg Gly Gly Leu Phe Ser Ala Gly Asn Tyr Gln Asn Asn Tyr Val Ser
            1060                1065                1070

Cys Cys Ile Ile Arg Gly Leu Tyr Phe Ile Ser Glu Glu Gly Val Val
        1075                1080                1085

Phe Trp Leu Lys Asn His Ser Asn Tyr Lys Val His Cys Leu Leu Lys
    1090                1095                1100

Asn Trp His Leu Lys Ser Ala Phe Arg Asn Ser Cys Ser Phe Trp Val
1105                1110                1115                1120

Phe Trp Glu Pro Thr Val His His Leu Thr Glu Tyr Ile Arg Leu Pro
                1125                1130                1135

Val Arg Leu Leu Glu Thr Val Thr Val Leu Phe Ser Asn Leu Phe Ile
            1140                1145                1150

Lys Thr Val Tyr Leu Glu Asn Val Met Cys Ser Asp Leu Ile Ile Thr
        1155                1160                1165

Asp Leu His Gly Asn Tyr Val Ile Asn Ile His Ile Leu Ser Lys Phe
    1170                1175                1180

Cys Phe Val Asn Val Arg Lys His Ser Tyr Phe Thr Asn Cys Phe Tyr
1185                1190                1195                1200
```

-continued

```
Cys Leu Leu Lys Lys Phe Leu Asn Thr Leu Leu Asn Gly Ile Ser Pro
                1205                1210                1215

Gly Gln Lys Asn Arg Ile Leu Gly Ala Ile Lys Gly Lys Asn Met Lys
            1220                1225                1230

Met Asn Gly Asp Gln Leu His Ala Ser Val Tyr Phe Val Phe Tyr Ile
        1235                1240                1245

Gln Phe Leu Leu Phe Phe Lys Asn Asn Val Phe His Thr Glu Tyr Lys
    1250                1255                1260

Lys Lys Lys Lys Lys
1265
```

(2) INFORMATION FOR SEQ ID NO: 75:

(i) SEQUENCE CHARACTERISTICS:
(A) LENGTH: 607 amino acids
(B) TYPE: amino acid
(C) STRANDEDNESS: single
(D) TOPOLOGY: linear (xi) SEQUENCE DESCRIPTION: SEQ ID NO: 75:

```
Ala Gln Ala Glu Val Leu Asn Leu Glu Ser Gly Ala Lys Gln Val Leu
1               5                   10                  15

Gln Glu Thr Phe Gly Tyr Gln Gln Phe Arg Pro Gly Gln Glu Glu Ile
            20                  25                  30

Ile Asp Thr Val Leu Ser Gly Arg Asp Cys Leu Val Val Met Pro Thr
        35                  40                  45

Gly Gly Gly Lys Ser Leu Cys Tyr Gln Ile Pro Ala Leu Leu Leu Asn
    50                  55                  60

Gly Leu Thr Val Val Val Ser Pro Leu Ile Ser Leu Met Lys Asp Gln
65                  70                  75                  80

Val Asp Gln Leu Gln Ala Asn Gly Val Ala Ala Ala Cys Leu Asn Ser
                85                  90                  95

Thr Gln Thr Arg Glu Gln Gln Leu Glu Val Met Thr Gly Cys Arg Thr
            100                 105                 110

Gly Gln Ile Arg Leu Leu Tyr Ile Ala Pro Glu Arg Leu Met Leu Asp
        115                 120                 125

Asn Phe Leu Glu His Leu Ala His Trp Asn Pro Val Leu Leu Ala Val
    130                 135                 140

Asp Glu Ala His Cys Ile Ser Gln Trp Gly His Asp Phe Arg Pro Glu
145                 150                 155                 160

Tyr Ala Ala Leu Gly Gln Leu Arg Gln Arg Phe Pro Thr Leu Pro Phe
                165                 170                 175

Met Ala Leu Thr Ala Thr Ala Asp Asp Thr Thr Arg Gln Asp Ile Val
            180                 185                 190

Arg Leu Leu Gly Leu Asn Asp Pro Leu Ile Gln Ile Ser Ser Phe Asp
        195                 200                 205

Arg Pro Asn Ile Arg Tyr Met Leu Met Glu Lys Phe Lys Pro Leu Asp
    210                 215                 220

Gln Leu Met Arg Tyr Val Gln Glu Gln Arg Gly Lys Ser Gly Ile Ile
225                 230                 235                 240

Tyr Cys Asn Ser Arg Ala Lys Val Glu Asp Thr Ala Ala Ala Leu Gln
                245                 250                 255

Ser Lys Gly Ile Ser Ala Ala Ala Tyr His Ala Gly Leu Glu Asn Asn
            260                 265                 270

Val Arg Ala Asp Val Gln Glu Lys Phe Gln Arg Asp Asp Leu Gln Ile
```

-continued

```
        275                 280                 285

Val Val Ala Thr Val Ala Phe Gly Met Gly Ile Asn Lys Pro Asn Val
    290                 295                 300

Arg Phe Val Val His Phe Asp Ile Pro Arg Asn Ile Glu Ser Tyr Tyr
305                 310                 315                 320

Gln Glu Thr Gly Arg Ala Gly Arg Asp Gly Leu Pro Ala Glu Ala Met
                325                 330                 335

Leu Phe Tyr Asp Pro Ala Asp Met Ala Trp Leu Arg Arg Cys Leu Glu
            340                 345                 350

Glu Lys Pro Gln Gly Gln Leu Gln Asp Ile Glu Arg His Lys Leu Asn
        355                 360                 365

Ala Met Gly Ala Phe Ala Glu Ala Gln Thr Cys Arg Arg Leu Val Leu
    370                 375                 380

Leu Asn Tyr Phe Gly Glu Gly Arg Gln Glu Pro Cys Gly Asn Cys Asp
385                 390                 395                 400

Ile Cys Leu Asp Pro Pro Lys Gln Tyr Asp Gly Ser Thr Asp Ala Gln
                405                 410                 415

Ile Ala Leu Ser Thr Ile Gly Arg Val Asn Gln Arg Phe Gly Met Gly
            420                 425                 430

Tyr Val Val Glu Val Ile Arg Gly Ala Asn Asn Gln Arg Ile Arg Asp
        435                 440                 445

Tyr Gly His Asp Lys Leu Lys Val Tyr Gly Met Gly Arg Asp Lys Ser
    450                 455                 460

His Glu His Trp Val Ser Val Ile Arg Gln Leu Ile His Leu Gly Leu
465                 470                 475                 480

Val Thr Gln Asn Ile Ala Gln His Ser Ala Leu Gln Leu Thr Glu Ala
                485                 490                 495

Ala Arg Pro Val Leu Ala Glu Ser Ser Leu Gln Leu Ala Val Pro Arg
            500                 505                 510

Ile Val Ala Leu Lys Pro Lys Ala Met Gln Lys Ser Phe Gly Gly Asn
        515                 520                 525

Tyr Asp Arg Lys Leu Phe Ala Lys Leu Arg Lys Leu Arg Lys Ser Ile
    530                 535                 540

Ala Asp Glu Ser Asn Val Pro Pro Tyr Val Val Phe Asn Asp Ala Thr
545                 550                 555                 560

Leu Ile Glu Met Ala Glu Gln Met Pro Ile Thr Ala Ser Glu Met Leu
                565                 570                 575

Ser Val Asn Gly Val Gly Met Arg Lys Leu Glu Arg Phe Gly Lys Pro
            580                 585                 590

Phe Met Ala Leu Ile Arg Ala His Val Asp Gly Asp Asp Glu Glu
        595                 600                 605
```

(2) INFORMATION FOR SEQ ID NO: 76:

(i) SEQUENCE CHARACTERISTICS:
(A) LENGTH: 1328 amino acids
(B) TYPE: amino acid
(C) STRANDEDNESS: single
(D) TOPOLOGY: linear (xi) SEQUENCE DESCRIPTION: SEQ ID NO: 76:

```
Met Thr Val Thr Lys Thr Asn Leu Asn Arg His Leu Asp Trp Phe Phe
1               5                   10                  15

Arg Glu Ser Pro Gln Lys Ile Glu Asn Val Thr Ser Pro Ile Lys Thr
            20                  25                  30
```

-continued

```
Leu Asp Phe Val Lys Val Lys Val Ser Ser Ser Asp Ile Val Val Lys
        35                  40                  45

Asp Ser Ile Pro His Lys Ser Lys Asn Val Phe Asp Asp Phe Asp Asp
    50                  55                  60

Gly Tyr Ala Ile Asp Leu Thr Glu Glu His Gln Ser Ser Ser Leu Asn
65                  70                  75                  80

Asn Leu Lys Trp Lys Asp Val Glu Gly Pro Asn Ile Leu Lys Pro Ile
                85                  90                  95

Lys Lys Ile Ala Val Pro Ala Ser Glu Ser Glu Glu Asp Phe Asp Asp
            100                 105                 110

Val Asp Glu Glu Met Leu Arg Ala Ala Glu Met Glu Val Phe Gln Ser
        115                 120                 125

Cys Gln Pro Leu Ala Val Asn Thr Ala Asp Thr Thr Val Ser His Ser
    130                 135                 140

Thr Ser Ser Ser Asn Val Pro Arg Ser Leu Asn Lys Ile His Asp Pro
145                 150                 155                 160

Ser Arg Phe Ile Lys Asp Asn Asp Val Glu Asn Arg Ile His Val Ser
                165                 170                 175

Ser Ala Ser Lys Val Ala Ser Ile Ser Asn Thr Ser Lys Pro Asn Pro
            180                 185                 190

Ile Val Ser Glu Asn Pro Ile Ser Ala Thr Ser Val Ser Ile Glu Ile
        195                 200                 205

Pro Ile Lys Pro Lys Glu Leu Ser Asn Asn Leu Pro Phe Pro Arg Leu
    210                 215                 220

Asn Asn Asn Asn Thr Asn Asn Asn Asn Asp Asn Asn Ala Ile Glu Lys
225                 230                 235                 240

Arg Asp Ser Ala Ser Pro Thr Pro Ser Ser Val Ser Ser Gln Ile Ser
                245                 250                 255

Ile Asp Phe Ser Thr Trp Pro His Gln Asn Leu Leu Gln Tyr Leu Asp
            260                 265                 270

Ile Leu Arg Asp Glu Lys Ser Glu Ile Ser Asp Arg Ile Ile Glu Val
        275                 280                 285

Met Glu Arg Tyr Pro Phe Ser Ser Arg Phe Lys Glu Trp Ile Pro Lys
    290                 295                 300

Arg Asp Ile Leu Ser Gln Lys Ile Ser Ser Val Leu Glu Val Leu Ser
305                 310                 315                 320

Asn Asn Asn Asn Ser Asn Asn Asn Asn Gly Asn Asn Gly Thr Val Pro
                325                 330                 335

Asn Ala Lys Thr Phe Phe Thr Pro Pro Ser Ser Ile Thr Gln Gln Val
            340                 345                 350

Pro Phe Pro Ser Thr Ile Ile Pro Glu Ser Thr Val Lys Glu Asn Ser
        355                 360                 365

Thr Arg Pro Tyr Val Asn Ser His Leu Val Ala Asn Asp Lys Ile Thr
    370                 375                 380

Ala Thr Pro Phe His Ser Glu Ala Val Val Ser Pro Leu Gln Ser Asn
385                 390                 395                 400

Ile Arg Asn Ser Asp Ile Ala Glu Phe Asp Glu Phe Asp Ile Asp Asp
                405                 410                 415

Ala Asp Phe Thr Phe Asn Thr Thr Asp Pro Ile Asn Asp Glu Ser Gly
            420                 425                 430

Ala Ser Ser Asp Val Val Val Ile Asp Asp Glu Glu Asp Asp Ile Glu
        435                 440                 445

Asn Arg Pro Leu Asn Gln Ala Leu Lys Ala Ser Lys Ala Ala Val Ser
```

-continued

```
    450                 455                 460

Asn Ala Ser Leu Leu Gln Ser Ser Ser Leu Asp Arg Pro Leu Leu Gly
465                 470                 475                 480

Glu Met Lys Asp Lys Asn His Lys Val Leu Met Pro Ser Leu Asp Asp
                485                 490                 495

Pro Met Leu Ser Tyr Pro Trp Ser Lys Glu Val Leu Gly Cys Leu Lys
            500                 505                 510

His Lys Phe His Leu Lys Gly Phe Arg Lys Asn Gln Leu Glu Ala Ile
        515                 520                 525

Asn Gly Thr Leu Ser Gly Lys Asp Val Phe Ile Leu Met Pro Thr Gly
    530                 535                 540

Gly Gly Lys Ser Leu Cys Tyr Gln Leu Pro Ala Val Ile Glu Gly Gly
545                 550                 555                 560

Ala Ser Arg Gly Val Thr Leu Val Ile Ser Pro Leu Leu Ser Leu Met
                565                 570                 575

Gln Asp Gln Leu Asp His Leu Arg Lys Leu Asn Ile Pro Ser Leu Pro
            580                 585                 590

Leu Ser Gly Glu Gln Pro Ala Asp Glu Arg Arg Gln Val Ile Ser Phe
        595                 600                 605

Leu Met Ala Lys Asn Val Leu Val Lys Leu Leu Tyr Val Thr Pro Glu
    610                 615                 620

Gly Leu Ala Ser Asn Gly Ala Ile Thr Arg Val Leu Lys Ser Leu Tyr
625                 630                 635                 640

Glu Arg Lys Leu Leu Ala Arg Ile Val Ile Asp Glu Ala His Cys Val
                645                 650                 655

Ser His Trp Gly His Asp Phe Arg Pro Asp Tyr Lys Gln Leu Gly Leu
            660                 665                 670

Leu Arg Asp Arg Tyr Gln Gly Ile Pro Phe Met Ala Leu Thr Ala Thr
        675                 680                 685

Ala Asn Glu Ile Val Lys Lys Asp Ile Ile Asn Thr Leu Arg Met Glu
    690                 695                 700

Asn Cys Leu Glu Leu Lys Ser Ser Phe Asn Arg Pro Asn Leu Phe Tyr
705                 710                 715                 720

Glu Ile Lys Pro Lys Lys Asp Leu Tyr Thr Glu Leu Tyr Arg Phe Ile
                725                 730                 735

Ser Asn Gly His Leu His Glu Ser Gly Ile Ile Tyr Cys Leu Ser Arg
            740                 745                 750

Thr Ser Cys Glu Gln Val Ala Ala Lys Leu Arg Asn Asp Tyr Gly Leu
        755                 760                 765

Lys Ala Trp His Tyr His Ala Gly Leu Glu Lys Val Glu Arg Gln Arg
    770                 775                 780

Ile Gln Asn Glu Trp Gln Ser Gly Ser Tyr Lys Ile Ile Val Ala Thr
785                 790                 795                 800

Ile Ala Phe Gly Met Gly Val Asp Lys Gly Asp Val Arg Phe Val Ile
                805                 810                 815

His His Ser Phe Pro Lys Ser Leu Glu Gly Tyr Tyr Gln Glu Thr Gly
            820                 825                 830

Arg Ala Gly Arg Asp Gly Lys Pro Ala His Cys Ile Met Phe Tyr Ser
        835                 840                 845

Tyr Lys Asp His Val Thr Phe Gln Lys Leu Ile Met Ser Gly Asp Gly
    850                 855                 860

Asp Ala Glu Thr Lys Glu Arg Gln Arg Gln Met Leu Arg Gln Val Ile
865                 870                 875                 880
```

-continued

```
Gln Phe Cys Glu Asn Lys Thr Asp Cys Arg Arg Lys Gln Val Leu Ala
                885                 890                 895

Tyr Phe Gly Glu Asn Phe Asp Lys Val His Cys Arg Lys Gly Cys Asp
            900                 905                 910

Ile Cys Cys Glu Glu Ala Thr Tyr Ile Lys Gln Asp Met Thr Glu Phe
        915                 920                 925

Ser Leu Gln Ala Ile Lys Leu Leu Lys Ser Ile Ser Gly Lys Ala Thr
    930                 935                 940

Leu Leu Gln Leu Met Asp Ile Phe Arg Gly Ser Lys Ser Ala Lys Ile
945                 950                 955                 960

Val Glu Asn Gly Trp Asp Arg Leu Glu Gly Ala Gly Val Gly Lys Leu
                965                 970                 975

Leu Asn Arg Gly Asp Ser Glu Arg Leu Phe His His Leu Val Ser Glu
            980                 985                 990

Gly Val Phe Val Glu Lys Val Glu Ala Asn Arg Arg Gly Phe Val Ser
        995                 1000                1005

Ala Tyr Val Val Pro Gly Arg Gln Thr Ile Ile Asn Ser Val Leu Ala
    1010                1015                1020

Gly Lys Arg Arg Ile Ile Leu Asp Val Lys Glu Ser Ser Ser Lys Pro
1025                1030                1035                1040

Asp Thr Ser Ser Arg Ser Leu Ser Arg Ser Lys Thr Leu Pro Ala Leu
                1045                1050                1055

Arg Glu Tyr Gln Leu Lys Ser Thr Thr Ala Ser Val Asp Cys Ser Ile
            1060                1065                1070

Gly Thr Arg Glu Val Asp Glu Ile Tyr Asp Ser Gln Met Pro Pro Val
        1075                1080                1085

Lys Pro Ser Leu Ile His Ser Arg Asn Lys Ile Asp Leu Glu Glu Leu
    1090                1095                1100

Ser Gly Gln Lys Phe Met Ser Glu Tyr Glu Ile Asp Val Met Thr Arg
1105                1110                1115                1120

Cys Leu Lys Asp Leu Lys Leu Leu Arg Ser Asn Leu Met Ala Ile Asp
                1125                1130                1135

Asp Ser Arg Val Ser Ser Tyr Phe Thr Asp Ser Val Leu Leu Ser Met
            1140                1145                1150

Ala Lys Lys Leu Pro Arg Asn Val Lys Glu Leu Lys Glu Ile His Gly
        1155                1160                1165

Val Ser Asn Glu Lys Ala Val Asn Leu Gly Pro Lys Phe Leu Gln Val
    1170                1175                1180

Ile Gln Lys Phe Ile Asp Glu Lys Glu Gln Asn Leu Glu Gly Thr Glu
1185                1190                1195                1200

Leu Asp Pro Ser Leu Gln Ser Leu Asp Thr Asp Tyr Pro Ile Asp Thr
                1205                1210                1215

Asn Ala Leu Ser Leu Asp His Glu Gln Gly Phe Ser Asp Asp Ser Asp
            1220                1225                1230

Ser Val Tyr Glu Pro Ser Ser Pro Ile Glu Glu Gly Asp Glu Glu Val
        1235                1240                1245

Asp Gly Gln Arg Lys Asp Ile Leu Asn Phe Met Asn Ser Gln Ser Leu
    1250                1255                1260

Thr Gln Thr Gly Ser Val Pro Lys Arg Lys Ser Thr Ser Tyr Thr Arg
1265                1270                1275                1280

Pro Ser Lys Ser Tyr Arg His Lys Arg Gly Ser Thr Ser Tyr Ser Arg
                1285                1290                1295
```

-continued

```
Lys Arg Lys Tyr Ser Thr Ser Gln Lys Asp Ser Arg Lys Thr Ser Lys
            1300                1305                1310

Ser Ala Asn Thr Ser Phe Ile His Pro Met Val Lys Gln Asn Tyr Arg
        1315                1320                1325


(2) INFORMATION FOR SEQ ID NO: 77:

     (i) SEQUENCE CHARACTERISTICS:
          (A) LENGTH: 659 amino acids
          (B) TYPE: amino acid
          (C) STRANDEDNESS: single
          (D) TOPOLOGY: linear

    (xi) SEQUENCE DESCRIPTION: SEQ ID NO: 77:

Met Ala Ser Val Ser Ala Leu Thr Glu Glu Leu Asp Ser Ile Thr Ser
1               5                   10                  15

Glu Leu His Ala Val Glu Ile Gln Ile Gln Glu Leu Thr Glu Arg Gln
            20                  25                  30

Gln Glu Leu Ile Gln Lys Lys Lys Val Leu Thr Lys Lys Ile Lys Gln
        35                  40                  45

Cys Leu Glu Asp Ser Asp Ala Gly Ala Ser Asn Glu Tyr Asp Ser Ser
    50                  55                  60

Pro Ala Ala Trp Asn Lys Glu Asp Phe Pro Trp Ser Gly Lys Val Lys
65                  70                  75                  80

Asp Ile Leu Gln Asn Val Phe Lys Leu Glu Lys Phe Arg Pro Leu Gln
                85                  90                  95

Leu Glu Thr Ile Asn Val Thr Met Ala Gly Lys Glu Val Phe Leu Val
            100                 105                 110

Met Pro Thr Gly Gly Gly Lys Ser Leu Cys Tyr Gln Leu Pro Ala Leu
        115                 120                 125

Cys Ser Asp Gly Phe Thr Leu Val Ile Cys Pro Leu Ile Ser Leu Met
    130                 135                 140

Glu Asp Gln Leu Met Val Leu Lys Gln Leu Gly Ile Ser Ala Thr Met
145                 150                 155                 160

Leu Asn Ala Ser Ser Ser Lys Glu His Val Lys Trp Val His Asp Glu
                165                 170                 175

Met Val Asn Lys Asn Ser Glu Leu Lys Leu Ile Tyr Val Thr Pro Glu
            180                 185                 190

Lys Ile Ala Lys Ser Lys Met Phe Met Ser Arg Leu Glu Lys Ala Tyr
        195                 200                 205

Glu Ala Arg Arg Phe Thr Arg Ile Ala Val Asp Glu Val His Cys Cys
    210                 215                 220

Ser Gln Trp Gly His Asp Phe Arg Pro Asp Tyr Lys Ala Leu Gly Ile
225                 230                 235                 240

Leu Lys Arg Gln Phe Pro Asn Ala Ser Leu Ile Gly Leu Thr Ala Thr
                245                 250                 255

Ala Thr Asn His Val Leu Thr Asp Ala Gln Lys Ile Leu Cys Ile Glu
            260                 265                 270

Lys Cys Phe Thr Phe Thr Ala Ser Phe Asn Arg Pro Asn Leu Tyr Tyr
        275                 280                 285

Glu Val Arg Gln Lys Pro Ser Asn Thr Glu Asp Phe Ile Glu Asp Ile
    290                 295                 300

Val Lys Leu Ile Asn Gly Arg Tyr Lys Gly Gln Ser Gly Ile Ile Tyr
305                 310                 315                 320

Cys Phe Ser Gln Lys Asp Ser Glu Gln Val Thr Val Ser Leu Gln Asn
                325                 330                 335
```

-continued

```
Leu Gly Ile His Ala Gly Ala Tyr His Ala Asn Leu Glu Pro Glu Asp
            340                 345                 350

Lys Thr Thr Val His Arg Lys Trp Ser Ala Asn Glu Ile Gln Val Val
        355                 360                 365

Val Ala Thr Val Ala Phe Gly Met Gly Ile Asp Lys Pro Asp Val Arg
    370                 375                 380

Phe Val Ile His His Ser Met Ser Lys Ser Met Glu Asn Tyr Tyr Gln
385                 390                 395                 400

Glu Ser Gly Arg Ala Gly Arg Asp Asp Met Lys Ala Asp Cys Ile Leu
                405                 410                 415

Tyr Tyr Gly Phe Gly Asp Ile Phe Arg Ile Ser Ser Met Val Val Met
            420                 425                 430

Glu Asn Val Gly Gln Gln Lys Leu Tyr Glu Met Val Ser Tyr Cys Gln
        435                 440                 445

Asn Ile Ser Lys Ser Arg Arg Val Leu Met Ala Gln His Phe Asp Glu
    450                 455                 460

Val Trp Asn Ser Glu Ala Cys Asn Lys Met Cys Asp Asn Cys Cys Lys
465                 470                 475                 480

Asp Ser Ala Phe Glu Arg Thr Asn Ile Thr Glu Tyr Cys Arg Asp Leu
                485                 490                 495

Ile Lys Ile Leu Lys Gln Ala Glu Glu Leu Asn Glu Lys Leu Thr Pro
            500                 505                 510

Leu Lys Leu Ile Asp Ser Trp Met Gly Lys Gly Ala Ala Lys Leu Arg
        515                 520                 525

Val Ala Gly Val Val Ala Pro Thr Leu Pro Arg Glu Asp Leu Glu Lys
    530                 535                 540

Ile Ile Ala His Phe Leu Ile Gln Gln Tyr Leu Lys Glu Asp Tyr Ser
545                 550                 555                 560

Phe Thr Ala Tyr Ala Ala Ile Ser Tyr Leu Lys Ile Gly Pro Lys Ala
                565                 570                 575

Asn Leu Leu Asn Asn Glu Ala His Ala Ile Thr Met Gln Val Thr Lys
            580                 585                 590

Ser Thr Gln Asn Ser Phe Arg Ala Glu Ser Ser Gln Thr Cys His Ser
        595                 600                 605

Glu Gln Gly Asp Lys Lys Asn Gly Gly Lys Lys Ile Gln Ala Thr Ser
    610                 615                 620

Arg Arg Arg Leu Gln Thr Cys Phe Ser Asn Leu Val Leu Arg Ile Gln
625                 630                 635                 640

Glu Leu Arg Lys Glu Lys Ser Met Met Pro Asp Met Asn Val Thr Lys
                645                 650                 655

Phe Ser Asn
```

(2) INFORMATION FOR SEQ ID NO: 78:

(i) SEQUENCE CHARACTERISTICS:
(A) LENGTH: 1417 amino acids
(B) TYPE: amino acid
(C) STRANDEDNESS: single
(D) TOPOLOGY: linear (xi) SEQUENCE DESCRIPTION: SEQ ID NO: 78:

```
Met Ala Ala Val Pro Gln Asn Asn Leu Gln Glu Gln Leu Glu Arg His
1               5                   10                  15

Ser Ala Arg Thr Leu Asn Asn Lys Leu Ser Leu Ser Lys Pro Lys Phe
            20                  25                  30
```

-continued

```
Ser Gly Phe Thr Phe Lys Lys Lys Thr Ser Ser Asp Asn Asn Val Ser
        35                  40                  45

Val Thr Asn Val Ser Val Ala Lys Thr Pro Val Leu Arg Asn Lys Asp
    50                  55                  60

Val Asn Val Thr Glu Asp Phe Ser Phe Ser Glu Pro Leu Pro Asn Thr
65                  70                  75                  80

Thr Asn Gln Gln Arg Val Lys Asp Phe Phe Lys Asn Ala Pro Ala Gly
                85                  90                  95

Gln Glu Thr Gln Arg Gly Gly Ser Lys Ser Leu Leu Pro Asp Phe Leu
            100                 105                 110

Gln Thr Pro Lys Glu Val Val Cys Thr Thr Gln Asn Thr Pro Thr Val
        115                 120                 125

Lys Lys Ser Arg Asp Thr Ala Leu Lys Lys Leu Glu Phe Ser Ser Ser
    130                 135                 140

Pro Asp Ser Leu Ser Thr Ile Asn Asp Trp Asp Asp Met Asp Asp Phe
145                 150                 155                 160

Asp Thr Ser Glu Thr Ser Lys Ser Phe Val Thr Pro Pro Gln Ser His
                165                 170                 175

Phe Val Arg Val Ser Thr Ala Gln Lys Ser Lys Lys Gly Lys Arg Asn
            180                 185                 190

Phe Phe Lys Ala Gln Leu Tyr Thr Thr Asn Thr Val Lys Thr Asp Leu
        195                 200                 205

Pro Pro Pro Ser Ser Glu Ser Glu Gln Ile Asp Leu Thr Glu Glu Gln
    210                 215                 220

Lys Asp Asp Ser Glu Trp Leu Ser Ser Asp Val Ile Cys Ile Asp Asp
225                 230                 235                 240

Gly Pro Ile Ala Glu Val His Ile Asn Glu Asp Ala Gln Glu Ser Asp
                245                 250                 255

Ser Leu Lys Thr His Leu Glu Asp Glu Arg Asp Asn Ser Glu Lys Lys
            260                 265                 270

Lys Asn Leu Glu Glu Ala Glu Leu His Ser Thr Glu Lys Val Pro Cys
        275                 280                 285

Ile Glu Phe Asp Asp Asp Asp Tyr Asp Thr Asp Phe Val Pro Pro Ser
    290                 295                 300

Pro Glu Glu Ile Ile Ser Ala Ser Ser Ser Ser Ser Lys Cys Leu Ser
305                 310                 315                 320

Thr Leu Lys Asp Leu Asp Thr Ser Asp Arg Lys Glu Asp Val Leu Ser
                325                 330                 335

Thr Ser Lys Asp Leu Leu Ser Lys Pro Glu Lys Met Ser Met Gln Glu
            340                 345                 350

Leu Asn Pro Glu Thr Ser Thr Asp Cys Asp Ala Arg Gln Ile Ser Leu
        355                 360                 365

Gln Gln Gln Leu Ile His Val Met Glu His Ile Cys Lys Leu Ile Asp
    370                 375                 380

Thr Ile Pro Asp Asp Lys Leu Lys Leu Leu Asp Cys Gly Asn Glu Leu
385                 390                 395                 400

Leu Gln Gln Arg Asn Ile Arg Arg Lys Leu Leu Thr Glu Val Asp Phe
                405                 410                 415

Asn Lys Ser Asp Ala Ser Leu Leu Gly Ser Leu Trp Arg Tyr Arg Pro
            420                 425                 430

Asp Ser Leu Asp Gly Pro Met Glu Gly Asp Ser Cys Pro Thr Gly Asn
        435                 440                 445
```

-continued

```
Ser Met Lys Glu Leu Asn Phe Ser His Leu Pro Ser Asn Ser Val Ser
    450                 455                 460

Pro Gly Asp Cys Leu Leu Thr Thr Thr Leu Gly Lys Thr Gly Phe Ser
465                 470                 475                 480

Ala Thr Arg Lys Asn Leu Phe Glu Arg Pro Leu Phe Asn Thr His Leu
                485                 490                 495

Gln Lys Ser Phe Val Ser Ser Asn Trp Ala Glu Thr Pro Arg Leu Gly
            500                 505                 510

Lys Lys Asn Glu Ser Ser Tyr Phe Pro Gly Asn Val Leu Thr Ser Thr
        515                 520                 525

Ala Val Lys Asp Gln Asn Lys His Thr Ala Ser Ile Asn Asp Leu Glu
    530                 535                 540

Arg Glu Thr Gln Pro Ser Tyr Asp Ile Asp Asn Phe Asp Ile Asp Asp
545                 550                 555                 560

Phe Asp Asp Asp Asp Asp Trp Glu Asp Ile Met His Asn Leu Ala Ala
                565                 570                 575

Ser Lys Ser Ser Thr Ala Ala Tyr Gln Pro Ile Lys Glu Gly Arg Pro
            580                 585                 590

Ile Lys Ser Val Ser Glu Arg Leu Ser Ser Ala Lys Thr Asp Cys Leu
        595                 600                 605

Pro Val Ser Ser Thr Ala Gln Asn Ile Asn Phe Ser Glu Ser Ile Gln
    610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
                645                 650                 655

Lys Ile Phe His Lys Lys Phe Gly Leu His Asn Phe Arg Thr Asn Gln
            660                 665                 670

Leu Glu Ala Ile Asn Ala Ala Leu Leu Gly Glu Asp Cys Phe Ile Leu
        675                 680                 685

Met Pro Thr Gly Gly Gly Lys Ser Leu Cys Tyr Gln Leu Pro Ala Cys
    690                 695                 700

Val Ser Pro Gly Val Thr Val Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
            740                 745                 750

Leu Ser Lys Lys Asp Pro Ile Ile Lys Leu Leu Tyr Val Thr Pro Glu
        755                 760                 765

Lys Ile Cys Ala Ser Asn Arg Leu Ile Ser Thr Leu Glu Asn Leu Tyr
    770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
                805                 810                 815

Leu Arg Gln Lys Phe Pro Ser Val Pro Val Met Ala Leu Thr Ala Thr
            820                 825                 830

Ala Asn Pro Arg Val Gln Lys Asp Ile Leu Thr Gln Leu Lys Ile Leu
        835                 840                 845

Arg Pro Gln Val Phe Ser Met Ser Phe Asn Arg His Asn Leu Lys Tyr
    850                 855                 860

Tyr Val Leu Pro Lys Lys Pro Lys Lys Val Ala Phe Asp Cys Leu Glu
```

-continued

```
865                 870                 875                 880

Trp Ile Arg Lys His His Pro Tyr Asp Ser Gly Ile Ile Tyr Cys Leu
                885                 890                 895

Ser Arg Arg Glu Cys Asp Thr Met Ala Asp Thr Leu Gln Arg Asp Gly
            900                 905                 910

Leu Ala Ala Leu Ala Tyr His Ala Gly Leu Ser Asp Ser Ala Arg Asp
        915                 920                 925

Glu Val Gln Gln Lys Trp Ile Asn Gln Asp Gly Cys Gln Val Ile Cys
    930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
                965                 970                 975

Ser Gly Arg Ala Gly Arg Asp Gly Glu Ile Ser His Cys Leu Leu Phe
            980                 985                 990

Tyr Thr Tyr His Asp Val Thr Arg Leu Lys Arg Leu Ile Met Met Glu
        995                 1000                1005

Lys Asp Gly Asn His His Thr Arg Glu Thr His Phe Asn Asn Leu Tyr
    1010                1015                1020

Ser Met Val His Tyr Cys Glu Asn Ile Thr Glu Cys Arg Arg Ile Gln
1025                1030                1035                1040

Leu Leu Ala Tyr Phe Gly Glu Asn Gly Phe Asn Pro Asp Phe Cys Lys
                1045                1050                1055

Lys His Pro Asp Val Ser Cys Asp Asn Cys Cys Lys Thr Lys Asp Tyr
            1060                1065                1070

Lys Thr Arg Asp Val Thr Asp Asp Val Lys Ser Ile Val Arg Phe Val
        1075                1080                1085

Gln Glu His Ser Ser Ser Gln Gly Met Arg Asn Ile Lys His Val Gly
    1090                1095                1100

Pro Ser Gly Arg Phe Thr Met Asn Met Leu Val Asp Ile Phe Leu Gly
1105                1110                1115                1120

Ser Lys Ser Ala Lys Ile Gln Ser Gly Ile Phe Gly Lys Gly Ser Ala
                1125                1130                1135

Tyr Ser Arg His Asn Ala Glu Arg Leu Phe Lys Lys Leu Ile Leu Asp
            1140                1145                1150

Lys Ile Leu Asp Glu Asp Leu Tyr Ile Asn Ala Asn Asp Gln Ala Ile
        1155                1160                1165

Ala Tyr Val Met Leu Gly Asn Lys Ala Gln Thr Val Leu Asn Gly Asn
    1170                1175                1180

Leu Lys Val Asp Phe Met Glu Thr Glu Asn Ser Ser Ser Val Lys Lys
1185                1190                1195                1200

Gln Lys Ala Leu Val Ala Lys Val Ser Gln Arg Glu Glu Met Val Lys
                1205                1210                1215

Lys Cys Leu Gly Glu Leu Thr Glu Val Cys Lys Ser Leu Gly Lys Val
            1220                1225                1230

Phe Gly Val His Tyr Phe Asn Ile Phe Asn Thr Val Thr Leu Lys Lys
        1235                1240                1245

Leu Ala Glu Ser Leu Ser Ser Asp Pro Glu Val Leu Leu Gln Ile Asp
    1250                1255                1260

Gly Val Thr Glu Asp Lys Leu Glu Lys Tyr Gly Ala Glu Val Ile Ser
1265                1270                1275                1280

Val Leu Gln Lys Tyr Ser Glu Trp Thr Ser Pro Ala Glu Asp Ser Ser
                1285                1290                1295
```

-continued

Pro Gly Ile Ser Leu Ser Ser Ser Arg Gly Pro Gly Arg Ser Ala Ala
1300 1305 1310

Glu Glu Leu Asp Glu Glu Ile Pro Val Ser Ser His Tyr Phe Ala Ser
1315 1320 1325

Lys Thr Arg Asn Glu Arg Lys Arg Lys Lys Met Pro Ala Ser Gln Arg
1330 1335 1340

Ser Lys Arg Arg Lys Thr Ala Ser Ser Gly Ser Lys Ala Lys Gly Gly
1345 1350 1355 1360

Ser Ala Thr Cys Arg Lys Ile Ser Ser Lys Thr Lys Ser Ser Ser Ile
1365 1370 1375

Ile Gly Ser Ser Ser Ala Ser His Thr Ser Gln Ala Thr Ser Gly Ala
1380 1385 1390

Asn Ser Lys Leu Gly Ile Met Ala Pro Pro Lys Pro Ile Asn Arg Pro
1395 1400 1405

Phe Leu Lys Pro Ser Tyr Ala Phe Ser
1410 1415

(2) INFORMATION FOR SEQ ID NO: 79:

(i) SEQUENCE CHARACTERISTICS:
(A) LENGTH: 87350 base pairs
(B) TYPE: nucleic acid
(C) STRANDEDNESS: single
(D) TOPOLOGY: linear (xi) SEQUENCE DESCRIPTION: SEQ ID NO: 79:

TATATTATGG CTATTTTTCT TTCTTATCTA TTTGTATTTT TATTGTTATT ACCTAAAAAA 60

AAATTTTCTA TGTCTTATCA CTAATTCTTC CCTAAAATTT CCCACAATTG TGTAAACTTA 120

CCTCAGTATA TTCATAGATA TGAGACATTC TATCAATTTT ACCCTCTTAA AGATGCAGAA 180

ATAATGCATT ATGTTTCATC CCACCATCTT TAATGAGAAG CTTCCATCTT AGATTAATAT 240

TAGAGAATGT TAAAATACTC TGCAATCAGG TAAGGACGCT TGAAACTTCA TCATAATGCA 300

AAAGTTTTCT TTAACACAAT AAATATTTTG AACCCCTTTT GTGTCTTGTA TTCATAGGAG 360

TTCAGATAGA CCACTTTATT TACTATTTTT TATAGAGAGT GAACAGAAAT CCCATTTCTA 420

GTCACCAGTC CTTAATCTGT AAATCAGGCA GATAATCTGT AAATGATTGG TTGAAATCAC 480

ATTGAATTCC ACTTTGTGCC AGGGACTTAA GTTAACGAAC AAATTATTCT TACAAAAAGG 540

TATAAATGTA AGGTTTTCAT TCCGCTAAAT ATGTTTGTCA AACTGTGTTG TGATTTGTTC 600

TCAGTGTGTC ATAGCTACCA TAGCTTTTGG AATGGGCATT AATAAAGCTG ACATTCGCCA 660

AGTCATTCAT TACGGTGCTC CTAAGGACAT GGAATCATAT TATCAGGAGA TTGGTAGAGC 720

TGGTCGTGAT GGACTTCAAA GTTCTTGTCA CGTCCTCTGG GCTCCTGCAG ACATTAACTT 780

AAATAGGTAA AAAAAATTTA TTGTTTTTAC TCTTGCAGAT TTCTTTCTTT CTTTCCATAT 840

AAACCTCAAA AGTGTTTGAG GCTATTTCCA GTATCCCAAG TAATTTGTGA GTGCATTTAA 900

AGTAAAAAAA AAAAAAAAAG AAAAATAAAA CCTCCCCAAA TCCAGAGGAC ATGTAAGAAG 960

AACATTTGTG GTAAGAGTTG CCACTTGGAG ATGAGCTAAT TTCAGCATGC CTTAGTTAGT 1020

GTGAGGAATT AACTAAATCA GGACAATACT TGGGCCTGTC ACAGAGATCC TATGGAATAC 1080

TTTCCTACCA TTGTGCATTA ATGAACAGGT TCTTTTCCTC TCCTCAGATC CTGTCAAGTT 1140

GCGATGTCTT CAGCCATAGT TACTTCAACT ACCACTGATT TTGTTACTGA TTCTTTCTTC 1200

CCATGCTACA GTGGTGATTA TTCCAGAGGA TTTCTCTCAG TCCCTATTTG ACTCTTGTTA 1260

CTATTTGTTT TCTTGGTTAG TTCCATGAGA CCATGCCAGT TCTCCTTGAC TGTGTATGAA 1320

-continued

```
TCATTGTGTT GCACTGTACT GACAGACTGC CGTAAGTCAA TATTAAGTGT TCAGTATCTA   1380

AGTGCAGGAG AACCTTTCTA CTTAAGTACT CAACAAGTAG TTTGTTGGCA CTTAAGTTCT   1440

ATGAGATTTT TTGTTGTAAA GGAAAACATT ATCTTGCAAA GATTTTGGGG CAGCATTTAC   1500

CAATACTTTG TTCCTTCATC CGTAGGAAAA AGAATCTCAG GAGAAAAACC TATACATGGT   1560

AACCAATGGG GCTGCCAAGC TGATGAAGTA TTTTCAGAGT ACACCTTTGT GTAGCTGAAT   1620

AAATTGAGAT CTTGAATGGA CATATTAGCT CATTTTAGTA AAATGATAAG AGAGTGCCTC   1680

CCACTACAGT TTTTGTTTTT ATGCATCATT AAACAATGTG TTTTTGATTG TCCACTGTGT   1740

TCCATGAACT ATGCTATGTG TGGGAGATAT AGTAGTAAAG AAAAGCAAAG TACCTGCTTC   1800

CATAGAATTC AGTATAATGG GAATGGTAAT TCTTTAGAGA ATCACATAAC TATGGATACA   1860

TAGGCTTCAT TTTACTGTTC TCCTTTTGTG TTTGAAAATG TCAACAATCA AAATTTTGTA   1920

AAAAAGGAAT CATGCAACAT ATTTAAAATT ATAACTGTGT TAAGTGTAAT GAAGGGAAAT   1980

TGCACTGAGT AGTAAGAATA TATAATGGTG TGTGGTATTT CCCAAGTTAA AAAGGTCAGA   2040

TAAGGCTTCC TTGTGGAAGT GATAGTTCAA ATCTGAAAGA AGAATAGGAA TTAATTAGGT   2100

AAAAATGTTT GATGCAAATT TTAAGATTTT CCTTCTGAGT AGTCAGTAGC TTTTCCTTCT   2160

TAACATAGAA GATGACAAAA CCATCCTTTT TTTGTACATA ACAATTCTTG TTTTCCTTTA   2220

GACAGTTGTA TCTGTCAAGC TTCTTATGAT CTAATTTAAA TAATTGGGAT AGAACACAGC   2280

TGTACATGTT ACTATTAAAT ATGGAATATA TCAAACATAA GTTGATTCCT ACCAGTTCTG   2340

ATTTTATTTG TGTATTTTGT TAAAGGTACT GAGGACATTA ATATCCAGTT TTATATTGTG   2400

CATTTGAAGG TTCATCAATA AATACAATTC TTGTTTCTCT GGGTCTTAAA AGATATTTTA   2460

AATGGTTATC TCATTAAGAT TTAACAGGAA ATAACAGTGA TTCAAATCAA ATAGTGGTGC   2520

CAGAAACCCA TACTTGAATT TTGGGTATAG ACAGGTTACC CTTTGCATCA ATCCTGAGGA   2580

AACTAAAACT ATAGGATTAA TCAGGATAAA AAAGAATTGA GCAAGGATTC AGGAGGGATC   2640

TGTATCATCC TGGTGACAAC CCTCTTCTAG AAAAAACTAG AAAGTCTAAG AATAAATGAA   2700

GTTGCTGGTT CTCACCTGGA AAGGTCAGTT ACTCACAAAA TTTTTAGAGT CTATCTTATG   2760

CCATAATTCT ATCACTGAGA GAAGAAACTT GTCCAGTCAT CATGTAATCT TCATGTAAAT   2820

TTATGTTTTT AATTGCAGAA TTCATACCAC AGGCAAAGTC CCAATGTCTG CATTTGCTGT   2880

TACCTTAAAT AGTCAAACCC CAAAGTTATT GTAATCTTTT TTTAACAGAG AATAATTTGC   2940

AGAGTAATCT CGGTCCGGTA GATCTTTCAG TGGATCCCAA ATGATTGCCA TGAATGGTTT   3000

AGAATTTTTT TAATTTTCAA GTTGTTTTTA TTCTGTGGAA TACTGGCTTA TTTTTGTAGT   3060

CCCAAAAGAA AAATAAATAT TTATTTATTT GCCGTTAAGA GTTGTAGTTT TGTTTTCTCA   3120

AATTTGTCCT GACACTGACG AGATTAGTTA AATGTAGGTC ATCTGAACCA AATACAAGGA   3180

AGGAAGGACC CAGTTCTGAA GAGTGTGGGC ATTTCTTTTC TTGTTTTTTT TTTTTTTTTT   3240

TTTTTTTTTT CTATAGGAGG GGAACGAGGT GAACTAAACA AACAAAATAA AGCAAAAAAG   3300

AACTGATTTT TATCCCTTGA GGTAGAAAGA ATGAGATTAC AGTGGACCCC CTTGTCTGCA   3360

TTTTCACTTT CTATGTTTTA GTTACTCACA ACCACGTCCA AAATGTTAAA TAGAAAATTC   3420

CAGAAATAAA CAATTTATAA ATTTTAAATC AGTGGTGGCT TTGAGTACTG TAATGAAATT   3480

TTGTGCCATC CCACTCAGTC GGCCTCGACT TCCCTTAGAA TCATCCCTTT GTCCGGTGCA   3540

TTCACGTTGT ATTTACTCCC TGTCTGTTAG TCACTTGTTG CAGTATCACA GTGCTTGTGT   3600

TCAAGTAACG CTTATTTTAC TTAAGAATGA CCCCAAAGCA CAAGAGTACT GTGCCTAATT   3660
```

-continued

```
TATAAATTAA ACTTTTTCAT AGGTATATAC ATATAGGAAA AAACATAATA CATACAGGAT   3720
TTGGTTGGTA CTATTCTGCG GCTTCAGGCA TCCACTGGAC GTCTTGGAAT GTATCCCTTG   3780
TGGATAAGGA GGAACTGTAT ATGGTTAACC TAGGAGCTAG AGTCAACAGT TGGAAGAGAC   3840
TTTGGGGATA ATTACATGGA AGGGCATGGT GGGTGGTCGT TTCAGATGAC AAGAATGTTT   3900
TTGAATAACG GATCATTTGT GTCTTCAGAC TTTCCAGAAC TCCTTGAGAA TTATGCAGAG   3960
GTATTTAATC AGTCAGAAGG TTGAATAGTC AAATTATTAG TGAGTGAAGT CTATTTTGAT   4020
GAGGATTTTA CTAATGCTGT CCCTTAGATG TTATAAGTAA ATCGTTGTTT TCTTTTGAAA   4080
TATCTGAAAC CTAGTTAACA TGGACTTTCA TTTGTTCTTG TAAAGATATG CAAAGCTATT   4140
TGGGAGATTG TCATCATCTG ATATTTGATA TTCATGGGCT TTCTTCACAG AAGACTAGAA   4200
ATTAACAGAG TCATGATGAA TTATGGCTGC ATTGACTTTA AAAAACAAAC ACCTCCTTAA   4260
TGTTATTTAA CAATTTTGAA TAAATTTGAT ATGGCAAACA AATCAGTTAT AATCGATTGA   4320
GAAAGGAACT TAATTCTAAT ACTTGACTGG TGTCCCATAA TAACCCATAA TACTAAGAGA   4380
CAGTTTTGGA GGGCGAGAAG TCCTGAAGAG CTGATAGAGA TAAAGGTTCA AATTTGAGCT   4440
TCTTTCAGTG TTCCTTACGT CAATGCTTTT AGTTTCTCAT ACAAAATAAA ATAAAGAATA   4500
ACCTTTTTAC TGGGAAAAGG TAAAAATTAA TAAATTGTAG AAGCATTGTT TGAAGCCAAA   4560
AAGTGTGTGA CATGTAAATT GAAATGAAAA ACCTTAGAGT TTTGATACT  TTTTCAAAGC   4620
AGCTAAAGAA TTGATACTTG GACACAGGAA GAATTTTTTT TCAAAAGCAA TTTTTATAAA   4680
ATCAGAAAAA TGTTTACCTC TTGTTGGGGG CATTGACTGG AAAGGAATAC AACAGAACTT   4740
TCTGAGATGC TAGAAATGTT TTTTTATCTT GATGGGGTGT GGGTTTTGTA GATAATGAAA   4800
AATAAACAGT AAAAAATAAG TAAAAAAAAA AGTAAGAAAG TTGCCAATAC AGTTTTACAT   4860
ATTCCTGTGA TGTTTTTAAT CGACAGGCAC CTTCTTACTG AGATACGTAA TGAGAAGTTT   4920
CGATTATACA AATTAAAGAT GATGGCAAAG ATGGAAAAAT ATCTTCATTC TAGCAGATGT   4980
AGGAGACAGT ATGTATTATT TATTTTATGC CAATAGTATG GATTTATGGA TGATGCTCTT   5040
TTAAGACAAC AATTTGGCTA AATAATTATC AGTATTTTGA AAAAATATTT TGTTGCTGTT   5100
ACATGTGTGC TGAATTTTTA AGGCTAACTT CTTTGTGTCT GAGTAAACTG AAGTCAAATA   5160
ATGAAGTCCC AAGTGAATCA ATTAATGGTG ATTTTACCTC ATTATTTTCA GGAATGAACT   5220
TAACATATAC GTTTCTGTTC TTTTATTTAA TTTAAAATTT TGTCTTGGGT AGAATCATCT   5280
TGTCTCATTT TGAGGACAAA CAAGTACAAA AAGCCTCCTT GGGAATTATG GGAACTGAAA   5340
AATGCTGTGA TAATTGCAGG TCCAGGTAAA GATTTCTTAT TATAGATGGA CATTCTAAAA   5400
GTCTTTCTTT CTCTTCCTTT TCATGTTTAA CTGAATTTTT GTTGAATGAT AAGTATTTCA   5460
GTTTTTTAAA CAAAACAATG AATGTGTTTA GATATGAGAA AGCAAACAAT ATTAAAGTAT   5520
TTTGCTTAAA AAATAGATAA AGCAATAAAA TGGTAGCCCT AAATCTAAAC ATATCAATAG   5580
TTATGTTAAA TGTAAATGAT CTAAAATATT ATTTAAAGGC GTAAATTGTA AGAATTGGTT   5640
TAAAAACATG ACCCTGTTCT GTACGTTGTC CACAAGAAAT CCACTGTAAT TATATAGATA   5700
GGTTTAAAAA AGAATGAAAC ATTACATTCC ATGAAAACAT TAATCAAAAG GAAGTTGGAG   5760
TTACTTTAAT ATCAGACAAT GGACACTTTG GAGCAAAGAA TATTATCAGG ATAAAGAAGG   5820
ATATTATATG ATGTAAAAGA ATCATTTCAC CAATGTATCA GTCAGGGTTC ACCAGAGAAA   5880
TAGGACGATT GATATTATGG AGATATATAT ATATATATAT ATATATATAT ATATATATAT   5940
ATATATATAT ATATATATAT ATGGGGAGGG AAAGGAAGAA CAAATATGGG GAGAGAGGGA   6000
TGAGGCGACT GATTTTGAAG AATTAGCTCA CGAAATTGTG GGGGTTGGCA AGTCTGAAAT   6060
```

-continued

```
TTGTAGAGCA GGTCAATAGG CTGGAAACTC AGGCAAGAGG TGATGTTGCA GTCTTGAGGC   6120
AGAATTTCTT CTCTAGCAAA CCTAGTTTTT GCCCTTTAGT CCTGCCACTG AGTGGATGAG   6180
GCCCACCCAC ATTATTGACA ATAATCTCCT TTACTTAAAG TCAACTGATT ATAAATGTTA   6240
ATCACGTCTA CAAAATATTT TACAGCAACA TCTAGATTAG TGTTTGACCA AACAACTGAG   6300
CATCATAGGC TAGCCAAGTT GATGCATAAT ATTAATCATC ACAACCAAGA AGACATCATC   6360
CTAAATATAT ATATATATCT ACTTAACAAA AAGACTGACA GAACTGAAAG GAGAAATAGA   6420
GAAATCTACA GTTACATTTG GTGACTTCCA GCATCTCTCA ATAATCAATA AAACTGACAG   6480
ACCAAAAAAT CAGTAAGAAG ACAGAAGAAA TGAACAGGAT TATCAGCATG CTGGATCTCA   6540
TTGACCTTTT TAGAACATTC TACCCAACAA CAGTAGAGTA CACATTCAAG TGCAGATGCA   6600
GTATTCATGA ACATGGATTA TATTCAGAGT CATAAAACAA ACCTTAACAA ATTTAAGAAT   6660
CTTGTATTTG TATATTTTTT GACTAGAATG GAATTAAACT AGAAAACAAT AACAGAAAGA   6720
TAACAGAAAA GTCTCTAAAC CTTAGAAATT AAATAACACA CTTATAAATA AATCCATGAG   6780
TCAAAGAGGA AGTCTCAAGG CAAATCAGAA AATGTTTTGA ACTGAATGAA ATGAAAATAC   6840
AAAATGTGTG AGATGCAGCT AATGCAATAC TGAGAAGGAA ATTTATAGCA TTAAATACCT   6900
ATGTAATAAA AGAAGAAAGG TCTCAAATCA GTACCTAAGC TTACATCTTA AGCAACAAGC   6960
AAATAAGAGC AAAATAAATC AAAATGAAGT AAACATAAGG AAATAACAAA GAACATAAGT   7020
CAATGAATAG AAAAGCTATG GTCATACCAC TGCTGTCCAG CCTGGGTGAC AGAGTGAGAC   7080
CCTATGTCAA AAAAATTTAA AAACAAAGCA GCATGCAGCA TTCATTGTCA GTGAATAGAA   7140
AATGGGAAAA CAATAGAGAA AATCAACTCA AAAGCTCATT CTGTATAAAG ATCAACAAAA   7200
TTGATATAAA CTTCTAACAA GACTGACGGN AAAGANGAAA AGACACAGAA GACCAATACC   7260
AGGAATGAAA GAGGGAATTT CACTACAGAC CTCCCAGGTA TTACTAGGGA TGATAAGGGA   7320
ACACTATGAA CAACTCAGAA CATAACTTTA ATAATTTAGA TGAAATGGAT CAATTTCTTG   7380
ATAATCTCAA GCTAATTAAA CTTACAGTGA ATTAGATAAC CTGCATAGTG TTACAACCAT   7440
TAGAGGGATT GAATTCTATG TTAAAAATCT CTGAAAATAA AATCCCCTAG CCCAAAGAAT   7500
TTCAATGACA AATTCTACCA AACATTTAGA AGACAAAATA ATACCAATTC TATAGCATGA   7560
TTCCATTTAT ATAATAGTCT TTGAAACATA AAACTATACT AGAGGGATGA AGAAAAGATC   7620
AGTGGTTATT AGAGATTGGG GGAGGGAGAA GGTATGATTC CAAAGGATAG TACAAGGCAG   7680
TATTTTGGAG TGATAGATTT ATCGTGCCCT GATTGTGATG GGAGTTAGAT GAATCTATGG   7740
ATATCTTAAA ATGTGTAGAA CTTTACACAT ACATACAACC AATTTGCCTA TGTTAATTGA   7800
AAAAATAAAA TAAAAACAAA TTATTTACCT GGTGGGTTAG CTACGTACCT AAGTTCAATA   7860
GCTGCGTTAC TGTAAGACAA AAGAAGCATT ATTAGGGATG GAGTTGTTNC TCTGTGTAAT   7920
GACAAATACT TCCTTCACTA AGAAGACAGA ATTGTTTTAT GCACCTTTAA AAAAAAACAA   7980
AAACAAAAAA AATACAACCA ACAAACAGTA ACTTGCTGGT GCGGTGGCTC ACACTTGTAG   8040
TATTAGCACT TTGGGAGGCT GAGGTGGGAG GATCACTTGA GACCAGGATT TTTAAGACCA   8100
GTCTGGGCAA AAAACCGAGA CTGTGTCTCT ACAAAAATAA AAAATAAATA AAAAAAATTA   8160
GCTAGGCATA GCATTATGTG CCTCTAGTCC CAGCTACTCT GGAGGCTAAG GTGGAAAGAT   8220
CGCTTGAGCC TGGAAGGTTG AGACTGCAGT TGCAGTGAGC CATGATGGCA CCACTACACT   8280
CCAGGCTGGG CATCAGAGTA AGACTCTGTC TCACATAAAA AAAATAATAA TAATGATAAA   8340
AACTAGTCTG GGCATGGTGG CTCACACCTG TAGTCCCAGT CCTTTGGAAG GCCGAGGCAA   8400
```

-continued

```
GAGAATTGCT TGAACCCAAG ACTTTGAGAA CAGCCTGGGC AACATAGCAA GACCCCATCT   8460
CTATTTAAAA AAAAAAACAA ACTTAAAAAT CCAGCAAATA CATAAAGCAC AAAGCCGACA   8520
GAAGAGGTGG AGAAATCAAC AAATCCACCA TCAAAGTGGG AGAATTTGAT ATAATTTTAA   8580
GTTATTGGTA GGGTAAACAA TCCAAAAATT AGTACACTGT AGAAAATTTG GTCAACATAG   8640
TAATAAGTTT GCTTATTACT ATTTATCAGT ATACATAGTA TACTGATTTA TCAGATACAT   8700
AGTATATGGA GCCCTAGAGC AAGCAACTAT AGCAGTGTAT CTCAAGTATT TTTACTTCAT   8760
GACCCACATA GCAAATGATA TGTGTATATA ACACACTGGG CTAATTGTCA GAGTTCAGTT   8820
TCTGTCCAAA ACCCTAAGAT CTGGAGTGAT TAACCTTTCA GCACTCTTAG AACTCACTTG   8880
TTTGTAGCAC ACTGATTGAG AAGCACTGAA AGACTTCACT CCTCAAACAT ACATGGAATA   8940
TTTCTAAAAA CTATGTATTG GGCCGGGTGC AGTGGCTCAT GCCTGTAATC CCAGCACTTT   9000
GGGAGGCCGA GGCGGGTGGA TCCCGAGGTC AGGAGATCGA GACCATCCTG GCTAACATGA   9060
TGAAACGCCG TCTCTACTAA AAATACAAAA AATTAGCCGG ATGTGGTGGC GAGTGCCTGT   9120
AGTCCCAGCT ACTCGGGAGG CTGAGGCAGG AGAATGGTGT GAACCCAGGA GGCGGAGTTG   9180
CAGTGAGCCG AGATCGTGCC ACTGCACTCC AGCCTGGGCA ACAGAGCGAG ACTCTGTCTC   9240
AAAAAAAACC AACCAACTGA ACAAACAAAA AAACTAAAAA ACAAAAACAA AAAAACTATG   9300
TATTAGAGCA TGGGTTGGCA AACTATGGCC TGTAGGCAAA TCTGCATGCT GTTTTATTTT   9360
TTTTATTTTT TTGACATAGG GTCACTACAG GCTGTCACAC AGGCTGGAGA GCAGTGGTAT   9420
GATCATAGCT CACTGTAACC TCAAATTCCT GGGCTCAAGC AATTCTCTTG CCTCACCTCA   9480
GCTTCCCAAG TAGCTACAGG CATGCACTAC CAGACCCAGT TAATTAAAAC AAATTTTTTT   9540
TTGGTAGAGA CAGTCTCAGT ATGTTGCCCA GGCTGGTTTT CAAACTCCTT GCCTCAATCA   9600
GTCCTCCTAC TTCAGCCTCC TAAAGTGCTG GGATTATAGG CCTGAGCCAT CACGCTTGAC   9660
TAATGTTTTT GTAAATAAAG TTTTCTCAGA ACACAGCCAT GCCTTTTGTT TATGTGTTAT   9720
GTAGGGCTGC CTGAGTTAAG TAGTTGGCTA CAAAGCCTAT CATGGCCTAT AAAGCCTGAA   9780
ATACTTACTA TCTGGTCCTT TATAGAAAGT GTTTTCTGAC CCTGTACTAG ACTAGCTTGT   9840
CTCAAAATTC TTCAATGAAT TTGGAAGTTT TCTCACCACA TTTTCTGACC ATAATGCACT   9900
TGAGTTAGAA GTAAATAAGC AGATAAACAA CAAAATCCTC ATGCATTTGG AAATTAAAAA   9960
TAACACTTAA ATAATTCATA TTCAAAGAAA AAATCAAACT GGAAATTAAA AAAAATTTTA  10020
AACCTACAGA TAACTACATT AATATGCATT AACATTTTTA GAACTTAGGG ATAGTTACAA  10080
TGATATACAT TAAAACTGGT AAGAGGCTGG GTGCGTTGGC TCACGCCTGT AATCCCAGCA  10140
CTTTGGGAGG CCGAGGCTGG GGGATCACGA GGTCAAGAGA TTGAAACCAT CCTGGCCAAC  10200
ATGGTGAAAT CCCGTCTCTA CTAAAAATAC AAAAATCAGC TGGGCGTGGT GGCACGCGCC  10260
TGTAGTCCCA GCTACTTGGG AGGCTGAGGC AGGAGAATCG CTTGAACCTG GGAGGCGGAG  10320
GTTGCCGTGA GCCGAGATTG GGCCACTGCA CTCCAGCCTG GCGACAGAGC GACACTCTTG  10380
TCTCAAAAAA AAAACAAAAA AAAAAACAAA AAAAAAAACT AGTAAGAGGT CCCAGTGGCT  10440
CACACCTGTC ATTCTAGCTC TTTGGGAGAC TGAGGAGAGA GGATCAGTTG AGGCCAGGAT  10500
TCAAGACCAG TCTGGGCAAC ATAACGAGAC CGCATCTCTA CAAAATTTTA ATAACAACAA  10560
CAAAAAAACT GGTAAGAGGC AACATTGAAT AGTACTTTGT GGGAGTTTAT TAGCTTGAAA  10620
TACTCATAAT AGAAAAGAAA ATTAATCAGC TAAGCATCTC ACTAAAGAGA TTAGGAGAAT  10680
AAACCTAAGC ATAGTTTTTT TCCCCCAAAC ATTATTATAT CTGGAATATT GAATGCATTC  10740
TTATTGCTAT TTCAAAGATA CTTACTCTAA GGAAAGCAAT TGAATTAGGT AGTTGAACTC  10800
```

-continued

TATAGTAGAT TTTCTTTAAT GAGTCCTTTT GTTCTCAACC TACTTAAATA ATTCTCATTT 10860

GAATTTATGA TAGTTTCAGA TCTACCCAAA GGGTGACTTA GGAATTTAAC TTCTAAATCT 10920

ATTTAAATGA AAGGTTTATA ATCTTTGTGT CATATTTTAC AGTCGTTAGC GTTTAACAAT 10980

TTATAGCATA GGATTTGGGT TTTTTTTTTT TTCATTTTAA AGAAGAAGTT TATTTAAGCA 11040

AGACACTTGA CTAAGGGAAG ACTATCTTGG AGTTATTATT ACTAGAGTAA TTTATTTCTA 11100

CTTAAAGACA GATTGCCCCA CAAGTAACAG CTACATAAAA AACAGTTGTA AAATTGTCCT 11160

TGGTTTTACA ATGATAAATG AAAAACATTA AAATTCTCTA ATTGAACAAG GTATGCAAGG 11220

ATTTTTATAT TGTTTTTTGC TAAAACTATG ACAGCAAAAT AACATCCTGG AGTATAAAGA 11280

TAAGAGCTGA ATGAGCAGGC CACTAGGGGA CAAAGGGAGT CTTTTCACAG AACCAATGCT 11340

TCTTTTGCCC ACCCCATCTC CATCGAAGTC AATCTAAACA TATTATTGGC CATTTAGTTA 11400

AAAAAAGAAA GAAAAGNAAA AGCAATATGC TTGTGGACAT ACACCAGTTA CTTTATGTGC 11460

AATAAAAGAG TAGGAAGGGG AAGGTGAAAG AATAGAGAAA ACTATGTAGT CAGGATGTGG 11520

TGGAACCAAA TTGCAACTTT CTTTTTTTTT TTTTTTTTTT TTTTTGAGAC AGAGTTTTGC 11580

TCTTGTCACC CAGGCTGGAG TGTAGTGGTG GCCCAATCTT GGCTCACTGC AACCTCCGCC 11640

TCTCAGATTC AAGCCATTCT CCTGCCTCAG CCTTCTGAGT AGCTGGGATT ACAGGTGCAT 11700

GCCACCATGC CTGGCTAATT TTTGTATTTT TAGTAGAGAT GGGTTTTCAC CATGTTGGCC 11760

AGGCTGGTCT TGAATGCCTG ACTTCAAGTG ATCCACCCGC CTCAGCCTCC CAAAGTGCTG 11820

GGATTACAGG CGTGAGCACT GCGCCTGGCC AAATTGTAGC TTTCTAATTG AGACTGTCTT 11880

CTTGGTCTGG AAGAGCAGAG TTCTGCAGTA AAATAACAGG TCCCCCTTTT AGTAGACATC 11940

TCCATGTCTG CTGCTGGAAC ACATCAGTTT TGTCTTAAGC CTCACTTCCA AATGTGCAGA 12000

TGTGTCTGGT TCATTGATTG GCTGCCTGTC AAATTGAAAC CTGATCTGCC TCATTGGCAA 12060

ACCGTGCCCC TTACAATAGG CTTTCATTGG TTTACTAAGC GGTGTGGTGC GTGGCTGTTC 12120

ATCTTAAACT GCACCACAGT TTAAGATGAA CCTTCAAATG AACATTATCC TTGTTCTCAG 12180

TCTTGACTTT CCTTGGGCTT TTTGTGGACC CTGGTGAGTG TGGCAGTCTC CTCAGCTGCT 12240

GCTTCACAAA AGAGGTACCA GGTCTGCCCC GAATGAGTGA GCCCCTAAAC AGGACCAGGA 12300

GTGGCAGAAG AAAGAGGCAG CAACTGAGAT GTGTTTTTTC TAAGCTGAAA GGCTTTTTTT 12360

TTTTTTTTTT GCAACACACC TTTAACACTA AAGTCCAATA TTTATATAAT TNGGTCAAGT 12420

AAGTGGAGCT GTTCTAGCTA TAAATATGGC AACTCTGCTT GCTCGTCCTA TTATTGACAT 12480

TATTCCTTTC TGTGGTCTGA GGTGCCTCCC ATGAAACTTG CTTCTAGGAC ACTAGGATTG 12540

AGAACCATNC AGCGTAACAT ATCTGTTACG CTACAATAGT TTATTTTCAT ATTTTAGCTA 12600

CTTTACATAC TCGGGTATAA TGAACTTTAT TCATAGCTTC TGAAGCAGTT GGCACATTTG 12660

AGATATTTTT TACTTGGCTA ATTGTTATGC TAAATCTTTT GATTTCTAAA GATACATGCC 12720

TTTGCTAAGC TTTCTTCAAA TGTTATTATT TTTATTTAGA TTGGATCATT GCTATTCCAT 12780

GGATGACTCA GAGGATACAT CCTGGGACTT TGGTCCACAA GCATTTAAGC TTTTGTCTGC 12840

TGTGGACATC TTAGGCGAAA AATTTGGAAT TGGGCTTCCA ATTTTATTTC TCCGAGGATC 12900

TGTAAGTATA TATCTGTGAA TTCCCTTCAT AGATCTTCTT TTACTTCTAT TACACTTTTC 12960

TTCAGAGGTT TGCAGTATTA TGATTGTAAC TTTGACTTCA GATGGGTGAC TAGGAACTCA 13020

TAGAGTCTTA CTAAGTTCCA GTTAAACACT ACATTCATTA CTTTGGATAA AACCCGTGTG 13080

TATGGCATCT TCTGCTGTTT TCATGTTCAA GCCGATGTTC AGCTCTGCAG CTCAGTCTGG 13140

-continued

```
AAGCATTGTG TTAATTTATC ACATTGCATT TGGGTGAATC CCTAGACTAG TCTTGCTTAG  13200
GATAATTAGG AAAAGTTAAC TTTCATTGTA TCAAGGGACA GGTAGAACAA AATTGTCCTT  13260
TTGTCCAGGA AACTATTAAA TTCTTCAAGG AAAACTTTAG TTATAGGGAT TATTTTTTAA  13320
ATGTCTAATT TCAGTAACAA TATTTGGGAC ATATTTATTT TTCCTTCTGT TTCCTATCAG  13380
AAGTATTTAA AGTTATAAGA AAATTGTGGT TTTTGCCTTT ACTAATGAAT AAATAATCAA  13440
TTAAATTCAG TTACTTTTTT TTGGAGTGAT TGATGTTCCA GTATTCTTCT AAACAACCAC  13500
GGGTACAAAT GTGAATAAGA TAGGACCGTT GCAGTCCAAG AGCTTGTTCT GTAGTCCTTT  13560
CCTTTATATG ATTTTTTCCC CTGATTTAGA AGTCTATAAA GCAAAGCTAA GTATTACACA  13620
CTGATAATGG CTGAATAAAT CAAGAGCAAG AGATAGGATA CTTTGCAAAT ATGCATATTT  13680
ATTAAAAATG TACTTTAAAA TAGAGATTAA AATTCTCGTA TTGAATGTAG AATAGGTAAG  13740
CATTTATTTG TGAAATACTC GAATGCTTCA TGTAAATACT TTCTGAGTTT GTATTTTTAG  13800
AAAGGAACAT TTTGGAGGCT GAGGCAGGAG AATGGCGTGA ACGTGGGAGG CGGAGCTTGC  13860
AGTGAGCTGA GATTGTGCCA CTGCACTCCA GCCTGCGCGA CAGAGCAAGA TTCTGTCTCA  13920
ATAAAAAAAA AAAAAGAAAC ATATTTATTA AATTAGTTGT GAAATATTTT TAATGAAATA  13980
TATTGAAAAC TTCTGTTGAT TTTTCATGTA CTGATGTTTT TAGATTCTAA ATGGAGTTTA  14040
AAATTTTGTT TGTAAATCAC AAGTTGGATT AGAAATTTAA TAGTAGAAGT GTTGCCTAAG  14100
GACTATTTTA GGTGCTGTGA GTGAAACTGT ATTTTTTATA ACAAGAATTT TAGTTGTAAG  14160
GGACAGCTTA AATATAATTG AGATCTGTGA AAATGTATTC TGTCTCTATC ACCTTCAGAA  14220
CCTGTGTATC TCAGTTGAAT GTATAATTTA TAAAAATTAT TCTTGTTTTA ATTTGGTGTA  14280
ATCCAGCCAT ATCCAGTATC AACAAATAAG TCTAAGTAGG CTCCTTGACA AACTTGAACT  14340
GGCCACAAGA GAGATCAGAT TTCACCTATT AAAAAACCAA ATCAGACCAC TTACACTGAC  14400
AGTCTCTTCT GGGAGTCCTC AAATTAAGAA GTCTATCCTT TGTGAAATAT TACACTACCC  14460
TTGCTAGATA AAACTTTTCT AAAAGTACCA CTTAATGAAA ATCTGTAGAC ACTAAATGCA  14520
ATGAAAATAA GGCATTGTTT TTTTTTCTCC CCATTTCAGT GATCTTGGTA TCCTGGGATA  14580
TTGTTTTTAA AATTATCGTT ATAATTCCTT TGAGAATTTA GTGAAACGTT CCCTTTAACC  14640
AACTTAGGAA AAATTAATAT CTTTGTACAT GATTTTGAGC TGTAAAATAA ACATTTTAAA  14700
CTGGGAATAA TTGGAGTTTA GTTAAAGAGA TAATGTATAT AAATATATAA CATAGTAGCA  14760
GCATATAATT CTGTCTTACA CAAGATTTTT CTGAATAGTA TAAACAGTTA TGTAGCCTAT  14820
CTAGGAGTTT GTGAATAGAG TTTAAAATTT TGTTTTGAAG CTGCAAATTT GATTAGAAAT  14880
TAAACAGTAA AGTTATTACT TAAGGAACTT CGTTTTAGCT GTCTGAACAA CTTACTGTAT  14940
AAAAATCTTT AAACATTCTG TATAAATATG TGATAAGATA TGCAATGACC TTAATTTTAT  15000
AGATTAGAAA ATAAAAACAC ACTCATTAAT TTACATAACT GACAGATTAA GTGAAACTTC  15060
TCTTCTGATC ACGTTAGCAG AATGCCAAAT CTTGTCGTGG CACTAGAATT AGACGGTAGT  15120
TTTGATAATA CATGATTTGA CTATAGACAT TTGTTGAAAC TATTGGTAGT TTTAATCACT  15180
CTTGTAATTT TCAAACTATC TAACGGGAGA GGATTATCCA TCCTGTTTTC TAGACAAACT  15240
GTTTCATCTG AATGAAATAT ATTCCTAGAG ATAATTATCA CTACTTCATC TTTTGGTTTT  15300
ATTTTGCACA TAGAATTATA GTTCACAATG ACTTTCTGAA GCTCTAAAGT TGCAGCTGTG  15360
AGCTTCTTTG GCCTGTAGGG ACTGGGAAAA AGCACCCCCG TCCTCCCCCA AGCCCCCCCA  15420
CCAAAAAAAG TTAAAGTGTT TTTAACAATA GCTGTGGGCT TTTTGTAGTT TCAGAACTTA  15480
GGAGTTGCCC AGGCTGGAAT GCAGTGGTGT GATCATAGCT TGATGCAGCC TTGAACTCCT  15540
```

-continued

```
GGGTTCAAGC AATCCTCCCA CCTCAGCCTC CAGAGTAGCT GGGACCACAG GTGCCACCCC  15600
ACCCAGCTAT TTTTTTTATT TTTTAATTTT TTTGTAGGTA TGGGGTCTCC CCATGTTGCC  15660
CTGCCTGTCT CAAACTCCAG GGCTCTCAGG TGATACCCAC CACCCTTGGC CTCCCAAAGC  15720
ACCGAGAGTC ACTGTGCCAG GCTGAGTTTA AAATTTCTTG AGTTGGAGTT TATGGCTATT  15780
TTTTCCACTA GTTATTAAAC ATGTATTTTT GTATAAGGCA CTGTATTACA TTTTGTGGGG  15840
GGATTCAAAG CTAAATTAGA TGAGACGCAT CATCTATTAT GGAAGATGTT ACTTAAGAAG  15900
AAATGAGTGT AATGTAGCAG AGAATTAGAT AAGGGACGTA TGAATACATA TAAATGCTGT  15960
TGAAGTTCTG AAGAGAGAGA GTGTTTAGAG AAATTAGAGG AGTCTTTGTG AAGTTATCAC  16020
TAGAACTTCC TATTTTTGTG GAATATATAG TAGATTTTGG TGTGATACTG TGGATTTGGA  16080
CATTCACTCA GAGAAGGAAT GAGGGAAGAA TGGTGGAGAA GAATGGCATT CACAGTACAA  16140
AAAGCAACTG TGACTTTTAA AGAAGTTAAT ATGGAGAAGT GGCAAGTCTT TTCTTCTCTC  16200
TTCTCTTCTC TTCTCTTCTC TCTTCTTTTT CTTTTTTCTT TTTTTCTCTG TCAGATACTG  16260
TTGTAAAGAC TTTGCTTTTA CCGGAAACTG ATACGTTGGG TCATGTACCC TGGCCAGTCA  16320
GTTCTCTTTA TTCTAACACT TAGCCGATCA ATTAGATTTC CACATTCCAT GATATGTCAG  16380
TTTTGGTGAC CCTTATTTTT CCACCTGGTT TATAAAGGGA AAGAATGTGA TATGTCACCC  16440
AGGCTCTGGA GTACAGTGGC ATGATCATAG GTCACAGCAG CCTCAAAGTT TCCAGTTCAA  16500
GCGATCCTAC CTCCTTGGCT TCCTGAGTAT GTGGCACTAC AGGTGCATGC CACCATGCCC  16560
AGCTAACTTT TTTGTAGAGA CAGGGTCTCC CTATGTTTCC CAGGCTGGTC TTGAACCCCT  16620
GACCTCAAGT GATCCGCCCA CCTTGGCTTC CCAAGATATT GGCATTACAG GCATGAGCCA  16680
CTGTGCCGGC CTGAAAATTT CTCTTTTGAG ATGGCATCCC ACAGAAGTAT ACCTGCTTAG  16740
AGCTAACACT GGTAAAAAGA CTATTTAACC CTATTGCCTT ATTTTACTGT AGTTGAGATT  16800
GAGTTAAACT GAAAGCTGAA TGACCTGTCC TAGGTCATAC TGTTACTTTG TGCCAGAGTC  16860
AGGATGAGCA AATGGATTTC CTGCCTGCTA GTCTAGTGTC TTTTCTATTT ATTGTGCTGT  16920
AACATACAGT TTTAAATTTG TATTTTTATG CCCAATGGAC ATGGTAGCTC ACACCTGTAA  16980
TTTCAGCACT TTTGGGAAGC CGAGGTGGGG GGATTGCTCG AGACCAGGAG TTCAAGATGA  17040
GCCTGGGCAA CATAGCGAGA CTCCGTCTCT ATAAAAAAAA ATTTAAAAAT TAGCTGAGTG  17100
GTGATGTGTG TGCGTGTAGT CCTCCTTGTG GGAGGTTGAG GTGGGAGGAT CGATTGAATC  17160
TAGGAATTCA GGACTGCAGT GAGCCATGAT TACACCACTG CACTCCAGCC TGGGTGACAG  17220
AGCAATACCC TGTCTCGAAT GAATGAATGA ATGAATGAAT GAATGAATGA ATGCCCAAAT  17280
CCGTAAGCTA TGTTCTGTAT AGCAGCTTTT TCATCATAGG CAGTTTTTAC TCTTATCAGT  17340
GGACAACCTA CAAAATTAAC TAAACACTTA AGCAATTAAC AGAGGAGGCC TTGTTCAGAG  17400
TGAGAAATCA TTAAGCATTT GTTGTTGAAA TTTCTTACTG TACTCTGTTT TAATTCTGTT  17460
TTTTTTTTTT TTTAATGTTA CTTGTTTTAG TTTGGATTCC TAGTTGAAAA GGGAATATGA  17520
TTCCTTTAAA ACAAAGATAC TCTGCTTTAA AGCAAAGGTA TATCATCCTC TTCATGGTGA  17580
TTGCCATGGA AACAAGACAA TGTAAATTTA TTCAAATAGT ACACAGTTTT TATAGTTATT  17640
GATCATGAGG GGAAGGGACA GTTAATCCCT ACTGATCAGA TAAAACCTCA TTGTTTCATA  17700
CTAATAAATG GTTTTTTTAT GCTTATGAAA GGAAAAGCCA GAAGGGTAAT TTTTAGTGTT  17760
TAGAGAGCTA GTGATTCTAG TTAGGGAACT TAATACCTTT GAAGTTATTA GTTTGCAAGC  17820
AATAGAATCT ACTACTACCA AGGTGACCCC TAGCAGATGT AGAGTACCAT TAACAAGTGT  17880
```

-continued

```
TCCAGGGAAG GAAAGCCAAC TAGATACCAA GTCATGCTTT TTACTCTTAG ATTAAGAAAT  17940
TCAGGTTGAG TTAAAGGATC AGCTGTTAAC TAATAAAAAG CAGATTAATA TTACAGAGCC  18000
AGGCTCTGTC CTGGTTATGG ACTTAATCTT CACAGCATCC TCAAGAGATA AAAATGAATA  18060
TACCTGCATA TTAGATGAGG AAATAGAAGA TAAGTAACTT GCCAGAGCTA TGACGTGAAC  18120
TCAGGTAATG TAGCTTAAGA GCCCCCACAT GTATGTATAT TGGGTGTGTG TGTGGAGGGG  18180
GTGCGTGTGA GTGCTTGTGC ATGCGTGTGG TATAATAAGA AAAAATTAGC ATTTATGCCT  18240
GTAATCCCAG CACTTTGGGA GACCGAGGCA CGAGGATCTC TCAACCCCAG GAGTTCAAGA  18300
CCAGTCTAGG CAACATAGCG AGACCCTACC TCTACAAAAA AAGTTTTAAA AATATTAGCG  18360
GGCATGGTGG AATACACCTG TAGTCTCAGC TGCTTGGGAC GCTGAGGTGG GAGGATCCTT  18420
GAGTCCAGGA GATTGAGGCT ACAGTGAGCT ATGATGACAC CTCTGCACTC CAGCTTGGGT  18480
GACAAAGAGA GACCCTGTCT CCAAAAAAAA AAATTAGAAC TAGTTATCTG GAGGCCTGTG  18540
TTCTAGTCCT AGCTTTAGTA CGGCTACACA GTGACACATT AGGCTACCAT TTAACATCTT  18600
TGAACCTCTG ATAATTTGTT AACAATATGG GTAAAAATGA CTAAGATAAA TCAAAGAGCT  18660
CCAGCATTCC CTCCAGCTCT GAAATTCTAT GATGTTTTAT CTTATTTTAC TTACAAAAAT  18720
AAATTATATT ATGTATATTT AAAGTATACA ATTTGATGTT ATGGGTTACC TATAGTAAAA  18780
TGATTACTAT AATGAAACTA ATTAACATAT CCATCATCTT ATATTGTTAA CCATTTTTTT  18840
GTTTTTGTGG CAAAAGCAGC TGAAATCCAC TCATTTAGCA GGAATCCCAA ATACAGTTCA  18900
GTTGTATTAA TTGTAATTCT CATGTTGTAC ATTCGATCTC TAGACTTGTT TATGCTACAT  18960
ATGTTTGACT TTTAAACATT CTACTCAAAT CAACCCTAAG TCAGGGTTAG CACAGACAGG  19020
ACTTGTTAAC AAGGTAGAAG GTGCCACATT GTACCTGGGT GTTTATATTT CTCTAAATCT  19080
TGTTCTGATC ATATTTTAAT AAATATAATC ATCAGGACAC CAAAATTCAT TCCTTAGCTA  19140
TTAAAAAATT CTATTCTATT TTATTGTTAA GATTTAGGAG AGCATGGTAC AGATTCTCTT  19200
AACTATACCT ATCAGAAGCC TATGTTTTAA GTCCAATGTA TAGGCACTGC TCTGTTTGTC  19260
TCTGGTGGGA ACTTACCCTG CTTTACCTAA TTTCATCCTA GCTTCCTTTT TGTGAAAGAT  19320
CACCCTTGCT TAGCCTATTT TTTGGCAAAT CTACACCTTG GAAATAGTAG TAAATGACAT  19380
AAGCATATTA ATATTTATGA TGTGATTTAT TTTTGTTTTC AAGTCATATA CTGGGGAAGA  19440
TTCTCAAATA TTAAAACAAT GTATCTTTAC ATTTATGTAT GTCGTTCTTG TTCTGTTTTA  19500
GAAGGCTTGT ATTTGCATTT TTAACATTCC AAAAGGTAAA CCTGTAATCA TAATGTTTTC  19560
ATCAATTCAA TAAAACCATT ACGTTTGTAA TAGAGAGCCC TATAGTTGCC TTAGTTAAGT  19620
TTGCTGCAAC TCATTTTATA TATTCTTTTA ATTTTGATCC CTGGATTTTT AATTGATTAT  19680
TAAACCTTCA TTAGGATATA TATGAAATGT AAAAATATTG AGTTATAATC TACCGTTTTC  19740
TAAAATTTTA TACTGCATTT TTATATAGAA ATTCAAATTG CTCATAATCA TTCTAGTGAA  19800
TTTAAGTAGA AAGGTATTTA TTACTAGGTA TTAAATGGCT TATAATATTG TTGACAAGGT  19860
TCCACTGCAA AATAGTTCAC CAAGGGAGCT GTGGCCTCTT CTGTGATCAA GAAGCCATCT  19920
GTCAACTTGG GAAGCTTCCA CTATAGCACC TAACCCCAGA CTACATTGAG TAGGAAGCTG  19980
TAATAATCAG GAAGCTTCTA CCTTTGCATG CTCTGCAAAC CAACGTGAAC CTGCTGTAAT  20040
TTGTAACCAC AAAATGGATG CCTGTTGATA CTTACGAAGC TCATCATTGT ATGCTGGGTT  20100
CTTTGCTAAT ACTTTCTTAT AAAAATTAAA TACCTCCACA ATCATGCATG CTAGCAGAAA  20160
CAGCAGAGGA GTAGCCTTAG CCTCACTTCC TGCTTATACC TGTCATGCAG ATATACAGAA  20220
CCCAGAACCC TAGCTGAAAG GGAGTTTGAG AACTAGTATT TGTATTGTCC CAGATTCTGC  20280
```

-continued

```
AGTGGAAGAA TTCATAGTGG ATGGAAGTTA GAATGACCCT TGAATTACAA TCGGCCACAT  20340
TCATCACAAA TACATTAAAT AAGAGTAATT TGCCATAAAG CTCTATGTTT GTATACTTCT  20400
TTGTTTTTTT TTTTTTTTTT TTTTTTTTTT GAGACAGGGT CTCACTCTGT TGCTCAGTCT  20460
GTAGTGCAGT GGTGTCATCA TAGCTCACTG CAGTCTTGAT CTCCTGAGCT CAAACGATTC  20520
TCCTGCCTCA GCTCCTGCTT CAGCCTCCTG AGTAGCGGAA CAACAGGTAC ACACCACCAC  20580
ACTTTGCTAA TTTTTTATTT TTTATTTTTT GTAGAGATGT GGGTCTCACT GTGTTGCCCA  20640
GGATGGTCTC GAACTCCTGG GCTTAAGTGA TCCTCCCAAA GTGTTGGGAT TACAGGCATG  20700
AACCACTGTG CCTGGCCCAT ATACTACATA TATTTAAAAG TAGTATTTAA ATGTGTAGGA  20760
TGAATGAAAG AGGCAGTAAG AGAACAAAGT GAATGAAAAA GTATTTCTAT ATGAAGTGAA  20820
AGCAGGAGAG TCCTCTCTGT TAGAGAACAA CAGAATTGCA TATGACAGAC TAGCTTTCTT  20880
AATATTTCTA GAACTTGATG GCTGTGAAGA GCGTCCCGTA GGAATTCTCC CTTCACTTAG  20940
GAAAACATAC CTCAAAACCA TCAGCTGTTT AGCATGCACC TGCTTTTCCT GGTATATCTC  21000
AGTGAAGCAG CTAAATTGTA AATGATTAAG TAAACTTTGC AGTGTATCAT GTGCAAAAGC  21060
ACAGTAAAAA CAAAAATGCA TTGGAAGCTG TGAGTTGTTG CACTGCACTC ATGGATGAAT  21120
AGCTGTTGGT TCGCATTGCG TTTTTTTGTT TTGTTTTGTT TTGTTTTTTT GAGATGGAGT  21180
CTTGCTCTGT TGCCCAGGCT GGAGTGCAGT GGCGTGATCT CGGCTCACTG CAAGCTCTGC  21240
CTCCCAGATT CACGCCATCC TCCTGCCTCA GCCTCCCGAG CAGCTGGGAC CACAGGTGCC  21300
CGCCACAACA CCTGGCTAAT TTTTTGTATT TTTAGTAGAG ACGGGGTTTC ACCATGTTAG  21360
CCATGATGGT CTCAATCTCC TGACCTCGTG ATCTGCCTGC CTTGGCCTCC CAAAGTGCTA  21420
GGATTACAGG CATGCCGCAT TGCGTTTTAT ATAATTCTCA TGGTTCTAGT CTCGAGCTGT  21480
AGGATTTTGA TCACTGTTTC AAACAATAAT GTGAGTTTGC TAAGAGGTCT AAATAACAAA  21540
AGCTAAGTGT CCAAACACAT ATCCAAACCT ATACACTGGG CAATGCATCT GAATTATATG  21600
TGAAATTTCC TGCCATTATT TAAGACACAA AAGGAACATT ATTTTGATAA TGTATTTATT  21660
TGTGAGTGGA GTGTTCAGAA TGAGCACGAT GGGTATAACA TTTTTGTAGG TTTTTAAAGT  21720
TGAAATTTAG TGTAAATCCA AAGAATCAAT AGACAAGTCT GTGTTTTACT TAACCTATAT  21780
GTTTAAATTA GCATTTTTAG ATACTGATTT TATTCCTAAT TTCAGAATTC TCAGCGTCTT  21840
GCCGATCAAT ATCGCAGGCA CAGTTTATTT GGCACTGGCA AGGATCAAAC AGAGAGTTGG  21900
TGGAAGGCTT TTTCCCGTCA GCTGATCACT GAGGGATTCT TGGTAGAAGT TTCTCGGTAT  21960
AACAAATTTA TGAAGATTTG CGCCCTTACG AAAAAGGTAA ACAGTGTAGG AGTCTGCCTG  22020
TTTGACTTAA TTTTGTTTCC CACTCCACAT TAAAAGATCC TTTTTGCTTT TAATAGGGTA  22080
GAAATTGGCT TCATAAAGCT AATACAGAAT CTCAGAGCCT CATCCTTCAA GCTAATGAAG  22140
AATTGTGTCC AAAGAAGTTT CTTCTGCCTA GGTTCATTTT TCAGTTTTTT TCTTGTAACT  22200
TCTGCATTTT TTGTTGCTAT TTATGTGATT CAAATTATAC CAGTTTATAG GCCTCTCACA  22260
AGTAAAATGA ATTGCCTGTT TGTTTTTGTA TGCCTATTTT AGTCAGTTTG GGGGAAGGGA  22320
TCTGTGAGGA AAGGATAAGT CATAGAGCAC TTTTCTTTTT TAAGAGACAG AGTCTCTCTG  22380
TGTTGCTCAA GCTGGAGTGC AGTGGTGCGA TCATAGCTTA CTGCAGCCTC GATCTCGTGG  22440
GCCCAAGTAA TCCTCAGCCA CCTGAGTAGA TGGGACTACA GACATGCACT ACTATGCCCA  22500
GCTAATATAT TTTAATTTTT TGTATAGAGA CAGGGTCTTC TAGTGCTTCC TAGGCTGGTC  22560
TTGAACTCCT GAGCTCAAGT GATCCTCCTG CCTCAGCCTC CCAAACTACT GGGATTACAG  22620
```

-continued

```
GCATGATCCA CCGCTCCCAG CCAGAACATT TTCTTGGTTG ATGGGAAGTA GCTGACCATG  22680
GTATTTAGAA AACTTCTTTC TCATCGATTA AAGAAGCAGT ACTGAAATCA ATGCGGAGGA  22740
ATCCATATAT CATATTTACT TCTGGTGTGT AGAAGTGGAA AGGGAATACA TTTGTTGCTT  22800
ACTTTTTTGT ACCTTTACAT GTGATTGATC ACTTGTGAGT TTTTTCTTTC AAACATCTTA  22860
AAGCTTCCAG AGCTTTTTCT AGAAAAAAAA ACCAGTTTTA AGAATCACCA GTTCTAAAAG  22920
GGTAATATCT TATTCATCTT TCTGAGAATG GAGTATCATG ATTCATGAAT TAGATACTTG  22980
CATCTTAACA TTTGAAATAA TTTAATTTTA TTATTTTTTA GTTCGAAAAC TGTATCTTCG  23040
GGCACCAAAG AGCATTGTTA TAATCAAGTA CCAGTTGAAT TAAGTACAGA GAAGAAGGTT  23100
TGTTTTAAAG AAATTGTTCT GACTTATTTC ATTCTTTATT GATTCAAATT CTGTTTAAAA  23160
TTTTATATTT TAATTCCTTT CCAATTAAAG AGAAAATGGC ATATATAACA AAGCATAAAA  23220
TTCGGCCAGG GAAGTGATGT GAACAGACTA AAATTTATTG TATATAATTT CTGGGGCTAA  23280
TAAAGAATTG GAGGTATTTG AGAAAGGAAT TAATTTGGGT TCTTTTAAAC CTATCTGCTA  23340
ACTCATTTGG CTTAGAGTAG TCACATGTTA TAATACTTAT AGTTGATCAA AAAATTGATT  23400
CCTAAGTGTT CTTATTAAAG ACACACACAC ACACACACAC ACACACACAC ATTCTTTCTC  23460
TCTCTCTCTC TCACACACAC ACACATGCAC ACACACTTAT GTACTTTCTT GCTTTTTTTG  23520
ACCTAAGATC TTAGATAACT ATTACAGATT AAATACTAAT CCACTGGCAG ACTTCAGCTA  23580
ATTAGAACAC TGGAATAATA GGCAAGCATA GTGAATTACA TTTTCTGGTG AACTTTTTCT  23640
GCTTTATTGA AGTATGCAGA ATGTAAATGA ATTGTTTTTA TAACTTTGGC ACTTGCTGTA  23700
TCTTAGAACA TTCTTTTGAT GATTTATTTT CTGTAGTTTT GGGAGAGATA AGACATTGGA  23760
ATGCGTTTCT AACTACCTTT AGAACTTTAG AAACTGATAA TTTAGGAGGT TATTTTCAGG  23820
TGATTAATTT GACAGCTTGA TTAGGCAAAG AAAAAATTGT GATTTTGAGA TTTTTGTTTC  23880
TTATTTTCTT CACATTTAAA AGTTTTTTGA AACTTTTTTT AATGGACCTT TATATGTTTA  23940
AATGCAGTCT AACTTGGAGA AGTTATATTC TTATAAACCA TGTGATAAGA TTTCTTCTGG  24000
GAGTAACATT TCTAAAAAAA GGTACAGAGT TCCATATTTC TATGTTCTAT ACTTGCTTTA  24060
TGAGTACTTT TTTTTCTAAA GAGAAAGAAC TGTCAGATGT TGGGCTATTT CATTGGCAAA  24120
AGGAAGTTAA ATTTAAAACA TAAGCTTTTC AGTATTAGAA TGATCAAAGT GAGCTATAAA  24180
AGAATAATGT TAATTTAATA GCTAACACTT CTTGGATATT ACTGTTTGTC AGGCATTATG  24240
TTAAATGCTA AGAACTTTAT ATGTGATATC TCATTTAATT CTTACAAGAG TCTAACAGCT  24300
GTTACTATTT ATCGCCATTT TATAGTTGAA GATACCAAGG GTTAAGAAGT TGACAAACTT  24360
GTTCAAGAGC ATACAGCTAA TGGCCGAGCT GGCTTTCAAG TCTATATTTG TCTACCTCTA  24420
GCATCAAGAC ACTATTTATT TTTCTTTGTA TGAAATATAT ACAGGCATAC TTTGTTTTAT  24480
TGTGCCTGGC TTTATTGTGA CTTGCAGATA TTGCATTTCT TATAAATTGA AGGTTTGTGG  24540
CAACCCTGCG TCAAACAGGT CATATTAGCC CCATTTTCCA ATAGCATGTT CTGTTGTCAT  24600
GTCTTTGTGT TATATTTTGG TAGTTCTTGA CTGGCCATTC ACCATTTCTC TCCCTCTCCT  24660
CGGGTCTCCC TGTTCCCTGA GATACAACAA AATTGAAATT AGGCCAATTA ATAACTCTAT  24720
AATAGTCTCT AAGTGTGTTT TTTTTTTTTT TCGAGACTGA GTCTCACTCT GTTGTTCAGG  24780
CTGGAGTGCA GTAGCACAAT CTCGGCTCAC TGCAATCTTC GCCTCCCGGG TTCAAGCGAT  24840
TCTCCTGTCT TAGCCTCCTG AGTAGCTGGG ACTACAGGCG CCCCCCGATC ATGTCTGGCT  24900
AATTTTTGTA TTTTTAGTAG AGATGGGTTT TTGCCGTGTT GGTCAGGTGG ATCTTGAACT  24960
CCTGAACTCA GGTGATCCGC CTGCCTTGGC CTCCCAAAGT GCTGGGATTA CAGGTGTGAG  25020
```

-continued

```
CCGCTGTGCC TGGCCCATCT CTAAGTGTTT AAGAGAAAGG AAGATTCACA TGTCTCTCAA  25080
TTTAAATCAA AAGCTAAAAG TGATTAGGCT TAGTGAGGAA GCCATGTCGA AAGCTGAGAT  25140
AGGCCAAAAG CTAGGCCCCT TGCACCAAAC AGTTAGTTTG CAAAGGCAAA AGTTCCTGAA  25200
GGAAATTAAA AATGCTACCC CAGTGAATAA AACAATGATA AGAAAGCAAA GCAGGCTTTT  25260
TGCTGATATG GAGAAAGTTT TAGTGGTCTT TATAGGAGAT TAAACCAGCC ACAACATTCC  25320
CTTGAGCCAA AGCCTAATCC AGAGCAAAGC CCTAACTCTC TTCAATTCTC TGAAAGCTGA  25380
GAGAGGTGAG GAAGCTGCAG AATAAAAGTT TGAGGCCAGC AGAGGTTGGT TCATGAGGTT  25440
TAAGGAAAGA AGCCATCTCC ATAACATAAA AGTGCAAAGT GAAACAGCAA GTGCTGGTAT  25500
AGAAGCTGTA GCAAGTTATC CAGAAGATCT AGCTAAGATC ATCGATGAAG GTGCCTGCAC  25560
TAACAGACTT TGAATGTAGA CCAAATGCTT TCTACCAGAA GAAGAAGCTG TCTAGTACTT  25620
TCATAGCTAG AGAGAAGTCA ATGCCTGGCT TCAAAGCTTC AAAGGACAAG CTGACTCTCT  25680
TGTTAGAAGC TGATGCAGCT GGTGACTTTA AGTTGAAGCC AGTGCTCAAT TAGCATTCTG  25740
AAAATCCTAG GGCCCTTAAG AATTATGCTA TATCTACTCT GCCTTTGCTA CATACATGTA  25800
ACAACAAAGT CTTGATGATA CCTGTTTACA GCATGGTTTC CTGAATACTT TAAGCCCATT  25860
GTTGAAACCT GCTTAGACAA AAGATTCCTT TCAAAATGTT ATTGCTCATT GACAACACTT  25920
AGTCACCAAG AGCCGTAATG GAGACATACA AGGAGACTAA CGTTGTTTTC ATGCCTGCTC  25980
GCTTAACATC CATTCTGTAG CTCATGGATC AAGAAGTAAA TTAACCTTTT AAGTATTATT  26040
ATTTAAGAAA TACAGTTTGT AATGCTTTAG CTTCTGTAGA TAGTGATTAT CAGAGATGGG  26100
TTTTTAAGAG GTTTTCCAGA AAACCTTCTG GAAAATATTC ACTATTCTAG AAGTCATGAA  26160
GAATATTTGT GATTCAGGAG AGTAGGTCAG AATATCAATA TTAATAGGAA TTTGGAAGAA  26220
GTCGATTCTT ATTAAAATCA AGAGTTTAGT GATAGACATA CTGAGTTTGG GATACCTGTG  26280
GAGTAGTCCA GAAGTTAATT TAAATATATG GGCTTAGTGT ACAGAAGTGA GCAGGGTGCT  26340
TATATATGAA TAAATATTAT TTTAAGATAT ATTTAAATTT TCCTTAAAAT AATACCTATA  26400
CTTGATATAA AAAGTTAATT GGAAATTAGT GGCTTATGAC AAGCATACCA GCCCACACTC  26460
TTCCCAAACC CACTTTGCTC TTATTCATAG AAGCTGTCAT CTTCAAATCT TCCAGCTGAT  26520
TTCCCTGGCG TGTGCCTTCT TATTTCTGAA TGACACGCTT AGAGTACTAT TTTTTTGACT  26580
TAGCAATTTT AGAAATTTTC TACTCATCTC CTATTATGGT AGATTTCCCC TCCTTCATTC  26640
CTCCTCCAAT ATAATTATAT TTCGTCATAT TAATAATTTG TTTATATATA TTTTTAATAT  26700
AATATGATAA TATTGTATTT ATATTATTAA AACTACACAA ATATTATATA CACACTACTA  26760
ACCCAACCGT GTTATTATGG CCACCACTAC CTTTATTTTT TTCCTTGTGT TAGTGATTGT  26820
CTTTGTTTTA TTTTCTTGGT TTTGAGTATT CCTTTTACTA ATTTTCTTTT TTCCTATTTC  26880
AATCTCTCAT TATTTGTTTA CTCATTTGGA GTGTTCCTTG ACTTTTATCC CCTCTTACCT  26940
AGTGACATTT TAATTTTAGT TATCAAATTT TTAATTTCTA AGAATGCTTC TTGTTCTCTT  27000
CTTGTTTCTT CTTCCCCACC AGCCAAAAAT CTATGATGTT ATAGCAAGGA TCATACATTG  27060
TTTCCCAGTA GGTTAAGAAA CCTTGGTTAA AACCTGTTGT ATCCCAGTAA GTTAAAAGAC  27120
GTTAACGTGT CATCTTCAGT ATGGATGAAA GAATATTTTC TTTCAAAAGC AGTTGGTTGA  27180
GGAAGAGAAT GGGACAAATG CTCTTTTTAA AACACCAATT TTGTGATGAA CTCAAATTGC  27240
AATTTTAACT TTACCATTAT AATGAATGTA TTTGATCCAA AATGTTTAAA ATCTAGGCTG  27300
TTGTCATTTA AATAACAAAT TACCTTACTG GTATCATGAA GAATAAATGT TTGTACTGAT  27360
```

-continued

```
TTGGAAAGAC ATTCTCATTT AGGGGATGAA ATAGAAAGTC AATGAGGAGA AAGAAAAGCT  27420
TTTATTATTT ATTTTCTTTT AAATATTTTA GTATCATGGT ACAGTCACCA GAAAAAGCTT  27480
ACAGTTCCTC ACAGCCTGTT ATTTCGGCAC AAGAGCAGGA GACTCAGGTA AGGCTTTTGT  27540
AAAAAGGTAA TTAGTTTATG ATAGGATAGT TATGATTCTA TGTATGCTTA AAATTCTGTA  27600
TTTTGCCAGC ATTTTAAAAA TTGTTCTTAA GCTAAGAGTC TGAGTTTATA TTTCAGTTTA  27660
TATTCATTCT AAGGAAAAAT GTGGTATCTG AAGCTCTAAA AATAAAGGAC TAGATCTTTT  27720
AAGTACACTT TAAAAAGTGT TGTTTCTTTG TTTTTTGTTC AGATTGTGTT ATATGGCAAA  27780
TTGGTAGAAG CTAGGCAGAA ACATGCCAAT AAAATGGATG TTCCCCCAGC TATTCTGGCA  27840
ACAAACAAGA TACTGGTGGA TATGGCCAAA ATGAGGTAAA CTATCTTTTG CATGTGTTCT  27900
CATTTATTTC CTTCTAACAA AATAGATTTG GAAAATATAT CTAAGTTGAT AATATGACCA  27960
TAGCTTCCAC TGTCACATCT GGGAGGTGAC TCAGATTCCC CCTGCTGCGA TGCTTATCTC  28020
TTTGCCAAGC TTTAGTACCG TGTTTCTGTA TGAATAAAAA CCAGTTACGT TTTCAGCAAT  28080
CATATTCAAT ATTTATAAAA TCTAACTCAT TATTTACCCA CCCTGCATTT TATCCAAATG  28140
CCGAAACTCC TCTTTTTGGA TTCTTTATTT TTGATTATCT TACCATCACA TTTGTAGTCA  28200
GAGGTTCCTA ATGCTTAAAA CCTCTGATCT GAATTTTCTC TCCTCCAATA TAAAACCCCT  28260
TCGTCTTCCT CTTCTTCTTC TTCATTTTTT TTTTTTTTTT TGTCTGAAGA CTTGTCTCAC  28320
TGTGTTGCCC AGGCTGGAGT GTAGTGGTGC GATCACTGCT CACTGCAGCC TTGACCCCCT  28380
GGACTCAAGC TATCCTCGCA CCTCAGCCTC CCGAGTAGCT GGGACTACAG AACATGCCAC  28440
CATGCTCAGC TAATTTTTGT ATTTTTTGTA GAGACAGGGT TTTGCCATAT TGCCTAGGCT  28500
GGTCTTGAAC TCCTAAGCTC AAGCAATCTT CCCGCCTCAG TCTCCAAAGT TCTGGCACTA  28560
CAGGTGTGAG CCACTGTGCC TGGCCTCTTT TTCTCATTTA AATACTTTTC ATACCTTTTG  28620
TAAAACGGGT TCCTTGTTGC CTGTCTATGC CTTCCTCCTC CTTCTTAATG ACACCACGTT  28680
AATTCTGACT GTTTTCCCTT GGCCTGTTGC AGAAGCCTCT TAACTATTAA CCCTTCATTC  28740
TCTCTCTCTG TTTCATCTGA TATATGAGTA CCAAACTAAA TCTTCCTTTA TCATATCTTA  28800
CTTCTGCTTA AATGTTTTTT TTCTAGCTTA GAATTCAAGG CCCTCTATTT ATGAACTTAA  28860
ACTTACTTTT CCCTCTAAGT TACAGAATTT GAAATGGTTT ATCTTACCTG GATTGTTTAT  28920
CACTTGTTGA AGATCCATTT TCAACTTCCA TATATTTATT TACAGTGTTG CTTCTCCTTG  28980
TAGTTTCCTT GATTCCTCAA AACTCCTTTT AAGAATTCTT GAAGATCTCG CTTTATTACT  29040
ATTTCTCGCT TTATTACTGT AAAGACTATG AGAAGGTCTT TCATGATCTT ATCAGCAAAG  29100
TAATTCCTCT CTCTTGAATT CATAGAGGAC TTTCAGATGA ATTCTAAAGA TGCTTCTGTA  29160
GCACTTACCA CACAATNGCT ATATTTTATT TTTTTGTAAT TAGTGGTAAA CAAGTATTAT  29220
TATATCTTNC TAGATTTTAA ACTCCAAATA AAGATACTAG CTCCTTACCT TTTTGTGTGT  29280
CTCCTGTAGC ACCTAGCACA ATGCCTCATA AACAGGAGGT GATCATTAAA TATTTAGAAG  29340
AAATTATTTC CCAAGAATAG TTGCTTGGTA ATTGTATTTG TCTTTTACTT CCTTTTAAAA  29400
AATTGTTTCT GTCACTAAAT TGCATCCAAT AGATGTTACT TGAGTGCAGA ATTTTCTAAT  29460
GACATTACAC AGTGCTACAT CTGACACTAA TTCTTTTGTT AAAAAATAAA TATTCTGGCC  29520
GGGCGCTGTG GCTCACGCTT GTAAATCCCA GGACTTTGGG AGGCCGAGGC GGGCGGATCA  29580
CGAGGTTAGG AGATCGAGGC CATCCTGGCT AACACGGTGA AACCCCGTTT CTACTAAAAA  29640
TACAAAAAAT TAGCCGGGCG TGGTGGCGGG TGCCTGTAGT CCCAGTTACT CTGGCGGCTG  29700
AGGCAGGAGA ATGGCGTGAA CCCGGGAGGC GGAGCTTGCA GTGAGCGGAG ATCGCGCCAC  29760
```

-continued

```
TGCACTCCAG CCTGGGTGAC AGAGCNNNAC TCCGTCTCAA AAAAAAATAA AAAATAAAAA  29820
TAAATAAATA TTCTAAGACC ATACTTTAAT GGAGGTGTTT TTTGTTTTTT TTTGTTTTTT  29880
TTTTTTTTTT TTGGTGATAG AGTTCTCACT CTGTCACCTA GGCTAGAGTG CAGTGGCGCG  29940
ATNCTCNGGC TCACTGCAAC CTCCGCCTCC TGGGTTCAAG CCATTCTCCT GCCTCAGCCT  30000
CCGGAATAGC TGGGACTACA GGTGCGCGCT GCCACCCCCG GCTAATTTTT TGTATTTTAG  30060
TAGAGATGAG GTTTCACTGT GTTGTCCAGG CTGGTGTTGA ACTCCTGAGC TCAGGCAATC  30120
CACCCGCCCC GGCCTCCCAA ATTGTTGGGA TTACAGGCGT GAGCCACAGT GCCTGGCCCA  30180
GAGGAGATAT TTAATGAAAA ATAATAATCA TTAGATAGGC AGATTTTTAG AAGGAGGGCA  30240
TCGAATGGGT TCTTGGATAT TGGACACAAT AAGAAATATT GAGCTAAAAG TCTGAAGGAA  30300
TTGGCAGATA TACTGTTACA GGTAAACACT TTGTAGAAGA AAATAATGAA TGAGACTTTC  30360
TTTTGAGATT TTCTTAGCCT CTTAGTTGTT CCCAGTTAAA GCCTCATATT TTTCCTTTTC  30420
ATGACAATAA AAATAATAAT AAAATCAGTA ATAAAGTGAA TATATGAGAT GTTAACCTGT  30480
TCCTTTATGA CAATGTCCTG TTTACCAATT AACAGTGTGT TTTTGTGGTG ATGGGGGCAA  30540
GACAAATCTT TAAATGGTGG AAAGCAAAGA AAGAAATTAT AAAACATGAT TAGTTGTATT  30600
ATACGTTGTT TTTGGTTGTT GGAAAAACTA TACATTTATT GAGAGAATCA TTAGGAAGCT  30660
GAACATCAGC TATATTGCTG GAGTGATACT GTTTCAGTGG TTTCTTGACC TTTTTGTTGT  30720
TGTTGTTGTT GTTGTTAAAC ACAGACCAAC TACGGTTGAA AACGTAAAAA GGATTGATGG  30780
TGTTTCTGAA GGCAAAGCTG CCATGTTGGC CCCTCTGTTG GAAGTCATCA AACATTTCTG  30840
CCAAACAAAT AGTGTTCAGG TAAAATACTG TGGTTTGCAG GAGCTCTTAG AGAATAAGCA  30900
TTTTTTGTAA CCATTTCAAA AGTACCCTCC AGAAGCAACA TTTGCTCACT TTATTTGCAT  30960
TTCCATACTG GACACTTAGA AAATGAATTA AAATTGTTTT TACAGTCAAT CNNTGTTGTA  31020
AAAACATGTC AGTTATCTAC TTTTAAAGAT GATACTAAAA AGTAGTTGTC CAGGCTGCTG  31080
ATGTCTTTCT ATTTCATTGG GAGGTTTTGT TTTTAAATTG GAAACATTAT TTTAGGTTGA  31140
TAAATTATAA TTTTACATTC AAATGTGGTA GTTGGAATTT AAAGCTGGAA AGTTATCCTT  31200
GCTATGAGTT GGTCAGGAGC TCAGCCACTT TCTTTTGGTT TAGCATCTTC TCTAATCTCC  31260
CTCCCCTTCC AGTAATGCTG TCTTTTGATA GTAAGTGGAT TTCATATTAT TCTCTTCAGT  31320
TTTAATAGTG TTTCCTTCAT ATCCTTTTAT TATTGCTTGT TCTGCCCTAA GTGACCATTT  31380
CCAGAAATGT CATTTAGGNA TTTTCTCTAA ACTCCACGTA GCAGACTCTA TAATGCATAC  31440
TCTGCAGAAG GTGAGGCAGT GGGAGGTAGA GGGGAGACTA CTAGACTAGG AGTCACGGAA  31500
TCAGGACTTT AGTTCTTCCT TACAGTTGTT CACCTGGTGA ACCTGCACAT GTCCTTTAAT  31560
TTCCTTGGGT CTCCATTTCC TCAGCTATAC AATGGAAATG ACACTTCCTC CCCCACATCC  31620
AGGAAACAAC AGATGACATT AGAAAATAGA AGACATGGGA TAAGTATAAA ATGTTGAAAG  31680
AGTTAAACAC ATTCAAGGCA ATATTAAGGG ATTATTTTTT ACTTCCAAGA AGCTCCTGGA  31740
AGCTTTGGGC AGGCACAGTT GGATCCTACT TTAGAAAAAT CTTTCTCTAA CTATAAGTAG  31800
AAAACCCTTC TGCTTTTTGA ATGTAGCATT TCCCTCTTTT GATATAGAGT ATCTTTGGCA  31860
ACTTTGAATT TTCTTTTTCA TACTCTTATA TAAGACATCA TGTGAAAATT CTTATTTCTT  31920
ACTGAGTTTT TGGAAATGAA ATTATAATGT CTTAATAGTT TGAGAAAGAA TATCATACCT  31980
ACCAGCGGTA ATTGAGTAAG TTCCCTCTCT TTGGACACTT GAAAGTAGTA TCTTCTTTCA  32040
TGAATTAGTG ATATTATTTA ATAATGAATG AGTGATCTCT CCTAACTCCC CTTCAGAAGA  32100
```

-continued

```
GGAAAATGAA GTAGGGGAAA AGGTAAATTC CCCAAGGGAT AGGTATGAAA CCTTTATGAA  32160
CCTTCTGGAT AGAGAAGATG ACTGCTGATT TCTGTGATTA GAAATTATAC TTGGGTTATT  32220
CTGCAAATTG AAATGAATTA TTTAAAAAAA AACAACTTTA ATGTTTATTA AGCAAGTTTT  32280
GTTATTCATG AGTTTCATTA GCCTTTTATT TTTTTTTTAA ATTTTGAAGT AAAATTTCTT  32340
GCTGTCACAA TACACATTAA AAATTACAAA TATGACACAT ATTAAACACA TTAAGATGGC  32400
CGAATAGGAA AAATATGCTA AAATATTTTT ATATAAATAC ATTTTTTGAG AATTTTGAGA  32460
ATTTCTGGAA CAAAGTAATG ATATAATCCA TAAATGTACA ATTAAAGAGT TTAAGGATAT  32520
CCAAAATACT TGGCAAAGTA ATCTGAAATA ATACTCTTAG GAAGGTAGGG CAAGAATGTG  32580
ATTCTAGTAA GCAAAAATGT AATCAAATCG TATTCTAGTC CCAGCTACTC GGGAGGCTGA  32640
GGCAGGAGAA TGGCGTGAAC CTGGGAGGCG GAGCTTGGAG TAAGCCGAGA TCGTGCCACT  32700
GCACTCCAGC CTGGGCGACA GAGCGAGACT CCATCTCAAA AAAAAAAAAA GACTATATGA  32760
ACTTGTATGG CATAAATATG TACAAATATT ATTTATTTTA AAAAAATTCA GGGGTAGGGA  32820
CAGGGTAGTT AGAAAATATC TAAGGATGTT CATGAAATAA TACTGGCTAT GAATGACAGT  32880
TGATGAAACC GGGTGGTGCC CNATCTTATT CCCTCGACTC GTGTATATGT TTGATATATC  32940
CCACAATAAA CCTTAAAAAA AAAAAGNATG AGTGGTCAAT TATAGGAAGA TATAAATAGA  33000
AAAGGCAATA AGGACAAAAG TTGGCAAAGC TTACCTAAGC ACTCTTCAGA TAAAAAGACA  33060
TTTTTGCTAA CTAGATTTGA ATATTATAGT TTAATTGTCA AGGAAAATGC CTCAACTTAA  33120
TCTTTGTTAA GAGACTACTT AAGGCACTAT CAGAAGTTCC CTCATGGCAA GGTGCAATCC  33180
CTCATGCCTG TAATCCCAGC ACTTTGGGAG GCCAAGGCAG GCAGGTTACC TGAGGCCAGG  33240
AGTTAGAAAA CAACCTGGGA AACATAGTGA GACCCGACCT CTACAAAAAC AATTTCTTAA  33300
AATTAGCCAG GCATGGTGGT GCTAGCCTGT AATCCCAGCT ATTTAGGATG CTTAGGCAGG  33360
AGGATTGCTT GAGCCCGGGG ATTTGAGGCT GCAGTGAGCC ATCATTGTGC CACAATACTC  33420
CAGCCTGAGT GATAGAAAAA AAAAAAAAAA GTGTCTTTGT TATATTCCAA ACTTGTTCTC  33480
AACTTTCAGG TGAGCTGGCT TCCTGTATAA CTCTTGTATA GGACAGAACA TACTGGTTGG  33540
GGCAAGTGAA ACTGTCTAGT TGTATGCCTC ATAAATTAAT GAATTTCCTT TCTAATATAT  33600
ACACTGATAT TTATACACAC ATACACATAA AACCAAGCTC AATAGATGGG TAGTGCAGCT  33660
CTATTCCCCA AAACCCAACT ACCCTGTAAC AAGACACATT AGACTTTTGA GATTGCAAGG  33720
ATGAGGACTG AAATGCTGGC CTAGACCATG GTGTTGCCAT AGTGGGGTGA CCAGTCTGAA  33780
TAGCCAACAA TGCTTCCTCA GTAAATACCC ATTTTGTCTT GGTGGGATTT CTACAAATTG  33840
CAAAATGCAG CTATTATGAA GCTGTAAAAG AGNAAACANG AAACATGTAA CACCTGGGAC  33900
TGTTTTATTA GGCCCACCGT ATGCTCAGAA CATGAAATCT CCACTGCTAG GGTTATTTGA  33960
TTGAAATTAT CTTTTGTGTT GATGTGAGAG TTTAGCTCTG AGATTCTTCC ACATGTAAAA  34020
TGTAATCCCC CAAAGTATTT GGCAAGCACA TTTTATTGCC TTGGGTCAGA TAATTGAAAC  34080
ATTAGGCATC ATATATATAG CATGTAAAAA GTAAAACAGA AACATTTATG TTTCTCACCA  34140
AGCAGTAAAT TAGTACTCAA CTAATAAATT TCTTAAACTC CCTAATAACA GAATATGGAA  34200
ACAAAAAATA AATCTTTCCA AAAGAAGAGC TCATGGACAC ATTTCCTCAT ATATGTATAC  34260
ATAATATAGT AGAACACATG ATAAATAACC TATAAAAATG ATACCAATAT CATTCATCAA  34320
GAGACGAGGC TCTTCTTTAA ATTATTAATT TCATCTGTTA CAGGTTTTAT TATGACTGTA  34380
GTATGCTGTT TTCATCTACC TTTTATGTGT AGTTAAAAAA ATAGTTTTCT ATCTCTTTAC  34440
CTTTATTTCA GCCTTTAAAA AGATTCCATT ATTTTTTCAT TAATCTTGTT TTTCAGTTTT  34500
```

-continued

```
TCCCATTTTT TCTTTTAAAC ATTTCTTAAG GAACCATATT TAAGATTTTA TAGAATACTT  34560
AGATTTCTAG TTGGGATGTA TCATTTAAAA TTAGATATGT AGAGAGAGTG TTATGATATA  34620
TTTCCTTACG ATATATTAGT GGTTATAGTA CCTAAATTTG AATAGTGATT CTGTTCATTC  34680
ATTCATTCAT TCATTCAATA TTCACTTCCA GGAGATTGGG GACTTATTTA AAGACAGAGT  34740
AGTTCACATT ATAGTTCCTT TTTTTAGTCC TTCTTATTCG TTAAAGAAAA GACTAGGAAA  34800
TGTTTGTTAT TACAAATATT TTATTAAAAT TTTGTGTGCT CTAGCATTAT TTTACCTTTT  34860
AAAATCAATA TGTTAAAAAT CCAACTTCTT TTTGAGCTCC CCATAAAAAG GGAATTATTT  34920
GTTGCTTATG GGTTTAACTT GTGTTATTTT TTTCTTAATG GCTAATTATC ATACATATAT  34980
TCTATTATTG TATTGATATT ACTGATCATT TGTGCTACAT TAAAAATTCT GTAGACAGAC  35040
CTCTTTTCAA GTACAAAACC TCAAGAAGAA CAGAAGACGA GTCTGGTAGC AAAAAATAAA  35100
ATATGCACAC TTTCACAGTC TATGGCCATC ACATACTCTT TATTCCAAGA AAAGAAGATG  35160
CCTTTGGTAA GTGTGACTTT CATGTTACAG GGAATTTTTT TAGTTTACTT AAACTTGTGT  35220
TTTATCAGCT TTTTAGTATT AAAGTTCTGA CTTGGGATCA ATTTCCTCCA ACCCTACAAT  35280
AAATCTCAGT TTATCTTTAA TTTTAAAAGA GAATGTTGTT TTCTTTTTCT GTTAAGCCTC  35340
CCTGTTAAGT AATAGCAGCA AGTTTAGTTT GGCCATGAAT ATCTTCTAGA GATTGTATCG  35400
GGGTACTGAT AAACACATTT ATAGCTCAGG GATACTGCAT CAGCCATATT TTAAAATGGG  35460
ACTAACAGTT TAAAAACTAT AAATATTCAC AGTGTTAAGA AACAATCTCA AGATGCATTA  35520
AGAAAAAGGA AGGTGCAAAA CAGAAAAACA AACGTAAACG TGTGTGCATA TGCATGCTTA  35580
TATAGTCACA TATTCTTGTA TGTGTACAAA AAATACACAC TGGATCTCTG CAAGCATAGC  35640
CAAGCAACTG GAAATATGTT TTTAAAAACT TGCTTTTCAT TCTATCTCTT CTAGTACTGT  35700
TTTGATGCTC TTTGAAAACA ATCTAATTGC TGTAACAAAT GACCATACGT AGGCCGGGTG  35760
TGGTGGCTCA TGCCTGTAAT CCCAGCACTT CGGGAGGCTG AGGCAGGCAG ATCATTTGAG  35820
GCCAGGGATT TGAGACCAGT TGGACAACAT AGGGAGACCC TGTCTTTACT AAAAATACAA  35880
AAATTAGCTG GGCGTAGTGA CGCATGCCTG TAATCCCAGA TACTTGGGAG GCGGAGACAT  35940
GGGACTTGCA TGAACCCAGG AGGCAGAGGT TGCAGTGAGC TGAGATTGCG ACACTGCATT  36000
CCAACCTGGG CGACCGAGCA AGACGCGGTC TCCAAAAAAA AAAAAAAAAA AGACCATATG  36060
TAATGTTTCT TCATTGTTCT AAGATAAATC TTTAAGGCTG TTGAGGTTTT TTGTATACAA  36120
AATGGAGAGT AAGTTTTAAT GGGATGGGAC AAAATGAGGC TTACAGTTGA GTTTAATTTG  36180
AGTTCACATC CTGTTGACAT TAAGTTGATT TGGAACAAGT GATATGGTCC AATGCCTGCT  36240
TTTCTATTGT CTGTGGTTCC ATCCACTAGT GCCTGTGTTA CACACCTCTT GTTCAGGTTT  36300
TATCATTTAA AATAAATAAG AATAAACAGT CCATAGCTTA TCTTACTTAC TGAATAAATG  36360
CTCTGATTTG ACAGTCATGT TTCTTAAAGT TCCTTACAAA GGCCATTGCC CAAGAAACCA  36420
AATAATTCCA TTATACTATT TTTGAAATAG AACACATAAT AAATGGGAAT TTTAAGTTCA  36480
GTTTCTTATG TAAACAATAA CTTCTATGTA CATGTTAAAT ATGCCTGTAT ATACCTAATT  36540
TGACCATGTA TGTATAGTAG AAATGAAAAC AGTTACTAAG AAAATTTGTT ATTGGCTCCA  36600
AATTTTCTGA ATTAAGTGTA TTNCTAATGC TCAGCCATAA TATGGGGTTT CATGTGTTAG  36660
TTTATGTATT CATGGTTAAA AATGTGAAGA CTGTTATATC TTCATTTGTG TCTTTTGGTA  36720
TTATTTGGTT GTATTTTATT GTGTGATATG GTGGTATAAT TATCCTTACC TCCCAGGAGT  36780
TTGAGAGGGT CTTGCCAGTT AACCGCAGAA TTAAACATGC CTAGGACTAA TTAATCAGGA  36840
```

-continued

```
GCAATACTAC AATTAATTGG AGGTAATTTG AAACCTGGTT TCAAATAACC CTGATATTAT  36900
GCACACATGG TGCACACTTT TCTAGTAGAC ATTTAATGAA AGTAATTTAA AACCTACCTT  36960
TGAAGGATGA AAAACATTGC CTTAAATGCT CTATTCTGTG AAAGTATCAA CATTTATGCA  37020
AATACAGTCT AAATTCAGAC TTTGAAAATG TATTGAAAGA GAGGATCATG AAATAAGTTA  37080
GAGCTGAGTG ACAAAGCTTT CTGAGTGTTT AAAAGAATGT TTTACCTAAT AAATATCTGA  37140
AATGTATTTG GAGCCACATT TGTTTAAAGA ACTGTATAAA TATGTAGCAC TGTTCATGTG  37200
AAGTTCAATA GTAGGAAAAT GCTGACAGCC CTTGTGGAAC TGTGGTTATT ATTATTTTAT  37260
GAATAGAGCC AATTTCAAAC ACCTATTAGA GTCTTCTCAG GAACATTTTA TAGAATGCAT  37320
CTGGAGCCTT ATGTTATCTC TAAGCATTTT AGGATTTGTC TTCTTGGAAA TTCATGTAAC  37380
CAAACCACCA TGTGTTATTT CAAGTGTATA TAGTATTGGG TTACAGTTTA CTATGTTTTC  37440
AGAAGGTTGT GACAACTATT AGACTTACAG AGAATGACTT CTCTGCCACT AACGGCTTTC  37500
TAAAGTGAAT AGAGAGGGGC GAGGATTGAA TTCTTCGGTA AAGCTGGGTG ATTTTGTTTT  37560
ATTCAATACA GTATAATAAG TATAAAAAGT AGAACCTATA GAGAGCTATA ATGGGGGTAG  37620
TTTTAAAGAA ATTCTGAAAA TGAAAAACTT AAGTAAAGGT TTAGTTCATT GTTTATTTCA  37680
CACTGAGCAT TTACTACCTG AATGTTTTGG ACATTTTATT TCCATGACTG GAGTGGACAC  37740
TTTTACAACT CACTGGGTTC TTTGCTGATC TTTCTCTAGA AGAGCATAGC TGAGAGCAGG  37800
ATTCTGCCTC TCATGACAAT TGGCATGCAC TTATCCCAAG CGGTGAAAGC TGGCTGCCCC  37860
CTTGATTTGG AGCGAGCAGG CCTGACTCCA GAGGTTCAGA AGATTATTGC TGATGTTATC  37920
CGAAACCCTC CCGTCAACTC AGGTGAGAGG CATGGCCTAG CTCTGCACCC TTAATGACTT  37980
GATGAAGTAA ACAAGCAATC CACTATATTT TTCACTGTTA ACAGCATTAA TCCTTTATGC  38040
TATTATGAAA ACCTTACTTT TGTGATTCTT TTTCTTGTTT TAGGAAAACA ATCTTTCTTC  38100
CCATTATCAC TCAGAGGAAA GTATACTGAG AAATTTTTTT GTTTTGTTTT GTTTTTTGAG  38160
ACAGAGTCTT GCTCTCTTGT CTAGGCTGGA GTGCAGTGGC GTGATCTTGG CTCGCTGCAA  38220
CCTCTATCTC CCAGGTTCAA GTGATTCTCT TGCCTCAGCT TCCTGAGTAG CTGGGACTAC  38280
AGGCGTGTGC CACCATGCCC AGCTACTTTT TGTATTTTTT GATAGAGACA GGGTTTTCCA  38340
TGTTGGCTAG GCAGGTCTCG AACTCCTGAC CTCTGATGAT CCGCCCACCT CAGCCTCCCA  38400
AAGTGCTGCG ATTACAGGTG TGAGCCATGG CACCTGGCCA ATACACTGAG AAATTTTTAT  38460
TTTCCTTTTC AGCTTAAGGT TACAACTTCC CCACCATCCA AAACGTGCAC TTTCATTTTT  38520
TTTCTAATTT CTATCTCATC ACTTGCAAAA ACCATATTTT TCTCCACATT CATTCCCAGT  38580
AGCTTCCTGA CTCCTAGTTC TTCCCTAAAT CCTTCTGAGT CCTTGTCATT GGTTTCGCTT  38640
GAGTAGCCTT TCTAATCAAC ACAGTCATTG GTATCAGTTA CTGTGACATG GAAGGGACAG  38700
ACCAAGTTCT GTGGGCCGCT ACGTAGAAGG ATTTCCTGTC ACTTTGCTGC AGAACCTCAG  38760
CTCGCGGAGA GCAAGCCCCT TTGCTTGCCC TGTAGAAATA TTTTAAATTA TTATCCTTTT  38820
TTTTTTNAAC AGAAGTAAAT AGGAGATACG TTAGAGGATT TTCTCTCCTA GATGTGTAAA  38880
TACAAACTTG GGGTCTTATA ACTCAATAAA TCTGATAAAT TTCTTTTGAC TGTTAGGATA  38940
GAGCAGTGGC CATACCAATA GCCTCATCTC CAAAGCTGCA GTGAAGATAC TTTTTACTAC  39000
CTTAAAGTCT TTCCCATTTG TGAACAACTT GTGAACAATT CCCCCCAAGA ATTTGGAAGA  39060
TCACTCTCTG AAAGCACAGT CAATACTGTA CTTAAATGGA TCTGAGCAAA AATAAGTCAC  39120
TTAGAAGACA GGATTATTTC TAGACTTGAG TGTGACTTGA CTGAAGGTCT AAAGAACAAA  39180
CAGCTCCTTC ACTTCCATTG ATCACGGTGG AAGCACAGGG AAAGGACAGA CACGGAGGCA  39240
```

-continued

```
AGTTGGAGTA GTGCTCATCT AAGTTCCAGG GATGCGGGGG AGTGGCCAGG GGACTTCAGG 39300
TATAGTAAAT AAATAACCTA TTTATAAGTT ATGTCAATGT CATGTTTGAA ATAGAAAACC 39360
AAATACTGCA TGTTCTTACT TACAAGCAGG AGCTAAAGTT GGTGCATATG GATATAAAAA 39420
TGAGAACAGG CCGGGCGTGG TGGCTTGTGT CTGTAATCCC AGCACTTTGG GAGACCTAGA 39480
TGGAAGGATT GCTTGAGCTC AGGAGTTCAA GACCAGCCTG AGCAACATAG TGTGACCCCC 39540
ATCTCTACAA AAAATAAGAA AATTAGCCAG ACGTGGTGGC ATATACCTAT AGTCTCAGCT 39600
ACTTGGGAGT CTGAGTCAGG AGGAGTGCTT GAGCTCAGGA GTTTGGGGTT ATAATAAGCT 39660
GTGATCATGC CACTGTGCTC CAGCCTGAGT GACACCCAGA GTGAGAACCT GTCTCAAAAG 39720
GAGAAAAAAA AAAAAGTAAC AGTAGACGCT GGGAACTACT GAGGGGAGGG AAGGAACAAT 39780
GGTTGAAAAG GTGGGAAGGG ACAGTGGTTG AAAAACTACG TGTTGGGTAC TATGCTCACT 39840
ATCTGGGTGA TGGGATCAAT TGTACCTCAA ACCTCAGCAT CCTGCAATAT ACTAATGTTA 39900
CAAACCTGCC CATGTACTAC CTGAATCTAA AGTAAAAGTT ATAATTTAAA AAAATTATAA 39960
TAAAATCAGA AAATAAAGGT CTGAGATGGA AAATTAAAAG ACCAAAGCCA CCCATAAGCA 40020
CAATAAATCC CTCCCCCCAA AAAATTATAT CTATTAAAAA AAGGTGTTGC GCCAGGCACT 40080
GTGGCTCATG CCTATTGCCT ATAATCCTAG CACTTTGGGA GGCCAAGACG GGCAGATGAC 40140
TTGACTTGAG GTCAGGAGTT CAAGACCAGC CTGGCCAACA TGGTGAAACC CTGTCTCTAC 40200
TGAAAATACA AAAATTAGCC AGCAGTGGTG GCATGCGCCT GTAATCCCAG CTACTCAGGA 40260
GACTGAGGCA GGAGAATCGC TTGAACTGGG GAGGCGGAGG TTGCAGTGAG CCGAGATCAT 40320
GCCACTGCAC TTCAGCCTGG GTGACAGAGT GAGACTCTGT CTCAAAAAAA AAAAAAAAAA 40380
AAGACCTTGT ACCCTGACAA GTTTTAGTTT GTGCAGGAAT GACACAATCT AGAATGACTC 40440
AAGATTGGAA AAATCTTTAA ATGTTAATTA CACAATAAGG GTAAAAGGAG AAAAATTACC 40500
TAATGTCATC TGAGCAACAA GAAGAAGAAA TGAAAGGCAT TAAAAATTGG GAAAAATTTA 40560
TATTTGACAG TATCTTAACA ACGAATTCTG CTTCTATATC ACTTCCTAGC TTTCTGATGA 40620
TAACTTCCCG TGCAGATCTG TATGTAAGGA ATGGACGTAG TAGTCATGCT AATCTGAGTA 40680
TTTATCTGTG TGATACTTAC GAATTAACGA TGTAAGTTAA TAAGTTAGCA TTTCGTGAAC 40740
CTGGTTAATA CCATTTGCTA AGGTTAAATT AGCCAAATCC TGAAGTAAGC TGTAAAACAT 40800
CCAAGGTAGG GTAGAGAGGC ATCTTATGAG AAAGCTGGCC AACTCTCCTG GTCACCTTCT 40860
AATCTTCCTA ACTTCAGAAA TCAAGGCAGA GAGAGGAAAA TAGTAATTAC TTTGTAGGAT 40920
TAGATTTATG GTTGTCGAAA CCTTTGTTTC TCCAGTGCAG AATGAGATAG CGTTTTAGGG 40980
AAAGCCAAAG ACTCAGATGT CTTCTTCATG CTCATCGTGT GGAATTTTTC TTCCTTTAGA 41040
AATGTATTGT CTCTCAGGGC TTAAAGCAAT TTGCATCTTT CGATGAGACA TTGAGTAATA 41100
GGCAATATTC TCTGAAATAA TTTGTGCAGG CTGGGCACAG TGGCTCACAC CTGTAATCCC 41160
AGCACTTTGG GAGGCCGAGG CGGGCAGGTC ACTGAGGTCA GGTGTTGGAG ACGAGCCTGA 41220
CCAACATGGT GAAACCCCGT CTCTACTAAA AATACCAAAA TTAGCTGGGC TTGGTGGCAC 41280
ACACCTGTAA TCCCAGCTAC TTGGGAGGCT GAGGCAGGAG AATTGCTTGA ACCCCCATGG 41340
AAGGTGGAGG TTGTGGTGAG CCAAGATTGT GTCATTGTAC TACAGTCTGG ACAACAGAGT 41400
GAGACTCTGT CTCAAAAAAA AAAAAATAGA ATTTGTGCAG TTCCCCCCAC CCCCTTTTTT 41460
TTTTCTGTTG GCATTTTTGC TATCATTTAG CTGCCTTCTT TATATCCTGA AACTTACAGG 41520
TGGTGTTGGT CTAGTCAGTA AGAGCAAAGG CTTTGGGAAT AGATAGATCT GTATTTAGAC 41580
```

-continued

```
CTTGGCTCTA GCATCTCATT GTTATGTGAC CTCCATCAAG TGACCTAATT TCCCTAATAT  41640
TCAATTTCCT CATCTCTAAG ACAGGGAGTT AATATTGCCT CTCTTATAGA ATTGTGAGAA  41700
ATATAGTCAT GTGTCGCTTG ATGATGGGGA TGAATTCTGA GAAATGTGTT GTTGGGCGAT  41760
TTCATTTTGT GGGAACCTCA CAGGGTGGAC TTAAACAAAC CTAGATGGTA TGGCCTACTA  41820
CACACCTAGG CTGTACGGTA TAGCTCCTGT CTTCAAACCT GTACAGCATG TGACTTTACT  41880
GAACACTGTA GGCAATTATA ACACAGTGGT ATTTGTATAT ATAAACATAG TGAAACATAG  41940
AAAAGGCCCA GTAGAAATAC AGTGTAAAAG NATTTTTTAA AAAAGCTGGG CATGGTGGCT  42000
CACGCCTGTA ATCCCAGCAC TTTGGGAGGC CGAGGCAGGC AGATCACTTG AGGTCAGGAG  42060
TTCAAGACCA GCCTGGCCAA CATGATGAAA CTCCGTTTCT ACTAAAAGTA CAAAAATTAG  42120
CTGGGCGTGG TGTTGGGTGC CTGTAATCCC AGCTATTCAG GAGGCTGAGG CAGGAGAATT  42180
GCTTGAACCC AGGAGGTGGA GGTTGCAGTG AGTCAAGATT GTGCCACTGC ACTTCAGCCT  42240
GGGAGACAGA GCGAGACTCT GTCTCNAAAA AAAAAAAAAA AAAAAAGAGA TAAAAAGGTA  42300
CATCTGTACA GGGCACTTAC CACGAATGGA GCTTGCACCC TGGGAGTTGC TCTGGGTAAG  42360
TCAGTGAGTG AGCGGTGAGT GAATGTGAAG ACCTAGGACT GTGCACTGCT GTAGACTTTA  42420
TAAACCCTGT GCACTTAGGC CACACTCACC CCTGTGATAC GAGTCTACCT ACTGTATAAC  42480
GTACCTGCAT ATGTACCCTT GAAACTAAAA CAAAAGTTAA AAAATTTATC TTCTTTTGCC  42540
AATAATAAAT TAACCTTAGC TTACTGTAAT GATTTTTCTT TATGAATTAA AATCTTTTTA  42600
CTCTTTTGTA ATAACACTTG GCTTAAAACA CAAACATATT GTACAGCTAT ACAAATATAT  42660
TTTCTTTATA TCCTTCTTCT CTAAGATTTT TTCTGTTTTT GATTTTGTTA AATTTGTTTT  42720
TACTTTTTAC ATTTTTTTTG TTAAAAACCA AGACAAAAAC CCACACATCA GCCTAGGCCT  42780
ACATGGGCTC AGGATCATCA GTCTCACTAT CTTCCACCTC CACATCTTGT CCCACCAGGT  42840
CTTCAGGGGC AGTCATATGC ATGGGGCTGT CATCTCCTGT GATAACAATG CCTTCTTCTG  42900
GACACCTCCA GAAGGGCCTG CGTGTTTTAC AGTGAACTTC TAAAAAATAA TAAAATGTAT  42960
AGTATAGCAA ACACATAAAC ATAGTAACAT AGTCATTTAT TATCATTTTC AAGTATTATA  43020
TACTGTACAT AATTGTACAT GCTAGACTTT TACACAGCTG GCAGCAAGGT GAGTTTGTTT  43080
ACACCATTAC CACCACAAAC ACATGGGTGA TGCTTTGCAT TGTGATGTTA CGATGGCATG  43140
ATGTCACTAG GTGGTAGGAA CTTTTCAGCT CCATGATAAT CTAATGGATA CTTGTTCCTG  43200
TTGGCTGCCC GTCGTTGACT GCAACATCAT TATGTGGTGC ATGACTGTAA ATTAGATACT  43260
GTTCAGAAAG CTTTGGCACA CTGGTAATAG CAAATGGTGG TGGCAAATAT GATGATGATG  43320
ATGATGATGA TTGAAGACAT AGATGGTAAA ATTTTATGGT GTCTTAAAAG TACCCTCTAA  43380
ATATGATTAT TTTTATAGTC TGTCCTTTTG AATAGGCACT TAAGAATGTA TGAACTTAAT  43440
AAGTATATAA GAAAGAATGT TCCCCAAAAT ATATCTTACA GAGGCATACA ATTTAAGAAT  43500
TCAAACAGGT TGTAATGGGG TGTGTGTGTG TGTGCACACG CGCACGCATG CGTGCTCATT  43560
CACACTAAAG AATTCTTGGG CATATGTTCC TGAATGTCCT AAATGGACAT TCTAACATCA  43620
CTTCATTATG GGCAGAGGGA AATGGTAAAG AAAAATTTCA TATTATATTA TTCAGCCACA  43680
TATTGACAGC ATCTGTTTTA TTTGCCTATG GTAAAGAATT GAAGCACTGT TAATTTGCTT  43740
TTTAAATCAT GTAGGCACAA AGTTATCGAA CTTTAGATTT AGAAATGAAA CTGGAAATCA  43800
TTACACTTTC CCTTTCCTAT CCCCACCCTG TTTTGGAGAG AAAGAGTGTG AGGCTTAGAG  43860
AGTTATAAAA CTGTTTTAAT ACCATGTCTA AGATTAATAA CTGAACAAGT TTCTCTTTTT  43920
ACTCGTGTTA AAGTTGTACT GCCAATTAAC TTAAAAGAAA GAAATATGCA ATTTCTAATC  43980
```

-continued

```
CTGATATAGG ATATGGGTAT ATAAACTCTA ACTTGATGAG TGAAACAAAT TAACTTATTT  44040
ATAATCAGTT TCATATCTTT ATTTATTGAG TGTCTTTAAA TACCCCTTAC CTTTAAAGTA  44100
AGAAATATTA AAATCAAGCA GAATATAATA ATGAAAAATT CTTAAGATAT ACTTACTAAA  44160
AACTTATCGT TCGGTTAATA CACTGTATGT AGGTTGTACA TACAATATGA AAAAGTATAT  44220
TTTTGTAGCC TACTTTTAAA TCCAGAATAG AGGAGGTTAA GAAGGTTGTG ATAACCATGA  44280
GCTCTTTTTT TTTTTTTTTT GAGACAAGGT CTTACTCTGT TTCCCAGGCT GGAGTGCCGT  44340
GGCACAATCA TAGCTTACTG CAGCCTTGAA CTCTTGGGCT CAAGCAAGCC TTCCACTTCA  44400
GCCTTCCAAG TAGCTGGGAC CACACCTGGC TAATTTTTAA GTATTTTTGT AGAGATGAGT  44460
TCTCACTACA TTGCCCAGGC TAGTCTTGAA CCCCTAGCCT TAAGCGATCC TCCCACCTCA  44520
GCCTGCCTAA GTGCTGGGAT TACAGGTGTG AGCCACTGAG CCCAGCCCTC TTTTATTTCT  44580
TTTGATAGTA CACTCATAAT CATTAAACTA TCATTTCTGG ATGTGAGATT GTGCTTTTGG  44640
ATTCTTATTT TTTCTTTATA AAATACTTTT TGTTCTCTTA CTGGAGAAAA CATTGTTGGA  44700
TTATAAATGA TATAACAAGG AATGAGGATA TACATACTAT AATAACGATT CAGATATGTT  44760
ATTTTCATAT TTTATTTAAC TGTAGCCATG CCACAATAAT TTAGAGTTTT AAAGAACAAG  44820
TTTGATTGAA ATCTAAACTT TGTACAATCC TGAATTGAGA AGTTTCCTGT ATTTTATTAT  44880
GACACAATAT TTACCTAAAA ATAGGGTAAT TATGAATTGA GAAAACATAG CTATTAATTT  44940
CATACTCTTA TTTGTTAAGT AGATTTTGTC TGGAAAACTG TTCATATTTA AAGGAGCTTT  45000
GTACCTTTGT ATTCTTTTTG TTTTTCCTTG TTTATATAAT TTTAAACTCT GTTTATGGAT  45060
TTGGGATTCT AACTATGCTA AATAATAAAT TAAGGCATTG AATGAAGTAC CTAGACAGTA  45120
TTTTGATTAA TTTTATTCCC CCATTCTTAA TGTGCATGTA ACTGGAAAAT TAAGAGTGGC  45180
TTCCAAGGGA TCTACTACAA AAGTAAGGTT AATATGATCT CTTTTAAAAC ACTGAAGGCG  45240
TGTAGCCAGT GTTGTCATTA ATTCTGCAGT AGATATTTTC AGCACTTATT TACATGGGAA  45300
GTTAGAGCAG AGTAAGATGC ACCTGTAAAG CTAAATGCCA CTTATTTGCA TATATATAAA  45360
ACGCAGGATG AATTTACCAT AGAAATATAA AGGGTACTTA TAGAAATGTA TTAGAAAAAT  45420
ATATGAATTT TTAACTTATA TCTAGAAGTT AACTTTATAC ATTTAACTTT AAATCATTAA  45480
TAGTGGTTTA ACACCATAAG CGGATGTTTA TGCATCATCA TTTTATGAAC AAAAGACATT  45540
CTAATTTTAG AAATAAAGTG ATTCAAAAGA GAATAAAATA TCTTACTTTT TCTTTTAAAA  45600
TTAATTTGTT TAGCGCATTA CATGATAATA GCTCAAGCTT GTGTGATTTT TCCCTAAAAA  45660
ATTGGTTTAT AAATATTACA TTTATAGTAT GAAGAAATTA ATCATACATA GTTTATTTAT  45720
CTAATTTCTA AATACCCATG GAAGAAAATG AATTTAATGG AATGTAGTTG TGTATTACTT  45780
GGTTTCGAGT GTGGGAAAAT TTATATGGTC TTTCTAAAAC AGCACTGTCA GTAGAAATAC  45840
AATGTGAGCT ACATATGCAA TTTTAAATTT TCTAGTAGCC ACATTTTAAA AAGTAAATGG  45900
ATGCAATTTA TTTTGATAAT ATAATTTAAT TAGTCTACTA TATTTAAAAT TTTATCATTT  45960
CAACATGTAA TCAATATGAA AATTATTAAT GAGATATTTT ACATACTTTT TTCTGTAATA  46020
AGCCTTTGTA ATCAGGTATG TACTTTATAT ATACAACAAA TCTTCTGATG CTAAATTTTA  46080
ACTGGAAATA CTTGATCTGT GTTTAGCTTT TGTAAAATTT ACTGTTGAAC AACGTGGACT  46140
AATGTGCCTA AGTGGTTCCA AACATATTTT AAAATTTGAA GACAAATAAA AGGGAACTCA  46200
AAGTAAATTG GGATACATAC ATACAACAGA ATACTGAGCC ATTAAAAAAT GATGAAATAG  46260
TAAAATTGGG GGAATTTTGA TGATACTAGG ATGATATAAT GACCAAGAGA CAAATACAAT  46320
```

-continued

```
TTTAGTTTGG TTGAGAGATG TGATCATCAC GTTGCTGATT TTACTATGTA TAGAGGTTAT  46380
CTTTTCCTTT CTAAGATTTT GAAACTTTAA TTAGTTAACC CACTTACCTA GTTTCTATTA  46440
GCTGTGTAAC TTTCTCTTCC TGTTTTTTGT TTTGTTTTGT TTTGTTTTTT GCTTTTTAAC  46500
TGCAGTATTT TGAGGAGTCT TGGAGTAGCA AGCTAATCTT TGGAAGAAAG GAAAATATAA  46560
ACCTGAAAAC TAATAATTTA AAGAACGTCT TTTCAGGTTG TCATTTGAAA AATANCTTGA  46620
TTTCTGATCN ACNTGATTTG AATTGAGTGT CAAATATTTG ATATGTTTTG TAAATTAGGT  46680
GAAGATGAGT GAGTAGGTTC TAAACTGCTT GGGTTTACCG CACTCTGGAG CATTGCAGGA  46740
GAATGTGATG TTGGAAGGAA GTGCTGAAAC ATAATTATTG GCTTGCCTAT AGGAGGGTGC  46800
TACATAATTT TAGAAGGTGT CAAGAAATTG ACACAGTCTG AATTAGTTCT GTTGAGTTGC  46860
AAAAAATGTA AAGTTTCTTG ATTCTGAAAA TAAGAAATAT GTTCCCAGAA ATCTCATCTA  46920
GTTAATGTGC TTTTAAAATC ATTGATGTCT CTTGTTATTA CAATAATAGC CATTGAAAGA  46980
ATCTTTTTTA TTAGAATGTT ATTTACAGGT ACGATTAGCT TCTATTTAAA TAAATTATTT  47040
TTATACTTGA TCTTAGGCAA AAGGCCAACA AGTGATCAGA ATAAATTATT TTAAGAGNAA  47100
AACTAATTAT AATTGATATT TGGAATTGGA AGCACAATTT CCTTTAGAAC AATTCCACGA  47160
ATGGTTGTTT TGATTCTCAA GGCAGCCCAC AAAAGACAGT TTGAAACACA ATTTATGCAG  47220
TGTCAATAGT ACTGACCTGA CTTTGGATCT TGGAGGCAGG GGCTTCAGGT GATACCCGAG  47280
TGGAGTTTTT ACTCCATTTC CATTCCGTAA GGCTATAGGC ATTTGAAAGA GGAAACTTTT  47340
CTTTGGCAAC CTTCCACCTT CCTTTCTACA GAATATTTCA GTATTTCTAG CTCATAGGTT  47400
TTCTAAAATA TTCTCTGTAA TTTATTTTGA AATGGAGTTT TTTTATCGTT TACAGATATG  47460
AGTAAAATTA GCCTAATCAG AATGTTAGTT CCTGAAAACA TTGACACGTA CCTTATCCAC  47520
ATGGCAATTG AGATCCTTAA ACATGGTCCT GACAGCGGAC TTCAACCTTC ATGTGATGTC  47580
AACAAAAGGA GATGTTTTCC CGGTTCTGAA GAGATCTGTT CAAGTTCTAA GAGAAGCAAG  47640
GAAGAAGTAG GCATCAATAC TGAGGTATTA ATTATATATA GAATTTTCAT AAAGTGTCAG  47700
TTTGTTCAAT TTGCATATCC TAGTACTAGA ATGCTGTATT TTTTTGAACT GTTATGAATT  47760
CTGATATGAT TACTTTCTCT ATGTGCTACA TTTCCTTTGC TTTTCATAAA TATGATCTGA  47820
GAAAAGTGAT TAAAAAAAAG ACAGTAAAAG GGAGGTTTAG TCCATCTGTT TAGCTTATTA  47880
TGTAGAATGT CAGCTTAAAT TTTACCTGTA CCTCATATTG ACCGTATAGC CTGGAAAATC  47940
TTTCGGAGGT ATAGTTAATG GATTTAAGCA TATGGCAGTT TATGTAGTTA ATGAAAGTGA  48000
AAACAAATTG TATTATAAAT ACCTCCCAAA CTGGTTTATT ATCATTCTAT CATTCTTCAT  48060
GCTCTGTTAG TATGATATTG AATATCTGAG GTACCAGGAT TATTGTTGCT TGTGGCTCTG  48120
AGCATTTCGT AGTGCTTTTG CATGATGAGA GAAAGATTAC AAATTTAGTA TTATGTTAGA  48180
TGGTACGTTT TATTAAAATC AAATGCTTCA AAAATAATTG CTCTGTGTAT GGCATGAGAT  48240
AAATAGCAAT CAGATATATT GTTTAATAAT ATGACTCTAT TAAATGATGG CATAAATTTG  48300
AAAATTTGAC CTTCGGTATC TTCCGGGTCT AAAATTATAT GACTCCATTA TAAATATTTT  48360
GGAAATGATT AACTAAAAAA TTGTTTCAAT TCTTAGTTGG TAAATTCAAT GTGGTAGTAG  48420
GTGGTGGTGA TTATTTTGTA TTAGAGAATT AGGAATTACA CTTAGTTCTA AGGTAATCTT  48480
TATAGGATGT CCAGCAATTA AACCCCTACT TTTTTGAATT GCTTAAAAAT AAGGGAACTG  48540
ATCTTTTTAA ATTCTGTACT TGAGTTACGT CTGTATATAT AGTCATGTCC TAGATAATCT  48600
AATGGAACTT AATTAGTTGG AAATCTTTAT ATTGTTTATA ACTGAACTAG CTATAAGAGG  48660
AACATTAAAG AAAACATATT TTGAGTGGAG GTAATGAAAT TTAGCTTCTA ATGCTCAGCC  48720
```

-continued

```
TTTTATTTCT GTAATCTATA CCAGATACCT AAGACCCTCT TATTGTTTCC CAGCTTCAAC  48780
CTGTCAGTAT AGAAAACGGT GTAACTTACT ATTTTTTCTC AATATTGAAG CACATTTGTA  48840
GTGAAATATT ATTTTAACTA TATATTGCCA TTTTTGCTTT TTCCCTATTT CAGTAACATT  48900
TTTCGCTATT TCAGTAACAT TACATGTCAA CAAGAGAATG GTGGGTATTT TGGGGGGGGT  48960
TGGGTGGGAA GAAATTTTAC TAAGCTTGCT AGATTCTAAA AGGTATACCT TATTTGGCCC  49020
CTTTTCCCCA TTTAGGGGAA CAAGGGTGTT GGGGCTGGGA AGTAGATAAG AGGTGAAGTA  49080
AGTCATCCAA AGCATATGTC TTCATTAGCC TCCCTGTATG AAAAGCTGAT TTCTGTAGAG  49140
TGTTGGAGGC CTACTTTCAG AATCTGTCAT ATGTTAACAT TCATCTTCTC TACTGACCTG  49200
ATTTATATCC CTTAGTCTAT TTCATTTTAT AATTATGACA AAGGATAAAG TCATTAGAAC  49260
AAATTCTTTT TATTAGTTGA CGTATTGTTG TGTTTATATC TCTTGTGTTT GTTATTAAGA  49320
TGGAAGCTCA ATCATGTCCT TGTTTAACAG AAAGGTGATG TCTTGGCATT GATAATTCTG  49380
ATTCAATATC CATAGGTACA TGGTGGATTC TTTAAATATT TAGTATTCTT TTATTTCTGG  49440
AAAGTTTTCT TAAATGATAG TTTTTTTAAA ATTTCATTTC TATAAAGTTT TCTTAAATCA  49500
TACTTTTTAG TGTTTTATTC CATTACTTCA TATTTCTTCT TCAGGAACTC CTGCTATACA  49560
TGTATGTTGG ATCTTCATTA CCCAGCTTCA ATATTTTTCA CTTTTCATGC ATTCTTTTTA  49620
TTTCTTCATT TCTCTTTAAA TTTTTTTCTT CCTTTTCACC TTCTATTTCT CTTTTAACAT  49680
AATTGTATTT ATTTCTGTAT TCCACATAGC TTAGTATTCA CTTATTTTAA AATTATTTTA  49740
AAACGTTTTT TAGATTTAAA AATTCTTTTT TTATTTATAT ATACATATTT TATTTTTACC  49800
AAAGGAGCAA CACTATTAAC TGAAGACTTC TATAATTTTT TTCTTTTATT TCTGATTCTT  49860
TCTTCGGTTT TCCCCCTCAG TTTTGAACTT TTCTAATTTT GATTTGTGAT GTCCTTTTGT  49920
ATTTTAGATA ATTTTCCTAA TGTTTTCCAG CTCATTTGGA AAGGCTACAG TTTTATTCTG  49980
TACCTAAGCA AGTCTTTCTG GTGTCAAAGA TTTGACCTTG ATACTTTTCT TTTGCTCATT  50040
TTCGTATGAG ATTAGTTTTC CTGTACTTTC AAAAGAAGGC GTGGTTCAAG ATGGCTTTCC  50100
CAATTTCACA TCTGTCTCTA ATGTTTTTGT GTAATGTCTA AAATATGGAA ACTTGGTTTA  50160
TGAGATCTAC TCTGCCATTT TTATCTGGGC TTTCTCTTCC TTTTGTCTCT GTTGTACCTG  50220
TCCTGCTTGG TTCTGATTTA ACCCCAGTGG TTTCTCCTGA ATGTGGAGCC TTCTCCTAGA  50280
AGGCAGCCTC GGCTAGTCCC AGGGTTCAGA GTAGCCAGCT GCTCTCTTCA CCTAAGAGAC  50340
CACTGTGGAT TCCTTGTACT CACTTGCTAT TGGCTTGGAC AAAAGCCCTC CCATTTTCAG  50400
ATGCTATTAT CAGATTAATC TCTCATTAAT CTGTCTTTCC AGTGTATGCC TGTGGGCTAT  50460
CTTGGGGTTC TCTTGTTATC AGACACCTCC CTGCTGGCCT CTGCTTTCTC CCGTACAGAT  50520
GTCAGTACTG TGCAGGTCTT AATTGCTGTT GGTGGTTTGC CCCTACATTC TTACAGTTTT  50580
AGTTTCCCAA GGATACCTTT AAACTTGGTT TTATTGTAAA TGTCGACAAT GGATTTTGGG  50640
TTTTACTATC TAGTTCTGTC TTAATTCTGG AATTCAGAAA GATTAAAAGC TCTGTTGTTG  50700
CAGCTGCTGC CACCTCTTCC CAGTACCCTC TCCTCCTATG TCATTTTTTT CTTCTTATTT  50760
TTCTTGACTG TATAAGAGAG AATGTATGAC ATTTCCTGCT TGACCGCTGA GTTTGATTAT  50820
AAATTAAAAT ACACAATATT TTATACAAAT TGTTTTGTAG AAGATTTATT TACAGATGCT  50880
CATTCACAGG TAAAATTGAC TTATGAAAAT AGTTTTCATG ACAAATGTAT CAGGCTCGGT  50940
AACTAAATAT ATGGATTGAT CTTGTTTATA AATGAAATTA AATGTGAATG TAACTTACAT  51000
ATTTCTGTAT TTGCTTACAT CCGTATGTAC ACATATAATC AGCAAATGAG TTGATGTTTC  51060
```

-continued

```
CTATTCGTAA CTTAATGGTA ATAGCTTGGT AACAGAGTTG GGAGTATTAA AAAGATGTAA  51120
AGAGCCCCTT AAAATTTTGT TGCTGGGAAT TTTAGTGTTC TACTGATGAA GGAAATAGAC  51180
ACTGGAAGGT GTTGTTTCTA TTAGGTAACT TAGATATCAT ACTGAAGACT TCAAATACTT  51240
ATTGTTGACA CTCAAAAGAC ACACTTAGTG TAAGTAAGCA TTTCCCCGCT TTTCCCAATG  51300
AAATAAGATC ATTATTATAA TTCCATTATA AATGCTGATG ATCATATTTA TAGAAATATA  51360
GAAGATAAGA CTTGAAATGA TATTCGCTAC CAATTAATGA GTTTGAAGAA GAAATCAGGA  51420
TGTGTTTTGC TATTTTACAT TTATTCTTAT TTAACTCCAA AGAATTCAGT GATGTTATGT  51480
ACTATTATTT CCATTTCTCT GTGAAGACGT TGAAGCTTAA GTAACACGCA TAATAAGGTC  51540
ATACATTTAG CAAGTGGCTC AATTAAAGTT CAAACCTGGT TCTGCCTGGT TTCAAAGTCT  51600
GTGCTACTCC ATGGTATTAG GCTACAACAT GACTTAGGGT TTCTTCCTCT GCTCTATTGC  51660
TGTTCAGATG TACTCCTCTT TTGGCAGAGT GGGAGAAAAT TTTTGCAATC TATGCATCTG  51720
ACAAAGGCCC AATATCCAGA ATCTACAAGG AACCTAAACA AATTTACAAG AAAAAAAAAA  51780
AAACATTAAA AAGTGGGCAA AGGACTTGAT CAGACACATC TCAAAAGAAG ACATTTATGT  51840
AGCCAACAAA CATATGAAGA AAAGCTCAAC ATCACTGATC ATTAGAAAGA TGCAAAATGC  51900
CTTTTCTGTA TGCCACCTTA TATCCCCAGT ATTTATTATT TCTAAGTCAT AGTATCTTAC  51960
AGTGTATATA AGTCTCATCC GTTCTTTTGA TTTTCTCTTC CCTGCTTGCA ATTGGGTACC  52020
TAGGAACAAA GTTGCAATCT TAGCCAGTTT TTTCTTTAGC CTTTGCTGAT GTGTGAAAAG  52080
CCCTTTTTTC TACCCTGGAT TTCTGTACTT AAGCTGGAAC AGCTAAGTTT TTACCTTTTT  52140
TAAATATAAA GTTTCAGAGT CTTCTGCCAA GGATCTTTTG CTGTTTTCCT ACTGTTAAAT  52200
ATTTCAAAGC CTTTTTTAAA CATAGGGAAT ATAATCAAAC ATAGCAAGCA GCTGATGAAC  52260
AATATCTAGA TAGTCTTCAT TATTGAAATG GAATAAATGG TATTTTTGTA TTTTAGGCTA  52320
ACAGACACCT TGTACCTTAG ATAAGGCCAA CCTTCTCATA AAATCCCTCA GTTACTTTTA  52380
TTAATAATAA CCAAATTAAC TCTGGATTCC AGGGTGTACT CATGATGGAA TGATTTCTCT  52440
GTCATGTTAT CCTGAGGATC TAGTACTCTG AGATAACATA AGTGTATGAC ACTTTAGGCT  52500
TATGAAACAC TTAGCTACTT AAATTATTTA ATTTTTTTTC ATGTGCAGAT GGTATTGTAC  52560
CCAAACACTA CCTTTGTGTG TGTGTGTGTG TGNNCGCCTG TGTGTGTGTT TTTGAGACAG  52620
GGTCTTACTC TGCTCAGGCT GGAGTGCAGT GGCGTGATTA TAGCTCACTA CAGCCTTGAC  52680
CTCCTGGGCT CCAGTGATCC TGCCAAAGTG TTGGGATTGC AGGCGTGAGC CACCTCACCC  52740
AGCCTTAAAT TATTTTTTTT TCAAGGATGT TTAACCTGAG GGTTAGAGGC TCTTTGGCAC  52800
GTGAGCTGCT GAAATGTGTG TGAAAGTGTT GTGCACGTGT ATGTTTCTCT TTTTTTCTGG  52860
GAAGTGGATC TGTAGTGATT CTTAGATGAG TCTATGAGAC AAGAAACTTT TATTTTTTTC  52920
ATTTATTTAG CGAATGTTTG TTAAGCGTAC TATGCCTTGG CCACTCTACA GGGTGCTGAT  52980
TGGACCAGTC TGTCTACCTA CCGTTGTAGA TGTTAGAAGC TATATTCTTT TCACATGCCT  53040
AATATAACTC TTTGTGTATG TATACATGCC CAGGCATGTT CCTTCCTCAG AACATTAAAT  53100
TCACCATTTT GGTCAACTCA AAGCAAGTAC ACCATGGGAC ACAGATCTGA AATAATGTCC  53160
AGATTTTTAC TTACTGAATG AGGTGTGTTG NAGTGTATAA GACTACATGA TGAGATGGCA  53220
AGTAATTGCC TGAAGAAATG ATGTAGTGAT TTTGTGTGTC TTATATTTAT TTACTTTTTG  53280
ATCCAGAAAT AAATTATATA GATACCACTA TTTTGTTTGG ATGGGGGAGA AAGGATGGGT  53340
GTGTATTCAG GAACTTATGT TACTTTTTTG CAACTAATAC CCCTTCTCAG TAGTACAAAG  53400
ATTTGATTTC TTTTTCTTTC TATTTCCTAC AGACTTCATC TGCAGAGAGA AAGAGACGAT  53460
```

-continued

TACCTGTGTG GTTTGCCAAA GGAAGTGATA CCAGCAAGAA ATTAATGGAC AAAACGAAAA 53520
GGGGAGGTCT TTTTAGTTAA GCTGGCAATT ACCAGAACAA TTATGTTTCT TGCTGTATTA 53580
TAAGAGGATA GCTATATTTT ATTTCTGAAG AGTAAGGAGT AGTATTTTGG CTTAAAAATC 53640
ATTCTAATTA CAAAGTTCAC TGTTTATTGA AGAACTGGCA TCTTAAATCA GCCTTCCGCA 53700
ATTCATGTAG TTTCTGGGTC TTCTGGGAGC CTACGTGAGT ACATCACCTA ACAGAATATT 53760
AAATTAGACT TCCTGTAAGA TTGCTTTAAG AAACTGTTAC TGTCCTGTTT TCTAATCTCT 53820
TTATTAAAAC AGTGTATTTG GAAAATGTTA TGTGCTCTGA TTTGATATAG ATAACAGATT 53880
AGTAGTTACA TGGTAATTAT GTGATATAAA ATATTCATAT ATTATCAAAA TTCTGTTTTG 53940
TAAATGTAAG AAAGCATAGT TATTTTACAA ATTGTTTTTA CTGTCTTTTG AAGAAGTTCT 54000
TAAATACGTT GTTAAATGGT ATTAGTTGAC CAGGGCAGTG AAAATGAAAC CGCATTTTGG 54060
GTGCCATTAA ATAGGGAAAA AACATGTAAA AAATGTAAAA TGGAGACCAA TTGCACTAGG 54120
CAAGTGTATA TTTTGTATTT TATATACAAT TTCTATTATT TTTCAAGTAA TAAAACAATG 54180
TTTTTCATAC TGAATATTAT ATATATATTT TTTAGCTTTC ATTTACTTAA TTATTTTAAG 54240
TACCTTTATT TTTCCAGGAT GTCAGAATTT GATTCTAATC TCTCTTATGT AGCACATGTG 54300
ACTTAATTTA AAACCTATAC TGTGACACAG AGTTGGGTAA ACGATGATTA TTTAACTTTA 54360
AGCAGTTCAC CATCCATTTC AAAGCCTTTG ATTGGCTTTT TTGTAAATAA AAATAACTTG 54420
TTAAGAAACA AATATATCTG TCATAGAAGA ACTAGAAAAT CCAGGGAAGT GAGAAAAATG 54480
AAAATAAAAA NTCATTCATA GTTTTACTAG TAGCTAATCA CAGTCAACCT CTTTTGTGTA 54540
TCCCACCAGA CTTTTTTATA TTCATTTGTT TTTAGGTAAA ATATAAAAGT CTCGTATATT 54600
CCCATTTTTC TGCATTGCAT TACCAGAAGG TAGTGGCGCC TATTAAATAT GTGATATGTT 54660
GTTGTCCAGC CATGGCTTCT GCATTTGCAT GCTTTTGTGT GTGCATCTGC AATACCCTGT 54720
GAATATCCTG TGTGATGGAG TGGCAAGTAC GCACAGACAC GTCTGCTGCA TGCCTAGGTA 54780
CGAGGCTGTC TCCAGGAGAA GCACTTGTTT GATTATTTGA GTTGCCAATT GAATTTGCTG 54840
CTTTTTTTCA TGGCTTGCCA TTTTCACTGA AAAGAATGAC TAATGAAAAA CGATGATTGG 54900
TTATTAGATT TGGATGTTTG GCAGACATTT TCTCAAAATT GAACTAAGTT GGCCTCTTCA 54960
CGGAAAACAA CTGGTATTTG TTGTGCCAAT GATAAAATTG GAGATTTCTA GCAAAATGTA 55020
TAATTTTGGA AAAGTTGTGT TCCTCCACTG GAAGCTTGAC AGCTTTCCTT AACATAAAGA 55080
CTTCTCTTTC TCTTCGCTTT CACTACTACT ACTACTAATT CTTCTTCTGA TTCTTCTTCT 55140
TCTCCTTCTT CCTTCTTCCT TCCTTCCTCC TCCTCCTCCT TCTTCTTCCT CTTCCTCTTC 55200
TTCTTTCTCT CTTTCCTTCC TTCCCTTCCC TTTCCCTTCC TTCCTTCCTT CCTTCCTGCC 55260
CGTCCGACCG CCCTGCCTTC CTTCCTTCCT TCCTCCCTCC CTCCCTCCCT CCCTCCTTTC 55320
TTTTTCTTTC TCTTTCTTTC TTTCTTTCTC TCTCTCTCTC TCTTTCTTTC TTTTTCTTTC 55380
TCTTTTTCTT TCTTTCAAGC AGTCCTCCCG CCTCAGTCCC CCAAAATAGT GGGATTATAG 55440
GTGTGAGCCA CCATGCACAG CCTTACATAA AGCCTTTTCT AATGAGATGG ATAGTAATTA 55500
ACAAATGTGA GTTTTTGATA TTATATAAAG ATTTTTTCTG TGTTTCGAAG ATCCGTATAA 55560
CTCAGTGAAT CAGTATGTTC TGGATGACTA ATATGTGATG TTAAGAAATC ATGACTGAGG 55620
CCGGGCGCGG TGGCTCACGC CTGTAATCCC AGCACTTTGG GAGGCCGAGG CGGGCGGATC 55680
ACGAGATCAG GAGATCGAGA CCACCCTGGC CAACATGGTG AAACCCCGTC TCTACTAAAA 55740
ATACAAAAAT TAGCTGGGTG TGTTGGTGCG TGCCTATAAT CCCAGCTACT CGGGAGGCTG 55800

-continued

```
AGGCAGGAGA ATCGCTTGAA CTCAGGAGGC GGAGATTGCA GTGAGCTGAG ACTGCGCCAC  55860
TGCACCCCAG CCTGGCGACA GAGCAAGACT CCGTCTCAAA AATAAAAAAA GAAATCATGA  55920
CTGGGTAAAA GATCTGTTCA GAGTACAAGA TGGACCAATG GATTTGATAT ATTTGAATAT  55980
AACAGAGTAT GAAAAAGTTT ATTGATATAG TTTCAGATTA CACACTGCAA CTAATCTTTA  56040
AGAAACTATT ACTTGTCCAC TTTTTGGTAA AATTTCAGAG AACAATGTCC ACCATTATCT  56100
GAACAGGCTA TTAAAATACT CTTCTCTTTT CCAACTACGT GCCTGTGCAA AGTCAGATTT  56160
TTTTCATATA CTTCAGCCAA AACAGCATAT CAAAATGGAT TGAATGCAGA AGTAGATCTG  56220
AGAATACAGC CACTTTTGTT AAGCCAGACA ATGAGATTTG CAAAATGTAA ACAATGCTGC  56280
TGTTCTCAGT TTTTAAAAAT ATGTTTTTTA AAAGTATTTA TGTTAATGTG TACTTGGTTT  56340
ACTACTGCTA TTTTTAAATA AAACAAGAAA CATTTTTAAA TGTCTGTTTT AATTTCTAAA  56400
GTGGTAGTGA TAGATATAAC CCATATTAAT AAAAGCTCTT TGGGGTCCTC AGTGATTTTT  56460
TTTTAAGAGT ATGGAAGGGT TCTCAGACCT AAGAGATTGA GAAATGCTGA TGTAATGTTT  56520
TATTATAAAG GTGTACCATG AATTATGTAC CTTACTTCAT ATTGTTGGAC ATTAAAGTTG  56580
CTTTCAGTTT TTTTGTTTTA AACAGCACTG CTTTGACCTT TTTTAAAAAA TGAGTCAGGG  56640
TCTTGCTGTG TTGCCCAGGT TGGAGTGCAG TGGCTATTCA CAGACATGAT CATAGCATGC  56700
TATAGCCTTG AATTCCTGGG CTCATGTGAT ACTTCTGCTT CAGCCTCCTG AGTAGCTGGG  56760
ACTATAGGCG TGCACCACTA TGCCCAGCTG CTTTGAATAT TCTTGAAATG AAATATGGTA  56820
TAGTCTCATA CCATATCATA GCCAGAGGGG GAGAGAGAGA ATTTTGTTGT TGTTGTTATG  56880
TTATCTGTAG TGGACTTTAT GCCTTCCCAG CATAAATTCT CTCTTTCCCC ATTTTTCGTG  56940
ACCCTTGATT TTTGTTGGGG TTCGTTCCAA GGAGAATAAT TTCCATCTGG ATATTGGATT  57000
GGCACCTGTG ACCTCTTCTG AGCTAGACCC TAGTAACAGC GTTTGGATCT GGGGTAGGTG  57060
TGTGGCCAAC TGAGCTGCTG GTTCATGCCT TTCCTGAAAT GAGCCCTACC TCTGAATATT  57120
TCAGAAACAT GGGACATTAA CTTCCCTTTA CTTACGTTAA ACCCCTTTGA ATGAGGAGTT  57180
GTTTTTCACT TCCAGTTGTG TTCAGTTGTC ACAGAAGCAC AGCGATGTGA TTGGTGGAAG  57240
GACCCGTCAA CAGACCCAGA AGATGTAAAG TGTTTTTAAT CTCAAAGGAT GTGGAATCTC  57300
AGAGATAGTT ACACCGAGTA GAGGATGAAG CGGCTCCTGG ATGGAGGCAG AGGCTTCCTG  57360
GATCTTCAAG TTCTGTATGG GTTGTTGTAT GAGGTTGGTG CAAAAGTGAG GCAGGAGAAT  57420
AGGGTCTGGA GGCAAGGAAA CTAAGGCCGA TTCACACTGA CTTCCTAGAA CTAAATCAAA  57480
AGGAAAACCC CAATTTTCCA GACCTAAATA ACAAAAGTAC CAGATGGCTC CTCCCTTTCA  57540
ACTGCCCCTC CCCCACACCT TTCTGCGTGA CACATGGAAA ATTGAAAGTA TCTCTGGTTG  57600
CTTCTGCGTA GGAATGTAAC TTTGTAACCA ATCAGACGGA TCGCAGGCCA AGTCGCCTGC  57660
ATAGAAATGT AACTTTGTAA CTTCACTTTA GCCTCTGATT GGTTGCTTTC CACAACCAAT  57720
CAGATGCTTG CATAGGGTGT ACCTGTTGTG ACTTCACAAA GTGGTGGAAG TGGTGGAAGT  57780
GGTGGAAGGG TGGAAGGGCT ATTTAAATTT TTATTCATCC TCTGATTGGT TGTTTCACTT  57840
AAGCCTCTAA TTGGTTCTTG AGTCCTGGAG CCTGTGAAGG GTACTTTATT TTCAGTAAAT  57900
GCATGCTTTT TTTGCTTCAT TCTTTCCTTG CTTTGTGCAT TTTGTTCAGT TCTTAGTTCA  57960
AGACACCAAG AGCCTGGACA CCCTCCACTG GTAACAAAAG TAACTGGTGT TTTTGCCATT  58020
AGAAGTAATG GCACAGAACA AGTACATGAG AGCGATTTCT TATGGAAAAT TAAATGGCGC  58080
ATAAGTCGTG TGCTCAGGTA AGGGAGCTGG GAACCGGTAG AGGAAGGTCT CCAACCCACA  58140
CCCGTGGGAT CTCTGAGTCT TTGAAAGTCC GTCCTCACCC TTTGTGAAGA ATGGGAGCAC  58200
```

-continued

GGCTGGACTC GTCACCGGGG GTTTTGGGGG GCTGAACTTG TCATTTGAGG GTGTAGGGAG 58260
GTTGGATGAA TCGCAGGGGT GCAGGGAGGG GGCCCACTGG AGCTCCACCA GGACCCCAGC 58320
ACCCTAGATC CAAACCTGGT CATGCTTCCC ATGCTCAGAG GCAAATCTCC CTCCCCTTGG 58380
GGGGCGGAGT CAGACGAGAC CCCCTCTCCA TCCTTTTCCA GGTCCGGTGG GGGCGGGACT 58440
TTAAAGGTAA AAACAGCAAT TACTTTTGCA CCAACTTATC TTCTAAGTTT CGCTCCCTAC 58500
CACCTGAGTG TGTTTGGAGG CTCTGGCTCA TTGTACCTGC CTGATCACCA GGTGCAAGTA 58560
GCTGGGCCAG AAGGACCTCG GCACGTTACG GAATATTTAC TACAGGAACA GGTGAGCTGA 58620
AGGCGAATTC CCCAGGTGTA GCCTGTGACC ATAGATTCAG ACAAAGCCCT GACTGTTGCC 58680
TGGAATTCAA AAAAGCTGTA GCCCTACCAG ATAGAATAAG AAAAGAATAT AGGATTCTTC 58740
CTATTCAAAT AGGTTGCATA TAATTAAGAG CATGAACGAT CCAATGGAAT GAACTCAAAG 58800
TAGTTTTTGA GTGTAATAGA CTTGAAGTGT CTTATGGAAA AGAATTGCAA AACCACAGAA 58860
ACAGTGAAGA AGGTTAGTTA TAGCCTTGAT GGGGTAGCTG ACTTCAGCAG TCTCAGCTAT 58920
CTGAAAAGTT ATTTACCAGA TTTTGGTTGG GAACATAATC CCTAAATCAT TTGAGATAAT 58980
GTACTTGTTT CCTTACTGGG TAAATGTGTT TAAACCTTGA GNAAAATGTA GACATAAGTA 59040
GNAATATANG AATAAATTAA ACCTTTGGTA GTTATGTTTT AGGATTAAGG ACTAATAAGT 59100
ACATATTTGA TATTTAAGCA TTTGTAATGC TTGAGATAAT TTATCCTACT CAAGTAACAG 59160
ATTACTCTTG TGACTCCAAT GTAAAATATA TCATTGAAAA ATTAGTATCT GCTTGTGATT 59220
TTTAAGTAGA AACCCTGCCA TTTGAAAGGT ATTTGCCTTT ATTATTGGAG ATATTTCATA 59280
TGAATGTTTA ACTTTGTTAT TGCATAGAAG TATTTAAACA GATTTCACTT GCAAGAGAAA 59340
GATATCTAAT AGGTTACTCT TAATCAGTAC TAAATTACTA CAATTACTAT ATTCTATTAA 59400
TATCGATTCA TTAAAACCCA GAGCTTTAAT TATGTCTCAG AAAATTAATT AAACTTTAGC 59460
CTCATAATCA GCTTTATTTT CTAACTCAAT GTTTAAAAAT TGACAAGTAT GTATTATACT 59520
TATTTATGTC TTCATTCAGT AAACATTTGC ATTTGTAGCA TGCAAGACAA CATGCTAGAC 59580
ACACGAAAGA TGGAATAAAT GGAAGAAAAT GCAACACAGA TCTCATGCTT AAGAGGGACA 59640
GATTTACTCT GAAGATTCAA TGAAAAAACA TCCACAAACA ACTTTTCTAC AAGAAACAAA 59700
ACATTTTAAA GAAAACATTT ACTTCAGCCG GGCGCGGTGG CTTACGCCTG TAATCCCAGC 59760
ACTTTGGGAG GGCGAGGTGG GTGCATCACG AGGTCAGAAG TTCGAAACCA GACTGGCCAG 59820
TATGGTGAAA CTGTGTCTCT ACTAAAAATA CAAAAATTAG CCTGGCGTGG TGGTGTGTGC 59880
CTGTGATCCC AGCTACTCAG GAGGCTGAGG CAGGAGAATC GCTTGAACCT GGGAGGCAGA 59940
GGTTGCAGTG AGCTGAGATC AGGCCATTGT GCTCCAGCCT GGGCAACAGA GCGAGACTCC 60000
GACTCAAAAA AAAAAAAAAG AAAAAAAAAA AGAAAACATT TACTTCACAT AATAAGATAT 60060
GAGAAAAAAT GGACTCTCTG AATGAAAAAA AGAGGAGATC ATGTGAAAGA TTTGCGCTTT 60120
TTTTTTTTTT AAAGTTATGG ACTGAAACAC TCCTAATCAT TAACATTTGT TATTTTAGGG 60180
GAGTGGAATT GGAAAGGTGG AAAGGGCTAT TTACATTTTT ATAATCTCCA TGTCTTTTAA 60240
ATCAATATAT ATTGCATTTA TTCTTTTAGT TAAAATTTTA AGAACTCTAT AAAAAATAGA 60300
GACAGGGACT CCCTTTGTTA CCCAGGCTGG TCTCAAACTC CTGGGATTAA GTGATCCTCC 60360
CACCTCAATT AGAAGGGTGG AAGGGCCAGC TGTTTAAGTT TCTATAATCT CTGTTAAATC 60420
AAATGTATAT TGCATTTATT ATTTTAAATT TTAAAAACTT TTTTAAAAAT AGAGATGGGA 60480
TCTTCCTATG TTGTCCAGGC TGGTTGTGAG CTCCTAGGAT CAAGTGATTC TCCCGCCTTG 60540

-continued

```
ACCTTTCAAA GAGCTGGGAT TACAGGCATG AGCCACCATG CCCAGCCTAT TTATTTGTTT  60600
ATTTATTTTT AGAGGCAGGG TCTCACTCTC ACTAGACTGA AGTGCAGTGG TGTGATCATA  60660
GCTCACTGCA GTCTCAAACT CCTGGACTCA AGCAATCAAC TAGCCTCAGC CTCTGAGTAC  60720
TGAGATGACA GGCATGTGCC TTCATACCCA GCTAATATTT TTGTAGAGAT GGGGTCTTCC  60780
TGTGTTGCCC GGAAGAGTCT CAAACTCTTG GCCTCAGCCT CCCAAAGCAC TGGGATTGCA  60840
GGCATGAGCC ACAACACATG GCCCTGCTTT TAAAAAATAT ATAGTGGGCC AGGCTTTCTG  60900
GGATGATGGG CAACCATTAC ATTTGCTTTC TCTCCATTCT GAATGTCAGC CTCCATACAC  60960
CTCTCTTGAG CCATCTCTTG ATGCCCAGGA CTGGCAGGCA AGCAGGATGT TAGGGTGCTG  61020
GCTGGAGGGC TGGAAAGCCC CAGGGCAAGG ATATGAACGT GAAGGATTTT AAGGAGATTC  61080
TTGGACCTCA AGGGAACTTT TGGTCCTGGT TTCCTAGAGT ATGTTAGATC TTCTTGGCCC  61140
CCAAAGAATC AAGGAAAAGC TGAATAGGTG GACCGAATCC TTTCCAGCAC TGAGGCTGGG  61200
AGAACTCTAT GACACCAGTG GGTGCTCATC CTGGTGCTGC CATGGACCTG ACTACCTACT  61260
TCCGCTAAAC TCTCCAGCAG CTGAGCCTTC AAGAGAAGAC GTCCTCCACC TTTTCCATGA  61320
GATGAAGAAT CCTTGGGGCC AGGGGATGTG CTCACTAGCT CACACCTGTC TCCATCCTCT  61380
AGACCATGCT TGCAGTACAC AGGACCCCAG AATGCCTGGC CCAAACACTC GTGAGCCTCC  61440
AGGGGCTGCA GGGGCTTCTG GCCTTGTTTC CCCATCTGAT GAGTTCGTTT CTTGGTCTGA  61500
AAGATTGTGA CAGTTACTAC GAGACTGAAT GAAGGGGGAT GAATGCAGAA ATGAAAACTT  61560
AAGACAAAAG TAACTTTTAA TGAGAGGGGC CGAGGGAAGA AGAAGAGGGC TCCCTGCTTC  61620
TAATGAGCAA AGGCAGCCAC CCTGAGCTTC TACAGCCCTT CGTATTTATT GAGTAGAAAG  61680
AGCAGGGAGG AGGAGGTAAT GATTGGTCAG CTGCTGGATT GATCACAGGT TCATATTATT  61740
GCTAACAGGC TTCAGATGTG CCTGATCACA AGAAACACTT GCGCCTGGGC ATGACTGCCC  61800
TCAGCATTCC TTCTGGGCGG CAGATGCAGT TTGTCAGTTT GCTAACAACC TGCTTTCATG  61860
AGAACAGTTT GCTGCTTACT TACACAGCCA CCAGTGATTT ACTGAGTTGA TCACGACCCT  61920
CACTCTTTCG GCCTCCAACA AAAGACGATC AAAGAATGGT TGTTTGCAGA GGTTATGGAC  61980
AAGACTTGAT GTCCAGGCCG AGTGTCCGTA TGCACAGGAG CCTCTTGGTG GTGCAGAGTG  62040
AAGCCAGAGG AGGAGGAGTG GGTTGTGTCC ATGGGCTGAT TCTCCCTGCA CCAACAGGAC  62100
AGAATCCTAA GGAATCCGAG CATTTGAAAT TCAAATCTGG TCTTACAGGT TGTTATGTAT  62160
TTGTCTAGGT AGGAGGCTAG AATGTATTGA AATGGGGTTA GCCTGACATA TTTATATATT  62220
TCATATTTAG GCTTCCATTT GTTCCTTTGT CTTGGGTCCC AAAAATATAT TAGAGGTGGG  62280
CCTGTCTGTT CTCTTGGACA CGAGGACCTC AACGAGTTTC CACTGTTCTC TGAATGTTTC  62340
CTTCCTGGTT TTCTGTGTAT ACAATAATTC CTAGTTTTCT GTTATTTACA ATTTTACTTC  62400
CACTTTTTAA AGACAAAAAT GTATGTTTTT TTAGTCAATA TTGATATAGT GGACCAATAT  62460
ATTTTACCGT TATTTTTGCT TACTGTTTTT GTTTTTTTGC CTTCCTCATC TTCTCACTAA  62520
GTTTGTCTGA CTACAGCCAC ACACCATTCA TTCAATACCA ACTCTTTTTT ATTTTTATTT  62580
TTTGGAGAGA GGGTCTCACT CTGTCACCCA GGCTGGAGTG CAGTGGCATG ATCTTGGTTC  62640
ACTGCAGTCT CAAACTCTTG GACTCAAATG TTCTTCCTGC CTCAGCCTCC TGAGTAGCTG  62700
GGACCACAGG TGCACACGAC CATGCCTGGC TAATTAAAAA CAAAACAATT TTTTTTTTTT  62760
TAGAGACGGG GTCTCACTAT GTTGCCTAGG CTGGTTTCAA ACTCCTGGGG TCAAGTGATC  62820
CAATACCAAC TCAACACGTG GTGAGACCCA GTGGTCTAGA CAAACAGCCA CATAGCAATA  62880
TGTTTTTCTC CATGATTCAT ATCCATGTTC GTTTGTTACA AATAACAGG CATGAACATT   62940
```

-continued

```
TTCTTCAGAG AGGGAGATCC CCACTTATCC ATTAATGACT CATTTGGTGT CCATTCCAAA  63000
CTATTAAACT GCAAAAGCAG ACATGAGAAA AGAAACTTAA GTCAATGTTT TTATCACATG  63060
TTGGTGCCAG CCTCCCATAG TGGTGCTAAA TTTATGNAAA TTGCAACAAA ACAAAAACCC  63120
AAACAACCCA ACAACGAAAA GCTATTTAGT GAACACCGTG ACTAACAAGC TTATTAGAAC  63180
TGCTTATCAG AGCTATGTGT GGATTTTGTA GGGGGAAAGA TTTTCTTCCC TCGTAGACAT  63240
TTTGCAAAAT AAAAGTAAAA TATTACCTTT ATGTACGTGG TAGATAGAAT TCCACAAGCT  63300
TCAAATTCAA CGACTCAAAA ATGTTGCTTT TACTTTCCAT ATCTCAGAAG TCACTTTTCT  63360
TTTATTTATT TTTTAGAGAT AGGGTCTCGC TCTGTTGCCC AAGCTGGAGT TGCAGTGGCA  63420
CAATCATAGC TCACTGCAGC CTTGAACTCC TGGGCTCAAG CAGTCCTCTT ATCTCAGCAT  63480
CCTGAGTAGC TGGGACTACA GGCGCATACC ACCACTCCTA GCTGATTTTT AAATTCTGTG  63540
TAGACATAGG ATCTTGCTGT ACTGCCCAGG CTAGTCTTGA ACTCTTGGCC TCAAGTGATC  63600
CTCCCACCTT GGCCTCCTAA AGTGCCGGGA TTGCAGGTGT GAGCCACCAT ACCTGCCCAG  63660
AAATCTCTTA TTTTAAACCC CAATTCCTCC TGATAGTAAA AAAAAAAAAA AAAAAAAAAT  63720
GTCATCTTGG TGTATTTTGG GTAGGCTGGA TCACTTCAAG TTTCCCCCTC CTCCTGAAGC  63780
TCCGACAGAG GCCTGCAAGC CCTGCTGGGA TCTGTCCTCA GTCCCTCTCG GGCTCATCTT  63840
CTACCATCTT GCTGTCACTC CATCTCCCTG TCCTTCCCTT TGCTTCACCC ATACCAGACC  63900
CTGTACTGTT TCTGGAAGAC ACCAGGCATG CTGTGTCTTA GGGGAGAATG TGATTTCACC  63960
AACTAGTGCC GCCCAAGTAA CATGCATTTG CCCTGACTGC TCTTTTCACC TGCTGTGCTG  64020
CTCCCCCAGA TAACCACAGG CAAACCCCGC CAACTCCTAG TTTATTGAAC TATACCATGA  64080
GTAACTTACT TAAAATCTCC ATACCTTGTC CCATTCTCTC TTACCTGTTC CAATACTTAT  64140
TTATGATGTT GATAGATGAT CTCCCTCTAC TAGACTGGAA GCTCCTTGAC AGCGGGGATT  64200
CTTGTCTGTT TTGTTCACTG CTGTGTCTTT AGCACCTGGA GAAATGCCTG GCACACAGCA  64260
GGAACTCAGT AAATAACTGC TGAATAAATA AACATGAATA AATCAATGAA TGGGGATGCC  64320
TAAGTGCTTC GGGATTCTGG TCAAAGCTTT GGCAACTAGG GACGCACAGG GACCCTCATC  64380
ATCTCTGCCT CCTAGGCAGG TATCCACTGA GATCCGCAAT CCCATCTGGT CCTTGGACCA  64440
GTTACCCTTC ATGTTGGCCT CTGTTAAGAT GTCCAGGTTG TATCTGGTCT CCCACACAGC  64500
ATCCCTTTAT TACTACCCCT GGACCTCAGC AGTCAGCCAC ACATTCAGTA AAGGCCACAG  64560
CTCTGCCATC TCCTAGCTAG GGGACTTTGG ACAAATTACT TAGACACTCT GAGCCTCGTT  64620
TGTAACATGC AGAGACGTTG CTGGGATTAG ACACAATGCC TGTAGACCAT TTAACAATTG  64680
CTGTCACACA TGGTTGGTAT TCACTCAGCT GTCGCTATGG AATTAGCAGA CAGAAAAGGC  64740
ACAGCGTCAG TGGCTGGGTG TCCAGAGAGA AGCAGCCTGT CTCTCTAGAT AATACTTGGC  64800
AAAATCACAG CAGTCCGGTG TGTGGCCCTT TACTGACCTT GATTAAAAAT CGGGTGTCAG  64860
CACCCCAAGT GGATCCTTCT TACAGGTGCA GATTCAGACT CATTATCCAA GTTGACAGAG  64920
ACAGAAGTAA ATATTCAACA AATATTTATT GAGCACTTAC TATGTGCCAG GCACTGTTGT  64980
TGTAGGTGCT GGAATACAGC AATGAACAAA AAAAGTGAAA CATTCTTCCT TAGATGGTGG  65040
TAAAGCGATA GGAGGACACA GCAGGGAAGG GGTTTGGACT ATTTCAATTT GGGACAGGAA  65100
ACGCCTTGCT GAGAGAGTGA GGGTTGAGCT CTGGAATTAG CCTGAGTTTG ACCACATGTA  65160
ACTGCAACTT TGAGCAAGTC GATCCACTGT AAGTCTCTTT TATTAACACC ATTGTGTGTA  65220
AGAGGAAATA GAAACTCAGC TAAAGTCGTT GGAGAATTGA ATGTGGTGCA GCATTTAGCA  65280
```

-continued

```
CAGCGCAGGA ATAATAAAAG CCAGCTGTTC TCATCCTTTG CCCATAGAAA AGCTATCCGG  65340
GAAGCCACAT TATAGTCTGA AGGCTGCCTA CTGGTTTGGT CAAAGAAAGG GCAGTTAGAT  65400
AATTTTCATG TTTAATTAAG GGCACGGGGC TAGATTTCTT GAGGTGCCAG AGTAATGCTT  65460
GCTTTTCATG AACAACGGAT ACAAGATATG GGCATTGCAG AACCTTTAAA GAACATAACT  65520
GGAATAATCA AATAACCGAA AGTTCATGAA ATATTCTGGC TCATGAATTA GTTATCTGGT  65580
AAATCACAGT CTGAAAGTCA CAGAATACAA ATTACTTTAA ATTTCCTCCA AAGCTTACTG  65640
AGTAAGGGGA GGGACATTTA AGATGCGGAG GAAGCGCTGA ACTTGCAAGA GGAACAAGGA  65700
GGACGGTGGC TGCTGGAACT CTGTAACCCT TAGAGAAGAT GTGGGTGGGA TTTGGCAAGC  65760
CCCCTAGACT CTCTTTGTTT TGGGTCTTAA TAGGGACAGT TTATTATTTT TAATGACTCG  65820
CGTGAATTGT ATACTGTTTT AAGCATCCAC CAAAAGCCTT TCGGCTTTTT CCCTAATTAG  65880
ACTCATTCTC ACACAGAGAG GAACTGAACT TTTTACCTCT TTGGTTCAAG AGCACCATCT  65940
ACTGGTCAGA TTTGGTAATT TCGGGTTTAT GGCACTGGAA AATCAAAGAG CATTTTGATT  66000
TGGTTGTGTT TGGTTTTGGT CCATTTATCA ATACAGGTTT TTTGGCGGAC AAAATAATGT  66060
GAAAATCAGG GGAATCAGGT GAGGGCATTG GATGTCTCTG TCACAGACGA TGGGGAGCTC  66120
AGCCGATTTT AAGCTTCTAA CCTCAGCTGG TCTGGAGAAG AGCAAACCTG ACAACCAGCA  66180
CGAAGAAAGT AGCTCTGCCT CTGTGGTGTG CTGGACATTC TGGTTACATA GATGGGAAGA  66240
CGAGGCCCTT TCCGACAAAT ATGCAAATCC CCCACATCTC CAAATTTGGT AGCTCTGGGG  66300
CTTAGGGCAG CTTCTGGAAA CAGAACTCAG ACCTAGCCTG CTGGAGCAGG AAGGGCTTCT  66360
GAGAAGATGA TATCTGGACC ATCTAAGGAG TGTAAATAAG AAATAGCCGC CAGGCATGGT  66420
NGCTCACGCC TGTAATCCCA GCACTTTGGG AGGCTGAGGC GGGCAAGTCG CTTGACAAAG  66480
TCAGGAGTTT GAGTCCAGTC GGGGCAACAT GATGAAACCC CATCTCTACA AAAAATACAA  66540
AAATTAGCTG GGTATGGTGG TGCATGCCTG TAGTCCCAGC TACTCTGGAG GCTGAGGTGG  66600
GAGGATCACT TGAGCCTGAG AGGTTGAGGC TGCAGTGAGT CGTGATGGCT GCACTCCAGC  66660
CCGGGCAACA GAGTGAGACC CTATCTTAAA AAAGAAAGAA AAAAGGAAGA GGTCAGGAGT  66720
TTGAGACCAG CATGGCCAAC ATGATGAAAC CCCATCTCTA CTAAAAATAA AAAAAAAATC  66780
AGCTGGGCGT GGTGCATGCG CCTGTAATCC CAGCTACTGG GGAGGTTGAA ACTGGAGGAT  66840
TCCTTGAACC CGGGAGGCGG ACGTTGCAGT GAGCCGAGAC CACACCACTG CACTCCAGCC  66900
TGGGCGATAG AGCGAGACTC CACCTCAAAA AAAAGAAAAA AGAAAAAAGAA AAGAAAAGAA  66960
ATAGCCAGAT GGAGAACAGG GGAAAGGCCA GAAGAGCAGG GGCGTAAAAG GCGTGGAATG  67020
GCATGCGGGG GAGTAACAAG GTTTTTTTTT TTTAAACGGA GTCTCACTCT GTTGCCCAGT  67080
TTGGAGTACA GTGGCGCGAT CTTGGCTCGC TGCAACCTCT ACCTCCCGGG TTCTAGCGAT  67140
TCTCCTGCCT CAGCCTCCTG AGTAGCTGGG ACTACAGGCG TGTGCCACCA CACCTGGCTA  67200
ATTTCTGTAT TTTTAGTAGA GATGGGGTTT CATCATGTTG GCCAGGCTGG TCTCGAACTC  67260
CTGACCTCAA GTGATCTGCC CGCCTCAGCC TCCGAAAGTG CTAGGATTAC AGGCGTGAGC  67320
ACCGTGCCCA GCTAGTAACA AGGTATTGAC TGAACCAGAG TGGGGTGTGT CAAGATCGGG  67380
AATCAGCAAG CAGCACAGGG GGTGTCCTGG GTGGGGATCT GGGGCTCAGG TCTTCCTGCT  67440
ATCCTGCTAC CCACCTGCAC ACTTGTTCGT TTTCTTTCCA CTCATTTTTC TCCCTTGCCC  67500
AGACTTCAGG TCTACCAGCT ACACTTCTTG ATTTCTTTGG CCTTCAAAAT TCGGTTCAAT  67560
AAGGAAAGTT TTAGCATTAT TTTCATATAG GTCCTTGACA TTTCTTGCTA AGGTTATCAT  67620
TAGATTTTTT TTTAATGGTG TAATAGTTCA GGCCTTCACT CAAATGTCAT CTCTCTAGAG  67680
```

-continued

AAGCCTTCCT TAACTACCAT ACCAAAAACG GTTCCAGCGC CGCTACCGTC TATCCCAGCC 67740

TATCCTCTCA CGTCCTGTGG TCCTGAGGTT CTGTGATAAT GTTCTATAAT TCTGTGCTGT 67800

CCAATATGGT AGCCACGAGC CACATGTATT CATATCGTCG TTATTGAGCA CTATATAATG 67860

TGGCTAGTGC AATTGACACA CTACAATTTT AGTTGAATGC AATTTAAATT AATTTACATT 67920

GAAATAGCCA CATGTTTGGC TCACACCTGT AATCCCAGCA CTTTGGGAGG CTGAGGCGGG 67980

TGGATCACCT GAGGTCAAGA GTTCGGGACC AGCCTGGCCA ACATGGTGAA ACCCCATCTC 68040

TACTAAAAAT ACAAAAATTA GCCGGGTGTG GTGGCACGCG CCTGCAATCC CAGCTACTCG 68100

GGAGGCTGAG GCAGGAGAAT CACTTGAACC TGGAGGGTGG AGGTTGCAGT GAGCCAAGAT 68160

TGCACCACTT CACTCCAACC TGGGCAAAAG AGTGACACTC TGTCCAAAAA AAAGAGAAAT 68220

AGCCATATGT GGCTGGTGGC TATTGTATTG GACAGCACAG CTCTGTTTCT CCCACTAGAA 68280

TGTAATTTGA TGAGGGTGGG GACTTGGACT TATTCACAGC TGAATACCTA GAATGGAACA 68340

TAACTGCTAT GTTTTGAATG TTTGTGTCCC TTCCAAAATG TATGTTGAAA CTTAATCCCC 68400

TATATAAGAG TTGAAGAACC TTTTAGAAGG TAATTAGGCC ATGAGGGCAG AGTCCTCATG 68460

GATGGGNATT AGGGTCTTAT AACAGGACTT GAGTCCTCTA TAANGGAACG GAGAGTTCAC 68520

CTTTNCCTTC CCTTCTGCCN ATGTGNAGGA CACAGCGTGT GTCCCCTCTG AAGGACACAG 68580

CGACAAGCCT CCATTTTGGA AGCAGAGAGC AGCCCTCACC AGACACTGAA CCTACTGGCG 68640

CCTTGATCTT GGACCTCCAG CCTCCAGAAC TATGAGAAAT AAACTACTGT TGTTTGTAAA 68700

TTGCCCAGTC TGTGGCATTT TGTTATGAAA ACAGCAAAAA CAGACTAAGA CAAATCAGTT 68760

CTGGCACATA CTAGTAACTC AGTGATTCTT TGTAGAGTGA GCAAACGTGT GAATGAATGA 68820

ATGAATACAT TGTCATGCGC AGCTTTCGTG GGTCGTGAGT ACAAATGAGA AAATACGATC 68880

ATGGTGCCAT TGCAATGGCT TGAAACCCCA GCACTTACTG GCAGGAAGTC TGTCATTTTT 68940

TGCAATTCTC CTTCCCAAGT GTTTCCAGAC TCCCGAGAAG TGCACATGTA TATTTAGGAA 69000

TCAGTTCTCA TCTGCTAGAA CATGGGAAGG GAGTTAGTTG ATAGCAGTTC AGCTGCTTCA 69060

AATGCAGTCC TAGCTGACCC TGGAGGATCC AGGTACCTAT GGGTGCCATC ACGGCCACCT 69120

TTGCACTATC CTGTGAGAAA CTCTCTCCCA TCCTTGGTGA TGTCCTCCTG TGGTAACCTC 69180

AGTGAGAGAA CTCCATTGAT TCCCTAAACC AGAGGTCCCC AACCTTTTTG GCACCAGGGA 69240

CTGGTTTTGT GGGAGACAAT TTTTCCATGG ACCATGGGTG GGGAGGGGGG GATGGTTTTG 69300

GAATAATTCA AGTGCATTAT AATACGTTTA TTGTGTACCT TGTTATTATT ATTACATTGT 69360

AGTATAGAAT AATTATACAA CACACGATAA TGTCTAATCA GTGGGAGCCC TGAGCTTGTT 69420

TTCCTGCAAC TAGACAGTCC CATCTGGGGG TGATGGGACA CAGTGGCAGA TCATCAGGCA 69480

TTAGATTCTC TTAAGGAACA TGCAACCTAG ATCCCTCGCA TACACAGTTC ACAATAGGGC 69540

TCATGCTCCT GTAAGAATCT AACGCTGCTG CTGATCTGAC AGGGGGCGGA GNTCAAGTGG 69600

TAATGTGATG GATGGGGAAC TGCTGTAAAT ACAGTTGAAG CCGCTCACCT CTTGCTTTGT 69660

GGCTGGGGCC TGGGTACCCC TGCCCTAGAC AGTAGACTTC TCAAGGGGAG GGGAAAGAAT 69720

GGGCCAAGGA ACTGTGTCAG TCAAGAGGGC CCCCACTCAA CGGAAACAGA CCAGCCACTG 69780

GTCTCACAGT GCAAGTCAAG GAAGCTGGTC TCAGAGCTGT CCTCAGAGGG GACGCGTGAT 69840

AAGCAGATCA CACCCGGGAA GACTCGGCAT CAAGATGGAG AGGAGGGAAT GCGATGCGCC 69900

TGGTGGCAGC CGTAGGATCT CCTTCCAAGG CCGCACTGGA GGAGAGCTGC CTCCTAAGAA 69960

CAGGAAAGTG AATCAGAGTG AGGCTGTCAT TATAGTAAGA TAAAGAAAGA TGAGTGCTTG 70020

-continued

```
TTTGGGAATC TGGACAGAAT TAGCATCTGC TTGCTTTAGG ATAGTGGCTT CTTTTCTCTC  70080
TTGAACAAAA TACTCTCCTT AATAACTGCA GACCCAGGAT AACATGGAGT CATTGTTCAA  70140
ATTCACCCCG TTGCAGAATT CTCCAGTTAT CAGCATTTGT GTGTGTGTGC GTGTGTACCT  70200
ACATGTGCAC AGATGTATAC ACACACAGAT AAACACACTC CAGGCTTTGG GGAAATCGTA  70260
TTCGTAGATG CCTGTCTCTA CCTTTATTAT GTTAAAGAGA ATTCTGACTC TCAGGTCGTG  70320
GACTTCATTC ATTGTGTTGC TCACATGCAG GAAAAAAAAA AACCAGAATG CAATAAGGAT  70380
AATTCATTGA TTTGTGGGGA AAGAGAAAAT TCATTGTTTT GGGGGGAAAG AGAGAATGTA  70440
TTGATTTGTG GGGAAAGAGT CAATAAGTGA ATGTTTCCTG TTCTAGGACT GGCTTTGCCT  70500
TGTCAATAAT TGATTTTGTT GTTGAGAATA CATTTCAAAG CCTTTAAAGC AGTGTGCAGT  70560
TAAGGATGAT ATTTTTGCTT GAAATGACTA CTTTGCATCA TGTAGAAGGA ATAGTGTCTT  70620
TTAAAGGCAA CAGATGCAAG TCTAGGACCC CAGAGCTTTA GAAGGCTCTG GGCTTCGGGT  70680
ATGTGTCTGA TGTGTTGAGA GTTGCAGGGG ACGGGAGGGA TGTCCACTGT GGGCCAGTTT  70740
CTACCAGCCA CCGAGAAGCT GGAATTTGTT TATTCATTTA TAGAGCAACA GGAACTGGAA  70800
TCGAAATCTG TCAGTCCCTA TGTGCAGGGT GTAATTGAAT TGACTTCTCT GCTCTCAATT  70860
GGAACTTCCT TTGACCTGTA GTGAGAACAT TTTATGGCTC CCTCTAATCT AAAAAGGGTT  70920
TTTTTTTTTT TTTTAACTTT CCTTCCTATT CCCTTGTCTG CTAACCAACA GAGAACTCAG  70980
CCCACAGCCT CACAGACAGA ATGAGAGCAA TGCTTAATCC TTGTTCAGTG AATCTCATGG  71040
CCTCCTCTAG TCTTCAAACT TGGATTCCAA GTGCCTTGAA GAGCCAGACA CAGTGGCTCA  71100
TGCCTGTAAT CCCAACACTA TCGGAGGCTG AGGCAAGGGT GGATCACTTG AGATCAGGAG  71160
TTTAAGACCA GCCTGGCCCA CATGGCGAAA CCCTGATTCT ACAAAACATA CAAAAATTAG  71220
CCAGTCCTAG TGGTGCATGC CTGAAATCCC AGATACTCCA GAGGCTGAGG GAGGAGAATC  71280
ACTTGAACCT GGGAGGTGGA GGTTGCAGTG AGTGGAGATC GCACTACTGC ACTCTACTCT  71340
GTCTCAAATA ATAATAATAT ATATTTTTAA GTGCCTAGAA GAAAGAACTG CACTTCTGCA  71400
GAGAGCGCCT CCAAAGCTCA GGGTAAGTGA CATGCTGCTT ACCATCCTAG AATGGAACCA  71460
GGCCACCCAT CCCCAGGTGG GACAACTGCA CTCCCAGGAT AACCCCTGAG TTATGGGCAG  71520
ACTTGTGTCT CTCCCCAGTT CAGATCTTGA AGTCCTAGAC CCAGTGCCTC AGGATGTAAC  71580
TGTAGATTCT TTAAAGAGTG AATTAAGATG AGGCCATTAC TAAAAGCCTA GACCTGACCA  71640
CTATGCAATC TATGCATGTA ACAAAATTGC ACATGTATCC CATCTCTACA AATTAAAATA  71700
AATAAATAAA ACTACGTCAT TACAGTGGGT CCTAATCCAG TATGACTAGT GTTTTTGTGT  71760
TTGTTTTTGT TTTGAGATGG AGTCTCTGTC ACCTAGGCTG GAGTGCAGTG ACACGACCTC  71820
GGCTCACTGC AACCTCCACT TCCCAGGTTC AAGCAATTCT CCTGCCTCAG CCTCCCGAGC  71880
AGCTGGGATT ACAGGCACGT GCCACCACAT TCAGCTAATT GTTTTGTAAT TTTTTTTTGA  71940
AGTTTTTATT TTTTATTTAT TTATTTTTAA TCTTTTTTTA TTTTATTTTA TTTTTTTACT  72000
TTAAGTTTTA GGGTACATGT GCACAACGTG CAGGTTAGTT ACATATGTAT ACGTGTGCCA  72060
TGCTGGTGCG CTGCACCCAC TAACTCGTCA TCTAGCATTA GGTATATCTC CCAATGCTAT  72120
CCCTCCCCCC TCCCCCCAAC CCACAACAGT CCCCAGAGTG TGATGTTCCC CTTCCTGTGT  72180
CCATGTGTTC TCATTGTTCA ATTCCCACCT ATGAGTGAGA ATATGCGGTG TTTGGTTTTT  72240
TGTTCTTGCG ATAGTTTACT GAGAATGATG ATTTCCAAAT AGAGACAGGG TTTCATCGTG  72300
TTGCCCAGGC TGGTCTCGAA CTCCTGACCT CAAGTGAGTT GCCTGCCTTG GCCTCCCAAA  72360
GTGCTGGGAT TACAGGCGTG AGCCACCACT CCCCGCCTGG TGTTATTAGA AGAAGAGATT  72420
```

-continued

```
AGGACAGAGA CACAGACACA GAGGAAAGGC TGAGTGAGGA CACAGGGAGA AGACAGCCAT  72480
CTGCAAGCCA AGGAGAGAGG CCTCAGAAGA AACCAACCCT ACTGACATCC TGAGCTTGGG  72540
CTTCCAGCAT CTAGAAACTG TGAAAAAATA AATGTCTGCT GTCTAAGCCA CCCAGCCAGT  72600
GGTATTTCGT TGTGGTAGCC CTAACAGACT AATACATGCT GAGTCTCTCA TTGTTCAAAT  72660
CATCCTGTAA AACTGACTCA ACAGGCTTTT TTTGAGCAGG GTTTTCTATT CATGTACTCA  72720
TTAATTTTCC TTAAATTAAA AGTTGCAAAT ACAATATACA AAATTAAAAG TTCAATTAGA  72780
AAAATGAGTT TCTATAATCA GCCTACTCAG AATTAACCAT GGTTTCAAAT AGGGGTTTTG  72840
CTGGTGTTTT TTGTTTTGTT TTGTTTTGAG AGAAAGTTTT GCTCTTGTCT CTCAGGCTGG  72900
AGTGCAATGA CGTGATCTCA TCTCACTGCA ACCTCCACCT CCGGGTTCAA GTGATTCTCC  72960
CGCCTCAGCC TCCCAAGCAG CTGGGATTAC AGGCAAGCGC CACCATGCCC AGCTAATTTT  73020
GTATTTTTAG TAGAGACGGG GTGATCTGCC CTCCTTGGCC TCCCAAAGTG CTGGGATTAC  73080
AGGCGTGAGC CACTGCGCCC GTTAGCTGTT TTGTTTTGAA ATCAACTTTG AAAAATGTTT  73140
TGATATCTCA TCATGTCCCC AATGCCATTT GTAATGGTCA CACAGCATTC TGTTGTATGA  73200
TGTACCATGC TTTATCTAAC CTGTGTCCTA TTTTTGGATA GTTCGAATTT TCCTATTTCT  73260
TTTCACTATT AGAAGCAAGG CTGCAATGGA CATCCTTTTA AATACTTTTT AAAAACAAAA  73320
ACCTTGGTAC AAGTACCTGT ATATAGACTT GCAGGGTCAA AACTTCCCAT TTGATGGCTA  73380
TTGATATGTA CTAACAAATT GTCCTCCAGA AAGTGGTCTT TTCCTCACCC TCATCAGTTC  73440
TTGGTGTTAC CACCTTTTTG CATTTTGCCA AGCTGATAGG TAAAAAAGTG TCTCTTACTA  73500
TTGTATGTAT TGAATTAAAT TTATTTATTT ATTTATTTAG ACAGGGTCTG GTTCTGTCCC  73560
CCAGGTAGGA GTGCAGTGGT GCAATCATAG CTCACTGCAG GCTTCAACTC CTGGGCTCCA  73620
GCAATCCTCC TGCCTCAGCT TCCTAAGTAG CTGGGACTAT AGGTGGGCCC AGCTAATTAA  73680
ATTTTTTTTT TTTTTTTTTT TTTAAGATAC AAGGTCTCAC TACTTCGCCC AAGCTGGTCT  73740
TGAACTCCTG AGCTCAAGAC ATCCTCCCAC CTCAGCCTCC TGAGTTGCTG GGATTACAGG  73800
CAGGAGCCAC TGTGCCTGCT TATTATATAT TTCAAAATAA CGAAAAGAGT GGAATTGCAA  73860
GTTCCTCACA CAAAGAAATG ACAAATGCTT GAGATAATGA TTATCATAAT TATCCTGATT  73920
TGATCACTAC AACTTGTATG CTTATATCAA AATATCACAT ATTTATATTT TTAAAAATTA  73980
TATTTATATT TATGTGATAT TTTGATATAT TTTGTAATGA TCATTTTACA TATGAACATA  74040
TTTATACATA TATACAAACC AAATAAACCA TACATATTTA TACATATGCA CCTATGTACA  74100
AACCAAAGAA ATTGGGATAT AGCTATCCCA GTTCTATTAA AAAATTGAGA TTTTTTTCTT  74160
CTCTATTGAT ATTTCCTACT TTTTTTTTGT TTTGAAAAAT AATTTATCCT TGAGTCAGTT  74220
GTGATGATTT ATACCTGTAT AGAGATTACT AGTTTGATCA AAATCATTTC ATTTATTGTT  74280
AAAAATTGTA TAATGATATT ATCTCCTAAC TGAAAATTTT CCTTTATCTC TGTGATTATA  74340
TTCCATTTCT CATTCATCAT ATTTTCATTT CATTCCAGTT TTCCTTGGTT AGACTTTCCT  74400
ATGATTTGTG TCTTTTACTG TTCTTTTCAA AGAACAGCCT TGGTATTTAT TTATCAATTC  74460
TATTTCTTTT TAATTTCACA ATTAATTGTT TTCTGTTTTT ACCATGACTA ATTCCCACCA  74520
CTGCTTTCAT AGATTAATTT TGTGTTCTTT TTCTAATTTC TTCAATTAAT TTATTTTCAT  74580
TTTTTAAAAA CTTAATAATA AAAGTTCTTA AAGTCCTAAA TCTTTTCCTG AGTACTGTGG  74640
GATTCTTTCC ATGTGCTTCT GCATGTAGTA TGACTATTGC AATTGGTATA GATGGTATTA  74700
CAGTTCTTAC TCCTTCTTAC ATCCAGGGAT TACTAAGGAG ACTGATTTTA AATTTGCAAG  74760
```

-continued

```
AAGTTTGACT TCTAAAAGTG CCAGGCTCCT TTTTGATGTC AAGTCTCACC TATTTCTTCT  74820
GTTTTTCTCT AGTAACTGAG CTCAGGTTTT GTTGAAGGCA GCAAACTACT GGCTAAAACT  74880
GCTCAATGTT TTCCAGCTAA AATTGCTCAA GTATTTCCTG CAGCTAGTTA GGGCAAGTTA  74940
CCTGGCTCTG TCTAGAGAGA TGGAGGTGCA GGTCCTTGGA GACAGAGTAC CCTCTGAACA  75000
AAAAGGCAAA GACTTACCAG CAGAAAACCC ATTTGCCTTT TCCCTTTCCT CCTCACTGAC  75060
ATGCAAGGGT TATGTCTGGA GGTACGAGAA AAGGAAAGCA TAAGGATAAA ATCTAACAGG  75120
CTAAGAATGA CAGGGCAGAA AGATAGAAAG GATCTGTGTC CCCGATGGCA TCGTTGTACC  75180
AGCAAGACTG ATGATCATGA TGTAAGTCAA ATGAATGCCC AGCTGCTGCT GGCTGTGTTT  75240
TTTGTTATTT GCGGCTGAAT GCATTGCTAA TGTAAACATT ACCTTGCAGC CAGAGAATAC  75300
GGCTTGCCAA AAGTCTAGTT TTGTATGTTA ATCATGATAC ACCAGCCAGA CAGAGTGGCC  75360
CTCAGCTGTA ATCCCAGCAC TTGGGGAGGC CAAGGCAGGC GGATCACTTG AGGTTAGGAG  75420
TTCGAGACCA GCCTGACCAA CATGACAAAC CCCCGTCTCT ACTAAAAATG CAAAAATTAG  75480
CTGGGCATGG TGGCTCCTGC CTGTAGTTCC AGCTACACGG GAGGCTGAGG CAGGAGAATC  75540
GCCTGAATGC AGGAGGAGGA GGTTGCAGTG AGCCAAGATG GTGCCATTGC ACTCCAGCCT  75600
GGGCGACAGA GTGAGACTCT GTCTCAAAAA ATAAAAATAA TAATAATAAT GATATGCCAA  75660
CTGCTATAGC ACCTAGACTG CAAAATGTAC ATCACAACAG TCCGATTCTC TGTTCTCTTT  75720
GTTCAGGGGT AAGCATGGAG CTTAATTTTG ATCTATGAGT CAACGTGGGA AGTCCGTTAG  75780
GTTAGAAGTG CTTCTGGTCA AGGTTTCTTT GCTTCTAAAA GAGGAATGTG AGGAAAAAGT  75840
CCCTGTCTTG GTGTGGATTT TGGTGTGGGG GGATGTATAT AAAGCCTGTA GCTATTGAAG  75900
CCATCTGGCA AACTTGAAGG GAGCAGCTGA CTCTGAGCTG GTAGAATATA GAAATGGAAA  75960
GGATTTAGAT CTTGATGTGG TTGAGAGGCT GCCCTCCCTT GGGACTTCTT TTTTGTGTGT  76020
GAGTTAACAA GTTTTCCTTA TTGTTAAGTT GCTTTAGTGG GTTTGCTATT ACTTGTAGTC  76080
AAAACATTTA TTATGGCATC ATCTACTTTA TTCTATCCTT CTGCTTTCCT TATTACAAGT  76140
ATATTTACAA GCTCATTGTC ATTCATGTCA TCATTTTAAT CAGCACCAAC AACAGCATCA  76200
CCAGTAACAT TTATTGAGTG TTTTTAAGTG CCAGGCCCTG TTGTTGTCAT TTAAATCTTA  76260
CACCAATCCC TACTGCTCAG ATACTATTCT TTTTAAAAAT TATTTTTTTT TTAGGCACAG  76320
GATCTTGCTC TGTTGCCCAG GCTGGAGTGC AGTGGCATAA TCATAGCTCA CTGCAGCCTC  76380
AAACTCCTGG GCTCCAGTGA TCTTCCTGCT TCAGTTTCCC AAAGTGCTGG GATTACAGGT  76440
GTGACCACTA CCCCCTGTCC TATTATTATT GATTCAGATT TACAGATGAG GAAAATAAGG  76500
CTTAGGAAGG CTACATAATT TCCTAGATTG CTTATTTAGT AAGCGGCAGA GCCAGGATTC  76560
AAACCCAGAC CTGAGGGACT CCTAGACTAG TCCATGCCAC TGTGATATGG CCTTTCACAT  76620
CTCTTCTTTC ATCCGTCATC ATGATATCTT TCTCCTCTGA GTTCTGGGGA AGTTTCTCAA  76680
GTTGGACTGC CAATTTTCTG CAGGATTTTC CTGTGATATA TAACTCCTTC ATTTACTGCT  76740
TCCATTTTAT TTCATATCAC CTACAATTTC CCTTATGTCT AAAACCAATT GCTCCTATAT  76800
CTAAGATGCA ACGTCCTTCT GAATTATAGT GTTAATGCAA TAGGGTATTT TGAAGGTTTC  76860
TGTATGTTTT CTGTAGAAAA GTTATCTCAA AGGGGGATAT ATACTTCCAT TTCCCAGTGG  76920
TCTACTTCTT TTAAGCCACA AATAGGGCAC TTTCTCTTGT TAGTTTAATC CTACGGGTAT  76980
ATAATTTTCA GTATTTCTAG TGTTAGAATT TGAGATTCAG AGAACTATGA GTCTCTGTTT  77040
TAATCTTTCA GTCCTAGGAA AAGGAGAAAT AGGGCTGCCT ATCTTTTCTG TGGTTTTATT  77100
TTGCCATTTA ATTTCTAATT GACTGTGAGA TGTATCAAGA GATCTGTAGC TCAAGGCAGT  77160
```

-continued

```
TGAATGTCCC AGAGCTTCAC AGCTGAGCCA AGTGACTTCT TTTCCATGTT TATTGTGGCA  77220
GCCAAGGTCA GCAGATGCCA TGCCTCTTGC TCTGAGTGCC TGGACCACCC CCATTAAGAG  77280
CCTCCCACAG CAACAACTCC ACTTGACCCA CGATAAGTGA GGTTGGCACT GTGTCTCTCT  77340
CTTTGTACAT TTTGTTTTCT AAGTTGCTTG TAGGGCCAAG CTTTGAGTCC TTGTTACCAT  77400
CAGCTTAAGC TCCGGCCTCT CTGAATTGGA GGATTTTGTT TGTGTTTGAT TAGAGCCTGT  77460
TGGCAGAAGC AAGTGCCAAA GTCAGACATA AAACAGAAAA CTCTAATGTG GTGTCAAGTC  77520
TTTTCCAGAT GTTACTGATC CTCTTTCTTT TCCTTCTTTT TTTTTTCTTT TTTGTTATTT  77580
TTGATCCCCT TCCTTTTTGC TTCCCTTAGG TTGACCTTTG CTGTCCTACG GGCAGTACAA  77640
AGATTGGGTC TTTCTGTCTC TGCCTCTCCT GCCCTCGGAC TCCTACCATG GGTCTTTTCT  77700
TTTTTTATAG AGATAGGGGT CTCACTTTGT TTATCGTGTT TTTTTTTTTG TTTGTTTTTT  77760
GAGGTGGAGT CTTACTCTGT CACCAGGCTG CAGTGCAGTG GCGTGATCTT GGCTCACTGC  77820
AACCTCCGCC TCCTGGGTTC AAGCGATTCT CCTGCCTCGG CCTCCTGAGT AGCTGGGACT  77880
ACAGGTGTGT GCCACTATGC CCAGTTAATT GTTGTATTTT TACTAGAGAC AAGGTTTCAC  77940
CATGTTGGCC AGGATGGTCT CAATCTCTTG ACCTTGTGAT CCACCCGCCT CAGCTTCCCA  78000
AAGTTCTGGG ATTACAGGTG TGAGCCACAG CGCTCAGCCT GAACTTTTAC TTTTAAGACA  78060
ATTGTAGATT CAAATCCTGT GTCCTCTCTT ACACAGTTTC CTCCAATGGG GGCATTTTAC  78120
AAATATAATA ACCAGGATAT TGACATTGAT ACATTTGATA CAGTCAAGTT ACATTTTCAT  78180
CACCACAAAG ATCCTGGTGT TACTCTTTTA TAGCCATACC TGCCTCCTTC TCCCCTCCCC  78240
CATCCCTCAC GCCGGCAACC ACTAATCTGT TCTCCATTTC TACAATTTTG TCGTTTCAAA  78300
AATGTTATGT AAACAGAATC ATACAGTTTC TCATCTTTAA GATTCGTTCT TTCCTGTTTT  78360
TTTTTTCTTT TTTTTCTTTT CTTTGTTTTT TTGAGATGGA GTCTCACTGT GCCACCCAGG  78420
CTGGAGTGCA CTGGTGTGAT CTCGGCTCAC TGCAACCTCC GCCTCCAAGT TGTGGGTTGA  78480
AGCGATTCTC CTGCCTCAGC CTCCCAAGTA GCTGGGATTA CAGGTGCCTG CCACCACGCT  78540
CGGCTAATTT TTTTTTTGTA TTTTTAGTAC AGACAAGGTT TCACCATGTT GGCCAAGCTG  78600
GTCTCGAGCT CCTGACCTCA GGTGATCTGC CTCGGCCTCC CAACTTGCTG GGATTACAGG  78660
CATGAGCCAC CGCACCCGGC TGAGATTGGC TCTTTCACTC AGCATAATTC CCTGGAGACT  78720
TCATCCAAGT TGTTGCATGT ATCAATAGCT TGTTTCTTTT CATTGCCACC TAGTTTTCAA  78780
TGGTATGAAT GCCGCATTGC TTGTTTCATC AGTCACCTGG TGGAAAACAT CAGGGTTGTT  78840
CCCAGTTTTT AACTATTATG AATAAAGCTG CTATGAACAT TTGTGTACAG GTTTTTGTGT  78900
GAACATATTA TCATTTCTCT GAGATGAATC AATGCCAAAG NAATGCAATG GTATGTTTAG  78960
TTTTATAAGA AACTGCCAAA CTGTTTTCCA GAGTGGCTAT ATGANTTTTG TATTCCTACT  79020
AGCAGTGTAT GAATAATCTA GTTTCTTTAC ATCCTCACCA GCATTTCATG TTCTCAGTAT  79080
TTTTTTTATT TTAGTTAATC CGATATGTAT GTAGTGCAAT ATCACTGTGG TCTTAATTTT  79140
TAGTTCACCA GTGCTAATGA TGTTGAATAT CTTTCATGTA CTTATTTGCC ATCTGTATAT  79200
CCACTTGGTG AAATACTTCA TGTCTTTAAA GAAGACCCAG GATTTCTAAA AAACTGTTGA  79260
GTTTTGAGAA TTTAAGAAAT ATATTCTAGA TACTGGTACT TTGTTGGATA CATGGTTTGT  79320
AAATATGTTC TCCTAGTTTG TAGCTTGTCT TTTCATATGT GTTAAAGCTT ATCTCCCATT  79380
TTATTATTTG TTTTCTGTTT ACTTTGTTTC TTATTCCTCT ATTCTCACTT TGGGTGGATT  79440
ATTTAAATAT TTTTTAAGGT TTCATCTTGA TTTATTTGTA GCATTTTGGG TACATCTCTT  79500
```

-continued

```
TGTACACTTT TCTTAGTGGT TGCCCTGGGT GTTACCATAT ACATATGTCA AGAGTCACAT  79560
TCTGCTGGTG TCAGTGTTTT TCCAGTTGAA GGCAAGTGTG GAAAACTTAC CTCCATTTAG  79620
ATTCCTTTAC TCTTCCCATT TTTAAAACAT GTGTCTCAAG TATTCCCTCT ACATTCATTG  79680
ATCAGCACAC TAGAGAGTGT TATTTTGGCT TTAACCTTCA AATATAATTT AAGACACTCA  79740
GGAGAATAGG ATCATCTATT ATGTTTACCC CTGTCTTTGC CTGTTTTGAT GTTCTTCATT  79800
CTTTTCTAAA GTTTCAAGCA TTCTTCTGTT ATCATTTCCT TTCTGTTTAA AGAACTTCCT  79860
TTAGTCGTTC TTTAAGGACA GATTTACTAG CAACAGATTC TCAGTTTTCC TTCATCTGAG  79920
AATGTCTTTA TTTCCCCTGC ATTCCTGAAG GATATTTTCA CCTGATATGG AATTTGTGAG  79980
TGATAGTTCT TTTTCCTCTA AGCACTTGAA AAATGTTATG CCACTTTCTG CTGTCTTTTA  80040
TGGTTTCCGA AGAGAAATCC ACTTTCATTC AAACTGTCAT TTCCCTGTAA GTAATGGATG  80100
TTTTCTGTCT AGTTGCCTTC AAGACTTTGT CTTTAGTTTT TACAAGTTTA ATTATGATAT  80160
GTCTTGGTGT GAATTTCTTT GAGTTTATCC TGCTTATGAT AGTTCACACA GCTTTTTGAA  80220
ACTGTAGGTT TATGTCTTCC ACCAAATTTT ACTGAATTTC TTCAGTTCTA TGGTCTTGCT  80280
CCTCTTCCTG AAGTATTCCA ATGATACCGT GTTCTCTTTT GTTACGGTCC CACTGGTCTT  80340
TGAGACTCTC TGTTCATTTT ATTTCGGTCT TTCTTTTCTC TGTTGTTCAG ATTGGGTAAA  80400
TTCCATTGAT CTACCTTCAA GCCCACTGAT TCTGTCCTCT ATCATCTCTA TTATTGAGCC  80460
CAACCACACA GTTTTAATTT TGATTATTGT ATTTCTCAGT TCTATAATTT CCATTTGGTT  80520
ATTTTTCAAT GACTTCCATT TTTGCTGAAA TTTTCACTTG TTTCAAGAGA ATTTGTAATT  80580
ACTTGTTGAA GCACTTTTAT AATATCTGTT TAAAATACTT GTCATATAAT TCCAGTAACT  80640
AATTCATCTT GGTGTTGACA TCTGTTTATT GCTCACTTAA AAATAAAAAA TAAAAAACAC  80700
CTAGACTTTA TTTTTTATAG CAGTTTAAGG TTCACAGCAA AATTGAGAAG AAAGTAAAGA  80760
GTGTGCCCAG AAAAATAGTA CCCCTATGCA GAACCTCCCT GATATTGTTT GGCTGTGTCC  80820
CCCACCAAAT CTCATCTTGA ATGGTAGCTC CCACAATTCC CACGTGTTGT GGGAGGGATC  80880
CAGTGGGAGG TAATTGGATA ATGGGGGCGA ATCTTTCCCA TGCTGTTCTC ATGATAGTGA  80940
ATAAGTCTCA TGAGATCTGA TGGTTTTATA AAGAGGGGTT CCCCTGCACA AGTCCTCTCT  81000
TGCCTGGCGC CAGGTAAGAA GTCCCTTTGC TCTTCCTTCA TCTTCCATTA TGATTGCGAG  81060
GTCTCCCCAG CCATGTGGAA CTGTAAGTCC ATTAAACCTC CTTTTCTGTA TAAAGTACCC  81120
AGTCTCAGGT ATGTCTTTAT TAGCAGTGTG AGAATGGACT AATACACTCC CTATCAACAT  81180
CCCCTACCAG ATTGGTATGT TTGTTGTAAT CGATGAACCT ATGTCAACAC AGCGTTATTT  81240
CCCAAGCTCC ATAGCTTATA TGAGGATTCG CTCTTGGTGT TTACATTCTG TGAGTATTGA  81300
CAAATGTATG ATGAAATGTA TTGACCATTA TAGTGTCATA CAGAATACAG GATAGTTTCA  81360
CTGTCTTAAA AAATCTTCTG TGCTCCCCTT ATTCATCCCT TCCTTCTGTG TAAGCCCTGG  81420
CAACCACCGA GCTTTTCACT GCCTCCATTG TTTTGCTTTT TCCAGGATGT CATAGAGATG  81480
GACTCATACA GTAGGTAGCC TTTTGAAATT GACTTCTTTC ACTTAGTAAT ATGATTCCTC  81540
CATGTCTTTT CATGGCTTGA TAGCTAATTT CTTTATAGTG CTGAGTAGTA TTCCATTCAC  81600
TTATAATTCC TTGAATTCAT TGTTTGGAAT ATTTTGCAGA TGATATGCTA TTCCCTAACT  81660
TTATGCATCT TCACTCACAG GATTGTTTTT TTCTCACCAA TGCTTATTTA TATAAAAGCC  81720
ATATCAACAA AATTTTACAC ATCAAAAATT TTCAGACTTC TGGTTGCTCC AAAGAAGGAA  81780
TGACCCCATT CTTCTCAGGT CCTCTTCCTC ATGACTAAAA AACTCTGAAC AAAGCACAGA  81840
AAGTTGCGGA AGGCTCTGAA AGGTGAAAGG AGGTGGACTG CCTAGGGACC TCAGGACTTG  81900
```

-continued

```
GAAAACAACT CAGTGGGGAA TTCCGTGGAT TTCCTTATCA CCTCCCTTAT ATCCTGGACA  81960
CGGAGCTGCA GAAGACTCCA ACCTACAGTC ACCAATGCGC ATAGAAGAAA AAAGCTCCAA  82020
GAAAAGCCTT TTCCTCCTGG CCAGATGACT GGACAAGGGT GGCCTGACAA CAGAAAACCC  82080
ACAACAAGGA ATTACAGGTA ACTCCAGAGA GGATCAGCTT GAGTGGTTAA AACAAGTACA  82140
TGGAAAACAA AAAGAAGCAT TTTTCTTTTT TTGTAAAAGA GCTTGTACTG TAATAACTTT  82200
GATTTTGTTT TTTGTTTTTT GTTTTTTGTT TTTTTTTTGA GACTGAGTCT CACTCTATTG  82260
CCCAGGCTAG AGTGCTGTGG CGCAATCTTG GCTTACTGCA ACTTTTGCCT CCTGGGTTCA  82320
AGTGATTCTC ATGTCTCAGC TTCCTGAGTA GTTGGGATTA CAGGCATGCA CCACCACACC  82380
AACTAATTTT TGTATTTTTA GTAGAGATGG GGTTTGACCA TGTTGGCCAG ACTGGTCTTG  82440
AACTCCTGAC CTCAAATGAT CTGCCCACCT TGGCCTCCCA AAGTGCTGAG ATTACAAGCC  82500
TGAGCCACCG CACCTGGCCA ACTTGGACTT ATTTTTATAA TAAGTAGATA TTGTTCACTG  82560
TAGATATTGA ATCAATTTTT ATTTAATCTT GATTTTTTTT CTTGAGCTGC ATTAGAAATT  82620
CATTACAATA TTTCAATTTA TAAATCTTAT TAAAAATTAC TACTACCTAG ATCTCATTGT  82680
TTTCTTTTTT CTTTTTTGAG ACATGGTCTT GCTCTGTCAA GCAGGAGTGC AGTGGGACAA  82740
TCATAACTCA CTGTAGCCTC CAACTCCTGG GCTCAAACGA TCCTGCTACC TCAGCCTCCT  82800
GAGTAGGTGG GACTATAGGT GCACGCCACC CATGTGTGGC TAATTTTCTT TATTTTTTTT  82860
TGTAGAGACA AGGTCTCACT GTGTTGCCCA AGCTGGTCTT GAATTCCTGG CTTCAATCAA  82920
TCCTCCCGCC TCAGCCTCCC AAGGTGTTGG GATTTCAGAC GTGAGCCACT GCACACCTGG  82980
CCCCATTTTT TTTCCTTGAA TAAAGTGTAC TGGTAAATTT TAGGCTCATG AGGGTATATA  83040
TGCATTATTT TCTTCAAATC AAGCCTGAAT CAAAGAAACT TCTGCTTTAG TTTTAGTGAT  83100
ATTTGTCCCA AATGTTTAAA GACTGTATCA TTCTGATGAA TTGGATATTC CCATTGAGAG  83160
ATATTCAATA GGCCTTGATT GAAATGTTCT TCATTTTCTT TTTAAATTCT ATTTACAGTA  83220
GTCTGCATGT GTTAGAACTT TCAGAAAGGG AGAGATTTCT GTCTGGGCTG TCCCCACCAG  83280
CCAGAAGGGT CTGAGAGGCA CTGACTTGCC CTGGGGTGAT ATTTCTGCAG GACTTTGCTC  83340
CTCTGTAGGA AGACAGCCTA GAACAGAGGT GAAGGATGCC TCGGGCCTGC CTAGACCAAC  83400
AGCCATTCCC TGGTGATGCT GTAGTGTGAA GACCCTTGTC TTTCCCAACA CCTGTGATAG  83460
CTTTCAAATT ATTCTTTTCA GACAAACTTT ATGCCTGTTT CTTTATCTCT ATTTTGCATC  83520
CTAACAGAAA AAGCCAATCA CCTAGAAGGG AAAGTCAGAC TGGTCCCTGC TGCTTTCCCC  83580
ACATCTCCAC TGCCCCCAAT ATTGAATGCC GTGACAATGG AATGAAATTC CAATGTCCAT  83640
GAAATTCTGA GGGGAGACAT TTTGACTCAA GATTATATAC TCAGTGAAGA TGTCCTTTAT  83700
TTATTTATTA AATTAATTTT TTTTGAGATG GAGTCTCTCT CTGTCTCCCA GTTTGGAGTG  83760
CAGTGGTGCG ATCTCGGCTC ACTGCAACCT CTGCCTCCTG GGTTAAAGTG ATTCTCCTGC  83820
TGCAGCCTCC TGAATAGCTG GGACTATAGG TACTCACCAC CACACCTAGC TAATTTTTTT  83880
TTTTTTTTTT TTTTTTTTGG TAAAGATGGG GTTTCACCAT GTTGGCCCGT CTGGTCTTGA  83940
ACTCCAGACC TCAGGTGATC TGCCCGCTTT GGCCTCCCAA AGTGCTGGGA TTACAGGCGT  84000
GAGCCACCTT GTCTGGCCAA AGACGTCCTT TAACTAAAGA CTTCTGGTGT ATGTTACCTT  84060
AAAAATATAA ATATAAAAGC ATGAAGAAAA TACAACCTCC ATGGAATTTT TTTGCCAATG  84120
AATCTAGAAA AATAAGAATT GATTCAAAAT AATGAATAGG GAAGCTGTAA TAAAATGACT  84180
TGAGGGTTCA TTGAGTCCAT TTAAATATAT ATCTCTTACT AAAATCACTA AGGGTCATAA  84240
```

-continued

```
TTAGACAATG AAGTAAGTGC CATAAATCTA AACAATGTAA ATAACAATAT ATCTAAAAAA  84300
AAAAAACTAA GGAGTTTGGA GAGAGGATAC GGGAGGATGT GTTCTTTCAT AGTAGGGAAT  84360
TAGTTAATAT TCTTTAAAAT GGAAACATGT AAGAAAAAAG ACCCTAATGA CTGAAAACTA  84420
AGTTTTCCTC AATCTTTTTT TCATATCCTT TGAAGGCTAT TTTAAGAAAT AATATCTAAA  84480
GAACATCGAT TTGATGTTCA CAATTCCAGT TGATTTTCCT TCTGTGAAAT TCAAATGAAA  84540
TTAAATAAAT ATGTTTTGTT AAAAATGGTG TCATCCCATT TAAGTAAATG TCCTTTCTTT  84600
TACCTATTTA TCCATCTATA ATCTGTATCT ATTCATCCAT CAATGGATAC ATGTGCACAG  84660
ATAAATGGCC CCTTTGGTGA AGGGCTGAGA GGGTATTGTT TTCTAACCCC AACCTGTGAC  84720
GGCTTCCATG AGGCCAATGG AATCATTTTG AAATGTGTTT ACCACAGCAG GGAGACACAG  84780
AAGACTGGGG TCTCACACCT GTGTGGGAAC TCCAGAGGGT GAGAAAAGGG CCAATGAACT  84840
GCTCCGGTGA CACAGCAGGG AGGGTGGCTG CCGTGCTGGG TGCGGCCTGC CTTCCTAGAG  84900
AATGTCAGGG AAAGGGATGT GGGGTCATTT CCTGTGGACA CATTTAAGCC AAGTAGGGGA  84960
GAGGTCTGGT ATGGGGTCCT CTTGGGGCCT GTTGGACAGG GTTGACCAGC AGAGAGAGGA  85020
TGCCCAAGGA TTGAAGGAGG AGTGGGTAAG AGGTTCTCTA GGTCATGGGA ACTTCTGAAT  85080
TTCCCATGGA AAGCACCACC ATAATCTGTG TGCAATGAAC AGCCAGACCC ACGTGGGAAT  85140
TCTAGGCCAG CAAGAATCCC TTACTTGCTC ACTGGCTGCC ACGTGGCTCT GACCATGGAG  85200
AGGTCTGGAA CTGTAGCTTC CCAGTGGGGG AGAAGTAGGC TGGGAGAGAG AAGGGGACAG  85260
AGGAACCACA CCCTCCTTCC CCACCTCCAA ACAGAAGCCA GTAAAAATTG AGGGATGGAG  85320
AAAAATATAA GGCTAAATTA AGTTTTGGAA CTTTGGCATG ATCAAGGCTC ACTGCAGCCT  85380
CAACCTCCTG GGCTCAAACA ATCCTCCCTT CTCAGCCTCC TGAGTAGCTG GGACTACAGG  85440
CACATACAAC CATGCTCACC TTTTTTTTTT TTTTTTTTTT GTAGAGATGG GGTATTGCTA  85500
TGTTGCTCAG GGCTGGTCTC AAACTCCTGG GCTCAAGCAA TTCTCCTGCC TCAGCCTCCA  85560
AAAGTGCTGG GATTACAGGT GTAAGCCATT GGCCCTGCCA AGTTTAAGAA CTTTTACAGT  85620
TATAAGAGAC TAGATATTTT AATTATTATT ATTATTTTTT AGACAGAGTC TTACTCCGTA  85680
TCCAGGCTGG AGTGCGGTGG CACAATCTTG GCTCACTGTA ACCTCCACCT TCTAGGTTTA  85740
AGCGATTCTC CTGTCTCGGC CTCCTGAGTA GCCAGAATTA GTAGAGACGG GGATTCGCCA  85800
TGTTGATCAG GCTGGTCTCG AACTCCTGAC CTCAAGTAAT CCACCTGCCT TAGCCTCCCA  85860
AAGTGCTGGG ATTACAGTAG ATATTTTAAT TTTTTTGCAT GGAGGCTATT TTTACTACTA  85920
AAAGTGAATG AAGTATATTT TGTATCTTCC AGGAGTTTGG AAAGTCAAGT CTATTTGCAC  85980
CCAGCCACGT GCCTGCCATG GTGCCCGCGG CCTCTCAATT TTTGACCTTT GTTTATGCTG  86040
CTCTGTCTAC CCAGAATGCT CTCCATCGAG GGAAACCTAC TCTCTCTTCA AGGCCAAATT  86100
CCAGCATCAC CTCCGCCATG AAGCCTTCAT AGATCTACTC AANGTAGAAA CTTCTTAACC  86160
CCTCTAAACT GTCTTAGCAT CTTGGTTGTA GTATTGGTTT AGAATAGCAC AAATTCTACC  86220
CAAAATCTCA CTAAGTCTAT TCTAAGCAAA TCTTGGATAA TTTGCTAACA CTAAAATTAA  86280
ACCTGTTCTC TTTTGGTTTT TTGCTAACAA TGAAACAAAC TTGGTCTTAC TCTTTTGCTC  86340
AAGCTGGAGT ACAGTGGTGT AATCATGTCT CACTGCAGCC AGGAATTCCC GGACTCAAGG  86400
GATCGTCCTA CCTCAGCCTC CTGAGTAGCC GGGACTACAG GTGTGCATAA CCGTGCCTGG  86460
CCAGTTTTAA AATTTTTATT TAGGGACAGA GTTTTGCTAT GTTGTCCAGG CTGGTCTTGA  86520
ACTATTGACC TCAAGTGATC CTCCCACCTT GGCCTTTCAA AGTGCTGGGA TTAGAGGTGT  86580
GAGCTGCCAC ACCCAGCCCC GTTCTCTCTT TTGCATCTAT ATTAGTCTCT GTGCTCTTGG  86640
```

-continued

```
GAAAAGTGGA CCAATATCAT TTCAAAACTT GATGAAAAAG AAAATTAAAA TCTCATCCTC  86700
GGGAACTGAA ATCACAAACC ACCCAGCAAG GTCCACACCT CTAGGAGACT GGCATTTAGA  86760
AGACAGGACC ACAGTTGAAG CAACGGTTCT TTCTTTACCC TCCCTGCCTG TGACAGACTG  86820
CATGTGCTGA TTATCCCTGC GTTTTCTGCA GAGCTTGCCT TCCTGGTGAT ACAGTACTTT  86880
ATTTTATTCT GAGGGCCCCT TCCTGCCAGG GGATATCTGT CAGGGGATAC ATAAAACTGC  86940
ACAAAATGGA ACAAGTTATA GGTCATATAA AATTTCAGGA CATTGTTGAG AAGGAGAAGT  87000
TGCTAAATTG GAGACACCAT GATGTGAAAT CCCAGGGTCC CAGAATATTG ATGGAACTAG  87060
TATGTTTTTC TTATGTAATA TTTTATGGTG TCTGGGAAAT GGAGTTGCCT AAGTGAACTC  87120
ATTTTTTATG TCTAGGGGAA TAGCAACATA ACTATCATCT AACACTAAAT AAAGAGGAGC  87180
AAAATGTGCT ACATTTAGAA AGTGATGGTA TTATCCCCAG CTGAGGCAGA CTTAGTGATG  87240
GTGTTAGAAA TAAAGTATGG TAGGAGGCTG AGGCAGGTGG ATTGCATGAG CTCAGGAGTT  87300
TGAGACCAGA CTGGGCAACA TGGCGGAAAC CCCATCTCTA CAAAAATCCA             87350
```

(2) INFORMATION FOR SEQ ID NO: 80:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 80:

CATTGGGAGA TAAATGCTCA GTAGA 25

(2) INFORMATION FOR SEQ ID NO: 81:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 81:

AGATGTACTT TGGCCATTCC AG 22

(2) INFORMATION FOR SEQ ID NO: 82:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 82:

GCCATGACAG CAACATTATC TC 22

(2) INFORMATION FOR SEQ ID NO: 83:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 83:

CTTACTGCTA CTGCAAGTTC TTC 23

(2) INFORMATION FOR SEQ ID NO: 84:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 84:

TCGATCAAAA CCAGTACAGG TG 22

(2) INFORMATION FOR SEQ ID NO: 85:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 85:

GCAGATGTAG GAGACAAATC ATC 23

(2) INFORMATION FOR SEQ ID NO: 86:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 86:

TCATCCAAAA TCTCTAAATT TCGG 24

(2) INFORMATION FOR SEQ ID NO: 87:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 87:

CTGAGGACCA GAAACTGTAT GC 22

(2) INFORMATION FOR SEQ ID NO: 88:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 88:

GCTGATTTGG TGTCTAGCCT GG 22

(2) INFORMATION FOR SEQ ID NO: 89:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 89:

TGCCTGGGTT GCAGGCCTGC 20

(2) INFORMATION FOR SEQ ID NO: 90:

-continued (i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 90:

TTGGAAACAA CTGCACAGCA GC 22

(2) INFORMATION FOR SEQ ID NO: 91:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 91:

GATCCAGTGA ATTCTAAGAA GGG 23

(2) INFORMATION FOR SEQ ID NO: 92:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 92:

AGGGCCTCCA CGCATGACGC 20

(2) INFORMATION FOR SEQ ID NO: 93:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 93:

AGTCTGTTTT TCCAGAATCT CCC 23

(2) INFORMATION FOR SEQ ID NO: 94:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 94:

CCTATGCTTG GACCTAGGTG TC 22

(2) INFORMATION FOR SEQ ID NO: 95:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 95:

GAAGTTTACA AGTAACAACT GACTC 25

(2) INFORMATION FOR SEQ ID NO: 96:

(i) SEQUENCE CHARACTERISTICS:

-continued (A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 96:

ACTATAAATT GAATGCTTCA GTGAAC 26

(2) INFORMATION FOR SEQ ID NO: 97:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 97:

GAACACACCT CACCTGTAAA ACTC 24

(2) INFORMATION FOR SEQ ID NO: 98:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 98:

GGTAAACCAC CATACCTGGC C 21

(2) INFORMATION FOR SEQ ID NO: 99:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 99:

GTACATATCC TGGTCATTTA GCC 23

(2) INFORMATION FOR SEQ ID NO: 100:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 100:

ATTCAGATAG AAAGTACATT CTGTG 25

(2) INFORMATION FOR SEQ ID NO: 101:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 101:

GTTAAGAAAT ACTCAAGGTC AATGTG 26

(2) INFORMATION FOR SEQ ID NO: 102:

(i) SEQUENCE CHARACTERISTICS:
(A) LENGTH: 25 base pairs

-continued (B) TYPE: nucleic acid
(C) STRANDEDNESS: single
(D) TOPOLOGY: linear (xi) SEQUENCE DESCRIPTION: SEQ ID NO: 102:

GGTTGTATTT TGGTATAACA TTTCC 25

(2) INFORMATION FOR SEQ ID NO: 103:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 103:

ATATTTTGGT AGAGTTTCTG CCAC 24

(2) INFORMATION FOR SEQ ID NO: 104:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 104:

CTCTTCGATT TTTCTGAAGA TGGG 24

(2) INFORMATION FOR SEQ ID NO: 105:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 105:

CCCTAATAGT CAGGAGTGTT CAG 23

(2) INFORMATION FOR SEQ ID NO: 106:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 106:

GGAAAGAAAA TGAAAATTTG ATCCC 25

(2) INFORMATION FOR SEQ ID NO: 107:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 107:

CAGCCTTAAT GAATAGTATT CTTCAC 26

(2) INFORMATION FOR SEQ ID NO: 108:

(i) SEQUENCE CHARACTERISTICS:
(A) LENGTH: 25 base pairs
(B) TYPE: nucleic acid

-continued (C) STRANDEDNESS: single
(D) TOPOLOGY: linear (xi) SEQUENCE DESCRIPTION: SEQ ID NO: 108:

ATTGATCTTT TAAGTGAAGG TCAGC 25

(2) INFORMATION FOR SEQ ID NO: 109:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 109:

CTGCAACAGA GACTGTATGT CCC 23

(2) INFORMATION FOR SEQ ID NO: 110:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 110:

GCTTTCGACA AAATTGTAGG CCC 23

(2) INFORMATION FOR SEQ ID NO: 111:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 111:

CCAAACCATC CAAAACTGGA TCC 23

(2) INFORMATION FOR SEQ ID NO: 112:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 112:

TAACCCATGG TAGCTGTCAC TG 22

(2) INFORMATION FOR SEQ ID NO: 113:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 113:

CTGTTGCTGT TAAGCAGACA GG 22

(2) INFORMATION FOR SEQ ID NO: 114:

(i) SEQUENCE CHARACTERISTICS:
(A) LENGTH: 24 base pairs
(B) TYPE: nucleic acid
(C) STRANDEDNESS: single -continued (D) TOPOLOGY: linear (xi) SEQUENCE DESCRIPTION: SEQ ID NO: 114:

TTGAATGGGA CATTGGTCAA ATGG 24

(2) INFORMATION FOR SEQ ID NO: 115:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 115:

GTAGTTGCAT TTGTATTTTG AGAGT 25

(2) INFORMATION FOR SEQ ID NO: 116:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 116:

GTAAAAAGAA ATGAAAGCAT CAAAGG 26

(2) INFORMATION FOR SEQ ID NO: 117:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 117:

TCACCCACAG AAGAAAAAAA GAGG 24

(2) INFORMATION FOR SEQ ID NO: 118:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 118:

CAAAAAAGAA AATTGCAAAG AACAGG 26

(2) INFORMATION FOR SEQ ID NO: 119:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 119:

CAGCAACATG TAATTCACCC ACG 23

(2) INFORMATION FOR SEQ ID NO: 120:

(i) SEQUENCE CHARACTERISTICS:
(A) LENGTH: 23 base pairs
(B) TYPE: nucleic acid
(C) STRANDEDNESS: single
(D) TOPOLOGY: linear -continued (xi) SEQUENCE DESCRIPTION: SEQ ID NO: 120:

GAAGAGACTG GAATTGGGTT TGG 23

(2) INFORMATION FOR SEQ ID NO: 121:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 121:

ATAGAGTATC ATGGGATAAG ATAGG 25

(2) INFORMATION FOR SEQ ID NO: 122:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 122:

TTCTCCTTTG GAGATGTAGA TGAG 24

(2) INFORMATION FOR SEQ ID NO: 123:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 123:

TCTTCAGCTT CTTTACCACT CCCCA 25

(2) INFORMATION FOR SEQ ID NO: 124:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 124:

CATGGTGTTT GACAACAGGA TGG 23

(2) INFORMATION FOR SEQ ID NO: 125:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 125:

GTTAAATATG CATTAGAAGG AAATCG 26

(2) INFORMATION FOR SEQ ID NO: 126:

(i) SEQUENCE CHARACTERISTICS:
(A) LENGTH: 23 base pairs
(B) TYPE: nucleic acid
(C) STRANDEDNESS: single
(D) TOPOLOGY: linear -continued (xi) SEQUENCE DESCRIPTION: SEQ ID NO: 126:

ATAAAACCAA ACGGGTCTGA AGC 23

(2) INFORMATION FOR SEQ ID NO: 127:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 127:

AAAAGAAGTA TTCAATAAAG ATCTGG 26

(2) INFORMATION FOR SEQ ID NO: 128:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 128:

AATTCCACTT TGTGCCAGGG ACT 23

(2) INFORMATION FOR SEQ ID NO: 129:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 129:

ACTTGGGATA CTGGAAATAG CCT 23

(2) INFORMATION FOR SEQ ID NO: 130:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 130:

TTTTTATCTT GATGGGGTGT GGG 23

(2) INFORMATION FOR SEQ ID NO: 131:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 131:

AAATTCAGCA CACATGTAAC AGCA 24

(2) INFORMATION FOR SEQ ID NO: 132:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 132:

-continued

CTGAAGTCAA ATAATGAAGT CCCA 24

(2) INFORMATION FOR SEQ ID NO: 133:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 133:

GTTTGCTTTC TCATATCTAA ACACA 25

(2) INFORMATION FOR SEQ ID NO: 134:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 134:

CTTGTGAGAG GCCTATAAAC TGG 23

(2) INFORMATION FOR SEQ ID NO: 135:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 135:

GGTAAACAGT GTAGGAGTCT GC 22

(2) INFORMATION FOR SEQ ID NO: 136:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 136:

GCTTGAAGGA TGAGGCTCTG AG 22

(2) INFORMATION FOR SEQ ID NO: 137:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 137:

TGTTCAGAAT GAGCACGATG GG 22

(2) INFORMATION FOR SEQ ID NO: 138:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 138:

-continued

CTTGTGAGAG GCCTATAAAC TGG 23

(2) INFORMATION FOR SEQ ID NO: 139:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 139:

GGTAAACAGT GTAGGAGTCT GC 22

(2) INFORMATION FOR SEQ ID NO: 140:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 140:

GCCATTTTCT CTTTAATTGG AAAGG 25

(2) INFORMATION FOR SEQ ID NO: 141:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 141:

ATCTTATTCA TCTTTCTGAG AATGG 25

(2) INFORMATION FOR SEQ ID NO: 142:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 142:

TGAAATAGCC CAACATCTGA CAG 23

(2) INFORMATION FOR SEQ ID NO: 143:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 143:

GATTAATTTG ACAGCTTGAT TAGGC 25

(2) INFORMATION FOR SEQ ID NO: 144:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 144:

TGAAATATAA ACTCAGACTC TTAGC 25

-continued (2) INFORMATION FOR SEQ ID NO: 145:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 145:

GTACTGATTT GGAAAGACAT TCTC 24

(2) INFORMATION FOR SEQ ID NO: 146:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 146:

GATGTGACAG TGGAAGCTAT GG 22

(2) INFORMATION FOR SEQ ID NO: 147:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 147:

GGAAAAATGT GGTATCTGAA GCTC 24

(2) INFORMATION FOR SEQ ID NO: 148:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 148:

AAGTGAGCAA ATGTTGCTTC TGG 23

(2) INFORMATION FOR SEQ ID NO: 149:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 149:

TCATTAGGAA GCTGAACATC AGC 23

(2) INFORMATION FOR SEQ ID NO: 150:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 150:

GTTGGAGGAA ATTGATCCCA AGTC 24

-continued (2) INFORMATION FOR SEQ ID NO: 151:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 151:

TGTTGCTTAT GGGTTTAACT TGTG 24

(2) INFORMATION FOR SEQ ID NO: 152:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 152:

TAAAGGATTA ATGCTGTTAA CAGTG 25

(2) INFORMATION FOR SEQ ID NO: 153:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 153:

TCACACTGAG CATTTACTAC CTG 23

(2) INFORMATION FOR SEQ ID NO: 154:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 154:

GCAAAGGAAA TGTAGCACAT AGAG 24

(2) INFORMATION FOR SEQ ID NO: 155:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 155:

AGGCTATAGG CATTTGAAAG AGG 23

(2) INFORMATION FOR SEQ ID NO: 156:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 156:

GTAGGCTCCC AGAAGACCCA G 21

-continued (2) INFORMATION FOR SEQ ID NO: 157:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 157:

GAAAGGATGG GTGTGTATTC AGG 23

(2) INFORMATION FOR SEQ ID NO: 158:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 158:

ACAGGCCATA GTTTGCCAAC CC 22

(2) INFORMATION FOR SEQ ID NO: 159:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 159:

TGGTATTAGA ATTTCCCTTT CTTCC 25

(2) INFORMATION FOR SEQ ID NO: 160:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 160:

TGAAAGAGAA TATGGAAAGA GGCTTG 26

(2) INFORMATION FOR SEQ ID NO: 161:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 161:

CTTTATGAAG CCAATTTCTA CCC 23

(2) INFORMATION FOR SEQ ID NO: 162:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 162:

TCAAAATCAG TCGCCTCATC CC 22

(2) INFORMATION FOR SEQ ID NO: 163:

-continued (i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 163:

CAATGTATCA GTCAGGGTTC ACC 23

(2) INFORMATION FOR SEQ ID NO: 164:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO: 164:

GATATTGTTT TGTATTTACC CATGAAGAC 29

(2) INFORMATION FOR SEQ ID NO: 165:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 165:

TCCGCTGCTG TGCAGTTGTT TCC 23

(2) INFORMATION FOR SEQ ID NO: 166:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 166:

TCAGTAGATT TATAAGCAAT ATCAC 25

(2) INFORMATION FOR SEQ ID NO: 167:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 167:

CTGGCAAGGA TCAAACAGAG AG 22

(2) INFORMATION FOR SEQ ID NO: 168:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 168:

CTTTATGAAG CCAATTTCTA CCC 23

(2) INFORMATION FOR SEQ ID NO: 169:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 169:

TTCTCGGGGT AAAGTGTC 18

(2) INFORMATION FOR SEQ ID NO: 170:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 170:

TACCTCTCAG TTTTCTTTAA AGAAAGGTAT GTTGTT 36

(2) INFORMATION FOR SEQ ID NO: 171:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 171:

TAAACTCAAG GCATGTGTGA TATTAGGTAA GTGATT 36

(2) INFORMATION FOR SEQ ID NO: 172:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 172:

CTCACTTTAG CATGAGTCCA TGTCAGGTTG GTATCT 36

(2) INFORMATION FOR SEQ ID NO: 173:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 173:

AATGTTACAG TTTTTCCCAT AAAAAGGTAA AAGCAA 36

(2) INFORMATION FOR SEQ ID NO: 174:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 174:

TCATTTCTAG CTGAAATGAT GCTTATGTAC GTGCTT 36

(2) INFORMATION FOR SEQ ID NO: 175:

(i) SEQUENCE CHARACTERISTICS:

-continued (A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 175:

TTTTTTATAG GCTGGTTTAA ATAAAGGTAT GTTAAG 36

(2) INFORMATION FOR SEQ ID NO: 176:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 176:

TTCCCCCTAG AGGAAGAACC ACGGAGGTTA AATATT 36

(2) INFORMATION FOR SEQ ID NO: 177:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 177:

TTTTTTTTAG GGTTTCTACT ACTGAGGTAC TAAAAT 36

(2) INFORMATION FOR SEQ ID NO: 178:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 178:

TTTTTTAAAG CATTTATCTG CTTAAGGGTA TGTTTA 36

(2) INFORMATION FOR SEQ ID NO: 179:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 179:

TTTTTTAAAG CATTTATCTG CTTAAGGGTA TGTTTA 36

(2) INFORMATION FOR SEQ ID NO: 180:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 180:

AAACTTTCAG TCTTTAGATG ATAAGGGTAA GCACTG 36

(2) INFORMATION FOR SEQ ID NO: 181:

(i) SEQUENCE CHARACTERISTICS:
(A) LENGTH: 36 base pairs

-continued (B) TYPE: nucleic acid
(C) STRANDEDNESS: single
(D) TOPOLOGY: linear (xi) SEQUENCE DESCRIPTION: SEQ ID NO: 181:

TTATTTCCAG ACTTTTTGTT TAAACCGTGA GTATAA 36

(2) INFORMATION FOR SEQ ID NO: 182:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 182:

CACCTTCAAG AGTTCAGTGG CAACTGGTAA GTTGTA 36

(2) INFORMATION FOR SEQ ID NO: 183:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 183:

TCATTTCAAG GATATGGACA GCTTAAGTAA GTCATG 36

(2) INFORMATION FOR SEQ ID NO: 184:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 184:

CTTCTTATAG AATGTCCAAT TAAATTGTGA GTAATT 36

(2) INFORMATION FOR SEQ ID NO: 185:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 185:

GTTTTTACAG AGGTAAATTG ATATTGGTAA GTGATA 36

(2) INFORMATION FOR SEQ ID NO: 186:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 186:

TTTTTTACAG GTATCACGTG CCAATGGTAA GCTTTG 36

(2) INFORMATION FOR SEQ ID NO: 187:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO: 187:

CATCATTCAG GTTCCAATAA AACAAGGTAA GGATTT 36

(2) INFORMATION FOR SEQ ID NO: 188:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 188:

TTTTCTTTAG TTCCCACTAA ATTCAGGTAT GAGGAT 36

(2) INFORMATION FOR SEQ ID NO: 189:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 189:

TTGTTCTCAG TGTGTCATTT AAATAGGTAA AAAAAA 36

(2) INFORMATION FOR SEQ ID NO: 190:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 190:

TAATCGACAG GCACCTTCAG GAGACAGTAT GTATTA 36

(2) INFORMATION FOR SEQ ID NO: 191:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 191:

TCTTGGGTAG AATCATCTAG GTCCAGGTAA AGATTT 36

(2) INFORMATION FOR SEQ ID NO: 192:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 192:

TTTTATTTAG ATTGGATCGA GGATCTGTAA GTATAT 36

(2) INFORMATION FOR SEQ ID NO: 193:

(i) SEQUENCE CHARACTERISTICS:
(A) LENGTH: 36 base pairs
(B) TYPE: nucleic acid
(C) STRANDEDNESS: single -continued (D) TOPOLOGY: linear (xi) SEQUENCE DESCRIPTION: SEQ ID NO: 193:

CTAATTTCAG AATTCTCACG AAAAAGGTAA ACAGTG 36

(2) INFORMATION FOR SEQ ID NO: 194:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 194:

CTTTTAATAG GGTAGAAACT GCCTAGGTTC ATTTTT 36

(2) INFORMATION FOR SEQ ID NO: 195:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 195:

TATTTTTTAG TTCGAAAAAG AAGAAGGTTT GTTTTA 36

(2) INFORMATION FOR SEQ ID NO: 196:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 196:

TTAAATGCAG TCTAACTTAA AAAAAGGTAC AGAGTT 36

(2) INFORMATION FOR SEQ ID NO: 197:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 197:

AATATTTTAG TATCATGGAG ACTCAGGTAA GGCTTT 36

(2) INFORMATION FOR SEQ ID NO: 198:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 198:

TTTTGTTCAG ATTGTGTTAA AATGAGGTAA ACTATC 36

(2) INFORMATION FOR SEQ ID NO: 199:

(i) SEQUENCE CHARACTERISTICS:
(A) LENGTH: 36 base pairs
(B) TYPE: nucleic acid
(C) STRANDEDNESS: single
(D) TOPOLOGY: linear -continued (xi) SEQUENCE DESCRIPTION: SEQ ID NO: 199:

TTAAACACAG ACCAACTAGT GTTCAGGTAA AATACT 36

(2) INFORMATION FOR SEQ ID NO: 200:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 200:

AATTCTGTAG ACAGACCTTG CCTTTGGTAA GTGTGA 36

(2) INFORMATION FOR SEQ ID NO: 201:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 201:

CTTTCTCTAG AAGAGCATCA ACTCAGGTGA GAGGCA 36

(2) INFORMATION FOR SEQ ID NO: 202:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 202:

TCGTTTACAG ATATGAGTAT ACTGAGGTAT TAATTA 36

(2) INFORMATION FOR SEQ ID NO: 203:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 203:

TTTCCTACAG ACTTCATC 18

(2) INFORMATION FOR SEQ ID NO: 204:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO: 204:

Phe Pro Gly Ser Glu Glu Ile Cys Ser Ser Ser Lys Arg
1 5 10

(2) INFORMATION FOR SEQ ID NO: 205:

(i) SEQUENCE CHARACTERISTICS:
(A) LENGTH: 4792 base pairs
(B) TYPE: nucleic acid
(C) STRANDEDNESS: single
(D) TOPOLOGY: linear -continued

```
    (ix) FEATURE:
          (A) NAME/KEY: CDS
          (B) LOCATION: 145..4347

    (xi) SEQUENCE DESCRIPTION: SEQ ID NO: 205:

GTATAAAGTT AGTAAATGTG AGGCCTCTCT CGATGCCTGG GTCCTGGGCT TTGGTTCTCA     60

GTCCTCCATA AATCATCCTG CTGGAGGAGA AGACCCTTAG ATCTGGCTCT TCTCAGGGGC    120

ATTTTAAAGA CAAATGAAAA TAAA ATG GAA ACC ACT TCA CTA CAG CGG AAA       171
                           Met Glu Thr Thr Ser Leu Gln Arg Lys
                             1               5

TTT CCA GAA TGG ATG TCT ATG CAG AGT CAA AGA TGT GCT ACA GAA GAA      219
Phe Pro Glu Trp Met Ser Met Gln Ser Gln Arg Cys Ala Thr Glu Glu
 10                  15                  20                  25

AAG GCC TGC GTT CAG AAG AGT GTT CTT GAA GAT AAC CTC CCA TTC TTA      267
Lys Ala Cys Val Gln Lys Ser Val Leu Glu Asp Asn Leu Pro Phe Leu
                 30                  35                  40

GAA TTC CCT GGA TCC ATT GTT TAC AGT TAT GAA GCT AGT GAT TGC TCC      315
Glu Phe Pro Gly Ser Ile Val Tyr Ser Tyr Glu Ala Ser Asp Cys Ser
             45                  50                  55

TTC CTG TCT GAA GAC ATT AGC ATG CGT CTG TCT GAT GGC GAT GTG GTG      363
Phe Leu Ser Glu Asp Ile Ser Met Arg Leu Ser Asp Gly Asp Val Val
         60                  65                  70

GGA TTT GAC ATG GAA TGG CCG CCC ATA TAC AAG CCA GGG AAA AGA AGC      411
Gly Phe Asp Met Glu Trp Pro Pro Ile Tyr Lys Pro Gly Lys Arg Ser
     75                  80                  85

AGA GTC GCA GTG ATC CAG TTG TGT GTG TCT GAG AGC AAA TGT TAC TTG      459
Arg Val Ala Val Ile Gln Leu Cys Val Ser Glu Ser Lys Cys Tyr Leu
 90                  95                 100                 105

TTT CAC ATT TCT TCC ATG TCA GTT TTC CCC CAG GGA TTA AAA ATG TTA      507
Phe His Ile Ser Ser Met Ser Val Phe Pro Gln Gly Leu Lys Met Leu
                110                 115                 120

CTA GAA AAC AAA TCA ATT AAG AAG GCA GGG GTT GGG ATT GAA GGG GAC      555
Leu Glu Asn Lys Ser Ile Lys Lys Ala Gly Val Gly Ile Glu Gly Asp
            125                 130                 135

CAG TGG AAA CTT CTG CGT GAT TTT GAC GTC AAG TTG GAG AGT TTT GTG      603
Gln Trp Lys Leu Leu Arg Asp Phe Asp Val Lys Leu Glu Ser Phe Val
        140                 145                 150

GAG CTG ACG GAT GTT GCC AAT GAA AAG TTG AAG TGC GCA GAG ACC TGG      651
Glu Leu Thr Asp Val Ala Asn Glu Lys Leu Lys Cys Ala Glu Thr Trp
    155                 160                 165

AGC CTC AAT GGT CTG GTT AAA CAC GTC TTA GGG AAA CAA CTT TTG AAA      699
Ser Leu Asn Gly Leu Val Lys His Val Leu Gly Lys Gln Leu Leu Lys
170                 175                 180                 185

GAC AAG TCC ATC CGC TGC AGC AAT TGG AGT AAT TTC CCC CTC ACT GAG      747
Asp Lys Ser Ile Arg Cys Ser Asn Trp Ser Asn Phe Pro Leu Thr Glu
                190                 195                 200

GAC CAG AAA CTG TAT GCA GCC ACT GAT GCT TAT GCT GGT CTT ATC ATC      795
Asp Gln Lys Leu Tyr Ala Ala Thr Asp Ala Tyr Ala Gly Leu Ile Ile
            205                 210                 215

TAT CAA AAA TTA GGA AAT TTG GGT GAT ACT GCG CAA GTG TTT GCT CTA      843
Tyr Gln Lys Leu Gly Asn Leu Gly Asp Thr Ala Gln Val Phe Ala Leu
        220                 225                 230

AAT AAA GCA GAG GAA AAC CTA CCT CTG GAG ATG AAG AAA CAG TTG AAT      891
Asn Lys Ala Glu Glu Asn Leu Pro Leu Glu Met Lys Lys Gln Leu Asn
    235                 240                 245

TCA ATC TCC GAA GAA ATG AGG GAC CTA GCC AAT CGT TTT CCT GTC ACT      939
Ser Ile Ser Glu Glu Met Arg Asp Leu Ala Asn Arg Phe Pro Val Thr
250                 255                 260                 265
```

-continued

```
TGC AGA AAT TTG GAA ACT CTC CAG AGG GTT CCT GTA ATA TTG AAG AGT      987
Cys Arg Asn Leu Glu Thr Leu Gln Arg Val Pro Val Ile Leu Lys Ser
                270                 275                 280

ATT TCA GAA AAT CTC TGT TCA TTG AGA AAA GTG ATC TGT GGT CCT ACA     1035
Ile Ser Glu Asn Leu Cys Ser Leu Arg Lys Val Ile Cys Gly Pro Thr
            285                 290                 295

AAC ACT GAG ACT AGA CTG AAG CCG GGC AGT AGT TTT AAT TTA CTG TCA     1083
Asn Thr Glu Thr Arg Leu Lys Pro Gly Ser Ser Phe Asn Leu Leu Ser
        300                 305                 310

TCA GAG GAT TCA GCT GCT GCT GGA GAA AAA GAG AAA CAG ATT GGA AAA     1131
Ser Glu Asp Ser Ala Ala Ala Gly Glu Lys Glu Lys Gln Ile Gly Lys
    315                 320                 325

CAT AGT ACT TTT GCT AAA ATT AAA GAA GAA CCA TGG GAC CCA GAA CTT     1179
His Ser Thr Phe Ala Lys Ile Lys Glu Glu Pro Trp Asp Pro Glu Leu
330                 335                 340                 345

GAC AGT TTA GTG AAG CAA GAG GAG GTT GAT GTA TTT AGA AAT CAA GTG     1227
Asp Ser Leu Val Lys Gln Glu Glu Val Asp Val Phe Arg Asn Gln Val
                350                 355                 360

AAG CAA GAA AAA GGT GAA TCT GAA AAT GAA ATA GAA GAC AAT CTG TTG     1275
Lys Gln Glu Lys Gly Glu Ser Glu Asn Glu Ile Glu Asp Asn Leu Leu
            365                 370                 375

AGA GAA GAT ATG GAA AGA ACT TGT GTG ATT CCT AGT ATT TCA GAA AAT     1323
Arg Glu Asp Met Glu Arg Thr Cys Val Ile Pro Ser Ile Ser Glu Asn
        380                 385                 390

GAA CTC CAA GAT TTG GAA CAG CAA GCT AAA GAA GAA AAA TAT AAT GAT     1371
Glu Leu Gln Asp Leu Glu Gln Gln Ala Lys Glu Glu Lys Tyr Asn Asp
    395                 400                 405

GTT TCT CAC CAA CTT TCT GAG CAT TTA TCT CCC AAT GAT GAT GAG AAT     1419
Val Ser His Gln Leu Ser Glu His Leu Ser Pro Asn Asp Asp Glu Asn
410                 415                 420                 425

GAC TCC TCC TAT ATA ATT GAA AGT GAT GAA GAT TTG GAA ATG GAG ATG     1467
Asp Ser Ser Tyr Ile Ile Glu Ser Asp Glu Asp Leu Glu Met Glu Met
                430                 435                 440

CTG AAG TCT TTA GAA AAC CTA AAT AGT GAC GTG GTG GAA CCC ACT CAC     1515
Leu Lys Ser Leu Glu Asn Leu Asn Ser Asp Val Val Glu Pro Thr His
            445                 450                 455

TCT ACA TGG TTG GAA ATG GGA ACC AAT GGG CGT CTT CCT CCT GAG GAG     1563
Ser Thr Trp Leu Glu Met Gly Thr Asn Gly Arg Leu Pro Pro Glu Glu
        460                 465                 470

GAA GAT GGA CAC GGA AAT GAA GCC ATC AAA GAG GAG CAG GAA GAA GAG     1611
Glu Asp Gly His Gly Asn Glu Ala Ile Lys Glu Glu Gln Glu Glu Glu
    475                 480                 485

GAC CAT TTA TTG CCG GAA CCC AAC GCA AAG CAA ATT AAT TGC CTC AAG     1659
Asp His Leu Leu Pro Glu Pro Asn Ala Lys Gln Ile Asn Cys Leu Lys
490                 495                 500                 505

ACC TAT TTC GGA CAC AGC AGT TTT AAA CCG GTT CAG TGG AAA GTC ATC     1707
Thr Tyr Phe Gly His Ser Ser Phe Lys Pro Val Gln Trp Lys Val Ile
                510                 515                 520

CAT TCT GTA TTA GAA GAG AGA AGA GAT AAT GTT GTT GTC ATG GCA ACT     1755
His Ser Val Leu Glu Glu Arg Arg Asp Asn Val Val Val Met Ala Thr
            525                 530                 535

GGA TAT GGG AAG AGT CTG TGC TTC CAG TAT CCG CCT GTT TAT ACA GGC     1803
Gly Tyr Gly Lys Ser Leu Cys Phe Gln Tyr Pro Pro Val Tyr Thr Gly
        540                 545                 550

AAG ATT GGC ATT GTC ATT TCA CCT CTC ATT TCC TTA ATG GAA GAC CAA     1851
Lys Ile Gly Ile Val Ile Ser Pro Leu Ile Ser Leu Met Glu Asp Gln
    555                 560                 565

GTC CTC CAG CTT GAG CTG TCC AAT GTT CCA GCC TGT TTA CTT GGA TCT     1899
Val Leu Gln Leu Glu Leu Ser Asn Val Pro Ala Cys Leu Leu Gly Ser
570                 575                 580                 585
```

-continued

```
GCA CAG TCA AAA AAT ATT CTA GGA GAT GTT AAA TTA GGC AAA TAT AGG     1947
Ala Gln Ser Lys Asn Ile Leu Gly Asp Val Lys Leu Gly Lys Tyr Arg
                590                 595                 600

GTC ATC TAC ATA ACT CCA GAG TTC TGT TCT GGT AAC TTG GAT CTA CTC     1995
Val Ile Tyr Ile Thr Pro Glu Phe Cys Ser Gly Asn Leu Asp Leu Leu
            605                 610                 615

CAG CAA CTT GAC TCT AGT ATT GGC ATC ACT CTC ATT GCT GTG GAT GAG     2043
Gln Gln Leu Asp Ser Ser Ile Gly Ile Thr Leu Ile Ala Val Asp Glu
        620                 625                 630

GCT CAC TGC ATT TCA GAG TGG GGC CAT GAT TTC AGA AGT TCA TTC AGG     2091
Ala His Cys Ile Ser Glu Trp Gly His Asp Phe Arg Ser Ser Phe Arg
    635                 640                 645

ATG CTG GGC TCT CTT AAA ACA GCG CTC CCA TTG GTT CCA GTC ATT GCA     2139
Met Leu Gly Ser Leu Lys Thr Ala Leu Pro Leu Val Pro Val Ile Ala
650                 655                 660                 665

CTC TCC GCT ACT GCA AGC TCT TCC ATC CGG GAA GAC ATT ATA AGC TGC     2187
Leu Ser Ala Thr Ala Ser Ser Ser Ile Arg Glu Asp Ile Ile Ser Cys
                670                 675                 680

TTA AAC CTG AAA GAC CCT CAG ATC ACC TGC ACT GGA TTT GAT CGG CCA     2235
Leu Asn Leu Lys Asp Pro Gln Ile Thr Cys Thr Gly Phe Asp Arg Pro
            685                 690                 695

AAT CTG TAC TTA GAA GTT GGA CGG AAA ACA GGG AAC ATC CTT CAG GAT     2283
Asn Leu Tyr Leu Glu Val Gly Arg Lys Thr Gly Asn Ile Leu Gln Asp
        700                 705                 710

CTA AAG CCG TTT CTC GTC CGA AAG GCA AGT TCT GCC TGG GAA TTT GAA     2331
Leu Lys Pro Phe Leu Val Arg Lys Ala Ser Ser Ala Trp Glu Phe Glu
    715                 720                 725

GGT CCA ACC ATC ATC TAT TGT CCT TCG AGA AAA ATG ACA GAA CAA GTT     2379
Gly Pro Thr Ile Ile Tyr Cys Pro Ser Arg Lys Met Thr Glu Gln Val
730                 735                 740                 745

ACT GCT GAA CTT GGG AAA CTG AAC TTA GCC TGC AGA ACA TAC CAC GCT     2427
Thr Ala Glu Leu Gly Lys Leu Asn Leu Ala Cys Arg Thr Tyr His Ala
                750                 755                 760

GGC ATG AAA ATT AGC GAA AGG AAG GAC GTT CAT CAT AGG TTC CTG AGA     2475
Gly Met Lys Ile Ser Glu Arg Lys Asp Val His His Arg Phe Leu Arg
            765                 770                 775

GAT GAA ATT CAG TGT GTT GTA GCT ACT GTA GCT TTT GGA ATG GGC ATT     2523
Asp Glu Ile Gln Cys Val Val Ala Thr Val Ala Phe Gly Met Gly Ile
        780                 785                 790

AAT AAA GCT GAC ATT CGC AAA GTT ATT CAT TAT GGT GCG CCT AAG GAA     2571
Asn Lys Ala Asp Ile Arg Lys Val Ile His Tyr Gly Ala Pro Lys Glu
    795                 800                 805

ATG GAA TCC TAT TAC CAG GAA ATT GGT AGA GCT GGC CGG GAT GGA CTT     2619
Met Glu Ser Tyr Tyr Gln Glu Ile Gly Arg Ala Gly Arg Asp Gly Leu
810                 815                 820                 825

CAG AGT TCC TGT CAC TTG CTC TGG GCT CCA GCA GAC TTT AAC ACA TCC     2667
Gln Ser Ser Cys His Leu Leu Trp Ala Pro Ala Asp Phe Asn Thr Ser
                830                 835                 840

AGG AAT CTC CTT ATT GAG ATT CAC GAT GAA AAG TTC CGG TTA TAT AAA     2715
Arg Asn Leu Leu Ile Glu Ile His Asp Glu Lys Phe Arg Leu Tyr Lys
            845                 850                 855

TTA AAG ATG ATG GTA AAG ATG GAA AAA TAC CTT CAC TCC AGT CAG TGT     2763
Leu Lys Met Met Val Lys Met Glu Lys Tyr Leu His Ser Ser Gln Cys
        860                 865                 870

AGG CGA CGA ATC ATC TTG TCC CAT TTT GAG GAC AAA TGT CTG CAG AAG     2811
Arg Arg Arg Ile Ile Leu Ser His Phe Glu Asp Lys Cys Leu Gln Lys
    875                 880                 885

GCC TCC TTG GAC ATT ATG GGA ACT GAA AAA TGC TGT GAT AAT TGC AGG     2859
Ala Ser Leu Asp Ile Met Gly Thr Glu Lys Cys Cys Asp Asn Cys Arg
```

-continued

```
890                 895                 900                 905

CCC AGG CTG AAT CAT TGC ATT ACT GCT AAC AAC TCA GAG GAC GCA TCC     2907
Pro Arg Leu Asn His Cys Ile Thr Ala Asn Asn Ser Glu Asp Ala Ser
                910                 915                 920

CAA GAC TTT GGG CCA CAA GCA TTC CAG CTA CTG TCT GCT GTG GAC ATC     2955
Gln Asp Phe Gly Pro Gln Ala Phe Gln Leu Leu Ser Ala Val Asp Ile
            925                 930                 935

CTG CAG GAG AAA TTT GGA ATT GGG ATT CCG ATC TTA TTT CTC CGA GGA     3003
Leu Gln Glu Lys Phe Gly Ile Gly Ile Pro Ile Leu Phe Leu Arg Gly
        940                 945                 950

TCT AAT TCT CAG CGT CTT CCT GAT AAA TAT CGG GGT CAC AGG CTC TTT     3051
Ser Asn Ser Gln Arg Leu Pro Asp Lys Tyr Arg Gly His Arg Leu Phe
    955                 960                 965

GGT GCT GGA AAG GAG CAA GCA GAA AGT TGG TGG AAG ACC CTT TCT CAC     3099
Gly Ala Gly Lys Glu Gln Ala Glu Ser Trp Trp Lys Thr Leu Ser His
970                 975                 980                 985

CAT CTC ATA GCT GAA GGA TTC TTG GTA GAA GTT CCC AAG GAA AAC AAA     3147
His Leu Ile Ala Glu Gly Phe Leu Val Glu Val Pro Lys Glu Asn Lys
                990                 995                 1000

TAT ATA AAG ACA TGT TCC CTC ACA AAA AAG GGT AGA AAG TGG CTT GGA     3195
Tyr Ile Lys Thr Cys Ser Leu Thr Lys Lys Gly Arg Lys Trp Leu Gly
            1005                1010                1015

GAA GCC AGT TCG CAG TCT CCT CCG AGC CTT CTC CTT CAA GCT AAT GAA     3243
Glu Ala Ser Ser Gln Ser Pro Pro Ser Leu Leu Leu Gln Ala Asn Glu
        1020                1025                1030

GAG ATG TTT CCA AGG AAA GTT CTG CTA CCA AGT TCT AAT CCT GTA TCT     3291
Glu Met Phe Pro Arg Lys Val Leu Leu Pro Ser Ser Asn Pro Val Ser
    1035                1040                1045

CCA GAA ACG ACG CAA CAT TCC TCT AAT CAA AAC CCA GCT GGA TTA ACT     3339
Pro Glu Thr Thr Gln His Ser Ser Asn Gln Asn Pro Ala Gly Leu Thr
1050                1055                1060                1065

ACC AAG CAG TCT AAT TTG GAG AGA ACG CAT TCT TAC AAA GTG CCT GAG     3387
Thr Lys Gln Ser Asn Leu Glu Arg Thr His Ser Tyr Lys Val Pro Glu
                1070                1075                1080

AAA GTT TCT TCT GGG ACT AAC ATT CCT AAA AAA AGT GCC GTG ATG CCG     3435
Lys Val Ser Ser Gly Thr Asn Ile Pro Lys Lys Ser Ala Val Met Pro
            1085                1090                1095

TCA CCA GGA ACA TCT TCC AGC CCC TTA GAA CCT GCC ATC TCA GCC CAA     3483
Ser Pro Gly Thr Ser Ser Ser Pro Leu Glu Pro Ala Ile Ser Ala Gln
        1100                1105                1110

GAG CTG GAC GCT CGG ACT GGG CTA TAT GCC AGG CTG GTG GAA GCA AGG     3531
Glu Leu Asp Ala Arg Thr Gly Leu Tyr Ala Arg Leu Val Glu Ala Arg
    1115                1120                1125

CAG AAA CAC GCT AAT AAG ATG GAT GTA CCT CCA GCT ATT TTA GCA ACA     3579
Gln Lys His Ala Asn Lys Met Asp Val Pro Pro Ala Ile Leu Ala Thr
1130                1135                1140                1145

AAC AAG GTT CTG CTG GAC ATG GCT AAA ATG AGA CCG ACT ACT GTT GAA     3627
Asn Lys Val Leu Leu Asp Met Ala Lys Met Arg Pro Thr Thr Val Glu
                1150                1155                1160

AAC ATG AAA CAG ATC GAC GGT GTC TCT GAA GGC AAA GCT GCT CTG TTG     3675
Asn Met Lys Gln Ile Asp Gly Val Ser Glu Gly Lys Ala Ala Leu Leu
            1165                1170                1175

GCC CCT CTG TTG GAA GTC ATC AAA CAT TTC TGT CAA GTA ACT AGT GTT     3723
Ala Pro Leu Leu Glu Val Ile Lys His Phe Cys Gln Val Thr Ser Val
        1180                1185                1190

CAG ACA GAC CTC CTT TCC AGT GCC AAA CCT CAC AAG GAA CAG GAG AAA     3771
Gln Thr Asp Leu Leu Ser Ser Ala Lys Pro His Lys Glu Gln Glu Lys
    1195                1200                1205

AGT CAG GAG ATG GAA AAG AAA GAC TGC TCA CTC CCC CAG TCT GTG GCC     3819
```

-continued

```
Ser Gln Glu Met Glu Lys Lys Asp Cys Ser Leu Pro Gln Ser Val Ala
1210                1215                1220                1225

GTC ACA TAC ACT CTA TTC CAG GAA AAG AAA ATG CCC TTA CAC AGC ATA     3867
Val Thr Tyr Thr Leu Phe Gln Glu Lys Lys Met Pro Leu His Ser Ile
                1230                1235                1240

GCT GAG AAC AGG CTC CTG CCT CTC ACA GCA GCC GGC ATG CAC TTA GCC     3915
Ala Glu Asn Arg Leu Leu Pro Leu Thr Ala Ala Gly Met His Leu Ala
            1245                1250                1255

CAG GCG GTG AAA GCC GGC TAC CCC CTG GAT ATG GAG CGA GCT GGC CTG     3963
Gln Ala Val Lys Ala Gly Tyr Pro Leu Asp Met Glu Arg Ala Gly Leu
        1260                1265                1270

ACC CCA GAG ACT TGG AAG ATT ATT ATG GAT GTC ATC CGA AAC CCT CCC     4011
Thr Pro Glu Thr Trp Lys Ile Ile Met Asp Val Ile Arg Asn Pro Pro
    1275                1280                1285

ATC AAC TCA GAT ATG TAT AAA GTT AAA CTC ATC AGA ATG TTA GTT CCT     4059
Ile Asn Ser Asp Met Tyr Lys Val Lys Leu Ile Arg Met Leu Val Pro
1290                1295                1300                1305

GAA AAC TTA GAC ACG TAC CTC ATC CAC ATG GCG ATT GAG ATT CTT CAG     4107
Glu Asn Leu Asp Thr Tyr Leu Ile His Met Ala Ile Glu Ile Leu Gln
                1310                1315                1320

AGT GGT TCC GAC AGC AGA ACC CAG CCT CCT TGT GAT TCC AGC AGG AAG     4155
Ser Gly Ser Asp Ser Arg Thr Gln Pro Pro Cys Asp Ser Ser Arg Lys
            1325                1330                1335

AGG CGT TTC CCC AGC TCT GCA GAG AGT TGT GAG AGC TGT AAG GAG AGC     4203
Arg Arg Phe Pro Ser Ser Ala Glu Ser Cys Glu Ser Cys Lys Glu Ser
        1340                1345                1350

AAA GAG GCG GTC ACC GAG ACC AAG GCA TCA TCT TCA GAG TCA AAG AGA     4251
Lys Glu Ala Val Thr Glu Thr Lys Ala Ser Ser Ser Glu Ser Lys Arg
    1355                1360                1365

AAA TTA CCC GAG TGG TTT GCC AAA GGA AAT GTG CCC TCA GCT GAT ACC     4299
Lys Leu Pro Glu Trp Phe Ala Lys Gly Asn Val Pro Ser Ala Asp Thr
1370                1375                1380                1385

GGC AGC TCA TCA TCA ATG GCC AAG ACC AAA AAG AAA GGT CTC TTT AGT     4347
Gly Ser Ser Ser Ser Met Ala Lys Thr Lys Lys Lys Gly Leu Phe Ser
                1390                1395                1400

TAANATGACN ACGATGGAAC AGTTTGTGTG TCCTACATCT TCATTCCTAT AAAGAATGAA   4407

NAGAAATATT TTAACCTCAA AATTATTTAA AGTCCAAAGT GAAGCTCACC TAAACGTCGA   4467

GCCATAGAGT CTTTAATTGN CCGTTGGCAG TTGAGCTACA GTATCTGAAC CTTCTGAGAC   4527

CCGGAGTGCA GCATAGACTG TGAAGTCGGC TTCCTTTCCG ATTGCCTTCC GAACCCGTGT   4587

CACTGTCAGG TTGCAGTCTT TCTCTTCTTG CAGCAGTGTG TGTTGGAAAT GGAGGCTGTG   4647

TCGCTTTGAC ATATAGAACA GATCAGTANT TGCATAGGGA CAGATATGAA GATNCAGCCG   4707

GTCTTTGCTT TCTTATGCAG ATGCCTGTAT GACAGTATCA GTGCACCAGC CCAGCCAGGG   4767

AGACATCAGC TTCCATTTAA AAAGG                                         4792
```

(2) INFORMATION FOR SEQ ID NO: 206:

(i) SEQUENCE CHARACTERISTICS:
(A) LENGTH: 1401 amino acids
(B) TYPE: amino acid
(D) TOPOLOGY: linear (ii) MOLECULE TYPE: protein (xi) SEQUENCE DESCRIPTION: SEQ ID NO: 206:

```
Met Glu Thr Thr Ser Leu Gln Arg Lys Phe Pro Glu Trp Met Ser Met
  1               5                  10                  15

Gln Ser Gln Arg Cys Ala Thr Glu Glu Lys Ala Cys Val Gln Lys Ser
```

-continued

```
                20                  25                  30

Val Leu Glu Asp Asn Leu Pro Phe Leu Glu Phe Pro Gly Ser Ile Val
            35                  40                  45

Tyr Ser Tyr Glu Ala Ser Asp Cys Ser Phe Leu Ser Glu Asp Ile Ser
    50                  55                  60

Met Arg Leu Ser Asp Gly Asp Val Val Gly Phe Asp Met Glu Trp Pro
65                  70                  75                  80

Pro Ile Tyr Lys Pro Gly Lys Arg Ser Arg Val Ala Val Ile Gln Leu
                85                  90                  95

Cys Val Ser Glu Ser Lys Cys Tyr Leu Phe His Ile Ser Ser Met Ser
            100                 105                 110

Val Phe Pro Gln Gly Leu Lys Met Leu Leu Glu Asn Lys Ser Ile Lys
        115                 120                 125

Lys Ala Gly Val Gly Ile Glu Gly Asp Gln Trp Lys Leu Leu Arg Asp
    130                 135                 140

Phe Asp Val Lys Leu Glu Ser Phe Val Glu Leu Thr Asp Val Ala Asn
145                 150                 155                 160

Glu Lys Leu Lys Cys Ala Glu Thr Trp Ser Leu Asn Gly Leu Val Lys
                165                 170                 175

His Val Leu Gly Lys Gln Leu Leu Lys Asp Lys Ser Ile Arg Cys Ser
            180                 185                 190

Asn Trp Ser Asn Phe Pro Leu Thr Glu Asp Gln Lys Leu Tyr Ala Ala
        195                 200                 205

Thr Asp Ala Tyr Ala Gly Leu Ile Ile Tyr Gln Lys Leu Gly Asn Leu
    210                 215                 220

Gly Asp Thr Ala Gln Val Phe Ala Leu Asn Lys Ala Glu Glu Asn Leu
225                 230                 235                 240

Pro Leu Glu Met Lys Lys Gln Leu Asn Ser Ile Ser Glu Glu Met Arg
                245                 250                 255

Asp Leu Ala Asn Arg Phe Pro Val Thr Cys Arg Asn Leu Glu Thr Leu
            260                 265                 270

Gln Arg Val Pro Val Ile Leu Lys Ser Ile Ser Glu Asn Leu Cys Ser
        275                 280                 285

Leu Arg Lys Val Ile Cys Gly Pro Thr Asn Thr Glu Thr Arg Leu Lys
    290                 295                 300

Pro Gly Ser Ser Phe Asn Leu Leu Ser Ser Glu Asp Ser Ala Ala Ala
305                 310                 315                 320

Gly Glu Lys Glu Lys Gln Ile Gly Lys His Ser Thr Phe Ala Lys Ile
                325                 330                 335

Lys Glu Glu Pro Trp Asp Pro Glu Leu Asp Ser Leu Val Lys Gln Glu
            340                 345                 350

Glu Val Asp Val Phe Arg Asn Gln Val Lys Gln Glu Lys Gly Glu Ser
        355                 360                 365

Glu Asn Glu Ile Glu Asp Asn Leu Leu Arg Glu Asp Met Glu Arg Thr
    370                 375                 380

Cys Val Ile Pro Ser Ile Ser Glu Asn Glu Leu Gln Asp Leu Glu Gln
385                 390                 395                 400

Gln Ala Lys Glu Glu Lys Tyr Asn Asp Val Ser His Gln Leu Ser Glu
                405                 410                 415

His Leu Ser Pro Asn Asp Asp Glu Asn Asp Ser Ser Tyr Ile Ile Glu
            420                 425                 430

Ser Asp Glu Asp Leu Glu Met Glu Met Leu Lys Ser Leu Glu Asn Leu
        435                 440                 445
```

-continued

```
Asn Ser Asp Val Val Glu Pro Thr His Ser Thr Trp Leu Glu Met Gly
    450                 455                 460

Thr Asn Gly Arg Leu Pro Pro Glu Glu Glu Asp Gly His Gly Asn Glu
465                 470                 475                 480

Ala Ile Lys Glu Glu Gln Glu Glu Glu Asp His Leu Leu Pro Glu Pro
                485                 490                 495

Asn Ala Lys Gln Ile Asn Cys Leu Lys Thr Tyr Phe Gly His Ser Ser
            500                 505                 510

Phe Lys Pro Val Gln Trp Lys Val Ile His Ser Val Leu Glu Glu Arg
        515                 520                 525

Arg Asp Asn Val Val Val Met Ala Thr Gly Tyr Gly Lys Ser Leu Cys
    530                 535                 540

Phe Gln Tyr Pro Pro Val Tyr Thr Gly Lys Ile Gly Ile Val Ile Ser
545                 550                 555                 560

Pro Leu Ile Ser Leu Met Glu Asp Gln Val Leu Gln Leu Glu Leu Ser
                565                 570                 575

Asn Val Pro Ala Cys Leu Leu Gly Ser Ala Gln Ser Lys Asn Ile Leu
            580                 585                 590

Gly Asp Val Lys Leu Gly Lys Tyr Arg Val Ile Tyr Ile Thr Pro Glu
        595                 600                 605

Phe Cys Ser Gly Asn Leu Asp Leu Leu Gln Gln Leu Asp Ser Ser Ile
    610                 615                 620

Gly Ile Thr Leu Ile Ala Val Asp Glu Ala His Cys Ile Ser Glu Trp
625                 630                 635                 640

Gly His Asp Phe Arg Ser Ser Phe Arg Met Leu Gly Ser Leu Lys Thr
                645                 650                 655

Ala Leu Pro Leu Val Pro Val Ile Ala Leu Ser Ala Thr Ala Ser Ser
            660                 665                 670

Ser Ile Arg Glu Asp Ile Ile Ser Cys Leu Asn Leu Lys Asp Pro Gln
        675                 680                 685

Ile Thr Cys Thr Gly Phe Asp Arg Pro Asn Leu Tyr Leu Glu Val Gly
    690                 695                 700

Arg Lys Thr Gly Asn Ile Leu Gln Asp Leu Lys Pro Phe Leu Val Arg
705                 710                 715                 720

Lys Ala Ser Ser Ala Trp Glu Phe Glu Gly Pro Thr Ile Ile Tyr Cys
                725                 730                 735

Pro Ser Arg Lys Met Thr Glu Gln Val Thr Ala Glu Leu Gly Lys Leu
            740                 745                 750

Asn Leu Ala Cys Arg Thr Tyr His Ala Gly Met Lys Ile Ser Glu Arg
        755                 760                 765

Lys Asp Val His His Arg Phe Leu Arg Asp Glu Ile Gln Cys Val Val
    770                 775                 780

Ala Thr Val Ala Phe Gly Met Gly Ile Asn Lys Ala Asp Ile Arg Lys
785                 790                 795                 800

Val Ile His Tyr Gly Ala Pro Lys Glu Met Glu Ser Tyr Tyr Gln Glu
                805                 810                 815

Ile Gly Arg Ala Gly Arg Asp Gly Leu Gln Ser Ser Cys His Leu Leu
            820                 825                 830

Trp Ala Pro Ala Asp Phe Asn Thr Ser Arg Asn Leu Leu Ile Glu Ile
        835                 840                 845

His Asp Glu Lys Phe Arg Leu Tyr Lys Leu Lys Met Met Val Lys Met
    850                 855                 860
```

-continued

```
Glu Lys Tyr Leu His Ser Ser Gln Cys Arg Arg Arg Ile Ile Leu Ser
865                 870                 875                 880

His Phe Glu Asp Lys Cys Leu Gln Lys Ala Ser Leu Asp Ile Met Gly
                885                 890                 895

Thr Glu Lys Cys Cys Asp Asn Cys Arg Pro Arg Leu Asn His Cys Ile
            900                 905                 910

Thr Ala Asn Asn Ser Glu Asp Ala Ser Gln Asp Phe Gly Pro Gln Ala
        915                 920                 925

Phe Gln Leu Leu Ser Ala Val Asp Ile Leu Gln Glu Lys Phe Gly Ile
    930                 935                 940

Gly Ile Pro Ile Leu Phe Leu Arg Gly Ser Asn Ser Gln Arg Leu Pro
945                 950                 955                 960

Asp Lys Tyr Arg Gly His Arg Leu Phe Gly Ala Gly Lys Glu Gln Ala
                965                 970                 975

Glu Ser Trp Trp Lys Thr Leu Ser His His Leu Ile Ala Glu Gly Phe
            980                 985                 990

Leu Val Glu Val Pro Lys Glu Asn Lys Tyr Ile Lys Thr Cys Ser Leu
        995                 1000                1005

Thr Lys Lys Gly Arg Lys Trp Leu Gly Glu Ala Ser Ser Gln Ser Pro
    1010                1015                1020

Pro Ser Leu Leu Leu Gln Ala Asn Glu Glu Met Phe Pro Arg Lys Val
1025                1030                1035                1040

Leu Leu Pro Ser Ser Asn Pro Val Ser Pro Glu Thr Thr Gln His Ser
                1045                1050                1055

Ser Asn Gln Asn Pro Ala Gly Leu Thr Thr Lys Gln Ser Asn Leu Glu
            1060                1065                1070

Arg Thr His Ser Tyr Lys Val Pro Glu Lys Val Ser Ser Gly Thr Asn
        1075                1080                1085

Ile Pro Lys Lys Ser Ala Val Met Pro Ser Pro Gly Thr Ser Ser Ser
    1090                1095                1100

Pro Leu Glu Pro Ala Ile Ser Ala Gln Glu Leu Asp Ala Arg Thr Gly
1105                1110                1115                1120

Leu Tyr Ala Arg Leu Val Glu Ala Arg Gln Lys His Ala Asn Lys Met
                1125                1130                1135

Asp Val Pro Pro Ala Ile Leu Ala Thr Asn Lys Val Leu Leu Asp Met
            1140                1145                1150

Ala Lys Met Arg Pro Thr Thr Val Glu Asn Met Lys Gln Ile Asp Gly
        1155                1160                1165

Val Ser Glu Gly Lys Ala Ala Leu Leu Ala Pro Leu Leu Glu Val Ile
    1170                1175                1180

Lys His Phe Cys Gln Val Thr Ser Val Gln Thr Asp Leu Leu Ser Ser
1185                1190                1195                1200

Ala Lys Pro His Lys Glu Gln Glu Lys Ser Gln Glu Met Glu Lys Lys
                1205                1210                1215

Asp Cys Ser Leu Pro Gln Ser Val Ala Val Thr Tyr Thr Leu Phe Gln
            1220                1225                1230

Glu Lys Lys Met Pro Leu His Ser Ile Ala Glu Asn Arg Leu Leu Pro
        1235                1240                1245

Leu Thr Ala Ala Gly Met His Leu Ala Gln Ala Val Lys Ala Gly Tyr
    1250                1255                1260

Pro Leu Asp Met Glu Arg Ala Gly Leu Thr Pro Glu Thr Trp Lys Ile
1265                1270                1275                1280

Ile Met Asp Val Ile Arg Asn Pro Pro Ile Asn Ser Asp Met Tyr Lys
```

-continued 1285 1290 1295

Val Lys Leu Ile Arg Met Leu Val Pro Glu Asn Leu Asp Thr Tyr Leu
1300 1305 1310

Ile His Met Ala Ile Glu Ile Leu Gln Ser Gly Ser Asp Ser Arg Thr
1315 1320 1325

Gln Pro Pro Cys Asp Ser Ser Arg Lys Arg Arg Phe Pro Ser Ser Ala
1330 1335 1340

Glu Ser Cys Glu Ser Cys Lys Glu Ser Lys Glu Ala Val Thr Glu Thr
1345 1350 1355 1360

Lys Ala Ser Ser Ser Glu Ser Lys Arg Lys Leu Pro Glu Trp Phe Ala
1365 1370 1375

Lys Gly Asn Val Pro Ser Ala Asp Thr Gly Ser Ser Ser Ser Met Ala
1380 1385 1390

Lys Thr Lys Lys Lys Gly Leu Phe Ser
1395 1400

(2) INFORMATION FOR SEQ ID NO: 207:

(i) SEQUENCE CHARACTERISTICS:
(A) LENGTH: 29604 base pairs
(B) TYPE: nucleic acid
(C) STRANDEDNESS: single
(D) TOPOLOGY: linear (xi) SEQUENCE DESCRIPTION: SEQ ID NO: 207:

TGAGGTTATT CTTTGAAGGG GACAGAATCC CATTTCACTT TTACTAGATA AGAATTTAGA 60

ACCTAACATC TGCCACCGTA GACTCTGAGT TATTAAATTG AGAGGAAATG GCCAAAGTGT 120

ATCCTGTAAT GAAATAATCC TCATATGAAA TTGTTCTTAT ATGACATTGG AAGACCTGTC 180

TTGCTCTGTC TTTTCAGTTT TGGATACATT TTCTTGACAC AAACCGGTAT CAGAGCCAGA 240

CTCTTTTCTG CTCTAACATC TTGCTTCTGT ACGTTATAAT CCTCAGTCCT CAAGCGGTCT 300

CTAACATCTT GCTTCTGTAC GTTATAATCC TCAGTCCTCA AGCGGTCTTC GGCGACGTCA 360

GCTACTCTTT TTTTGTACAG AGTGATGGTT ATAAAGTCTT CTTGTTGAAA ATCACTGTGA 420

ACTTAGTAGC TATAGTAAAA TTTTCATAAA GATCCGTAGA AATTAAAATT ATAGCATAAA 480

TATACAACTA GCTTTTTCTA ACATTTTGTT ATCAGATTTC AGAATAATCA TACATTTTTT 540

ACATTTTTAC TAAAAAATGA GTATTTACAT ATTTGACCAA AATAAAATTG AACCATTTTA 600

GATAATTATT GAAACAATTT CCACATTAAG CAGTATAACT GCCAATTAGT TAATTGCTGA 660

ATGATTACAT ATTAGTTATT AATATTGTCT AGCAACAACT TTATCTTATA CTCAAAATGA 720

TTATATTGGC CATTTAACTT AATTAAGTTT CTCGCTTTTT TAATGCTTTT AGAAAAGATT 780

GGGATGCCTT ATTTAGTTTA GCCCTCAAGC AATTAGGTGA GGCAATTACC ATGGTAACAG 840

AAGGTATTCA TTTCCTTACC TTAGCTAAAG GTTTTGGGAA CAAAGAAACC TCTCAGCTCA 900

TCCATTGAAA CCCAACTTTC TCCTGAGCCT GGCATTAAGT GTTTGTTCTC TAAAAGAGGA 960

CTTAATTTTA AGTGGGGAAA ACATGCCCCT GAGCTGAGTC TCTTTGTCAT AGGGCGATTA 1020

AAAAGCTACC TCTTCTTAAT AGGAAGTGTG GTCTTAACTT TTATATTTCA CATTTTATAT 1080

TGAGAATTTC TACACTCATA TAATGTTTTG ATCAAACTTT CCCTTTAAAT CCTTGCCTTC 1140

CCTATCCTCT TTCTTCCTTT GTTTCCTTCT TTGTTTGTTT CTCTCTCTCT CTCTCTCTCT 1200

CTCTCTCTCT CTCTCTCTCT CTCTTTCTTT CTTTCCTTCA AATGCCCTGA ACGTCCTTAC 1260

GCTGCTTCTC GCTGCATGAG TACAGGATCA CCTGAGATAC CTACCTAGCT GTCAGGAACC 1320

ACATCCTGAA GAAGACAGAC CCTTGCTTCC CCAGTGGCTG GCTATCTGTT GCCAATACTG 1380

-continued

```
TAGGCTTCAT GAGCTTCCCC TCAGTGCACG CTGAGATTTG GCTGGCTTGA TTTTTTTGCA   1440
TGCAGACATA GCCTCTGAGA TGGACAATAA TCCTGCCAAC AGTCTTCCTG CCCCTCTTCT   1500
GCAATGATTC CCAAGCCTTG TGACATGGGA GTCACATTTA GAGCTGGTCA GTTTTTGTTC   1560
TTTTTTCTTT TGTTTTGAAT TAAACTCGAA ATCTCATTGG TATGCTCTCT TTTGACAAAA   1620
GGATACCAGA CCACCTCTCC TAACGGTCTA ATTGCTGTCA AATAAAATCA CTTAAGGTGT   1680
ATTTTTCAAC ACATAATTTA TAGTTTTTGA CAGGTAATTT ATTAATATTT ATTTGGCTAG   1740
TTCTACCATT CCCAAGCAGA AAGTCTACTT ACTAAATTAG CTATCATGAG GCAAATTTTG   1800
TAACTAATTT ATCAAAAATT CTGGTCATGG TGGTGCATAT CTATAATCCT ATCACCCAGG   1860
ATTGTGGTTC AAGGCCAATC TCAAAGGAAA CTTTGTCTCA AAACAAACAA ACAAACAAAC   1920
AAACAAATTA ACATGAAACA GAACACATTA AAAAAACCCA GGGTTTTTAC CAGAAATTTA   1980
ATTATTAAAT ATATCTTGGA AATTAAAACC AGACAACAAC AACAACAACA TCAACCCACC   2040
CTGAGTATGC TGTTAAAAAT ACCAGTACTA GAGGCCTGGA GACATTGCTC ATGCTTGAGA   2100
CTATTAAGCA TTCTTACAGA AGAATGGGTT CTGTTTCTTG CAACCTCATG GTGGCTCACA   2160
GCTCCCAGTA TATGGACATC TGAGACTGGA AATGATAGGA AGAATTAAGG CTTTACACAA   2220
ATATCTGTCT AAAAACACGC ATGCGCCAGG CTGTCTATAT ACAGCGACTC CTGAATATTC   2280
ACACTTGCAT TTAATTTGAA TTCTGCATTG TGATGCCATA TAAACTGTTA AGTGCAGTGG   2340
AATTCAGGAA CTTGTGGTAC TTTCTGTTTA GTTTAAGATT AAAAGTGCAG TTACTATGTA   2400
GTGGGTAAAG GTGCTTGCTT TGCAAGCCTG ACAGCCTGGC TCAGGGTTCA GCCTCTGTGT   2460
GATGTAGGAG AGAAGCACAC CAGAGCATCA GTAACACTGT CAGGCATTGG TGCCTCTCAT   2520
GAGCTGGATC CCAAGTTGGG CCTGTCATTC CTGTTCCCCA GGCTCTTCTC CATATTTTTC   2580
CCTGCAGTTC CTTTAGACAG GAACAATTCT GAGTCAGAGT TTTTGACTGT GGGATGACAA   2640
CCCCATCCCT CCACTTGGTG CCCTGTCTTT CTATTGGAGG TGGACTCTAC AAGTTCCCTC   2700
TCCCCACTTT TGAGCATTTC GTCTAAGGTC CCTTGCTTTG AGTCCTGAGA GTCTCTCACC   2760
TCCGAGGTCT CTGGTACTTT CTAGAGGGTC CCCCCATTTG AGGGCAACTG ACAGTGCATT   2820
GAGCTTACCA AATATTTTGT AAACTTCTTG TTGTTCAGAT TTAATTACAT CTTTAAAGAG   2880
TTTTGTCCCT AGCTATCGTT CTCGCCGGCA AGAACACACG CGGACAACCG GATTCTTCTG   2940
CGGCAAGCTT TATTGCTTCT TAAGGAGGGA AGACCCAGAC CCTGGAAAAT GGTGCTGCTT   3000
ATATAGCCCT CAGCGTGGCG TTTCAGCACC TGATGTGGCA TGTCACCTCC TGATTTGTTG   3060
CTCGCCCATC ACTTCATTAC TATGCCCCGA GATGGGCAGT GACTAGGCGT GAGTTCACTC   3120
TTGCACTTGC GCACAAGGCT TGTTTATTAG GCACAGCGGA AGCCAGCGCC ATCTTATAAT   3180
GGTGATTACT CGCGGCACGG CTCTCCACAG AGTTTACCAG AAAATGTATT CATAAAATGA   3240
GTGTTATATT ACTTTCCTGT TATATTTATT CCCAATAATA TTGTTTATTT TATTGTATAG   3300
CTTTTTGCTA TTGTAAATAT AATTTTGACT CTGCCCTAAT TTCTGAGGAT GCATTGTCAT   3360
ATCAGAAAAA GTTTTATTAT AGTTTCTATT GTGTTTCTAT AGTTTTTATT ATAGTTTCTA   3420
GTTCAAACCA TATTACTGTT TTCTTTATCA ATTGAAAAAG AGCTACTTTT TAAATTATAG   3480
GCTCCTTGGT TCTCTGGTTA TAAACAATGG TATGCAAAAT AAAACCATTT ACCACTGTGT   3540
CTCTTAAAAA GAAAGTAGGA GATAACTGAC TTCACAAAGT TGCTCTGTGA TCCCCCACGC   3600
ATGTGTCATG GTGGGAGCTT GCTGGCATTC AAACATAAAC ATATCACAAA CGCACACACA   3660
TGCACACATA CTCTCTCTCT CTCACACATG CACACACACA CAATTTGTTA TTTCACTATT   3720
```

-continued

```
GAAGTCTTGA GAGACCAAAA GAAGGTTTTA CACTAAAAGG AACATTTTTA ATTATCCCCT   3780
CTGTTTCCTT TTTGAAGACT TGTAATATAA TTACATTATA GTTAAAACTG TAGCAATCAC   3840
AGATCACAGG GAAGATGCCC TGATAGCCCA GAAGTAGTAG CATGAAACAA TGTTTAATTA   3900
ATGCTGTCTG ACTCTCAAAT AATAACTAAT AGTACTAACA GAGCAGATGA GAGCTTTTAA   3960
TAGTATTTTG AAAATATTTT ATATAAAATT TAGTCATATT CAAAGCTGTC TATATGATTG   4020
GAAGGAATTA ACATGTCTCC TCTTTAAGGA AACAGAGACT CTCTTAGCTT TAAGGGCTTT   4080
GTGCCCTTGG TAATCCATGT AAGGGGCCTG AACTGCTGCA CAGCAGTTGG TTGTAAAGAA   4140
GTTTTTAGAC TGCCAAGCGA GACACTCCTC CTGCTGTTTG CTACCACTTG ATTAGAAAAT   4200
AGTTTGTGTG GTGGTTGTTA AATAAAATTC AAGTCATGAT CAAAAGTAAG CATAAAGTCC   4260
AATATATAGT AACCTTAATA ATGGGGGGAG GAGAGTGAGT ACTTGTCGAG TGTTCAAGAA   4320
GTCTCAGGTT CCGTCCACAG TCCCACATAC ACCAGGCACA GGGGCACAGA CCTGTCATCT   4380
CATCTCAGTA CGCGGGCAAG AAAATCAGGA GTTCAAAGCC ATCCTTGGCT ACATAGCAAG   4440
TTTGAGGCCA GCGTAGACGT CATGACATTC TGTCTCAATA AAACAAGCAA CAACAAGAAC   4500
ACTCCCCAAA CAACAACCTT CCCTCAAGTC CAAAGAAGAC TGAGACATGC GAGATGCACA   4560
GTAAACTAAG GTCATCAGGA GTGTGAGGGG CTTAGAGAGG ATGGGTGGGG GGGACTACAC   4620
TGTATGAAGC TGTCACAAAG ATGCACACTA GACAAGGGAA AATGTCTTTA AAATGCAGAC   4680
ATATAATCTT ATTTATTATT GTGTGTGAGT GTGGGTAGAC ACATGCCATG GCATGCATGT   4740
CAACTTTGTG GAGTTGCTTC TCTTTTTCTA CCTTTCCATG GATTCTGAGT CTCCAATTCA   4800
GGTCACCACA CCTGTGGAGT TAATACCCTT ATCTGCTGGG CTGTCTCATC AGCGCCAAAG   4860
AACTTGTTTT TAATACTGCC TGTGAATGAG ATGAATGGCA CTACTGAAAA ACTGTAAATT   4920
AATATAAATT ATGCTGATCC CTGCTTAGCC TCAAATGAAT GAGACCCAAA CTATAATTTA   4980
TTTATTGGGC TCTGCTCAAT TACCTCGGGA TGACCCCAAA TCTATTCTCT AATGCTAGTC   5040
TGGCTACTTC CCCAACTGTG CTCCCCAAAT ACTTGCCGTC TGAATCTTCC TGGGTGATTC   5100
CTGCTCTAGC AGCCTGGTGT CCCAGGAAGG CATTTCACTC AGGCAGTGCT GCTGGTCCAT   5160
CAGGACTAAT GGAGATCTCC TCTTTTCTAT GTCTTCTTCC CCATTCCCAC CCCACCCTTG   5220
TAATTGGTTG TTGCCAGTTT TACTTAACTA ATAGTTTTAA ATTGGATAAG TTTGCACAAC   5280
AAAGGTGGGT TGTAACTAGG GATTTGCTTG TCTTGGCGCA ACCAGATCAT GGAGTACAGA   5340
ATTTAACATA TGGATACAAG TAGCACCAGA CCAACCCACA ATAAAAAACA GACAAAAAAA   5400
AAAAAAAAAA AAAAAACCAG CAAAAAAAAC CCCCATAGAC AGTCTTTAAA TGATAAGAGC   5460
GGAAAAGTTG TAGGTGGTAA TAGATGGTTA GACAGGATAA TTTCAGGGAA GATTTAAGTT   5520
ATTTAAAAAA AATCTATTTA TATATGCATG CAATTGTGTG TGAGTGTGTG TGTGCGCACG   5580
TGATTGTATG AGTATGTGAT GGCCAGTGCT CTTGGAGGTC AGGGTGTCAG ATCTGGTAGC   5640
TGGAGTCTCA ACTTGGGTAG AAACTTTTAA CCTCTGAGCC ATCTTTCTAG CCCCAAGATA   5700
CTGGTTTTGT AAATAAATTT ACCTTTAAAT TCTCTTCCTG GGGGGTATCT AGATCCAATT   5760
TTGTACGTAA GCAGATATTT CAAATTAAAA TGATGCTGGT GTCACACAGC TGCCGATTAG   5820
TTACTGAGAT TTACGTTTGC TTCAACATTG TGCTGAACTA CATGCATAGC TTTTGTAAAA   5880
GGTTATTTGC TGAAACTAGC TTTCTGGTAT TTCACCAGTA ATATACTCTG GGCACAGAAC   5940
AAACTTGTTT TCTGACTCAA TATAAATATA TTGCGTGTGT GTGTGTGTGT GTGTGTGTGT   6000
GTGTGTGTGT GTGTGTGTGC ATGTTATAAA ATCCTGTCTT CTGCTCATGA CATAGCTGTT   6060
TCATTAACTC ACAGCAGTTT GTATTTGCCT GCATGAGACC TATATAAGAT CAAGCCAGTC   6120
```

-continued

```
TGAATCCCAG CATGCAAAGG GGAGATGCTA TCTGGGACCC ACCCTTCATG GGAGATACAG   6180
GAATTGGTGG CTCCTGGGGG AGGGAAGAGT AATTTTTCTT TGGGAGTGTG GCCATTGTCA   6240
TCTTGTCCAT GTTCCAGTGG ATAGCCCTAC ACTCATACAC AGAAGCAACA GTAACTGGAC   6300
TTAGTGGGTT ATAAAAAATA TTAGAAATGG AATTTGTATA CAACCGAGCC GTATCACTCC   6360
TGATCATATA CCCAAAGGAC TTTACCATAC AATAGAAGTA TTTGCTTAGC CATGTTTATT   6420
GCTAATCTTT TCATAATAGT GAGTATGTGA ATAAGTGGAT GAGTGGATAG AGAGTCTGGA   6480
ACTAGGTAGG AGACCATGAA CGGGAACAGT AGGTGTTGAG AAGGGGCAGG AGCAGAAAGC   6540
AAAAGGTCAC ATTGGGCATT GTCTTAGTTA GGCTTACTAT CGTTGTGACA AAACACAAAA   6600
TAAAATCTCC AAAAGCAACT TGGGGAGGAA AAGATTAGAA TTTACGACTC TTGAGTTCAT   6660
ACTCCATCAC TGTGGGAAGT CAGAGCAGGA ACTCTAGGCA GGAACTGAAG GAGAGGCCAA   6720
GGAGGAACAC TGCTTACTGG CTTTCTCTTC ATGGCTTGCT CAGCCTGTTT TCTTAGACAC   6780
CAAGAACAAC CTGCCCTGGG GTGACATCAC TTACTGTAGA CCAGGCCCTC CCACATTAAT   6840
CATGTGTCAA GAAAATGTCC CACATGCTTT CTTTAAGGCC AATCTTATAG AGCTGTGGGA   6900
AGCCACATGT GCCGTTGCAG AGTGGCACCG GCTACTGCTG GCTACCACGC ATAAGTTTGG   6960
ACAAACAACC AATGTGTACA TATGCAGTAA AGCTTTTTGC CAAGTCACTG CCTGGCCCCG   7020
GCATGTTAAT GAGGTACTGA GAATATAACC AATCAGATGT GAGACATGCA AATGAGGTAT   7080
GATAATGAGG TTCTGTGAGG TACTGAGAGA GAGTAGCCAA TCAGATGAGG AACATGCAAA   7140
TGAGGCATAG TGCATAACCA ATCCGTGTGT GAGACACGCC TCTCCTAGGC CTATATAAGC   7200
AGCACCAGTT CTGGGCTCAG GGTCTCTTTG CCTCTGCAAT CAAGCTCTCC CAGAAGGATC   7260
CTGTTGCAGC GTCGTTCTTG CTGGTCAAGT CGGGCGAGCA CAAAATAGAG CCTTTTTTTT   7320
TTTTTAAATT GAGAGTCCCT CCTCCCAAAT GACTCCCGCT TGTGTCAGGT GGACAGTAAA   7380
CTAGCCAGGA CAGATGACCC CCTTGTCAAC TTGGCACACC AGTACTTATT ATGAAAACAT   7440
AACCTTTCCC TTTTTGTTCA TTTTTAAGGT CTCATATTAA TATTATAATA TAAGCTATAA   7500
ATAACTTTAA AAGTTTCATA TTCTTTAAAA ATTCAAAAAA TTTACAAGTT AAGTCTCTTT   7560
AAAATATCCA AAATTTCTCT AAAATTACCA AGTTTCTTTG AAATATCCAA GGCCTCATAA   7620
ATGGATGTTT CTGTAAAATT AAAATAAATT ACTTTCTTAT TCCAAGAGAG AAGAAGCAGG   7680
GCACAGCCAC AGAAAATTCT GAGTGCACAT TAATAACTAA GTAAGATAAT GCCCCATAGG   7740
GTTGTCTTCT GTCGGCCTGT CTTACAGAGG CAATTTCTCA ATTATGCTTC CCTTTTCTCA   7800
GACAACACAT ACTTGTGTCA CATTGGCAAA AATCTAGCCA ACAAAGGCTT GAAAGCAGAA   7860
GGCTACTGGG GATGGCAGGG CTCAAGGACT GGGGACTTGG TGATTAGGGA GAAATAGGGC   7920
ATAGGAAGAG AAACCGCAAA AACAAAAATT TCTTGTAAAA ATGCTACAAT GAAACCTAAT   7980
CATCTGTATA TAATAAAAAG TGAATAGAAC AGATTGTACA TCTGTAATTT GCTATCATCT   8040
TTTGACTTCT GTTAGTGGTT TTGAAATCTT GGCAAAAAGC AACTTAACCA TTAACAGTTC   8100
TAAATTGCTT TAGGGTTTAT AAAACCTGCA TTTTCACATG AGATTGTCTT ATTACATTAA   8160
AGTTGGGTGG ATCTGGGAAG AGTTACACTA TGTATGCAAT TCTCAAAGAA CCGAGGAAAG   8220
GAAGATAAAA TTTCTTTATA TTATTTAATA GTGCTGAGTG TAGTAGGCTG TTCCTCCATC   8280
TTAAATGCGT GCTCTGATTT CTTCATGGTA ACAGAGGTTT CATCAGGAGA CTCTTCCAAA   8340
ACATATTTAA AACTTTACTC CCCACAAGAC ATTTGGGTAA CAGGAACTTT CCGGANGTGT   8400
GAGGAGTTTA TTACTTGGCT TTAGTATAAA TCATGTAGGA GCATGGATGC ATTTCATTAT   8460
```

-continued

```
TGAAAAAATA ATATATTTGG AGTCTCATAC TTGAAGTCTG GGTTATATTC CAGAGAGCCC   8520

TCAAAACTAG TAACAGCTTA AGAGAAAGAT CATCCAAGAA ACCCTTTCTT TTTAGGGAAG   8580

TGTCTCTTAC TCAGCCAAGA GCACAGTGAA AGGGCTTAGT ATTGGACAGC TATTATATCT   8640

TCAAAACTAG GTCTTTATTT TATTTTACGA ATAAATCCAG TAGTTGCTCT GAGTCAGCTT   8700

ATACCTTATG AGAGATGATA ATTATACAGA AAATCAAAGA TGCTGAAAAT GTAATACCTC   8760

ACATACTGAG GGATCCTGTT CATTAAGGAG ATAAAAATTA TTCTTTTGAA GGAGCAAAGC   8820

TATACACATA ACATATTAGA ATTTTGAAAC AGCCACAATC ATAGAACTTA ATTTGTTATA   8880

AAAGGAAGAA GTAATGTATA GTTAATAAGT GGTTTAAGCC TTGTCCTTGA GGCTAGATGT   8940

TATAACTCAT ACTAAATATG TATGTTTGTT TCAGGCTAGG TATCATATCC TACACGAAAT   9000

ATGTATGTAT GTTTCAGGTT AGATGCTATA TCCTACACTA ATTATATATG TTTGTTTCAT   9060

TTTCAGTCCT ATCTATGGAG CTGTCTCTGA GCTTTCTATC AAATATTTGT CATATTTATT   9120

CATAGATATT GTTTATTGGA ATTTGCAAAC AGGGCATTTT AAAGACAAAT GAAAATAAAA   9180

TGGAAACCAC TTCACTACAG CGGAAATTTC CAGAATGGAT GTCTATGCAG AGTCAAAGAT   9240

GTGCTACAGA AGAAAAGGTA ATTGTTCATT GATTATTTGT CTAAATGGGC AATCTTGTTT   9300

GAGTTTGACT ATGCAGTGAG TCACATCATT GCTTGTGAGC TTTGGGTCAT TGTTGAGGTA   9360

AAACTTTCTG TTGTGTGAAT GAACCAGAAC TAAGTTGTTC AAAGGTAAAT GAGACTCAAT   9420

TTTATACATG TTTTATAAAA TGAGATTCCC TAGAGTATAT TCTTTCTTTT TATAGTTAGC   9480

ATTCTTAGTT GAAGTTATTG GTTTGTTCAA ATTCAAGTAA TAATTTATAC AATATTAATG   9540

TTGGCATTTT TTGGTTAAAA TAGTTTGAGT CCTTAGAGGC TTAAGATCTG ATAATTAGCC   9600

ACCAACATTT TTTTGTTTTC TTTTTCAATA TTTTATTAGA TATTTTCTTC ATTTACGTTT   9660

CAAATGCTAT CCCGAAAGTC CCTTATACTC CCTCACTCCA CCCACTCCCC TACCCACCCA   9720

CTCCCACTTC TTGGCCCTGG CGTTTCCCTG TACTGGGGCA TATAAAGTTT GCAAGACCAA   9780

GGGGCCTCTC TTCCCAATGA TGGCTGACTA GGACATCTTC TGCTACATAT GCATCTAGAG   9840

ACATGAGCTC TGGGGGGTAC TGGTTAGTTC ATATTGTTGT TCTACCTATA GGGTTGCAGA   9900

TCCCCCCAGC TCCTTGGGTA CTTTCTCTAG CTCCTCCATT GGGGGCCCTG TGATCCATCC   9960

TATAGATGAC TGTGAGCATC CACGTCTGTG TTTGCCAGGC ACTGGCATAG CCTCACACGA  10020

GACAGCTATA TCAGGGTCCT TTCAGCAAAA TCTTGCTGGC ATGTGCAATA GTGTCTGCGT  10080

TTGGTAGCCA CCAACATTTT AAGGTTACAT TATTGCATCT AGCATGCTAA TATAATTATG  10140

AGGAAAAAAC AAGTAAATTA AGTGACTTCA CAAAAGAAAG ATTGGATGTT TGAAAATAGA  10200

ATTGTGTGGA AAAATAACTT TATGTTTACC CTTGTTAATC TGACCTTATG AATTCTTACT  10260

CTATAATATA AAATGTAGTG CTATAAATTT CTTCAGTGAA CTTTATTATT TCAGTTAACA  10320

CTACAACTTA CTGTGATATT TATTTGTGCC TGTTTTGAAT TTTGCTCAAC TCAAGGCCTG  10380

CGTTCAGAAG AGTGTTCTTG AAGATAATCT CCCATTCTTA GAATTCCCTG GATCCATTGT  10440

TTACAGTTAT GAAGCTAGTG ATTGCTCCTT CCTGTCTGAA GACATTAGGT AAGGGATTGG  10500

AAGTTCTTAC CATTAAGTTT GTACCCGTAA GAAATAGCGA TATTTATGAG TGCCTAGTTT  10560

TACAATGGAA GTATATCTCA GAAGTATATT TACATACATC ATATCACAGT TGTATTCTAC  10620

TTTTTAAAAT ATAAAATAAA CTCACTAAAT TAAATTAGTA AGGTTCCTAT TTGTTAATTA  10680

GTAACCTTTT CTACTTTATT AGATACTTTT TTTTTCTTTT AGTGCTTTAG ATGTAAATAC  10740

AGGTAAAACT ATTGAAGACA ACTGTTTACC AATTTAGGAA AAAATGGAAA ATGTTATTTA  10800

ATGTCGAACT ATTTTCATAT CTTAAAACAT CAATGTATTA AGTAATGTTT ATGATTCTCT  10860
```

-continued

```
GTTTTATTTT TTTTAATTTA TTTTTAGCTT TTAAAATTGT GTTAGGATGC CTCCTCTGCG  10920
TGTATGTTTG TATACCACAT GGTTACGGTG TCCACAGAGG CCAGGAGAGG GCTTTGGATC  10980
CCCTTGAACT GGAGTTGTGA GCGATCTTAT GGGTGCCGGG AATCAAGCCT AGGTTCTCTG  11040
GAAGAGCAGC CAGTGCATTC AGCTGCTGAA CCATTTTAAA AGATAGTGAT AGTTCCTGCA  11100
AATGGTCCAT GAAAAGAGCT TTAGCAATGA CTGTTGGTAC TTTAAGAGTT GCCTGTCTTT  11160
GTTTTTCTAA GGCTATAACA AAATCCATGG CCTGAGTAAA TTATAAAAAA ATACATATAA  11220
GTAAATTCAT AAATAAATTT ATTCCTTACA GTTTTGGAGG CTATAGAGCC CCCAGAGAAT  11280
GGGATTGGCA TTTGTAAGGG GACCATTTTT TTTTTTAAAT TGGATATTTT CTTTATTTAC  11340
ATTTCAAATG TTATCATCTT TTCTGGTTTC CTTCCCTCCT GGAAACCCCC TATCACATCC  11400
TCCGTCTCTC TGCTTCTGTA AGAGTGTTCC TCTACCCACC CACCCACCCA CCCACCCACT  11460
CCCACCTTCC TGCCCTTGAT TCACCTACAC TGATGCATCT ATTGAGCCTT CATAGGACCA  11520
CGGACATCTC CTCCCACTGA TGAATGACAA GGCCATCCTC TGCAACATAT GCAGCTGGAG  11580
CTATGTGTAC TCCTTGGTTG ATGGCTTAGT CCCTAGTTTT CTGGGGGTGG GGGAGGTGTG  11640
ATCTGGTTGG TTTATGTTGT TGTTCTTCCT ATGGGATTTC AAACCCTTTC AACTCTTTCA  11700
GTCCCTTCTC TAACTCCTCT ATTAAGGACC CTGCGCTCAG TCCAATGGTT GGCTGTTAAC  11760
ATCCACCTCT GTATTTGTAA GGCTCTGGCA GGGCCTCTCA GGAGCAGGCT CCTTTCAGCA  11820
TGCACTTCTT GGCATCCACA ATAGTGTCTG GGTTTGGTAA CTGTATATGG AATGAATCCC  11880
CAGGTGAGAC AGTTTCTGGG TGGTCTTTCC TTCAGTCTCT GCTCTTCACT TTATCTCCAT  11940
ATTTGCTCCT GTGAGTATTT TGTTCTCCTT CTAAGAAGGA CCGAAGCACC CCCACTTTGG  12000
TCTTCTTTCT TATTGACCTT CATGTAGTCT GTGAATTGTA TCCTGGTCAT TTGGAGCTTT  12060
TGGGCTAATA TCCACTTATC AATGAGTGTA TAATATTTGT GTTCTTCTGC GATTGGGTTA  12120
CCTCACTCAG GATGATATTT TCTGTCCATT TGCCTAAGAA TTTCATGAAT TCATCATTTT  12180
TAATAGCTGA GTAGTAAGTA CTCCATTGTG TAAATGTACC ACATTTTCTG TATCTATTCC  12240
TCTTTTGAAG GACATCTGGC TTCCTTCCAG CTCCTGGCTA TTATAAATAA ATATATAAAC  12300
ATAGTGGAGC ATGTGTTCTT ATTACATATT GGAACAGAAA GAGCAATTTG CAAATTCATT  12360
TGGAATAACA AAAAAAAAAA AAAAAAAAAC CCAGGATAGC GAAAACTATT CTCAACAATA  12420
GAAGAACTTC TGGGGGAATC ACCATCCTGA CCTCAAGTTG TATTACAGAG CAATAGTGAT  12480
AAAGACTGCT TGGTAATGGT TCAGAGACAG GCAGGAAGAT CAATGGAATA GAATTGAAGA  12540
CCCAGAAATG AACCCACACT CATATGGTCA CTTAATCTTT GACAAAGGAG CTAAAACCAT  12600
CCAGTGGAAA AATGACAGCA TTTTTAACAA ATGGTGTTAG TTTAACTGGT AGTCAGCATG  12660
TAGAAGAATG CAAATCGACC CATTTTTTTC TTTTCTTTTC TTTATTTACA TTTCAAATGT  12720
TATTCCCTTT CCTGGTTTCC CCTCTAACCC CCCCCCCCCC CCACACACAC ACACACACAC  12780
ACCAACCCAC TGGCTTCCTC TTCCTGGCCC TGGCATTCCT CTATACTGGG GCATAGAGCC  12840
TTCAAAAGAC CAAGGGCCTC TCCTCCCATT GATGACCAAC TAGGCCATCC TCAGCTACAT  12900
ATGTAGCTGA AGCCATGAGT GTGCTCTTTG GTTAGTGGTT TAGTCTCTGA GAGCTCTGGT  12960
GGTACTGGTT AGTTCATATT GTTGTTCCTC CAATGGGGCT GCAAACCTCT GCTACTCCTT  13020
GGTTACTTTC TCTAACTCCT TCACTGGGGA TCCTGTGCTC AGTCCAATGG ATGGCTGTGA  13080
GCATCCATTT CTGTATTTGA AGTTGACCCA TTCTTACCTC CTTGTACAAA GCTCAAGTCC  13140
AAGTGGATCA AGGACCTTCA CATAAAACCA GATACACTGA AACTTATAGA GAAGAAAGTG  13200
```

-continued

```
GGGAAGAGCC CCAAACATAT GGGCACAGGG GAAAAATTCC TGAACAGAAC ACCAATGGCT  13260
TATGCTGTAA GATAAAGAAT CAACAAATGG GACCTCATAA AATTGCAAAG CTTCTGTAAG  13320
GCAAAGCACA TTGTCAATAA GAAAAAAAGG CCACCAACAG ATTGGGAAAA GATCTTTACC  13380
AATCCTACAT CTGATAGAGG GCTAATATCC AATATATTCA AAGAACTCAA GAAGTTAGAC  13440
TTCAGAGAAC CAAATAACCC TATTAAAAAT GGGGTTCAGA GCTGTCTTAG TCAGGGTTTC  13500
TATTCCTGCA CAAACATCAT GACCAAGAAG CAAGTTGGGG AGGAAAGGGT TTATTCGGCT  13560
TACATTTCCA TATTGCTGTT GATCACCAAA GGATGCAGGA CTGGAACTCA AGCAGGTCAG  13620
AAAGCAGGAG CTGATGCAGA GACCATGGAG GGATGTTCTT TACTGGCTTG CTTCCCCTGG  13680
CTTGCTCAGC CTGCTCTCTT ATAGAACCCA AGACTACCAG CCCAGAGATG GTTCCACCTA  13740
CAAGGGGCCT TTCCCCCTTT ATCACTAATT GAGAAAATGC CTTAGAGTTG GATCTCATGG  13800
AGGCATTTCC TCAACTGAAG CTCCTTTCTC TGTGATAACC CCAGCTGTGT CAAGTTGACA  13860
CAAAACCAGC CAGTACAAGA GCTAAACAAA GAATTTTCAA CTGAGGAATA CTGAATGGCT  13920
GAGAAGCACC TAAAGAAATG TTCAACATCC TTAATGATCA GGGAAATGCA AATCAAAACA  13980
ACCATGAGAT TCCACCTCAC ACCAGTCAGA ATGGCTAAGA TCAAAAACTC AGGTGACAGC  14040
AGATGCTGGC AAGGATGTGG AGAAAGAGGA ACACTCCTCC ATTGCTGGTG GGATTGCAGG  14100
CTTGTACAAC CACTCTGGAA ATCAGTCTGG CGGTTCCTCA GAAAACTGAA CATAGTACCT  14160
ACTACCTGAG GACCCAGCTA TACCACTCCT GGGCATATAT CCAGAAGATG CTGCAACATC  14220
TAAGGGAACT TTGTACTGCG TCTGTATCAG GGTAGAGGCT AAGATGGGTT GGGATTAAGC  14280
CAGTTCTCTG GATACCTGTT CTGGGAGTGG AGCCCTGATG AGCCAAACAC TTGTGTTTAG  14340
GCCCCACCTC CACGCCCTGC TCCATTAAGG ATTCCATTTT AACAGGGACT ATGAATAGGA  14400
TATTCATGAC CCAGCACCTT GTGTAATTCG GGTTCTGGAG TAATGCAATC TAAGCCTCTT  14460
GATGCAACTT ACACTGAGAA GTAGTAAATC AATTCAGATC ATTGAAATGA CTGCGTGTGT  14520
CCTTTTGGTT TTTAACTATT TTCATGAAAA GCAGAAGTGA ATAAAGTTGT TCATCAGTGC  14580
CCTCCTGGTG GTTGGTAAAT GTGATCTAGA AGTGGCATTT AGGTATCTTT ACTTCCACTG  14640
CATTTACTGG TTATGTGTGG GCTTCATTTT GCTGAACTAA AATTAGACTT ACAGAATAAG  14700
TAAATCTATT ACACACGGTT ATATATTGTC CTCACCATGT TACCTTTGTC TTCCTACGGT  14760
ATGACATGTG TTTTATTAGT CAGAGGGTTT TTTTTTTTTG GTTTGTTTGT TTATCTTTTG  14820
TTTTTAAAGG AATAGAACTG GCAGAATGAA CGTATATATA TATCAAACAG GGATTTATTA  14880
GTGTGGCTTT GCAGACTGAG GTCTCTTGTC CAACAATGGC TGTGCCTCAT CAAAGCCAAG  14940
AATCCTTTTT TCTCGTAGTT GTTCATTCGA GGAGCCTGGG TGTCTAAGTC AGTCTTCAGT  15000
CTGCATGGGC TTCCTGAAGA AGGAATTTCT AACACCAGCT AAGTAGTGCC TTAGTAGCAA  15060
GACAGACGAA CTTGCCAGCC AGACTGAGGA CAGGCTGACA AAAAGCCAAA GCTTCCCTCT  15120
TCCGTGCCCC TTCAGAAGTG GGCCGCCATC AGAAAGCGTA ACCTAGATTT AGGATGCTCT  15180
TCTCCTGTCA CATAATCTAA TCAAGAAAAG CCCTCATAGG TGAGCCCAGG GCTTATATTT  15240
TAGATGATTC CAAATGGAGT CAGGTTGCCA GCCAAGATCA GCTCAGCACA GTAAGTTGAA  15300
GTGGTCTGAA TGAAGCTCTG TGTTCATTTT GAAGTGCAAG ACGGGCTTGG TTTGCTTTGC  15360
ATTACTTTTC ATATGGCCAC TTTGGAGATC CTCGCATCAG GGGCTGGAAA CATGGCCCCC  15420
CATTAAGAGC AGGAAGCGCT ATTGCAGAGG ACCCCAGTCT GGTTCCCAGT ACCCATAATG  15480
GTGGCTCACA GACCTCTGTT TTCTATGACT CCAGCTCCAG GGTGCTGAGT CCCTCTTCTG  15540
CCCTCTACAG GCACCTGTGC TTATGTGCAC ATATGTACCC CTCTTCCCAT ACACACCTGG  15600
```

-continued

```
TTAGAAAAAT AAAAATCTTA AAGAATATTT TTACACCAGG GCCAGTGACA TGGCTCAGCG  15660
GGTAACAGGG CCTGCCACCA AGACTGGAGA TCTGAGTTCT AATCCCATTT CAACCTCAGA  15720
GGCTCATGGT GGAAGCCAAG AGCTGATCCT GAATTCAACA TGCATGGGGC CACCAAAAAA  15780
GAAAGAAAGA AAGAAAGCAA TTTAAAAAGA TGTTTACCCC ATGGGGTTTC AACAGTTTGA  15840
TATGACATAC CTTTGTGTGC TGAAGTTTGT GCTGATCCTG CTTGGGGACC ATCGACCTTT  15900
TTTTTTTTTT TTTTTAAATT TGTGGGTTTA ATAGTTTTTG TCCAATTTGA AAATCATCTT  15960
CAGTTTTTAT TTTTTTCAGT ACTGTGCTTT TCTGGGACTC TGATATACAT ACACTAGGTT  16020
GCTGGATACT ATGTCTTAAC TTCTTTTCTC TTTTTGTTTA TGCTTTGGTT TGAATGTTTC  16080
TTCTGCTGTG TCTTTAAGTT AATCACCTAT ATTTCTTCTG TAGTGGCTGA TCTACTGTAT  16140
ATCCTCCCTG TGTATTTTTA ATTTTCATTG TGTTTTTCTC TTTTTTGTTA TTGAAAATGA  16200
TTTTTTTAAA AATACAACAC ATTTGGACTG TGGTTTCCCT TTCCACAACT CACCCCAAAT  16260
CCTCTCCACC TCAACAGAAA AAGAAAGGGC CAGAGAAGAA GCACAGGAAA CACATACAGA  16320
TGCAGGCCAC ACACGTGTAC ACACAGGAAT CTCATAAGTA CACAAAATCA GAAACCAGAT  16380
ATATAAAAAT TATATAAGCA AAAGACTTGC TAGATTAACA AAATAAAGGT TCATTCTCTG  16440
TTGGCCATTT ACTGCTGGGC CTAGGGCCTG CTGGTGAGTG TGGTTTGTAT ACCCAGTGAG  16500
TCTGGTGGAG AAACTAGTTT TTCCTTTGTG AGTGGTTATA AATAGGAGAT AATTTCTGGG  16560
TGAGGGATAG GATCGGCGCT GGGACTTTAT CTGGTTAGAC CTGGGTAGAC CCTGTGTGTG  16620
CTCCCACATG AAAGCTCTTC TGTGCTTTAT CAGCCCTGCT GTGTCTTGAA GGGCTTCTTG  16680
CCTTGGTGTC TTCCATCCCA CTGGGTCTTA CAACCTCTCT GCCCCCTCTT TTGCAAAGTT  16740
CCCTGAGCCA TGCGGGGAGG GGTCTGTCAT TGTTCCCATC TCCTGCAGGA GGCAGTGTCT  16800
CTGACATTGG CTGGGCAAGA CACTGAGCCA TGAGCATAAA AAAACCCTGC CAATTTGCTA  16860
TTCATTGTGT GCATGCTTTC CTTTAAATTC CTGAACATAT TTACAATTTA TAATAGTTTT  16920
CGTTTGTCTT GTTTTGAGCA GGGGCTTATG TAGCCTAGGC TGGCCTTGAA TGTACTCTGT  16980
CGCCAAGGCT GATCTTAGTT CCTGATCCTA TTGCCTATGC CACCAAGTGC TGGGATCACT  17040
GACTTGTGCC AGCAGGCCCT GCTGTGACCA TAATGCAAAT TTCAGTGATA TTTTAGCTCT  17100
ATTTTTGCCT CTATTGAGTG ATCACCCCGC CAACTGATTA TGTTTATGTT TGATATGTGT  17160
CAGGGCTGTT GAGGTTTTTT TTCTTTTTCT TTTTTTTTTT TTTTTTTTGG TCTGCTGTTG  17220
TGATTTTACC TTGCTCAATA TATATATATA TATATATATA TATATATATT TTTTTTTTTT  17280
TAGTTTGCTT TCTAAGAAAA GAGGTTTTGC CAGAGGGCTC ACCCAGAGAT GGGTTTTGTA  17340
TTCGGAGGCT TGCTTTTAGA CCTCATTAGG CCGGCAATTG CTTTTCCTCC AAAGGTAATT  17400
TAGTTCTCTC AGGTGCGATC ATAAGGGAGG CTGCTGCATG TTCCTAGAGT TCAGCAAGAA  17460
TGTCTGCTGG GACTTGGGAA CTTACGCTCT TACCTCTGTC TGTGTCCCCA CCTCAGGGCT  17520
GTCCTTTCTC TGTTGTCTGT AAGGCATTCT AGGAGAACCA GGGACAACGA CAGAGACTGT  17580
CCTCTTGTTC AGAGAACAGT AAATTTAGAC GTGTTTGTAC AATTTATTGT TTCTTTTTAG  17640
TGGAAAAAGA AGTACTTGTA AATTTTATCT TAGCCTGAGG TATTAGTTGA TATTCTTTTA  17700
TGTTTGTAAT AAATTTTTAA TCAAAACTTG TGAACTAGGC ATAGAAACAA TAGTAAACAA  17760
AACCGTATCT TCTTATTTAA TTATATCAAA TCTTTATTAT TTAGTGTGTA TGTGTGTGTG  17820
CTCATGTATG TAGATATATA CTTGGTCAGA GGACAACTTT CAGGAGTAGT TTTCTTCTAT  17880
TATTTATGTC TAAAATTAAA TAGAAAATAA AAGCTCATGT ATACCCTTTT TAATTTATTT  17940
```

-continued

```
TCTTCCAACC CCCGTGCTAC TTTAAATAAC ATGTCATGAA TTTAGTATTT ATCATTTCTT  18000
TATATTGTGT TATTTGCCAA CTTAGAAACT ATATGGTTTT CCTGAAGCTT GTCTTTTTCA  18060
CTCAAGTTTT GAGAATTTTT CATTTTGATA TATGTAGTTC CATTATTTTA TATGCTATAT  18120
TATGTTTTGG CATGCCACAA TTTCTTTATT TTTTTGTTTT ATGGAAACAT AGTTTTTCCA  18180
ATTCCCCCGT CTGCAAAAGG ATCAGGGTTG TAGTGAACAT TCTTTCTTTG CTGTGTTGGT  18240
TAGTGTTTCT TGTCCATTTG GCACAGCCTA GAGTCGTCTG AGGCTAAGGA ACCCAACTGA  18300
GAGAATGCCC CATCAGATTG GTGTATAGGC AAGCGTGGGA ATAGGGTTTT CTTGACTGAT  18360
GATTGATGTG GGAGGGACCA GCTCACCTTG GGCAATGTCA TCCCTTGGGA GTTGGTCCTA  18420
CCTTGTATAA GAAAGCAAAC CTAGCAAGCC AGTTAGCAGT GTTTCTCCAT GGCCTCTACT  18480
TCCGCTCCTG CTTCTAGGGA CCTGCCTTGA GTTCCTGCCC TGACTTCCTT TTCTTCCCAA  18540
ATTGCTTTTG GACATGGTGA TGATCACAGC AATAGATGGC AAACTAAGAC ATTAATCAAT  18600
TGAGCTGTCT CACCTTTTAG AGTGGTTTGA ATAAGCATGG CCCTCAAAGG CTCATATATA  18660
GAATGGCTAA TCACCGAGGA GTGGAACTCT TTGATAGGAT TGGAACAGTG GTTCTCAACT  18720
TGAGAGTCTT GATGTCTTTG GACATTAAGC GACCCTTTCA CAGATATCCT GAATATCAGG  18780
TATTTACATC GTGATTCATA GCAGTAACAA AATTACAGTT ATGAAGTACC AATGAAATCA  18840
TTTTATGGTT GGCGTCATTA GGAAGGTTGA CAACCACTGG ATTAGAAGAA TTAGGACTTA  18900
TGACCTTGTT GGGGGAAGTG TGTCACTTGG GGTGGGCTTT GAGGCTTCAA AAGCCTAGAC  18960
TTTGAACAGA CCTTTTGCAC AAGAACAGGC CTCTTGTTCT CTCTACTGCT GCTCAGGGTA  19020
TAGCTCTCAG CTGCTGCCGC AGTGCCGTGC TTTACACCAT GATAATGGAC TAAGCCTCTG  19080
AGCTGTAAGC CAGCCACCAA TTACATGCTT TCTTTTATGA GAGTTGCCAT GGTCATGGTG  19140
TCTCTGCAGC AGTACAACAG TGACTAAGAC AGAAGGAAAC ATAGAAACAT TCACGCAGTT  19200
AATCCACACA ATTTTTCCTT TGATAGCATG CGTCTGTCTG ATGGCGATGT GGTGGGATTT  19260
GACATGGAAT GGCCGCCCAT ATACAAGCCA GGGAAACGAA GCAGAGTCGC AGTGATCCAG  19320
TTGTGTGTGT CTGAGAACAA ATGTTACTTG TTTCACATTT CTTCCATGTC AGGTTGGTAT  19380
CTCTGCTTCA TTGTCATATG GCCATCAATA ATACCATATC AACTTTCTTC CTGCAAAGTT  19440
AAGTTCTTTC ATTAGCAGGC CTTCTTTCAT GATCTTGTAT TTGTTTAAGT ATTTATATTT  19500
TTACTTGATT TTTATACCTT TTCCCTTGGT TAGAGAATAG AGAACTGAAG TTTAGAGGTG  19560
TAAATGACTA GGAATAATAC CCTATTACTG TTACTACAGG TGGCGTTCGA ACTCATTCTA  19620
TCTAGTCAAA TTTCAGTCTG GACTCTGCAT TAGCTAAGAA AAGAGATAGT TAAGGTGAAT  19680
GTGATTCTAA ATTTAAGCTT AATATAAACA GTTTACCACA CATTCCGTGT GCATTAAAAT  19740
AGTAAATCCA TTATATTAAA GAGTTTTATG GAAATAATAA TGAAATGTTT TAGTTTTCCC  19800
CCAGGGATTA AAAATGTTAC TAGAAAACAA ATCAATTAAG AAGGCAGGGG TTGGGATTGA  19860
AGGGGACCAG TGGAAACTTC TGCGTGATTT TGACGTCAAG TTGGAGAGTT TTGTGGAGCT  19920
GACGGATGTT GCCAATGAAA AGGTAGGCGT AATAAATGCA GTATTTTAAT AAACATGATA  19980
ACCTGAGTTT CATAGAATGT GCATTTTCAT CTAAATGTTA AGTTTCTTTT TTTTTCCATT  20040
TTTTATTAGG TATTTAGCTC ATTTACATTT CCAATGCTAT ACCAAAAGTC CCCCATACCC  20100
ACCCACCCCC ACTCCCCTGC CCACCCACTC CCCCTTTTTG GCCCTGGCGT TACCCTGTAC  20160
TGGGGCATAT AAAGTTTGCA AGTCCAATGG GCCTCTCTTT CCAGTGATGG CCGACTAGGC  20220
CATCTTTTGA TATATATGCA GCTAGAGTCA AGAGCTCCGG GGTACTGGTT AGTTCATAAT  20280
GTTGTTCCAC CTATAGGGTT GCAGATCCCT TTAGCTCCTT GGCTACTTTC TCTAGCTCCT  20340
```

-continued

```
CCATTGGGAG CCCTATGATC CATCCATTAG CTGACTGTGA GCATCCACTT CTGTGTTTGC  20400
TAGGCCCCGG CATAGTCTCA CAAGAGACAG CTACATCTGG GTCCTTTCAA TAAAATCTTG  20460
CTAGTGTATG CAATGGTGTC AGCGTTTGGA TGCTGATTAT GGGGTGGATC CCTGGATATG  20520
GCAGTCTCTA CATGGTCCAT CCTTTCATCT CAGCTCCAAA CTTTGTCTCT GTAACTCCTT  20580
CCATGGGTGT TTTGTTCCCA AATCTAAGGA AGGGCATAGT GTTCACACTT CAGTCTTCAT  20640
TCTTCTTGAG TTTCATGTGT TTAGCAAATT ATATCTTATA TCTTGGGTAT CCTAGGTTTG  20700
GGGCTAATAT CCACTTATCA GTGAGTACAT ATTGTGTGAG TTTCTTTGTG AATGTGTTAC  20760
CTCACTCAGG ATGATGCCCT CCAGGTCCAT CCATTTGGCT AGGAATTTCA TAAATTCATT  20820
CTTTTTAATA GCTGAGTAGT ACTCCATTGT GTAGATGTAC CACATTTTCT GTATCCATTC  20880
CTCTGTTGAG GGGCATCTAG GTTCTTTCCA GCTTCTGGCT ATTATAAATA AGGCTGCTAT  20940
GAACATAGTG GAGCATGTGT CCTTCTTACC AGTTGGGGCA TCTTCTGGAT ATATGCCCAG  21000
GAGAGGTATT GCTGGATCCT CCGGTAGTAA ATATGTCCAA TTTTCTGAGG AACCGCCAGA  21060
CTGATTTCCA GAGTGGTTGT ACAAGCCTGC AATCCCACCA ACAATGGAGG AGTGTTCCTC  21120
TTTCTCCACA TCCACGCCAG CATCTGCTGT CACCTGAATT TTTGATCTTA GCCATTCTGA  21180
CTGGTGTGAG GTGGAATCTC AGGGTTGTTT TGATTTGCAT TTCCCTGATG ATTAAGGATG  21240
TTGAACATTT TTTCAGGTGT TTCTCTGCCA TTCGGTATTC CTCAGGTGAG AATTCTTTGT  21300
TCAGTTCTGA GCCCCATTTT TTAATGGGGT TATTTGATTT TCTGAAGTCC ACCTTCTTGA  21360
GTTCTTTATA TATGTTGGAT ATTAGTCCCC TATCTGATTT AGGATAGGTA AAGATCCTTT  21420
CCCAATCTGT TGGTGGTCTT TTTGTCTTAT TGACGGTGTC TTTTGCCTTG CAGAAACTTT  21480
GGAGTTTCAT TAGGTCCCAT TTGTCAATTC TCGATCTTAC AGCACAAGCC ATTGCTGTTC  21540
TGTTCAGGAA TTTTTCCCCT GTGCCCATAT CTTCAAGGCT TTTCCCCACT TTCTCCTCTA  21600
TAAGTTTCAG TGTCTCTGGT TTTATGTGAA GATCCTTGAT CCACTTAGAT TTGACCTTAG  21660
TACAAGGAGA TAAGTATGGA TCGATTCGCA TTCTTCTACA CGATAACAAC CAGTTGTGCC  21720
AGCACCAATT GTTGAAAATG CTGTCTTTCT TCCACTGGAT GGTTTTAGCT CCCTTGTCGA  21780
AGATCAAGTG ACCATAGGTG TGTGGGTTCA TTTCTGGGTC TTCAATTCTA TTCCATTGGT  21840
CTACTTGTCT GTCTCTATAC CAGTACCATG CAGTTTTTAT CACAATTGCT CTGTAGTAAA  21900
GCTTTAGGTC TGGCATGGTG ATTCCGCCAG AAGTTCTTTT ATCCTTGAGA AGACTTTTTG  21960
CTATCCTAGG TTTTTTGTTA TTCCAGACAA ATTTGCAAAT TGCTCCTTCC AATTCGTTGA  22020
AGAATTGAGT TGGAATTTTG ATGGGGATTG CATTGAATCT GTAGATTGCT TTTGGCAAGA  22080
TAGCCATTTT TACAATGTTA ATCCTGCCAA TCCATGAGCA TGGGAGATCT TTCCATCTTC  22140
TGAGATCTTC CTTAATTTCT TTCTTCAGAG ATTTGAAGTT TTTATCATAC AGATCTTTCA  22200
CTTCCTTAGT TAGAGTCACG CCAAGATATT TTATATTATT TGTGACTATT GAGAAGGGTG  22260
TTGTTTCCCT AATTTCTTTC TCAGCCTGTT TATTCTTTGT ATAGAGAAAG GCCATTGACT  22320
TGTTTGAGTT TATTTTATAT CCAGCTACTT CACCGAAGCT GTTTATCAGG TTTAGGAGTT  22380
CTCTGGTAGA ATTTTTAGGG TCACTTATAT ATACTATCAT ATCATCTGCA AAAAGTGATA  22440
TTTTGACTTC CTCTTTTCCA ATTTGTATCC CCTTGATCTC CTTTTCTTGT CGAATTGCTC  22500
TGGCTAATAC TTCAAGTACT ATGTTGAAAA GGTAGGGAGA AAGTGGGCAG CCTTGTCTAG  22560
TCCCTGATTT TAGTGGGATT GCTTCCAGCT TCTCTCCATT TACTTTGATG TTGGCTACTG  22620
GTTTGCTGTA GATTGCTTTT ATCATGTTTA GGTATGGGCC TTGAATTCCT GATCTTTCCA  22680
```

-continued

```
ACACTTTTAT CATGAATGGG TGTTGGATCT TGTCAAATGC TTTTTCTGCA TCTAACGAGA  22740
TGATCATGTG GTTTTTGTCT TTGAGTTTGT TTATATAATG GATTACATTG ATGGATTTTC  22800
GTATATTAAA CCATCCCTGC ATCCCTGGAA TAAAACCTAC TTGGTCAGGA TGGATGATTG  22860
CTTTAATGTG TTCTTGGATT CGGTTAGCGA GAATTTTATT GAGGATTTTT GCATCGATAT  22920
TCATAAGAGA AATTGGTCTG AAGTTCTCTA TCTTTGTTGG GTCTTTCTGT GGTTTAGGTA  22980
TCAGAGTAAT AGTGGCTTCA TAAAATGAGT TGGGTAGAGT ACCTTCTACT TCTATTTTGT  23040
GAAATAGTTT GTGCAGAAGT GGAATTAGAT CTTCTTTGAA GGTCTGATAG AACTCTGCAC  23100
TAAACCCATC TGGTCCTGGG CTTTTTTTGG TTGGGAGACT ATTAATAACT GCTTCTATTT  23160
CTTTAGGTGA TATGGGACTG TTTAGATAGT CAACTTGATC CTGATTCAAC TTTGGTACCT  23220
GGTATCTTTC CAGAAATTTG TCCATTTCGT CCAGGTTTAC CAGTTTTGTT GAGTATAGCC  23280
TTTTGTAGAA GGATCTGATG GTGTTTTGGA TTTCTTCAGG ATCTGTTGTT ATGTCTCCCT  23340
TTTCATTTCT GATTTTGTTA ATTAGGATTT TGTCCCTGTG CCCTCTAGTG AGTCTAGCTA  23400
AGGGTTTATC TATCTTGTTG ATTTTCTCAA AGAACCAGCT CCTCGTTTGG TTAATTCTTT  23460
GAATAGTTCT TCTTGTTTCC ACTTGGTTGA TTTCACCCCT GAGTTTGATT ATTTCCTGCC  23520
GTCTACTCCT CTTGGGTGAA TTTGCTTCCT TTTTTTCTAG AGCTTTTAGA TGTGTTGTCA  23580
AGCTGCTAGT ATGTGCTCTC TCCCGTTTCT TCTTGGAGGC ACTCAGAGAT ATGAGTTTTC  23640
CTCTTAGAAA TGCTTTCATT GTGTCCCATA GATTTGGGTA CGTTGTGGCT TCATTTTCAT  23700
TAAACTCTAA AAAGTCTTTA ATTTCTTTCT TTATTCCTTC CTTGACCAAG GTATCATTGA  23760
GAAGAGTGTT ATTCAGTTTC CACGTGAATG TTGGCTTTCC ATTATTTATG TTGTTATTGA  23820
AGATCAGCCT TAGGCCATGG TGGTCTGATA GGATACATGG GACAATTTCA ATATTTTTGT  23880
ATCTATTGAG GCCTGTTTTG TGACCAATTA TATGGTCAAT TTTGGAGAAG GTCCCGTGAG  23940
GTGCTGAGAA GAAGGTATAT CCTTTTGTTT TAGGATAAAA TGTTCTGTAG ATATCTGTCA  24000
GGTCCATTTG TTTCATAACT TCTGTTAGTT TCACTGTGTC CCTGTTTAGT TTCTGTTTCC  24060
ACGATCTGTC CTTTGAAGAA AGTGGTGTGT TGAAGTCTCC CACTATTATT GTGTGAGGTG  24120
CAATGTATGC TTTGAGCTTT ACTAAAGTGT CTCTAATGAA TGTGGCTGCC CTTGCATTTG  24180
GTGCGTAGAT ATTCAGAATT GAGTGTTCCT CTTGGAGGAT TTTACCTTTG ATGAGTATGA  24240
AGTGTCCCTC CTTGTCTTTT TTGATAACTT TGGGTTGGAA GTCGATTTTA TCCGATACTA  24300
AAATGGCTAC TCCAGCTTGT TTCTTCAGTC CATTTGCTTG GAAAATTGTT TTCCAGCCTT  24360
TTACTCTGAG GTAGTGTCTG TCTTTTTCCC TGAGATGGGT TTCCTGTAAG CAGCAGAATG  24420
TTGGGTCCTG TTTGTGTAGC CAGTCTGTTA GTCTATGTCT TTTTATTGGG GAATTGAGTC  24480
CATTGATATT AAGAGATATT AAGGAAAAGT AATTGTTGCT TCCTTTTATT TTTGTTGTTA  24540
GAGTTGGCAT TCTGTTCTTG TGGCTTTCTT CTTTTTGGTT TGTTGAATGA TTACTTTCTT  24600
GGTTGTTCTA GGGCGTGATT TCCGTTCTTG TATTGCTTCT TTTCTGTTAT TATCCTTTGA  24660
AGGGCTGGAT TCGTGGAAAG ATATTGTGTG AATTTGTTTT TGTCGTGGAA TACTTTGGTT  24720
TCTCCATCTA TGGTAATTGA GAGTTTGGCC TGGTATAGTA GCCTGGGCTG GCATTTGTGT  24780
TCTCTTAGTT TCTGTATAAC ATCTGTCCAG GCTCTTCTGG CTTTCATAGT CTCTGGTGAA  24840
AAGTCTGGTG TAATTCTGAT AGGCCTTCCT TTATATGTTA CTTGACCTTT CTCCCTTACT  24900
GCTTTTAATA TTCTATCTTT ATTTAGTGCA TTTGTTGTTC TGATTATTAT GTGTCGGGAG  24960
GAATTTCTTT TCTGGTCCAG TCTATTTGGA GTTCTGTAGG CTTCTTGTAT GATCATGGGC  25020
ATCTCTTTTT TTATGTTTGG GAAGTTTTCT TCTATTATTT TGTTGAAGAT ATTAGCTGGC  25080
```

-continued

```
CCTTTAAGTT GAAAATCTTC ATTCTCATCA ATTCCTATTA TCCGTAGGTT TGGTCTTCTC  25140
ATTGTGTCCT GGATTACCTG GATGTTTTGA GTTAGGATCC TTTTGCATTT TGTATTTTCT  25200
TTGACTGTTG TGTCGATGTT CTCTATGGAA TCTTCTGCAC CTGAGATTCT CTCTTCCATT  25260
TCTTGTATTC TGTTGCTGAT GCTCGCATCT ATGGTTCCAG ATCTCTTTCC TAGGATTTCT  25320
ATCTCCAGCG TTGCCTCGCT TTGGGTTTTC TTTATTGTGT CTACTTCCCC TTTTAGTTCT  25380
AGTATGGTTT TGTTCATTTC CATCACCTGT TTGGATGTGT TTTCCTGTTT TTCTTTAATG  25440
ATTTCTACCT GTTTGGCTGT GTTTTCCTGC TTTTCTTTAA GGGCCTGTAA CTCTTTAGCA  25500
GTGCTCTCCT GTAATTCTTT AAGTGACTTA TGAAAGTCCT TCTTGATGTC CTCTATCATC  25560
ATCATGAGAA ATGTTTTTAA ATCTGGGTCT AGATTTTCGG TTGTGTTGGG GTGCCCAGGA  25620
CTAGGTGGGG TGGGAGTGCT GCGTTCTGAT GATGGTGAGT GGTCTTGATT TCTGTTAGTA  25680
GGATTCTTAC GTTTGCCTTT CGCCATCTGG TAATCTCTGA AGCTAGCTGT TTTAGTTGTC  25740
ACTGTTAAGA GCTTGTTCTT CAGGTGACTC TGTTAGCCTC TATAAGCAGA CCTGGAGGGC  25800
AGCACTCTCC TTAGTTTCAG TGAGCAGAGT ATTCTCTGCA GGCAAGCTCT CTTCTTGCAG  25860
GGCAGGTACC CAGATATCTG GTGTTCGAAC CAGACTCCTG GCAGAAGTTG TGTTCCACTC  25920
ACTAGAGGTC TTAGGATCTT GTGTGGAATC CTGTGTGGGC CCTTGCAGGT GTCAGGCGAC  25980
TCTGCTGGCA AGGTAGCCCG GGGCTCGAGT CGAGTGGAAG GGACTTGTGC CCCAGATCAG  26040
GCCCGGGTAG CCTGCTTCCC TATGTACTGC AGTCTCAGGT TCCGCGCGAT TGGATTGGGG  26100
CAGGCACTGT GTTCCACTCA TCAGAGGTCT TAGGATCCTG TGGGGGGTCC CGTGTGGGCC  26160
CTTGCGGGTG TTGGGCAAAC TCTGCTGGCA AGGTAGCCCT GGGCTCGAGT CGAGCGGAAG  26220
GGACTTGTGC CCCAGATCAG GCCAGGGTAG CCTGCTTCCC TATGTACTGC AGTCTCAGGT  26280
TCCGCGCGAT TGGATTGGGG CAGGCGCTGT GTTCCACTCA CCAGAGGTCT TAGGATCCCG  26340
TGGGGGGTCC CGTGTGGGCC CTTTCGGGTG TTGGGCAAGA CTCTGCTGGC AAGGTAGCCC  26400
GGGGCTCGAG CTCTTTTTTT TTCTTTAAAA AAAAATTTTT TTTATTAGGT ATTTTCCTCA  26460
TTTACATTTC CAATGCTATC CCAAAAGTCC CCCATACCCT CCCCCTGACT CCCCTACCCA  26520
CCCACTGCCA CTTCTTGGCC CTGGCGTTCC CCTGTACTGA GGCAGATAAA GTTTGCACGA  26580
CCAATGGGCC TCTCTTTCCA CTGATGGCCT GCTAGGCCAT CTTCTGCTAC ATATGCAGCT  26640
AGAGACAAGA GCTCCAGGGG GTACTGGTTA GTTCATATTG TTGTTCCACT TATAGGGTTG  26700
CAGATCCCTT TAGCTCCTTG GATACTTTCT CTAGCTCCTC CATTGGTGCC CTGTGATCCA  26760
TCCAATAGCT GACTGTGATC ATCCACTTCT GTGTTTGCTA GGCCCCGGCA TAGTCTCACA  26820
AGAGACAGCT ATATCAGGGT CCTTTCAGCA AAATCTTGCT AGTGTATGCA ATGGTATCTG  26880
TGTTTGGCGG CTGATTATGG GATGGATCCC CGGATATGGT AGTCTCTAGA TGGTCCATCC  26940
TATTGTCTCA GCTCCAAACT TTGTCTCTGT AACTTCTTCC ATGGGTGTTT TGTTCCCAAT  27000
TCTAAGAAGG GGCAAACTGT CCACACTTTG GTCTTCATTC TTCTTGAGTT TCATGTGCAT  27060
TGTATCTTGT ATCTTGGGTA TTCTAAGTTT CTGGGCTAAT ATCCACTTAT CAGTGAGTAC  27120
ATATCATGTG AGTTCTTTTG TGATTGGGTT ACCTCACTCA GGATGATGCC CTCCAGGACA  27180
ATCCATTTGC CTAGGAATTT CATAAATTCA TTCTTTTTAA TAGGTGAGTA GTACTCTGTT  27240
GTGTAAATGT ACCACATTTT CTGTATCCAT TCCTCTGTTG AGGGGCATCT GGGTTCTTTC  27300
CATCTTCTGG CTATTATAAA TAAGGCTGCT ATGAACATGG TGGGGCATGT GTCTTTCTTA  27360
CCAGTTGGAA CATCTTCTGG ATATATGCCC AGGAGAGGTA TGTCGGGATC CTCTGGTAGT  27420
```

-continued

```
ACTATGTCCA TTTTTCTGAG GAACCGCCAG ACTGATTTCC AGAGTGGTTG TACAGCTTTC  27480
AATCTGACCA GCAATGGAGG AGTGTTCCTC TTTCTCCACA TCCTCACCAG CATCTGCTGT  27540
CACCTGAATT TTTGATCTTA GCCATTCTGA CTGGTGTGAG ATGGAATCTC AGGGTTGTTT  27600
TGATTTGCAT TTCCCTGATG ATTAAGGATG CTGAACATTT TTTCAGGTGC TTCTCGGCCA  27660
TTCGGTATTC CTCAGGTGAG AATTCTTTGT TTAGCTCTGA GCCCCATTTT TAATGGGGTT  27720
ATCTGATTTT CTGGAGTCCA CCTTCTTCAG TTCTTTATAT ATATTAGATA TTAGTTCACT  27780
ATCTGATTTA GGATAGGTAA AGATCCTTTC CCAGTCTGTT GGTGGCCTTT TTGTCTTATT  27840
GACGGTGTCC TTTGCTTTAC AGAAGCTTTG CAATTTTATG AGGTTCCATT GGTCAATTCT  27900
AGATCTTACA GCACAAGCCA TTGCTCTTCT ATTCAGGAAT TTTTCCCCTG TGCCCATATC  27960
TTCAAGGCTT TTCCCCACTT TCTCCTCTAT AAGTTTAAGT GTCTCTGGTT TTATGTGGAG  28020
TTCCTTGATC CTATTAGATT TAACCTTAGA ACAAGGAGAT AGGAATGGAT TAATTCGTAT  28080
TCTTCTATAT GTTAACCACC AGTTGTGCCA GCACCATTTG TTGAAAATGC TGTCATTTTT  28140
CCACTGGATG GTTTTAGCTC CCTTGTCAAA GATCAAGTGA CCATAGGTGT GTGGGCTCAT  28200
TTTTGGGTCT TCAATTCTAT TCTACTGGTC TACTTGTCTG TCACTATACC AGTACCATGC  28260
AGTTTTTATC ACAATTTAGG TCAGGCATGG TGATTCCACC AGAGGTTCTT TTATCCTTGA  28320
GAAGAGTTTT TGCTAACCTA GGGTTTTTGT TATTCCAGAT GAATTTGCAG ATTGCTCTAA  28380
TTCATTGAAG AATTGAGTTG AAATTTTGAT AGGGATTGCA TTGAATCTAT AGATTGCTTT  28440
TGGGAAGATA GCCATTTTTA CTATATTGAT CCTGCCAATC CATGAGCATG GGAGATCTTT  28500
CCATCTTCTG AGATCTTCTT TAATTTCTTT CTTCAGAGAC TTGAAGTTTT TTTTCATACA  28560
GATCTTTCAC TTAGTTAGAG TCACACCAAG GTATTTTATA TTATTTGTGA CTATTGAGAA  28620
GGGTGTTGTA TCCCTAATTT CTTTCTCAGC CTTTTTATTC TTTGTGTAGA GAAAGGCCAT  28680
TGACTTGTTT GAGTTAATAT CCAGCCACTT CACCGAAGCT GTTTATCAGG TTTAGGAGTT  28740
CTCTGGTGGA ATTTTTAGGG TCACTTATAT ATACTATCAT ATTATCATCT GCAAAAAGTG  28800
ATATTTTGAC TTCTTCTTTC CAATTTGTAT CCCCTTGATC TCCTTTTCTT GTCGAATTGC  28860
TCTGGCTAGG ACTTCAAGTA CAATGTTGAA TAGGTAGGGA GAAAGTGGGC AGCCTTGTCT  28920
AGTCCCTAAT TTTAGTGGGA TTGCTTCCAG CTTCTCACCA TTTACTTTGA TGTTGGCTAC  28980
TGGTTTGCTG TAGATTGCTT TTATCATGTT TACGTATGGG TCTTGAATTC CTGATCTTTC  29040
CAAGACTTTT ATCATGAATG GGTGTTGGAT TTTGTCAAAT GCTTTCTCCT CTTCTAACAA  29100
GATGATCATG TGGTTTTTGT CTTTGAGTTT GTTTATATAA TGGATTACGT TGCTGGATTT  29160
CCATATATTA AACCATCCCT GCATCCCTGA AATAAAATCT ACTTGGTAAG GATGGATGAT  29220
TGTTTTAATG TGTTCTTGGG TTCGGGTAGC GAGAATTTTA TTGCTTATTT TTGCATCAAT  29280
ATTCATAAGG GAAATTGGTC TGAAGTTCTC TATCTTTGTT GGATCTTTCT TTGTTTTAGG  29340
TATCAGAGTA TTGTGTCTTC ATAGAATGAA TTGGGTAGAG TACCTTCTGC TTCTATTTTG  29400
TGGAATAGTT TGTGCAGAAC TGGAATTAGA TATTCTTTGA AGGTCTGATA GAACTCTGCA  29460
TTAAACCCAT CTGTCCCTGG GCTTTTTTTG GTTGGCAGAC TATTAACGAC TGCTTCTATT  29520
TCTTTAGGGG ATATAGGATT GTTTAGATCA TTAACCTGAT CTTGATTTAA TTTTGGTACC  29580
TGGTATCTGT CTAGAAACTT GTCC                                          29604
```

(2) INFORMATION FOR SEQ ID NO: 208:

(i) SEQUENCE CHARACTERISTICS:
(A) LENGTH: 16442 base pairs

-continued (B) TYPE: nucleic acid
(C) STRANDEDNESS: single
(D) TOPOLOGY: linear (xi) SEQUENCE DESCRIPTION: SEQ ID NO: 208:

TGTTCTTGTG GCTGTCTTTT TGGTTTGTTG AAGGATTACT TTCTTATTTT TTCTAGGGCG 60

TGGTTTCTAT CCTTGTATTG GGTTTTTTTT TTTTTTCTGT TATTATCCTT TGAAGGGCTG 120

GATTCGTGGA GAGATAATGT GTGAATTTGG TATTGTCATG GAATACTTTG TTTTCTCCAT 180

CTATGGCAAT TGAGAGTTTG GTTGGGTATA GTAGCCTGGG CTGGCGTTTG TGTTCTCTTA 240

GGGTCTTTAT AACATCTGTC TAGGATCTTC TGGCTTTCAT AGTCTCTGGT GCAAAGGTCT 300

GGTATAATTC TGATAGGCCT GCCTTTATAT GTTACTTGAC TTTTTTCCCT TACTGCTTTT 360

AATATTCTAT CTTTATTTAG TGCACTTGTT GTTCTGATTA TTATGTGTGG GGAGGAATTT 420

CTTTTCTGGT CCTGTCTATT TGGAGTTCTG TAGGCTTCTT GTATGTTCAT GTGCATCTCT 480

TTAAGTTTGG GAAGGTTTCT TCTATTATTT TGTTGAAGAT ATTTGTTGGC CCTTTAAGTT 540

GAAAATCTTC ATTTTCATCT ACTCCTATTA TCCGTANGTT TGGACTTCTC ATTGTGTCCT 600

GAATTTCCTG GATGTTTTAA GTTAGGATCT TTTTGCATTT TGCATTTTCT TTGATTGTTG 660

TGCCTATGTT CTCTATGGAA TCTTCTGCAC CTGAGATTCT CTCTTCCATG TCTTGTATTC 720

TGCTGCTGAT GCTTGCATCT ATGGTTCCAG ATTTCTTTCC TAGGGTTTCT ATCTCTAGCG 780

TTGCCTCATT TTGGGTTTTC TTTATTGTGT CTACTTCGCT TTTTAGGTCT ACTATGGTTT 840

TGTTCATTTC CATCACCTAT TTGGATGTGT TTTCCTGTTT TTCTTTAAGG ACTTCTACCT 900

GTTTGGTTAT TTTTTCGTGT TTTTCTTTAA GGACTTGTAA CTCTTTAGCA GTGTTCTCCT 960

GTATTTCTTT GAGTTATTAA AGTCCTTCTT GATGTCCTCT ACTATCATCA TGAGATATGC 1020

TTTTAAATCC GGGTCTAGCT TTTCGGGTGT GTTTGGGTGC CCAGGACTGG GTGAGGTGGG 1080

AATGCTGCAT TCTGATGATG GTGAGTGGTC TTGGCTTCTG TTACTAAGAT TCTTACGTTT 1140

GCCTCTCACC ATCCAGTAAT CTCTGGAGTC AGTTGTTATA GTTGTCTCTG GTTAGAGCTT 1200

GTTCCTCTTG TGATTCTGTT AGTGTCTATC AGCAGACCTG GGAGACTAGC CTTCTCCTGA 1260

GTTTCAGTAG TCAGAGCACT CTCTGCAGAT AAGCTCTCCT CTTGTAGGGA CGGTGCCCAG 1320

ATATCTGGCA TTTGAACCTG CCTCCTGGCA GATTTTGTGT TCCACTCACC AGAGGTCCTA 1380

AGATCTCGTG GAGAGTGTTC TGGGTACCTT GGGGGTGTCC GACAACTCCG TGTCCGACAA 1440

TTCTAGTGCT GGGGCCGACT GGAAGGGACC TCTTTTTCTT TTATAAAGTA ATGAAAGCTA 1500

TGTGTTGATT TTGGTGGCAA AAGAGAAGTT CAAAGTGCAA TAATGAAACC CTCCATTTCT 1560

GAAACTCCAT CTCAGCGTCC AGTTGCCTGA ACTAACGCCC GTTCATCTTT CCTGCCAACC 1620

TTAGTATTTT GTATATTGCA CACTTGAATG TTTATTGTAT CTAACGGATT TATTCCAATA 1680

GCACGTCTTT GGAAAAGATG ACTACAGGGC AACTCTCAAT ATAGAATGTT GAGTGTCTGT 1740

TTGACCTTTA ACATCATCAC CTATGTTTCC ATCATTTTAT TGATGAGATG ATTACATCCT 1800

TATATTCAGC CACGTATTCA TTTGGTTTTG AGATCAAAAC CATTCTTGCC TATTCCGCTG 1860

CCTTCTAGGA ACAGCATCTT TAACGTTTCA GCCCTTTGAT ACCCACATTA TGGAACCTCG 1920

GAGTTAAATT CCTACTGTCC ACTATGAATG AGGTCTCAGA TGGGAGGCTT GTTTTTTTTG 1980

TGGTCCCTGG GGACAGCTGA CTATGACTGT GAATGTTTGC TCTGTCCCCC TTTCACTCCT 2040

TCCAGTTGAA GTGCGCAGAG ACCTGGAGCC TCAATGGTCT GGTTAAACAC GTCTTAGGGA 2100

AACAACTTTT GAAAGACAAG TCCATCCGCT GCAGCAATTG GAGTAATTTC CCCCTCACTG 2160

AGGACCAGAA ACTGTATGCA GCCACTGATG CTTATGTATG TATTTAAAGA CCTTTAATAT 2220

-continued

```
GACATCATTC TCATTTCTCG GACCAAATCA CTTTAGTAAA AATGTATTGG GGTTATGTCC   2280
TTAGCTGAAA TATTTTATTA TAGTTTGGCA TTAAAATTTG CTTAGGAATA CATCAAGTGA   2340
AATTCTTCAT GTTAATTAGA AAATACCAAT TAATAGGTTG TTTAGCAGTA GTTATTTCTA   2400
CTATTACGAT GTAAAGTGAT GTCCAATTCC TGTGTAAAAG AATGTGAACT TACTGAAAAC   2460
ATGAAAGGCT TTGAGCTTAG CAGGCACAAA TAGTTTGATG ATGTATTTTG TATATAAGCA   2520
ACTCAGAATC AGAAAAATCA CAGGCTTTCC ATATTTAAAC TAGCCTTATT CCCTACATTT   2580
ATATTTAAAA TGTGGAAATT TAGATAAATT GCCTCCAAAT TTAGTTGCTG CTGTTCTTAG   2640
ATGTATTTTC ATATGTGTAA TCTGTACATA CTGGCATCTA GGCTTGTCTT TATATATAGT   2700
ACTGTGGTCT GTGTGTGCTT TACCTTAAGA AATGTTTCTT TTGTAAATTT CTTTGCCCTA   2760
GATCATACTT ATTGCTCATA TTTAAATAGT ATTTATTGAT AAATATCTTG TTAATTTTCC   2820
ACCTTACATT TATTTTTAAG ACATCGATAC TCTAACTTTT AGCCAGAAAA ACAAAGGAAA   2880
ACCAACTGTC TTAGTCAGGG TTTCTATTCC TGCACAAACA TCATGACCAA GAAGCAAGTT   2940
GGGGAGGAAA GGGTTTATTC AGCTTACACT TCCATACTGC TGTTCATCAC CAAGGAAGTC   3000
AGGGCTGGAA CTCAAGCAGG TCAGAAAGCA GGAGCTGATG CAGAAGCCAT GGAGGGATGT   3060
TCTTTACTGG CTTGCTTCCC CTGGCTTGCT CAGCCTTCTC TCTTATAGAA CCCAAGACTA   3120
CCAGCCCAGA GATGGTCCCA CCCACAAGGT GTCTTTCCCC CTTGATCACT AATTGAGAAA   3180
ATACCCCACA GCTGGATCGC ATGTAGGCAC TTCCTCAACT GAAGCTCCTT TCTCTGTGAT   3240
AACTCCAGCC TGTGTCAAGT TGACACAAAA CTAGCCAGTA CAGCAACAGA TGCTTTTTGT   3300
CAGGAGAACA GCTGGATGAG TTGGGATGTG CTGTTGTTCC TTTGGCTTCC TTTGCTTCCT   3360
TGCTTACTTG CTTTAAAAAA AATAACAGAC TCTCTTGCAG CTTATTCCAC TCTTGAACTG   3420
TTCATGCAGC CGAGGCTGCC CTTAATGTCC AGATCCTCTT GCCCCTGTTT CCTTGCTATG   3480
GAGATTACAG GCTGTAGTGT CTATATTCTT GACAGTTTGT ATGACTTGAT CAAGTCTGTG   3540
AAAAATACCC AGCATGCATT GTTGTTCATA CACTGACCAG CATTCTCAGT TGGTTTAATG   3600
AAATCTCAAG AATTGGATAG GATCTGTCAC CAAAACAGAT GTTTCTTACT AGATGGTAGT   3660
TATTAGATTT TGTTTACAGA TCATTTCATT TGGATACCTA TTTACAATAC TGAAAATTAG   3720
TAAGTGAAAA TTTAAAGCTG TATTTTATAG CCTAGGCAGC TTTTGTTTCC CCATTGGGTA   3780
GTGCTTACAT GAAGACCCGA GTCTTTGCAT ACTGAAATAG TTTTACTTCA TTTTTGGAGA   3840
GTATTTTGGA AATCATTCTT GTAGATGTTG CTTGAGATAT CACATATATA TATTTATTTT   3900
GGTAATCTTT AACTTGCACT TTGTTTTTCT TTTGTCTTTT TATAGGCTGG TCTTATCATC   3960
TATCAAAAAT TAGGAAATTT GGGTGATACT GTGCAAGTGT TTGCTCTAAA TAAAGGTATG   4020
TTGTGGCCTA AAATAAAAGA TAAAAATATG AATTTGCTAT TTTGTGAGAT TCATTTAAAA   4080
AAGTCAAAGT ATTATGTATC TTTGCAAAGT ATTATGGTAC TTCTTAAATG TCTGAGCAGT   4140
GTTGCTGTAA AGGTGACATC CATCAGGATC AGAAATTAGA GTTGTAGATC TTCCCTTGTG   4200
AAAAGCAGGG ATTCCATTGC TAGTTTGATA GTGTTGCTGC TCTTCTTGTC CATGGAGTGG   4260
CCATGTTATT GTCCTTGATA ACATCAGTTA GCCAGCCAGC TGCCTCTTGG CTGGTAACAT   4320
CCACATTCTT TCTACACTTG TTTAAAACGG ATTTGCCTCG ACTATTCCTG TGTATATGGT   4380
GCACTGTAGT GTTCTGCCTT TCTGTGTTCG GTTGCTGTTT TCTTCACTCA GCTTCATTGA   4440
CCTTGTCAGA TGCTTTGATC TGTTAGTGAT TACAGGCAGA GTCAGCCAGT AGGTGGATAA   4500
GCACCAGCTT TTGTGCTGCA GAACCTCTGT GGTGGAGCCT TAGCCATCTG ACCTGTAAGA   4560
```

-continued

```
TGTCCCTTTC CCCATGCTTG TAATGTGGAC AATAGATAAG TGTCTATCTC ATGGATTGGT   4620
TGTGACCACT AAAGGGACAG ATGTTCAAAG TAAGATGGTC AGAGAAAATT GTTAAATAGA   4680
TTGAACAGTC CTATAATACA TGATCTGAAA TGCTTTGAAA TCGGAAACTT TTTGGTGATA   4740
ACATGATTTA CGTATTCATT AGTATATTTC ATTGAAAATA TTTCCTGGAA GAAGCAATAC   4800
TTGAGAAGCC TGAAATAGGA ACAGAAATTT GCCAGCCAAA GCCAGAGGGA AAGTGATAGA   4860
CAGGTACAAA GCCTCAGAGG GCAGCTCTCT GGAACTTATG CAGTGTAAGG AAACTGTTGA   4920
CTGTGACAGT GTAATGTAGG AGAAGCAGAA AAATGAGACA GGCCTCACTA AAGAGGTTAC   4980
ATGTAGCCTT CCAAAGAGCA AATTGAAGCT GTTATTGACG GTTCTAAATG TGGAAGTGAA   5040
ATGCGCTGGA TTGAAAACAA GCTAACAAAA CAAGCTGTAG AATAAAACAC ACTAACTAAG   5100
CGAGCCACAG AGAAAGAAAG TGGATCTTAG GATTACAAAA GAATGGTGGG AAAGGCTTTT   5160
TGGAGGCTAT GATGGTAAGC CAAGAAAGAG GAATTGGTAC CTTGAATTGG TTATTTGTGT   5220
CAAGGGTCGG CACAGTGGGT AGCGTCANCC TACATTTAAT GGAGGCAACA GAATCTGCTG   5280
TAATGACAGG CACACGCCAA GGATCCTCCT GGCTTTTGGC TGCACGACAG ATTAAAATCC   5340
AGGGTAAAGA CTCACTTTAT ATAGACCAGG CTGGCCTAGA ACTCAGAGAC CTACCTGCCT   5400
CTGCCTCCTG AGTGCTGGGA TTAAAGGTGT GCACCACCAC CACTCAGCTG GAAGTAAAGT   5460
TTTATAGTTG TTTTTTTAGA CATGTTCAAG GAGAGTAACA TCTCAGGTAG CAAGAGGGTT   5520
GTAGCCTGTG GACACCTAGA TATGTAGGTT GTATCTCAGA AGACAGTTTG TCTGAGATAA   5580
AATGTAAGCA CTAAGTGTCC TAAGAAACTG CTGGCGTCTA ATCTTTGTGT GGGGGAGGGG   5640
ACCCTATAGG AGTTGCCCTG GGTGTGGAAG GAGATGAGAA AGTGCTGGAC AATTCAAGTA   5700
CCAGTGTGCT GAAAGTCAAG GGAGGGCTAG GTTTGAGGGA GGAGGATGTT ATCAACTGCT   5760
TTGAATTCTG CTGAGATTTT GGCAAAGTGA AGGCTTGTAG GCAATCATCA GATTTGGCAC   5820
AATGGCCACT ATCATTTGTA ACCTTCTACA CCAGTGGTTC TCAACCTTCC TGTACTGTGA   5880
CCCTTTAATA CAGTTCCTCG TGCTGTGATG GCACCAACCA TGACATTATT TCCTTTGCTA   5940
CTTCTTGACT GTAATTTTGC CACCGTTATG AATTGTGATG TAACTATCTG ATATACAGGA   6000
TGTTTGATTT GTAAACCCTG TGAAAGAGCC ATTTGATCAA TCATTGTTCT GTGCTCTACT   6060
TCTGGTGTCC TGGGTGTTGA CAAAAGAGTA TTGCAATCAG AGGGTGAACT TCTAGAGCAG   6120
ACAGGGTCCA GAGGCTTTGG TAGTATAAAA ATATTATAGG CATAGCAAGA ATAAAGTAGT   6180
TTAATGAGGT AGGTAGAAAC CAGTACTAAA ATTATATCAA TCATATTACT GCAAATAGTG   6240
GAGAAAGATG TAAGGAATTG ATTTTAAGTG TATATAAATA ATATTTTTTA AAGACTTAAT   6300
TTAGAAAGGG AACGTTCATA AAACACAGGT TTGTCTAGTG TTTGCTATAT TTTAGTGTTC   6360
ATTATGTATT GATTTTATTT GACAAGCAAG GTAACATGCT ATTTGGCTCT CTGAAGGAAG   6420
AGAGCCAAAT GCTTAGAGCT GAGAAAGTAC AAAGCCACTG AGGGCAACTG CTTCCCTAGT   6480
GTAAGGAACA GAAATATAAC CAAAGAGAAA CGAGTGTGAG GGAGACTTGT AGGAAACAAG   6540
GCTGGAAAAG AGGCTTGGGG CCAGTCAGTT AGGGCATCAG ATTGTGTGAA TTGGACTTGA   6600
TGTTTTAATA CTCAAAACCA TCAACAACCA CGGTACAACG ATGGCCAATA GGAAACCCTT   6660
AGTTTGGGTG TGTGGAGCAG CAGAGTAAAA TGATCCAGAT TTTGTCTTAA AGTGTTTTTT   6720
TTTTCTCACT GCTGTAAGAA GGTCAGGAAG TTAGATAGGA GGCTTTTTCA ATTGTCCAGA   6780
AATAGAAGAT AGTTGTACTG GGCCAGTGGA GGTAGCAAGA AATGTAAATG CAGTAGGTAT   6840
TCTGAAGGCA TACACTGAAG AATTCTAGGT GAATTCCTTA TAAAGGGTGA GGAAAAGACT   6900
GCTAGGATGG CCAAGGTATT TTTCTTTTCT TTTCTTTTTC AGTTTTTCGA GACAGGGTTT   6960
```

-continued

CTCTGTGTAG CCCTGGCTGT CCTGGAGCTC ACTCTGTAGA CCAGGCTGGC CTTGAACTCA 7020

GAAATCTGCC TATCTGCGCC TCTCAAGTGT TGGGATTAAA GGCGCCCGGC TTAAGGTATT 7080

TTTCTTGAAT GACCTGATGA CTGGCAGTGC AGGATGATAT GAAGAGTATG TTTTGGTTGG 7140

AAAAAATCCA CCAAAGTTGC AACGTGGACA TGAAAAAAAA CTAGAGGTGG ATTTTGATAT 7200

CCACGAACGG CTCCATACTA GTTATTTTCT GTTACTGTGA TAAAACACCG TGACCAGAGA 7260

GGTCTTTAAG GAAAGGAGTT TCTTTTTGCT CACAGTCCCA GAGGGAAGTC TTCAGTGGCT 7320

CTGCGGGAGC ATGGCAGAAA GCAGCCGGCT TGGCAGTGGG GCAGGAAACT GTTAGGTCAC 7380

ATCTTGAACA GCAGTCTTGA AGCAGAGAGA GCAAACAGGA AGTAGGGTGA AGCTGTGCAC 7440

TCTCAAAGCC ACCCCCAGTG TCAAACTTAC TCCCGGAAGG TTGCACCACC TAAACCTCTC 7500

CAAATGGAGT CACCAACTGA GCATCCAGTG TTCCACTGCC CGCGAGCCTG TGGGAAATAT 7560

TTCCCACCTA ACCACCACTG CACTGTGAGA AATGGAATTC CAGAGTACAC GGCGGAAGTT 7620

GGGGTTAGAA ATATAGATTG TCCAGTGGTG AAACTGGAGA TAAAACTGGG AGTGAATAAA 7680

CTGAAGAATA TAGGTGGTGT CAGCTTCAAG GTCACACTGA CATTTAGAAA ATGAGAGTGG 7740

CTTGAGGGCG GAGACGGGGC ATCAGTGAAT GAGGAGGGGG GCGAAGGACA TGCTTTAAAT 7800

AGGAAGGAGA CATCAGCCCC TTAAACCTCG GAGGAGTTGA ACGATGCACA GATCGTGGAT 7860

TAACTATTAG GGTTGATAAT GTGGTAGCCT TCCCAGAGGA AGCTGTGCTG CTGAGGGCAA 7920

AACTCTTGAG TTGGAGTTAG TTTAGGAGAA AATAAGAGCA GAACATTCGA GGATGAGCAG 7980

CAGGCGTTGG AAACGTAAAA GAGAAAGAAG AGGTGTAAAA TTGTCATCTT AAGATAAGCG 8040

GGGTCTGCGT CATGAGTTTA AAACTAAACC GGCCATTATC ATTTTGTTTT AATTTCAAGA 8100

ATGTCCAGCT ACTTAGGCAC CGATTAGCTA AAGAAGTTGA GTATGATTAG AGTAGATTTT 8160

GCCCCGTGAG TTCCACGGAG TTGGGTAAAG AAGGCAGAAG TGGAGAGTCT GTATCAAATG 8220

AATGGCTAAG AAAGGAAAGG AGACCAGGTA GGGAGAGTAG GAGTGGGTGC TGGAGGGGGC 8280

GGATTCAACA GGTTTCATTC TGAAGTGTTA ACTCACTGAG CTGGGGTAAG CAAGCCAGAA 8340

AGAGCGGTGG GATGGCTCTA TTTATGGTGG AAAGTGTTTG TAATAGAAGG TTTGGGTGCA 8400

GTGGAGGTTT TATTGGGCAG TTTTAAGGTC GAGAGTCTGA TTGTGGGAAT GAGTAGCTCA 8460

GATTAGATGA GGAAGATTGT TGGAATGAAG GGTGACCCTT GGGCAAGGGT TCCAAACGGT 8520

GTTAAGTTTG AACGTGCCTG GATTGGGGCT TACTGACTTC CAAGTCAGAA ACAGTGTCGG 8580

GTGAGTTTAG AGTCCCAGGC TTGTCCTCTG GCCCAGGTCA GTAACATTTA GATTGGATAA 8640

TGTATACATT TGGAATTCAC TCTAAATTTC AAATAGCAAA AATTTGAAAG GAACATTAAA 8700

ACAAGGGAGT AAAGAGGAAA GTGATTTAGA GATCCGAGAG GGAAGTGTTC TGTTAGAATT 8760

CATTGTGCGA ATAGATGAAA ATCTGGATAC TAATACTATG CTGTGATGTG GTTAAATAAA 8820

ATCTCTGCTT TCTAATTTTA ATATTAATCT TTTCTCTCTC TCTCTCTCTC TCTCTCTTTC 8880

TCTCTCTCTC TCTCTCTTCT TTTATTTAGC AGAGGAAAAC CTACCTCTGG AGATGAAGAA 8940

ACAGTTGAAT TTAATCTCCG AAGAAATGAG GGATCTAGCC AATCGTTTTC CTGTCACTTG 9000

CAGAAATTTG GAAACTCTCC AGAGGTTAAA TATTGTGCTT TTTAAAATAT TTATTTTATT 9060

TTTAATTGTA TGTGTATGCG CGTTCAGTCA CCTTTTATGC TATTTTCTTA AACATGGAAT 9120

TCTGATTTTT ACAGAATGCC TGCTTGTTAT AAATTACATA TACCTACAGC TTGGCTTTAT 9180

AACAGCAAGT TAAGTAGGAT TTATTAGCAT CAAGAACTCA CAACAGAGTG GTTTGAAGTT 9240

TATTGTAGGA AGGAACAGTT GTTTTTGTCT CAGAGGACCC TAATAGAATC GATGTGATTT 9300

-continued

```
AGTATTGTTT AGTCATTTAT TTACATTCAG TGTGCTGCGG TGTTGCTGCA GTGTGATTAG    9360
CACTCTACTG GCTGTTGAGC TTGTCTGCTG CTAACTAATG AGCAGGATAG AAATCTTAAG    9420
GAAGGAAATG TGCATGCCAC CATGTATGCC TTCCTAGTCC AGCCTTTAAC GTTAGAGTAA    9480
GTGGTTATGT CTTACTCTGA TGTGAGTGCT TGGTAAATAA GATATTATAA TAGTATCACT    9540
GTTGCTATAG CAACACATTT ATTTCACAAT TAAATTGAAT CATAACTTCT CATACCATAT    9600
TATTTATACA CAGTTGTTAT ATATAAGCAG TATATGTATA TACATATAAT TATATACTGT    9660
GTATGTAGTA AAATTTACAA AATTGCCAGG CACCACGGTA CATACCTGTA ATCTGTGCAT    9720
TCAGGAGGCA GAGGCAGGAG AATTCCAAGC TCAAGGCCAG CCTGACTAAT AAAAAGCTTT    9780
ATAAATTTTT ATTATTTTAA AATAACTTGT TATTAGATTT TGAATTTAGT TAATAGTTTT    9840
AAAAGTTTTT TTTTTGTATC ATTTTATGTG TATGGCTGTC TTTGCCTGCA TGTATGTCTC    9900
TGTACAACTT ATGTGATGTA TTCCTGAGAG GTGCAGAGGA GGGTATTGGA TCTTCTGGAA    9960
CTGGTGTTAC ACACAGTTGA AAGCTGCCAT GTGGGTGCTG GGAATCAAAC CTGGGTCCTC   10020
TAGAAGAGCA GCCAATGCTC TTAACTGCTG AGCTATCTTT CCAGCCCTGA ATTTAATTTT   10080
GATCTTGATT TTTGCTTATG TTAATATAGA CTTTGACAGT TTAAGGTTGA GCTAAAGTTG   10140
GGAGAGTTGA TAATTGTGTA GTTTTGTTTT TTTGAGTATT TTTGTACATT TTATTATGAT   10200
CATAATTACT TTCCATTACA CTCTCTTATC CCCCTGATTC CTGCTGACTC CCTCTTACTT   10260
AAGTAGCTCC TTTCCTTCTT TCACGTCTCA TGTGTGTTTG TGTATTTGTG TGTGCATGTG   10320
TGTGCATGTG TGTGTGTGTG TGTGTGAGTG TGTGTGAGTG GCACTGTGTT TATTTAGGAG   10380
TATTTGTATG AGCATGGTTA AGAGGCTGCT GACTAAGCAC TGGCAACTTT ACCAGTGACT   10440
ACTGAAGAGA ATGATGACTG TTTGCCTAGA AGCCAAGCAA AAGCTCCCTA GGGAAGGATG   10500
GGGTGGGTCA CTTTTGAGCT TCACCATCCA CGTGGGAGCG GCAGAAGGCC CTGTGTTTTG   10560
TGGGTTTTAT GCAGATATCC ATAGCTGCTG CGTGTTTATG ATTTCAGTAG CCATGCAATG   10620
TCTACATGGC AATGTTTCAC AGCACTCCCC CACATCGTCT GACTCTTACG GTTTGTCCAT   10680
CCATCCTGTT ATGTCCACTG GGCCATTGAA GGAGTTTTAT GTACAGGCTG GTCCCAATTC   10740
AGGCAGAGCA CCCAGTATTC ATTTATGCTC AACACTTTGA TCATTGTGAG TCTTCTTTAG   10800
CCAAAAGCTT CTTTGACCAA GACTGAGAGT AGCACTCTGG ATAAGAACAA GAGTTCGAAG   10860
GCAATATGAT ATGTGTCTAT CTAGCAATGT GTCAGCAGTT GGTACCCCTC TGCTATGGCC   10920
TGTGATCTCC CCAGCCAAAG GCTTCTGACC AGATTTATAC TTCCAGTCAC GTATTCCCTC   10980
CTGAAGGTCC AGGCTTCAAA TGCCTCGATT GCTGATTGAT GTGACCCACC CCCAGTCATG   11040
TCATTGGTTC TCCAGCAGAC ATACCTTGCC TGGCAGGTTG GTACTGTAGC ATGCAGGGTA   11100
CAGAGTTGGG TAAGACCCTT GATGACCATC GCCACCCCTC CCCCCTGGCA GGTGGCATAG   11160
TACCTTTTCC AAGTATGAAT GCTGACTGGC AGGATGAAAC TGAAGCATCC GGTCAGTTCC   11220
AGTTTGATTT TTCTGTGTCT TGTAAGAATG AGCTCCCAGT GTAGGACCAA CCCCTGGACA   11280
AACTCAGACT TTGATGGTTT ATTCTCATAG AAGAGCAGAG TTTCATCTGA ACCATTAAAA   11340
TAAAAATTAG CTGGAACTAC CTGAACATTT CTGGTTTTAT AAATCATTGA GTTAAATATT   11400
GGAAAATTAG AATACATAGT CCAAAGCACT TATTACATAA CAACATACGT CTCTTTGTTT   11460
ATTACCATCT TTTGTCTTTC TCTAATTTCC TCACTTATTT AGGTAATTTT TCTTTCTTTA   11520
GTGCTGAGGA TTGAGCTTGA AGCCTTGTGC ACTCCAGGCA AGCATCACAG AGTTGTCTTT   11580
AAAGTAGTCC TGTTGTTTGG TGTTCTGCAC AGTGTTTCTT ATTTACACTA CGTTCAGAAT   11640
GTATTACCTA CAATTTCTAC TTTTAGTTTC TTTAAAGTGG AATGATAATT CAATATACTT   11700
```

-continued

```
GAAGTCATGT GACTACAAAG TCCTAAGAAT TTTTAAGTTT TTTTCTTATG AGCTTTTGCA  11760
GTTATTTTGA CTATGGGGCA TAATTTTTTG ATTATAATTT TTATGTAATA GATAATTATA  11820
TTTTTCCTAT CCCCCAACCC TTTCCAGATC CTAACCACCT CCCTATCCAC CCAAGGTTTG  11880
AGCCCCTTTC TATCAACAAT GAACAATCTA ACAAAGAAAA ATCAGAACAA AAAACCAGTA  11940
AGGAAAAACA GATACCTCAA CAAAATGAAA TTAAAAGCCT ACAAAAAAAA AAAAAAAAAA  12000
AAAAACCAAA ACAAAACAAG GCGTTCATTT TGTGTTGGTT ATCTTCTCCT GGGCATGGGG  12060
CCTGCCCTGG ACTGTTGCCA ATACATCCAG TGACACGTAA TTAGAGAAAG CAGATTTTTT  12120
TTCTTTCCCA GCTTTTGCAA AGAAGTTTTT AGTTAGGAGT GCTGGGATTT TGTCTAGATT  12180
GAACCTTTGC TATTCATGTG CAAGCTACCA CAGTCTCTGG GAGTTCATAT GTGCATCAGT  12240
CTTGTGTCTG GAAGACAGTG TTTCTGTGTC ATTTTATTGT AAAATTTACT ACTTAACTGA  12300
GAGTTATCAA TAATTTTTTT TTCTTTTTTA GTTTTGTTTT TTGACTTTGT TATTTTGTGG  12360
TTAAAGTGTG GCTTGCTTCC TCCTCTTCTG ATTTACTGGT CTGGGATTGT TCCTTCTGTT  12420
TTCTTGGATG TGATTAACTG CTTCAGACTA AAGTTTTCCT TCTAATGCCT TCAGTAGTGT  12480
TGGTTTAGTA GACTGATATG CTTAAAATTG GTTTAATCAC AGAATGTCCC CCTCGCCCCC  12540
AAGCTACTGT GATTGATAGT TTTGCTGGGT ATAGTAGTCT GGGCAGGGAT TTGTGATCTT  12600
TCAGAGCTTG TAGACTATTT GCCCAGGTCC TTTATGGGTT TTTAAAATCT CCATTTAAAA  12660
GCCAGAAGAT ATTTTAATAG CTCTGCCTTT ATATGTTATA TGGTCTTTAA ACCTTGTAGC  12720
CTTTAATATT CTTTCTTTCC TCTGTATGTT TAGTATTTTG ATTATGTGGC GAGGGATTTC  12780
TATTCCTATC TATTTTGTTT TCTGTATACT TCTTGTACCT TAAAACGCAT TTCCTGCTTT  12840
AGATTGGGAG AAATTTCTTG TATGGTTTTG TTAATAATAT TTTCTGTGAC TTTACATGGA  12900
TTTCTTCTCC TTCCTTTATA TCTACTTTTT ATAAGTTTGA TCCTTTCATT GTATTACAGG  12960
ATTTCCAAAT GGCTTGTGCC TGCGTCTTTT TAGATTTAAC ATTTTTTGAC TGAACTGTAC  13020
ATTTTTTTCT ACCTTGTTTT TAAGACTTGA ACTTCATTCT TCCATGTTGT GTGATATGTT  13080
GATGACACTT ACCTCTCAAG TTTTTCTTTA ACACCCTGAG TTTTTCATTT TAGAAAATTT  13140
ATTAACAAAT AACAAATTTA CGAACAGAAC TTTATTGGCT TTTCCCATGT GTTTAGTCCA  13200
GAATAGAATG AAATAGTTTT TGCTTTGTTT TTTGTCATAT CTTATTGCTG CAGTTTACAT  13260
TTCATTAAAT TAATTATCAA AAAGGGCCAT CTGGCATAAA GGGGATGGGG ACTCAGAGTT  13320
AGTAAACTCT GAGTGAGTAT GCAAGGCTAC TTCTACAATG AGAAGCACCT GATCACACAG  13380
GCAAGTTGGC TGTTACTCAT ATTCACGTGT GGCCACATGG AAATAAGGAA CAGTTTTAGT  13440
CCCAATGGGT CTCCTCAGTA AGCCTTCGTT CAGTAAGAAC TTTTAAAGCT CATCTTTACA  13500
ATGAATAAAA TTAGAGCTGA ATAATGCTTA TTGAATTTTT TTTAGGGTTC CTGTAATATT  13560
GAAGAGTATT TCAGAAAATC TCTGTTCATT GAGAAAAGTG ATCTGTGGTC CTACAAACAC  13620
TGAGACTAGA CTGAAGCCGG GCAGTAGTTT TAATTTACTG TCATCAGAGG ATTCAGCTGC  13680
TGCTGGAGAA AAAGAGAAAC AGATTGGAAA ACATAGTACT TTTGCTAAAA TTAAAGAAGA  13740
ACCATGGGAC CCAGAACTTG ACAGTTTAGT GAAGCAAGAG GAGGTTGATG TATTTAGAAA  13800
TCAAGTGAAG CAAGAAAAAG GTGAATCTGA AAATGAAATA GAAGATAATC TGTTGAGAGA  13860
AGATATGGAA AGAACTTGTG TGATTCCTAG TATTTCAGAA AATGAACTCC AAGATTTGGA  13920
ACAGCAAGCT AAAGAAGAAA AATATAATGA TGTTTCTCAC CAACTTTCTG AGGTACTGAA  13980
TCAAGAGGGA ATAATATATT CATCAGTGGT TGGTTTACTT TGTTGTATAA ATGCACAAAG  14040
```

-continued

```
AACAAATATT TTAGTTTTTG TGGGATGCAT GGTCTCTGTT GTACCTATCC AGTTCATCCG  14100
TTGTAAAGCT GCCATAGACA CATGCAAGCA GTGGTACCTG TGTGCTTCAG TAAAACTTTA  14160
TTTAAAAATA CAAACAGAGG GCCATGTTAA CTTGTGAGAT CCACTTAATA CAATAAGTAG  14220
AATTGTATAA GTGAAAAATT TTGCTGCTTT ACTATTTATG TTTTTTATAT GATAGGTAAT  14280
AGTTTTTTGG TGGATTCTTC CTAAGTATTT ACTCATTCAA ACTTGATTTG GGGGGTGGGT  14340
GGGTTTTATT CCTTCAAATA GAAATTATTT GTTAGGGTGA AAGGGTCCTT TGATTTACAG  14400
GCATCCATAC TGTGACCTGG AGAGCCAGGA AGCTCTTGTC TCCTTCCTAA TTCTTATTAG  14460
CTTGCAAATT ACTGAAGACA TTTATCATTT CTGGGAGGTT TTTCTTTTTC TTTTCTTTTC  14520
TTTTCTTTTC TTTTTTTTTC TTTTCTCTTC TCTCTTTTTT TTTGCAATAA CAAATTTCAT  14580
TTTAGATTTT GAAAAGATTG TATAGGTTTA AACCTCTCAA TTTCATTACA GAAGTGGAAA  14640
CCCAGTCTTA TATACAATTC TTTGATTTTT TTTTTACAGG AGTTTTTCAA TTGTTTCTAT  14700
TGAGTATATA AATGTAAATT GTTTTAAAAA TTTCAAAATA TTCTCATTCT AATTTTTTGT  14760
GAACCAGATT CCCTCTCTAG AAAATGCTGT CTTTCACTTA CATGTGCATC ATTCTAATTC  14820
TGTAGAAATT TCTAATTAGA TCTGCACTTT CATATTTTTA TATATTAGAG AATTATGCTC  14880
ATGAGTTTGA TTTGACTGAT ATCTTTTATA TCAATTATTG CCATTTTATT ATGTAATGAT  14940
TAGCATCATT TTTATTATTT AAGACTGCGT TTAGAAGTCA AGAAAACCTT ACTCAGTTAA  15000
AAGTGTACTT TAATACATTT TAATAGCTTT AAATTAGCAT GTTAATTAAG GCTATTTTCA  15060
TTTTCCCATT AACAAATTAA ATATGAAGCA TTTGGGGAGA TATTCCTTCA AGTTTCTTCT  15120
TGATTTGTGT GTGTGTGTGT GTGTGTGTGT GTGTGTGTGT GTGTGAAGGG TAGATTTGCA  15180
GCTTGTTAGG CACCCGGTTC CTTGGGATTG CCAAATTATT GTAAAGATTC TTCATATCCA  15240
AACATCAACA ACAGATCAAG AAAATAATAT ATTTAGTATT TTTTCAAATA GATGGTCTTT  15300
GTAAAACACT AATTTATTGA AAGATTATTA TGTATTAGTC TTTGGTATTT TTAAGTCAGT  15360
GTATGTAAGA AAACCATTGA TTTTCTTGGT TTGTACAGAC TTTTTTCAAC ATTGATTAGA  15420
ATGCCATCTA TTGGAAAGTT GGGGAGACCC AGGTTGACCT GGTTGACCTT CAACTTGCAC  15480
TTTCTCTTCT TTTGCATGTA GATTCTACTT GACGTCTGTT TATCTAACTT GCCTGTCTTT  15540
TTAATTACGC TCTCTCTCTC TCTCTCATTA TTTGAAGATT AAAACACTCA TTCTCCTTTC  15600
TCTCCCGTCC TCTCTGTGCT CATGCTGTGA ACATATAAAT ATGCTTTAAA CATCTGCCTA  15660
TTAAAGAAGA GGAAGATGTC TAAATACTTC AGTGAAAGCA GCTGAGAGCA TAGTGTCACT  15720
CTCGCAGAAC GTTAATCTTT GAAATCCTTT TCTTTAAAGC ATTTATCTCC CAATGATGAT  15780
GAGAATGACT CCTCCTATAT AATTGAAAGT GATGAAGATT TGGAAATGGA GATGCTGAAG  15840
GTATGTTTGA ACACAAGAGA AAGTTACTTC AAGTTTTTAA AAGAACACTT TAATAATTAA  15900
AATATTATCC ACTTCCAAAT CAGATGCCAC CACAATGATA TTCATACCCA TTATTTAATG  15960
TTAGACTTTA AGTTTTCAAT TTACATGTCC TCATCTGTAA GTAGTCTTAG GTGTAACGTT  16020
GGGAGTTCTC ACGGGAGTTC TGTGTCCTCA TACGTCTCTC TCTCTGGAAA CTGGGCAGTA  16080
ACTAAGCACT TGAGCAGGAA ACTCATTATT TCTTCTTCTT CTTCTTCTTC TTCTTCTTCT  16140
TCTTCTTCTT CTTCTTCTTC TTCTTCTTCT TCTTCTTCTT CTTCTTCTTC TTCTCCTTCT  16200
ACTCCTCCTC CTCCTCCTCC TCCTCCTGCT CCTGCTCCTC CTCCTCCTGC TCCTCCTGCT  16260
CCTCCTCCTC CTGCTCCTGC TCCTCCTCCT GCTCCTCCTC CTCCTCCTGC TCCTCCTGCT  16320
CCTCCTCCTC CTCCTGCTCC TCCTGCTCCT GCTCCTCCTC CTGCTCCTGC TCCTGCTCCT  16380
CCTCCTCCTC CTGCTCCTGC TCCTCCTCCT CCTCCTCCTG CTCCTGCTCC TCCTCCTGCT  16440
```

-continued

CC 16442

(2) INFORMATION FOR SEQ ID NO: 209:

(i) SEQUENCE CHARACTERISTICS:
(A) LENGTH: 51259 base pairs
(B) TYPE: nucleic acid
(C) STRANDEDNESS: single
(D) TOPOLOGY: linear (xi) SEQUENCE DESCRIPTION: SEQ ID NO: 209:

GCTCCTCCTC CTCCTGCTCC TCCTGCTCCT GCTCCTGCTC CTCCTCCTCC TCCTGCTCCT 60

GTTCCTGCTC CTGCTCCTCC TCCTCCTCCT CCTCCTCCTC CTGCCCCTCC TTCTCCTCCT 120

TCTCCTTCTC CTCCTTCTCC TCCTCCTCCT GCTCCTCCTC CTCCTCCTGC TCCTCCTTCT 180

TCTCCTCCTC CTCCTCTTCC TCCTCCTCCT CCTGCTCCTC CTCCTCCTCC TCCTCCTCCT 240

CCTCCTCCTC CTCCTCCTCC TTCTTCATGT ATTTGTTGTG TTTTAGACAT TCTGTGTTTT 300

ACTCATTCAA TCATTTACAG GGTCTGGATT TTCTTATTGT GTGTTTTTTT TTTTTTAAAT 360

ACTGATTATA TATAATGGCT GTTTACTCTG TTATCAAAGC TGAAGTATGG ATCTGTGCAT 420

TTCTATCCTG TCACTCATCC TCCAGCTTAT CAAGTGTCGT AAGCCATGTG CAGACAGAAA 480

AATCCAGACT GAGAGAGTAA GGGAAAGCAC AGTTTAGTTA AATCAAATGA AAAATAAAAA 540

GAAATAGAAG TATGCTTTTG TGTCTGCCTT TTAAGCTGCC ACCTGTAGGT TAGTGTGCTT 600

TTTCTTTTCA TTAAATGAGA GTAATTTTCT AGTTCTTTAG TTTTGAGTTT TAGATAAATA 660

AGGATAAATA AAGATGTGGA TTCCTAATTG AATGTAGACC TGAGTCCTCC CTTCCCCATT 720

GGTGTCCATT GCTAACATCA CAGTTTACCA GGGAGCCTGT CTCCTATTTA AGAAATATGA 780

GCTAAATCAC AATCTATTCA CTAGGTATCC ATTTTTCTAG TGCATTCAGT TCAAGTGGTA 840

CCAAGTGTAG GATGCTTGTA GACATCTGTA CCATATATTA TACACTGGAC ATCTCTGTTC 900

TCTGGATATG TTGGTAGAGT TAAAGAAATA TCATCACCTC TTTTTTCCCC TCATTTTTCT 960

TTTATAGGAC GGAAATATTA TACTTTAAAG GACATTCTTA AAACCAAACT AAAAAAATAGA 1020

ACGCCTCATA AAAAGTGAAG ATAACTTGTG TTAAATGAAT AGTCTATGTA ACTCCTTAGT 1080

AAAAAGTTTT ATAGATACAG CGATTTGAAA TATACTAATA TTTTTGAAAT AGTGGAGAAA 1140

ATACATATCA AAACACCTTT TTTTCACATC AGTAATATTT CTTTCCTAAA ATTATTTGAA 1200

TCCTTTTTTA CAATTCCAAA ACACATTTAT TGCTTGCTCA TAATTTAAGC ATCATCTTTA 1260

CTCAAGAAAA ATGCAATTGA CATGTAACAT AGAGAAATCT ATGATAAAAA TAGCATTAAA 1320

ATGTTTCATT TTACCACTTA GAATTCTAAA ACGTTGAAGT CCAATAAGAA AAACTGGTTA 1380

AATTATGCAA ATTTTAAATT TACGATACGT TTCCCAGAGG CCGTTCATTA TGTGCTATTA 1440

CTGAACCTTG TTTATGCTGG CCATGCTCCA TCCTGGCCTC GTGCCTTGGA GCATCTTCAG 1500

CACGTATTTA TAGAGGAGCA CACATGTTCT TTTGTGCTGT TGTTTGCACA TCTGCCGGTT 1560

TTCAACCAAA TTGTAGGCTT TGTTAATAAC CCTCCTTTTG TACTCAGTAA AAAGATACTG 1620

TATTGTCAGT GTTCTGCCTC AAATTTCTTT TAAACTTCCA GTCTTTAGAA AACCTAAATA 1680

GTGACATGGT GGAACCCACT CACTCTAAAT GGTTGGAAAT GGGAACCAAT GGGTGTCTTC 1740

CTCCTGAGGA GGAAGATGGA CACGGAAATG AAGCCATCAA AGAGGAGCAG GAAGAAGAGG 1800

GTAAGAATCA GGGTGGAAAC AAACTCACCT TTCATGGATT TCGTGTCAGT TTTCCCGTGT 1860

TTGGAAGTTT AACAAGTTGG TGGCACGTAG TTACTTATCC AGTCTATAAA CCAACCACTT 1920

AAGTCCTTAG TGCTCCTGTC TCTCGGGAAC TGTGGATGAT GAAACCTTTA ATCCTGAAGT 1980

-continued

```
GAAAGATTTG GTTTGGGTCC CAATGACAGT GGTGAAATAG TTTACTAATT GTTCATATTG   2040
AATGCCCTTG TTGGTGATAC AAATACATGC AGTCTGCTAC CCACCAGGAG CTTATGGTTT   2100
AAACAAGTGC CACACCATAT GTTCAATTAA ATGTATAGAA TAGTAAATGA GTGTGCAAGT   2160
GATAGAACTG TCATCTACGT GTAACCAATC ATGGTCATTC GGTCAACTTT GTAGTACTAT   2220
CACTATACTT ACAATATATT GTGGTGGGAA AATGTGGGCA TTTCAAAATC ATTTTGTAGG   2280
TAGAAGGTAC TTATAAATGT ATTGATGAGT TATTCTCCTT TGTTTCCTTT TATTAAGTGT   2340
AGCCATCTGT TTGTTAAGAT GTGCCATAGC ACTTATTTTT CATGTTTAAT GATAGCTTAT   2400
CTAGAATCTG TGTTTTATCC TTTCTTGGCT GCTTGTGAAT CTTTGCATCA ATGGACAGAC   2460
AGTGGTGGGA CTTAGGGAGA GCTAACATAG TCCACCATGT GGTACCATTA AAATTTTTGG   2520
CTAAAGATTT AAGTAGCTAT ATTAACCTAA CTAAATAGGA TAGGTAGCTA AATTAGATCC   2580
AGGTAACTTA ATTTATATAA CTAGATTTAG TTTTAAACAG CTAAATGAAA ATTTTATTTT   2640
TTTTCTGTAC ACTTAATTTG GGATACTAAT ATAATTCATG TTTATCATTA ATTGAAAATT   2700
ACTTCTAATA TAAAATTTTT ATCGGCATTT CTATTGTTTG CTTGGTTCGC TTCATTCTGG   2760
ATTGTAGATC CTGCAAGTTT CCCAATTACA GGATGTTGGG CCTCTTCTTA CCACTATTGC   2820
TAAAGCGGGC CACAAGGATA GGTCTAGTTT GTAAGTAGTG ATCAGAGGAT TTGCCTGGTG   2880
TCATGCTAGA TATCTGTAGA GTCAAGTGTG ACTGGGATGG AAACAGTGGA TGTCACCCAT   2940
CACTCTGTTC TTTATCACAG CAATGGAATG AACATTTTCC TCTTCTTGCA TAGCATATTT   3000
GCTTTTGAAC ATAAATGTCA ATTTTATTAT TTTATTTATT TTTAAGACCA TTTATTGCCG   3060
GAACCCAACG CAAAGCAAAT TAATTGCCTC AAGACCTATT TCGGACACAG CAGTTTTAAA   3120
CCGTGAGTAT GATCTCAATT AACTATATTA TGTACATATT TTTTTTTCAC AAAGAGAAAG   3180
AGTAAATAAT CCATCCCCAT ATCCTAACAG CAGCAGCCTA ATTTTATTGT AGGCATATAT   3240
GTCAGGTATA GATTATATAC AACTGTAAAA TTATTGGAAA TATTAATTAC ATAAGTTTCT   3300
TTGTCCTTTT AATAGGAAAG GAAGCGGTTC TATTTTTCTT TAACTGAGTG CTTCTATGCA   3360
AAAACTATAT AATAATAAAA AAAGAATTTT TCTCACTGCT GAGTTATCTT TTATTGAGTA   3420
TGAATTCAGA GGAAAGGCAC ATTGCTTACT GCTTTCTGCA GGTGTTGCAA GGCACACTGT   3480
TGTGAGTCTC TGAGAGAACA GTTTGAGAAG CTGAAGGTTT ATTGTTTTAA CATTTCAAAA   3540
TATATTTCCA TCTAAAGGGC TGTCTTAGTC CATGTCCCAT TGTCGTGAAG GGACACCATG   3600
ACTACAGCAA CTCCGATAAA GGAAAACATT TGATCAGGGC TGGCTTACCA GTTCAGAGGT   3660
TTAGTCCATT ATCATGGAAG GCATGGCAGT GTACAGGCAG ACATGGTGCT GGAGAAGGAG   3720
CTGAGAGTTC TACATCCCAA TTGGCGGGCA GGAGGAAGAG AGAGTGAGAC ACTGGTTGTG   3780
GCTTGAGCTT TTGACACCTC AAAGCTCACA TCTGGTGACA TACTTCCTCC AACAAGGCCA   3840
CACCTGGTCC AACAAGGCCA CACCTCCTAA TCTGTTCAGA TACTGCCAAT CCCTGTGAGC   3900
CTTAGGGGAG TGTTTTCATT CCAACCATCA CAAGGGCACA CTAATAACTA GAAACAATGA   3960
GATGAACACA AACGAGATTA GGAACAAGTG CATTTGAATA AGACCAGTAA GTAACTAACA   4020
ATCTAGACAG GGTTTTTTCA ATTTTTTTTA TAACTTTTTT TTGGGGGGGG GTGCGTGTTT   4080
CGAGACAGGG TTTCTCTGTG TAGCCCTGGC TGTCCTGGAA CTCACTCTGT AGACCAGGCT   4140
GACTTTGAAC TCAGAAATCT GCCTGCCTCT GCCTCCCAAG TCCTGGGATT AAAGGCGTGC   4200
ATCACCACTG CCCGTTTTTT GTTTTTTTTT TTAAATAACT TTAAAAAGAA TTCATCGGAA   4260
CATTTTTCCT TCTTTTAATA AACTATCACC TCCAGTTGAT TTCACCTTAG TCCATCACTT   4320
```

-continued

```
TACACAGGTC TCATTTCAAA CCTATAGCAG TCCTCTTATT TATTCTAAAA TATTAACTTT   4380
TCGGTCTATA GTACAAAGCT GGGTATTTGT TTTATACTTT AGATATATGT AATAAAATTA   4440
CATATACATA CTATATGGCA ACTCATGGTT ATTCAGTCAG TCTGAATGAA AAGTTAATCA   4500
AATGATCAAA TTTTTTCTCT CAAATTTCTA GGATTTGAAT ATATTTTTAT AGGTAGCTCC   4560
AAAAAAAAAT CTGAGTTTAT TGGAGAGAAG TTAAATAGAT TTGAACTTGT GCTTTGGATG   4620
CTATTGATAA AACATTTTAC TTTGTACCTT CAAGGGTTCA GTGGAAAGTC ATCCATTCTG   4680
TATTAGAAGA GAGAAGAGAT AATGTTGTTG TCATGGCAAC TGGTAAGCTA TACTTAAAGT   4740
AAATAATTTA ATCATCTAAA AGTCATAAAG GGTCTAAAGT GCTTAATCTT TCAGAAACTT   4800
ATAAAATATA GGAAGGAATG ATTGGGGGAA AAGCCTTCAA ACTTATGCAT GAATTACCAT   4860
GTCAGTCCAC TTATTCTGCT ATATAAGCAC ACTGTAAGAA GAAAGTAAAG CATCAAGAGT   4920
TTCTTTTTAT TTTTTTGTGT TATTTTTTTT TTATTCAAGG ATATGGGAAG AGTCTGTGCT   4980
TCCAGTATCC GCCTGTTTAT ACAGGCAAGA TTGGCATTGT CATTTCACCT CTCATTTCCT   5040
TAATGGAAGA CCAAGTCCTC CAGCTTGAGT AAGTAATGCT TGCACTGCTG CAGCGTCGCC   5100
TTGGATAAGC AAGTGGAAAG AACATGGCAA GGCAGGATCT TACTACACAG GCTTAGCTAG   5160
GCTCTTCTCT CAGTGCAGTG GCCCTTTGCC CAGTTGTCCC TCTCTGTTCT ATCGATGAAA   5220
TATCAGAAGA TGAACGTGAA TCTAGGTCAC AGGATTACGT TTTGGGAAGT AACTTGATCT   5280
TCTTTATTTC TATTTTTAAT TTTTGAGATA GGGTCTTGAT ATATATATAG TCCAGGGTGG   5340
TGTCGCTCTG GCCTCTTGCC TTGCCCTTCA TGCCTTGGGC TCACAGAGCA TGCACTAGCA   5400
CCCCTGGCTG CATTCATTAG TAGCAAACGA AGTGTTAGTG GAAGAGTTTA CATTCATTCT   5460
TGAGGTCTCC AATGCAAGGC TACCTGTTTT CTCTGATCAG GGTTTAAAAG GACTGATTGC   5520
TTTATGCTAG TTAGCTGTCT CAAATTCTTT TTTTTTTGTT CTGCTCTCTG GGCTCCCAAG   5580
CTTGCAATGA GATATATATA AAAGTTTACT TTTTAAGATA TGTTTTTATT AGTTCTTTGA   5640
AAATCTCCTA CATGTTTTGA TTATAGTCAC CCCTCTTCTA ACCCTAAGTT CACCTTTCTA   5700
TTCCTTCTTG AAAGATCCAC ATTAAAGACT TGCCTCCTCA TCAGGCTTTT GAAGGAATAT   5760
ATCAAGTTAT ATAGACACAA AAAGGAAGAA CATTAGAAAG ATGAGGAACA TAGGAGGTTC   5820
ATGTTTATGT GTGTATTCAT CAGAGCGTTT GTCTCTTGTA GGCTATCCAA TGTTCCAGCC   5880
TGTTTACTTG GATCTGCACA ATCAAAAAAT ATTCTAGGAG ATGTTAAATT GTGAGTAACT   5940
TATATCATGT CACATAATAT TGTAAGATGT ATATAGAGTA AGAGAATTTT GTATATATGT   6000
TTACTTATAT GAGTAAATTG CCCATATTTG AAAACATACT TTAAAAAGCC TTATTTCTGA   6060
AATAATAACA TAGTTCCATT TCTTCCTTTC CTTTCTTCCT TCCAAACTCT GCCAAACATC   6120
CTTCCTTGTT CTCTTTCAGA TTGATGGATT TTTTTCCCAT TAGTTGTCAT TACATGGATC   6180
CATGTTTATA CATATGTATT ACCAAATGCC CCGTTTTTTC TCAGCAGAAG TCATGTAAAA   6240
CTCCTTTATC CTTAAGATAA ATATTCACTT TTGGGGGGCT GGTAAGATGG CTCAGTGGTT   6300
GAGAGCATAC TGAGTGCTTT TCTGGAGGTT ATGAGTTCAA ATCCCAGCAA CCACATGGTG   6360
GCTCACAACC ATCTGTAATG AGAAACAAAT AAAAAAAATC CCTATGGGCC AGAACGAGTG   6420
GGGCCCCGGA GTGAGTGGGG TCAGAGCAAG AGGGAGAGAA AGGGAAGTGG ATTTTTATTC   6480
ACTTTTTGTT TAAATTATTA TTGTATTTGT ATTATTAACT TGTCTTCCAT TATCTTATTG   6540
TATCATATCT AGTATTATAT GTTATACATA TATATCGTAT ATATGTATTT ATATGTATCA   6600
TACTTTATAT TATATGGTTA ATTTGCTATT ATGATAATTT TTATAAAAGA AGGCTAGAAA   6660
TTACTTATGG CATGTCTCTA CCATATAAAA GCAGATAAAA TTAAATTAAA AATTTTAATA   6720
```

-continued

```
TAAAAGTTCT TTAAGTTTTT AATTTATCTA TTCCACTAGT ATTTTAGTGT CTATTACATG   6780
CTAAACATTA TGTTTTCACT AGTAATTTAT TAGGCATGTA ATAAATTTTA TCGTATCTCC   6840
AGGAAATTGA TGCAGTTTTC TAATTACTGT AAGAAACAAT AAAAATAATG AAGGCTAACA   6900
TCACTGTACC CAGGTTTGGA ATCAGTTCTC CGTCCGACTA GGAAACTGAT CTGAGATGAG   6960
CCAGTCAACT CCAGTGTATC CCAGTTTCTT GAAAATTAGC TGTTTACTTA CAGAGACAGA   7020
CTTAGGACAT CTCAGTTAAG AAACGGACAC TGGAACCTTC ATGGAACCAA AGAGCAGCCA   7080
GGAAAACTAA CACACCCCTG AAAACAAAGA GCATAACTGG GGGCTTGTCA TCGAGACTTG   7140
CAGGCTTTTA CTGTAGCTAC AGCAGCCAAC ACAGGCAGAC GGAGCCACAG AAGCAGATCT   7200
CAGCAAGGAA TCTGCACATG CCTACAAAGC TCATCATCTG AGAAAGGCTC AAAGGTGATC   7260
CAGTGGAAAA GAGACAATCC AGAATAATGG CTTATATGAA AACAATGGCC TTATAAGAAA   7320
AACAAACCAA ACAAACCAAA CCAAAACAAA CAAAACCCCC CAAACTAATA CACCACACAA   7380
TATAAACATT TTTTGCTAAA AGCGAATTAT GCGTCCAAGC ATAAAATTGT GAAATGTTTA   7440
AGGAAAAGCA TGCCATCTTT ATAACCTTCA GTTAGGGAGA CTTCTTAAAT ACCCAAAGCA   7500
AAATCTATAG GAACAAACTA GCAGCTGGAC TTTTACAAAC TGAAAACCTA CTTCTCTTCA   7560
AAAGAATTAT TGAAAAAGGA AGAAAGGCCA TAAACTAGCA AAGTATATGC AAAGTACATA   7620
TCCATACAAG ATTTCTACCT ATAATATAGA AATTACCACC AAAAGAGAAT TAAAAAAAAT   7680
TAAAGTGTCA AAAGATTGGA ACAGACACTA GCACAAAGAT ATACAAACAG CAATAAGTAT   7740
AAGATGCTTA TATAATTGGT CACCAGGCAA AAACAAATTC AAGGTACAGT GAGATTCTTT   7800
CCAAGTGGCT AAAGCCAATG ACTGGCTAAG AAATGTCAGG GGTAGTGAGC AACAAGACTT   7860
TTCACACACC ACTTCTAGGG ATGAGAGATG GTAGAATGTT TGTTTGGGGA GTAGACTGTT   7920
AGAAACCATA ATTTGGCTTA TAATTCCAGC TTAGTGGTGA ATCCTACACA TCAAGAATTG   7980
TTATATTTTA TTTTGGTGAA TTGAAGATAA ATGAAAGGAC TAACATCTGA ATTATGTATA   8040
TATATAAAAT ATTCCTTTGG ATTTTAATAA TCAGCATGAT GCATTACTTA AAAACCTATT   8100
GAATGCTTCT TTCCAGTCTA GGGCAGGGAC CTTAGCTGAC CTTGGGTGCT AACTCTGCAC   8160
CCAGCCCCAC AATACCCAAA GGAAGCTCCA CTTCTAGGCG CTCTAACACG CCAAGTCCGC   8220
AGGATTCCAG GATCCCAGGA ACTTGGTCAC ACCAGGATCT CAGGGTTTTA GAGGAACCTT   8280
GGCTCCCAGG AGCTCTGACA CACCCAGGAT CTCAGGATCA CAGGATCACA GAGACAGCTG   8340
AACTCTGAGA AGGTCTGACA CGACCAGGAT CACAGGAAGG ACAGGCTCCA GTCAGATATA   8400
GTGAAGGCAG GTAGCACTAT AGATAACCAG ATGGTGGGAG GCAAGGGGAA GAACATAAGC   8460
AACAGAAACC AAGGTTACTT GGCATCATCA GAACCCAGTT CTCTCACCAT AGCAAGTCCT   8520
GGATACCCCA ACACACTGGA AAAGCAAGAT TCAGATCTAA AAATCACTTC TCAGGATGAT   8580
GATAGAGGAC ATTAAGAAGG ACATCAACAA CTCCCTTAAA GAATACAGGA GAACACAAGT   8640
AAACAACTAG AAGCCCTTAA AGAGGAAACA CAAAAATCTT TTAAAGAACT ACAGGAGAAC   8700
AAAATCAAAC AGGTGAAGGA AATGAACAAA ACCATCCAGG ATCTAAAAAT GGAACTAGAA   8760
ACAATAAAGA AATCACAAAG GGAGACAACG CTGGAGACAG AAAACCTAGG AAAGAGATCA   8820
GCAGTCATAT ATACAAGCAT CACCAACAGA ATACAAGAGA TAGAAGAGAG AATCTCAGGT   8880
GCAGAAGATA CCATAGAAAA CATTGACACA ACAGTCAAAG AAAATACAAA ATGCAAAAAG   8940
CTCCTAACCC AAAACATCCA GGAAATATAG GACACAATGA GAAAATGAAA CCTAAGGATA   9000
ATAGGTATAG AAGAAAGTGA AGATTCCCAA CTCAAAGGGC CAGTAAATAT CTTCAACAAA   9060
```

-continued

```
ATTATAGAAG AAAACTTCCA TAACCTAAAG AAAGCGATGT CCATGAACAT ACAAGAAACC   9120
TCCAGAACTC CAAATAGACT GGACAAGAAA AGAATTCCTC CTGTCACATA ATAATTGAAA   9180
CATCAAATGC ATTAAACAAA GAAAGAATAA TGAAAGCAGT AAGGGAAAGA AGTCAAGTAA   9240
CATATAAAGG CAGACCTATC AGATATAGGA CTAGACTTCT CACCAGAGAC TATGAAAGCT   9300
AGAAGATCCT AGGCAGATGT CATACAGACC CAAAGAGAAC ACAAATGCCA GCCCAGGCTA   9360
CTATACCCAG CAAAACTCTG AATTATCATA GATGGAGAAA CCAAGATATT CCATGACAAA   9420
ACCAAATTTA CACAATATCA TTCCACAAAT CCAGCTCTAA AAAGGATAAT AGATGGAAAA   9480
CACCAACACA AGGAGGGAAA CTACACCCTA GAAGAAGCAA GAAAGTAATC TTTCAACAAA   9540
CCCAAAAGAA GATAGCCACA CAAACATAAT TCCACCTCTA ACAACAACAA AAATAACAGG   9600
AAGTAACAAT CACTTTTCCT TAATATCTCT TAACATCAAT GGACTCAATT CCTCAAAAAA   9660
GGACATAGAC TAACAGACTG GATGTGTAAG CAGGACCCAG CATTTTGCTG CATACAGGAA   9720
ATGCACCTCA GTGACAAAGG CAGACACTAC CTCAGAGTTC AAGGTTGGAA AACAATTTTC   9780
CAAGCAAATG GTTGTTTCCC AAGAAACAAG CTGGAGTAGC CATTCTAATA TGGAATAAAT   9840
TCAACTCTCA ACCAAGTTAT CAAAAAAAAA AAAAGATAAG GAAGGACACT TCATACTGGT   9900
CAAAGGAAAC ATCTGCCAAG ATGAACTCTC AATTCTGAAC ATGTATGCTA CAAATGCAAG   9960
GGCACCCACA TTCATAAAAG AAACTTTACT AAATCTCAAA GCACACATCA CACCCGATAC  10020
AATAATAGTG GGAGATTTCA GCACCCCACT CTCAGCAATG GACAGGATCA CGGAAACAGA  10080
AACTAATCAG AGACACAGTG AAACTAACAG ATGTTATGAA CCAAATGGAT CTAACAGATA  10140
TTTATAGAAC ATGTCATCCA AAAGCAATAA ATATACCTTC TTCTCAGCAC CTCATGGAAC  10200
CTTCTCCAAA ACTGACCATA TAGCTGGTCA CAAAACAGAC TTCTACAGAT TCAAGATGAT  10260
GGAAATCATC CCATGCACCC TATCATCAGA CCACCACGGC CTAAGATTGG TCTTAAATAC  10320
CAACACAAAC AACGGAAAGC ACACATACAT ATGGAAGCTG AACAGCGCTC TACTCAATGA  10380
TACCTTGGTC AAGGCAGAAA TGAAAATGAA GACACATCAT ACCAAAACTT CCGGGACACA  10440
GTGAAAGCAG TGGTAGGAGG AAAACTCATA GCTCTAAGTG CTTCCAAAAA GAAACTGAAG  10500
AGAGCTTACA CTAGCAGCTT GACAGCTCAC CTGAAAACTC TAGAACTAAA AGAAGCAAAA  10560
ACACTCAAGA GGAGTAGACT GCAGGAAATG ATCAAACTCA GGGCTGAAAT CAACCAAATA  10620
GAAGCAAAAA GAACTATACA AAGAATCAAC AAAACCAGGA GCTCGTTCTT TCAAGAAATC  10680
AACAAGATAG ATAAATCCTT AGCCAGAGTA ACCAGAGGGT ACAGAAACAG TATCCAAATT  10740
AATAAAATCA GAAAGGAAAA AGGAAACATA ACAACAAAGT ATATCTTAAA ATAACTATTC  10800
TGTTTGTTGA ATATCAATAG TTGAAAATAT TAAAATCATG TTCTACAAAC ATCATGGAAA  10860
TATTATTGAT AATTTTTCTC ACTGTGCTTG AAATTAGCAT TTTCTTAATG TTTATGTCAA  10920
AGTGTTTTTG CTATTTTGAA ATGTTTAAAA TATACTTACT GATAAAATAA TTTCTCTCCT  10980
AGAAACACTG ATAATCTTTT TTCTGTAAAC TGATTTTTGG ACAATGTACA CAGATATAAA  11040
ATGTGTTTTA AATACTCTCT CACTATGTCA GGTGTTATTA TATAAAGGCT TTCAAATATA  11100
TTTCTTAGTG ATTCTTTTTA AATATTTTAT GCTCTTTTAC TATGCCTAGC TCCCAAAGAA  11160
TATTCTGTAT GTTTTGAAAC AATTTAGTAT TCAATATTAG GTACAGGATC CTCAGTTATG  11220
GATAGTATTA AATATTAATT AATGATATTT TTAGGATATG AAAGGATATG AATATAAAAG  11280
TTGGACAAAA TTTTAAAGTA TTATCTGATA TCAAAATACT CAATATTATT GATATGTTTG  11340
ATGTATAAAA TACATTTAAA TAATAAGTTT TAAAAAATGT CTATTGAACA TTTTGATTTT  11400
GTTATCATTC ATTGACTGCC TTTTTTTCCT ATTAGAGTGT TTCAATTTAT GTTTCTATTT  11460
```

-continued

TTGTTTGTCT TTACAGAGGC AAATATAGGG TCATCTACAT AACTCCAGAG TTCTGTTCTG 11520

GTAACTTGGA TCTACTCCAG AAACTTGACT CTAGTATTGG TAAGTAATGA AGTAGGACTT 11580

CGGTGAATAC AAAGTAACCC ATTTATGGTT GAAGACCAGA TTCCAGTTTT GTTAAAGGCT 11640

TATTTCAAAC ATTTGCTCCT CTAGGAAATT TCTAATCAGT TTTACATTTG TCCCATTTTA 11700

CAATGCTGTA TAATTCCTCA TTCCATAGAG GTGGTACTCC TGGGTGGGTG TCATATTTGT 11760

ATATAAGCAT GTATGTATCC CTGTCACACT CAACCCTTTT GAGGCTTCTC TGCTCTTACT 11820

GGCCTCCCAA CTCCTTCATG CAGGATGTGG CACACAGTTG TCTATCCTGT GCATTGCTGC 11880

ATGAACGCTG AGTCTTGTTT CATATTCTGA GTCTAAATGA AATCAGTGTG TGGTTCCTCA 11940

TTCTTGCTCG TCAGAATCGC CCTTCAAGCT CTAGAACAAT GCTGTTAAAT GGCGTATTTC 12000

TTAGAAAATA TAAATATAAA ATAGGTTAAA TGCTGTGATA TTGTTTATGC TGAAACTTTT 12060

GTTTTTTGGT GGTGGAAGTG TGGTCAGGTT TAGCTAAGAG CTCCAAAGGA AACAAACATT 12120

ATCCATATTC AAAACTTTCA TTTAAATTTT ATCCAACTTA TCAGATAAAA TTGTTTTCCC 12180

AATTTGTGGG ATTTTCGTTT TTGAAGAATT AGGTATTAAG TAATTTCATA TAGGTTAAGT 12240

TTTCAGTATT GTACTGGACT AGCTAGTGGA GTGTCAACTT GATTTAAGCT ATGGTCTTCA 12300

AAGAGGAGGA AACTCAGTTA AGAAAATGTC TCCTTAAGTC AAGATGAAGG CAATCCTGTA 12360

GAACATTTTC TCAATTACGG ATTGATGGTA GAGGGCCATT GTGGATGGTA CTATCTCTGG 12420

CCTGGTGGTC TTGGGTGCTA TAAGAAAACA GGCTGAACAT GCCATGGAGA GCAAGCCTGT 12480

AAGCAGCATC CCTCCGTGGG CTCTGCATCA GCTTGTATTG ATTGGTGTTG CTTGTTGGTG 12540

CCACAGTAGA GAGAGGAGCT CACCAAGTTC CTAAGCCATC CTTTTTGGAA GGAGCAGAGG 12600

GGTTCAGCCT TCCTGGGAAG GCTCACTCCA GTTACTTTAT TCAAGCATTG TTCAAGGTTA 12660

ATTGGGGCTG GGAAAGGTTT CAACCACCAC AGTTGTTATC TTGTGTTTGC TGCTCAAGAG 12720

ACAACATGAC CCACACAGAT CTTAGTCCCT TTTGACCATG GCTAGGCATA ATCAAAGGTA 12780

AGAACTCCAG GTTTGCCAGG AGTGTCTTAG GACCAAGGTT GATGCAGCTG CAGGCCTTCA 12840

GGTAGTACTG AGTGCAGACT TTGCAGGGAG ACAACATTTC TTCAAATAAT CTCAAAACAA 12900

TTTCTCAGCC TCTACTCATT AACCCAAACA CAGCAGAGGC TTCGCTGAAA CATTTCACTC 12960

AAAGCTAGGC ACAAAGGCTT CACTGAACAT TTCACTTCAG GCTCCTGCCT CCAGGTCGCT 13020

TCCCTGCTTG AGTTCCCACA TTGGCTTCCA TCAATAATGA GGATGATGTG GAAGTGTAAG 13080

CCAAATAAAC CCTTCCTCCA CAAATCGCTT TGGTCATGGT AACAAAGACA TGTACCCTAT 13140

CACTTAATAG TATTTCTCTT ATCAGGCATC CATGGGAGGA GGGGCCCTTG GTCCTGTGAA 13200

GGCTCCATGC CCCAGTGTAG GGGAATTCGA GGCTAGGGAG GCAGGAGTCG GGGGTGGGGG 13260

GAACACCCTT ATGGAGGCAG GGGGATGGAG AATGGGACAG GGGATAACAT TTGAAATGTA 13320

AATAATGAAA ATATCCAATA AAAATAAATA AATAAATAAA TAAATAAATA AGGAAATTGA 13380

AAAAAAAAAC AAAACAAAAA GAGAGTAGAC TTTTATATTT CAGTATGTGT TGAAAGCAGC 13440

AAAGAATGAG GACCTACATT AATATTTATG GAAATATATT ATCACAGTGT ACCTATGCTC 13500

TCTCTCTGTT AGCTCTCATT GCCATGTTTT TGCCTGTAAT GGAAAACAAG TTTGATGTCC 13560

AGTCTGTAAT AGCTGGAAGG TGTTCCTTCA AGCATCTCTC TATGGGTTTA GCCTTATAGA 13620

TTTACCTTAT AGATCTATAG CCTTATAGAT CTACCTTATA GGTCAATTTC ATGGTTGGAT 13680

CTAAAAACCT GGTTATCAGT AACTCTGTAT TCTGAGTATA TTTTTTTCCA CTTTCAGTGT 13740

TTATTTGTTT TAATTTATAA TGATGTTAAA TTAATAACTC CTGTAAGTAA ATAAACATTA 13800

-continued

```
AGAGCCTTTG ACAAGTAGTT ATAACTTTTT ATGAGGTAAA TGGTCATTGC TGCCGAGCTG  13860
AGGACACTGT TCAATGATTC TGTTTGCCTA GCATGTTCCA GGCCTGGCTT CAAACCTCAT  13920
TCAGTTTCAC TTATTTTTGT TTTTACTCCA TGTGTTGGTG TTTGTGGTCA CAGGGTAACT  13980
TGAAGGAGAA GGGGAGATGG TCCTCTCCGT CAACCATGTG GGTTCTGGGC ATTTGCTGTT  14040
ATGCCAAAGG GAAGTGGTTT TACCCACTCC CTCTTGCTCA CCTTAGACAC TGTATGTTTT  14100
GTTTATTGTG CTTTTCTCCC CCCCCCCCCG TGAATCAGTT TAGGAGAATG ATACAGGAGG  14160
ATCAGATAGT CTGACCTCCC TTCTGTTTTA AAAACATACA CACAAGTGAG CAAACAAAAC  14220
CAGATAACAC GTGTAAGTTT TTCATCACTA GAGCAGAATT GTTTGCTTTT AATAGATAAA  14280
AATATTTCCC TGGGTGATTT AGAAAAAGGG ATAAGGAAAA TGAAAATTAT TTTTTTTAAA  14340
TATTTCCACT GGCTTTTGTT TGCAGGAAAC AGTAAAAAGT CTACAAAAAT GAATATACTT  14400
GGGATGTTAT TTGTACAGTA GTCTGACATT TAACTAATCA GATTTGTCAT TTTTAGGTAA  14460
ATGTTACATT TTTTTTTAAA GTAGTCCGGG TCTATAACAG AAATAGCAAG CATACTTCAT  14520
GGGGTGCCTT CCCAGGCGTA CTTGTGATTG TCTTTTAACT TTGGGAATGA GACTTGAATG  14580
GCAGATGCCT AAATGAAATC TCTACAGGAC CTTGGAAGAC CCTTGAACTT TTGCATTCAG  14640
AGTGAATTTT GCCAAAGCTT GTCTGAACTA ACTGTGTAGG TGAAAGTTCA ACTCTATTAA  14700
CTGCTTGTCA GATCTCTTTT AACTTAAAGT CTAGCCATGT TAATTTCTAC ATTCAGAATA  14760
AGTGTATGAG TGACACTGGA ATTTCCGCAG TCACTCAGTG GTATAAAGTC AGCGTTTGCC  14820
TCTTCGCTTC CTTCCTTCTC GCAGTCTGAG GACATTGGTG TAATCTCAAT GAGTTGCTCT  14880
TGTTTCTTTT GTTTCCTCTC TGGATTGTGA GACCCTTGAG GTCAAGTATA CTTTGGTTAC  14940
CAAGAAAAGG GTTAATTCAG TTTTCTTATT TAGATAGAGC CTCCAGCAGC TCAGGCCGGT  15000
CTTGAACTTT CTATGTGGCT GAAGAGAGCC TTGAATTCCT GATCCTGAAT TACATGCGTG  15060
TGGCTCTTAA AAGGGCTTTA AATCATAATG ACCATGTAGT AATAACCGCT GAAGTATATT  15120
TTTATTAAGC TCTTTTTGGG CCCATCCTTA TCTGAGTGTT TTATGTGAAT GTTCTAATTT  15180
AACCTTAGAG GAGTAAGAAG TATTAGGTGC TGTTACTACC TACCGTGTTT TATTTTTGCT  15240
TACGATGCTG TTTGTGCTGC TGGTGCTGCT GGGGGTGATG GTGGTGATGG TGATGGTGAT  15300
GGTGGTAGTG GTGGTGATGA TGTTTGTGGT GGTAGTGGTC AGTGTGTGTG TGTGTGTGTG  15360
TGTGAAATAC CACAGTGTGT TTGTAGAGGT CAGAGAACAC CTGTGTAAGT GGGAGACAGT  15420
TCTCTCTGTG GTTTCTGAGG GTTGAACTCA AGTTCTCAGA CTTTTACCCA CTGAGCCTTC  15480
TCAGCAGGTC CACGATGTAG TTTTGAGGAA ACTGAGAACT GAAAAGATTT GTAGCTTGCT  15540
CAAGGCTTTG TGTACAGCTA ATCTAATTCT AAAGCACATG TTTTAAATCA TCTCACTGAT  15600
AGGGTATATC AGCAAATAAC AGAAGGTTAT TTTTCTCTTA AAAGTACTAA TTTGATAAGG  15660
GTAAAGGCAT TACTAGTCAG TTCTTTGAAA TGTCTGAAGA TGTCATGATG ATTACATAAT  15720
GAAGCCCTTT CAGATGCATT AAGACACCAT TGATCTTGTA TTAGTGTGTG GTGTGGGGCC  15780
CCGTGGAGGG TTATGTTCTT TTTCACTACT TACTTTGCAC ACGGTGGGAA TTAGTTCTCC  15840
CCAAGCCGTT TTATGTTAGC CAATGTGGAT GTCATCTCGT CTTCAGTTAT TGGCATTTCA  15900
GAGGAACTTC CTGTAATATG ATATGTGCCG GATTGCAGAT AACGATGTAC TTAATCTCAG  15960
TAGAAATGTG CTGACTATTT GTCTCCGTTG ATAGCTAATC TATGAGATAA GATTAACATT  16020
ATTGCCAAAA AGAAATGGAA CAATTCTTTT GAAAGGATAT TGTTGTAGAT GTTATAAGTG  16080
ATAATTTTGG GACACAGTAA TAATAAGCAA TTTATGTCTT TGAGGAATAG TAATGAAAAC  16140
TGAAAGATAG TGTGTTGTTT CAATTACGAC GTAAATATTT CCTGTATGCG AACCTCTTTT  16200
```

-continued

```
ATTCATTTCT CCTCTTACCT CCTATTCTGC CTTCGGAAGT TTGATGTTAT CTGGTATTAT  16260
TTATGCTTCT TATATGTGTG TGTGTTTGAG CCCAATACTT TGATTTGACT TATACTTTCT  16320
GTGAGGTATA TGTTCTAATA GGAACAGACA ATATTGACTT AGCTAGCATT TTCCTTCTGA  16380
GCCTTATTTC TCCTGTATAT TTTCTTCTGT GTAGGCATCA CTCTCATTGC TGTGGATGAG  16440
GCTCACTGCA TTTCAGAGTG GGGCCATGAT TTCAGAAGTT CATTCAGGAT GCTGGGCTCT  16500
CTTAAAACAG CGCTCCCATT GGTAAGCCTT GCCAGATCTC ATGCCCCCAC CCCACCCATC  16560
TCAGCTGAGG ACTGACCCCA GGGCTCCTAC CACCAGGCTA GACCCTCAAT CCCGAATTTA  16620
CTGAAGTGAC ATTTTCATCA AGGCCTTTCC AGGACTGGGT AATGTCCACC CATCTCAAGA  16680
CTTCTCTATA AAAGGGATCA GATGTGAGCA ATGGGGCATA TTTAGTTTTA AAATTTTTTA  16740
AATTCTCACG CTGGCTTCCT TTTGAGGTTG ACGTGTAGCT TACTAAGGAA TACTCTTAAC  16800
AGGAGTGTCC AGGCTGTGAC ATTGAGCTAC TCCAGTGTCA TCTTCAAGGT TCTCCCTCAA  16860
GAACCACAAA ATTGTGTTAT TCAAAGACAT CACAAAGATG CCTCTGTTTT AGTTCACGTG  16920
TGACTTTGTG TTGTGCCACA TTCCTACTGT CAGGGCACGG GCTGGATGCT CTTCACTAGG  16980
ACAAGAGCTG GAAAACAAGT TTTGAACATG GCAGATAAAA ATGGCAGTTA CTATTCCTTA  17040
GTGAAAGGGG ATACAGTTTC AAGAATCCGT GGATGCCTGG AAACACCCCC TCAGTGTAAA  17100
TTATGCACAG TAGAAGAATT TTTAAAATGA CTATCTGTGA CAATATACTA TAGCAAAAAT  17160
GACCACAGTC ATTATTCTTG ACCGCGTGGC TCATGATTAA GTAGAGTAGG TAGCACCCAA  17220
CCACAAGCAC TTCCTAGTCT CCTAACTGAG ATGGTTAGTC AGTAGGTAAT GGGGGAGGCT  17280
GTGGATTGTG TGGAAACTTT GGACCAAGGG GAGAATGGGG TGATATCTTT GAGAGTACAG  17340
TGCAGAATTT CATCATGTTA CTCAGCACGC CTTTAATCCC AGCACTCGGG AGACAGAAGC  17400
AGGTGGATCT CTGAGTTTGA GGCAGCCTAC TTTAGTCCTG TCTTAGGAGA AAGATAAAGG  17460
AAAATGTAAG TTGGGTTTTA GGTTTTTTTG GTTTTTTTTT TTTTCTATTT GTTTGTTTTT  17520
GTTTTGTTTT TTGTTTTTTG GTATAACTTT TCATTTAGTA TATTCAGATT TGGTTGTTCA  17580
CAAGAATCTG AAATCAGAAA ACGCCATTGT GGATAGAGAA GGTGGGTGTG AAGTGGATGA  17640
GAGGGCGGGT GTGTGGTGGA TAGAGATGGG AGTGTAGTAG ATGGAGGGGG CGGGTGTGTG  17700
GTAAATGGAA AGGGCGGTGC GTAGTATAGT ATGGCTTTCA CATACAGTTC TCTTTTCTTA  17760
AATAGTCCAT AAAAAATGTA GTTACCTGGT GTTCCTCACT AATGGCCTCT GTAAAATGGG  17820
CTGGGGACTG CGATAGTTCT ACTTATCACA GTTTGTAGAA ACTTTTAGGT TGTTTGTTGG  17880
AGTTAGGATA TTATGAATGG GGATACTGTA AACATTTGTC TATAGTCCCA GGGTCCAGGT  17940
CAGCGGTTAC AAAGTTTGTG AACATAAGTT TTAGTTTTCT GGGATAAATG ATGTTCTGGG  18000
TTCTATGGGA AGTGCTGGTT TCACTTTTAG GAAGACCCCA GTGCTACTCT CTAGACTGGC  18060
TGCTCTGTTT TGTATCGTCC CCTCCCCAGC AGCTTAGGAA CAATAGCTTC TTCTCTTTTT  18120
TGCCACTGTT TAGTCTTATT ACTATGTAGT ATTTTAGCAA TTATGATACG AGTGGAGTGG  18180
TAGCTTGTGT TTTCAATTTG CATTTCTCTA ATAGCTAGTG GTGTTGAACA TCTTTTGTGA  18240
GCTTCTTATT TGGTTAAATG CCTAGTTTAA TTGGGTTGTA TTTTTTCTGT TAAGCACATG  18300
GGGGAGGTGG AGGGAGAGAA AGGGAGGGAG AGGGATAAGG AAGGAGAGGA GAGAGAAGGA  18360
AGGAGAGAGG GAGGGGGAGG GTTGTGCTTA TGCACATATA CCTCTGCGGT GTGCTCTACA  18420
GTGCAGCCCC TGCAGGCGCC AGATGTTGAC GCTGCTGTCC TCCTCTGTTA CTCTCTACCC  18480
CATTTTATTT GAAACACAGT CTCAGTAGCC AGGGAGCTCC TCATTTGTGC TAGACTAGCA  18540
```

-continued

```
GGCCACCAAG CCCCTGGGCT CTTCCTACTT TGGAACATTG GGCTCCTAGG TGTGCACGCT  18600
GTGCCTGGCT TTTCTGTTGG TTCTGGGAAT CCTTGCTCAT GTCCTGATAC TCACTGAGCC  18660
ATCTCTTCAG TCCCTCTGTT AACTGCTAAG AATTAAATGT TTATAAGTGT GAGTTATTGG  18720
TTGGATATTG AGCTTGTAAA TATTTCTTTG TAAATTTTAT TTTTTTCTCC TATTTTCACA  18780
ATCTTTTATA AAAAATATTA TAAGTTGGGT AAAATTCAGA ATATTTTTTT TCCTTTATGG  18840
GCTTTCTTTC TCAGTCTCAG ATCTTGAAAG TTTGTCCCTG TAGTTTTTCC TAAAATGTAA  18900
ATGATGTAAA TTTAGGTCCG ACAGGGTACA GAGATGTCAT GGCAGGTAAA GAGCTTGCCG  18960
TGCAAGTGTG AAGACATGAG CTTGAGTCTG TGAAGTACAG TGACATGTGC CCCATCCCAC  19020
ACTATATGGC AGAGGAGACC CAAGGGCCCA CTCCTCCCCT AACTGGGTAA AAAGAGGGCT  19080
TTTTATCTAC TTAATTGCTT TTGCCTCTTT GTTGAGAATC TTTTGAGTGT GTTTTGTCAG  19140
CCTGTTTCTC TGGGCTGTAG TCATTTGGAT TGAATTAACG AAGCGGCCTA TATTTAGGTC  19200
CTGGTGCTAG AGAGACGGTG TGCACAAGCC TCACAGTTAA ATGGGTCAAA CCAAGAGGAG  19260
CATTCAAAGT TCTTATCCTT TTGGCGAGAT TGTCTGACTT AGTTCCCTTA ATCATCAATC  19320
TTACACATTA ATAGCAAATT GCTATGTTTA AAATGACTTC TTTCTGTTCG GGTTTTCTCG  19380
TCAAGATTTG ATTGAGCAGT GATTAAGTAA GTCAAAAACA GTAGGAGACA GGTAATGCTA  19440
CAGCTAGCAG ATACTACATC AAAGGAAAAG AAACTAATGT ATTTGGGGTC TAAGTATGCG  19500
TCTGGCCTTG GGTCAGACAC TCTTGTCTCA GTCTTCAGGA CTGTTAATTA AGTTAGCTTT  19560
AATGCCATCA TATTTCATCA TTTGTCAAAG GACAGCTCAT TCCCCTTGCT TTCTTTCCCA  19620
GCATAACCTT CTCCTCAAGT CTCTTCTGTT CCTTTGTACC TTCTTGTTTT ATTAGGGTTG  19680
GTGTCCTGGT CCCTGTTTTA GACTTACTCT CTCTCTCTTC TGTGCTCTCT TTTCTGTGCA  19740
TAATTGGATA CCATCCATCC CATTATGGAG AACCCTCAAA TCTACAACTT GGATTAGTAC  19800
CAGATGTGAC TGAGTTCCTC CGCCTACTTA CCGGCACTTG CTGTTGTACT ACATTTTGTT  19860
TTAGCAATTT TATTGCATAT AAATCACACA TATTATAGGG GATTTATAGG ATATGTATAT  19920
ATACACAATT GTCAACTTGA GGGTTTGCTC TTTGGGTTCC TAATAGGTAT CTCAAACTTA  19980
ACCCCTCCAA AACTGGCTCC TGATGTTCTT CGCACTCTGA GTGCTTTTCC CGCAGACTCC  20040
ATCACCTTGT TTAATAGCAG CACCAGAGTG TTTTGCTATG CAGCCCGGAC TAAACAAGAG  20100
ATCCTCCTGC CTCAGTGTAC CCAGTTGCCT GGAATGCAAG TGTGTACTAC TCTGCCTGGG  20160
AGCTTGATTA TTGTTACCAC TCTGCAGCAT ACATTTCACC AGTAAGGAAA GCCTGTGAGT  20220
GATCTTCCGA GCCTATACAG CTGCTAATCG CTTCCCTCTT GATCCCTGCC GTAGCCCCGG  20280
TGCTGGCTTA CATCTTCCTT CATGTAGGCT GTTACAATAA TCGCCTGGTT TCCACCTTTA  20340
GTCTATTTCT ATACAGCGTT CAAAGTGATA CTTCTGAATC TGTCCCCTAG TTCTGTGTCT  20400
TCTGTGCAGG ATGTGATGGC ATCGCCCCTC ACTGAGGTTA TGCTATGTCG TCTTTCACTT  20460
TCATGCCCGA ATGGTGATGT TAGCTTCTTA ATGCAATCCA TCAGTGAATT AAGTCTTTGG  20520
GTCAGGTTAC AGCCATCGTT ATCTAATCAC CTCTCCGTGG TTGGGTCTGT GACTTGGGGA  20580
TTTTCACCCT TCTACACACA GAGAGGGCAG TTTGTATCTA AACCATAACA AGAGGGAGTT  20640
TTTCTTTTTC TTTTTGTTTA TATAAGCAGG GGTACTATCT GACTCATAGC AGTTGCTTAA  20700
TAATTACACG AATCAATTAA TTCTGGTCAG AAAGCTGGGA ATTAGCGAAG TAACTTTCCT  20760
ATATAGGTAG TTATAAAAGA GTTGGGTAAT AAATAGCTAT ACCATAATAT ACTGTGCCGA  20820
TTTCAACACA AATGATTTGA AAGAGACAAG CTATATTTTC TACCCTTAGG TAGTTCATAG  20880
CCCCGAGAGG GAGTTGAGAT CCACATCCAG GAAAGTAGAG GCAATAGAAA CAAACTGTGC  20940
```

-continued

```
ACCATGCATG GAAAGATGAG TAGTGCCCAT AGCACAGTCG CACATGGGAG GGCAAGTGAA  21000
GGTGTCCCAC AGTGCAGTCA CTGAGCGCTG CTCTGAAGGA CTGGTTCCCA CTGACTTAGG  21060
AAGATTTAAT GAGACAGAGC GAGCTGTGGA ATTGAAAAGC AAGAGGATGC TTGTGTAAGC  21120
CTTTCTTAGG CCTTTGATTC TAGGATTGCG TTAAAGGAGT TTTAAATAAT TTAAGTGGTT  21180
CTCAAATATT CTTCAGGTGG AAAAAAAAAG AATTAAATCT TTTATTATAT CTAACTCTGG  21240
ACATAATGAG ATCGCTTTCA GTTCTTGCAG TGATGAAACA GCGTATTCCT TCAGCTGAGA  21300
GTCTTGGCAG GTTGTTCCTC CTGCAGAGGC CGAGGATCCT TAGCCCCTGT GCTTTTAAAG  21360
ATGGACTCTG TTGGGGGTGG TAAGAAACGC CACCTGGTGG ATATTCCTTT TCTTATTGAC  21420
CTTGATCTTA CTGTTTTAAC CCTGTTATGC TGGGATTACT GTTGGGTTCA TTACACCAAA  21480
TTAGTATAGC AAATCTAAAA GTGCTGGAAA CCACCAAACA ATTAACACAG AGGACCCATT  21540
TGGAAGGAAT CACAAAAGTG AGCCCAGAGA GGTGAAAGCC AGGTGAAAGT TCTGCATAGC  21600
CGTCAAAGTT TATATCTAAC CAGGAGGACG GACTTTTGAA GACTATGAGG TATATTGACT  21660
CTTCCCACTA ATTTGTCGTA AGGACCCATT AAAAAGATCA GAATAGTAGA CACTAAATAA  21720
CTGGAAGAAG AGATTAACTA AAATCTGTGT GCAGAGTGTG AAGTAGTTAT GTCATCCAAT  21780
TTAGAAAAAA GATTGTTATG TTTTCTTTCA ACCGTTGTTT CATGGAGCAT GTAGTTAAGA  21840
TTCATCTCAA TGTACAGTGT CATAAGATTA ATCTGCATTA TATATTCATT GGGTTTTGTT  21900
GCTTACTTTG TCAACAACTG GTGTCTCTTA CCAAGGAAAT CAAGGCAGGC AAACTTAAAG  21960
AACAAATTCC TGGTGCTAAG TGCTTGATAT ATGTAGACAC CAGTATAATT CAGCACATGA  22020
CCAGCTTTCT TCTCAAACAG GTTACACTAT TTATAATTGT GCTGTAGCCA CAAAAACGAC  22080
CTGGAAATAG CCCATCCAAC AAGGGCATAT GGTCCCATTT CTCAGTACTG ACCCATGTGC  22140
TATTTGTAAG CATTGTCCTT GACTAAAATT TTCACATTAT AAAATGCTGC AGACTTCTGA  22200
GGGATCCGTT CTAGTCACAT TCATTTTCAT GAAGACTGTT ATTTTTTATT CTACTTTTTA  22260
GTTGGAAGAG CAGTATTCCT CTCTGTGTCT TTGGAATGTT GTAGTGAGTT TACAATATTT  22320
TCCCTGCTAG CAGTCTGCTT GACTTTTTGA GGACCTTATA AGAAAAATGA AAATTTTTAC  22380
TAAAAGATCT ATCAATCTTG TAGCTCTGTG TCTCTCACTT CACTTTTCCT TAAGTTGAGC  22440
CCTTGCTGGA GTCAGTGGGG AATGCGCTAG CATTTGAAAT TCTCCACCAT TGACATTTCC  22500
ATGCAGAAAG AAATGTCTTC TGTTGTTTTG TGACTGCACT AGTTATAAGG AACATTTTAG  22560
GTGCTGGCTC TAATACCCTG AATAGAATTA AGCACTTAGC ATGCTTTTGT AGATATGTTT  22620
ATGTGTTTTG TGTGGAGTCC AGGTGTGTAT AAAGACTACA GGTCATTCTT GGGTGTTGTT  22680
CCTCAGGTAC AATCCACATT GTCTTTGAGA AACAGGATCT TTCACTGGCC TGGAGCTAGC  22740
CAAGTAGGAT GGAGTGACTG GCCCTAGAGT CCTGGGAACC TCCATATTTC TTTTATATTT  22800
GGCATAAGAC CGCTGTCCTT TTTCTTTGAT TCTTAAAATA TTGTTCAGCC TCTTTGCTTA  22860
TGCAAAGGCG ATCTATCAAT CAGTAAAGTT CTGGCCTGAG AAGTCTGTTC AGGAAGACAG  22920
GCCATTGGCT GAGATCATCT ACCCAGTGCC GGTATTACAA ACTGGAATTT CAAGTGTGTG  22980
TCACAACATC TAGGTGTGTG TGTGTGTGTG TGTGTACACA TATATATGTA TATATGGTGA  23040
TGCCCAGCGT CCTGAAGGCG CTGTTTGACA AAGTTCCAGT TCTTGGACCA AGCCTTCACT  23100
GCCCTTGGTG GATATTCGCT GCACACCTCT TGCTAGTCTT ATGTTTCTCA CTGTTAAAGG  23160
CCTCTCTCTG AAAGCTAGAG GTGGGATAAC AAGAAGCTAG TGTAAACAAG AATCAAGTTA  23220
ATTAAAGTTC CCTGGGGGGG GGGAAGTTAT GCAGAAAATT GAGTCTCTTC TAAGAAGTTA  23280
```

-continued

```
TTTCTTAAAT AAACATTTAG ATCATTAATG AATGTTGTTA GTAAGCATGA GATAGAAGAT  23340
TTGAGAAGAA TTATTAAAGA AGTAAAACTT AGGGAGAACT TAGAAGTTGA GAAGTTGTAT  23400
TTGGATTGCT AGGTTTTTAA GGTTCAACTT GAGAAACGAG CAGTTTGTAT GTATAGGACG  23460
GGATTTGGAT CATGCAGGTT TATGACAAGC CTCGGTGCCT TCCTGAAGGC AAAAGTAAGC  23520
AGGTTTAGGA ACCCTGATGT TCTTCTGTTC TTCACAGAAT TGTTGTAAAG ATAGGGATTG  23580
TATTGAAACA AGGGTTCAAG ACAGAGACAC AGAAGAAGGC ACTCTGGCTC AGTGAACTAC  23640
CTGCCTTCCT GAACATGTAA GGTTAAAAAT GTAAATTCCT AGGAAACTGT TATATTTCTT  23700
TTTAAAATGT TAGGTTTTGT TTGTTTGTTT GTTTGTTTTG TTTTTTAGTT TTAGTTTTAC  23760
TTTTTTTTAG ACAGGGTCTC ACTGTGTAGC TGGGGACAAG CTCCACCCCT GTTCCCCTTT  23820
TCCTCACCCT CCTGAGTGCT GGGATCACAG GCGTGTGCCA CCACCCCTGT CAGGGTCCTC  23880
TACACACCCA GGAGTCCTTA CTGTCAGGCT GTGTCTGTTA TCGTATCTTA TATCAACCAC  23940
TAATCAACCA TTGTAATGCT TGATTAGAGA ATCTGATTTC TTCAAAACAA ACAAGGCTCT  24000
GCATGACTTA ATCACTACAT ATACATTCCT AACGCAGAGA GCAGTCGGAT TATTGGCCTG  24060
AAGATTAATG TGGGGTTACA TTTTAAAGTG GTTTCACAAA TTTAAAAATA GACAATACAA  24120
AAAATTATCC TAATTACTTG GTTTCATTGA GTTTATTTTT GTATGACTTT GGATAGGTTT  24180
TAATCTAATT AAGTTATTTT AATCGTAAGA GTAGCTGTTT CTTAATTAAT TTACTGCTGA  24240
AGACCAAACC CAAGGCCTTG ACAGGCTCGT ACATTCCCAA TGAGCCATGC CTTCAGCCAC  24300
TTAACTATTC CTTTCTGTGT GTGACTGAAA ATAAGCTTTA TTTTTCTAAG CCAACAAAAA  24360
TGAAATAATG CTTGAAGCTT TGTCCAAGTC TATATTATTT TATGGGTAAT ATTTATTTTA  24420
TATTGAACAC TTTTATTTTT TAACTATGAA GGTCTTTTAT TTTCATAGAT ATCTATTGCG  24480
GTAAAAATTT AAAGGTAATA AACTATGATA AATTGAGCTA AAGATGTGGC TCAGTGGTTA  24540
GATGTTCATA TTGCTCTTAC ATGAGAGGAG AGTTCAATTC CGATCACCCA CATTAGGTGG  24600
CTCACACCTA ACCATAACCC CAGCTCCAGG GGTGTCTGAA AGCTCTGGCC TTTGAGGAGG  24660
ACTTCACACA CACACACACA CACACACACA CACACACACA CACACACAAA GTAATAAATA  24720
AAAATGATCC CTAAGTACAT AAATCATAAT TGAAGTAACA TTCAATGTTG TTATGGAGGA  24780
TCAGCTTATT GGGAGGTTAT GTAACTATAA TATTTACATT TTTAAAGAAT AGAAAAAATC  24840
TATTTCTATA ACAAAGCTAA CTGAAACAGT AGAATATAAA AGGCAAAAAC ATTGATATTA  24900
ATATTTTGTG AAATTTAAAT AAAAACCAGC AATCAACTGA AACTGAAAAT ACCATAAATG  24960
ACAATGCTCT TTCTTAGGTA TTTCTTAGTA GTTTTGTTTC GCATTCTTAA TTTACATTGT  25020
TGTATAAAGA AGAATAAACC GAGTTACTGA ACAGAGCAGC AAAGCTTGTA ATCTAAAATT  25080
TAAAGATGTT TATGTTTTAG TTTTCGAATT AACAATTTAT AATTCTGAAG ATAATTTTTT  25140
CTTAATTTGT TTATTATCTA AATGCATTTT ATACATCAAC CATATTAATA ATATTGAACA  25200
TTTTGAGACT CAAATAATAC ATAAAAAATT TGTTCAACTT TTATTTTCAT ATCCTGAAAG  25260
TATCATTAAT GAATATTTAA TACTATCCAT AACTGAGGAT CCTATATCTA ATGTTAAATA  25320
CTAAATTGTT TCAAAACATA CAGAATATGC TTAGGGAGTT AAGCATAGTA AAAGAGCATA  25380
GAATATTAAA AATGAATCAT TAAAAAATAC ATTAAAAAGC CCTTATATGA TACCACATGA  25440
CATAGTGAGA GAGTATTTAA AACGCATTAT ATATCTGTGT GCATTGTCTA ACAATCAGTT  25500
TACTTAAAAA AGATTATCAG TGTTTCTAGG AGAGAAATTA TTTTATCAGT AAGTATATTT  25560
TAAAAATTAC AAAATAGCAA AAACTCTTTG AAGTTAACAG TAAGAAAATG CTAATTTCAA  25620
GCACAGTGAG AAAAATTATC AATAATATTT CCATGATGTT TGTAGAACAT GATTTTAATA  25680
```

-continued

```
TTTTCAAATG TTGATATTCA ATAAACAGAA AAGTTATTTG AAGATATATT TCATTGTTAT  25740
GTCTCCCTTT TAATTTTTGA TTTTATTAAT TTGGATACTG TCTCTATGCC CTCTGGTTAC  25800
TCTGGCTTAG GGTTTATCTA TCTTGTTGAT TTTTTTTTCA AAGAACCAGC TCCTAGTTTT  25860
GTTGATTCTT TGTATAGTTC TTTTTGCTTC TATTTGGTTG ATTTCAGCCC TGAGTTTGAT  25920
TATTTCCTGC AGTCTACTCC TCTTGAGTGT TTTTGCTTCT TTTAGTTCTA GAGTTTTCAG  25980
GTGAGCTGTC AAGCTGCTAG TGTAAGCTCT CTTCAGTTTC TTTTTGGAAG CACTTAGAGC  26040
TATGAGTTTT CCTCCTACCA CTGCTTTCAC TGTGTCCCGG AAGTTTTGGT ATGATGTGTC  26100
TTCATTTTCA TTTCTGCCTT GACCAAGTTA TCATTGAGTA GAGCGCTGTT CAGCTTCCAT  26160
ATGTATGTGT GCTTTCCGTT GTTTGTGTTG GTATTTAAGA CCAACCTTAG TCCGTGGTGG  26220
TCTGATGATA GGGTGCATGG GATGATTTCC ATCATCTTGA ATCTGTAGAA GTCTGTTTTG  26280
TGACCAGCTA TATGGTCAGT TTTGGAGAAG GTTCCATGAG GTGCTGAGAA GAAGGTATAT  26340
TTTTTGCTTT TGGATGACAT GTTCTATAAA TATCTGTTAG ATCCATTTGG TTCATAACAT  26400
CTGTTAGTTT CACTGTGTCT CTGCTTAGTT TCTGTTTCCG TGATCCTGTC CATTGCTGAG  26460
AGTGGGGTGC TGAAATCTCC CACTATTATT GTATCAGGTA TGATGTGTGC TTTGAGATTT  26520
AGTAAAGTTT TTTTATGAAT GTGGGTGCCC TTGCATTTGG AGCATACATG TTCAGAATTG  26580
AGAGTTCATC TTGGCAGATG TTTCCTTTGA CCAATATGAA GTGTCCTTCC TTATCTTTTT  26640
TTTGATAACT TGGTTGAGAG TTGAATTTAT TCCATATTAG AATGGCTACT CCAGCTTGTT  26700
TCTTGGGAAA CAACCATTTG CTTGGAAAAT TGTTTTCCAA CCTTGAACTC TGAGGTAGTG  26760
TCTGCCTTTG TCACTGAGGT GCATTTCCTG TATGCAGCAA AATGCTGGGT CCTGTTTACA  26820
CACCCAGTCT GTTAGTCTAT GTCTTTTTTT GAGGAATTGA GTCCATTGAT GTTAAGAGAT  26880
ATTAAGGAAA AGTGATTGTT ACTTCCTGTT ATTTTTGTTG TTGTTAGAGG TGGAATTATG  26940
TTTGTGTGGC TATCTTCTTT TGGGTTTGTT GAAAGATTGC TTTCTTGCTT TTTCTAGGGT  27000
GTAGTTTCCC TCCTTGTGTT GGTGTTTTCC ATCTATTATC CTTTTTAGAG CTGGAAAGAT  27060
ATTGTGTAAA TTTGGTTTTG TCATGAAATA CCTAGCAGCT TGACAGCACA CCTGAACACT  27120
CTAGAACTAA AAGAAGCAAA TACACCCAAG AGGAGTAGAC TGAGATTGGG AGTTTTGCCT  27180
GGGCTGGCAT TTGTGTTCTC TTAGGGTCTG TATGACATCT GCCTAGGATC TTTTAGCTTT  27240
CATAGTTTCT GGTGAGAAGT CTGGTGTAAT TCTGATAGGC CTGCCTTTAT ATGTTACTTG  27300
ACCTTTTCCA TTGCTGCTTT TAATATTCTT TCTTTGTTTA GTGCATTTGG TGTTTTGATT  27360
ATTATGTGAC AGGAGGAATT TCTTTTCTGG TCCAGTCTAT TTGGAGTTCT GGAGGCTTCT  27420
TGCATGTTCA TGGGCATCGC TTTTTTTAGG TTAGGGAAGT TTTCTTCTAT AATTTTGTTG  27480
AAGATATTTA CTGGCCCTTT GAGTTGGGAA TCTTCACTCT CTTCTATACA TATTATCCTT  27540
AGGTTTGGTC TTCTCATTGT GTCCTGGATT TCCTGGATGT TTTGGGTTAG GAGCTTTTTG  27600
CATTTTGTAT TTTCTTTGAC TGTTGTGTCA ATATTTTCTA TGGTATCTTC TGCACCTGAG  27660
ATTCTCTCTT CTATCTCTTG TATTCTGTTT GGTGATGCTT GCATCTCTGA CTCCTGATCT  27720
CTTTCCTAGA TTTTCTAACT CCAGGGTTGT CTCCCTTTGT GATTTCTTTA TTGTTTCTAG  27780
TTCCATTTTT AGACTCTGGA TGGTTTTGTT CATTTCCTTT GCCTGTTTTA AAGTGTTTTC  27840
TGGTAATTCT GTAAGGAATT TTTGTGTTTC CTCTTTAAGG GCTTCTAGCT GTTTACCTGT  27900
GTTCTCCTGT ATTTCTTTAA GGGAATTATT TGTGTCCTTC CTAACGTCCT CTATCATCAT  27960
CATGAGAAGT GATTTTCGAT CTGAATCTTG CTTTTCCAGT GTGTTGGGGT ATCCAGGACT  28020
```

-continued

```
TGCTATGGTG GGAGAATTGG GTTCTGATGA TGCCAAGTAA CTTTTGTTTC TATTGTTTAT  28080
GTTCTTCAGC TTGCCTCCCG CTATCTGATT ATCTCTAGTG CTACTTGCCC TCGCTCTGTC  28140
TGACTGGAGC CTGTCCTTCC CGTGATCCTG GTTGTGTCAG AACTCCTCAG AGTTCAGCTG  28200
TCTCTGGGAT CCTGTGATTC TGGAATCCTG TGATCCTGAG ATCCTGGGTG TGTCAGAGCT  28260
CCTGGGACTC AAGCTGCCTC TAGGAACCTG AGATCCTGGT GTGACCAAGC TCCTGGGATC  28320
CTGGGATCCT GGGATCCTGT GGACCTGGGT GTGTTAGAGC TCCTGGGAGT AGAGCTTCCT  28380
TTGGGTGTTG TGCTACTGGC TGTGGAGTTT GCTCTCAAGA TCTGCTCTGG GCAACGGCTC  28440
AGAGTGGATG GGACCTGTGC CGCTGGTCAG GTGGAGTTCC TGGGTGCCTG GGTTCCACTG  28500
CTCCCAGTTA CTCCCGGTGT TGGGGCAGAT GTTGTGCCCT CCTCACCTCT GATCCTATGA  28560
TCCTGGGAAT GTTTAGGGCA CTTGGGAGTG AGCTTCCTCT GGGTGTTGTG GGACTGGCTG  28620
CGGAGTTAAT GCCCAAGGTC TCTGCTCAGG GCACTGGCCC TGACTGGAAG GAACCTGTGC  28680
CAGTGGTGGG GCGGATTTCC TGGGCACCAG CCCAGACTGG AACAGAACAC TTTTATTTTT  28740
ATTCATTTAT ATTGTTCAAA ATAATGAGTT TCGTTTCATT TCCATAACAT ATTTAATGTA  28800
CTTTGGTCAT ACTTATTCCC TAAGAGATCG TATTTTGTTT TAATTTTAAG TCAAATTATA  28860
TACATATTTC TTTGTAAATT AGCAAACTGC ATACACATTT ATACTTAGAT ACAAGATAAA  28920
TGCTTAAATT ATTTTATGAG GTATTTACCG TTATGTTTGA ATAATTTTAT TAGGATGTTG  28980
TTTCCTCTAT CTGTAACAGG TAATAAAATA AAAAATTGAA TTCTTAGCAA TAGAATAGCT  29040
AATGATTTAG AAATAAATTT TAAGACAGCC TTTTTCTTTT CTGATAATGA AATGGTTGAG  29100
TACCCTGGTT GAGTGTGTCC CCATTGTAAT AGTTATAAAA CATGAGCCAT CTACATGGAA  29160
GATACCTTGC TCACCTACAT GTGAATTTCT GAACGAAATA TTCATGGTCT TCCTGCCTCC  29220
TATTGTGCCT CTTGATTTTG ATGCTCACCC TATGGAGAAA TGCTAGAAAA TAGCCTATGA  29280
GTCAGTTGCT TAAAGAATCG GGTAGTCATA CATGTCTCAC TTTCTACATA TTGATTACAT  29340
CCAGAATGGC ACTGAGAACT CAGTAAGACA GGAGAGAGGT TGTAATGGCT GTTGGGAGAC  29400
TTGCTTCCAC AGCTGGAAAG CCACATGCCA ATATAATTTT GAAGAACGCT TCTCACAAAA  29460
TAAAAGATAA ATTGTTTTAT GTAGCTAGGC TATTAATTTA TAACCCTGCC AGGGCTTATG  29520
TATTGCAAGT TACAGATTAT TAAAAAAGAA CGAGATGTAT TAATCCCCAC TTCTATTAGC  29580
ACTAAAGTAT AAATGGCTAA TAAGTAGTTT TAATTTAGTG GGACAAGATA AATTGCATTG  29640
AAATCTCATG ATTTAGTGTT TGATTTATTA AGTAGGAGAT AACTTTTCTC GTTTAAAAAC  29700
ATTTTTTTTT CTCTTTACGT AGGGCTCGTA GCTTGGTGGT AGAGCACCCA CTAAGCATGC  29760
CCAAGGTCCT GGGTACCATC CCCAACATGA CAAAAAGAAA TAAATATTCT AATAAACCAA  29820
AACGTTAGCA TGTGTGTCTT GGCCATGGTT CCTGTATGGT TGTGACTGTG GATGTGTCAG  29880
AAGACAGTGA GAAGTCAATG CGCCTTTTAA ACGTCCGTTT GTATTGGATT TCCCCCCAGG  29940
TTCCAGTCAT TGCACTCTCC GCTACTGCAA GCTCTTCCAT CCGGGAAGAC ATTATAAGCT  30000
GCTTAAACCT GAAAGACCCT CAGATCACCT GCACTGGATT TGATCGGCCA AATCTGTACT  30060
TAGAAGTTGG ACGGAAAACA GGGAACATCC TTCAGGATCT AAAGCCGTTT CTCGTCCGAA  30120
AGGCAAGGTA AAGATAGGAC GCTAGACGAA AGGATCTTTT AAAGAAGTTA TTTTATTTTT  30180
TTCTATTTCT TTTTTTGATA TATATTTAAT GTCTCAAATT TTATGTAGCC TTGGCTCAAA  30240
TGAGTGTAAT ACTACATAAT CAATTCAGTG ACCAATATGA AACCACTAAA AGAAATATTT  30300
CCATTCATTC TTTTAGAATT TCATATAGTA TACTTTGATC ATATCCACCC CTTATTACTT  30360
TCCCAACTTC TCAACGGAAA CTAGCTCTCC CTCTCCCAGA AGCTATCAGC TGTCTACAGT  30420
```

-continued

```
CTACTGCTTG GTTAGGGGTA GGGGCTTGGT CTAGTGTAGA CAAGGGTTCA TGAGCGCAGT  30480
GGTCCTGCCA TGACCAGGAC ACATGGCTTT GCTTCAGTTT TCTCTGACCA TTGGCCTTTG  30540
TGTTCTATTT GTCCACTCTC CCATGGTGTT CAAAGCATTT GTATTTTGCA AGGGCAGAGG  30600
AGATGTGGCC AGGAACTAAT TTGTCTAATA TTATTTTTCT TTTATATTGT TATTCAAATA  30660
AGAGATATTC TTTTAATAAT TTACAACTAA ATGAACAAAT ATGACATGAG CATTTCTTAT  30720
GAGTTCTGTC TGCTTTCATA TTTAGATGAT CTACCTCTGC TGGAGGGGCT TTTTAATAGT  30780
CAGTATAGAG TCTGTCCATG TTCCAAGGAC TGTCCTAGAT GCTTTATACA AGTGATCTTG  30840
TTAAATCCTC TAGCATAAGG AAGTTCCTGT GTACATCTAT ATTTTACTGA TGAAACTGTC  30900
CATTACACTT CTAAGATTTG TATTTTAAAA TATACTTTAT GCTTTATTTT GTATGCGAAG  30960
AACCTTTGTA ATGCCATTAT TCTCTGTCCT GCCTGCTGAG TTAAAAGTTG ATATTTTCCT  31020
TATATTAAGT ATTCTGAATA ATGAAAAATA ATTTTCTCCT ACCAATACCA ATGCAAACCA  31080
AGTCCAAGCA AGAAAGAGCT GAGAGCATTG TTAGTGTTTT CCTCGTCCAG AAAGGATGTA  31140
AATGGGAAGA GAGATCCTAG GTTAAGGAAG TGATAGTGTT TGTTGTAGAT ACTAGGAAGT  31200
AGTTTAAGTA CCACCTGAGA AGTGCTCGCT ATTCCGAGTA GAATAGGAAG ATGGGGAATG  31260
TATTGATAGG GTTTTGCTGC TCAAGCTGCC TCCTTGAACC TGCTGTTCCA TGGTCCTTTC  31320
CAGTAAAGGA AAAGTTCTCT TGTCAAAGGC TTCTTCTAAA CTGGATGTTT CTACACTCAT  31380
GTCATTACTA ACCCCTGATC TTTTAGTTCT TGTCAATGCA CATTATTTTT AATATCTATG  31440
GCTAATTTTT ATAGTGACCC TCTTCTTTCA TATGTATATG TGTGTGTGTG TGTGAGTGTG  31500
TGTGTGTGTA TGTATATATG TGTGAGTGTG TGTGTATGTA TGTATATGTG TGTGTGTACG  31560
TGAGTGTGTG TGTGAGTGTG TATCTGTGTG TGTGTGTGTG TATGTGTGTA CACACACGTT  31620
AAAGTGCCTT CCCCCATCTT TTCTTGTGAT GTTTTGTTTT CCCATTTTTG GCATCATTTG  31680
CCTTACAATA TCTTATGCAA ATGCCTTCTT CCCAATTTAT ATTGATATTC TGGTAACGAT  31740
GATTAATTTA ATTTTTAGCC CAGATTTTTC TGATCACTCA TAACACATCT ATATCCTCGG  31800
TGCTACTTGA TATATTCCAC AGATAACTTT CAGGTTTATC ATCTGCAGAC ACGTCCTTAA  31860
ACCTTGGAGT AAAATTTTAT TTTTAAACCT TGTATAATAT TTTATGCAAC AGTGAAATTA  31920
TTCTCTCACC TCTTAAATAA GAATAGATTA ATCTATTGTG CTGCCTTTCT AGACTCATTT  31980
TTATCCATAC CTTGTAAGTT TTAGAATCAT TTTTTTCCTA AAACAAAGTG ATTCCTGGTT  32040
TTAACTTTAA TTTGGGCCAA TGTTGAGTGC CAGAGTTTTG CTTTCACACA ATACGTTTCT  32100
ACGTTTGTCT TTCCAGAATG TTCTGGAGTT TCAGGGAGTT GAAGTGTTTT TCAGTCTGCT  32160
GACTTCTTTA AGACTTTTGC TTAGTGAAAG CAAAGATTAT GAAAGATGAA TCCCAAACTG  32220
CGATGAAACA TACATGTAAC AGGCGTGTTT GCTTTCTCTG TCTCCCTACC TCTTCCCCAC  32280
CCTTCCACAG TTCTGCCTGG GAATTTGAAG GTCCAACCAT CATCTATTGT CCTTCGAGAA  32340
AAATGACAGA ACAAGTTACT GCTGAACTTG GGAAACTGAA CTTAGCCTGC AGAACATACC  32400
ACGCTGGCAT GAAAATTAGC GAAAGGAAGG ACGTTCATCA TAGGTTCCTG AGAGATGAAA  32460
TTCAGGTGTG CAGAGCAACC ATCTTTCTCT GAATTCTTCA CAGGAAGTAT ACGTATCTGT  32520
CAAACATTTA TGTCACCAAT TTTTTTTTTA AAATTGTTGT ATTAAGCACA GTTTCACCAC  32580
TCTGATAAAG GTAATGACTG TATAGTGAAA TTGGATTAAA TAAACCCTAC AGCTTAGTGT  32640
AAATAGCAAA GACTGTCATC TGTTACTGGG CTACACAGAG AATCAACACC AGTTCTGTCA  32700
GAGTAGGTTA TGTAATGAGA GTGGTCATCA GGAAGCTGAA ATCTGAGAAG AGTCTTAAGT  32760
```

-continued

```
ATGTCAAGTT TACCAGGTCA GTAGGTAACG AGGGCTGTAG AGTCCCAGGA AGCAGCAGCA  32820

GGTGCAGAGA CACACGTTGA GTGCATCCTG GGCTCAGAGA GGAAGAGCCT GAGGTGATCG  32880

GAGGAGAAGA TGAGCGGTAG GAATGGCACA GTCAGGGGAC ACAATGAGAA GGTTAGACAC  32940

TCTCAGGAAG GCTGCGTTGG ATGGTTGGCC AGCTTAAAGA TGAGAAGGAT CCCTGGTTAA  33000

TGGTGCTCGC CCCCTACCAG AAAGCATCTA TTGTCACTCT TCCTGTAGGA ACGGCACTAA  33060

TGCTTATGAG AGGTTGTTGT GCACACTTAT TAATACTTTT ATTACTTTAG CGACTGGGTC  33120

CTTTGGATGC ATCTGGCATA CTGCCTGTCT TAGGTACTTT TCTGTTCTAC TACTGACTGA  33180

GGCAACTTAC AGAAGAAATA GTTTATTGGG GCCTACAGTT TCAGAGAGGG GGTCTGTGGT  33240

CACTGTGGAG AGTGTGCAGC AAGCAGATAG GCATGGTGCT GGCGCAGCGG GTAGGCAAGG  33300

TGCTGGAGCA GCGGGTAGGC AAGGTGCTGG AGCAGCGGGT AGGCAAGGTG CTGGAGCAGC  33360

GGGTAGGCGT GGTGCTGGAG CAGCGGGTAG GCGTGGTGCT GGAGCAGCGG GTAGGCGTGG  33420

TGCTGGAGCA GGAGCTGGCA GCTTGAGCAC CAAGAGAGAG AGCTAGCTGG AATGGCACGG  33480

ACCTTTGAAA TTTCAAGGCC AGCCTTTAAA GCCTGCTCTT CCCCACAAGG ACACACGTCC  33540

TAACTCTTCC CAAACAGTTC TCTCACCTAT GGATCAGCGT CCAAACATAT GAACCTATCA  33600

GGGCCATTCT TGTTCAAACC ACCACACTGC CAATGTATAA CTTGATTGAA GCATTAAATT  33660

TATATATATT AGTTTTTTGA GACAGGGTTT CTCTGTATAG CCCTAGCTGT TCTGTGGAAG  33720

TATTAATATT TTAAAAGAAG GCTTAAAAAT CTTTAGTGAT CTTTCATTAC AGTTAATTTT  33780

GAAGGTTATC TATCTACCTA CCTACCTACC TACCTACCTA CCTACCTACC TACCTACTTA  33840

TCTACCTACC TACCTACCTA CCTACTTACC TACCTATCTA TATTTTGCAT GCCCTGCTGA  33900

ATTTTCTCTT TCTAGTACAG GAAGTCATCA ATTCGAATCC ATATTATAAA AATTAAAGTT  33960

TAGATGAATA GTTGCATTCT AGGTAGCCCG AGGTAGTGTT TTGTCTAACA GCTGAACCGA  34020

TAGACTCCTT CCTGGTCACA ATTCAGAAGC CTGGCATATG CTTCGAACCT TCCCCTTTCT  34080

TAGCACAGTG AAAGGCATGT TGTCATCAGT GTAGACTTAT CTGGACTCTT AGAGCTGATT  34140

ACTTTTTGTT GGGTGTTCGT TGAGTGCCGA CTGAATTCAT AAATGTAATG ACTTCTAGAT  34200

AGCTACTTCC TGACCATTTT ACAGTGGATT TTTACTGTAT GGCAGGCACA GAGGCTGACC  34260

TCTGTAGCTC TTCATATGTT AGACTGATGC ATAAAGCCAT TTTCTGTTTT ACAATTTTAG  34320

AAACAAAGGG AATTTCCTTT ATGTCATATA TACTCAAATC CCATGCACAT TAGCTTTCCA  34380

TGATTTGTTT ATAACTGTCT GTTCTCAAAT TTTATCCCAA CCCTTAGTTT CGTCCTTCCT  34440

ACATTTGCCA TTTTAAGGTG GCTTTTTAAA AAATGAAATG ATGAATAACT TATTTGGTAG  34500

AATAGTTTTC ATTTATATCT AAAAGTTTAT AGGGACAGTG TGAAAATCTG GTTAATAGAA  34560

TAGTTAACAT CAAATGAAAG AATAATCCGG TGAAGCTTAG AATTCCATTG GTTATTGACT  34620

GCTAGCTGGA CTGAGCTGTT AGAATTCCAT TGGTTATTGA CTGCTCGCTG GACTGAGCTG  34680

TTAGAATTCC ATTGGTTATT GATTGCTCGC TGGACTGAGC TGTTAGAATT CCATTGGTTA  34740

TTGACTGCTA GCTGGACTGA GCTGTTAGAA TTCCATTGGT TATTGACTGC TAGCTGGACT  34800

GAGCTGTTAG AATTCCATTG GTTATTGACT GCTCGCTGGA CTGAGCTGGC TTCTTGCACC  34860

AAAGCTTTTG CTTCCCACGT CTGTGCCGTT ATCCCCGCTC CCTCACCCCT CACCCATCCT  34920

TTGCGTGTTT CCTATGCTCT TCCTTTCTCC TTTCTGTCAA TCTCCTGGGC CATCCTAGAA  34980

CATACCCTAT GAGCTTATTT TACTGTTGTC TCTTCAATGA GGCGTCTTCT CCCCTCCCCT  35040

CTCCTAAGCC TTCGATCTGA CTTTGGAGGT GTTTATTGCT CTACCCTGAC ACAATTTACT  35100

TATACTGCTA TCTTAATTTA TTGTCAGTTT TTATGATTCT CTATTGATTC CCCACTAAAA  35160
```

-continued

```
ATGCCGGAAA TTCACCAGCC TTTCCTCTGT GTTCCTGCAG CCCTGGACCC CTTTCCCTTT  35220
GCCTGTTGGT TTATATCTTA ATTCTGCTTA AATGTCATAT GGTTATCAAC TTAAGCATCT  35280
TACCTTTAAT TTTTATAATA TATGGTTATA GTTCTCACAT ATATTTTTGT ATTCTTGTTA  35340
TTAAAGGATT TTTTTTCTGA GTATTTGTCC CTAATTCTCC TGTGAGTTTT TTCCAACCAT  35400
ATGAACTTTA TTTTGTTAGG TTCATTCACA TTAGGTCATT TGACAGTTTT ATCCTCTTGG  35460
TATTATACCC GTCTTTTTTG TTTTTGTTTC TGTTTTTGTT TTGTTTTGTT TTGTTGTTTT  35520
CTATTGTACC CATCTTAATG ATGCTTCATT AGCTGTATTT CTCTTTGCAG TAGTGAATGG  35580
TATTATACTT AGATTCTGTC ATCAGGAGAG GACATTCGAA ACTTGATAAT AATACAATAG  35640
TTTTATTCAC TACAGTAACT GTTTCTCATA GCTTCGGGTC TCCAGAGAAA CTCCTTTATT  35700
TGCTCCTTTT TATAGAGATG AAGAGAAGTC ACATTTTTTT TTTTAAAGAC AGGGTTTCTC  35760
TGTATAGCCT TAGCTGTCCT GGAACTCACT CTGTAGATCA GGCTGGCCTC AAACTCAGAA  35820
ATCCGCCTGT CTCTGCCTCC CAAGTGCTGT GATTAAAGGC GTGCACCACC ACTGCCCGGC  35880
CAGAAATCAC ATTTTTATAG CCACTATTTA TCCAAATCTG TATTTGGATA GATTATCTTT  35940
TAGTCTGTAA GTAAAGTTAT ATTTAATTTA GTTTTACACT GGCGGGCAAG CTGCTGTTTT  36000
ATTTTGTAAG TTTTAGTTAA GTTGAAATGT GATTCTTACT CTGCGTTGTT GTTCATTCTC  36060
AGTGTGTTGT AGCTACTGTA GCTTTTGGAA TGGGCATTAA TAAAGCTGAC ATTCGCAAAG  36120
TTATTCATTA TGGTGCGCCT AAGGAAATGG AATCCTATTA CCAGGAAATT GGTAGAGCTG  36180
GCCGGGATGG ACTTCAGAGT TCCTGTCACT TGCTCTGGGC TCCAGCAGAC TTTAACACAT  36240
CCAGGTATAA ATGCTTATTG TTTTCACCTT ACAAATTCCT TTTTCCTTTC CAAGAAAGTA  36300
TTTGAGGGAG TATCCAAAAT ATCAAGTGAC CCCTGAGTAT ATTTAAAGGG GTCGCCACCG  36360
GAAAGTGAGC AAAATGAACA GAATATCCCT GAAGAGTGTT TTTGGTAAGT CTTCCCACAT  36420
AGCAGGTGAT CCAGTTGGAG TTAACAAGAT CGGGACTGCA CTTGGACGTA TAACATAGGT  36480
CTTATGGCAT CCTGTCCTAT TGTGCAGCAG TAAGCAGTTC CCACATTTTA AATCCTCCAG  36540
TCATATGGCT CTAGGTTTAA GTAAGTACCA TGTGTCCAGT GCTATAATGG TGGTTATTCT  36600
AAAAGATGTA TCCAATTCTT GTTTAACTCT CTTTACTATT GTTTCTGTGA TTAGTTCCGT  36660
AAGTGCATGC CACTGCTCAT AGACTGAAAA CTCACCTGGT TGATAGTGCC TAAATAATGT  36720
AACAGCGTAG TGTTAGAGTG CTGTCATAAA ATAGTATATG TTCGTGGTTT AAATTCAAGG  36780
AAAGGGAAAC TGCCTACTTA AATGCTAACT AAATTGTAAC TTACATCCTG CCAGATTATA  36840
TTAGAAGCAA CAGCTTCAAT TTCCAAAATC ATAGGGACAT TATTTACCAG TTATCTATCT  36900
ATAGGGAACC AGGAAAAGAA GCCAGTGCAG CCCAGCCAGT GAACGTGCCA ACATAAAGGA  36960
CCTTTCAGTG CTCCTCCAGG CTGATGAGTA AGCTAGACAC TGGTAGCTAA AAGAGTAGGA  37020
TTAGATAAGT AAAAAGGGTT GTTACAAAAT CTAAGATCTT GCTAGGAATA GTCAGTATAT  37080
TTTACTTTGT AATAAGTAGA GCTGAACTCT GATCCCCTGA AAGCAAGCAT TCTTAGCCAC  37140
TGAGCCATCT CTCCAGACCA GGCGCCAGAG TCTTTACCCA GCCTTTTAAA AACCAATTTA  37200
AAGTAAGTTG GATAGAACAC ATCTCTGCAA GCTACTATTA AATTTGGAAT ATATCAAATA  37260
TCACTTGGTT AAGACCAGAT CTTATTTTAT TTGTGTATTA TGCTAACATG CTGGAAACAT  37320
TATAGGCCTG AGTTGTATAA TGCAATCTCA CCCGTGGATA TAGTGTTGAT TTATGTGGGT  37380
TTTGAAAGAT ATGCTGAGTG GTTTATCTCA TTAAGATTGA TCAGGAAATA ATAGTTGTGC  37440
CAGAATACCC GTGCAATTGT TACTTAGTAT CCATGGTGAC TGGTTCTGAG TTCCTTAAGA  37500
```

-continued

```
TAGAAATAAA TAAATAATCT CCCTATACAT GAGGCTCTTA TACAACATAG TATTTGTATA  37560
CAGGCTGTGT ACTCTTCTAC ATACTATCTT CCTAGCTCAC ATATAACATC TATTATAAAG  37620
TAATTGATGT GTAAGCATTT AGTTTTACAC TGTAATCTTT AGAGAATAAC AATAAGAAGA  37680
ATGTCTCAAT GTGTTTAGTA CAGATGCAAC TACTGTAAGC CTAATTGGGG TTTAACTTGG  37740
GGTTGACCGA CTCTCAAGTG CTGAACTAGT GGGTGCAGAG CTGAACCACT CGCTCTTTTA  37800
GTACAGATAG GCTACTCTGT GTATCAGAGA CAAAGGAGAA AAACTGTAAA AGGATAAACA  37860
GGAGAGAGCC AAGGATTAAG GGTGAGTTTG TACCATCGAG ATCTTGAAGC AGAAGAAAGC  37920
AGTGAGATTC TGGGTCTCAG CTCTAAGGGT CATTGTAACT TATAAAGTTG TAGTCTCGCG  37980
TATGCTAAAA TTCTGTGACA AGGGAAGAGT CTTGTTTGAG GGATCATGCC GTGATTTTAA  38040
CTAACTAATG TTTATTTGTT AGTTTTGTGA TGCTGGGTAT CAAATCTGGG CCACCCTCAT  38100
GCTAGACAGC CTATGTAAGC CACATCCTCA GAGACGATTA TGTAGTTTTA TGTTCCCTTA  38160
TTGTGTGATT TTTGTGTTTC TTACTGCCGA GCCGTAACAA GGCAGTGTCC CAGTGATTAT  38220
GTTTATTATA TTTGTAGTCA TACCCAGTAG TTACTGCCAT CTTTTGTTTC AAAGTGAAGA  38280
ACTTAGAGAA TAATCTCTAA TAAATCTTTG AATTCTCTTA AAGTTAATGA ATTGTTAGAA  38340
TTTATGGTTT TTTTGGTGAA ATAAGTTGTA TTGCGCATTT AATAGTAGCA AAAGAAGAAT  38400
AAACTAATAA ATATTTAATT GAGTTTCTTT TTCTCAAATG AACATGTAAA TGAGCATGGA  38460
TGAAATCAAA TAAATATATT TCATCTCAAT CCAATATACT AAGATATAGT TCTGAGTATT  38520
GTTGACTTTA TCTCTGAAGG ACAAGGGAAC TAAATGAAAC TGATTTTTTT ACAAATCTAT  38580
GATCCATTAA GTATGGGCTT GGATAATAGC TCAGGTTAGT ATTTTTAGTT CAGGGTATTT  38640
GGAGGAGAAA ATTCATGTGA AGGGTGTTAT CCATTGAGAA CATATCTTTG AATAATGGAT  38700
CATTTGTACA TTCAAATTTT CTAGAATAGA GATTGTATAC AGATATTTTG ATTAATCAGA  38760
AGGCTGGATG TTACAAACAT TAGTGAGCAA AGTCCCTAAT GATGAAGTTC AGTATTATCA  38820
TTTAGTTCTT GTATATTAAA TCAGAATGTT ATATTGCAAT ATCTAAAATT CATTTCATGC  38880
AGGTTTTTTT TTATTATTAT TCTTGGAAAG ATGTGGAACA CTGCCTGGAA GATTTCATGG  38940
CCTAATGCAA TAGCACTGAT GTTTAAAGAT AAAAACAAAC ATACTGGTAC TGTTATTTCA  39000
CAATTATAAA CAACTTCATT ATTGTGACCA AAAAAATTCA TTACAACTCA CCAAGGAAAA  39060
CACTCAATTC TAATACTTTA CTCCTGTCCT CAAGGGCTTC GCAATACAGA GGGACAGCTT  39120
TGGAGCTGAG CTGTCCTCTG AAAAGCCAGT AGGAGTAGAT GAAGGTTCAG ACTGGAGTGA  39180
CGGGGATGGA GACTAGAGCG ATGGGGATGA AGGGTCATAC AGACTAATGA GCCTCTTTCA  39240
GTTTTCCTTA CATAGATATT TTAACTTTCT CAGAGAACAT TTATTAAAAT AAAAGATGAA  39300
TTTCCAGTGA AAGGTCCAGG ATCCATGTGC TAGAAGGCTT ACTAGAAACT GTGATGAATG  39360
AGGTCTGTAA ATCAAAAGGA AACCTTGAAA GTTATCAGTG GAACTCTCTT GTCCAGGGCA  39420
TGATTAGGAA GAATGCAGGC ATTTGGGGGA GCAAAATAAT AAAATTAACA GTATAATTTT  39480
AGATATTCTT GTGATTTTTC CATTGGCAGG AATCACCTTA TTGAGATTCA TGATGAAAAG  39540
TTCCGGTTAT ATAAATTAAA GATGATGGTA AAGATGGAAA AATACCTTCA CTCCAGTCAG  39600
TGTAGGCGAC GGTATGTATT ACCTGCTTTT TCCAATTGGA AGCATAGGTC TTTAGCTGGT  39660
ACTTTTTTTG TTGTTTGTTT TTTTGAGACA GGGTTTCTCT GTGTAGCCCT GGCTGTCCTG  39720
GAACTCACTC TGTAGACCAG GCTGGCCTCG AACTCAGAAA TCTGCCTACC TCTGCCTCCT  39780
GAGTGCTGGG ATTAAAGGCG TGTGCCACCA CTGCCCGGCT AGATGGTACT TTTTTTTTTT  39840
TAAAGTTAAT TAAAAGTGTT TTTAAAGAAT GTTTGCTGTA TACATGCTGA ACTTTAGGGC  39900
```

-continued

```
AGGCTTATTT CTGTTTAAAT AAATTAATAT GAAATAATGC TGAGACAAGT AAATACAGTA  39960
GTGGTACTAT CGTGTCATTT TGGGTGGTGG GTGTAGTATG TCTATATTTG TTCTTTAATT  40020
TAAGATTTTC CCTTCATCAG AATCATCTTG TCCCATTTTG AGGACAAATG TCTGCAGAAG  40080
GCCTCCTTGG ACATTATGGG AACTGAAAAA TGCTGTGATA ATTGCAGGCC CAGGTAAAAA  40140
TATCTTCCTG ACGAACCTTC TAGAAACTGT CGATTCTCTT TCTGTTCAAC TCCTGCTTCA  40200
TTAAATTTTT GTTTAATATA AGTATTTTAG GTTTTGTTTT GTTTTGTTTT GTTTTGTTTT  40260
TTTCGAGACA GGGTTTCTCT GTATAGCCCT GGCTGTCCTG GAACTCATTT TGTAGACCAG  40320
GCTGGCCTCG AACTCAGAAA TCCACCTGCC TCTGCCTCCC GAGTGCTGGG ATTAAAGACA  40380
TGCTATTTTA GTTTTTTTAA ATGACATAGT TACTTTATTT AAAATAAAAC AAAGTGAAGA  40440
GGTTTACTTT TATACAATAA AGTCTTAAAA CGGTAGGCCT AGTTAGTCAA TAGTTGCGTT  40500
TCAATATGAT TAGCCTAAAA ATACTCATTA AAGGCATAAT TTATCAAAAT TGATTTGAAA  40560
GGCATTCTAC TTGATGTTTA CCATAAGGGC AAGTACAATT ATGTAGATAG TTTTAAAAAA  40620
TGAAATAGAA AACACTGCAA AAACACTAGC CAAAAGAAAC CGTACGTTAC TGTTTTAGTA  40680
TTTAGTGGTA TGGACTTTGG AGCAAAGCAT GCTATCAGGG ATGAATCAAG ACACCGACCA  40740
GTGTGAAGTA TCAGCGTTCT GCAGAGAAGT GGCACCAAGG AGAGAGCAAG AGGGGCAGGA  40800
GAGGTGTGGG ATGGAAAGAA CAGGACAGAG GTGACAGGCA TCAGTGAGGT GGCAAATCTT  40860
AAAACTTGTA GCCAAGTTTT GGTCTGAACC CTGCGTCAGG CACACGCTAA TGTTAGTGTT  40920
GAAACAAAGT TTATTGCCCA GCAAGCTTGT TTGTATTAAG GCTTTCAACC CAAAGAGGGT  40980
AGTTATTGGG CATGATTTCC ATTGTTGAAG TCGTCTCATC ATAAGTAATA TTCACATCTA  41040
CAAAATACAT TTGCTGTGGC ATCTAAATTA TTTTCTGATC AAACAACAGC CCCACTTTGA  41100
CATGCAAGCT ATACAGCCCA GAAGACATAA TCCCAAGTGG GCACATAAGA ACCTGCACAT  41160
AAGAACCTGC ACATAAGTAC CACAGAAGCA GAAGGCGGGG GGATCAGAAA CCCACGTGTA  41220
TTAGGTGACG TCGGCGTCTG CTTACAAGGC AGTGGAATTA ATGGACAAGA ATGAGTAGGG  41280
CTGCGGGGAG CGATGGGCGT GTCTGCAATG GCAAATTCAG AGGTTCAGAC GGGAGATCAA  41340
GAGACTGAGA CCAGCCTGTG ATGCAAGTGA TCTCAAAAAG AACCCAGGTC CCATAGTGAG  41400
ACTGTGTCTC AAGATCCCGA GAACAAAAGC AAGCGTAAGA CTCAACAGCA AGCATGACCC  41460
ACCCCAAAGC CCCCAAACAG CCCCCTACCC CCACCCCACT GACTCTATGA GGAGATGAAG  41520
GAATGAAGAG GGTGTCAGCA AACCAGTTCT AATTAATTTC TTGAAAGCAT TTCAGCCACT  41580
TGTTCCAATG GCGGCTTATA CACACATGTT TACATAAAGC TAACCTTGAC AAATGAGGAA  41640
CTATTCGATT TGGATCAAGT ATGCTTTTTG CTTTAATGGC ATCAATCTAG AAAGCAGCAG  41700
TGGGAAGAAA AGAGAAATCT CCAAACCCTT AGAAACCGTA CCTCCAAATA ATCTTACAGC  41760
CACTCAGAAA ATGATCTGAA CCGACGAAGA AGAATATGAA GTACCTGGGA TACAGCTAGA  41820
ATGACTCTGC AAAGATAATT TATAGTGTTA ATACAACATG GAAGAGCACA GGCTTCAGAC  41880
ACATAACTAG CATTCACTTT AAGAAACGGG CAGAGCCGGG CGTGGTGGCA CAAAACAAAC  41940
AAACAAACAA ACAAACAAAA AACAAAAAAC AAAAACAAAA AAGAAATGGG CAAATATGAG  42000
GAAGATGAAC AGGAAGGGAG TTAAAAAGAG AAGTGCGTAG ATCAATGCCG TAGACGACAA  42060
AGCCAATAGA GGGGAGTCGG CGAGCTCACA GGCTTCATAT TTTCCAAGAC TGGTGGGGAA  42120
AGGGGAGGAC AGTACCAATA TCAAAATGAA GGAATTTCAC TGCAGACCCC ATGAATGCTC  42180
TGAACAAGCC AGGTTACTGG AAATGCAGTA AAACTGATCT AATAGACCAG TTTCTTAGTG  42240
```

-continued

```
GGCTCTAATT GACAGTGCTC AGGCATGGTG AAACTTAGGA AGAATACTCC TCTAACTGTT  42300
ATAAGGATTG AGTTCTTCCT TAAAAAACCT CTGAAAAGAG AACTCTCTAG CCCACCTGGC  42360
TTTAGTGACA AATTCCAGCA CCAGAAGAGG ACATCAAACT CATTACAGAT GGTTGTGAGT  42420
CACCATGTGG TTGCTGGGAT TTGAACTCAG GACCTTCAGA AGAGCTGTCA GTGCTGAACC  42480
ACTGAGCCAT CTCGCCAGCC CTCCAGCAAA CATTTAAATG AGGAGATATC CCTGCTTCTG  42540
TAGTGTGGCT GCACATGCAC ACTCTCTGAA AGGCAGAGCT GTAGGGAAGA TCAGCCGCTG  42600
GCAGAGGTTA AAGGCAGGCA GAATAGATCT GAGAGCAGGG CATTCAGTGG GTCTTGAGTG  42660
TGACGAAGGT TCGATGGGTC TGCTTATAGG GATATGTACG CTTTATTATA CTGTAAATAA  42720
AATAAGTATA AGTGGTGCCT CTTTGAGTTA ATCGTGTCTC TAGGTACAGT AGCTGTATGC  42780
CAGAAGCAGC GCTGTTAGAG ATAGAAATCT AAAGATGTTT GGAAATTAGT GATAACCACA  42840
ATAACATATA TTTAAGGTGG TAAGATAATA TGTATAGGTC ATACTTCATG GGAACTTGAT  42900
AACTTTAAAT TCTCTGAAGA AAGTCACCTG AGCATCCTAC TAAAGAGGTA AATGGGAGAA  42960
TAAACCTAAG GCAGGGGATT TCTTCTTTAA ATCAAAACAT AATGGCTTTA ACTGGAATAC  43020
TGACTGCATT CTTATTGCTA CTTTAAAGAT ATATGTGATG TGGAAAGTAG TTGAATTTCG  43080
TAATTGAATA TATTAGTTGA TAGTCTCTAA GGACTTCTTT TGTTCTCAAG CTAAAAAAAA  43140
AATCCTCATT TACACCAATG ATAATTTTAC ATCTACTTGG AGGATGACTA AGGAATTTAA  43200
CTGCTGAATG TACCAGCAGG ACAAGCTTAT AGGCTCGGTG CTCTGTTGTA AAATTATTAG  43260
GGTTCAAGCT AACATGTTAC TGCATAGCAG CTTTTTACTT AAAACCAATT TTACCCTTCC  43320
TGGTGTAACG TAGCACAAGC TTCCGTATTT ATATAACTGA TCGTGTGGAG CTGCCCTAGC  43380
CGGGATGCTT TCCTTGAGCC TGGCATCTTC CCAGCGCCTC CATAACATTT AGCTTCTGGG  43440
TGCCACAAGA AAGCGCTGTC TGTAGTGCCG TATTTGTTAT TTGTGTCTCA TACGCATAGA  43500
TCACACACAT GCCCTTGATT GTAATAAGCT TTATGTGTAG AGTTGGAAGT GTCAGACACA  43560
TTTGAGAATT TTTTTTTTTA CGTGGTCTAT GTTTGTATCT TTCTATTTCT AAGGGAGCAT  43620
GCTTTTGTCA GTGTTTTCTT AGGCTGTTCT TACTTTCCTT CAGGCTGAAT CATTGCCTTA  43680
CTGCTAACAA CTCAGAGGAC GCATCCCAAG ACTTTGGGCC ACAAGCATTC CAGCTACTGT  43740
CTGCTGTGGA CATCCTGCAG GAGAAATTTG GAATTGGGAT TCCGATCTTA TTTCTCCGAG  43800
GATCTGTGAG TGTATCTGTG ATAGCTCCTG GGACTGTTTC TGACAGTGCT TTCCACTGTG  43860
TGGCTATGGC TTTGGCTTTC TTTAGATGGC TAACTAGCAA CCCGTGTTAG CAACACCTTG  43920
AGTTCCATCC TAACCCTGCA TTCATTGTCT TGGACAAATC TTGTCTCACG TCAGACGCTG  43980
TTTTGCTATG TTGGATGCTG GCGGTCAGCT GTGTGCTGCA GTCTGAAAAT AGCCTATTCG  44040
TTTACCACAC TGCAATTGCA TTAATCCCTA GACTGGTTTT TCTTAGGATA ATTAGGGAAA  44100
GTTAACTCCC AGTGTGTCAA GGGACTGGTA GAACAAAGTT GCAGCTTCTG GTGCCCAGAT  44160
ACGATTATGT TCTTTGCGCA AAACTTGAAT TTCAGGGATT ATGTTGTCAG AGGCTGGGTT  44220
CAGCAACAGT GTACAGCAAC ATAGTCTCCC TCCGATGGTG TTTTATGTCA GAAGTACTTA  44280
ACATGCTAAG AAAGGGCTTT TGCTTGTTTT AGTGGTTTAC CAGTGAATAC CTGATTTAAC  44340
TGGACTCCTT TCTGTTTTGA GTGATTCATG TGGCCTCATT ATGCTGCCAA ATGTCACTTA  44400
CAAAGTGACA ATAATAAGGT ACAAATACAC ATACAGAGCT GGTTTTCTGT AGTCCTTCTG  44460
CTTTTATGAT AATTTTATTT CTGAATTAAG AGTCTGTAAA TTTAAGAATT GTATATTAAT  44520
ATCACTTAAA TAAACCAAGA GTAGAAGAAG GCAGAGTACT TTGTAGATGG ATCTATCTGC  44580
TTATTTAAAA CATGCTTTAG AGTAGAGGCT AAATGTTCAT TTTGTATATA GAATTTTAAA  44640
```

-continued

ATAATTTAGG TAAGCTTTTG CTGCTTAAAT ACTCAAGAGC TTCATGTAAA TGCATTTGCT 44700
TGTGCTTGCT TGTGCTTAGA AAGTAATCTA TGGAGTTAGT TATGAAATAT TTTTAATGAA 44760
ACACATTGAA AACTTGTACT ATCCTTTCAA GTGTCAGTGC TTTCAAGATA ATAGAGTTTA 44820
AATTTTTGGT TTTAAATGGC AAAAAAGCAT ATAAATGTAA CAATAGAAGT GTTACTTAAG 44880
CAGTTTTTAT TTCTATCAGC TCTGCAAGAA ATCTCAAATG CCACTGAAAT CCGTACATTC 44940
GTTTTCTATC TTTGTCACCT TTAAAATCCC TGTAGCCAGT GTGAGTATTT AATTTATGAA 45000
AAGTGTCCTT GTTTTGGTTT GGTGCGATCT AGCTGTATCC AATATCAATA AATAAGTTTG 45060
TTTCTCGTCA AACTTTCAGT GGTCACAGGA GGGATCAGGT TTCACTTATT ATTTGAAAAC 45120
CAAGTCAGAC GTCCTCTACC GGCAGTGTCT TCTGGGAGTC CTCAAATTAA GCAGTTCATC 45180
CTTAGTGAAA CTTTATACTA CCCTTGCTAG CGCAACGTGT AAAGCTTTTA AAAAGTATCA 45240
CTTAATGAAA ATGTGTAGAT GCTAACAATA GTGAAAATAA GACAGGCTTC CTTTCTCTGC 45300
TTTCAGTGAC TTTGATATCT ATTGGGATAT CGGTGAAAAA GTATGACTGT AATTCTCTTG 45360
AGAACTGAGC AAGTTGTTCC CCTTAACCAA TTTAGGACAA GCTAATACCT TTGTAATTTT 45420
AATTTGTAAG ATGATATATC AAACTGTCTT GGAGTTATTT TGAAGAGATA ATTTTTATAA 45480
GCATAAATTC GGTTTTGGTA GTGCTTGATT CTCTCCTACA TGTTTTTTTA ATATTATAAA 45540
CACTTAATTT ATCCATAAAT TTGTTAAATT TAGTTTAAAA ATTTGTTTTA ATGTGTCTAA 45600
TTAGAAAGTA ACCAAGATTG TCTAGAGAAC TTTGTTTTAA CTGACTAAAC AGTTCACCAT 45660
GTTCAGCAAT CTTTGACATT GCTCAAACGT GTCATAACAT AATCAATAGC CATAATTTAA 45720
GGGAAAAAAA CCACATTGAT CATTTGCATA CCAAGATTAG CATCTTCCCA AATGCCTTAT 45780
CCAAGTGCTA ATCTTTATCA TGGCCTCAGG AGTAGGTACC ACTTAATATT TTAGGATGTG 45840
TGTATATGCA CGTGTTCAGG TGCTCTCACA TCTGTGTGTG CATATGAACA CCAGAGGTGG 45900
ACATTGGATG TCTCCCTCTG GTACCCTCCA TTTCATTCGT ACTCTTTTGA CCCAGTTTGT 45960
CACCGAACCA GGAGCTCAGT GTCTTGGTTA GACTGGCTTG CCATTAGTCC CTGACATTCT 46020
CCTGCCTCCG TTTCCTGCCA GCCAGCTGAC ACTGTAGTAA CAGCACCCAG CTTGTCTTCT 46080
TAAATTATAG TTTACTGGCG TTTCAAGAAC ATCATAACGG ATGCAGTGTA TTTTGGTTAT 46140
AATCAACCTC AGTATTCTCC CAGCTCTTCC CAGACTGATC CCACTGCCTC TTCACCAATC 46200
CCAACTTTAT GACCTCCCCC GCCCAACTTC CCCAGCCATG GGTATGGGCA TCTGTTAGAA 46260
TGTGGTCAAC CTATCAGGAG CTATGCCCGT AAAGAATGAC GATCTCCCTG AAGAGCCGTC 46320
AGCTGTGAAT AGTTGTTCCC CAGGAGCTCC TGAACCCTTT TCTCCATCCC TTGATGAAAA 46380
TTTTGCTAAC TTGGTTCTGT GCAGGCAGCC ACAGATGCTG TGGGTTAACG GGTGCAGTGG 46440
TCTGTCATGC CCAAAAGACA CTGTTTGGTT CTGGTTCTAC ATGACCTCTG GCTCTAACAA 46500
TCTCCTTTTG GGACGAACCC TGAGCCTTGA GGGAAAGGAG TGTGACCCAG ATCTCCCATT 46560
TGTAGATGAA CACTCTATAT AGACAATATC CTCTGTGCTG TGCTTTGACC AGATGTGAGA 46620
TTCTGCGTTA ACCGCCATCC ACTGCACAAA GAACCTTCTC TGATGAGGCT TGAGAGTGGG 46680
ACCAATCTAT GGCTATAGGA ACAGGAACTT AGAGACAAGT ATAATTCTAT GTCAGTTTAG 46740
CAAAATAATA GTAAGAAATA TACTGCTGGG GCCGTGAGCT CCTTGACCAA ATGTTCTGGC 46800
CAGATTTACA GCATCCTGTA TGGAATGGGT GTGGGAACGG TAGGGAGAGG ATGGTACTTC 46860
TTAAATCCTG TCAGAAAGTG CTATGATATT GAGGCCACTT TTGCACCCAT GGGCATATCT 46920
GCCATGCTGG TTGTCATTTT AGTGTACAGG GTTAATAACT GGAGGAGAAA TTGACTTTTT 46980

```
CTTCCCCAGT AGCCTGCATA GCACCTTCTG GTATTGTGAA AGCTAGCCAG CAGAAAGGAA    47040

ACTTCTGGGC CAGGACCAGC GTGATTTCTC CATGTTCTAT GGCCAAAGCA GGTGGTGTCT    47100

TCAGCAATAC AGCCTTACCA CTAAGTTCTG ATGAGAAACC AAGAACAGTA GCGGTGACCT    47160

GTATTATTTG AGGTGGGGCA TCTGTAGGAA AAACTGAGCA ACAGTTTGAG AGGAGGTATC    47220

TCACACTGGA CTATTTGTTT GGTGACCTGT GGCTTCCTTG AGTAACATTA GCTTTTATGT    47280

AGCCTGATTC CAATTAAACT CTTATATAAG TGTGTGTGAG TTTAGGAAGC TTATAAATAG    47340

TAAGTTTCCA TATGGGTTTT AATTTTTTTT TAATTTTATT TTGTGATTTT ACTAATTCGC    47400

TTTACATCCC GCTCACTGCC CTACTCCTGG TCACTCCCTC CCACAATCCT TTCCTTATCC    47460

CTCCTCCCCC CTTCTCCTCT GAGAAGTTGG GCCCCCCTGG GTATCCCTCC ACCCTGGCAC    47520

TTCAAGTCTA TGCGAGGATA GGGTCTTCCT CTCCAATTGA GGCCAGACAA GGTAGCCCAG    47580

CTAGTAGAAC ATATCCCACG TACGGGCAAC AGCTTTGGGA TAGCCCCCAC TCCAGTTGTT    47640

TGGGACCCAC ATGAAGACCA AGCTGGACAC CTGCTACATA TGTGTAAGGA AACCTAGCTC    47700

CATATGTTCT TTGGTTCGTG GTACAGTTTC TGAGAGCTCC AAGGGTCAGG TTAGTTGGCT    47760

CTGTTGGTTT TCCTGTGGAG TTCTATCCCT TTCTGGGCTG CAATCCGTCT TCCTAGTTTT    47820

CCAAGAGTCC CCAAGCTCCA TTCACTGTTT GGCTGTGGGT GTCTGCATCT GTCTAAGTCA    47880

GCTGCTGTGT GGAGCCTCTC AAAAGACAAC ATGCTCCTGT CTGCAAGCAT AACAGAATAT    47940

CATTAATAGT GTCAAGGATT GGTGCTTGCC CATGGGATGG GTCTCAAGTT GGACCGGTTA    48000

TTGGTTGGCC ATTCCCTCAG TCTCTGCTCC CTCCCCTGTG CCTATATTAC TTGTAGACAG    48060

GATAAATTTT GGGTTGATAA TTTTGTGGGT GGGTCAGTGT CTTTATTGCT CTACTTGGGT    48120

TGCTGCCTGG CTACAGGAGG TGGCCTCTTC AAGTTCCATA TCCCCAGTGT AGTAAGTCAC    48180

AGCTAAGGTC ACACCTATTA ATCCTTGGAT GCCTCCCTTA TCCCAGGTTT CTGTCTCATC    48240

CTGTAAATGC CACCCACTTC CCCACTTTTC CTCTGCAGAT TTCCATTCAT TCTCATTACA    48300

TCTAGCTCTC TCCCTGCCCT TCCCTACACC CAATCCTGAA CTCCCATCTC CCTCCGCATC    48360

CCCCGTCCTA GTTCCCTCTT TCCATGTGCC TCTTATAACT ATTTTATTCC CACTTCTAAA    48420

TGAGATTCAA GCATCCTTCT GCCTTCCTTC TTGTTTAGCT TCTTTGGGTC TATGGAGTGT    48480

ACCATGGTAC TTGTATGTTT TGGCTAATGT CCGCTTATAA GTAAGTACAT ATCATGCATC    48540

TCCTTTTGGG GTTGGGTCAC CTCACTCAGG ATGATATTCT CAAGTTCCAG CCATTGGCTT    48600

GCAAAATTCA TGATGTCTTT CTTTTTAATA GCGGAATGGT ATTCCATTCT GTAGATGTAT    48660

CACATTTTAT CCATTCTTCA GTTGAGGGAC AGCTAGGTTG TTTCCAGCTT CTGGCTATTA    48720

TGAATAAAGC TTTAGGAACA TAGTTGGGTA TGTGTCTTTA TGGGATGTTG GAGCATCTTT    48780

TGGGTATGTG CCCAGGAATG GTATAGCTGG GTCTTGAGGT AGGACTATTC CCAGTTTTCT    48840

GAGAAACTGC CAAAGTTTCA AGTGGTTGTA TAAGTTCCCC TCACTCCACA CCCTTGCCAG    48900

CCTGTGTTAT CTTTTGAGTT TTTGATCTTA GCTATTCTGA TGGGTATAAG ATGGAACATC    48960

AATGTTGTTT TGATTTGCAT TTCCCTCATG ACTAAGGACT TTGAACATTT CTCTAAGTGC    49020

CTTTCAGCCA TTTGAGAGTC CTCTTTTGAG AATTCTCTGT TTAGCTCTGT TTCCCATTTT    49080

TAAATTGGGT TATTTGGGTC ATTGTTGTCC AACTTCTTGA ATTCTTCGTA AATTTTAGAT    49140

ATTTGCCTTC TGTCCGATGT AGGATTGGTG AAGATTCTTT TCCAATCTGA AGATTGCCTT    49200

CTTGTCCTAT TGACAGTGTC CTTTGCCTTA CAGAAGCTTT GCAATTTCTT GGGGTCCTAT    49260

TTATCAGTTG TTGATCTTAG AGCCTGAGCC ATTGGTGTTC TGTTCAGGAA CTTGTCTTCT    49320

GTACCAATGC ATTCAAGGTA TTTCCCTCTT TCTCTTCTAT GATATTTAGT GTATATAGTT    49380
```

-continued

```
TTAAGTCGAG GTCTTTCATC CACTTGGACT TGACTCTTTT AATAAATGTG TGTGTGTGTG  49440
TATGTGTGTG TTTAGGAAGC TTATAAATAG TAAATTTCCA TGTGTTTTTT TTAAACTTTT  49500
TTTTTTACCT CTCTCTCTCT CCCTACCTCT CCACTCTGCC CTCGCATCCC ACTCTACACC  49560
TTAAACCTCT TCCCCCTTTA TATCACATAT TGTTCCAGTA TCCCCGTCAT AATGTTTTTT  49620
TCTTTCACCT ACCTCTACCA ATAAATGGTC CCTTTCTAGT TTCTTGGATT CTTCAGGCAC  49680
TCCAAGTTAA ACACACTATG TGAAACATTC AATGGTAGGA TCACATGTGC GAACATGTGA  49740
TGATGTTTGT CCTTCTGGGT CTGGGTTCCC TGAATCACTA TTGTTCCCCA GCTCCATCAG  49800
TTTCCCTGCA AATTGTTATG ATTGTAGTTT TCTTTATAGC CAAATAAAAC GGCATTGTGT  49860
ATAGGTGGTC CCACACTTTC GTGATCTATT TTGTAATTTA ATGGCTGTTT TCATGTCCTA  49920
GCAGTCATGA ACATAGCAGC TAGACCATGG CTGAGCATGC ATCTCTCTGG TAGGAAATAG  49980
AGGCCTTTGG TTATATACCC AGGGGTGATT TATGTGGGCC ATCGGATTCA TCATTTTAGC  50040
TGTTTGAGGA TTCTCTTTAC TGATTTCGAA GGAGCTGCAC CAGCTTTCTG TCTCACCAAC  50100
GGTGCACAGG GGTTCCCCAG ATCATCACCT GCATTTCTTG TCTTTTATGT TTTTTAATCT  50160
TATCCTCGAA GTAGTTTCAA CTTGAGTTAA GGATGGTAAA CTCTCCTGAA AGCATTTCAT  50220
TTCCTAGGCA CCTGCATTTC TTCTTCTGCA ACTTCTGTTT CATTCTATAA CTCACTTTTT  50280
GTTTTTAGTT TTTTCAACTC TTTTTTGTAT TCTGTAGACT AACCCTCTGT CAGATGTGTA  50340
GCTGGAATTA TACTCTAGGC TGCTCCTTTG GTCATGTAAT GGTTTCTTTC TTAGTAGCAC  50400
CTTTTCATTT ATAAAATTCT ATTTGTTGAT TAGTGGTCAT ATTTTGTAGA TGACAGGGCT  50460
CCTTTTCAGA GTCCTTACCT GAGCTGGTAT ACTGAGGCAT ACTTCACATT CTTCTGGGAG  50520
TTTCAGATCT AGCATTGAAA CCTTTGATTT CATTTGGAAT TTATTTGCCA TATCTTACAG  50580
GTCCTGGGGA TCCAATCTCA GGTGCTTATA TTTAGACATA GAGCCCTTTG TCTCATGAGC  50640
TATCTCCCCA ACCCAGATAA TGCTTTTAAG AAAAGATTGG ACCTATTCAG CTGTTAGAAC  50700
TGTTGATAGA TTTGTGTGTG TATGTGTGTG TGTGTGTGTG TGTGTGTGTG TGTACATGTG  50760
TGTACCTATA TGCACACATC TGTATGTATC TATTTTAAAG ACAAGATCAT GCCTAGGTTG  50820
ACTCTCACTC AACTGGAAAT TCTCCTGTCT AAGCCTCCTG ATTACAGCAG TAGGATTACA  50880
GGCATGTACT ACTATAGTCA ACGGCAATTG CTGTAGTTCT AATCACTCTC CAAAGTTATA  50940
AGAACATGTA GCTGGGGTGG GCTATTTCGT TTAATTTTCT AGACAAATAT TGAGTCTGAT  51000
AGAAATATAT TACTATGGGT TAGGTCTGCT TTTCAGGACT AAAGAACTTG GCTAAATGCA  51060
CAAGGCACTT GGTTCATGAA GAATTACCTA TTGAACCCCT GAAATGGCAG CTGGGACTAT  51120
CTCTGGACTA TAGGAGCTGG AAAGGGGCAG GGCTGGTGGG AGGAGAAGGT GGAGAGGGTA  51180
GCTAGGAACT TAAATGTCTT TGAGCTATTG AGCATCTGTT TTTATGTAAG GCATGACATT  51240
GATTTTGTAG AGGATACAC                                               51259
```

ANTIBODIES AGAINST GENE PRODUCTS RELATED TO WERNER'S SYNDROME

CROSS-REFERENCES TO RELATED APPLICATIONS

This application is a divisional of U.S. application Ser. No. 09/618,166, filed Jul. 17, 2000, now U.S. Pat. No. 6,583,112, now allowed; which is a continuation of U.S. application Ser. No. 08/781,891, filed Dec. 27, 1996, now issued as U.S. Pat. No. 6,090,620; which is a continuation-in-part of U.S. application Ser. No. 08/632,175, filed Apr. 12, 1996, now abandoned; which is a continuation-in-part of U.S. application Ser. No. 08/594,242, filed Jan. 30, 1996, now abandoned; which is a continuation-in-part of U.S. application Ser. No. 08/580,539, filed Dec. 29, 1995, now abandoned; which application claims priority from U.S. application Ser. No. 60/009,409, filed Dec. 29, 1995 and U.S. application Ser. No. 60/010,835, filed Jan. 30, 1996, all of which applications are incorporated herein by reference in their entireties.

BACKGROUND OF THE INVENTION

1. Field of the Invention

The present invention relates generally to Werner's Syndrome and more specifically to methods and compositions suitable for use in diagnosis and treatment of Werner's Syndrome.

2. Description of the Related Art

Werner Syndrome (WS) is an autosomal recessive disorder with a complex phenotype. The disorder manifests itself in premature occurrence of age-related diseases and premature appearance of some of the physical features of normal aging. The onset of symptoms usually occurs after adolescence. The disorder progresses throughout life and typically patients have a shortened life expectancy with a modal age of death at 47. The prevalence of Werner Syndrome is estimated for heterozygotes to be 1-5 per 1,000 individuals, and for homozygotes to be 1-22 per 1,000,000 individuals.

Clinical symptoms of Werner Syndrome include both a prevalence of age-related diseases and physical features of aging. Such diseases include arteriosclerosis and heart disease, both benign and malignant neoplasms (usually sarcomas), diabetes mellitus, osteoporosis, and ocular cataracts. The physical appearance of WS patients is often manifest as a short stature, premature graying or loss of hair, hypogonadism, altered skin pigmentation, hyperkeratosis, tight skin, bird-like facies, cutaneous atrophy, cutaneous leg ulcers, and telangiectasia. Most of these diseases and features are present in from 40-90% of WS patients. Diagnosis of WS relies mainly upon the appearance of a certain number of these diseases and features. One biochemical test, excessive excretion of hyaluronic acid in urine, may also be used to assist diagnosis.

In addition to the noted signs and symptoms of aging, Werner Syndrome mimics normal aging as evidenced by the replicative potential of fibroblasts isolated from WS subjects. Replication potential of fibroblasts is reduced in these patients compared to fibroblasts isolated from age-matched controls, and is comparable to the replicative potential of fibroblasts taken from elderly subjects. Moreover, an increased mutation rate has been described in WS patients. Such abnormality is manifest as chromosomal instability, such as inversions, reciprocal translocations, deletions, and pseudodiploidy, and as increased mutation rate at the hypoxanthine phosphoribosyl transferase (HPRT) gene.

Werner Syndrome has been recognized as an autosomal recessive disorder. Goto et al. (Goto et al., *Nature* 355:735-738, 1992) mapped the WS gene onto the short arm of chromosome 8, using 21 affected Japanese families. The gene is located between marker D8S87 and ankyrin (ANK1). More recently, more refined mapping has pinpointed the WS gene to a region between marker D8S131 and D8S87, an 8.3 cM interval. Identification of the gene and gene product should add considerably to understanding the basis of Werner Syndrome and enable biochemical and genetic approaches to diagnosis and treatment.

The present invention provides a novel, previously unidentified gene for Werner Syndrome and compositions for diagnosis and treatment of WS, and further provides other related advantages.

BRIEF SUMMARY OF THE INVENTION

Briefly stated, the present invention provides isolated nucleic acid molecules encoding the WRN gene, as well as portions thereof, representative of which are provided in the Figures. The protein which is encoded by the WRN gene is referred to hereinafter as the "WRN protein". Within other embodiments, nucleic acid molecules are provided which encode a mutant WRN gene product that increases the probability of Werner's Syndrome (in a statistically significant manner). Representative illustrations of such mutants are provided in Example 3.

Within other aspects of the present invention, isolated nucleic acid molecules are provided, selected from the group consisting of (a) an isolated nucleic acid molecule as set forth in the Figures, or complementary sequence thereof, (b) an isolated nucleic acid molecule that specifically hybridizes to the nucleic acid molecule of (a) under conditions of high stringency, and (c) an isolated nucleic acid that encodes a WRN gene product (WRN protein). As utilized herein, it should be understood that a nucleic acid molecule hybridizes "specifically" to an WRN gene (or related sequence) if it hybridizes detectably to such a sequence, but does not significantly or detectably hybridize to the Bloom's Syndrome gene (Ellis et al., *Cell* 83:655-666, 1995).

Within other aspects, expression vectors are provided comprising a promoter operably linked to one of the nucleic acid molecule described above. Representative examples of suitable promoters include tissue-specific promoters, as well as promoters such as the CMV I-E promoter, SV40 early promoter and MuLV LTR. Within related aspects, viral vectors are provided that are capable of directing the expression of a nucleic acid molecule as described above. Representative examples of such viral vectors include herpes simplex viral vectors, adenoviral vectors, adenovirus-associated viral vectors and retroviral vectors. Also provided are host cells (e.g., human, dog, monkey, rat or mouse cells) which carry the above-described vectors.

Within other aspects of the present invention, isolated proteins or polypeptides are provided comprising a WRN gene product, as well as peptides of greater than 12, 13 or 20 amino acids. Within another embodiment, the protein is a mutant WRN gene product that increases the probability of Werner's Syndrome.

Within yet another aspect of the present invention, methods of treating or preventing Werner's Syndrome are provided (as well as for related diseases which are discussed in more detail below), comprising the step of administering to a patient a vector containing or expressing a nucleic acid molecule as described above, thereby reducing the likelihood or delaying the onset of Werner's Syndrome (or the related disease) in the patient. Within a related aspect, methods of treating or preventing Werner's Syndrome (and related diseases) are provided, comprising the step of administering to a patient a protein as described above, thereby reducing the likelihood or delaying the onset of Werner's Syndrome (or a related disease) in the patient. Within certain embodiments, the above methods may be accomplished by in vivo administration.

Also provided by the present invention are pharmaceutical compositions comprising a nucleic acid molecule, vector, host cell, protein, or antibody as described above, along with a pharmaceutically acceptable carrier or diluent.

Within other aspects of the present invention, antibodies are provided which specifically bind to an WRN protein or to unique peptides derived therefrom. As utilized herein, it should be understood that an antibody is specific for an WRN protein (or peptide) if it binds detectably, and with a $K_d$ of $10^{-7}$M or less (e.g., $10^{-8}$M, $10^{-9}$M, etc.), but does not bind detectably (or with an affinity of greater than $10^{-7}$M, (e.g., $10^{-6}$M, $10^{-5}$M, etc.) to an unrelated helicase (e.g., the Bloom's Syndrome gene, supra). Also provided are hybridomas which are capable of producing such antibodies.

Within other aspects of the present invention, nucleic acid probes are provided which are capable of specifically hybridizing (as defined below) to an WRN gene under conditions of high stringency. Within one related aspect, such probes comprise at least a portion of the nucleotide sequence shown in the Figures, or its complementary sequence, the probe being capable of specifically hybridizing to a mutant WRN gene under conditions of high stringency. Representative probes of the present invention are generally at least 12 nucleotide bases in length, although they may be 14, 16, 18 bases or longer. Also provided are primer pairs capable of specifically amplifying all or a portion of any of the nucleic acid molecules disclosed herein.

Within other aspects of the invention, methods are provided for diagnosing a patient having an increased likelihood of contracting Werner's Syndrome (or a related disease), comprising the steps of (a) obtaining from a patient a biological sample containing nucleic acid, (b) incubating the nucleic acid with a probe which is capable of specifically hybridizing to a mutant WRN gene under conditions and for time sufficient to allow hybridization to occur, and (c) detecting the presence of hybridized probe, and thereby determining that said patient has an increased likelihood of contracting Werner's Syndrome (or a related disease). Within another aspect, methods are provided comprising the steps of (a) obtaining from a patient a biological sample containing nucleic acid, (b) amplifying a selected nucleic acid sequence associated with a mutant WRN gene, and (c) detecting the presence of an amplified nucleic acid sequence, and thereby determining that the patient has an increased likelihood of contracting Werner's Syndrome (or a related disease). Suitable biological samples include nucleated cells obtained from the peripheral blood, from buccal swabs, or brain tissue.

Within another aspect, peptide vaccines are provided which comprise a portion of a mutant WRN gene product containing a mutation, in combination with a pharmaceutically acceptable carrier or diluent.

Within yet another aspect, transgenic animals are provided whose germ cells and somatic cells contain a WRN gene (or lack thereof, i.e., a "knockout") which is operably linked to a promoter effective for the expression of the gene, the gene being introduced into the animal, or an ancestor of the animal, at an embryonic stage. Within one embodiment, the animal is a mouse, rat or dog. Within other embodiments, the WRN gene is expressed from a vector as described above. Within yet another embodiment, the WRN gene encodes a mutant WRN gene product.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIGS. 2A and 2B are the DNA (SEQ ID No. 70) and predicted amino acid (SEQ ID No. 71) sequences of the WRN gene transcript. The one-letter amino acid code is used in FIG. 2B.

FIGS. 3A-3C are the DNA and predicted amino acid sequence of an alternate WRN gene transcript (SEQ ID Nos. 72 and 73).

FIGS. 4A-4G are an alignment of the WRN gene product (SEQ ID No. 74) with known helicases from *S. pombe* (SEQ ID No. 76), *E. coli* (SEQ ID No. 75), human (SEQ ID No. 77) and the Bloom's Syndrome gene "BLM" (SEQ ID No. 78).

FIGS. 5A-5U are the genomic DNA sequence of the region containing a WRN gene (SEQ ID No. 79).

FIG. 6 presents a cDNA sequence of the mouse WRN gene (SEQ ID Nos. 205 and 206).

FIG. 7 is a genomic DNA sequence of the mouse WRN gene (SEQ ID Nos. 207-209).

FIG. 10 shows the alignment of the mouse and human WRN gene products.

DETAILED DESCRIPTION OF THE INVENTION

Definitions

Figure 1:
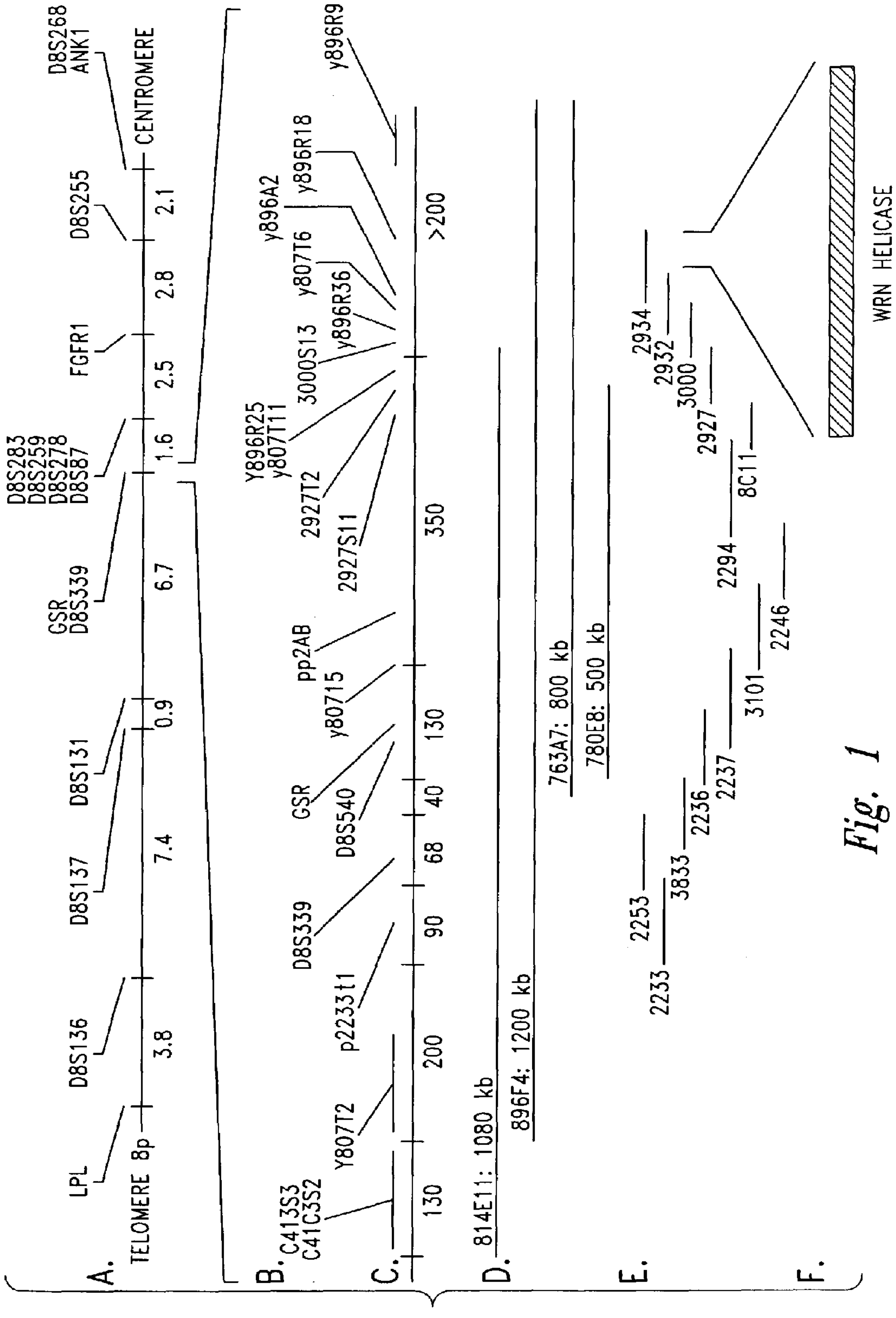
FIG. 1 is a genetic and physical map of the WRN region. The genetic map (A) of the region is sex-equal with distances given in cM. The polymorphic loci used (B) are di-nucleotide and tri-nucleotide repeat STRP loci. The physical map presented (C) has approximate distances determined from sizes of over-lapping non-chimeric YACs, and from genomic DNA sequence from overlapping P1 clones 2233, 2253, 3833, 2236, and 3101. Marker order was determined from the sequence-tagged site (STS) content of YACs, P1 clones, and cosmid clones and from genomic DNA sequence from P1 clones. The YACs presented (D) represent the minimal tiling and are the YACs used for cDNA selection experiments. The P1 and cosmid clones needed for the minimum tiling path are shown (E). Clones shown are P1 clones except for 8C11, which is a cosmid clone. Clone order was established by STS content.

Prior to setting forth the invention in detail, it may be helpful to an understanding thereof to set forth definitions of certain terms and to list and to define the abbreviations that will be used hereinafter.

"Genetic marker" is any segment of a chromosome that is distinguishably unique in the genome, and polymorphic in the population so as to provide information about the inheritance of linked DNA sequences, genes and/or other markers.

"Vector" refers to an assembly which is capable of directing the expression of a WRN gene, as well as any additional sequence(s) or gene(s) of interest. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Abbreviations: YAC, yeast artificial chromosome; EST, expressed sequence tag; PCR, polymerase chain reaction; RT-PCR, PCR process in which RNA is first transcribed into DNA at the first step using reverse transcriptase (RT); cDNA, any DNA made by copying an RNA sequence into DNA form.

As noted above, the present invention provides methods and compositions for the detection and treatment of Werner's Syndrome, as well as related diseases. These methods and compositions include a family of Werner's Syndrome-related genes, and the proteins encoded thereby, that have been implicated in the onset of Werner's Syndrome. These genes and proteins, including genetic markers, nucleic acid sequences and clones, are also useful in the creation of in vitro and animal models and screening tests useful for the study of Werner's Syndrome, including the possible identification of other genes implicated in Werner's Syndrome. The present invention also provides vector constructs, genetic markers, nucleic acid sequences, clones, diagnostic tests and compositions and methods for the identification of individuals likely to suffer from Werner's Syndrome.

Genes and Gene Products Related to Werner's Syndrome

The present invention provides isolated nucleic acid molecules comprising a portion of the gene which is implicated in the onset of WS. Briefly, as can be seen from FIG. 4, this gene encodes a protein that is similar in amino acid sequence to several known ATP-dependent DNA helicases (enzymes that unwind the DNA duplex). It is less similar to known RNA-DNA helicases. Helicases are involved in the replication of DNA, often binding the replication origin, and/or the replication complex. In addition, the single stranded DNA that is involved in recombination can be generated by DNA helicases.

Although various aspects of the WRN gene (or portions thereof) are shown in the Figures, it should be understood that within the context of the present invention, reference to one or more of these genes includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of the described genes and includes, for example, portions of the sequence or allelic variations of the sequences discussed above, or alternatively, encodes a helicase-like activity (Bjornson et al., *Biochem.* 3307:14306-14316, 1994); (b) the nucleotide sequence is capable of hybridization to nucleotide sequences of the present invention under high or very high stringency (see Sambrook et al., *Molecular Cloning: A Laboratory Manual*, 2nd ed., Cold Spring Harbor Laboratory Press, NY, 1989); or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent) while very high stringency means conditions of hybridization such that the nucleotide sequence is able to selectively hybridize to a single allele of the WS-related gene.

The WRN gene may be isolated from genomic DNA or cDNA. Genomic DNA libraries constructed in chromosomal vectors, such as YACs (yeast artificial chromosomes), bacteriophage vectors, such as λEMBL3, λgt10, cosmids, or plasmids are suitable for use. cDNA libraries constructed in bacteriophage vectors, plasmids, or others, are suitable for screening. Such libraries may be constructed using methods and techniques known in the art (see Sambrook et al., *Molecular Cloning: A Laboratory Manual*, Cold Spring Harbor Press, 1989) or purchased from commercial sources (e.g., Clontech, Palo Alto, Calif.). Within one embodiment, the WRN gene is isolated by PCR performed on genomic DNA, cDNA or DNA from libraries, or is isolated by probe hybridization of genomic DNA or cDNA libraries. Primers for PCR and probes for hybridization screening may be designed based on the DNA sequence of WRN presented herein. The DNA sequence of a portion of the WRN gene and the entire coding sequence is presented in the Figures. Primers for PCR should be derived from sequences in the 5' and 3' untranslated region in order to isolate a full-length cDNA. The primers should not have self-complementary sequences nor have complementary sequences at their 3' end (to prevent primer-dimer formation). Preferably, the primers have a GC content of about 50% and contain restriction sites. The primers are annealed to cDNA and sufficient cycles of PCR are performed to yield a product readily visualized by gel electrophoresis and staining. The amplified fragment is purified and inserted into a vector, such as λgt10 or pBS (M13+), and propagated. An oligonucleotide hybridization probe suitable for screening genomic or cDNA libraries may be designed based on the sequence provided herein. Preferably, the oligonucleotide is 20-30 bases long. Such an oligonucleotide may be synthesized by automated synthesis. The oligonucleotide may be conveniently labeled at the 5' end with a reporter molecule, such as a radionuclide, (e.g., $^{32}P$) or biotin. The library is plated as colonies or phage, depending upon the vector, and the recombinant DNA is transferred to nylon or nitrocellulose membranes. Following denaturation, neutralization, and fixation of the DNA to the membrane, the membranes are hybridized with the labeled probe. The membranes are washed and the reporter molecule detected. The hybridizing colonies or phage are isolated and propagated. Candidate clones or PCR amplified fragments may be verified as containing WRN DNA by any of various means. For example, the candidate clones may be hybridized with a second, nonoverlapping probe or subjected to DNA sequence analysis. In these ways, clones containing WRN gene, which are suitable for use in the present invention are isolated.

The structure of the proteins encoded by the nucleic acid molecules described herein may be predicted from the primary translation products using the hydrophobicity plot function of, for example, P/C Gene, Lasergen System, DNA STAR, Madison, Wis., or according to the methods described by Kyte and Doolittle (*J. Mol. Biol*. 157:105-132, 1982).

WRN proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the WRN proteins disclosed herein include conjugates of the proteins along with other proteins or polypeptides. This may be accomplished, for example, by the synthesis of N-terminal or C-terminal fusion proteins which may be added to facilitate purification or identification of WRN proteins (see U.S. Pat. No. 4,851,341; see also, Hopp et al., *Bio/Technology* 6:1204, 1988.) Alternatively, fusion proteins such as WRN protein-β-galactosidase or WRN protein-luciferase may be constructed in order to assist in the identification, expression, and analysis of WRN proteins.

WRN proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and Sambrook et al. (supra). Deletion or truncation derivatives of WRN proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual*, 2d Ed., Cold Spring Harbor Laboratory Press, 1989).

Mutations of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

WRN proteins may also be constructed utilizing techniques of PCR mutagenesis, chemical mutagenesis (Drinkwater and Klinedinst, *PNAS* 83:3402-3406, 1986), by forced nucleotide misincorporation (e.g., Liao and Wise *Gene* 88:107-111, 1990), or by use of randomly mutagenized oligonucleotides (Horwitz et al., *Genome* 3:112-117, 1989).

Proteins can be isolated by, among other methods, culturing suitable host and vector systems to produce the recombinant translation products of the present invention. Supernates from such cell lines, or protein inclusions or whole cells where the protein is not excreted into the supernate, can then be treated by a variety of purification procedures in order to isolate the desired proteins. For example, the supernate may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to sodium dodecyl sulfate-polyacrylamide gel electrophoresis (SDS-PAGE) analysis followed by Coomassie blue staining. Within other embodiments, the desired protein can be isolated such that no other (undesired) protein is detected pursuant to SDS-PAGE analysis followed by silver staining.

Expression of a WRN Gene

The present invention also provides for the manipulation and expression of the above described genes by culturing host cells containing a vector capable of expressing the above-described genes. Such vectors or vector constructs include either synthetic or cDNA-derived nucleic acid molecules encoding WRN proteins, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

Nucleic acid molecules that encode any of the WRN proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci. USA* 75:1929-1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual*, 2nd edition, Cold Spring Harbor Laboratory Press, 1989; for plant cells see Czako and Marton, *Plant Physiol.* 104:1067-1071, 1994; and Paszkowski et al., *Biotech.* 24:387-392, 1992).

Bacterial host cells suitable for carrying out the present invention include *E. coli, B. subtilis, Salmonella typhimurium*, and various species within the genera *Pseudomonas, Streptomyces*, and *Staphylococcus*, as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20-77, 1983 and Vieira and Messing, *Gene* 19:259-268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera *Pichia* or *Kluyveromyces* and various species of the genus *Aspergillus* (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035-1039, 1978), YEp13 (Broach et al., *Gene* 8:121-133, 1979), pJDB249 and pJDB219 (Beggs, *Nature* 275:104-108, 1978) and derivatives thereof.

Preferred promoters for use in yeast include promoters from yeast glycolytic genes (Hitzeman et al., *J. Biol. Chem.* 255:12073-12080, 1980; Alber and Kawasaki, *J. Mol. Appl. Genet.* 1:419-434, 1982) or alcohol dehydrogenase genes (Young et al., in *Genetic Engineering of Microorganisms for Chemicals*, Hollaender et al. (eds.), p. 355, Plenum, New York, 1982; Ammerer, *Meth. Enzymol.* 101:192-201, 1983). Examples of useful promoters for fungi vectors include those derived from *Aspergillus nidulans* glycolytic genes, such as the adh3 promoter (McKnight et al., *EMBO J.* 4:2093-2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci. USA* 75:1929-1933, 1978), Yelton et al. (*Proc. Natl. Acad. Sci. USA* 81:1740-1747, 1984), and Russell (*Nature* 301:167-169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes an WRN protein as described above. A wide variety of promoters may be utilized within the context of the present invention, including for example, promoters such as MoMLV LTR, RSV LTR, Friend MuLV LTR, adenoviral promoter (Ohno et al., *Science* 265: 781-784, 1994), neomycin phosphotransferase promoter/enhancer, late parvovirus promoter (Koering et al., *Hum. Gene Therap.* 5:457-463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morpho-genetic protein promoter, human alpha1-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite.

Thus, WRN proteins of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215-219, 1994; Kass-Eisler et al., *PNAS* 90(24):11498-502, 1993; Guzman et al., *Circulation* 88(6): 2838-48, 1993; Guzman et al., *Cir. Res.* 73(6):1202-1207, 1993; Zabner et al., *Cell* 75(2):207-216, 1993; Li et al., *Hum Gene Ther.* 4(4):403-409, 1993; Caillaud et al., *Eur. J. Neurosci.* 5(10:1287-1291, 1993; Vincent et al., *Nat. Genet.*

5(2):130-134, 1993; Jaffe et al., *Nat. Genet.* 1(5):372-378, 1992; and Levrero et al, *Gene* 101(2):195-202, 1991), adeno-associated viral vectors (WO 95/13365; Flotte et al., *PNAS* 90(22):10613-10617, 1993), baculovirus vectors, parvovirus vectors (Koering et al., *Hum. Gene Therap.* 5:457-463, 1994), pox virus vectors (Panicali and Paoletti, *PNAS* 79:4927-4931, 1982; and Ozaki et al., *Biochem. Biophys. Res. Comm.* 193(2):653-660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Mammalian cells suitable for carrying out the present invention include, among others: PC12 (ATCC No. CRL1721), NIE-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59-72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm $5AHT_2B$ (Orskov and Nielson, *FEBS* 229(1):175-178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521-530, 1985), cytomegalovirus immediate late promoter, SV40 promoter (Subramani et al., *Mol. Cell. Biol.* 1:854-864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse $V_\kappa$ promoter (Bergman et al., *Proc. Natl. Acad. Sci. USA* 81:7041-7045, 1983; Grant et al., *Nucl. Acids Res.* 15:5496, 1987) and a mouse $V_H$ promoter (Loh et al., *Cell* 33:85-93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719-3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, Somatic Cell Genetics 7:603, 1981; Graham and Van der Eb, *Virology* 52:456, 1973), electroporation (Neumann et al., *EMBO J.* 1:841-845, 1982), or DEAE-dextran mediated transfection (Ausubel et al. (eds.), *Current Protocols in Molecular Biology*, John Wiley and Sons, Inc., NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference).

Mammalian cells containing a suitable vector are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215-224,1990).

Numerous plant host cells known in the art can also be useful within the present invention, in light of the subject specification. For example, the use of *Agrobacterium rhizogenes* as vectors for expressing genes in plant cells has been reviewed by Sinkar et al., (*J. Biosci.* (*Bangalore*) 11:47-58, 1987).

WRN proteins may be prepared by growing (typically by culturing) the host/vector systems described above, in order to express the recombinant WRN proteins. Recombinantly produced WRN proteins may be further purified as described in more detail below.

Within related aspects of the present invention, WRN proteins may be expressed in a transgenic animal whose germ cells and somatic cells contain a WRN gene which is operably linked to a promoter effective for the expression of the gene. Alternatively, in a similar manner transgenic animals may be prepared that lack the WRN gene (e.g., "knockout" mice). Such transgenics may be prepared in a variety non-human animals, including mice, rats, rabbits, sheep, dogs, goats and pigs (see Hammer et al. *Nature* 315:680-683, 1985, Palmiter et al. *Science* 222:809-814, 1983, Brinster et al. *Proc. Natl. Acad. Sci. USA* 82:4438-4442, 1985, Palmiter and Brinster *Cell* 41:343-345, 1985 and U.S. Pat. Nos. 5,175,383, 5,087,571, 4,736,866, 5,387,742, 5,347,075, 5,221,778, and 5,175,384).

Briefly, an expression vector, including a nucleic acid molecule to be expressed together with appropriately positioned expression control sequences, is introduced into pronucleli of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Vectors of the present invention may contain or express a wide variety of additional nucleic acid molecules in place of or in addition to an WRN protein as described above, either from one or several separate promoters. For example, the viral vector may express a lymphokine or lymphokine receptor, antisense or ribozyme sequence or toxins. Representative examples of lymphokines include IL-1, IL-2, IL-3, IL-4, IL-5, IL-6, IL-7, IL-8, IL-9, IL-10, IL-11, IL-12, IL-13, IL-14, IL-15, GM-CSF, G-CSF, M-CSF, alpha-interferon, beta-interferon, gamma-interferon, and tumor necrosis factors, as well as their respective receptors. Representative examples of antisense sequences include antisense sequences which block the expression of WRN protein mutants. Representative examples of toxins include: ricin, abrin, diphtheria toxin, cholera toxin, saporin, gelonin, pokeweed antiviral protein, tritin, *Shigella* toxin, and *Pseudomonas* exotoxin A.

Within other aspects of the invention, antisense oligonucleotide molecules are provided which specifically inhibit expression of mutant WRN nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004-1012 (1993); WO 95/10607; U.S. Pat. No. 5,359,051; WO 92/06693; and EP-A2-612844). Briefly, such molecules are constructed such that they are complementary to, and able to form Watson-Crick base pairs with, a region of transcribed WRN mutant mRNA sequence containing an WRN mutation. The resultant double-stranded nucleic acid interferes with subsequent processing of the mRNA, thereby preventing protein synthesis.

Within other related aspects of the invention, ribozyme molecules are provided wherein an antisense oligonucleotide sequence is incorporated into a ribozyme which can specifically cleave mRNA molecules transcribed from a mutant WRN gene (see generally, Kim et al. *Proc. Nat. Acad. Sci. USA* 84:8788 (1987); Haseloff, et al. *Nature* 234:585 (1988), Cech, *JAMA* 260:3030 (1988); Jeffries, et al. *Nucleic Acids Res.* 17:1371 (1989); U.S. Pat. Nos. 5,093,246; 5,354,855; 5,144,019; 5,272,262; 5,254,678; and 4,987,071). According to this aspect of the invention, the antisense sequence which is incorporated into a ribozyme includes a sequence complementary to, and able to form Watson-Crick base pairs with, a region of the transcribed mutant WRN mRNA containing an WRN mutation. The antisense sequence thus becomes a targeting agent for delivery of catalytic ribozyme activity specifically to mutant WRN mRNA, where such catalytic activity cleaves the mRNA to render it incapable of being subsequently processed for WRN protein translation.

Host Cells

As discussed above, nucleic acid molecules which encode the WRN proteins of the present invention (or the vectors which contain and/or express related mutants) may readily be introduced into a wide variety of host cells. Representative examples of such host cells include plant cells, eukaryotic cells, and prokaryotic cells. Within preferred embodiments, the nucleic acid molecules are introduced into cells from a vertebrate or warm-blooded animal, such as a human, macaque, dog, cow, horse, pig, sheep, rat, hamster, mouse or fish cell, or any hybrid thereof.

Preferred prokaryotic host cells for use within the present invention include *E. coli, Salmonella, Bacillus, Shigella, Pseudomonas, Streptomyces* and other genera. Techniques for transforming these hosts and expressing foreign DNA sequences cloned therein are well known in the art (see, e.g., Maniatis et al., *Molecular Cloning: A Laboratory Manual*, Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155-164, 1983), lac (Casadaban et al., *J. Bacteriol.* 143:971-980, 1980), and phage $\lambda$ (Queen, *J. Mol. Appl. Genet.* 2:1-10, 1983) promoter systems. Plasmids useful for transforming bacteria include the pUC plasmids (Messing, *Meth. Enzymol.* 101:20-78, 1983; Vieira and Messing, *Gene* 19:259-268, 1982), pBR322 (Bolivar et al., *Gene* 2:95-113, 1977), pCQV2 (Queen, ibid.), and derivatives thereof. Plasmids may contain both viral and bacterial elements.

Preferred eukaryotic cells include cultured mammalian cell lines (e.g., rodent or human cell lines) and fungal cells, including species of yeast (e.g., *Saccharomyces* spp., particularly *S. cerevisiae, Schizosaccharomyces* spp., or *Kluyveromyces* spp.) or filamentous fungi (e.g., *Aspergillus* spp., *Neurospora* spp.). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.), Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

The nucleic acid molecules (or vectors) may be introduced into host cells by a wide variety of mechanisms, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841-845, 1982), retroviral, adenoviral, protoplast fusion-mediated transfection or DEAE-dextran mediated transfection (Ausubel et al., (eds.), *Current Protocols in Molecular Biology*, John Wiley and Sons, Inc., NY, N.Y., 1987).

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5-6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the nucleic acid molecules of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M.

Cultured mammalian cells are generally cultured in commercially available serum-containing or serum-free media. Selection of a medium and growth conditions appropriate for the particular cell line used is well within the level of ordinary skill in the art.

Antibodies

Antibodies to the WRN proteins discussed above may readily be prepared given the disclosure provided herein. Such antibodies may, within certain embodiments, specifically recognize wild type WRN protein rather than a mutant WRN protein, mutant WRN protein rather than wild type WRN protein, or equally recognize both the mutant and wild-type forms of WRN protein. Antibodies may be used for isolation of the protein, establishing intracellular localization of the WRN protein, inhibiting activity of the protein (antagonist), or enhancing activity of the protein (agonist). Knowledge of the intracellular location of the WRN gene product may be abnormal in patients with WRN mutations, thus allowing the development of a rapid screening assay. As well, assays for small molecules that interact with the WRN gene product will be facilitated by the development of antibodies and localization studies.

Within the context of the present invention, antibodies are understood to include monoclonal antibodies, polyclonal antibodies, anti-idiotypic antibodies, antibody fragments (e.g., Fab, and $F(ab')_2$, $F_v$ variable regions, or complementarity determining regions). As discussed above, antibodies are understood to be specific against an WRN protein if it binds with a $K_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660-672, 1949).

Briefly, polyclonal antibodies may be readily generated by one of ordinary skill in the art from a variety of warm-blooded animals such as horses, cows, various fowl, rabbits, mice, or rats. Typically, an WRN protein or unique peptide thereof of 13-20 amino acids (preferably conjugated to keyhole limpet hemocyanin by cross-linking with glutaraldehyde) is utilized to immunize the animal through intraperitoneal, intramuscular, intraocular, or subcutaneous injections, an adjuvant such as Freund's complete or incomplete adjuvant. Merely as an example, a peptide corresponding to residues 1375 through 1387 of the WRN polypeptide sequence is used to raise a rabbit polyclonal antiserum. Following several booster immunizations, samples of serum are collected and tested for reactivity to the WRN protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference).

Briefly, within one embodiment a subject animal such as a rat or mouse is injected with an WRN protein or portion thereof as described above. The protein may be admixed with an adjuvant such as Freund's complete or incomplete adjuvant in order to increase the resultant immune response. Between one and three weeks after the initial immunization the animal may be reimmunized with another booster immunization, and tested for reactivity to the protein utilizing assays described above. Once the animal has reached a plateau in its reactivity to the injected protein, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see Glasky and Reading, *Hybridoma* 8(4):377-389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3×63-Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as fetal bovine serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against an WRN protein. A wide variety of assays may be utilized to determine the presence of antibodies which are reactive against the proteins of the present invention, including for example countercurrent immuno-electrophoresis, radioimmunoassays, radioimmunoprecipitations, enzyme-linked immunosorbent assays (ELISA), dot blot assays, western blots, immunoprecipitation, Inhibition or Competition Assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the WRN protein may be isolated.

Other techniques may also be utilized to construct monoclonal antibodies (see William D. Huse et al., "Generation of a Large Combinational Library of the Immunoglobulin Repertoire in Phage Lambda," *Science* 246:1275-1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-5732, August 1989; see also Michelle Alting-Mees et al., "Monoclonal Antibody Expression Libraries: A Rapid Alternative to Hybridomas," *Strategies in Molecular Biology* 3:1-9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli.*

Similarly, portions or fragments, such as Fab and Fv fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423-426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Assays

Assays useful within the context of the present invention include those assays for detecting agonists or antagonists of WRN protein activity. Other assays are useful for the screening of peptide or organic molecule libraries. Still other assays are useful for the identification and/or isolation of nucleic acid molecules and/or peptides within the present invention, the identification of proteins that interact or bind the WRN protein, for diagnosis of a patient with an increased likelihood of contracting Werner's Syndrome, or for diagnosis of a patient with susceptibility to or manifestation of a WRN-related disease.

Nucleic Acid Based Diagnostic Tests

Briefly, another aspect of the present invention provides probes and primers for detecting the WRN genes and/or mutants thereof. In one embodiment of this aspect, probes are provided that are capable of specifically hybridizing to DNA or RNA of the WRN genes. For purposes of the present invention, probes are "capable of hybridizing" to DNA or RNA of the WRN gene if they hybridize to an WRN gene under conditions of either high or moderate stringency (see Sambrook et al., supra) but not significantly or detectably to the an unrelated helicase gene such as the Bloom's Syndrome gene (Ellis et al., *Cell* 83:655-666, 1995). Preferably, the probe hybridizes to suitable nucleotide sequences under high stringency conditions, such as hybridization in 5×SSPE, 1× Denhardt's solution, 0.1% SDS at 65° C., and at least one wash to remove unhybridized probe in the presence of 0.2×SSC, 1× Denhardt's solution, 0.1% SDS at 65° C. Except as otherwise provided herein, probe sequences are designed to allow hybridization to WRN genes, but not to DNA or RNA sequences from other genes. The probes are used, for example, to hybridize to nucleic acid that is present in a biological sample isolated from a patient. The hybridized probe is then detected, thereby indicating the presence of the desired cellular nucleic acid. Preferably, the cellular nucleic acid is subjected to an amplification procedure, such as PCR, prior to hybridization. Alternatively, the WRN gene may be amplified and the amplified product subjected to DNA sequencing. Mutants of WRN may be detected by DNA sequence analysis or hybridization with allele-specific oligonucleotide probes under conditions and for time sufficient to allow hybridization to the specific allele. Typically, the hybridization buffer and wash will contain tetramethyl ammonium chloride or the like (see Sambrook et al., supra).

Nucleic acid probes of the present invention may be composed of either deoxyribonucleic acids (DNA), ribonucleic acids (RNA), nucleic acid analogues (e.g., peptide nucleic acids), or any combination thereof, and may be as few as about 12 nucleotides in length, usually about 14 to 18 nucleotides in length, and possibly as large as the entire sequence of a WRN gene. Selection of probe size is somewhat dependent upon the use of the probe, and is within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as [α-$^{32}P$]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al., supra.)

Probes can be labeled by a variety of markers, including for example, radioactive markers, fluorescent markers, enzymatic markers, and chromogenic markers. The use of $^{32}P$ is particularly preferred for marking or labeling a particular probe.

It is a feature of this aspect of the invention that the probes can be utilized to detect the presence of WRN mRNA or DNA within a sample. However, if the relevant sample is present in only a limited number, then it may be beneficial to amplify the relevant sequence so that it may be more readily detected or obtained.

A variety of methods may be utilized in order to amplify a selected sequence, including, for example, RNA amplification (see Lizardi et al., *Bio/Technology* 6:1197-1202, 1988; Kramer et al., *Nature* 339:401-402, 1989; Lomeli et al., *Clinical Chem.* 35(9):1826-1831, 1989; U.S. Pat. No. 4,786,600), and DNA amplification utilizing LCR or polymerase chain reaction ("PCR") (see, U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:348-352, 1994). PCR may also be used in combination with reverse dot-blot hybridization (Iida et al., *FEMS Microbiol. Lett.* 114:167-172, 1993). PCR products may be quantitatively analyzed by incorporation of dUTP (Duplàa et al., *Anal. Biochem.* 212:229-236, 1993), and samples may be filter sampled for PCR-gene probe detection (Bej et al., *Appl. Environ. Microbiol.* 57:3529-3534, 1991).

Within a particularly preferred embodiment, PCR amplification is utilized to detect the WRN DNA. Briefly, as described in greater detail below, a DNA sample is denatured at 95° C. in order to generate single-stranded DNA. The DNA sample may be a cDNA generated from RNA. Specific primers are then annealed to the single-stranded DNA at 37° C. to 70° C., depending on the proportion of AT/GC in the primers. The primers are extended at 72° C. with Taq DNA polymerase or other thermostable DNA polymerase in order to generate the opposite strand to the template. These steps constitute one cycle, which may be repeated in order to amplify the selected sequence. For greater specificity, nested PCR may be performed. In nested PCR, a second amplification is performed using a second set of primers derived from sequences within the first amplified product. The entire coding region of WRN may be amplified from cDNA using three sets of primers to generate fragment lengths that are a convenient size for determining their sequence. In a preferred embodiment, nested PCR is performed.

Within an alternative preferred embodiment, LCR amplification is utilized for amplification. LCR primers are synthesized such that the 5' base of the upstream primer is capable of hybridizing to a unique base pair in a desired gene to specifically detect an WRN gene.

Within another preferred embodiment, the probes are used in an automated, non-isotopic strategy wherein target nucleic acid sequences are amplified by PCR, and then desired products are determined by a calorimetric oligonucleotide ligation assay (OLA) (Nickerson et al., *Proc. Natl. Acad. Sci. USA* 81:8923-8927, 1990).

Primers for the amplification of a selected sequence should be selected from sequences that are highly specific to WRN (and not, e.g., the Bloom's Syndrome gene, supra) and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplàa et al., *Anal. Biochem.* 212:229-236, 1993; Higuchi et al., *Bio/Technology* 11:1026-1030).

Within one embodiment of the invention, nucleic acid diagnostics may be developed which are capable of detecting the presence of Werner's Syndrome, or of various related diseases that may be caused by Werner's Syndrome. Briefly, severe mutations in the WRN gene may lead to Werner's Syndrome, as well as a host of related diseases, including for example, increased frequency of some benign and malignant neoplasms (especially sarcomas), cataracts, cardiovascular disease, osteoporosis, type I or type II diabetes, cataracts, sclerodoma-like skin changes and hyperkeratosis. Less severe mutations of the gene may lead to the onset of the same set of diseases, but at an older age. In addition, many of the related diseases may be associated with mutations in the WRN gene. For example, diabetes and osteoporosis are often associated with aging. Aging population and individuals with these (or other) diseases are screened for mutations in WRN. Any of the assays described herein may be used. RT-PCR is especially preferred in conjunction with DNA sequence determination. To correlate a mutation or polymorphism with disease, sibling pairs in which one sibling has disease are preferred subjects. Once a mutation is identified, other convenient screening assays may be used to assay particular nucleotide changes.

Since the sequences of the two copies of the gene from non-Werner's affected individuals can be correlated with the medical histories of these patients to define these correspondences, these alleles can therefore be used as diagnostics for susceptibilities to these diseases, once the relationship is defined. Certain non-null forms of the gene, for example, in either the homozygous or heterozygous state may significantly affect the propensity for the carriers to develop, for example, cancer. These propensities can be ascertained by examining the sequences of the gene (both copies) in a statistically significant sample of cancer patients. Other diseases (see above) can be similarly examined for significant correlations with certain alleles. To detect such a causal relationship one can use a chi-squared test, or other statistical test, to examine the significance of any correlation between the appropriate genotypes and the disease state as recorded in the medical records, using standard good practices of medical epidemiology. The sequences that define each of the alleles are then valuable diagnostic indicators for an increased susceptibility to the disease. Thus, from the nucleic acid sequences provided herein, a wide variety of Werner's Syndrome-related diseases may be readily detected.

Another cellular phenotype of the cells from Werner's patients is the increased frequency of deletion mutation in these cells. Clearly, the defective helicase in these cells leads to a specific mutator phenotype, while not rendering the cells hypersensitive to a variety of chemical or physical mutagens that damage DNA, like ionizing radiation. Disease states, or sensitivities that result from an elevated deletion frequency can therefore be controlled, in part, by alterations of the Werner's gene, and some alleles may therefore be diagnostic of this class of medical conditions.

Assays for Agonists and Antagonists

An agonist or antagonist of the WRN gene product comprising a protein, peptide, chemical, or peptidomimetic that binds to the WRN gene product or interacts with a protein that binds to the WRN gene product such that the binding of the agonist or antagonist affects the activity of the WRN gene product. An agonist will activate or increase the activity of the WRN gene product. An antagonist will inhibit or decrease the activity of the WRN gene product. The activity of the WRN gene product may be measured in an assay, such as a helicase assay or other assay that measures an activity of the WRN gene product. Other assays measure the binding of protein that interacts with WRN and is necessary for its activity.

Agonists and antagonists of the WRN gene product may be used to enhance activity or inhibit activity of the gene product. Such agonists and antagonists may be identified in a variety of methods. For example, proteins that bind and activate WRN may be identified using a yeast 2-hybrid detection system. In this system, the WRN gene is fused to either a DNA-binding domain or an activating domain of a yeast gene such as GAL4. A cDNA library is constructed in a vector such that the inserts are fused to one of the domains. The vectors are co-transfected into yeast and selected for transcriptional activation of a reporter gene (Fields and Song, *Nature* 340: 245, 1989). The protein(s) that bind to WRN are candidate agonists. Three different proteins that bind WRN have been identified in an initial screen using the 2-hybrid system.

When the binding site on WRN gene product is determined, molecules that bind and activate WRN protein may be designed and evaluated. For example, computer modeling of the binding site can be generated and mimetics that bind can be designed. Antibodies to the binding site may be generated and analogues of native binding proteins generated as well. Any of these molecules is tested for agonist or antagonist activity by a functional assay of the WRN gene product. For example, to test for antagonist activity, yeast are co-transfected with the WRN and binding protein each fused to a DNA binding domain or an activation domain. The test molecule is administered and activation is monitored. An antagonist will inhibit the activation of the reporter gene by at least 50%. Similarly, agonist activity may be measured by either enhancing WRN activity in a yeast 2-hybrid system or by coupling the test compound to a DNA binding or activation domain and monitoring activity of the reporter gene.

Labels

WRN proteins, nucleic acid molecules which encodes such proteins, anti-WRN protein antibodies and agonists or antagonists, as described above and below, may be labeled with a variety of molecules, including for example, fluorescent molecules, toxins, and radionuclides. Representative examples of fluorescent molecules include fluorescein, *Phycobili* proteins, such as phycoerythrin, rhodamine, Texas red and luciferase. Representative examples of toxins include ricin, abrin diphtheria toxin, cholera toxin, gelonin, pokeweed antiviral protein, tritin, *Shigella* toxin, and *Pseudomonas* exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the WRN proteins, nucleic acid molecules which encode such proteins, anti-WRN protein antibodies and agonists or antagonists, as discussed above, with the representative labels set forth above may be readily accomplished by one of ordinary skill in the art (see Trichothecene Antibody Conjugate, U.S. Pat. No. 4,744,981,; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification*: Part B, Jakoby and Wilchek (eds.), Academic Press, New York, p. 30, 1974; see also Wilchek and Bayer, "The Avidin-Biotin Complex in Bioanalytical Applications," *Anal. Biochem.* 171:1-32, 1988).

Pharmaceutical Compositions

As noted above, the present invention also provides a variety of pharmaceutical compositions, comprising one of the above-described WRN proteins, nucleic acid molecules, vectors, antibodies, host cells, agonists or antagonists, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treating or Preventing Werner's Syndrome

The present invention also provides methods for treating or preventing Werner's Syndrome (or related diseases), comprising the step of administering to a patient a vector (e.g., expression vector, viral vector, or viral particle containing a vector) or nucleic acid molecules alone, as described above, thereby reducing the likelihood or delaying the onset of Werner's Syndrome (or the related disease).

Similarly, therapeutic peptides, peptidomimetics, or small molecules may be used to delay onset of Werner's Syndrome, lessen symptoms, or halt or delay progression of the disease. Such therapeutics may be tested in a transgenic animal model that expresses mutant protein, wild-type and mutant protein, or in an in vitro assay system (e.g., a helicase assay such as that described by Bjornson et al., *Biochem.* 3307:14306-14316, 1994).

As noted above, the present invention provides methods for treating or preventing Werner's Syndrome through the administration to a patient of a therapeutically effective amount of an antagonist or pharmaceutical composition as described herein. Such patients may be identified through clinical diagnosis based on the classical symptoms of Werner's Syndrome.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Within other embodiments of the invention, the vectors which contain or express the nucleic acid molecules which encode the WRN proteins described above, or even the nucleic acid molecules themselves may be administered by a variety of alternative techniques, including for example administration of asialoosomucoid (ASOR) conjugated with poly-L-lysine DNA complexes (Cristano et al., *PNAS* 92122-92126, 1993), DNA linked to killed adenovirus (Curiel et al., *Hum. Gene Ther*. 3(2):147-154, 1992), cytofectin-mediated introduction (DMRIE-DOPE, Vical, Calif.), direct DNA injection (Acsadi et al., *Nature* 352:815-818, 1991); DNA ligand (Wu et al., *J. of Biol. Chem*. 264:16985-16987, 1989); lipofection (Felgner et al., *Proc. Natl. Acad. Sci. USA* 84:7413-7417, 1989); liposomes (Pickering et al., *Circ.* 89(1):13-21, 1994; and Wang et al., *PNAS* 84:7851-7855, 1987); microprojectile bombardment (Williams et al., *PNAS* 88:2726-2730, 1991); and direct delivery of nucleic acids which encode the WRN protein itself either alone (Vile and Hart, *Cancer Res*. 53: 3860-3864, 1993), or utilizing PEG-nucleic acid complexes.

The following examples are offered by way of illustration, and not by way of limitation.

EXAMPLES

Example 1

Cloning of the WRN Gene from Chromosome 8

The WS locus (WRN) was initially localized to 8p12 by conventional mapping methods (Goto et al., *Nature* 355: 735-738, 1992) and the genetic position refined using both meiotic and homozygosity mapping (Schellenberg et al., 1992; Nakura, et al., *Genomics* 23:600-608, 1994; Thomas, *Genomics* 16:685-690, 1993). The latter approach is possible since many WS subjects are the offspring of consanguineous marriages (Table 1). Initial mapping work (Nakura, et al., *Genomics* 23:600-608, 1994; Oshima et al., *Genomics* 23:100-113, 1994) placed the WRN locus in an 8.3 cM interval flanked by D8S137 and D8S87 (FIG. 1). D8S339, a marker within this interval, was the closest locus tested (q=0.001, $Z_{max}$=15.93). Multipoint analysis placed WRN within 0.6 cM of D8S339, although the region between D8S87 and FGFR could not be excluded. Subsequently, the short tandem repeat polymorphism (STRP) markers at glutathione reductase (GSR) and D8S339 were found to be in linkage disequilibrium with WS in Japanese WS subjects (Yu, *American Journal of Human Genetics* 55:356-364, 1994).

To clone the WRN gene, a yeast artificial chromosome (YAC) P1, and cosmid contig was generated starting at the GSR/D8S339 region and extended by walking methods to cover approximately 3 Mb. An additional 16 STRP markers in the YAC contig (FIG. 1B) were identified to define recombinants and to delineate the boundaries of the linkage disequilibrium region. For marker ordering and gene identification, cosmids and P1 clones were also isolated and used to construct a small-clone partial contig of the region (FIG. 1E). The WRN region was defined by obligate recombinants at C41C3S3 excluding the region telomeric to this marker, and at y896R9 excluding the region centormeric to this marker. Thus, the region from C41C3S2 to y896R9, which is approximately 1.2 Mb (FIG. 1C), was considered the minimal WRN region.

Genes in the WRN region were identified by exon trapping using vector pSL3 (Buckler et al., *Proc. Natl. Acad. Sci. USA* 88:4005-4009, 1991; Church et al., *Nat. Genet.* 6:98-105, 1994), hybridization of cDNA libraries to immobilized YACs (Parimoo et al., *Proc. Natl. Acad. Sci USA* 87:3166-3169, 1991), and comparison of the genomic sequence to DNA sequence databases using BLAST (Altschul et al. *J. Mol. Biol.* 215:403-410, 1990) and the exon-finding program GRAIL (Uberbacher and Mural, *Proc. Natl. Acad. Sci. USA* 88:1261, 1991). The genomic sequence was determined for the region defined by P1 clones 2233, 2253, 3833, 2236, 2237, 2932, 6738 and 2934 and cosmid clone 176 C6. Each method identifies short segments of expressed sequences, which were then used to screen an arrayed fibroblast cDNA library to identify longer cDNA clones. This library was selected because WS fibroblasts have a premature senescence phenotype in vitro, indicating that the WRN gene is probably expressed in this cell type. Genes identified by this process were screened for WRN mutations using reverse transcriptase-polymerase chain reaction (RT-PCR). Seven subjects were initially screened for mutations; 5 WRN subjects (2 Caucasians and 3 Japanese) and 2 control subjects (1 Caucasian and 1 Japanese). Prior to identification of the WRN gene, the following genes from the region were screened for mutations; GSR, PP2AB, TFIIEB, and genes corresponding to other expressed sequence tagged sites (ESTs).

The candidate WRN locus gene was initially detected by using the genomic sequence of P1 clone 2934 to search the EST database. A single 245 bp EST, R58879, was detected which is homologous to 3 segments of the genomic sequence separated by presumed intronic sequence. Sequence from R58879 was used to identify longer cDNA clones from a normal fibroblast cDNA library. An initial 2.1 kb cDNA clone containing EST R58879, which corresponds to the 3' end of the gene, was obtained by screening an array of clones by PCR, using the primers A and B (see below). Primers A and B are derived from R58879 sequence and yield a 145 bp fragment after amplification. Longer clones were identified by PCR screening with primers 5EA and 5EB, which were derived from sequences within a predicted exon located in p2934 and 5' to sequences contained in the initial 2.1 kb clone. Six additional clones were identified. An additional 8 clones were obtained by plaque hybridization. The longest clone is 4.0 kb in length. Additional sequence was obtained by the RAGE method using primer 5EA to prime first strand cDNA synthesis. A 2.5 kb product was obtained that contained an additional 1.4 kb of sequence.

Evidence that R58879 is expressed was obtained by Northern blot analysis, in which 6.5 kb and 8 kb transcripts were detected in a variety of tissues, including heart, placenta, muscle, and pancreas. Also, transcripts were detected by RT-PCR products from fibroblast and lymphoblastoid cell line RNA.

Example 2

Cloning of the WRN Gene from Subjects

The WRN gene may be isolated from patients and mutations or polymorphisms determined by sequence analysis. Peripheral blood cells are obtained by venipuncture and hypotonic lysis of erythrocytes. DNA or RNA is isolated from these cells and the WRN gene isolated by amplification. The gene sequence may be obtained by amplification of the exons from genomic DNA or by RT-PCR, followed by determination of the DNA sequence. Primers suitable for determining the DNA sequence and for performing RT-PCR are listed below (Primers A-R are SEQ ID Nos. 1-18 respectively, and primers 5EA-5EG are SEQ ID Nos. 19-25 respectively). Two cDNAs were identified and are shown in FIGS. 2 and 3. There is some uncertainty regarding the identity of a few bases in the 5' untranslated region in FIG. 2.

Two RT-PCR reactions are used to obtain the gene from different tissues. First strand cDNA synthesis is carried out according to standard procedures (e.g., with a Stratascript Kit from Stratagene). The cDNA is subjected to a pair of nested PCR amplifications, the first with primers I and J (SEQ ID Nos. 9 and 10), followed by primers K and L (SEQ ID Nos. 11 and 12), and the second with primers 5ED and P (SEQ ID Nos. 22 and 16), followed by primers 5EE and B (SEQ ID Nos. 23 and 2). These fragments are isolated and used for sequencing to identify differences in the gene sequence or splicing pattern. Primers A-H (SEQ ID Nos. 1-8) and K-R (SEQ ID Nos. 11-18) are used for sequencing the first RT-PCR fragment. Primers B, 5EA, 5EB, 5EC, 5EE, 5EF and 5EG (SEQ ID Nos. 2, 19, 20, 21, 23, 24, and 25, repectively) are used for sequencing the second RT-PCR fragment. Sequencing is done on an ABI373A using Applied Biosystems Division of Perkin-Elmer FS sequencing kits according to the instructions of the manufacturer.

| | |
|---|---|
| A | 5'-CTGGCAAGGATCAAACAGAGAG |
| B | 5'-CTTTATGAAGCCAATTTCTACCC |
| C | 5'-TGGCAAATTGGTAGAAGCTAGG |
| D | 5'-AAATAACTATGCTTTCTTACATTTAC |
| E | 5'-CTCCCGTCAACTCAGATATGAG |
| F | 5'-CTGTTTGTAAATGTAAGAAAGCATAG |
| G | 5'-GAGCTATGATGACACCACTGC |
| H | 5'-ACTGAGCAACAGAGTGAGACC |

-continued

| | |
|---|---|
| I | 5'-GGATCTGGTCTCACTCTGTTGC |
| J | 5'-TTGCCTAGTGCAATTGGTCTCC |
| K | 5'-AGTGCAGTGGTGTCATCATAGC |
| L | 5'-CCTATTTAATGGCACCCAAAATGC |
| M | 5'-CAGTCTATGGCCATCACATACTC |
| N | 5'-ACCGCTTGGGATAAGTGCATGC |
| O | 5'-GAGAAGAAGTCTAACTTGGAGAAG |
| P | 5'-TTCTGGTGACTGTACCATGATAC |
| Q | 5'-CCAAAGGAAGTGATACCAGCAAG |
| R | 5'-ACAGCAAGAAACATAATTGTTCTGG |
| 5EA | 5'-GAACTTTGAAGTCCATCACGACC |
| 5EB | 5'-GCATTAATAAAGCTGACATTCGCC |
| 5EC | 5'-CATTACGGTGCTCCTAAGGACATG |
| 5ED | 5'-GATGGATTTGAAGATGGAGTAGAAG |
| 5EE | 5'-TGAAAGAGAATATGGAAAGAGCTTG |
| 5EF | 5'-GTAGAACCAACTCATTCTAAATGCT |
| 5EG | 5'-AATTTGCGTGTCATCCTTGCGCA |

The exons of the 3'-end of the WRN gene can be amplified from DNA samples using the primers listed below (Primers E1A-E13B are SEQ ID Nos. 26-57, respectively). The DNA sequence is determined using the same primers and an ABI373A automated sequencer using Applied Biosystems Division of Perkin-Elmer FS sequencing kits according to the instructions of the manufacturer.

| | |
|---|---|
| E1A | 5'-TCCTAGTCACCCATCTGAAGTC |
| E1B | 5'-CATGAAACTTGCTTCTAGGACAC |
| E2A | 5'-CCCAGGAGTTCGAGACCATCC |
| E2B | 5'-TTACAATCGGCCACATTCATCAC |
| E2C | 5'-TGTAATCCCAACACTTTGGGAGG |
| E2D | 5'-AGTGGAAGAATTCATAGTGGATGG |
| E3A | 5'-TAGCTTTATGAAGCCAATTTCTACC |
| E3B | 5'-AATCCAAAGAATCAATAGACAAGTC |
| E3C | 5'-GCTTGAAGGATGAGGCTCTGAG |
| E3D | 5'-TGTTCAGAATGAGCACGATGGG |
| E4A | 5'-CTTGTGAGAGGCCTATAAACTGG |
| E4B | 5'-GGTAAACAGTGTAGGAGTCTGC |
| E5A | 5'-GCCATTTTCTCTTTAATTGGAAAGG |
| E5B | 5'-ATCTTATTCATCTTTCTGAGAATGG |
| E6A | 5'-TGAAATAGCCCAACATCTGACAG |
| E6B | 5'-GATTAATTTGACAGCTTGATTAGGC |
| E7A | 5'-TGAAATATAAACTCAGACTCTTAGC |
| E7B | 5'-GTACTGATTTGGAAAGACATTCTC |

-continued

| | |
|---|---|
| E8A | 5'-GATGTGACAGTGGAAGCTATGG |
| E8B | 5'-GGAAAAATGTGGTATCTGAAGCTC |
| E9A | 5'-AAGTGAGCAAATGTTGCTTCTGG |
| E9B | 5'-TCATTAGGAAGCTGAACATCAGC |
| E10A | 5'-GTTGGAGGAAATTGATCCCAAGTC |
| E10B | 5'-TGTTGCTTATGGGTTTAACTTGTG |
| E11A | 5'-TAAAGGATTAATGCTGTTAACAGTG |
| E11B | 5'-TCACACTGAGCATTTACTACCTG |
| E12A | 5'-GTAATCATATCAGAATTCATAACAG |
| E12B | 5'-CTTTGGCAACCTTCCACCTTCC |
| E12C | 5'-GCAAAGGAAATGTAGCACATAGAG |
| E12D | 5'-AGGCTATAGGCATTTGAAAGAGG |
| E13A | 5'-GTAGGCTCCCAGAAGACCCAG |
| E13B | 5'-GAAAGGATGGGTGTGTATTCAGG |

Example 3

Identification of Mutant Alleles

The cDNA sequence (FIG. 2) was aligned to the genomic sequence to identify the exon structure, and primers synthesized for PCR amplification of each exon. DNA sequence of all 13 exons were determined for 5 patients and two unaffected individuals. In 4 of 5 patients, single base pair changes lead to splicing defects or stop codons in the open reading frame of the gene. In the fifth patient, a single base pair change results in a cysteine to arginine transition, which may disrupt gene function. Each of the exons was also sequenced in 96 unaffected control individuals (48 Caucasians and 48 Japanese), and none of the mutations were found in any of the control individuals.

The first mutation is a mutation at a splice acceptor site. In the sequence below, the GGTAGAAA sequence begins at nucleotide 2030 (FIG. 2). The g to c change results in a deletion of 95 bp.

Preparation of DNA for RT-PCR mutational analysis revealed that for one subject, the amplification product was shorter than observed in products from other WS and control subjects. DNA sequence analysis of the RT-PCR product revealed that 95 bp were missing compared to other samples. The missing sequence corresponds to a single exon. This exon and flanking genomic segments were sequenced from the WS subject and controls and a single base change (G→C) at the splice donor site was detected. The subject was the offspring of a first cousin marriage and was, as expected, homozygous for this mutation. The same mutation was found in a total of 18 out of 30 Japanese WS subjects and, thus, is the most common Japanese WS mutation. Deletion of this exon results in a change in the predicted open-reading frame and a premature stop codon. This mutation was not observed in 46 Japanese and 46 Caucasian controls. Among mutation carriers, 12/16 had the 141 bp allele at the GSR2-STRP.

```
wild type:   ttttaatagGGTAGAAA    (SEQ ID No.58)
Werners:     ttttaatacGGTAGAAA    (SEQ ID No.59)
```

The second mutation changes a C to T at nucleotide 2384 (FIG. 2) changing a glutamine to a stop codon, which results in a predicted truncated protein. This mutation was observed in a single subject. Primers E11A and E11B flank this sequence and amplify a 360 bp fragment.

```
                       gln
wild type:   GAAGCTACGCAGAAACAT    (SEQ ID No.60)
Werners:     GAAGCTAGGTAGAAACAT    (SEQ ID No.61)
                       ter
```

The third mutation changes a C to T at nucleotide 2804 (FIG. 2), which alters an arginine codon to a stop codon resulting in a predicted truncated protein. Four Japanese WS subjects and 1 Caucasian W5 subject had this mutation. Primers E8A and E8B flank this sequence and amplify a 267 bp product.

```
                    arg
wild type:   TTGGAGCGAGCA    (SEQ ID No.62)
Werners:     TTGGAGTGAGCA    (SEQ ID No.63)
                    ter
```

The fourth mutation is a 4 bp deletion across a splice junction. The exon sequence shown below begins at nucleotide 2579 (FIG. 2). This mutation was identified in a Syrian W5 kindred. Primers E4A and E4B flank this mutation and amplify a 267 bp fragment.

```
wild type:   ctgtagACAGACACCTC    (SEQ ID No.68)
Werners:     ctgt----AGACACCTC    (SEQ ID No.69)
```

The fifth mutation is a missense mutation. A T is altered to a G at nucleotide 2113 (FIG. 2), changing the wild-type phe codon to a leu codon. This change is a polymorphism with each allele present at a frequency of approximately 0.5 It does not appear to correlate with WS.

```
                    phe
wild type:   AAGAAGTTTCTTCTG    (SEQ ID No.64)
Werners:     AAGAAGTTGCTTCTG    (SEQ ID No.65)
                    leu
```

The sixth mutation is a missense mutation changing a T to a C at nucleotide 2990 (FIG. 2) and a cys codon to an arg codon.

```
                    cys
wild type:   CCTTCATGTGAT    (SEQ ID No.66)
Werners:     CCTTCACGTGAT    (SEQ ID No.67)
                    arg
```

These point mutations may also be identified by PCR using primers that contain as the 3'-most base either the wild type or the mutant nucleotide. Two separate reactions are performed using one of these primers and a common second primer. Amplification is detectable in the reaction containing a matched primer.

Example 4

Characterization of the WRN Gene and Gene Product

The 2 kb WRN cDNA hybridizes to a 6.5 kb RNA and a less abundant 8 kb RNA on a Northern blot, suggesting that a full length coding region is about 5.2 kb long. An overlapping cDNA clone has been isolated that extends the sequence by 2 kb. The insert from this clone is used to probe cDNA libraries to identify other clones that contain the 5' end of the cDNA or full length sequence. Alternate splicing events are detected by sequencing the full cDNA sequence from a number of different tissues, including fully differentiated cells and stem cells, and the full range of gene transcripts identified by sequence comparison. Additional exons are identified as above by further genomic sequencing and GRAIL analysis.

Figure 8:
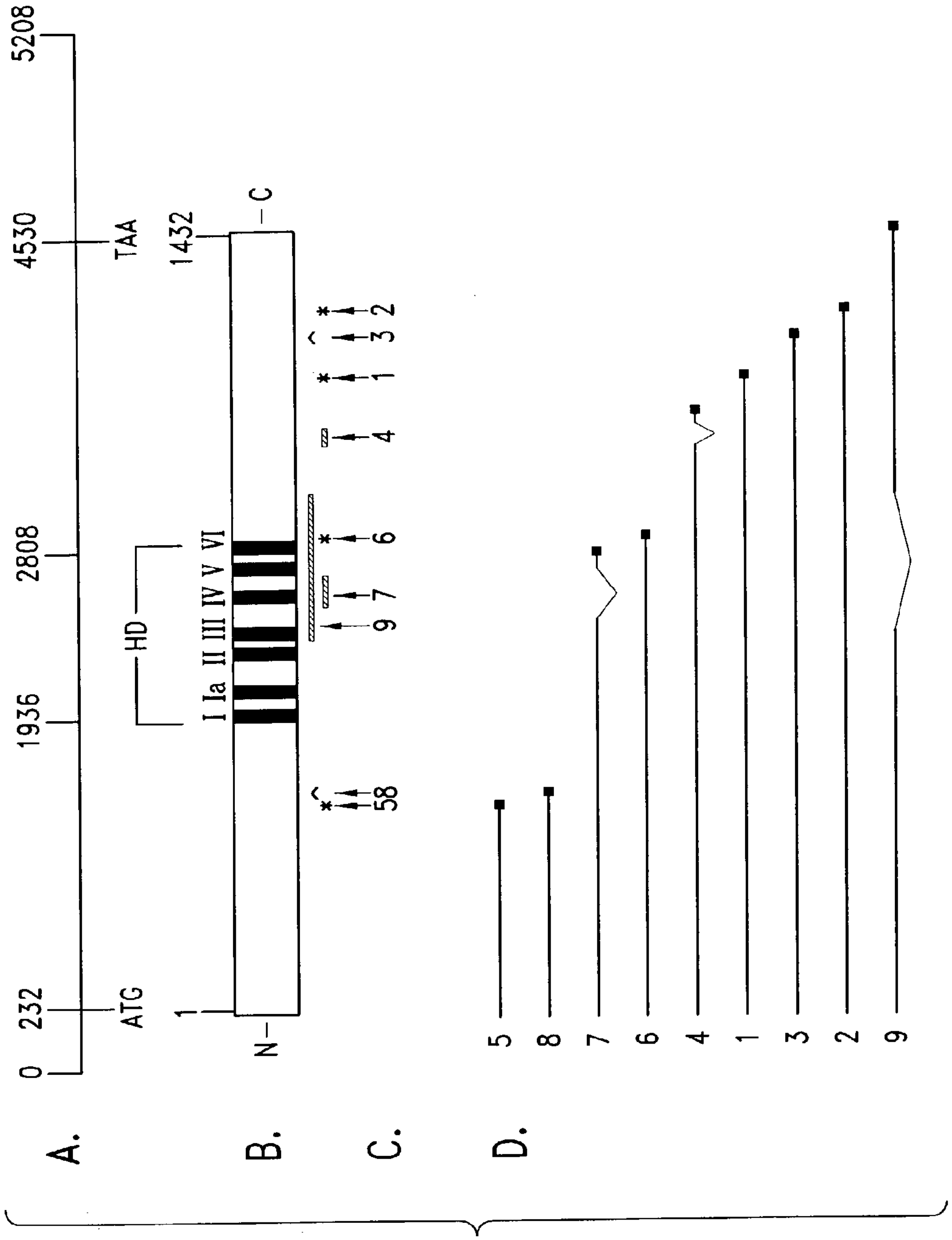
FIG. 8 is a diagram of the WRN gene product with location of mutations. A, WRN cDNA. Numbering across the top refers to the cDNA sequence as numbered in GenBank L76937. B, Predicted WRN gene product. The helicase domain is designated as "HD", motifs from I to VI are indicated. C, Location of mutations. Numbering across the bottom refer to the mutations. *: nonsense mutation. ^: frame shift mutation caused by a single base deletion. Gray lines: frame shift mutations causing deletion of exon(s). D, Predicted proteins. Lines represent the different predicted truncated proteins produced from mutations in the WRN gene.

The predicted amino acid sequence is shown in FIGS. 2B and 3. FIG. 2 shows cDNA and predicted amino acid sequences of the WRN gene. FIG. 3 presents cDNA and predicted amino acid sequences of a less abundant transcript of the WRN gene. The longest open reading frame is shown from the first methionine in that frame. The predicted WRN protein consists of 1,432 amino acids divided into three regions: an N-terminal region, a central region containing 7 motifs (I, Ia, II, III, IV, V and VI) characteristic of the DNA and RNA superfamily of helicases (Gorbalenya et al. *Nucleic Acid Res*. 17: 4713, 1989), and a C-terminal region (FIG. 8). Unlike the central region, the N-terminal and C-terminal domains of the predicted protein do not show amino acid identity to other helicases or to any previously described protein. Because many helicases function as part of a multiprotein complex, the N-terminal and/or the C-terminal domain may contain interaction sites for these other proteins, while the central helicase domain functions in the actual enzymatic unwinding of DNA or RNA duplexes.

The N-terminal region, encompassing approximately codons 1 to 539, is acidic; there are 109 aspartate or glutamate residues, including a stretch of 14 acidic residues in a 19 amino acid sequence (codons 507-526). Stretches of acidic residues are found in the Xeroderma pigmentosum (XP) complementation group B helicase, the Bloom's syndrome helicase, and the X-chromosome-linked $\alpha$-thalassemia mental retardation syndrome helicase. In the WRN gene, this region also contains a tandem duplication of 27 amino acids in which each copy is encoded by a single exon. Because this duplication is exact at the nucleotide level, and because flanking intronic sequences for the two exons that encode the duplication are also highly similar, this duplication is presumed to be the result of a relatively recent event. The duplicated regions are also highly acidic with 8 glutamate or aspartate residues out of 27 amino acids and only 2 basic amino acids (one histidine and one lysine residue).

The central region of the WRN gene, spanning approximately codons 540-963, is highly homologous to other helicases from a wide range of organisms including the ReqQ gene from *E. coli*, the SGS1 gene from *S. cerevisiae*, a predicted helicase (F18C5C) from *C. elegans*, and several human helicases. Thus, by sequence similarity, the WRN gene is a member of a superfamily of DExH-box DNA and RNA helicases. The principle conserved sequences consist of 7 motifs found in other helicases. These motifs include a predicted nucleotide binding site (motif I) and a $Mg^{2+}$ binding site (sequence DEAH, motif II). Some or all of the 7 motifs are presumed to form the enzymatic active site for DNA/RNA unwinding. The presence of the DEAH sequence and an ATP-binding motif further suggests that the WRN gene product is a functional helicase.

The C-terminal end of the WRN gene, from codons 964 to 1432, has limited identity to other genes. The only identity identified is a loose similarity to *E. coli* ReqQ gene and *C. elegans* gene F18C5.2.

Example 5

Identifying and Detecting Mutations in the WRN Gene

Mutations or polymorphisms of WRN may be identified by various methods, including sequence analysis. Although any cell (other than erythrocytes) may be used to isolate nucleic acids, peripheral blood mononuclear cells (PBMC) are preferred. Peripheral blood mononuclear cells are obtained by venipuncture and subsequent hypotonic lysis of erythrocytes. RNA is isolated and first strand cDNA synthesis is performed using a Strata-script RT-PCR kit according to the manufacturers instructions (Stratagene, La Jolla, part numbers 200347 and 200420). Three RT-PCR fragments are amplified using an LA PCR Kit Ver. 2 using buffer containing 1.5 mM Mg+2 (TaKaRa Shuzo Co., Ltd., Japan, part number RR013A). Nested PCR is performed. In this reaction, a second PCR is performed using a pair of primers within the sequence amplified by the first PCR reaction. The cycling conditions for each amplification are: 10 min at 95° C., 35 cycles of 1 min at 60° C., 1 min at 72° C., and 1 min at 95° C., followed by 7 min at 72° C. in a Perkin-Elmer 9600 PCR machine. The amplified fragments are purified using 96-well plate spin columns (Wang et al., *Anal. Biochem*. 226:85-90, 1995). DNA sequence is determined using an FS Dye-Terminator sequencing kit (Applied Biosystems Division of Perkin Elmer) and the specific primers described below. An automated Applied Biosystems ABI373A DNA Sequencer is used to determine the sequence. The amplified fragments and the appropriate primers are listed in Table 1, and the primer sequences are listed in Table 2.

The DNA sequences are aligned with the known sequence (FIG. 2A) using the program Sequencher (Gene Codes, Michigan) to identify any discrepancies between patient samples and the reference sequence.

TABLE 1

PCR and sequence primers

| | Primers Nested on cDNA | | | |
|---|---|---|---|---|
| Fragment | 1st PCR | 2nd PCR | Coordinates | Sequence primers |
| I | 5EC, J | 5EN, L | 2947–5065 | 5EN, L, M, N, O, P, Q, R |
| II | 5ED, P | 5EE, B | 1379–3391 | 5EE, 5EJ, 5EK, 5EL, 5EM, 5EB, 5EA, 5EN, B |
| III | 5ES, 5EK | 5ET, 5EH | 75–1516 | 5ET, 5EX, 5EI, 5EP, 5EO, 5ED, 5EH |

TABLE 2

| Primer sequences | | |
|---|---|---|
| B | 5'-CTTTATGAAGCCAATTTCTACCC | (SEQ ID No.2) |
| J | 5'-TTGCCTAGTGCAATTGGTCTCC | (SEQ ID No.10) |
| L | 5'-CCTATTTAATGGCACCCAAAATGC | (SEQ ID No.12) |
| M | 5'-CAGTCTATGGCCATCACATACTC | (SEQ ID No.13) |
| N | 5'-ACCGCTTGGGATAAGTGCATGC | (SEQ ID No.14) |
| O | 5'-GAGAAGAAGTCTAACTTGGAGAAG | (SEQ ID No.15) |
| P | 5'-TTCTGGTGACTGTACCATGATAC | (SEQ ID No.16) |
| Q | 5'-CCAAAGGAAGTGATACCAGCAAG | (SEQ ID No.17) |
| R | 5'-ACAGCAAGAAACATAATTGTTCTGG | (SEQ ID No.18) |
| 5EA | 5'-GAACTTTGAAGTCCATCACGACC | (SEQ ID No.19) |
| 5EB | 5'-GCATTAATAAAGCTGACATTCGCC | (SEQ ID No.20) |
| 5EC | 5'-CATTACGGTGCTCCTAAGGACATG | (SEQ ID No.21) |
| 5ED | 5'-GATGGATTTGAAGATGGAGTAGAAG | (SEQ ID No.22) |
| 5EE | 5'-TGAAAGAGAATATGGAAAGAGCTTG | (SEQ ID No.23) |
| 5EH | 5'-CATTGGGAGATAAATGCTCAGTAGA | (SEQ ID No.80) |
| 5EJ | 5'-AGATGTACTTTGGCCATTCCAG | (SEQ ID No.81) |
| 5EK | 5'-GCCATGACAGCAACATTATCTC | (SEQ ID No.82) |
| 5EL | 5'-CTTACTGCTACTGCAAGTTCTTC | (SEQ ID No.83) |
| 5EM | 5'-TCGATCAAAACCAGTACAGGTG | (SEQ ID No.84) |
| 5EN | 5'-GCAGATGTAGGAGACAAATCATC | (SEQ ID No.85) |
| 5EO | 5'-TCATCCAAAATCTCTAAATTTCGG | (SEQ ID No.86) |
| 5EP | 5'-CTGAGGACCAGAAACTGTATGC | (SEQ ID No.87) |
| 5ES | 5'-GCTGATTTGGTGTCTAGCCTGG | (SEQ ID No.88) |
| 5ET | 5'-TGCCTGGGTTGCAGGCCTGC | (SEQ ID No.89) |

TABLE 2-continued

| Primer sequences | | |
|---|---|---|
| 5EX | 5'-TTGGAAACAACTGCACAGCAGC | (SEQ ID No.90) |
| 5EI | 5'-GATCCAGTGAATTCTAAGAAGGG | (SEQ ID No.91) |

Example 6

Isolation of Genomic DNA Containing Werner's Syndrome Gene

To facilitate mutational analysis of the WRN gene, the intron-exon structure is determined. The WRN gene is located in the genomic sequence of P1 clone 2934. However, this clone only contains the 3' end of the gene (exons 21 to 35). Genomic clones containing the 5' end are obtained from a chromosome 8-specific cosmid library LA08NC01 (Wood et al. *Cytogenet. Cell Genet*. 59: 243, 1992) by screening for clones adjacent to P1 clone 2934. Briefly, this library is arrayed for PCR screening as described in Amemiya et al. (*Nucl. Acids Res*. 20: 2559, 1992). WRN containing cosmids are identified using primer sets 5E6/5EY, 5ED/5E12, and CD-A/CD-B (Table 3), which are derived from the WRN cDNA sequence (FIG. 1; GenBank Accession No. L76937). Four walking steps yielded cosmids 193B5, 114D2, 78D8 and 194C3, which contained the remaining exons. Primers derived from the WRN cDNA were used for the initial sequence analysis of the cosmid clones. The resulting sequence (FIG. 5) is compared to the cDNA sequence to identify intron-exon boundaries. Sequencing primers are then designed from the intron sequences to obtain sequence in the reverse direction and to obtain the second boundary defining the intron-exon junction. This strategy is used to define the exons not present in P1 clone 2934.

TABLE 3

Primer sequence and PCR conditions for WRN analysis

| Region | | Primer Sequence | | Product Size (bp) | $Mg^{+2}$ (mM) | pH |
|---|---|---|---|---|---|---|
| N- | 5F6 | 5'-GATATTGTTTTGTATTTACCCATGAAGAC | (SEQ ID No.164) | 106 | 1.5 | 8.3 |
| domain | 5EY | 5'-TCCGCTGCTGTGCAGTTGTTTCC | (SEQ ID No.165) | | | |
| center | 5ED | 5'-GATGGATTTGAAGATGGAGTAGAAG | (SEQ ID No.22) | 158 | 2.0 | 8.3 |
| domain | 5E12 | 5'-TCAGTAGATTTATAAGCAATATCAC | (SEQ ID No.166) | | | |
| C- | CD-A | 5'-CTGGCAAGGATCAAACAGAGAG | (SEQ ID No.167) | 144 | 2.0 | 8.3 |
| domain | CD-B | 5'-CTTTATGAAGCCAATTTCTACCC | (SEQ ID No.168) | | | |

The annealing temperature was 60° C. for all primer sets.

Table 4 presents a summary of the structure of the genomic WRN gene. The first column identifies the exon, the second column indicates the base numbers of the cDNA that are derived from the exon, the third column denotes the size of the exon in bp, the fourth column shows the sequence of the boundaries with intron sequences in lower case letters and exon sequences in upper case letters, the fifth column shows notable features of the exons.

TABLE 4

,Intron-Exon Structure of the WRN Gene

| Exon | cDNA Location | Exon Size (bp) | Intron-Exon Boundary Sequences | Exon Features |
|---|---|---|---|---|
| 1 | 1-155 | >155 | ...TTCTCGGGgtaaatgtc (SEQ ID No. 169) | 5'UTR |
| 2 | 156-327 | 172 | tacctctcagTTTTCTTT....AAGAAAGgtatgttgtt (SEQ ID No. 170) | 5'UTR, ATG codon |
| 3 | 328-440 | 113 | taaactcaagGCATGTGT....GATATTAGgtaagtgatt (SEQ ID No. 171) | |
| 4 | 441-586 | 146 | ctcactttagCATGAGTC....CATGTCAGgttggtatct (SEQ ID No. 172) | |
| 5 | 587-735 | 149 | aatgttacagTTTTTCCC....ATAAAAAGgtaaaagcaa (SEQ ID No. 173) | |
| 6 | 736-885 | 150 | tcatttctagCTGAAATG....ATGCTTATgtacgtgctt (SEQ ID No. 174) | |
| 7 | 886-955 | 70 | ttttttatagGCTGGTTT....AAATAAAGgtatgttaag (SEQ ID No. 175) | |
| 8 | 956-1070 | 115 | ttccccctagAGGAAGAAA....CCACGGAGgttaaatatt (SEQ ID No. 176) | |
| 9 | 1071-1500 | 430 | ttttttttagGGTTTCTA....CTACTGAGgtactaaaat (SEQ ID No. 177) | |
| 10 | 1501-1581 | 81 | ttttttaaagCATTTATG....TGCTTAAGggtatgttta (SEQ ID No. 178) | duplicated exon |
| 11 | 1582-1662 | 81 | ttttttaaagCATTTATC....TGCTTAAGggtatgttta (SEQ ID No. 179) | duplicated exon |
| 12 | 1663-1807 | 145 | aaactttcagTCTTTAGA....TGATAAGGgtaagcactg (SEQ ID No. 180) | |
| 13 | 1808-1883 | 76 | ttatttccagACTTTTTG....TTTAAACCgtgagtataa (SEQ ID No. 181) | |
| 14 | 1884-1951 | 68 | caccttcaagAGTTCAGT....GGCAACTGgtaagttgta (SEQ ID No. 182) | helicase motif I (5' end) |
| 15 | 1952-2060 | 109 | tcatttcaagGATATGGA....CAGCTTAAgtaagtcatg (SEQ ID No. 183) | helicase motif I (3' end) and Ia |
| 16 | 2061-2129 | 69 | cttcttatagAATGTCCA....ATTAAATTgtgagtaatt (SEQ ID No. 184) | |
| 17 | 2130-2212 | 83 | gtttttacagAGGTAAAT....TGATATTGgtaagtgata (SEQ ID No. 185) | |
| 18 | 2213-2319 | 107 | ttttttacagGTATCACG....TGCCAATGgtaagctttg (SEQ ID No. 186) | helicase motif II |
| 19 | 2320-2504 | 185 | catcattcagGTTCCAAT....AAAACAAGgtaaggattt (SEQ ID No. 187) | helicase motif III |
| 20 | 2505-2679 | 175 | ttttctttagTTCCCACT....AAATTCAGgtatgaggat (SEQ ID No. 188) | helicase motif IV |
| 21 | 2680-2861 | 182 | ttgttctcagTGTGTCAT....TTAAATAGgtaaaaaaaa (SEQ ID No. 189) | helicase motifs V and VI |
| 22 | 2862-2963 | 102 | taatcgacagGCACCTTC....AGGAGACAgtatgtatta (SEQ ID No. 190) | |

TABLE 4-continued

,Intron-Exon Structure of the WRN Gene

| Exon | cDNA Location | Exon Size (bp) | Intron-Exon Boundary Sequences | Exon Features |
|---|---|---|---|---|
| 23 | 2964-3056 | 93 | tcttgggtagAATCATCT....AGGTCCAGgtaaagattt (SEQ ID No. 191) | |
| 24 | 3057-3198 | 142 | ttttatttagATTGGATC....GAGGATCTgtaagtatat (SEQ ID No. 192) | |
| 25 | 3199-3369 | 171 | ctaatttcagAATTCTCA....CGAAAAAGgtaaacagtg (SEQ ID No. 193) | |
| 26 | 3370-3464 | 95 | cttttaatagGGTAGAAA....CTGCCTAGgttcattttt (SEQ ID No. 194) | |
| 27 | 3465-3540 | 76 | tattttttagTTCGAAAA....AGAAGAAGgtttgtttta (SEQ ID No. 195) | |
| 28 | 3541-3614 | 74 | ttaaatgcagTCTAACTT....AAAAAAAGgtacagagtt (SEQ ID No. 196) | |
| 29 | 3615-3690 | 76 | aatattttagTATCATGG....AGACTCAGgtaaggcttt (SEQ ID No. 197) | |
| 30 | 3691-3803 | 113 | ttttgttcagATTGTGTT....AAAATGAGgtaaactatc (SEQ ID No. 198) | |
| 31 | 3804-3918 | 115 | ttaaacacagACCAACTA....GTGTTCAGgtaaaatact (SEQ ID No. 199) | |
| 32 | 3919-4050 | 132 | aattctgtagACAGACCT....TGCCTTTGgtaagtgtga (SEQ ID No. 200) | |
| 33 | 4051-4213 | 163 | ctttctctagAAGAGCAT....CAACTCAGgtgagaggca (SEQ ID No. 201) | |
| 34 | 4214-4422 | 209 | tcgtttacagATATGAGT....ATACTGAGgtattaatta (SEQ ID No. 202) | |
| 35 | 4423-5190 | 768 | tttcctacagACTTCATC.... (SEQ ID No. 203) | TM codon.3'UTR |

Note.
Exons are in uppercase and intron sequences are in lowercase letters.

As shown above, WRN contains a total of 35 exons ranging in size from 68 bp (exon 14) to 768 bp (exon 35). The coding region begins in the second exon (Table 2). As noted previously, there is a duplicated region in the WRN cDNA sequence which is 27 amino acids in length. This duplication is exactly conserved at the nucleotide level in cDNA. At the genomic level, the duplicated sequences were present as 2 exons (exons 10 and 11), each exon containing only the duplicated nucleotides. The intronic sequences adjacent to these 2 exons are also highly conserved, suggesting that the a relatively recent duplication event is responsible for these repeated exons. In addition, because the surrounding intronic sequences were conserved, it was not possible to design primers which could specifically amplify exons 10 and 11.

The helicase region of the WRN gene is contained in exons 14-21. Helicase motif 1 is split between exons 14 and 15 while the remaining motifs are each in an individual exon (Table 4). This region, from codon 569 to 859, has sequence similarity to the 7 signature helicase motifs. In addition, though the sequences between the motifs are not conserved, the spacing is very similar in genes from a wide range of species. For example, the helicase domains in the *E. coli* RecQ gene are found in a stretch of 288 amino acids compared to 291 amino acids for the WRN gene.

Example 7

Identification of Mutations

Initially, 4 different mutations in the C-terminal domain of WRN were identified. These mutations accounted for more than 80% of the Japanese WS patients examined. All 4 mutations are in the C-terminal domain region of WRN and the resulting predicted protein contained an intact helicase domain. Additional WS subjects are screened to identify further mutations. Genomic structure information is used to design PCR-primers for amplifying each exon, which is then subjected to DNA sequence analysis. Five additional WRN mutations are described; 2 are located in the consensus helicase motifs and another 2 are predicted to produce truncated proteins without the helicase domains. These mutations suggest that in at least some WS subjects, the enzymatic helicase activity is destroyed and support that complete loss-of-function of WRN gene product causes Werner's syndrome.

Although any cell may be used to isolate DNA, PBMC are preferred. As above, PBMC are obtained by venipuncture and subsequent hypotonic lysis of erythrocytes. PBMC are lysed by the addition of detergent, such as 0.5% NP-40, 0.5% Triton-X100, or 0.5% SDS. If a non-ionic detergent is used, no further purification of DNA is necessary, but proteinase K treatment, and subsequent heat killing of the enzyme (95° C. for 10 minutes) is required. Genomic DNA is amplified according to the PCR conditions recited above using the primers listed in Table 5. Exons 9 and 10 are contained in a region of DNA that is duplicated. The primer pair for exon 9 and 10 anneals to sequences outside the duplication. Amplified product is analyzed by DNA sequence determination, hybridization with allele-specific probe, or other mutation detection method. When DNA sequences are determined, the sequence of the amplified exon is aligned with the known sequence (FIG. 2A) and any discrepancies between patient samples and the reference sequence are identified.

TABLE 5

| PCR Fragment | Primer Sequence | Product Size (bp) | $Mg^{+2}$ (mM) | pH |
|---|---|---|---|---|
| exon 1 | A 5'-AGGGCCTCCACGCATGACGC (SEQ ID No. 92) | 583 | 1.5 | 8.3 |
| | B 5'-AGTCTGTTTTTCCAGAATCTCCC (SEQ ID No. 93) | | | |
| exon 2 | A 5'-CCTATGCTTGGACCTAGGTGTC (SEQ ID No. 94) | 339 | 1.5 | 8.3 |
| | B 5'-GAAGTTTACAAGTAACAACTGACTC (SEQ ID No. 95) | | | |
| exon 3 | A 5'-ACTATAAATTGAATGCTTCAGTGAAC (SEQ ID No. 96) | 316 | 1.5 | 8.3 |
| | B 5'-GAACACACCTCACCTGTAAAACTC (SEQ ID No. 97) | | | |
| exon 4 | E 5'-GGTAAACCACCATACCTGGCC (SEQ ID No. 98) | 691 | 1.5 | 8.3 |
| | F 5'-GTACATATCCTGGTCATTTAGCC (SEQ ID No. 99) | | | |
| exon 5 | B 5'-ATTCAGATAGAAAGTACATTCTGTG (SEQ ID No. 100) | 369 | 1.5 | 8.3 |
| | E 5'-GTTAAGAAATACTCAAGGTCAATGTG (SEQ ID No. 101) | | | |
| exon 6 | A 5'-GGTTGTATTTTGGTATAACATTTCC (SEQ ID No. 102) | 374 | 1.5 | 8.3 |
| | B 5'-ATATTTTGGTAGAGTTTCTGCCAC (SEQ ID No. 103) | | | |
| exon 7 | A 5'-CTCTTCGATTTTTCTGAAGATGGG (SEQ ID No. 104) | 291 | 1.5 | 8.3 |
| | B 5'-CCCTAATAGTCAGGAGTGTTCAG (SEQ ID No. 105) | | | |
| exon 8 | A 5'-GGAAAGAAAATGAAAATTTGATCCC (SEQ ID No. 106) | 316 | 4.0 | 8.3 |
| | B 5'-CAGCCTTAATGAATAGTATTCTTCAC (SEQ ID No. 107) | | | |
| exon 9 | C 5'-ATTGATCTTTTAAGTGAAGGTCAGC (SEQ ID No. 108) | 668 | 1.5 | 8.3 |
| | D 5'-CTGCAACAGAGACTGTATGTCCC (SEQ ID No. 109) | | | |
| exon 12 | A 5'-GCTTTCGACAAAATTGTAGGCCC (SEQ ID No. 110) | 337 | 1.5 | 9.0 |
| | B 5'-CCAAACCATCCAAAACTGGATCC (SEQ ID No. 111) | | | |
| exon 13 | A 5'-TAACCCATGGTAGCTGTCACTG (SEQ ID No. 112) | 285 | 1.5 | 8.3 |

TABLE 5-continued

| PCR Fragment | Primer Sequence | Product Size (bp) | $Mg^{+2}$ (mM) | pH |
|---|---|---|---|---|
| | B 5'-CTGTTGCTGTTAAGCAGACAGG (SEQ ID No. 113) | | | |
| exon 14 | C 5'-TTGAATGGGACATTGGTCAAATGG (SEQ ID No. 114) | 348 | 1.5 | 8.3 |
| | F 5'-GTAGTTGCATTTGTATTTTGAGAGT (SEQ ID No. 115) | | | |
| exon 15 | C 5'-GTAAAAAGAAATGAAAGCATCAAAGG (SEQ ID No. 116) | 246 | 4.0 | 8.3 |
| | D 5'-TCACCCACAGAAGAAAAAAAGAGG (SEQ ID No. 117) | | | |
| exon 16 | A 5'-CAAAAAAGAAAATTGCAAAGAACAGG (SEQ ID No. 118) | 282 | 4.0 | 8.3 |
| | B 5'-CAGCAACATGTAATTCACCCACG (SEQ ID No. 119) | | | |
| exon 17 | 5'-GAAGAGACTGGAATTGGGTTTGG (SEQ ID No. 120) | 532 | 1.5 | 8.3 |
| | 5'-ATAGAGTATCATGGGATAAGATAGG (SEQ ID No. 121) | | | |
| exon 18 | A 5'-TTCTCCTTTGGAGATGTAGATGAG (SEQ ID No. 122) | 273 | 4.0 | 10 |
| | B 5'-TCTTCAGCTTCTTTACCACTCCCCA (SEQ ID No. 123) | | | |
| exon 19 | A 5'-CATGGTGTTTGACAACAGGATGG (SEQ ID No. 124) | 396 | 4.0 | 9.0 |
| | B 5'-GTTAAATATGCATTAGAAGGAAATCG (SEQ ID No. 125) | | | |
| exon 20 | A 5'-ATAAAACCAAACGGGTCTGAAGC (SEQ ID No. 126) | 342 | 4.0 | 8.3 |
| | B 5'-AAAAGAAGTATTCAATAAAGATCTGG (SEQ ID No. 127) | | | |
| exon 21 | A 5'-AATTCCACTTTGTGCCAGGGACT (SEQ ID No. 128) | 397 | 1.5 | 9.0 |
| | B 5'-ACTTGGGATACTGGAAATAGCCT (SEQ ID No. 129) | | | |
| exon 22 | A 5'-TTTTTATCTTGATGGGGTGTGGG (SEQ ID No. 130) | 356 | 1.5 | 9.0 |
| | B 5'-AAATTCAGCACACATGTAACAGCA (SEQ ID No. 131) | | | |
| exon 23 | A 5'-CTGAAGTCAAATAATGAAGTCCCA (SEQ ID No. 132) | 360 | 4.0 | 8.3 |
| | B 5'-GTTTGCTTTCTCATATCTAAACACA (SEQ ID No. 133) | | | |
| exon 24 | A 5'-CTTGTGAGAGGCCTATAAACTGG (SEQ ID No. 134) | 267 | 1.5 | 8.3 |
| | B 5'-GGTAAACAGTGTAGGAGTCTGC (SEQ ID No. 135) | | | |
| exon 25 | C 5'-GCTTGAAGGATGAGGCTCTGAG (SEQ ID No. 136) | 461 | 1.5 | 8.3 |
| | D 5'-TGTTCAGAATGAGCACGATGGG (SEQ ID No. 137) | | | |

TABLE 5-continued

| PCR Fragment | Primer Sequence | Product Size (bp) | $Mg^{+2}$ (mM) | pH |
|---|---|---|---|---|
| exon 26 | A 5'-CTTGTGAGAGGCCTATAAACTGG (SEQ ID No. 138) | 267 | 1.5 | 8.3 |
| | B 5'-GGTAAACAGTGTAGGAGTCTGC (SEQ ID No. 139) | | | |
| exon 27 | A 5'-GCCATTTTCTCTTTAATTGGAAAGG (SEQ ID No. 140) | 274 | 1.5 | 8.3 |
| | B 5'-ATCTTATTCATCTTTCTGAGAATGG (SEQ ID No. 141) | | | |
| exon 28 | A 5'-TGAAATAGCCCAACATCTGACAC (SEQ ID No. 142) | 291 | 1.5 | 8.3 |
| | B 5'-GATTAATTTGACAGCTTGATTAGGC (SEQ ID No. 143) | | | |
| exon 29 | A 5'-TGAAATATAAACTCAGACTCTTAGC (SEQ ID No. 144) | 303 | 1.5 | 8.3 |
| | B 5'-GTACTGATTTGGAAAGACATTCTC (SEQ ID No. 145) | | | |
| exon 30 | A 5'-GATGTGACAGTGGAAGCTATGG (SEQ ID No. 146) | 307 | 1.5 | 8.3 |
| | B 5'-GGAAAAATGTGGTATCTGAAGCTC (SEQ ID No. 147) | | | |
| exon 31 | A 5'-AAGTGAGCAAATGTTGCTTCTGG (SEQ ID No. 148) | 304 | 1.5 | 8.3 |
| | B 5'-TCATTAGGAAGCTGAACATCAGC (SEQ ID No. 149) | | | |
| exon 32 | A 5'-GTTGGAGGAAATTGATCCCAAGTC (SEQ ID No. 150) | 351 | 1.5 | 8.3 |
| | B 5'-TGTTGCTTATGGGTTTAACTTGTG (SEQ ID No. 151) | | | |
| exon 33 | A 5'-TAAAGGATTAATGCTGTTAACAGTG (SEQ ID No. 152) | 360 | 1.5 | 8.3 |
| | B 5'-TCACACTGAGCATTTAGTACCTG (SEQ ID No. 153) | | | |
| exon 34 | C 5'-GCAAAGGAAATGTAGCACATAGAG (SEQ ID No. 154) | 491 | 1.5 | 8.3 |
| | D 5'-AGGCTATAGGCATTTGAAAGAGG (SEQ ID No. 155) | | | |
| exon 35 | A 5'-GTAGGCTCCCAGAAGACCCAG (SEQ ID No. 156) | 406 | 1.5 | 8.3 |
| | B 5'-GAAAGGATGGGTGTGTATTCAGG (SEQ ID No. 157) | | | |
| mutation 7 | GD A 5'-ACAGGCCATAGTTTGCCAACCC (SEQ ID No. 158) | 426 | 1.5 | 9.0 |
| | GD D 5'-TGGTATTAGAATTTCCCTTTCTTCC (SEQ ID No. 159) | | | |
| DJG RT-PCR | 5EE 5'-TGAAAGAGAATATGGAAAGAGGCTTG (SEQ ID No. 160) | 2002 | 1.5 | 8.3 |
| | B 5'-CTTTATGAAGCCAATTTCTACCC (SEQ ID No. 161) | | | |

TABLE 5-continued

| PCR Fragment | Primer Sequence | Product Size (bp) | $Mg^{+2}$ (mM) | pH |
|---|---|---|---|---|
| P2934AT1 | A 5'-TCAAAATCAGTCGCCTCATCCC (SEQ ID No. 162) | 168 | 2.0 | 8.3 |
| | B 5'-CAATGTATCAGTCAGGGTTCACC (SEQ ID No. 163) | | | |

The annealing temperature was 60° C. for all primer sets.

Mutations are detected by amplifying WRN exons from genomic DNA and directly cycle-sequencing the PCR products by dye-terminator cycle sequencing (Perkin Elmer) and an AB1373 automated DNA sequencer. Prior to sequencing, the PCR-amplified exon fragments were purified using a QIAquick 8 PCR purification kit (Qiagen). The resulting sequences are aligned by FASTA analysis (GCG). Nucleotide differences between WS and controls are subsequently confirmed by sequencing the reverse strand.

Reverse transcriptase PCR (RT-PCR) based methods used to identify some mutations (mutations 1-4 and 9, Table 6) and to confirm the predicted consequences of splice-junction mutations. RT-PCR products were synthesized from mRNA isolated from lymphoblastoid cell lines (Qiagen Oligotex, Qiagen). The large genomic deletion was detected in genomic DNA using long-range PCR (Expand Long Template PCR System, Boehringer Mannheim).

Diagnostic Criteria. WS patients were from an International Registry of Werner's Syndrome subjects. Diagnostic criteria are based on the following signs and symptoms (Nakura et al. 1994). Cardinal signs are: 1) bilateral cataracts; 2) characteristic dermatological pathology (tight skin, atrophic skin, pigmentary alterations, ulceration, hyperkeratosis, regional subcutaneous atrophy) and characteristic facies ("bird" facies); 3) short stature; 4) paternal consanguinity (3rd cousin or greater) or affected sibling; 5) premature greying and/or thinning of scalp hair; 6) positive 24-hour urinary hyaluronic acid test, when available). Further criteria are: 1) diabetes mellitus; 2) hypogonadism (secondary sexual underdevelopment, diminished fertility, testicular or ovarian atrophy); 3) osteoporosis; 4) osteosclerosis of distal phalanges of fingers and/or toes (X-ray diagnosis); 5) soft tissue calcification; 6) evidence of premature atherosclerosis (e.g. history of myocardial infarction); 7) mesenchymal neoplasms, rare neoplasms or multiple neoplasms; 8) voice changes (high pitched, squeaky or hoarse voice); 9) flat feet. Diagnostic classifications are as follows: "Definite", all cardinal signs (#6 when available) and any 2 others; "Probable", the first 3 cardinal signs and any 2 others; "Possible", either cataracts or dermatological alterations and any 4 others; "Excluded", onset of signs and symptoms before adolescence (except short stature since current data on pre-adolescent growth patterns is inadequate) or a negative hyaluronic acid test. Family designations are as previously used (Nakura et al. 1994; Goddard et al. 1996; Yu et al. 1996).

Mutations in WS Subjects. Initial screening of the WRN gene was based on sequence from only the 3' end of the gene (exons 23-35). Thus the first 4 mutations (designated 1-4, Table 3) were in the region 3' to the helicase domains. In this mutation screening, primers amplify exons 2-35 along with approximately 80 bp of flanking intronic sequence (Table 5). Initially, 9 WS subjects (Caucasian subjects DJG, EKL, and FES, and Japanese subjects IB, KO, OW, KUN, WKH, and WSF) were screened for mutations. These subjects were selected based on haplotype analysis that suggested that each subject might have a different mutation (Yu et al. 1994; Goddard et al. 1996). A total of 30 Japanese and 36 Caucasian subjects were ultimately screened for each mutation by DNA sequence analysis of the appropriate exon.

TABLE 6

Summary of WRN Mutations

| Mutation | Codon | Exon | Type of Mutation | Nucleotide Sequence | Comment | Predicted Protein Length |
|---|---|---|---|---|---|---|
| none | | | | | | 1432 |
| 1 | 1165 | 30 | substitution | CAG (Gln) to TAG (terminator) | nonsense | 1164 |
| 2 | 1305 | 33 | substitutions | CGA (Arg) to TGA (terminator) | nonsense | 1034 |
| 3 | 1230 | 32 | 4 bp deletion | gtag-ACAG to gt-AG | 4 bp deletion at splice-donor site | 1247 |
| 4 | 1047-1078 | 24 | substitution | tag-GGT to tac-GGT | substitution at splice-donor site | 1060 |
| 5 | 369 | 9 | substitution | CGA (Arg) to TGA (terminator) | nonsense | 368 |
| 6 | 889 | 22 | substitution | CGA (Arg) to TGA (terminator) | nonsense | 888 |

TABLE 6-continued

Summary of WRN Mutations

| Mutation | Codon | Exon | Type of Mutation | Nucleotide Sequence | Comment | Predicted Protein Length |
|---|---|---|---|---|---|---|
| 7 | 759-816 | 20 | substitution | CAG-gta to CAG-tta | substitution at splice-receptor site | 760 |
| 8 | 389 | 9 | 1 bp deletion | AGAG (Arg) to GAG (Glu) | frame-shift | 391 |
| 9 | 697-942 | 19-23 | deletion (>15 kb) | — | genomic deletion | 1186 |

TABLE 7

Mutation Status of WS Subjects[1]

| Nutation | Japanese WS Subjects | | Non-Japanese WS Subjects | |
|---|---|---|---|---|
| | Homozygous | Heterozygous | Homozygous | Heterozygous |
| 1 | SY[D] | | | |
| 2 | HH[D], HM[D], MH[M], NN[D] | | GAR[D] | |
| 3 | | | SYR[1] | |
| 4 | FJ[D], FUW[D], HA[1], HW[D], IU[D], JOI[D], JO2[D], KAKU[P], KY[D], MCI[D], MIE2[1], SK[D], ST[D], TH[1], TK[M], TO[D], ZM[D], 78–85[1]. | | | |
| 5 | KO[D], OW[P] | KUN[1] | EKL[D], AG0780[1], AG4103[M] | DJG[P], CP3[1], NF[M] |
| 6 | | | CTA[D] | SUG1[P] |
| 7 | WKH[D] | | | |
| 8 | | | | FES[1] |
| 9 | | | | DJG[P], SUG1[P] |

[1]The diagnostic classification is as previously described (Nakura et al. 1994).
Diagnosis categories:
[D]Definite;
[P]Probable;
[M]Possible;
[I]Insufficiant data.
The country of origin (ethin group) of non-Japanese subjects are: AG00780, USA (Caucasian); AG04103, USA (Caucasian); CTA, England (India, East African, Asian); CP3; France (Caucasian); DJG Germany (German); EKL, Switzerland (German); FES, Germany (German); NF, France (Caucasian); SUG, USA (Caucasian); SYR, Syria (Syrian). AG04103 and AG00780 were obtained as cell lines from the Aging Cell Repository (Camden, New Jersey).

Five new WS mutations were detected in the WRN gene (designated 5-9, Table 6). Two of the mutations (5 and 6) were single base substitutions creating nonsense codons. Mutation 5 results in a C→T transition changing an Arg to a termination codon (Table 6, FIG. 6). The predicted protein is truncated at 368 amino acids, excluding the helicase region, which begins at codon 569. Three Japanese and 3 Caucasian subjects were homozygous, and 1 Japanese and 4 Caucasians were heterozygous for this mutation (Table 7). Mutation 6 is also a C→T transition changing an Arg to a nonsense codon. One Caucasian WS subject was homozygous for this mutation, and a second was a compound heterozygote. The predicted protein product is 888 amino acids. A third substitution mutation (mutation 7) was a G→T change at a splice-receptor site, generating a truncated mRNA devoid of exon 20 and a prematurely terminated WRN protein at amino acid 760. A single Japanese WS subject was homozygous for this mutation.

Two deletions were observed. One (mutation 8) is a 1 bp deletion at codon 389 resulting in a frame shift and a predicted truncated protein 391 amino acids long. This mutation is found in one Caucasian patient as a heterozygote. The second (mutation 9) is a much larger deletion. This deletion was first observed in RT-PCR experiments when 2 different RT-PCR products were obtained from RNA prepared from subject DJG. RT-PCR products produced by primers 5EE and B (Table 5) yielded 2 different products, one with the expected size of 2009 bp, and a second, shorter product approximately 700 bp smaller. The DNA sequence of the shorter product revealed that exons 19 through 23 were missing. To further establish the nature of this mutation, primers (exon 18A and exon 24A, Table 5) derived from the exons flanking this potential gross deletion (exons 18 and 24) were used to amplify genomic DNA from subject DJG using a long-range PCR protocol. A single 5 kb fragment was observed corresponding to the shorter RT-PCR product. (The normal fragment, which is estimated to be >20 kb was not observed.) The complete DNA sequence of this 5 kb fragment was determined and contained the expected 3' and 5' ends of exons 18 and 24, respectively. The exonic sequences were separated by intronic sequences adjacent to the 3' and 5' end of exons 18 and 24, respectively. No sequences from exons 19-23 were found in the 5 kb fragment. In other subjects and controls, the intronic sequence in the intron 3' to exon 18 contained 531 bp of unique sequence followed by a 241 bp Alu repeat element. Likewise, for the region 5' to exon 24, there is an Alu repeat element separated from exon 24 by 3,460 bp of unique sequence. The 4938 bp fragment from subject DJG contained these unique exon-flanking intronic sequences separated by a single Alu element. Thus, this deletion presumably occurred by a recombination error at 2 highly homologous Alu elements within the WRN gene. A primer set, GD-A and GD-D (Table 5) was designed to specifically amplify a short fragment (426 bp) across this junction point. A single additional Caucasian WS patient, SUG, was shown to contain this genomic deletion. Further PCR amplification of the exons within this deleted region demonstrated that both DJG and SUG are heterozygous for this mutation.

Origins of WRN Mutations. Because multiple subjects have the same mutation and because the same mutation was observed in different ethnic groups, at least some of the mutations likely originated in common founders. Evidence for a common founder was examined using 2 short tandem repeat polymorphisms (STRPs) within the WRN gene. These STRPs, D8S2162 and p2934AT1, were isolated from the same P1 clone (p2934) and are within 17.5 kb of each other. While D8S2162 is not particularly polymorphic (heterozygosity=54% in Japanese and 70% in Caucasians) and is primarily a 2 allele system (140 and 142 bp alleles), p2934AT1 is highly polymorphic (heterozygosity=78% in both Japanese and Caucasian populations). For mutation 4, which has only been observed in Japanese subjects, all but 1 subject had the D8S2164/p2934AT1 haplotype of 140-148 (Table 8). The single exception, JO2, has the haplotype 140-150, with the p2934AT1 allele being 2 bp different from the 148 bp allele observed in other subjects with mutation 4. This 2 bp difference may be the result of a 2 bp mutation, as is commonly observed in dinucleotide repeat STRP loci (Weber and Wong, 1993). The haplotype data is consistent with a common Japanese founder and is consistent with the linkage disequilibrium observed in the same Japanese subjects for other markers in the WRN region (Yu et al. 1994; Goddard et al., 1996). For mutations 2 and 5, in the Japanese, the 896R18-p2934AT1 haplotypes for the small number of available subjects, are consistent with common founders for each mutation. However, the non-Japanese subjects with mutations 2 and 5 have discordant p2934AT1 genotypes when compared to Japanese subjects with the same mutations. These results do not support a common founder for both Japanese and non-Japanese subjects with mutations 2 and 5. Within the non-Japanese subjects, for mutation 5, there may be as many as 3 different founders since in both cases, different subjects with mutation 5 are discordant for p2934AT1 (e.g. compare AG00780 to EKL). It should be noted that absence of evidence for a common founder does not necessarily exclude the possibility of a single originating mutational event. Intragenic recombination and/or mutations creating new alleles at the 2 STRP loci could, over time, obscure the origins of the different WRN mutations.

TABLE 8

STRP Genotypes at the WRN gene[1].

| Subject | Ethnic Group | Mutation | y896r18 | p2934at1 |
|---|---|---|---|---|
| FJ, FUW, HA, HW, JO1, KAKU, KY, MIE2, TO | Japanese | 4 | 140/140 | 148/148 |
| JO2 | Japanese | 4 | 140/140 | 150/150 |
| HM, MH, NN, | Japanese | 2 | 140/140 | 144/144 |
| GAR | Hispanic | 2 | 140/140 | 156/156 |
| OW, KO | Japanese | 5 | 140/140 | 148/148 |
| AG00780 | Caucasian | 5 | 142/142 | 136/136 |
| EKL, AG04103 | Caucasian | 5 | 142/142 | 128/128 |
| CP3 | Caucasian | 5/? | 142/150 | 128/142 |
| KUN | Japanese | 5/? | 140/142 | 128/148 |
| DJG | Caucasian | 5/9 | 140/142 | 128/del[2] |

[1]Gentype data for HH, SK, ST, TH, TK, and ZM was not available.
For y896R18, alleles in bp (frequency for Caucasian, frequency for Japanese) were as follows: 136 (0.030, 0.025); 138 (0.020, 0.010); 140 (0.460, 0.576); 142 (0.337, 0.359); 144 (0.084, 0.010); 146 (0, 0.010); 148 (0.009, 0.010); 150 (0.059, 0).
For p2934AT1, alleles in bp (Caucasian frequency, Japanese frequency) were as follows: 114 (0.006, 0); 122 (0, 0.009); 124 (0.011, 0); 128 (0.253, 0.079); 130 (0, 0.018); 132 (0.006, 0.009); 134 (0.046, 0.096); 136 (0.086), 0.009); 138 (0.011, 0); 140 (0.034, 0); 142 (0.052, 0.035); 144 (0.023, 0.061); 146 (0.023, 0.053); 148 (0.034, 0.0132); 150 (0.034, 0.105); 152 (0.057, 0.123); 154 (0.063, 0.088); 156 (0.086, 0.070); 158 (0.098, 0.070); 160 (0.046, 0.018); 162 (0.029, 0.009); 166 (0, 0.009); 168 (0, 0.009).

The 5 mutations identified here demonstrate that WS mutations are not restricted to the 3' end of the gene, but are also found in other regions of WRN. In addition, mutations 5 and 7-9 each disrupt either part or all of the helicase region. Thus the WS subjects homozygous for this mutation will completely lack the WRN helicase domains as well as the 3' end of the protein. Though the possibility exists that the truncated 368 amino acid protein has some partial remaining function, mutation 5 probably results in complete loss of all activity of the WRN protein. However, the WS phenotype in these subjects is not appreciably distinct from the WS phenotype generated by the other mutations described here. Thus, all mutations in the WS gene may be complete loss of function mutations.

Example 8

Identification of Mouse WRN Gene

The mouse WRN cDNA was isolated by screening a mouse splenocyte cDNA library at low strengency with human WRN cDNA as probe. The mouse cDNA sequence is presented in FIG. 9. The homology between human and mouse WRN cDNA sequence is about 80%. On the amino acid level, the human and mouse WRN gene product show about 90% identity. Notably, the repeated exon in human WRN cDNA (exons 10 and 11) is only present once in mouse WRN cDNA.

Genomic mouse WRN clone was isolated by using mouse WRN specific primers to screen mouse genomic BAC library. The genomic DNA sequence is presented in FIG. 6.

The genomic DNA sequence is presentd in FIG. 7 and SEQ ID NOS: 207-209. The DNA sequence is presented in FIG. 6 and SEQ ID NOS: 205 and 206.

Example 9

Localization of the WRN Gene Product

A rabbit polyclonal antiserum raised to a peptide of WRN gene product is used in an indirect immunofluorescence assay to determine the intracellular localization of the WRN protein.

A rabbit polyclonal antiserum is raised to the peptide Phe-Pro-Gly-Ser-Glu-Glu-Ile-Cys-Ser-Ser-Ser-Lys-Arg (FPGSEEICSSSKR) (SEQ ID NO: 204) by standard methods (see Harlow and Lane, *Antibodies, A Laboratory Manual*, CSH Press, Cold Spring Harbor, 1989*; Current Protocols in Immunology*, Greene Publishing, 1995). The peptide corresponds to residues 1375 through 1387 of the WRN polypeptide.

Cells, such as epithelial cells, are grown on a plastic or glass surface, fixed with 3% paraformaldehyde and permeabilized for 2 min with a buffer containing 0.5% Triton X-100, 10 mM PIPES, pH 6.8, 50 mM NaCl, 300 mM sucrose, and 3 mM $MgCl_2$ (see for example, Fey et al., *J. Biol. Chem*. 98: 1973, 1984). The cells are then stained for 20 min with a suitable dilution of the anti-peptide antibody (1:1500), washed, stained with a suitable second antibody (e.g., FITC-conjugated goat anti-rabbit antibody), washed, and mounted for visualization by gluorescence microscopy. Control stains include bis-benzimidine (Sigma, St. Louis, Mo.), which stains DNA, and phalloidin (Molecular Probes, OR, BODIPY 558/568 phalloidin), which stains filamentous actin.

Figure 9C:
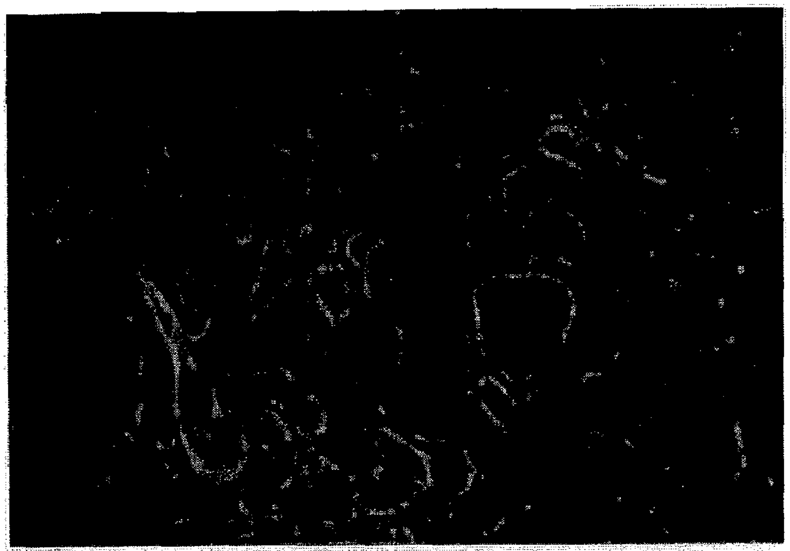
FIGS. 9A, 9B, and 9C are photomeceographs showing localization of the WRN gene product by fluorescent antibody staining (panel A), nuclei (panel B), and the size of cells (panel C) expressing the WRN gene.
Figure 9B:
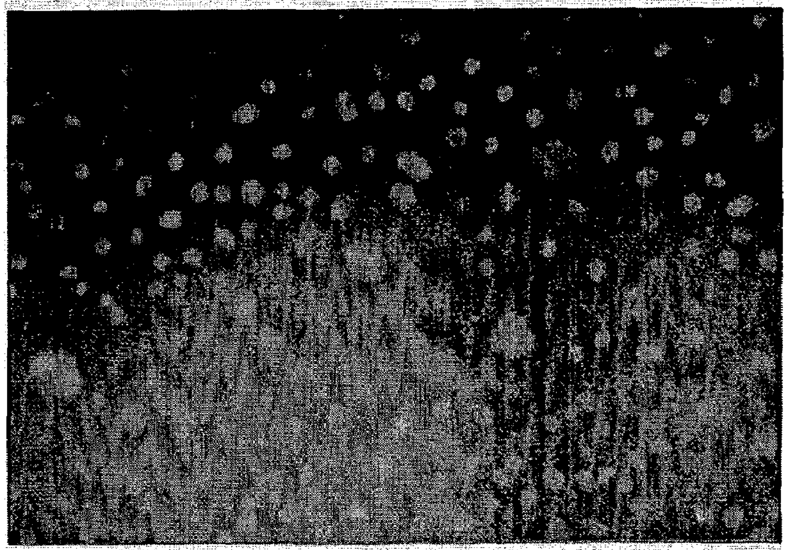
Figure 9A:
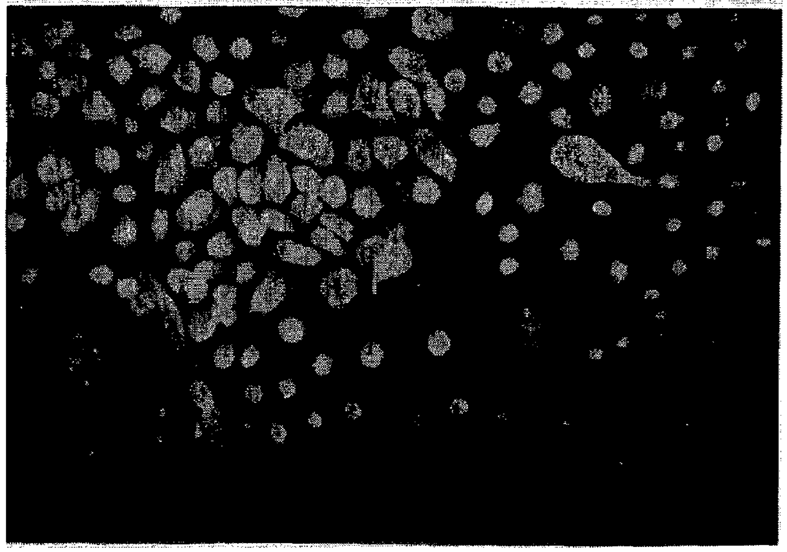

As seen in FIG. 9, the WRN gene product is almost entirely located in the nucleus. Nuclear staining is readily noted in the epithelial cells at the bottom left in panel A. These cells are close to the periphery of the expanding clone of human prostate epithelial cells. Cells that are not rapidly dividing (e.g., cells closer to the center of the clone), such as those seen in the upper right of panel A, are stained in both the cytoplasm and nucleus. The location and size of the nuclei in these cells is shown by staining DNA with the intercalating dye bis-benzimidine (Hoeschst 33258), panel B. The overall size of the cells and in some cases key cytoskeletal features are revealed by staining for F-actin as shown in panel C.

Example 10

Isolation of a Protein that Binds to the WRN Gene Product

A yeast 2-hybrid interaction screen (Hollenberg et al., *Mol. Cell Biol*. 13: 3813, 1995) is used to identify and isolate a cellular protein that binds to the carboxy-terminal 443 amino acids (residues 990 through 1432) of the WRN gene product.

A library of 1.1×106 independent cDNA clones generated from RNA isolated from stimulated human peripheral blood mononuclear cells is generated in pACT-2 (Clontech, Palo Alto, Calif.) that creates cDNA/GAL4 activation domain fusions is co-transfected into yeast containing pLEXA with the WRN gene fragment to generate WRN/LEXA DNA-binding fusion. Host yeast cells, L40, are grown on medium lacking leucine, tryptophan, and histidine and containing 4 mM 3AT, a toxic catabolite for histidine. 67 colonies grew on this medium. Of these, 60 were cured of the pLEXA plasmid by growth on medium containing cycloheximide and mated with a yeast strain expressing a fusion of a "sticky" laminin and the GAL4 activation domain. 19 clones did not activate the sticky protein and underwent DNA sequence analysis. Of these, 6 contained sequences that did not match any sequence in GenBank by BLAST search. Two other clones encoded camitine palmitoyl transferase I and prolyl 4-hydroxylase B subunit. Six independent clones encoded a 70K component of the U1 snRNP complex (GenBank Accession No. M22636). Moreover, all six derived from the RNA recognition motif region of the 70K protein.

From the foregoing, it will be appreciated that, although specific embodiments of this invention have been described herein for the pruposes of illustration, various modifications may be made without departing from the spirit and scope of the invention. Accordingly, the invention is not limited except by the appended claims.

We claim:

1. A purified antibody which specifically binds to a WRN gene product comprising the amino acid sequence set forth in SEQ ID NO:71.

2. A purified antibody that specifically binds to a WRN gene product peptide, wherein the peptide consists of the amino acid sequence set forth in SEQ ID NO:204.

3. The antibody of claim 2 wherein the antibody is a monoclonal antibody.

4. The antibody according to either claim 1 or claim 2 wherein said antibody is a monoclonal antibody.

5. The antibody according to either claim 1 or claim 2 wherein said antibody is selected from the group consisting of an Fab fragment, an Fv fragment and a single chain antibody.

6. A hybridoma capable of producing the antibody according to claim 4.

* * * * *